(12) United States Patent
Rajeev

(10) Patent No.: US 12,274,753 B2
(45) Date of Patent: *Apr. 15, 2025

(54) COMPOSITIONS AND METHODS FOR TARGETED RNA DELIVERY

(71) Applicant: Verve Therapeutics, Inc., Boston, MA (US)

(72) Inventor: Kallanthottathil G. Rajeev, Wayland, MA (US)

(73) Assignee: VERVE THERAPEUTICS, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/470,280

(22) Filed: Sep. 19, 2023

(65) Prior Publication Data

US 2024/0100169 A1    Mar. 28, 2024

Related U.S. Application Data

(60) Continuation of application No. 17/533,461, filed on Nov. 23, 2021, now Pat. No. 11,801,306, which is a division of application No. 17/192,709, filed on Mar. 4, 2021, now Pat. No. 11,207,416.

(60) Provisional application No. 63/078,982, filed on Sep. 16, 2020, provisional application No. 62/984,866, filed on Mar. 4, 2020.

(51) Int. Cl.
*A61K 47/54* (2017.01)
*A61K 47/69* (2017.01)
*A61P 9/10* (2006.01)
*C12N 15/113* (2010.01)

(52) U.S. Cl.
CPC ........ *A61K 47/549* (2017.08); *A61K 47/6929* (2017.08); *A61P 9/10* (2018.01); *C12N 15/113* (2013.01)

(58) Field of Classification Search
CPC ..... A61K 47/549; A61K 47/6929; A61P 9/10; C12N 15/113
See application file for complete search history.

(56) References Cited

U.S. PATENT DOCUMENTS

| | | |
|---|---|---|
| 3,687,808 A | 8/1972 | Merigan, Jr. et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,138,045 A | 8/1992 | Cook et al. |
| 5,149,782 A | 9/1992 | Chang et al. |
| 5,214,136 A | 5/1993 | Lin et al. |
| 5,218,105 A | 6/1993 | Cook et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,272,250 A | 12/1993 | Spielvogel et al. |
| 5,292,873 A | 3/1994 | Rokita et al. |
| 5,317,098 A | 5/1994 | Shizuya et al. |
| 5,371,241 A | 12/1994 | Brush |
| 5,391,723 A | 2/1995 | Priest |
| 5,414,077 A | 5/1995 | Lin et al. |
| 5,416,203 A | 5/1995 | Letsinger |
| 5,451,463 A | 9/1995 | Nelson et al. |
| 5,486,603 A | 1/1996 | Buhr |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van et al. |
| 5,525,465 A | 6/1996 | Haralambidis et al. |
| 5,541,313 A | 7/1996 | Ruth |
| 5,545,730 A | 8/1996 | Urdea et al. |
| 5,552,538 A | 9/1996 | Urdea et al. |
| 5,565,552 A | 10/1996 | Magda et al. |
| 5,567,810 A | 10/1996 | Weis et al. |

(Continued)

FOREIGN PATENT DOCUMENTS

| | | |
|---|---|---|
| EP | 4114360 A1 | 1/2023 |
| GB | 2213818 A | 8/1989 |

(Continued)

OTHER PUBLICATIONS

Baker; K.E. et al.: Nonsense-mediated mRNA decay: terminating erroneous gene expression. Current Opinion in Cell Biology 16(3):293-299 (2004).

(Continued)

*Primary Examiner* — Genevieve S Alley

(74) *Attorney, Agent, or Firm* — Wilson Sonsini Goodrich & Rosati

(57) ABSTRACT

Provided herein are compositions, methods of making the same, and methods for targeted delivery of therapeutic agents for modifying expression and function of target genes, e.g. proteins involved in lipid and cholesterol metabolism such as PCSK9. Further provided herein are compositions and methods of treating conditions related to coronary disease.

20 Claims, 12 Drawing Sheets

Specification includes a Sequence Listing.

(56) References Cited

U.S. PATENT DOCUMENTS

| | | | |
|---|---|---|---|
| 5,574,142 | A | 11/1996 | Meyer, Jr. et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,371 | A | 12/1996 | Sessler et al. |
| 5,591,584 | A | 1/1997 | Chang et al. |
| 5,595,726 | A | 1/1997 | Magda et al. |
| 5,597,696 | A | 1/1997 | Linn et al. |
| 5,599,923 | A | 2/1997 | Sessler et al. |
| 5,599,928 | A | 2/1997 | Hemmi et al. |
| 5,608,046 | A | 3/1997 | Cook et al. |
| 5,672,662 | A | 9/1997 | Harris et al. |
| 5,688,941 | A | 11/1997 | Cook et al. |
| 5,714,166 | A | 2/1998 | Tomalia et al. |
| 5,885,613 | A | 3/1999 | Holland et al. |
| 6,153,737 | A | 11/2000 | Manoharan et al. |
| 6,172,208 | B1 | 1/2001 | Cook |
| 6,214,345 | B1 | 4/2001 | Firestone et al. |
| 6,300,319 | B1 | 10/2001 | Manoharan |
| 6,335,434 | B1 | 1/2002 | Guzaev et al. |
| 6,335,437 | B1 | 1/2002 | Manoharan |
| 6,395,437 | B1 | 5/2002 | Wollesen |
| 6,444,806 | B1 | 9/2002 | Veerapanani et al. |
| 6,486,308 | B2 | 11/2002 | Kutyavin et al. |
| 6,525,031 | B2 | 2/2003 | Manoharan |
| 6,528,631 | B1 | 3/2003 | Cook et al. |
| 6,559,279 | B1 | 5/2003 | Manoharan et al. |
| 7,745,651 | B2 | 6/2010 | Heyes et al. |
| 7,799,565 | B2 | 9/2010 | MacLachlan et al. |
| 8,017,804 | B2 | 9/2011 | Keil et al. |
| 8,106,022 | B2 | 1/2012 | Manoharan et al. |
| 8,192,753 | B2 | 6/2012 | Essler et al. |
| 8,193,246 | B2 | 6/2012 | Panzner et al. |
| 8,202,983 | B2 | 6/2012 | Dellinger et al. |
| 8,357,722 | B2 | 1/2013 | Keil et al. |
| 8,877,901 | B2 | 11/2014 | Govindan |
| 9,365,610 | B2 | 6/2016 | Payne et al. |
| 9,549,983 | B2 | 1/2017 | Brown et al. |
| 9,879,265 | B2 | 1/2018 | Albæk et al. |
| 10,358,643 | B2 | 7/2019 | Albaek et al. |
| 11,207,416 | B2 | 12/2021 | Rajeev et al. |
| 11,801,306 | B2 | 10/2023 | Rajeev et al. |
| 2009/0239814 | A1 | 9/2009 | Manoharan et al. |
| 2012/0101148 | A1 | 4/2012 | Aking et al. |
| 2012/0114696 | A1 | 5/2012 | Pang et al. |
| 2012/0183602 | A1 | 7/2012 | Chen et al. |
| 2013/0020652 | A1 | 1/2013 | Huang et al. |
| 2013/0202652 | A1 | 8/2013 | Manoharan et al. |
| 2014/0287024 | A1 | 9/2014 | Wang et al. |
| 2015/0126718 | A1 | 5/2015 | Prakash et al. |
| 2015/0273068 | A1 | 10/2015 | Maier et al. |
| 2015/0291958 | A1 | 10/2015 | Albaek et al. |
| 2016/0060354 | A1 | 3/2016 | Avila et al. |
| 2017/0143631 | A1 | 5/2017 | Chen et al. |
| 2018/0290965 | A1 | 10/2018 | Brito et al. |
| 2018/0312846 | A1 | 11/2018 | Albaek et al. |
| 2019/0032087 | A1 | 1/2019 | Cullis et al. |
| 2019/0316127 | A1 | 10/2019 | Schlegel et al. |
| 2021/0207146 | A1 | 7/2021 | Prakash et al. |
| 2022/0152210 | A1 | 5/2022 | Rajeev et al. |
| 2024/0131166 | A1 | 4/2024 | Rajeev et al. |

FOREIGN PATENT DOCUMENTS

| | | |
|---|---|---|
| WO | WO-9819705 A1 | 5/1998 |
| WO | WO-2006007712 A1 | 1/2006 |
| WO | WO-2008103276 A2 | 8/2008 |
| WO | WO-2009120878 A2 | 10/2009 |
| WO | WO-2009134487 A2 | 11/2009 |
| WO | WO-2010006282 A2 | 1/2010 |
| WO | WO-2010088537 A2 | 8/2010 |
| WO | WO-2010093395 A1 | 8/2010 |
| WO | WO-2012016188 A2 | 2/2012 |
| WO | WO-2013076844 A1 | 5/2013 |
| WO | WO-2013176844 A1 | 11/2013 |
| WO | WO-2014118272 A1 | 8/2014 |
| WO | WO-2015089354 A1 | 6/2015 |
| WO | WO-2015095340 A1 | 6/2015 |
| WO | WO-2016168286 A1 | 10/2016 |
| WO | WO-2017070632 A2 | 4/2017 |
| WO | WO-2017173054 A1 | 10/2017 |
| WO | WO-2018027078 A1 | 2/2018 |
| WO | WO-2018136620 A2 | 7/2018 |
| WO | WO-2019145543 A1 | 8/2019 |
| WO | WO-2020097540 A1 | 5/2020 |
| WO | WO-2020160397 A1 | 8/2020 |
| WO | WO-2020219276 A1 | 10/2020 |
| WO | WO-2021178725 A1 | 9/2021 |
| WO | WO-2022060871 A1 | 3/2022 |
| WO | WO-2022271806 A1 | 12/2022 |
| WO | WO-2023015223 A2 | 2/2023 |

OTHER PUBLICATIONS

Behm-Ansmant; I. et al.: Quality control of gene expression: a stepwise assembly pathway for the surveillance complex that triggers nonsense-mediated mRNA decay. Genes & Development 20(4):391-398 (2006).

Brown, Jonathan et al.: Ligand Conjugated Multimeric siRNAs Enable Enhanced Uptake and Multiplexed Gene Silencing. Nucleic Acid Therapeutics 29:5 (2019), Mary Ann Liebert, Inc., DOI: 10.1089/nat.2019.0782.

Chadwick, A.C. et al.: In Vivo Base Editing of PCSK9 (Proprotein Convertase Subtilisin/Kexin Type 9) as a Therapeutic Alternative to Genome Editing. Arterioscler. Thromb. Vasc. Biol. 37(9):1741-1747 (2017).

Chang; Y. F. et al: The nonsense-mediated decay RNA surveillance pathway. Annual Review of Biochemistry 76:51-74 (2007).

Crooke; S.T. et al.: Pharmacokinetic properties of several novel oligonucleotide analogs in mice. J. Pharmacol. Exp. Ther. 277(2):923-937 (1996) (Abstract).

Damha, Masad J. et al.: Protocols for Oligonucleotides and Analogs. Methods in Molecular Biology 20:81-114 (1993).

Dellinger; Douglas J.: Streamlined process for the chemical synthesis of RNA using 2'-O-thionocarbamate-protected nucleoside phosphoramidites in the solid phase. J. Am. Chem. Soc. 133(30):11540-11556 (2011). doi: 10.1021/ja201561z. Epub Jul. 11, 2011 (Abstract).

Ding et al. Permanent alteration of PCSK9 with in vivo CRISPR-Cas9 genome editing. Circ. Res. 115:488-492 (2014).

Finn, et al., A Single administration of CRISPR/Cas9 lipid Nanoparticles Achieves Robust and Persistent in Vivo Genome Editing. Cell Reports 22(9):2227-2235 (2018).

Flajolet, M. et al.: Woodchuck Hepatitis Virus Enhancer I and Enhancer II Are Both Involved in N-myc2 Activation in Woodchuck Liver Tumors. J. Virol. 72(7):6175-80 (1998).

Harlow; Ed: Antibodies: A Laboratory Manual. Cold Spring Harbor Laboratory (1988).

Hu, Johnny H. et al.: Evolved Cas9 variants with broad PAM compatibility and high DNA specificity. Nature 556(7699):57-63 (2018). doi: 10.1038/nature26155.

Kramer, et al.: In vitro and in vivo comparative study of chimeric liver-specific promoters. Molecular therapy.Molecular Therapy 7(3):375-385 (2003).

Krutzfeldt, J. et al.: Silencing of microRNAs in vivo with antagomirs. Nature 438:685-689 (2005).

Kumar; Ravindra et al.: Template-directed oligonucleotide strand ligation, covalent intramolecular DNA circularization and catenation using click chemistry. J. Am. Chem. Soc. 129(21):6859-6864 (2007). doi: 10.1021/ja070273v. Epub May 9, 2007 (Abstract).

Matsuda et al., "siRNA Conjugates Carrying Sequentially Assembled Trivalent N-Aceytlgalactosamine Linked Through Nucleosides Elicit Robust Gene Silencing In Vivo in Hepatocytes", ACS Chem Biol., 2015, vol. 10, No. 5, 7 pages.

Miller et al.: Non-Viral CRISPR/Cas Gene Editing In Vitro and In Vivo Enabled by Synthetic Nanoparticle Co-Delivery of Cas9 mRNA and sgRNA. Angew Chem Int Ed Engl. 56(4): 1059-1063 (2017).

(56) References Cited

OTHER PUBLICATIONS

Mishra; Rakesh Kumar et al.: Improved leishmanicidal effect of phosphorotioate antisense oligonucleotides by LDL-mediated delivery. Biochimica et Biophysica Acta (BBA)—Gene Structure and Expression 1264(2, 7):229-237 (1995).
Nair et al., "Multivalent N-Acetylgalactosamine-Conjugated siRNA Localizes in Hepatocytes and Elicits Robust RNAi-Mediated Gene Silencing", Journal of the American Chemical Society, 2014, vol. 136, pp. 16958-16961. (4 pages).
Onopchechko, Anatoli et al.: The Reaction of Phthalic Anhydride with Diethylenetriamine and Triethylenetetramine. A Literature Correction. Bulletin of the Chemical Society of Japan 71(3):717-721 (1998). https://doi.org/10.1246/bcsj.71.717.
Prakash, TP et al.: Lipid nanoparticles improve activity of single-stranded siRNA and gapmer antisense oligonucleotides in animals. ACS Chemical Biology 8(7):1402-1406 (2013). Abstract.
Pratesi, Alessandro et al.: Biotin Derivatives Carrying Two Chelating DOTA Units. Synthesis, in Vitro Evaluation of Biotinidases Resistance, Avidin Binding, and Radiolabeling Tests. J. Med. Chem. 53:432-440 (2010). DOI: 10.1021/jm9014372.
Rajeev et al., "Hepatocyte-Specific Delivery of siRNAs Conjugated to Novel Non-nucleosidic Trivalent N-Aceytlgalactosamine Elicits Robust Gene Slicing in Vivo", ChemBioChem, 2015, vol. 16, pp. 903-908.
Ran et al.: In vivo genome editing using Staphylococcus aureus Cas9. Nature. 520(7546):186-191 (2015).
Rossidis, A.C. et al al: In utero CRISPR-mediated therapeutic editing of metabolic genes. Nat. Med. 24(10):1513-1518 (2018).
Yin et al.: Therapeutic genome editing by combined viral and non-viral delivery of CRISPR system components in vivo. Nat Biotechnol. 34(3):328-333 doi:10.1038/nbt.3471 (2016).
Zhang, M. et al.: Lactosylated gramicidin-based lipid nanoparticles (Lac-GLN) for targeted delivery of anti-miR-155 to hepatocellular carcinoma. J. Control Release 168(3):251-261 (2013). doi:10.1016/j.jconrel.2013.03.020.
Zufferey et al., Woodchuck Hepatitis Virus Posttranscriptional Regulatory Element Enhances Expression of Transgenes Delivered by Retroviral Vectors. Journal of Virology 73(4): 2886-2892 (1999).
Akinc, et al., "A combinatorial library of lipid-like materials for delivery of RNAi therapeutics" Nat. Biotechnol 2008, 26, 561-569.
Akinc et al. Targeted Delivery of RNAi Therapeutics With Endogenous and Exogenous Ligand-Based Mechanisms. Mol Ther 18(7):1357-1364 (2010).
Bae et al.: Cas-OFFinder: a fast and versatile algorithm that searches for potential off-target sites of Cas9 RNA-guided endonucleases. Bioinformatics 30(10):1473-1475 (2014). https://doi.org/10.1093/bioinformatics/btu048.
Batzer et al.: Enhanced evolutionary PCR using oligonucleotides with inosine at the 3'-terminus. Nucleic Acids Res. 19(18):5081 (1991). doi: 10.1093/nar/19.18.5081.
Betz et al.: KlenTaq polymerase replicates unnatural base pairs by inducing a Watson-Crick geometry. Nature Chemical Biology 8:612-614 (2012).
Catalog # 880151P, Avanti Polar Lipids Inc, https://avantilipids.com/product/880151.
Catalog # PG1-CLS-2k, Nanocos, http://www.nanocs.com/PEG/LPEG.htm.
Chari et al.: Unraveling CRISPR-Cas9 genome engineering parameters via a library-on-library approach. Nat Methods 12(9): 823-826 (2015). doi:10.1038/nmeth.3473.
Delcheva et al.: Crispr RNA maturation by trans-encoded small RNA and host factor RNase III. Nature 471(7340):602-607. doi: 10.1038/nature09886.
Diebold, Sandra S.: Recognition of viral single-stranded RNA by Toll-like receptors. Advanced Drug Delivery Reviews 60(7):813-823 (2008). https://doi.org/10.1016/j.addr.2007.11.004.
Doench et al.: Rational design of highly active sgRNAs for CRISPR-Cas9-mediated gene inactivation. Nat Biotechnol. 32(12):1262-7 (2014). doi: 10.1038/nbt.3026. Epub Sep. 3, 2014.

Englisch et al.: Chemically Modified Oligonucleotides as Probes and Inhibitors. Angewandte Chemie International Edition in English 30(6)613-629 (1991) (abstract).
Farboud et al.: Dramatic Enhancement of Genome Editing by CRISPR/Cas9 Through Improved Guide RNA Design. Genetics 199(4):959-971 (2015). https://doi.org/10.1534/genetics.115.175166.
Fusi et al.: In Silico Predictive Modeling of CRISPR/Cas9 guide efficiency. bioRxiv 021568 (2015). doi: https://doi.org/10.1101/021568.
Gaudelli et al.: Programmable base editing of A•T to G•C in genomic DNA without DNA cleavage. Nature 551(7681):464-471 (2017). doi: 10.1038/nature24644.
Gehrke et al.: An APOBEC3A-Cas9 base editor with minimized bystander and off-target activities. Nat. Biotechnol. 36(10):977-982 (2018). doi: 10.1038/nbt.4199. Epub Jul. 30, 2018.
Haeusslet et al.: Evaluation of off-target and on-target scoring algorithms and integration into the guide RNA selection tool CRISPOR. Genome Biology 17:148 (2016). DOI 10.1186/s13059-016-1012-2.
Housden et al.: Identification of potential drug targets for tuberous sclerosis complex by synthetic screens combining CRISPR-based knockouts with RNAi. Sci Signal. 8(393):rs9-rs9 (2015).
Hsu et al.: DNA targeting specificity of RNA-guided Cas9 nucleases. Nat Biotechnol. 31(9):827-32 (2013). doi: 10.1038/nbt.2647. Epub Jul. 21, 2013.
International Search Report and Written Opinion for corresponding PCT application PCT/US2021/020955, dated Jul. 1, 20214.
Jayaraman, et al., "Maximizing the Potency of siRNA Lipid Nanoparticles for Hepatic Gene Silencing In Vivo" Angew. Chem. Int. Ed. 2012, 51, 8529-8533.
Jinek et al.: A Programmable Dual-RNA-Guided DNA Endonuclease in Adaptive Bacterial Immunity. Science 337(6096):816-821 (2012). DOI: 10.1126/science.1225829.
Kananov et al.: A new class of antivirals: antisense oligonucleotides combined with a hydrophobic substituent effectively inhibit influenza virus reproduction and synthesis of virus-specific proteins in MDCK cells. FEBS Letters 259(2):327-330 (1990). https://doi.org/10.1016/0014-5793(90)80039-L.
Komor et al.: Improved base excision repair inhibition and bacteriophage Mu Gam protein yields C:G-to-T: A base editors with higher efficiency and product purity. Science Advances 3:8 (2017). DOI: 10.1126/sciadv.aao4774.
Komor et al.: Programmable editing of a target base in genomic DNA without double-stranded DNA cleavage. Nature 533(7603):420-424 (2016). doi:10.1038/nature17946.
Letsinger et al.: Cholesteryl-conjugated oligonucleotides: synthesis, properties, and activity as inhibitors of replication of human immunodeficiency virus in cell culture. PNAS 86(17):6553-6556 (1989). https://doi.org/10.1073/pnas.86.17.655.
Loakes, David: Survey and Summary: The applications of universal DNA base analogues. Nucleic Acids Research 29(12):2437-2447 (2001). https://doi.org/10.1093/nar/29.12.2437.
Makarova et al.: An updated evolutionary classification of CRISPR—Cas systems. Nat Rev Microbiol. 13(11):722-36 (2015). doi: 10.1038/nrmicro3569.
Manoharan et al.: Cholic acid-oligonucleotide conjugates for antisense applications. Bioorganic & Medicinal Chemistry Letters 4(8):1053-1060 (1994) Abstract.
Manoharan et al.: Lipidic nucleic acids. Tetrahedron Letters 36(21):3651-3654 (1995) Abstract.
Manoharan et al.: Oligonucleotide Conjugates: Alteration of the Pharmacokinetic Properties of Antisense Agents. Nucleosides and Nucleotides 14:3-5 (1995) Abstract.
Merriam-Weber, "lipid" definition, accessed Sep. 17, 21. (Year: 2021).
Moreno-Mateos et al.: CRISPRscan: designing highly efficient sgRNAs for CRISPR-Cas9 targeting in vivo. Nature Methods 12(10):982-988 (2015).
Nishida et al.: Targeted nucleotide editing using hybrid prokaryotic and vertebrate adaptive immune systems. Science 353:6305 (2016 ). DOI: 10.1126/science.aaf8729.

(56) References Cited

OTHER PUBLICATIONS

Oberhauser et al.: Effective incorporation of 2'-O-methyl-oligoribonucleotides into liposomes and enhanced cell association through modification with thiocholesterol. Nucleic Acids Research 20(3):533-538 (1992). https://doi.org/10.1093/nar/20.3.533.

Ohtsuka et al.: An alternative approach to deoxyoligonucleotides as hybridization probes by insertion of deoxyinosine at ambiguous codon positions. Journal of Bilogical Chemistry 260(5):2605-2608 (1985). https://doi.org/10.1016/S0021-9258(18)89400-5.

Pubchem, SID 233374427, Available Date: Feb. 12, 2015 [retrieved on Apr. 21, 2021]. Retrieved from the internet: URL: https://pubchem.ncbi.nlm.nih.gov/substance/233374427 entire document.

Rossolini et al.: Use of deoxyinosine-containing primers vs degenerate primers for polymerase chain reaction based on ambiguous sequence information. Mol. Cell. Probes 8(2):91-8 (1994). doi: 10.1006/mcpr.1994.1013.

Sabnis, et al., "A Novel Amino Lipid Series for mRNA Delivery: Improved Endosomal Escape and Sustained Pharmacology and Safety in Non-human Primates" Molecular Therapy 2018, 26,1509-1519.

Sambrook et al.: Molecular cloning: a laboratory manual. Sec. Ed., Cold Spring Harbor Press, Plainview, NY.

Sato, et al., "Highly specific delivery of siRNA to hepatocytes circumvents endothelial cell-mediated lipid nanoparticle-associated toxicity leading to the safe and efficacious decrease in the hepatitis B virus" Journal of Controlled Release 266 (2017) 216-225.

Sharma et al.: Novel Cluster and Monomer-Based GalNAc Structures Induce Effective Uptake of siRNAs in Vitro and in Vivo. Bioconjugate Chem. 29(7): 2478-2488 (2018).

Shea et al.: Synthesis, hybridization properties and antiviral activity of lipid-oligodeoxynucleotide conjugates. Nucleic Acids Research 18(13):3777-3783 (1990). https://doi.org/10.1093/nar/18.13.3777.

Shmakov et al.: Discovery and Functional Characterization of Diverse Class 2 CRISPR-Cas Systems. Molecular Cell 60:385-397 (2015). DOI:https://doi.org/10.1016/j.molcel.2015.10.008.

Sorrentino, S.: Human extracellular ribonucleases: multiplicity, molecular diversity and catalytic properties of the major RNase types. Cellular and Molecular Life Sciences CMLS 54(8):785-794 (1998).

Springer, et al., "GalNAc-siRNA Conjugates: Leading the Way for Delivery of TNAi Therapeutics" (2018) Nucleic Acid Therapeutics, vol. 28, No. 3.

Srinivasarao et al.: Ligand-Targeted Drug Delivery. Chem. Rev. 17(19): 12133-12164 (2017).

Svinarchuk et al.: Inhibition of HIV proliferation in MT-4 cells by antisense oligonucleotide conjugated to lipophilic groups. Biochimie 75(1-2):49-54 (1993) Abstract.

Wang et al.: Genetic screens in human cells using the CRISPR/Cas9 system. Science 343(6166):80-84. doi:10.1126/science.1246981.

Zetsche et al.: pf1 is a single RNA-guided endonuclease of a Class 2 CRISPRCas system. Cell 163(3):759-71 (2015). doi: 10.1016/j.cell.2015.09.038. Epub Sep. 25, 2015.

Bae, Sangsu et al. Cas-OFFinder: a fast and versatile algorithm that searches for potential off-target sites of Cas9 RNA-guided endonucleases, Bioinformatics vol. 30,10: 1473-1475 (2014), https://doi.org/10.1093/bioinformatics/btu048.

Batzer, M A et al. Enhanced evolutionary PCR using oligonucleotides with inosine at the 3'-terminus. Nucleic Acids Research vol. 19, 18: 5081 (1991).

Brown, E A et al. Secondary Structure of the 5' Nontranslated Regions of Hepatitis C Virus and Pestivirus Genomic RNAs. Nucleic Acids Research vol. 20,19: 5041-5045 (1992).

Clement, Kendell et al. CRISPResso2 Provides Accurate and Rapid Genome Editing Sequence Analysis. Nature Biotechnology vol. 37,3: pp. 224-226 (2019).

Co-pending U.S. Appl. No. 18/420,112, inventors Rajeev; Kallanthottathil G. et al., filed on Jan. 23, 2024.

Co-pending U.S. Appl. No. 18/470,264, inventors Rajeev; Kallanthottathil G. et al., filed on Sep. 19, 2023.

Co-pending U.S. Appl. No. 18/470,280, inventors Rajeev; Kallanthottathil G. et al., filed on Sep. 19, 2023.

Dellinger, Douglas J. et al. Solid-phase chemical synthesis of phosphonoacetate and thiophosphonoacetate oligodeoxynucleotides. Journal of the American Chemical Society 125,4: 940-950 (2003). Epub Jan. 3, 2003. DOI: 10.1021/ja027983f.

Ding, Qiurong et al. Permanent Alteration of PCSK9 With In Vivo CRISPR-Cas9 Genome Editing. Circulation Research 115,5: 488-492 (2014).

Doench, John G et al. Rational design of highly active sgRNAs for CRISPR-Cas9-mediated gene inactivation. Nature Biotechnology vol. 32: 1262-1267 (2014).

Gehrke, Jason M et al. An APOBEC3A-Cas9 base editor with minimized bystander and off-target activities. Nature biotechnology vol. 36,10 (2018): 977-982.

Guo, Jian, et al. Protecting groups in carbohydrate chemistry: influence on stereoselectivity of glycosylations. Molecules vol. 15,10:7235-7265 (2010).

Harris, J Milton., Poly(Ethylene Glycol) Chemistry: Biotechnical and Biomedical Applications. SpringerLink :20 Pages (1992).

Jacobs, Frank, et al. The Role of Liver Sinusoidal Cells in Hepatocyte-directed Gene Transfer. The American Journal of Pathology vol. 176, 1: 14-21 (2010).

Katzmann, Julius L et al. Targeting RNA With Antisense Oligonucleotides and Small Interfering RNA: JACC State-of-the-Art Review. Journal of the American College of Cardiology vol. 76,5: 563-579 (2020).

Manoharan. et al. Chemical Modifications to Improve Uptake and Bioavailability of Antisense Oligonucleotides. Annals of the New York Academy of Sciences vol. 660: 306-309 (1992).

Manoharan. et al. Introduction of a Lipophilic Thioether in the Minor Groove of Nucleic Acids for Antisense Applications. Bioorganic & Medicinal Chemistry Letters vol. 3: 2765-2770 (1993).

Manoharan. et al. Oligonucleotide Conjugates: Alteration of the Pharmacokinetic Properties of Antisense Agents. Nucleosides & Nucleotides vol. 14: 969-973 (1995).

Onopchenko, A. The Reaction of Phthalic Anhydride with Diethylenetriamine and Triethylenetetramine. A Literature Correction. Bull. Chem. Soc. Japan 71(3): 717-721 (1998).

PCT/US2022/074493 International Search Report and Written Opinion dated Jul. 28, 2023 (Pub. No. WO2023015223).

Qu, Shuai, et al. Non-viral Nucleic Acid Therapeutics: Revolutionizing the Landscape of Atherosclerotic Treatment. Nano Today, vol. 45, 101514: 1-14 (2022).

Ramzy. et al. Clinical Cytopathology and Aspiration Biopsy: Fundamental principles and practice. McGraw Hill Professional, 2001.

Rejman, Joanna et al. Characterization and Transfection Properties of Lipoplexes Stabilized With Novel Exchangeable Polyethylene Glycol-lipid Conjugates. Biochimica et Biophysica Acta vol. 1660,1-2: 41-52 (2004).

Roberts, Thomas C et al. Advances in Oligonucleotide Drug Delivery. Nature Reviews Drug Discovery 19(10):673-694 (2020).

Romberg, Birgit et al. Sheddable Coatings for Long-Circulating Nanoparticles. Pharmaceutical Research vol. 25, 1: 55-71 (2008).

Sabnis, Staci et al. A Novel Amino Lipid Series for mRNA Delivery: Improved Endosomal Escape and Sustained Pharmacology and Safety in Non-human Primates. Molecular Therapy 26(6):1509-1519 (2018).

Saison-Behmoaras et al. Short Modified Antisense Oligonucleotides Directed Against Ha-ras Point Mutation Induce Selective Cleavage of the Mrna and Inhibit T24 Cells Proliferation. The EMBO Journal vol. 10,5: 1111-1118 (1991).

Singh, Mohan et al., Primary cilia are present on human blood and bone marrow cells and mediate Hedgehog signaling. Experimental Hematology vol. 44, 12: 1181-1187.e2 (2016).

Singleton et al., Dictionary of Microbiology and Molecular Biology. 3rd Edition Wiley & Sons New York, N.Y. (2001).

Troy. Pancreatic Enzymes. Remington: The Science and Practice of Pharmacy, 21st edition. Lippincot Williams & Wilkins, 2006. p. 1304.

Wang, Xinmei et al. Enhanced hepatic delivery of siRNA and microRNA using oleic acid based lipid nanoparticle formulations.

(56) References Cited

OTHER PUBLICATIONS

Journal of Controlled Release : Official Journal of the Controlled Release Society vol. 172,3: 690-698 (2013). doi:10.1016/j.jconrel.2013.09.027.

Willoughby, Jennifer L S et al. Evaluation of GalNAc-siRNA Conjugate Activity in Pre-clinical Animal Models with Reduced Asialoglycoprotein Receptor Expression. Molecular therapy : the journal of the American Society of Gene Therapy vol. 26,1: 105-114 (2018).

Yin, Hao et al. Therapeutic Genome Editing by Combined Viral and Non-viral Delivery of CRISPR System Components in Vivo. Nature Biotechnology 34(3:328-333 (2016).

Zufferey, R et al. Woodchuck hepatitis virus posttranscriptional regulatory element enhances expression of transgenes delivered by retroviral vectors. Journal of Virology vol. 73,4: 2886-2892 (1999).

Office Action dated Aug. 8, 2024 issued in Canadian Patent Application No. 3,174,708.

Search and Examination Report dated Sep. 23, 2024 issued in Great Britain Patent Application No. GB2411424.1.

Search and Examination Report dated Aug. 15, 2024 issued in Great Britain Patent Application No. GB2411424.1.

COMPOSITIONS AND METHODS FOR TARGETED RNA DELIVERY

CROSS-REFERENCE TO RELATED APPLICATION

This application is a continuation of U.S. patent application Ser. No. 17/533,461 filed on Nov. 23, 2021 which is a divisional of U.S. patent application Ser. No. 17/192,709 filed on Mar. 4, 2021, now U.S. Pat. No. 11,207,416 issued on Dec. 28, 2021 which claims the benefit of U.S. Provisional Application No. 63/078,982 filed on Sep. 16, 2020 and U.S. Provisional Application No. 62/984,866 filed on Mar. 4, 2020, which are hereby each incorporated by reference in their entirety.

SEQUENCE LISTING

The instant application contains a Sequence Listing which has been submitted electronically in XML format and is hereby incorporated by reference in its entirety. Said XML copy, created on Aug. 25, 2023, is named 53989-706_301_SL.xml and is 261,452 bytes in size.

FIELD OF THE DISCLOSURE

The instant disclosure relates to compositions and methods for targeted delivery of therapeutic agents such as CRISPR-guide RNA and other nucleic acid agents.

BACKGROUND

All publications herein are incorporated by reference to the same extent as if each individual publication or patent application was specifically and individually indicated to be incorporated by reference. The following description includes information that may be useful in understanding the present disclosure. It is not an admission that any of the information provided herein is prior art or relevant to the presently claimed invention, or that any publication specifically or implicitly referenced is prior art.

SUMMARY

In one aspect, described herein is a receptor targeting conjugate, comprising a compound of Formula (V):

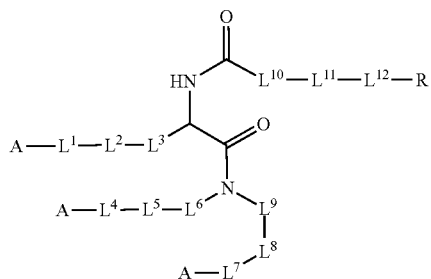

Formula (V)

wherein,
a plurality of the A groups collectively comprise a receptor targeting ligand;
each $L^1$, $L^2$, $L^3$, $L^4$, $L^5$, $L^6$, $L^7$, $L^8$, $L^9$, $L^{10}$ and $L^{12}$ is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O) O—, —NR$^1$C(=O)NR$^1$—, —C(=O)NR$^1$C(=O)—, —S(=O)$_2$NR$^1$—, —NR$^1$S(=O)$_2$—, —NR$^1$—, or —N(OR$^1$)—;
$L^{11}$ is substituted or unsubstituted —(CH$_2$CH$_2$O)$_n$—, or substituted or unsubstituted —(OCH$_2$CH$_2$)$_n$—;
each $R^1$ is independently H or substituted or unsubstituted $C_1$-$C_6$alkyl;
R is a lipid, nucleic acid, amino acid, protein, or lipid nanoparticle;
m is an integer selected from 1 to 10; and
n is an integer selected from 1 to 200.

In some embodiments, each $L^1$, $L^4$, and $L^7$ is independently substituted or unsubstituted $C_1$-$C_{12}$ alkylene. In some embodiments, each $L^1$, $L^4$, and $L^7$ is independently substituted or unsubstituted $C_2$-$C_6$ alkylene. In some embodiments, each $L^1$, $L^4$, and $L^7$ is $C_4$ alkylene. In some embodiments, each $L^2$, $L^5$, and $L^8$ is independently —C(=O) NR$^1$—, —NR$^1$C(=O)—, —OC(=O)NR$^1$—, —NR$^1$C (=O)O—, —NR$^1$C(=O)NR$^1$—, or —C(=O)NR$^1$C (=O)—. In some embodiments, each $L^2$, $L^5$, and $L^8$ is independently —C(=O)NR$^1$— or —NR$^1$C(=O)—. In some embodiments, each $L^2$, $L^5$, and $L^8$ is —C(=O)NH—. In some embodiments, each $L^3$, $L^6$, and $L^9$ is independently substituted or unsubstituted $C_1$-$C_{12}$ alkylene. In some embodiments, each $L^3$ is substituted or unsubstituted $C_2$-$C_6$ alkylene. In some embodiments, $L^3$ is $C_4$ alkylene. In some embodiments, each $L^6$ and $L^9$ is independently substituted or unsubstituted $C_2$-$C_{10}$ alkylene. In some embodiments, each $L^6$ and $L^9$ is independently substituted or unsubstituted $C_2$-$C_6$ alkylene. In some embodiments, each $L^6$ and $L^9$ is $C_3$ alkylene. In one aspect, described herein is a receptor targeting conjugate, comprising a compound of Formula (VI):

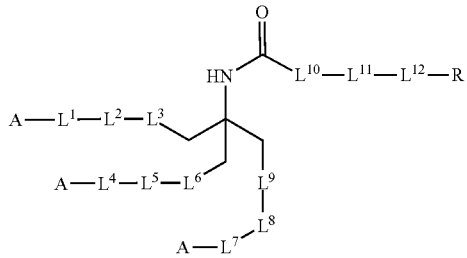

Formula (VI)

wherein,
a plurality of the A groups collectively comprise a receptor targeting ligand;
each $L^1$, $L^2$, $L^3$, $L^4$, $L^5$, $L^6$, $L^7$, $L^8$, $L^9$, $L^{10}$ and $L^{12}$ is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR¹C(=O)—, —OC(=O)NR¹—, —NR¹C(=O)
O—, —NR¹C(=O)NR¹—, —C(=O)NR¹C(=O)—,
—S(=O)₂NR¹—, —NR¹S(=O)₂—, —NR¹—, or
—N(OR¹)—;

$L^{11}$ is substituted or unsubstituted —(CH₂CH₂O)$_n$—, or substituted or unsubstituted —(OCH₂CH₂)$_n$—;

each $R^1$ is independently H or substituted or unsubstituted $C_1$-$C_6$ alkyl;

R is a lipid, nucleic acid, amino acid, protein, or lipid nanoparticle;

m is an integer selected from 1 to 10; and n is an integer selected from 1 to 200.

In some embodiments, each $L^1$, $L^4$, and $L^7$ is independently substituted or unsubstituted $C_1$-$C_{12}$ alkylene or substituted or unsubstituted $C_1$-$C_{12}$ heteroalkylene. In some embodiments, each $L^1$, $L^4$, and $L^7$ is independently substituted or unsubstituted $C_1$-$C_{12}$ heteroalkylene. In some embodiments, each $L^1$, $L^4$, and $L^7$ is independently substituted or unsubstituted $C_1$-$C_{12}$ heteroalkylene comprising 1-10 O atoms. In some embodiments, each $L^1$, $L^4$, and $L^7$ is independently —(CH₂CH₂O)$_{p1}$—(CH₂)$_{q1}$—; wherein p1 is 1-8; and q1 is 1-6. In some embodiments, each $L^1$, $L^4$, and $L^7$ is —(CH₂CH₂O)₃—(CH₂)₂—. In some embodiments, each $L^1$, $L^4$, and $L^7$ is independently substituted or unsubstituted $C_1$-$C_{12}$ alkylene. In some embodiments, each $L^1$, $L^4$, and $L^7$ is independently substituted or unsubstituted $C_2$-$C_6$ alkylene. In some embodiments, each $L^1$, $L^4$, and $L^7$ is $C_4$ alkylene. In some embodiments, each $L^2$, $L^5$, and $L^8$ is independently —C(=O)NR¹—, —NR¹C(=O)—, —OC(=O)NR¹—, —NR¹C(=O)O—, —NR¹C(=O)NR¹—, or —C(=O)NR¹C(=O)—. In some embodiments, each $L^2$, $L^5$, and $L^8$ is independently —C(=O)NR¹— or —NR¹C(=O)—. In some embodiments, each $L^2$, $L^5$, and $L^8$ is —NHC(=O)—. In some embodiments, each $L^2$, $L^5$, and $L^8$ is —C(=O)NH—. In some embodiments, each $L^3$, $L^6$, and $L^9$ is independently substituted or unsubstituted $C_1$-$C_{12}$ heteroalkylene. In some embodiments, each $L^3$, $L^6$, and $L^9$ is independently substituted or unsubstituted $C_1$-$C_{12}$ heteroalkylene comprising 1-10 O atoms. In some embodiments, each $L^3$, $L^6$, and $L^9$ is independently —(CH₂CH₂O)$_{p2}$—(CH₂CH₂CH₂O)$_{q2}$—; wherein p2 is 1-8; and q2 is 1-6. In some embodiments, each $L^3$, $L^6$, and $L^9$ is —(CH₂CH₂O)—(CH₂CH₂CH₂O)—. In some embodiments, each $L^3$, $L^6$, and $L^9$ is independently —(CH₂CH₂CH₂O)$_{q3}$—; wherein q3 is 1-8. In some embodiments, each $L^3$, $L^6$, and $L^9$ is —(CH₂CH₂CH₂O)₂—. In some embodiments, $L^{10}$ is substituted or unsubstituted $C_1$-$C_{12}$ alkylene. In some embodiments, $L^{10}$ is substituted or unsubstituted $C_1$-$C_4$ alkylene. In some embodiments, $L^{10}$ is $C_2$ alkylene. In some embodiments, $L^{11}$ is —(OCH₂CH₂)$_n$—. In some embodiments, n is 1-100. In some embodiments, n is 2-50. In some embodiments, n is 2, 12, 37, or 45. In some embodiments, $L^{12}$ is —O—, —C(=O)O—, —C(=O)NR¹—, —NR¹C(=O)—, or —NR¹C(=O)O—. In some embodiments, $L^{12}$ is —C(=O)O— or —NR¹C(=O)O—. In some embodiments, $L^{12}$ is —C(=O)O—. In some embodiments, $L^{12}$ is —NHC(=O)O—. In some embodiments, $L^{12}$ is —NHC(=O)—. In some embodiments, A binds to a lectin. In some embodiments, the lectin is an asialoglycoprotein receptor (ASGPR). In some embodiments, A is N-acetylgalactosamine (GalNAc) or a derivative

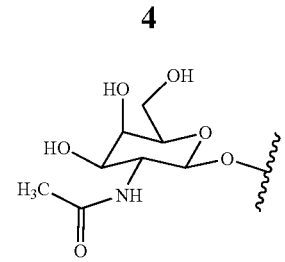

or a derivative thereof. A is N-acetylgalactosamine (GalNAc)

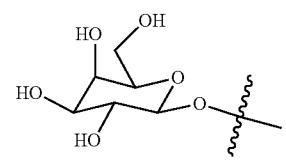 [SMILES: *OC1OC(CO)C(O)C(O)C1O]

or a derivative thereof. In some embodiments, each $R^1$ is independently H or —CH₃. In some embodiments, each $R^1$ is H. In some embodiments, the R comprises one or more of fatty alcohols, fatty acids, glycerolipids, glycerophospholipids, sphingolipids, saccharolipids, polyketides, sterol lipids, and prenol lipids. In some embodiments, the R comprises one or more fatty alcohols. In some embodiments, each fatty alcohol is independently a saturated, monounsaturated, or polyunsaturated fatty alcohol. In some embodiments, the fatty alcohol comprises one or more a $C_2$-$C_{26}$ fatty alcohol. In some embodiments, the fatty alcohol comprises two or more a $C_2$-$C_{26}$ fatty alcohol. In some embodiments, each fatty alcohol is a $C_{12}$, $C_{14}$, $C_{16}$, $C_{18}$, $C_{20}$, or $C_{22}$ fatty alcohol. In some embodiments, each fatty alcohol is independently docosahexaenol, eicosapentaenol, oleyl alcohol, stearyl alcohol, (9Z,12Z)-octadeca-9,12-dien-1-yl alcohol, (Z)-docos-13-en-1-yl alcohol, docosanyl alcohol, (E)-octadec-9-en-1-yl alcohol, icosanyl alcohol, (9Z,12Z,15Z)-octadeca-9,12,15-trien-1-yl alcohol, or palmityl alcohol. In some embodiments, each fatty alcohol is a stearyl alcohol. In some embodiments, the R comprises one or more sterol lipids. In some embodiments, the R comprises one or more of vitamins. In some embodiments, each vitamin is independently a vitamin A, vitamin D, vitamin E, or vitamin K. In some embodiments, the R comprises a nucleic acid. In some embodiments, the nucleic acid is a mRNA, guide RNA, siRNA, antisense oligonucleotide, aptamer, microRNA, immunostimulatory oligonucleotide, splice switching oligonucleotide, self-amplifying RNA, circular RNA or DNA, but not limited to the aforementioned. In some embodiments, the R comprises a protein. In some embodiments, the protein is a gene editor protein, an antibody, an antigen-binding antibody fragment or a peptide, but not limited to the aforementioned.

In one aspect, described herein is a receptor targeting conjugate, comprising a compound from Table 4.

In one aspect, described herein is a nanoparticle composition comprising: (a) one or more nucleic acid molecular entities; and (b) a receptor targeting conjugate as described herein. In some embodiments, the receptor targeting conjugate comprises from about 0.001 mol % to about 20 mol % of the total lipid content present in the nanoparticle composition. In some embodiments, the receptor targeting conjugate comprises from about 0.01 mol % to about 1 mol % of the total lipid content present in the nanoparticle composition. In some embodiments, comprising a sterol or a derivative thereof, comprising from 10 mol % to 70 mol % of the total lipid content present in the nanoparticle composition. In some embodiments, the sterol or the derivative thereof is cholesterol or a cholesterol derivative. In some embodiments, the cholesterol or the cholesterol derivative comprises from 20 mol % to 50 mol % of the total lipid content present in the nanoparticle composition. In some embodiments, the nanoparticle composition comprises a phospholipid, comprising from 1 mol % to 20 mol % of the total lipid content present in the nanoparticle composition. In some embodiments, the phospholipid comprises from about 5 mol % to about 15 mol % of the total lipid content present in said nanoparticle composition. In some embodiments, the phospholipid is selected from 1,2-distearoyl-sn-glycero-3-phosphocholine (DSPC), 1,2-dipalmitoyl-sn-glycero-3-phosphocholine (DPPC), 1,2-dimyristoyl-sn-glycerophosphocholine (DMPC), 2-oleoyl-1-palmitoyl-sn-glycero-3-phosphocholine (POPC), 1,2-dioleoyl-sn-glycero-3-phosphoethanolamine (DOPE), and sphingomyelin. In some embodiments, the phospholipid is DSPC. In some embodiments, the nanoparticle composition comprises a stealth lipid, comprising from 0.1 mol % to 6 mol % of the total lipid content present in the nanoparticle composition. In some embodiments, the stealth lipid comprises about 2.0 mol % to about 2.5 mol % of the total lipid content present in said nanoparticle composition. In some embodiments, the stealth lipid is a PEG-lipid that has a number average molecular weight of from about 200 Da to about 5000 Da. In some embodiments, the nanoparticle composition comprises an amino lipid, comprising from about 10 mol % to about 60 mol % of the total lipid content present in the nanoparticle composition. In some embodiments, the nanoparticle composition comprises an antioxidant. In some embodiments, the antioxidant comprises ethylenediaminetetraacetic acid (EDTA). In some embodiments, the one or more nucleic acid molecular entities comprise a single guide RNA (sgRNA) or guide RNA (gRNA) targeting a disease causing gene of interest produced in the hepatocytes. In some embodiments, the one or more nucleic acid molecular entities comprise an mRNA that encodes a Cas nuclease. In some embodiments, at least one of the one or more nucleic acid molecular entities comprises a chemical modification. In some embodiments, the chemical modification is a 2'-F modification, a phosphorothioate internucleotide linkage modification, acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), 4'-O-methyl, or a 2'-ara-F modification. In some embodiments, the chemical modification is a 2'-O-methyl modification.

In one aspect, provided herein is a pharmaceutical composition comprising a herein described receptor targeting conjugate or a herein described nanoparticle composition, and an excipient or carrier. In some embodiments, the pharmaceutical composition comprises an mRNA encoding a gene editor nuclease. In some embodiments, the pharmaceutical composition comprises one or more guide RNA molecules. In some embodiments, the pharmaceutical composition comprises two or more guide RNA molecules. In some embodiments, the two or more guide RNA molecules target two or more genes of interest. In some embodiments, the mRNA encodes Cas9 nuclease. In some embodiments, the mRNA encodes a base editor nuclease. In some embodiments, the mRNA and the one or more guide RNA molecules are present in the same nanoparticle composition. In some embodiments, the mRNA and the one or more guide RNA molecules are present in different nanoparticle compositions. In some embodiments, a ratio of the gRNA molecules to the mRNA in the pharmaceutical composition is from about 0.01 to about 100 by weight or by mole. In some embodiments, a ratio of said gRNA molecules to said mRNA in said pharmaceutical composition is about 50:1, about 40:1, about 30:1, about 20:1, about 18:1, about 16:1, about 14:1, about 12:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 by weight or by mole.

In one aspect, provided herein is a pharmaceutical composition comprising: (a) a first receptor targeting conjugate or a first nanoparticle composition as described herein, and (b) a second receptor targeting conjugate or a second nanoparticle composition as described herein. In some embodiments, the first nanoparticle composition comprises a gene editor mRNA. In some embodiments, the second nanoparticle composition comprises one or more guide RNA molecules. In some embodiments, a ratio of guide RNA molecules to mRNA in said pharmaceutical composition is about 50:1, about 40:1, about 30:1, about 20:1, about 18:1, about 16:1, about 14:1, about 12:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 by weight or by mole.

In one aspect, provided herein is a method of delivering a nucleic acid to a cell, the method comprising contacting the cell with a nanoparticle composition or a pharmaceutical composition as described herein, whereby the nucleic acid is delivered to said cell. In some embodiments, the cell is contacted in vivo, ex vivo, or in intro.

In one aspect, provided herein is a method of producing a polypeptide of interest in a cell, the method comprising contacting said cell with a nanoparticle composition or a pharmaceutical composition as described herein, whereby the nucleic acid is capable of being translated in said cell to produce the polypeptide.

In one aspect, provided herein is a method of treating a disease or condition in a subject, the method comprising administering to the subject a therapeutically effective amount of a pharmaceutical composition as described herein. In some embodiments, the disease or condition is a coronary disease. In some embodiments, the subject is low-density lipoprotein receptor (LDLR)-deficient. In some embodiments, the subject has heterozygous familial hypercholesterolemia (HeFH), homozygous familial hypercholesterolemia (HoFH) or clinical atherosclerotic cardiovascular disease (ASCVD). In some embodiments, the subject is at high risk of cardiovascular events. In some embodiments, the subject requires additional lowering of low-density lipoprotein cholesterol (LDL-C) despite maximally tolerated lipid-lowering therapy.

In one aspect, provided herein is a method of delivering a nucleic acid molecular entity to the liver of a subject, comprising administering to the subject a pharmaceutical composition as described herein, thereby delivering the nucleic acid molecular entity.

In one aspect, described herein is a nucleotide conjugate comprising: (a) a nucleic acid, and (b) a targeting moiety connected to the nucleic acid in (a), wherein the targeting moiety comprises a structure of Table 1. In some embodiments, the targeting moiety further comprises a coupling sequence that hybridizes with the nucleic acid in (a). In one aspect, described herein is a nucleotide conjugate comprising: (a) a nucleic acid, and (b) a targeting moiety connected to the nucleic acid in (a), wherein the targeting moiety comprises a coupling sequence that hybridizes with the nucleic acid in (a). In some embodiments, the nucleic acid comprises a single stranded, double stranded, a partially double stranded, or a hairpin stem-loop nucleic acid, and wherein the targeting moiety is a receptor targeting moiety. In some embodiments, the targeting moiety binds to a lectin. In some embodiments, the lectin is an asialoglycoprotein receptor (ASGPR). In some embodiments, the targeting moiety comprises one or more N-acetylgalactosamine (GalNAc) or GalNAc derivatives. In some embodiments, the targeting moiety comprises one or more N-acetylgalactosamine (GalNAc) or GalNAc derivatives and a spacer. In some embodiments, the targeting moiety comprises one or more galactose or galactose derivatives. In some embodiments, the targeting moiety comprises one or more galactose or galactose derivatives and a spacer. In some embodiments, the spacer comprises polyethylene glycol, substituted or unsubstituted $C_1$-$C_{12}$ alkylene, or both, wherein the polyethylene glycol has from 1 to 5 repeating units. In some embodiments, the targeting moiety is linked to one or more strands of the nucleic acid through one or more linkers. In some embodiments, the targeting moiety comprises a structure of Table 1. In some embodiments, the coupling sequence hybridizes with the nucleic acid in (a). In some embodiments, the coupling sequence hybridizes with an extension in the nucleic acid in (a). In some embodiments, the targeting moiety is attached to the 5' end of the nucleic acid sequence, the 3' end of the nucleic acid sequence, or the middle of the nucleic acid sequence. In some embodiments, the targeting moiety comprises at least two GalNAcs or GalNAc derivatives. In some embodiments, the targeting moiety comprises at least three GalNAcs or GalNAc derivatives. In some embodiments, the GalNAcs or GalNAc derivatives are connected to the nucleic acid in (a) via a linker in the targeting moiety, via hybridization of the coupling sequence in the targeting moiety that hybridizes with the nucleic acid in (a), or via a combination thereof. In some embodiments, the targeting moiety comprises at least two galactose or galactose derivatives. In some embodiments, the targeting moiety comprises at least three galactoses or galactose derivatives. In some embodiments, the galactoses or galactose derivatives are connected to the nucleic acid in (a) via a linker in the targeting moiety, via hybridization of the coupling sequence in the targeting moiety that hybridizes with the nucleic acid in (a), or via a combination thereof. In some embodiments, the targeting moiety comprises at least two coupling sequences that hybridize with the nucleic acid in (a). In some embodiments, the at least two coupling sequences are identical. In some embodiments, the at least two coupling sequences are different. In some embodiments, the nucleotide conjugate further comprises a second targeting moiety. In some embodiments, the second targeting moiety binds to an asialoglycoprotein receptor (ASGPR). In some embodiments, the second targeting moiety is linked to one or more strands the nucleic acid through a spacer and/or through one or more linkers. In some embodiments, the second targeting moiety comprises a GalNAc or GalNAc derivative. In some embodiments, the second targeting moiety comprises at least three GalNAc moieties or GalNAc derivatives. In some embodiments, the GalNAc or GalNAc derivatives are connected to the nucleic acid in (a) via a linker in the targeting moiety, via hybridization of the coupling sequence in the targeting moiety that hybridizes with the nucleic acid in (a), or via a combination thereof. In some embodiments, the second targeting moiety comprises a galactose or galactose derivative. In some embodiments, the second targeting moiety comprises at least three galactose moieties or galactose derivatives. In some embodiments, the galactose or galactose derivatives are connected to the nucleic acid in (a) via a linker in the targeting moiety, via hybridization of the coupling sequence in the targeting moiety that hybridizes with the nucleic acid in (a), or via a combination thereof. In some embodiments, the second targeting moiety comprises a structure of Table 1. In some embodiments, the second targeting moiety comprises a coupling sequence that hybridizes with the nucleic acid. In some embodiments, the second targeting moiety is attached to the 5' end of the nucleic acid, the 3' end of the nucleic acid, or the middle of the nucleic acid. In some embodiments, the nucleic acid in (a) comprises RNA or DNA. In some embodiments, the coupling sequence comprises RNA, DNA, chemically modified RNA, chemically modified DNA, or a hybrid of DNA and RNA. In some embodiments, the coupling sequence comprises one or more of (a), (c), (g), (u), (A)n, (T)n, (U)n, (a)n, or (u)n, wherein n is an integer no less than 3, wherein a is 2'-O-methyladenosine (2'-OMe A), wherein c is 2'-O-methylacytidine (2'-OMe-C), wherein g is 2'-O-methylacytidine guanine (2'-OMe-G), and wherein u is 2'-O-methyluridine (2'-OMe-U). In some embodiments, the coupling sequence comprises one or more of (a), (c), (g), (u), (A)n, (T)n, (U)n, (a)n, or (u)n, wherein n is an integer no less than 3, wherein a is 2'-O-methyladenosine (2'-OMe A), wherein c is 2'-O-methylacytidine (2'-OMe-C), wherein g is 2'-O-methylacytidine guanine (2'-OMe-G), and wherein u is 2'-O-methyluridine (2'-OMe-U). In some embodiments, the (a), (c), (g), or (u) is scattered along the nucleic acid or the coupling sequence. In some embodiments, the nucleic acid and the coupling sequence comprise one or more G-C base pairing within a hybridization duplex wherein the coupling sequence hybridizes with the nucleic acid and wherein said one or more G-C base pairing increases stability of the hybridization duplex. In some embodiments, the linker comprises a covalent linker. In some embodiments, the linker comprises a non-covalent linker. In some embodiments, the linker comprises a monovalent linker, a bivalent linker, a trivalent linker, or a combination thereof. In some embodiments, the linker comprises a biocleavable linker. In some embodiments, the linker comprises a non-biocleavable linker. In some embodiments, the linker comprises a phosphate, phosphorothioate, amide, ether, oxime, hydrazine or carbamate. In some embodiments, the linker is a phosphate or phosphorothioate. In some embodiments, the nucleic acid in (a) comprises a chemical modification. In some embodiments, the nucleic acid in (a) comprises a 2'-F modification, a phosphorothioate internucleotide linkage modification, acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), 4'-O-methyl, or a 2'-ara-F modification. In some embodiments, the nucleic acid comprises a 2'-O-methyl modification. In some embodiments, the nucleic acid comprises a phosphorothioate internucleotide linkage modification. In some embodiments, the nucleic acid is capable of hybridizing with a target sequence within a target gene of a genome. In some embodiments, the nucleic acid comprises a mRNA, siRNA, shRNA, antisense oligonucleotide, microRNA, anti-microRNA or antimir, supermir, antagomir, ribozyme, triplex-forming oligonucleotide, decoy oligonucleotide, splice-switching oligonucleotide, immunostimulatory oligonucleotide, RNA activator, U1 adaptor, guide RNA, or any combinations thereof. In some embodiments, the nucleic acid encodes a protein. In some embodiments, the nucleic acid is a CRISPR enzyme. In some embodiments, the nucleic acid is a guide RNA capable of forming a complex with a CRISPR enzyme. In some embodiments, the guide RNA is a single guide RNA or a dual guide RNA. In some embodiments, the CRISPR enzyme is selected from the group consisting of Cas9, Cpf1, CasX, CasY, C2c1, C2c3, and base editor fusion protein. In some embodiments, the nucleic acid further comprises a mRNA encoding the CRISPR enzyme. In some embodiments, the CRISPR enzyme results in an alteration in the target sequence. In some embodiments, the target gene is involved in a lipid metabolism pathway. In some embodiments, the target gene is selected from the group consisting of PCSK9, ANGPTL3, APOC3, LPA, APOB, MTP, ANGPTL4, ANGPTL8, APOA5, APOE, LDLR, IDOL, NPC1L1, ASGR1, TM6SF2, GALNT2, GCKR, LPL, MLXIPL, SORT1, TRIB1, MARC1, ABCG5, and ABCG8. In some embodiments, the guide RNA comprises a sequence selected from sequences of Table 3. In some embodiments, the guide RNA comprises a sequence selected from sequences of Table 5.

In one aspect, described herein is a particle comprising the described nucleotide conjugate and the described CRISPR enzyme. In some embodiments, the particle is a lipid nanoparticle, a liposome, an inorganic nanoparticle, or an RNP.

In one aspect, described herein is a cell comprising the nucleotide conjugate of any one of the preceding claims. In some embodiments, the cell is a prokaryotic cell, a eukaryotic cell, a vertebrate cell, a mouse cell, a non-human primate cell, or a human cell.

In one aspect, described herein is a pharmaceutical composition comprising the described nucleotide conjugate, the particle, or the cell. In some embodiments, the pharmaceutical composition comprises a pharmaceutically acceptable adjuvant, diluent, carrier, preservative, excipient, buffer, stabilizer, or a combination thereof. In some embodiments, the carrier comprises solvents, dispersion media, dispersion or suspension aids, surface active agents, isotonic agents, thickening or emulsifying agents, preservatives, lipids, lipidoids, polymers, lipoplexes, core-shell nanoparticles, hyaluronidase, nanoparticle mimics, or combinations thereof.

In one aspect, described herein is a kit comprising the described nucleotide conjugate.

In one aspect, described herein is a method for reducing the risk of coronary disease in a subject in need thereof, comprising administering to the subject an effective amount of the described nucleotide conjugate. In one aspect, described herein is a method for reducing the risk of coronary disease in a subject in need thereof, comprising administering to the subject an effective amount of a pharmaceutical composition, said pharmaceutical composition comprising (a) a nucleic acid, and (b) a targeting moiety connected to the nucleic acid in (a), wherein the targeting moiety comprises a structure of Table 1. In one aspect, described herein is a method of delivering a nucleic acid to the liver of a subject, comprising administering to the subject said nucleic acid connected to a targeting moiety, wherein the targeting moiety comprises a structure of Table 1. In some embodiments, the targeting moiety further comprises a coupling sequence that hybridizes with the nucleic acid in (a). In one aspect, described herein is a method for reducing the risk of coronary disease in a subject in need thereof, comprising administering to the subject an effective amount of a pharmaceutical composition, said pharmaceutical composition comprising (a) a nucleic acid, and (b) a targeting moiety connected to the nucleic acid in (a), wherein the targeting moiety comprises a coupling sequence that hybridizes with the nucleic acid in (a). In one aspect, described herein is a method of delivering a nucleic acid to the liver of a subject, comprising administering to the subject said nucleic acid connected to a targeting moiety, wherein the targeting moiety comprises a coupling sequence that hybridizes with the nucleic acid. In some embodiments, the nucleic acid comprises a single stranded, double stranded, a partially double stranded, or a hairpin stem-loop nucleic acid, and wherein the targeting moiety is a receptor targeting moiety. In some embodiments, the targeting moiety binds to a lectin. In some embodiments, the lectin is an asialoglycoprotein receptor (ASGPR). In some embodiments, the targeting moiety comprises one or more N-acetylgalactosamine (GalNAc) or GalNAc derivatives. In some embodiments, the targeting moiety comprises at least three GalNAc or GalNAc derivatives. In some embodiments, the targeting moiety comprises one or more galactose or galactose derivatives. In some embodiments, the targeting moiety comprises at least three galactose or galactose derivatives. In some embodiments, the nucleic acid comprises (i) a guide RNA and a nuclease mRNA or (ii) a guide RNA complexed in a nuclease RNP, and wherein the guide RNA is capable of directing the nuclease to a target sequence in a target gene. In some embodiments, the guide RNA comprises a single guide RNA or a dual guide RNA. In some embodiments, the nuclease is a CRISPR enzyme. In some embodiments, the CRISPR enzyme selected from the group consisting of Cas9, Cpf1, CasX, CasY, C2c1, C2c3, and base editor fusion protein. In some embodiments, the CRISPR enzyme results in an alteration in the target sequence. In some embodiments, the administration results in reduced expression of the target gene in the liver of the subject. In some embodiments, expression of the target gene in the liver of the subject is reduced by at least 1%, at least 5%, at least 10%, at least 20%, at least 30%, at least 40%, at least 50%, at least 60%, at least 70%, at least 80%, at least 85%, at least 90%, at least 95%, at least 96%, at least 97%, at least 98%, at least 99%, or greater than 99.99% as compared to a control tissue of the subject. In some embodiments, the target gene is associated with a coronary disease. In some embodiments, the target gene is selected from the group consisting of PCSK9, ANGPTL3, APOC3, LPA, APOB, MTP, ANGPTL4, ANGPTL8, APOA5, APOE, LDLR, IDOL, NPC1L1, ASGR1, TM6SF2, GALNT2, GCKR, LPL, MLXIPL, SORT1, TRIB1, MARC1, ABCG5, and ABCG8. In some embodiments, the coupling sequence comprises RNA, DNA, chemically modified RNA, chemically modified DNA, or a hybrid of DNA and RNA. In some embodiments, the coupling sequence comprises (A)n, (T)n, (U)n, (a)n, or (u)n, wherein n is an integer no less than 3, wherein a is 2'-O-methyladenosine (2'-OMe A), and wherein u is 2'-O-methyluridine (2'-OMe-U). In some embodiments, the nucleic acid in (a) comprises (A)n, (T)n, (U)n, (a)n, or (u)n, wherein n is an integer no less than 3, wherein a is 2'-O-methyladenosine, and wherein u is 2'-O-methyluridine. In some embodiments, the targeting moiety is linked to the nucleic acid in (a) via a linker in the targeting moiety, via hybridization of the coupling sequence in the targeting moiety that hybridizes with the nucleic acid in (a), or via a combination thereof. In some embodiments, the linker comprises a covalent linker. In some embodiments, the linker comprises a phosphate, phosphorothioate, amide, ether, oxime, hydrazine or carbamate. In some embodiments, the linker is a phosphate or phosphorothioate. In some embodiments, the nucleic acid in (a) comprises a chemical modification. In some embodiments, the nucleic acid in (a) comprises a 2'-F modification, a phosphorothioate internucleotide linkage modification, acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), or a 2'-ara-F modification. In some embodiments, the nucleic acid comprises a 2'-O-methyl modification. In some embodiments, the nucleic acid comprises a phosphorothioate internucleotide linkage modification. In some embodiments, the level of the nucleic acid in the liver of the subject is at least 1.5, at least 2, at least 2.5, at least 3, at least 5, at least 10, at least 15, at least 20, at least 30, at least 40, at least 50 folds higher as compared to other tissues of the subject at least 1 hours, 2 hours, 6 hours, 12 hours, 24 hours, 2 days, 1 week, 2 weeks, 3 weeks, 6 weeks, or 8 weeks post delivery. In some embodiments, the effective amount is about 1 mg/kg to about 10 mg/kg. In some embodiments, the administration results in reduced blood triglycerides and/or reduced low-density lipo-protein cholesterol in the subject in need thereof. In some embodiments, the administration is performed intravenously, intrathecally, intramuscularly, intraventricularly, intracerebrally, intracerebellarly, intracerebroventricularly, intraparenchymally, subcutaneously, or a combination thereof.

In one aspect, described herein is a method for reducing the risk of coronary disease in a subject in need thereof, the method comprising administering to the subject a pharmaceutical composition comprising (a) (i) a single guide RNA and a nuclease mRNA, (ii) a dual guide RNA and a nuclease mRNA, (iii) a single guide RNA and an RNP, or (iv) a dual guide RNAs and an RNP; and (b) a asialoglycoprotein receptor (ASGPR) targeting moiety connected to the nucleic acid in (a), wherein the single guide RNA or the dual guide RNA comprises 4 or more 2'-O-methyl modifications and 2 or more phosphorothioate internucleotide linkages, wherein the targeting moiety comprises a structure of Table 1, and wherein the guide RNA hybridizes with a PCSK9 gene. In one aspect, described herein is a method for reducing the risk of coronary disease in a subject in need thereof, the method comprising administering to the subject a pharmaceutical composition comprising (a) (i) a single guide RNA and a nuclease mRNA, (ii) a dual guide RNA and a nuclease mRNA, (iii) a single guide RNA and an RNP, or (iv) a dual guide RNAs and an RNP; and (b) a targeting moiety connected to the nucleic acid in (a), wherein the single guide RNA or the dual guide RNA comprises 4 or more 2'-O-methyl modifications and two or more phosphorothioate internucleotide linkages, wherein the targeting moiety comprises a coupling sequence that hybridizes with the single guide RNA in (a), and wherein the guide RNA hybridizes with a PCSK9 gene. In some embodiments, the nuclease mRNA and/or the single guide RNA comprises at least one chemical modification. In some embodiments, the chemical modification is selected from the group consisting of a 2'-F modification, phosphorothioate internucleotide linkage modification, acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), 4'-O-methyl, and a 2'-ara-F modification. In some embodiments, administrating of the nucleic acid conjugate results in a reduced level of immune response as compared to a control nucleic acid conjugate without said chemical modification.

In one aspect, described herein is a nucleotide conjugate comprising a structure of Formula (IV)

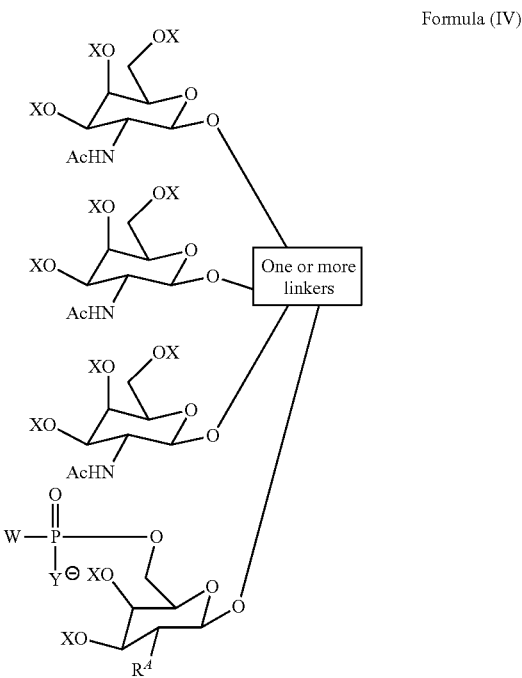

Formula (IV)

wherein each X is independently H or a protecting group, $R^4$ is —OX or —NHAc, Y is O or S, and W represents
(a) (i) a single guide RNA and a nuclease mRNA, (ii) a dual guide RNA and a nuclease mRNA, (iii) a single guide RNA and an RNP, or (iv) a dual guide RNAs and an RNP; or
(b) a coupling sequence.

In some embodiments, the one or more linkers comprise a structure selected from the group consisting of:

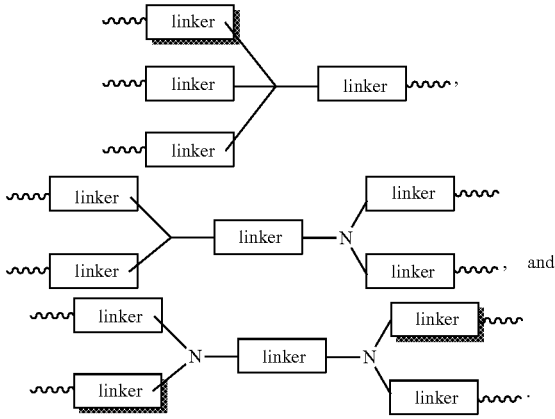

In some embodiments, each of the linkers independently has a structure of $-(L^1)_{k1}-(L^2)_{k2}-(L^3)_{k3}-(L^4)_{k4}-$, wherein each of k1, k2, k3, and k4 is independently 0, 1 or 2, and each of the $L^1$, $L^2$, $L^3$ and $L^4$ is independently selected from —O—, —S—, $S(=O)_{1-2}$—, —C(=O)—, —C(=O)—, —C(=S)—, —NR$^L$—, —OC(O)—, —C(O)O—, —OC(O)O—, —C(=O)NR$^L$—, —OC(=O)NR$^L$—, —NR$^L$C(=O)—, —NR$^L$C(=O)NR$^L$—, —P(=O)R$^L$—, —NR$^L$S(=$_0$)(=NR$^L$)—, —NR$^L$S (=O)$_2$—, —S(=O)$_2$NR$^L$—, —N=N—, —(CH$_2$—CH$_2$—O)$_{1-6}$—, linear or branched C$_{1-6}$ alkylene, linear or branched C$_2$-6 alkenylene, linear or branched C$_2$-6 alkynylene, C$_3$-C$_5$ cycloalkylene, C$_2$-C$_7$ heterocycloalkylene, C$_6$-C$_{10}$ arylene, and C$_5$-C$_9$ heteroarylene, wherein the alkylene, alkenylene, alkynylene, cycloalkylene, cycloalkylene, arylene, or heteroarylene is substituted or unsubstituted, and wherein each R$^L$ is independently H, D, cyano, halogen, substituted or unsubstituted C$_1$-C$_6$ alkyl, —CD$_3$, —OCH$_3$, —OCD$_3$, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl. In some embodiments, each R$^L$ is independently H, substituted or unsubstituted C$_1$-C$_6$ alkyl, —OCH$_3$, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, or substituted or unsubstituted C$_2$-C$_7$ heterocycloalkyl. In some embodiments, the sum of k1, k2, k3, and k4 is 1, 2, or 3.

In one aspect, described herein is a method of preparing a formulation comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, the method comprising: (a) providing a first solution comprising the one or more nucleic acid molecular entities; (b) providing a second solution comprising at least one of the one or more lipids; (c) mixing the first solution and the second solution, thereby producing a mixture comprising nanoparticles that comprise the one or more nucleic acid molecular entities and the one or more lipids; (d) mixing the receptor targeting conjugate with the nanoparticles produced in step (c); (e) incubating the nanoparticles; and (f) optionally carrying out a buffer exchange process. In some embodiments, the receptor targeting conjugate is combined with the one or more lipids after the mixing step in (c). In some embodiments, the receptor targeting conjugate is added in a dilution buffer, and wherein the dilution buffer is mixed with preformed nucleic acid-lipid nanoparticles coming out of an inline mixing chamber thereby forming the nanoparticles. In some embodiments, the receptor targeting conjugate is introduced after an addition of a dilution buffer to the mixture and holding the diluted mixture for a period of time. In some embodiments, the holding time is between 1 and 120 minutes. In some embodiments, the holding time is between 1 and 90 minutes, between 1 and 60 minutes, or between 10 and 40 minutes. In some embodiments, the holding time is about 30 minutes. In some embodiments, the receptor targeting conjugate is introduced to the nanoparticles after buffer exchange. In some embodiments, the receptor targeting conjugate is introduced to the nanoparticles after buffer exchange and concentration, but prior to storage. In some embodiments, the receptor targeting conjugate is introduced to the nanoparticles after storage and thawing, and prior to dosing or evaluation. In one aspect, described herein is a method of preparing a formulation comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, the method comprising: (a) providing a first solution comprising the one or more nucleic acid molecular entities; (b) providing a second solution comprising at least one of the one or more lipids; (c) inline mixing of the first solution and the second solution, thereby producing a mixture comprising nanoparticles that comprise the one or more nucleic acid molecular entities and the one or more lipids; (d) inline mixing of the receptor targeting conjugate to the mixture of step (c), thereby producing a mixture comprising nanoparticles that comprise the one or more nucleic acid molecular entities, the one or more lipids, and the receptor targeting conjugate; (e) diluting the mixture of step (d) by adding a dilution buffer; and (f) optionally carrying out a buffer exchange process. In some embodiments, the inline mixing of step (c) and the inline mixing of step (d) are performed successively. In one aspect, described herein is a method of preparing a formulation comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, the method comprising: (a) providing a first solution comprising the one or more nucleic acid molecular entities; (b) providing a second solution comprising (i) at least one of the one or more lipids and (ii) at least a portion of the receptor targeting conjugate; (c) mixing the first solution and the second solution, thereby producing a mixture comprising nanoparticles; (d) optionally incubating the nanoparticles; and (e) optionally carrying out a buffer exchange process. In some embodiments, the second solution comprises all the receptor targeting conjugate. In one aspect, described herein is a method of preparing a formulation comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, the method comprising: (a) providing a first solution comprising the one or more nucleic acid molecular entities; (b) providing a second solution comprising at least one of the one or more lipids; (c) mixing the first solution and the second solution, thereby producing a mixture comprising nanoparticles that comprise the one or more nucleic acid molecular entities and the one or more lipids; (d) combining the receptor targeting conjugate with the one or more lipids, wherein at least a portion of the receptor targeting conjugate is combined with the one or more lipids prior to or concurrently with the mixing step; (e) optionally incubating the nanoparticles; and (f) optionally carrying out a buffer exchange process. In some embodiments, at least a portion of the receptor targeting conjugate is combined with the one or more lipids concurrently with the mixing step. In some embodiments, at least a portion of the receptor targeting conjugate is combined with the one or more lipids prior to the mixing step. In some embodiments, the receptor targeting conjugate is combined with the one or more lipids in the second solution. In some embodiments, a portion of the receptor targeting conjugate is combined with the one or more lipids in the second solution and a portion of the receptor targeting conjugate is combined with the one or more lipids after the mixing. In some embodiments, a portion of the receptor targeting conjugate is combined with the one or more lipids in the second solution and a portion of the receptor targeting conjugate is combined with the one or more lipids after the incubating step. In some embodiments, a portion of the receptor targeting conjugate is combined with the one or more lipids in the second solution and a portion of the receptor targeting conjugate is combined with the one or more lipids after the buffer exchange step. In some embodiments, the method further comprises diluting the mixture produced by mixing the first and the second solutions by adding a dilution buffer. In some embodiments, the mixture is diluted inline. In some embodiments, the dilution buffer comprises at least a portion of the receptor targeting conjugate. In some embodiments, the dilution buffer comprises at least a portion of the stealth lipid. In some embodiments, the first solution comprises an aqueous buffer. In some embodiments, the second solution comprises ethanol. In some embodiments, the mixing comprises laminar mixing, vortex mixing, turbulent mixing, or a combination thereof. In some embodiments, the mixing comprises cross-mixing. In some embodiments, the mixing comprises inline mixing. In some embodiments, the mixing comprises introducing at least a portion of the first solution through a first inlet channel and at least a portion of the second solution through a second inlet channel, and wherein an angle between the first inlet channel and the second inlet channel is from about 15 to 180 degrees. In some embodiments, the mixing comprises introducing a portion of the first solution through a third inlet channel. In some embodiments, the buffer exchange comprises dialysis, chromatography, or tangential flow filtration (TFF). In some embodiments, the method further comprises a filtration step. In some embodiments, the receptor targeting conjugate comprises one or more N-acetylgalactosamine (GalNAc) or GalNAc derivatives. In some embodiments, the receptor targeting conjugate comprises one or more galactose or galactose derivatives. In some embodiments, the receptor targeting conjugate is selected from Table 4. In some embodiments, the receptor targeting conjugate is a targeting conjugate described herein. In some embodiments, the nanoparticles comprise a first nanoparticle composition described herein. In some embodiments, the formulation is a pharmaceutical composition described herein.

In one aspect, described herein is a pharmaceutical composition comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, wherein the formulation is prepared by a method described herein. In one aspect, described herein is a pharmaceutical composition comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, wherein the formulation is prepared by a method comprising: (a) providing a first solution comprising the one or more nucleic acid molecular entities; (b) providing a second solution comprising at least one of the one or more lipids; (c)mixing the first solution and the second solution, thereby producing a mixture comprising nanoparticles that comprise the one or more nucleic acid molecular entities and the one or more lipids; (d)mixing the receptor targeting conjugate with the nanoparticles produced in step (c); (e) incubating the nanoparticles; and (f) optionally carrying out a buffer exchange process. In one aspect, described herein is a pharmaceutical composition comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, wherein the formulation is prepared by a method comprising: (a) providing a first solution comprising the one or more nucleic acid molecular entities; (b) providing a second solution comprising at least one of the one or more lipids; (c)mixing the first solution and the second solution, thereby producing a mixture comprising nanoparticles that comprise the one or more nucleic acid molecular entities and the one or more lipids; (d) combining the receptor targeting conjugate with the one or more lipids, wherein at least a portion of the receptor targeting conjugate is combined with the one or more lipids prior to or concurrently with the mixing step; (e) optionally incubating the nanoparticles; and (f) optionally carrying out a buffer exchange process. In one aspect, described herein is a pharmaceutical composition comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, wherein the formulation is prepared by a method comprising: (a) providing a first solution comprising the one or more nucleic acid molecular entities; (b) providing a second solution comprising at least one of the one or more lipids; (c) inline mixing of the first solution and the second solution, thereby producing a mixture comprising nanoparticles that comprise the one or more nucleic acid molecular entities and the one or more lipids; (d) inline mixing of the receptor targeting conjugate to the mixture of step (c), thereby producing a mixture comprising nanoparticles that comprise the one or more nucleic acid molecular entities, the one or more lipids, and the receptor targeting conjugate; (e) diluting the mixture of step (d) by adding a dilution buffer; and (f) optionally carrying out a buffer exchange process. In one aspect, described herein is a pharmaceutical composition comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, wherein the formulation is prepared by a method comprising: (a) providing a first solution comprising the one or more nucleic acid molecular entities; (b) providing a second solution comprising (i) at least one of the one or more lipids and (ii) at least a portion of the receptor targeting conjugate; (c)mixing the first solution and the second solution, thereby producing a mixture comprising nanoparticles; (d) optionally incubating the nanoparticles; and optionally carrying out a buffer exchange process.

INCORPORATION BY REFERENCE

All publications, references, patents, and patent applications mentioned in this specification are herein incorporated by reference to the same extent as if each individual publication, patent, or patent application was specifically and individually indicated to be incorporated by reference. In the event of inconsistent usages between this document and those documents so incorporated by reference, the usage in the incorporated reference(s) should be considered supplementary to that of this document; for irreconcilable inconsistencies, the usage in this document controls

BRIEF DESCRIPTION OF THE DRAWINGS

Novel features of the invention are set forth with particularity in the appended claims. A better understanding of the features and advantages of the present invention will be obtained by reference to the following detailed description that sets forth illustrative embodiments in which the principles of the inventions are utilized, and the accompany drawings of which:

FIG. 1A shows reference LNP with no GalNAc-lipid present and FIG. 1B shows LNP constituted with GalNAc-lipid.

DETAILED DESCRIPTION

Figure 1A:
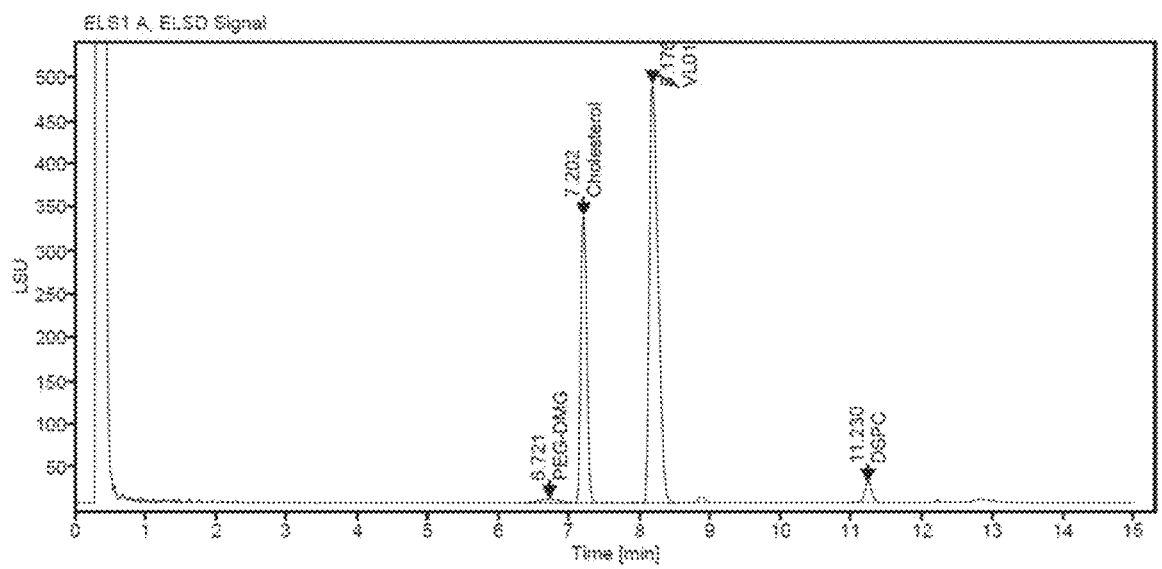
FIG. 1A-FIG. 1B illustrate the HPLC chromatogram of GalNAc-lipid incorporation of compositions herein.

Certain specific details of this description are set forth in order to provide a thorough understanding of various embodiments. However, one skilled in the art will understand that the present disclosure may be practiced without these details. In other instances, well-known structures and/or methods have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure. The section headings used herein are for organizational purposes only and are not to be construed as limiting the subject matter described.

Efficient delivery to cells requires specific targeting and substantial protection from the extracellular environment, particularly serum proteins. One method of achieving specific targeting is to conjugate a targeting moiety to active agents or pharmaceutical effector such as a nucleic acid agent, thereby directing the active agent or pharmaceutical effector to particular cells or tissues depending on the specificity of the targeting moiety. One way a targeting moiety can improve delivery is by receptor mediated endocytotic activity. In some cases, this mechanism of uptake can involve the movement of nucleic acid agent bound to membrane receptors into the interior of an area that is enveloped by the membrane via invagination of the membrane structure or by fusion of the delivery system with the cell membrane. This process is initiated via activation of a cell-surface or membrane receptor following binding of a specific ligand to the receptor. Many receptor-mediated endocytotic systems are known and have been studied, including those that recognize sugars such as galactose, mannose, mannose-6-phosphate, peptides and proteins such as transferrin, asialoglycoprotein, vitamin B12, insulin and epidermal growth factor (EGF). Lipophilic moieties, such as cholesterol or fatty acids, when attached to highly hydrophilic molecules such as nucleic acids can substantially enhance plasma protein binding and consequently circulation half life. Lipophilic conjugates can also be used in combination with the targeting ligands in order to improve the intracellular trafficking of a targeted delivery approach.

The Asialoglycoprotein receptor (ASGP-R) is a high capacity receptor, which is highly abundant on hepatocytes. The ASGP-R shows a 50-fold higher affinity for N-Acetyl-D-Galactosylamine (GalNAc) than D-Gal. Previous work has shown that multivalency is required to achieve high affinity, while spacing among sugars is also crucial. The inventors here recognized that there is a clear need for new receptor specific ligand conjugated RNA or DNA agents and methods for their preparation, that address the shortcomings of in vivo delivery of therapeutics with nucleic acids or nucleic acid involved complexes as described above. The present disclosure is directed to this very important objective.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All references cited herein are incorporated by reference in their entirety as though fully set forth. Singleton et al., Dictionary of Microbiology and Molecular Biology 3rd ed., J. Wiley & Sons (New York, NY 2001); March, Advanced Organic Chemistry Reactions, Mechanisms and Structure 5th ed., J. Wiley & Sons (New York, NY 2001); and Sambrook and Russel, Molecular Cloning: A Laboratory Manual 3rd ed., Cold Spring Harbor Laboratory Press (Cold Spring Harbor, N Y 2001), provide one skilled in the art with a general guide to many of the terms used in the present application.

Specific Definitions

When indicating the number of substituents, the term "one or more" refers to the range from one substituent to the highest possible number of substitution, e.g. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "nucleic acid molecular entity" is used interchangeably with "nucleic acid."

The term "nucleic acid" as used herein generally refers to one or more nucleobases, nucleosides, or nucleotides, and the term includes polynucleobases, polynucleosides, and polynucleotides. A nucleic acid can include polynucleotides, mononucleotides, and oligonucleotides. A nucleic acid can include DNA, RNA, or a mixture thereof, and can be single stranded, double stranded, or partially single or double stranded, and can form secondary structures. In some embodiments, a nucleic acid has multiple double-stranded segments and single stranded segments. For example, a nucleic acid may comprise a polynucleotide, e.g. a mRNA, with multiple double stranded segments within it. DNA may be in the form of e.g., antisense molecules, plasmid DNA, pre-condensed DNA, a PCR product, vectors, expression cassettes, chimeric sequences, chromosomal DNA, or derivatives and combinations of these groups. RNA may be in the form of siRNA, asymmetrical interfering RNA (aiRNA), microRNA (miRNA), mRNA, tRNA, rRNA, tRNA, viral RNA (vRNA), CRISPR RNA, base editor RNA and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J Biol. Chem., 260:2605-2608 (1985); Rossolini et al., Mal. Cell. Probes, 8:91-98 (1994)). "Nucleotides" contain a substituted and/or unsubstituted sugar deoxyribose (DNA), or a substituted and/or unsubstituted sugar ribose (RNA), or a substituted and/or unsubstituted carbocylic, or a substituted and/or unsubstituted acyclic moiety (glycol nucleic, for e.g.), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "polynucleotide", as used herein generally refers to a molecule comprising two or more linked nucleic acid subunits, e.g., nucleotides, and can be used interchangeably with "oligonucleotide". For example, a polynucleotide may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides include nucleotides in which the sugar is ribose. Deoxyribonucleotides include nucleotides in which the sugar is deoxyribose. A nucleotide can be a nucleoside monophosphate, nucleoside diphosphate, nucleoside triphosphate or a nucleoside polyphosphate. For example, a nucleotide can be a deoxyribonucleoside polyphosphate, such as a deoxyribonucleoside triphosphate (dNTP), Exemplary dNTPs include deoxyadenosine triphosphate (dATP), deoxycytidine triphosphate (dCTP), deoxyguanosine triphosphate (dGTP), uridine triphosphate (dUTP) and deoxythymidine triphosphate (dTTP). dNTPs can also include detectable tags, such as luminescent tags or markers (e.g., fluorophores). For example, a nucleotide can be a purine (e.g., A or G, or variant thereof) or a pyrimidine (e.g., C, T or U, or variant thereof). In some examples, a polynucleotide is deoxyribonucleic acid (DNA), ribonucleic acid (RNA), or derivatives or variants thereof. Exemplary polynucleotides include, but are not limited to, short interfering RNA (siRNA), a microRNA (miRNA), a plasmid DNA (pDNA), a short hairpin RNA (shRNA), small nuclear RNA (snRNA), messenger RNA (mRNA), precursor mRNA (pre-mRNA), antisense RNA (asRNA), and heteronuclear RNA (hnRNA), and encompasses both the nucleotide sequence and any structural embodiments thereof, such as single-stranded, double-stranded, triple-stranded, helical, hairpin, stem loop, bulge, etc. In some cases, a polynucleotide is circular. A polynucleotide can have various lengths. For example, a polynucleotide can have a length of at least about 7 bases, 8 bases, 9 bases, 10 bases, 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. A polynucleotide can be isolated from a cell or a tissue. For example, polynucleotide sequences may comprise isolated and purified DNA/RNA molecules, synthetic DNA/RNA molecules, and/or synthetic DNA/RNA analogs.

Polynucleotides can include one or more nucleotide variants, including nonstandard nucleotide(s), non-natural nucleotide(s), nucleotide analog(s) and/or modified nucleotides. Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl) uracil, (acp3)w, 2,6-diaminopurine and the like. In some cases, nucleotides may include modifications in their phosphate moieties, including modifications to a triphosphate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thiotriphosphate and beta-thiotriphosphates). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as amino ally 1-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A. Nat. Chem. Biol. 2012 July; 8(7):612-4, which is herein incorporated by reference for all purposes.

As used herein, the terms "polypeptide", "protein" and "peptide" are used interchangeably and refer to a polymer of amino acid residues linked via peptide bonds and which may be composed of two or more polypeptide chains. The terms "polypeptide", "protein" and "peptide" refer to a polymer of at least two amino acid monomers joined together through amide bonds. An amino acid may be the L-optical isomer or the D-optical isomer. More specifically, the terms "polypeptide", "protein" and "peptide" refer to a molecule composed of two or more amino acids in a specific order; for example, the order as determined by the base sequence of nucleotides in the gene or RNA coding for the protein. Proteins are essential for the structure, function, and regulation of the body's cells, tissues, and organs, and each protein has unique functions. Examples are hormones, enzymes, antibodies, and any fragments thereof. In some cases, a protein can be a portion of the protein, for example, a domain, a subdomain, or a motif of the protein. In some cases, a protein can be a variant (or mutation) of the protein, wherein one or more amino acid residues are inserted into, deleted from, and/or substituted into the naturally occurring (or at least a known) amino acid sequence of the protein. A protein or a variant thereof can be naturally occurring or recombinant.

As used herein, the term "intercalating" or "intercalation" refers to the actions of agents (e.g., small molecules) that insert themselves between successive bases in DNA. In some cases, the intercalation prevents the proper functioning of the DNA.

As used herein, "complement" means the complementary sequence to a nucleic acid according to standard Watson/Crick pairing rules. A complement sequence can also be a sequence of RNA complementary to the DNA sequence or its complement sequence, and can also be a cDNA. Complements may be fully complementary or partially complementary such that the two sequences will hybridize under stringent hybridization conditions. The skilled artisan will understand that complementary or substantially complementary sequences need not hybridize along their entire length. In particular embodiments, complementary or substantially complementary sequences may comprise a contiguous sequence of bases that do not hybridize to a target sequence, positioned 3' or 5' to a contiguous sequence of bases that hybridize to a target sequence.

As used herein, "hybridize" refers to a process where two nucleic acid strands anneal to each in accordance with Watson-Crick base pairing rules. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to determine the appropriate stringency of hybridization/washing conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J, all of which are incorporated herein by reference in their entireties. In certain embodiments, hybridizations may occur between nucleic acid molecules of 20-100 nucleotides in length. In some embodiments, hybridization may occur between at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 consecutive nucleotides. In some embodiments, the hybridizing nucleic acid molecules may contain up to 1, 2, 3, 4, 5, 6, 7, 8, 9, 10, 11, 12, 13, 14, 15, 16, 17, 18, 19, or 20 mismatches that are tolerated.

As used herein, the term "biological sample" means any biological material from which polynucleotides, polypeptides, biomarkers, and/or metabolites can be prepared and examined. Non-limiting examples encompasses whole blood, plasma, saliva, cheek swab, fecal specimen, urine specimen, cell mass, or any other bodily fluid or tissue.

The terms "administer," "administering", "administration," and the like, as used herein, refer to the methods that may be used to enable delivery of compounds or compositions to the desired site of biological action. These methods include, but are not limited to oral routes (p.o.), intraduodenal routes (i.d.), parenteral injection (including intravenous (i.v.), subcutaneous (s.c.), intraperitoneal (i.p.), intramuscular (i.m.), intravascular or infusion (inf.)), topical (top.) and rectal (p.r.) administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated; for example a reduction and/or alleviation of one or more signs, symptoms, or causes of a disease, or any other desired alteration of a biological system. For example, an "effective amount" for therapeutic uses can be an amount of an agent that provides a clinically significant decrease in one or more disease symptoms. An appropriate "effective" amount may be determined using techniques, such as a dose escalation study, in individual cases.

The terms "enhance" or "enhancing," as used herein, means to increase or prolong either in amount, potency or duration a desired effect.

As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

The term "monosaccharide" embraces radicals of allose, altrose, arabinose, cladinose, erythrose, erythrulose, fructose, D-fucitol, L-fucitol, fucosamine, fucose, fuculose, galactosamine, D-galactosaminitol, N-acetyl-galctosamine, galactose, glucosamine, N-acetyl-glucosamine, glucosaminitol, glucose, glucose-6-phosphate gulose glyceraldehyde, L-glycero-D-mannos-heprose, glycerol, glycerone, gulose idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tartaric acid, throse, xylose and xylulose. The monosaccharide can be in D- or L-configuration. The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or C=O replaced by C=S, or a ring oxygen of cyclic form replaced by sulfur), a seleno sugar, a telluro sugar, an aza sugar (ring carbon replaced by nitrogen), a imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, preferably galactosamine, glusamine, mannosamine, fucosmine, quinavosamine, neuraminic acid, muramic acid, lactosediamine, acosamine, bacillosamine, daunosamine, desosamine, forosamine, garosamine, kanosamine, kanosamine, mycaminose, myosamine, persosamine, pneumosamine, purpurosamine, rhodosmine. It is understood that the monosaccharide and the like can be further substituted.

As used herein, the "N/P ratio" is the molar ratio of ionizable (e.g., in the physiological pH range)nitrogen atoms in a lipid (or lipids) to phosphate groups in a nucleic acid molecular entity (or nucleic acid molecular entities), e.g., in a nanoparticle composition comprising a lipid component and an RNA. Ionizable nitrogen atoms can include, for example, nitrogen atoms that can be protonated at about pH 1, about pH 2, about pH 3, about pH 4, about pH5, about pH 6, about pH 7, about pH 7.5, or about pH 8 or higher. The physiological pH range can include, for example, the pH range of different cellular compartments (such as organs, tissues, and cells) and bodily fluids (such as blood, CSF, gastric juice, milk, bile, saliva, tears, and urine). In certain specific embodiments, the physiological pH range refers to the pH range of blood in a mammal, for example, from about 7.35 to about 7.45. In some embodiments, ionizable nitrogen atoms refer to those nitrogen atoms that are ionizable within a pH range between 5 and 14.

The terms "disaccharide", "trisaccharide" and "polysaecharide" embrace radicals of abequose, acrabose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose diginose, digitalose, digitoxose, evalose, evemitrose, fructooligosaccharide, galto-oligosaccharide, gentianose, genitiobiose, glucan, gluicogen, glylcogen, hamamelose, heparin, inulin, isolevoglucosenone, isomaltose, isomaltotriose, isopanose, kojibiose, lactose, lactose, lactosamine, lactosediamine, laminarabiose, levoglucosan, levoglucosenone, β-maltose, maltriose, mannan-oligosacchardie, amnninotriose, melezitose, melibiose, muramic acid, mycarose, mycinose, neuaminic acid, migerose, nojirimycon, noviose, oleandrose, panose, paratose, planteose, primeverose, raffinose, rhodone, rutinose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trahalosamine, turanose, tyvelose, xylobiose, umbelliferose and the like. Further, it is understood that the "disaccharide", "trisaccharide" and "polysaccharide" and the like can further substituted. Disaccharide also includes amino sugars and their derivatives, particularly, a mycaminose derivatized a the C-4' position or a 4 deoxy-3-amino-glucose derivatized at the C-6' position.

The term "subject" or "patient" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. The term "animal" as used herein comprises human beings and non-human animals. In one embodiment, a "non-human animal" is a mammal, for example a rodent such as rat or a mouse. In one embodiment, a non-human animal is a mouse or a monkey.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically. The term "treating" further encompasses the concept of "prevent," "preventing," and "prevention," as stated below. It is appreciated that, although not precluded, treating a disorder or condition does not require that the disorder, condition, or symptoms associated therewith be completely eliminated.

The term "preventing" or "prevention" of a disease state denotes causing the clinical symptoms of the disease state not to develop in a subject that can be exposed to or predisposed to the disease state, but does not yet experience or display symptoms of the disease state.

The terms "pharmaceutical composition" and "pharmaceutical formulation" (or "formulation") are used interchangeably and denote a mixture or solution comprising a therapeutically effective amount of an active pharmaceutical ingredient together with one or more pharmaceutically acceptable excipients to be administered to a subject, e.g., a human in need thereof.

The term "pharmaceutical combination" as used herein, means a product that results from mixing or combining more than one active ingredient and includes both fixed and non-fixed combinations of the active ingredients. The term "fixed combination" means that the active ingredients, e.g., a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., administration of three or more active ingredients.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use. "Pharmaceutically acceptable" can refer to a material, such as a carrier or diluent, which does not abrogate the biological activity or properties of the compound, and is relatively nontoxic, e.g., the material may be administered to an individual without causing undesirable biological effects or interacting in a deleterious manner with any of the components of the composition in which it is contained.

The terms "pharmaceutically acceptable excipient", "pharmaceutically acceptable carrier", "pharmaceutically acceptable vehicle" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents, excipients, preservatives or lubricants used in formulating pharmaceutical products.

The term "base editing" and "base correction" are used interchangeably to indicate a base change or mutation at a target sequence within the target gene leading to base modification. In certain embodiments, base editing occurs at a single base of the target sequence. In preferred embodiments, base editing does not involve double strand breaks of the target sequence.

As used herein, the term "siRNA" refers to an agent that mediates the targeted cleavage of an RNA transcript. These agents associate with a cytoplasmic multi-protein complex known as RNAi-induced silencing complex (RISC). Agents that are effective in inducing RNA interference are also referred to as siRNA, RNAi agent, or iRNA agent, herein. As used herein, the term siRNA includes microRNAs and pre-microRNAs. As used herein, the terms "siRNA activity" and "RNAi activity" refer to gene silencing by an siRNA.

The term "2'-O-methoxyethyl" (also 2'-MOE, 2'-O(CH2) 2-OCH3 and 2'-O-(2-methoxyethyl)) refers to an O-methoxy-ethyl modification of the 2' position of a furosyl ring. A 2'-O-methoxyethyl modified sugar is a modified sugar.

The term "2'-O-methoxyethyl nucleotide" means a nucleotide comprising a 2'-O-methoxyethyl modified sugar moiety.

The term "5-methylcytosine" means a cytosine modified with a methyl group attached to the 5' position. A 5-methylcytosine is a modified nucleobase.

The term "oxo" refers to the =O substituent.

The term "alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —CH(CH$_3$)$_2$ or —C(CH$_3$)$_3$. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

The term "alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

The term "alkylamino" refers to a radical of the formula —NHR or —NRR where each R is, independently, an alkyl radical as defined above. Unless stated otherwise specifically in the specification, an alkylamino group may be optionally substituted as described below.

The term "alkenyl" refers to a type of alkyl group in which at least one carbon-carbon double bond is present. In one embodiment, an alkenyl group has the formula —C(R) =CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$. Depending on the structure, an alkenyl group can be monovalent or divalent (i.e., an alkenylene group).

The term "alkynyl" refers to a type of alkyl group in which at least one carbon-carbon triple bond is present.

Accordingly, "alkynylene" can refer to a divalent alkynyl group. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$, —C≡CCH$_2$CH$_3$, —CH$_2$C≡CH.

The term "aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be monovalent or divalent (i.e., an "arylene" group). Unless stated otherwise specifically in the specification, the term "aryl" or the prefix "ar-" (such as in "aralkyl") is meant to include aryl radicals that are optionally substituted. In some embodiments, an aryl group is partially reduced to form a cycloalkyl group defined herein. In some embodiments, an aryl group is fully reduced to form a cycloalkyl group defined herein. In some embodiments, an aryl group is a $C_6$-$C_{14}$ aryl. In some embodiments, an aryl group is a $C_6$-$C_{10}$ aryl.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopropyl, cyclobutyl, cyclopentyl or cyclohexyl. In some embodiments, the monocyclic cycloalkyl is cyclopentenyl or cyclohexenyl. In some embodiments, the monocyclic cycloalkyl is cyclopentenyl. Polycyclic radicals include, for example, adamantyl, 1,2-dihydronaphthalenyl, 1,4-dihydronaphthalenyl, tetrainyl, decalinyl, 3,4-dihydronaphthalenyl-1(2H)-one, spiro[2.2]pentyl, norbornyl and bicycle[1.1.1]pentyl. Unless otherwise stated specifically in the specification, a cycloalkyl group may be optionally substituted. Depending on the structure, a cycloalkyl group can be monovalent or divalent (i.e., a cycloalkylene group).

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or-propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "heteroalkylene" refers to an alkyl radical as described above where one or more carbon atoms of the alkyl is replaced with a 0, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$OCH$_2$CH$_2$O—.

The term "heterocycloalkyl" refers to a cycloalkyl group that includes at least one heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 12 carbons in the ring. In some embodiments, heterocycloalkyls have from 2 to 10 carbons in the ring. In some embodiments, heterocycloalkyls have from 2 to 10 carbons in the ring and 1 or 2 N atoms. In some embodiments, heterocycloalkyls have from 2 to 10 carbons in the ring and 3 or 4 N atoms. In some embodiments, heterocycloalkyls have from 2 to 12 carbons, 0-2 N atoms, 0-2 O atoms, 0-2 P atoms, and 0-1 S atoms in the ring. In some embodiments, heterocycloalkyls have from 2 to 12 carbons, 1-3 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted. As used herein, the term "heterocycloalkylene" can refer to a divalent heterocycloalkyl group.

The term "heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-6 N atoms in the ring. In some embodiments, a heteroaryl contains 1-4 N atoms in the ring. In some embodiments, a heteroaryl contains 4-6 N atoms in the ring. In some embodiments, a heteroaryl contains 0-4 N atoms, 0-1 O atoms, 0-1 P atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, a bicyclic heteroaryl is a $C_6$-$C_9$ heteroaryl. In some embodiments, a heteroaryl group is partially reduced to form a heterocycloalkyl group defined herein. In some embodiments, a heteroaryl group is fully reduced to form a heterocycloalkyl group defined herein. Depending on the structure, a heteroaryl group can be monovalent or divalent (i.e., a "heteroarylene" group).

The term "substituted," "substituent" or the like, unless otherwise indicated, can refer to the replacement of one or more hydrogen radicals in a given structure individually and independently with the radical of a specified substituent including, but not limited to: D, halogen, —CN, —$NH_2$, —NH(alkyl), —N(alkyl)$_2$, —OH, —$CO_2H$, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —$NH_2$, —NH($CH_3$), —N($CH_3$)$_2$, —OH, —$CO_2H$, —$CO_2$($C_1$-$C_4$ alkyl), —C(=O)$NH_2$, —C(=O)NH($C_1$-$C_4$ alkyl), —C(=O)N($C_1$-$C_4$ alkyl)$_2$, —S(=O)$_2NH_2$, —S(=O)$_2$NH($C_1$-$C_4$ alkyl), —S(=O)$_2$N($C_1$-$C_4$ alkyl)$_2$, $C_1$-$C_4$ alkyl, $C_3$-$C_6$ cycloalkyl, $C_1$-$C_4$ fluoroalkyl, $C_1$-$C_4$ heteroalkyl, $C_1$-$C_4$ alkoxy, $C_1$-$C_4$ fluoroalkoxy, —S$C_1$-$C_4$ alkyl, —S(=O)$C_1$-$C_4$ alkyl, and —S(=O)$_2$($C_1$-$C_4$ alkyl). In some embodiments, optional substituents are independently selected from D, halogen, —CN, —$NH_2$, —OH, —NH($CH_3$), —N($CH_3$)$_2$, —NH(cyclopropyl), —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (=O).

The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can also be stated as mg/kg or g/kg.

"Modified internucleoside linkage" refers to a substitution or any change from a naturally occurring internucleoside bond. For example, a phosphorothioate linkage is a modified internucleoside linkage.

"Modified nucleobase" refers to any nucleobase other than adenine, cytosine, guanine, thymidine, or uracil. For example, 5-methylcytosine is a modified nucleobase. An "unmodified nucleobase" means the purine bases adenine (A) and guanine (G), and the pyrimidine bases thymine (T), cytosine (C), and uracil (U).

"Modified nucleoside" means a nucleoside having at least one modified sugar moiety, and/or modified nucleobase.

"Modified nucleotide" means a nucleotide having at least one modified sugar moiety, modified internucleoside linkage and/or modified nucleobase.

"Modified oligonucleotide" means an oligonucleotide comprising at least one modified nucleotide.

"Modified sugar" refers to a substitution or change from a natural sugar. For example, a 2'-O-methoxyethyl modified sugar is a modified sugar.

"Motif" means the pattern of chemically distinct regions in an antisense compound.

"Statin" means an agent that inhibits the activity of HMG-CoA reductase.

"Symptom of cardiovascular disease or disorder" means a phenomenon that arises from and accompanies the cardiovascular disease or disorder and serves as an indication of it. For example, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever are symptoms of cardiovascular disease or disorder.

"Target nucleic acid," and "target sequence" refer to a nucleic acid capable of being targeted by a genome editing composition. For example, a target DNA sequence within or adjacent to the ANGPTL3 gene may be targeted by a guide nucleotide associated with a Cas9 nuclease.

Methods for detection and/or measurement of polypeptides in biological material are well known in the art and include, but are not limited to, Western-blotting, flow cytometry, ELISAs, RIAs, and various proteomics techniques. An exemplary method to measure or detect a polypeptide is an immunoassay, such as an ELISA. This type of protein quantitation can be based on an antibody capable of capturing a specific antigen, and a second antibody capable of detecting the captured antigen. Exemplary assays for detection and/or measurement of polypeptides are described in Harlow, E. and Lane, D. Antibodies: A Laboratory Manual, (1988), Cold Spring Harbor Laboratory Press.

Methods for detection and/or measurement of RNA in biological material are well known in the art and include, but are not limited to, Northern-blotting, RNA protection assay, RT PCR. Suitable methods are described in Molecular Cloning: A Laboratory Manual (Fourth Edition) By Michael R. Green, Joseph Sambrook, Peter MacCallum 2012, 2,028 pp, ISBN 978-1-936113-42-2.

A ribonucleoprotein (RNP) refers to a nucleoprotein that contains RNA. A RNP can be a complex of a ribonucleic acid and an RNA-binding protein. Such a combination can also be referred to as a protein-RNA complex. These complexes can function in a number of biological functions that include, but are not limited to, DNA replication, DNA modification, gene expression, metabolism and modification of RNA, and pre-mRNA splicing.

The term "nucleobase editors (BEs)" or "base editors (BEs)," as used herein, refers to a composition, e.g. a fusion protein comprising a polypeptide capable of making a nucleobase modification and a Cas protein. In some embodiments, the fusion protein comprises a nuclease-inactive Cas9 (dCas9) fused to a deaminase. In some embodiments, the fusion protein comprises a Cas9 nickase fused to a deaminase. In some embodiments, the fusion protein comprises a D10X mutation or a H840X mutation of a Cas9 as numbered in a wild type Cas9 sequence, e.g. SEQ ID NO: 1, which renders Cas9 capable of cleaving only one strand of a nucleic acid duplex. In some embodiments, the base editor comprises a programmable DNA nuclease domain fused or linked to a deaminase domain (e.g., adenosine deaminase domain or cytidine deaminase domain). Details of base editors are described in International PCT Application Nos. PCT/2017/045381 (WO2018/027078) and PCT/US2016/058344 (WO2017/070632), each of which is incorporated herein by reference in its entirety. Also see Komor, A. C., et al., "Programmable editing of a target base in genomic DNA without double-stranded DNA cleavage" Nature 533, 420-424 (2016); Gaudelli, N. M., et al., "Programmable base editing of A·T to G·C in genomic DNA without DNA cleavage" Nature 551, 464-471 (2017); Komor, A. C., et al., "Improved base excision repair inhibition and bacteriophage Mu Gam protein yields C:G-to-T:A base editors with higher efficiency and product purity" Science Advances 3:eaao4774 (2017); Nishida, K. et al. "Targeted nucleotide editing using hybrid prokaryotic and vertebrate adaptive immune systems", Science 353, aaf8729 (2016); Gehrke J M, Cervantes O, Clement M K, Wu Y, Zeng J, Bauer D E, Pinello L, Joung J K. An APOBEC3A-Cas9 base editor with minimized bystander and off-target activities. Nat Biotechnol. 2018 November; 36(10):977-982, the entire contents of which are hereby incorporated by reference.:

As used herein, the term "biomarker" or "marker" are used interchangeably to refer to any biochemical marker, serological marker, genetic marker, or other clinical or echographic characteristic that can be used to classify a sample from a patient as being associated with an pathological condition, such as a cardiovascular disease or disorder.

As used herein, the term "antibody" includes but is not limited to a population of immunoglobulin molecules, which can be polyclonal or monoclonal and of any class and isotype, or a fragment of an immunoglobulin molecule. There are five major classes of immunoglobulins: IgA, IgD, IgE, IgG, and IgM, and several of these may be further divided into subclasses (isotypes), e.g., IgG1, IgG2, IgG3, IgG4, IgA1 (human), IgA2 (human), IgAa (canine), IgAb (canine), IgAc (canine), and IgAd (canine). Such fragment generally comprises the portion of the antibody molecule that specifically binds an antigen. For example, a fragment of an immunoglobulin molecule known in the art as Fab, Fab' or F(ab')$_2$ is included within the meaning of the term antibody.

The term "label," as used herein, refers to a detectable compound, composition, or solid support, which can be conjugated directly or indirectly (e.g., via covalent or non-covalent means, alone or encapsulated) to a monoclonal antibody or a protein. The label may be detectable by itself (e.g., radioisotope labels, chemiluminescent dye, electrochemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label employed in the current disclosure could be, but is not limited to alkaline phosphatase; glucose-6-phosphate dehydrogenase ("G6PDH"); horseradish peroxidase (HRP); chemiluminescers such as isoluminol, fluorescers such as fluorescein and rhodamine compounds; ribozymes; and dyes. The label may also be a specific binding molecule which itself may be detectable (e.g., biotin, avidin, streptavidin, digioxigenin, maltose, oligohistidine, e.g., hexa-histidine (SEQ ID NO: 114), 2,4-dinitrobenzene, phenylarsenate, ssDNA, dsDNA, and the like). The utilization of a label produces a signal that may be detected by means such as detection of electromagnetic radiation or direct visualization, and that can optionally be measured.

"Substantial binding" or "substantially binding" refer to an amount of specific binding or affinity between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted to distinguish specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, e.g. less than 10%, e.g., less than 5% of the reactivity exhibited toward a third molecule under a particular set of assay conditions, which includes the relative concentration and incubation of the molecules. Specific binding can be tested using a number of widely known methods, e.g, an immunohistochemical assay, an enzyme-linked immunosorbent assay (ELISA), a radioimmunoassay (RIA), or a western blot assay.

As used herein, the term "substantially the same amino acid sequence" includes an amino acid sequence that is similar, but not identical to, the naturally-occurring amino acid sequence. For example, an amino acid sequence, e.g., polypeptide, that has substantially the same amino acid sequence as a flagellin protein can have one or more modifications such as amino acid additions, deletions, or substitutions relative to the amino acid sequence of the naturally-occurring flagellin protein, provided that the modified polypeptide retains substantially at least one biological activity of flagellin such as immunoreactivity. The "percentage similarity" between two sequences is a function of the number of positions that contain matching residues or conservative[YEG1][CY2] residues shared by the two sequences divided by the number of compared positions times 100. In this regard, conservative residues in a sequence is a residue that is physically or functionally similar to the corresponding reference residue, e.g., that has a similar size, shape, electric charge, chemical properties, including the ability to form covalent or hydrogen bonds, or the like.

The term "targeting moiety" refers to any molecule that provides an enhanced affinity for a selected target, e.g., a cell, cell type, tissue, organ, region of the body, or a compartment, e.g., a cellular, tissue or organ compartment. Some exemplary targeting moieties include, but are not limited to, antibodies, antigens, carbohydrate base moieties, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands. Carbohydrate based targeting moieties include, but are not limited to, D-galactose, multivalent galactose, N-acetyl-D-galactosamine (GalNAc), multivalent GalNAc, e.g. GalNAc2 and GalNAc3; D-mannose, multivalent mannose, multivalent lactose, N-acetyl-gulucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

The term "heterologous" refers to any two or more nucleic acid or polypeptide sequences that are not normally found in the same relationship to each other in nature. For instance, a heterologous nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion protein).

As used herein, the term "fragment" includes a peptide, polypeptide or protein segment of amino acids of the full-length protein, provided that the fragment retains reactivity with at least one antibody in sera of disease patients.

An "epitope" is the antigenic determinant on a polypeptide that is recognized for binding by a paratope on antibodies specific to the polypeptide, for example, an IBD-associated antibody.

The term "clinical factor" includes a symptom in a patient that is associated with a cardiovascular disease. Examples of clinical factors include, without limitation, angina; chest pain; shortness of breath; palpitations; weakness; dizziness; nausea; sweating; tachycardia; bradycardia; arrhythmia; atrial fibrillation; swelling in the lower extremities; cyanosis; fatigue; fainting; numbness of the face; numbness of the limbs; claudication or cramping of muscles; bloating of the abdomen; or fever. In some embodiments, a diagnosis of a cardiovascular disease is based upon a combination of analyzing the presence or level of one or more markers in a patient using statistical algorithms and determining whether the patient has one or more clinical factors.

The term "prognosis" includes a prediction of the probable course and outcome of a pathological condition, for example a cardiovascular disease, or the likelihood of recovery from the disease. In some embodiments, the use of statistical algorithms provides a prognosis of cardiovascular disease in a patient. For example, the prognosis can be surgery, development of one or more clinical factors, or recovery from the disease.

Provided herein are methods and compositions for targeted delivery of therapeutic agents such as nucleic acid agents. The therapeutic agents as used herein may be connected to or associated with a targeting moiety to assist targeted delivery. For example, the therapeutic agent and the targeting moiety may form a conjugate. The therapeutic agent may comprise a nucleic acid guided programmable nuclease system complexed with nucleic acids, such as guide RNAs. In some embodiments, the guide RNAs may be chemically modified. In some embodiments, the modified guide RNAs can be used for the preparation of a medicament for the treatment of any disease, disorder or condition relating to a gene where the gene may be altered, manipulated, edited, and modified by insertion or deletion of DNA. According to a further aspect of the disclosure, the modified guide RNA may be used for altering genes by deleting, substituting, repairing or inserting DNA. This can be done in microorganisms, or animals, in particular mammals and more particularly in humans. Human cells or tissue may be genetically altered or amended using the guide RNAs of the present disclosure and the CRISPR/Cas system known in the art in vitro and then inserted back into the patient in need thereof. In another aspect of the disclosure there is provided a pharmaceutical composition comprising a modified guide RNA according to the disclosure and a CRISPR-Cas system and a pharmaceutically acceptable carrier or excipient. The pharmaceutical composition may include a vector or a cell with the modified guide RNA of the disclosure. In a still further aspect of the disclosure there is provided a composition comprising a modified guide RNA and at least one delivery means selected from GalNAc, polymers, liposomes, peptides, aptamers, antibodies, viral vectors, folate or transferrin.

Nuclease Systems

Provided herein are compositions and methods for targeted delivery of active agents, or therapeutic agents, including nucleic acids, polynucleotides or oligonucleotides. The active agent can be a pharmaceutic composition, a drug, a polynucleotide, an oligonucleotide, an RNP, a lipid nanoparticle, or a protein-RNA complex. Targeted delivery as described herein may direct the active agent to a particular desired location, for example, to specific in vivo positions, cells, tissues, or organs, recognition locations in an intracellular matrix, specific locations within a cell. In some embodiments, the active agent comprises a guide RNA associated with a nuclease, for example, a CRISPR nuclease. In some embodiments, the active agent comprises a nuclease system capable of modifying the activity and/or function of one or more target genes, e.g. a PCSK9 or ANGPTL3gene.

In some embodiments, the active agent comprises a genome editing composition comprising a nuclease system. In some embodiments, the genome editing composition is a target specific genome editing composition. In some embodiments, the genome editing composition comprises a nucleic acid guided programmable nuclease or a portion thereof. In some embodiments of the present disclosure, a nuclease system includes at least one nuclease. In some embodiments, the nuclease system comprises at least one programmable nuclease. In some embodiments, the nuclease may comprise at least one DNA binding domain and at least one nuclease domain. In some embodiments, the nuclease domain may be heterologous to the DNA binding domain. In certain embodiments, the nuclease is a DNA endonuclease, and may cleave single or double-stranded DNA. In certain embodiments, the nuclease may cleave RNA.

In some embodiments, a nuclease system may include a Cas protein domain (also called a "Cas nuclease") from a CRISPR/Cas system. The Cas protein may comprise at least one domain that interacts with a guide nucleic acid, for example, a guide RNA (gRNA). Additionally, the Cas protein may be directed to a target sequence by a guide RNA. The guide RNA interacts with the Cas protein as well as the target sequence such that, the Cas protein is directed to the target sequence and may be capable of cleaving the target sequence. In certain embodiments, e.g., Cas9, the Cas protein is a single-protein effector, an RNA-guided nuclease. In some embodiments, the guide RNA provides the specificity for the targeted cleavage, and the Cas protein may be universal and paired with different guide RNAs to cleave different target sequences. The terms Cas protein and Cas nuclease are used interchangeably herein.

In some embodiments, the CRISPR/Cas system may comprise Type-I, Type-II, or Type-III system components, or any orthologues thereof. Updated classification schemes for CRISPR/Cas loci define Class 1 and Class 2 CRISPR/Cas systems, having Types I to V or VI. See, e.g., Makarova et al., Nat Rev Microbiol, 13(11): 722-36 (2015); Shmakov et al., Molecular Cell, 60:385-397 (2015). Class 2 CRISPR/Cas systems have single protein effectors. Cas proteins of Types II, V, and VI may be single-protein, RNA-guided endonucleases, herein called "Class 2 Cas nucleases." Class 2 Cas nucleases include, for example, Cas9, Cpf1, C2c1, C2c2, and $C_2c3$ proteins. Cpf1 protein, Zetsche et al., Cell, 163: 1-13 (2015), is homologous to Cas9, and contains a RuvC-like nuclease domain. S3.

In some embodiments, the Cas protein may be from a Type-II CRISPR/Cas system, i.e., a Cas9 protein from a CRISPR/Cas9 system. In some embodiments, the Cas protein may be from a Class 2 CRISPR/Cas system, i.e., a single-protein Cas nuclease such as a Cas9 protein or a Cpf1 protein. The Cas9 and Cpf1 family of proteins are enzymes with DNA endonuclease activity, and they can be directed to cleave a desired nucleic acid target by designing an appropriate guide RNA, as described further herein.

A Type-II CRISPR/Cas system component may be from a Type-IIA, Type-IIB, or Type-IIC system. Cas9 nuclease structure and sequences are known to those skilled in the art (Jinek et al. Science 2012, 337: 816-821; Delcheva et al. Nature 2011, 471: 602-607, incorporated herein by reference). In some embodiments, wild type Cas9 corresponds to *Streptococcus pyogenes* Cas9 (NCBI Ref No. NC_002737.2, SEQ ID NO: 2) and Uniprot Reference Q99ZW2 (SEQ ID NO: 1).

*Streptococcus pyogenes* Cas9 (wild type) protein sequence
(SEQ ID NO: 1)

MDKKYSIGLDIGTNSVGWAVITDEYKVPSKKFKVLGNTDRHSIKKNLIGALLF

DSGEAEATRLKRTARRRYTRRKNRICYLQEIFSNEMAKVDDSFFHRLEESFLVEEDKKH

ERHPIFGNIVDEVAYHEKYPTIYHLRKKLVDSTDKADLRLIYLALAHMIKFRGHFLIEGD

LNPDNSDVDKLFIQLVQTYNQLFEENPINASGVDAKAILSARLSKSRRLENLIAQLPGEK

KNGLFGNLIALSLGLTPNFKSNFDLAEDAKLQLSKDTYDDDLDNLLAQIGDQYADLFLA

AKNLSDAILLSDILRVNTEITKAPLSASMIKRYDEHHQDLTLLKALVRQQLPEKYKEIFFD

QSKNGYAGYIDGGASQEEFYKFIKPILEKMDGTEELLVKLNREDLLRKQRTFDNGSIPHQ

IHLGELHAILRRQEDFYPFLKDNREKIEKILTFRIPYYVGPLARGNSRFAWMTRKSEETIT

PWNFEEVVDKGASAQSFIERMTNFDKNLPNEKVLPKHSLLYEYFTVYNELTKVKYVTE

GMRKPAFLSGEQKKAIVDLLFKTNRKVTVKQLKEDYFKKIECFDSVEISGVEDRFNASL

GTYHDLLKIIKDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDSLTFKEDIQKA

QVSGQGDSLHEHIANLAGSPAIKKGILQTVKVVDELVKVMGRHKPENIVIEMARENTTK

GQKNSRERMKRIEEGIKELGSQILKEHPVENTQLQNEKLYLYYLQNGRDMYVDQELDIN

RLSDYDVDHIVPQSFLKDDSIDNKVLTRSDKNRGKSDNVPSEEVVKKMKNYWRQLLNA

KLITQRKFDNLTKAERGGLSELDKAGFIKRQLVETRQITKHVAQILDSRMNTKYDENDK

LIREVKVITLKSKLVSDFRKDFQFYKVREINNYHHAHDAYLNAVVGTALIKKYPKLESEF

VYGDYKVYDVRKMIAKSEEIGKATAKYFFYSNIMNFFKTEITLANGEIRKRPLIETNGET

GEIVWDKGRDFATVRKVLSMPVNIVKKTEVTGGFSKESILPKRNSDKLIARKKDWDPKK

YGGFDSPTVAYSVLVVAKVEKGKSKKLKSVKELLGITIMERSSFEKNPIDFLEAKGYKE

VKKDLIIKLPKYSLFELENGRKRMLASAGELQKGNELALPSKYVNFLYLASHYEKLKGS

PEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGD

-continued

Streptococcus pyogenes Cas9 (wild type) nucleotide sequence
(SEQ ID NO: 2)

```
ATGGATAAGAAATACTCAATAGGCTTAGATATCGGCACAAATAGCGTCGGATGGGC
GGTGATCACTGATGAATATAAGGTTCCGTCTAAAAAGTTCAAGGTTCTGGGAAATAC
AGACCGCCACAGTATCAAAAAAAATCTTATAGGGGCTCTTTTATTTGACAGTGGAGA
GACAGCGGAAGCGACTCGTCTCAAACGGACAGCTCGTAGAAGGTATACACGTCGGA
AGAATCGTATTTGTTATCTACAGGAGATTTTTTCAAATGAGATGGCGAAAGTAGATG
ATAGTTTCTTTCATCGACTTGAAGAGTCTTTTTTGGTGGAAGAAGACAAGAAGCATG
AACGTCATCCTATTTTTGGAAATATAGTAGATGAAGTTGCTTATCATGAGAAATATC
CAACTATCTATCATCTGCGAAAAAAATTGGTAGATTCTACTGATAAAGCGGATTTGC
GCTTAATCTATTTGGCCTTAGCGCATATGATTAAGTTTCGTGGTCATTTTTTGATTGA
GGGAGATTTAAATCCTGATAATAGTGATGTGGACAAACTATTTATCCAGTTGGTACA
AACCTACAATCAATTATTTGAAGAAAACCCTATTAACGCAAGTGGAGTAGATGCTA
AAGCGATTCTTTCTGCACGATTGAGTAAATCAAGACGATTAGAAAATCTCATTGCTC
AGCTCCCCGGTGAGAAGAAAAATGGCTTATTTGGGAATCTCATTGCTTTGTCATTGG
GTTTGACCCCTAATTTTAAATCAAATTTTGATTTGGCAGAAGATGCTAAATTACAGC
TTTCAAAAGATACTTACGATGATGATTTAGATAATTTATTGGCGCAAATTGGAGATC
AATATGCTGATTTGTTTTTGGCAGCTAAGAATTTATCAGATGCTATTTTACTTTCAGA
TATCCTAAGAGTAAATACTGAAATAACTAAGGCTCCCCTATCAGCTTCAATGATTAA
ACGCTACGATGAACATCATCAAGACTTGACTCTTTTAAAAGCTTTAGTTCGACAACA
ACTTCCAGAAAAGTATAAAGAAATCTTTTTTGATCAATCAAAAAACGGATATGCAG
GTTATATTGATGGGGGAGCTAGCCAAGAAGAATTTTATAAATTTATCAAACCAATTT
TAGAAAAAATGGATGGTACTGAGGAATTATTGGTGAAACTAAATCGTGAAGATTTG
CTGCGCAAGCAACGGACCTTTGACAACGGCTCTATTCCCCATCAAATTCACTTGGGT
GAGCTGCATGCTATTTTGAGAAGACAAGAAGACTTTTATCCATTTTTAAAAGACAAT
CGTGAGAAGATTGAAAAAATCTTGACTTTTCGAATTCCTTATTATGTTGGTCCATTGG
CGCGTGGCAATAGTCGTTTTGCATGGATGACTCGGAAGTCTGAAGAAACAATTACCC
CATGGAATTTTGAAGAAGTTGTCGATAAAGGTGCTTCAGCTCAATCATTTATTGAAC
GCATGACAAACTTTGATAAAAATCTTCCAAATGAAAAAGTACTACCAAAACATAGT
TTGCTTTATGAGTATTTTACGGTTTATAACGAATTGACAAAGGTCAAATATGTTACTG
AAGGAATGCGAAAACCAGCATTTCTTTCAGGTGAACAGAAGAAAGCCATTGTTGAT
TTACTCTTCAAAACAAATCGAAAAGTAACCGTTAAGCAATTAAAAGAAGATTATTTC
AAAAAAATAGAATGTTTTGATAGTGTTGAAATTTCAGGAGTTGAAGATAGATTTAAT
GCTTCATTAGGTACCTACCATGATTTGCTAAAAATTATTAAAGATAAAGATTTTTTG
GATAATGAAGAAAATGAAGATATCTTAGAGGATATTGTTTTAACATTGACCTTATTT
GAAGATAGGGAGATGATTGAGGAAAGACTTAAAACATATGCTCACCTCTTTGATGA
TAAGGTGATGAAACAGCTTAAACGTCGCCGTTATACTGGTTGGGGACGTTTGTCTCG
AAAATTGATTAATGGTATTAGGGATAAGCAATCTGGCAAAACAATATTAGATTTTTT
GAAATCAGATGGTTTTGCCAATCGCAATTTTATGCAGCTGATCCATGATGATAGTTT
GACATTTAAAGAAGACATTCAAAAAGCACAAGTGTCTGGACAAGGCGATAGTTTAC
ATGAACATATTGCAAATTTAGCTGGTAGCCCTGCTATTAAAAAAGGTATTTTACAGA
```

```
-continued
CTGTAAAAGTTGTTGATGAATTGGTCAAAGTAATGGGGCGGCATAAGCCAGAAAAT

ATCGTTATTGAAATGGCACGTGAAAATCAGACAACTCAAAAGGGCCAGAAAAATTC

GCGAGAGCGTATGAAACGAATCGAAGAAGGTATCAAAGAATTAGGAAGTCAGATTC

TTAAAGAGCATCCTGTTGAAAATACTCAATTGCAAAATGAAAAGCTCTATCTCTATT

ATCTCCAAAATGGAAGAGACATGTATGTGGACCAAGAATTAGATATTAATCGTTTAA

GTGATTATGATGTCGATCACATTGTTCCACAAAGTTTCCTTAAAGACGATTCAATAG

ACAATAAGGTCTTAACGCGTTCTGATAAAAATCGTGGTAAATCGGATAACGTTCCAA

GTGAAGAAGTAGTCAAAAAGATGAAAAACTATTGGAGACAACTTCTAAACGCCAAG

TTAATCACTCAACGTAAGTTTGATAATTTAACGAAAGCTGAACGTGGAGGTTTGAGT

GAACTTGATAAAGCTGGTTTTATCAAACGCCAATTGGTTGAAACTCGCCAAATCACT

AAGCATGTGGCACAAATTTTGGATAGTCGCATGAATACTAAATACGATGAAAATGA

TAAACTTATTCGAGAGGTTAAAGTGATTACCTTAAAATCTAAATTAGTTTCTGACTTC

CGAAAAGATTTCCAATTCTATAAAGTACGTGAGATTAACAATTACCATCATGCCCAT

GATGCGTATCTAAATGCCGTCGTTGGAACTGCTTTGATTAAGAAATATCCAAAACTT

GAATCGGAGTTTGTCTATGGTGATTATAAAGTTTATGATGTTCGTAAAATGATTGCT

AAGTCTGAGCAAGAAATAGGCAAAGCAACCGCAAAATATTTCTTTTACTCTAATATC

ATGAACTTCTTCAAAACAGAAATTACACTTGCAAATGGAGAGATTCGCAAACGCCCT

CTAATCGAAACTAATGGGGAAACTGGAGAAATTGTCTGGGATAAAGGGCGAGATTT

TGCCACAGTGCGCAAAGTATTGTCCATGCCCCAAGTCAATATTGTCAAGAAAACAG

AAGTACAGACAGGCGGATTCTCCAAGGAGTCAATTTTACCAAAAAGAAATTCGGAC

AAGCTTATTGCTCGTAAAAAAGACTGGGATCCAAAAAAATATGGTGGTTTTGATAGT

CCAACGGTAGCTTATTCAGTCCTAGTGGTTGCTAAGGTGGAAAAAGGGAAATCGAA

GAAGTTAAAATCCGTTAAAGAGTTACTAGGGATCACAATTATGGAAAGAAGTTCCTT

TGAAAAAAATCCGATTGACTTTTTAGAAGCTAAAGGATATAAGGAAGTTAAAAAAG

ACTTAATCATTAAACTACCTAAATATAGTCTTTTTGAGTTAGAAAACGGTCGTAAAC

GGATGCTGGCTAGTGCCGGAGAATTACAAAAAGGAAATGAGCTGGCTCTGCCAAGC

AAATATGTGAATTTTTTATATTTAGCTAGTCATTATGAAAAGTTGAAGGGTAGTCCA

GAAGATAACGAACAAAAACAATTGTTTGTGGAGCAGCATAAGCATTATTTAGATGA

GATTATTGAGCAAATCAGTGAATTTTCTAAGCGTGTTATTTTAGCAGATGCCAATTT

AGATAAAGTTCTTAGTGCATATAACAAACATAGAGACAAACCAATACGTGAACAAG

CAGAAAATATTATTCATTTATTTACGTTGACGAATCTTGGAGCTCCCGCTGCTTTTAA

ATATTTTGATACAACAATTGATCGTAAACGATATACGTCTACAAAAGAAGTTTTAGA

TGCCACTCTTATCCATCAATCCATCACTGGTCTTTATGAAACACGCATTGATTTGAGT

CAGCTAGGAGGTGACTGA
```

Non-limiting exemplary species that the Cas9 protein or other components may be derived from include Streptococcus pyogenes, Streptococcus thermophilus, Streptococcus sp., Staphylococcus aureus, Listeria innocua, Lactobacillus gasseri, Francisella novicida, Wolinella succinogenes, Sutterella wadsworthensis, Gamma proteobacterium, Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Lactobacillus buchneri, Treponema denticola, Microscilla marina, Burkholderiales bacterium, Polaromonas naphthalenivorans, Polaromonas sp., Crocosphaera watsonii, Cyanothece sp., Microcystis aeruginosa, Synechococcus sp., Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum

*thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Streptococcus pasteurianus, Neisseria cinerea, Campylobacter lari, Parvibaculum lavamentivorans, Corynebacterium diphtheria*, or *Acaryochloris marina*. In some embodiments, the Cas9 protein may be from *Streptococcus pyogenes*. In some embodiments, the Cas9 protein may be derived from *Streptococcus thermophilus*. In some embodiments, the Cas9 protein may be derived from *Neisseria meningitidis*. In some embodiments, the Cas9 protein may be derived from *Staphylococcus aureus*.

In some embodiments, a Cas protein may comprise more than one nuclease domain. For example, a Cas9 protein may comprise at least one RuvC-like nuclease domain (e.g. Cpf1/Cas12a) and at least one HNH-like nuclease domain (e.g. Cas9). In some embodiments, the Cas9 protein may be capable of introducing a DSB in the target sequence. In some embodiments, the Cas9 protein may be modified to contain only one functional nuclease domain. For example, the Cas9 protein may be modified such that one of the nuclease domains is mutated or fully or partially deleted to reduce its nucleic acid cleavage activity. In some embodiments, the Cas9 protein may be modified to contain no functional RuvC-like nuclease domain. In other embodiments, the Cas9 protein may be modified to contain no functional HNH-like nuclease domain. In some embodiments in which only one of the nuclease domains is functional, the Cas9 protein may be a nickase that is capable of introducing a single-stranded break (a "nick") into the target sequence. In some embodiments, a conserved amino acid within a Cas9 protein nuclease domain is substituted to reduce or alter a nuclease activity. In some embodiments, the Cas protein nickase may comprise an amino acid substitution in the RuvC-like nuclease domain. Exemplary amino acid substitutions in the RuvC-like nuclease domain include D10A (based on the *S. pyogenes* Cas9 protein). In some embodiments, the nickase may comprise an amino acid substitution in the HNH-like nuclease domain. Exemplary amino acid substitutions in the HNH-like nuclease domain include E762A, H840A, N863A, H983A, and D986A (based on the *S. pyogenes* Cas9 protein). In some embodiments, the nuclease system described herein may comprise a nickase and a pair of guide RNAs that are complementary to the sense and antisense strands of the target sequence, respectively. The guide RNAs may direct the nickase to target and introduce a DSB by generating a nick on opposite strands of the target sequence (i.e., double nicking). Chimeric Cas9 proteins may also be used, where one domain or region of the protein is replaced by a portion of a different protein. For example, a Cas9 nuclease domain may be replaced with a domain from a different nuclease such as Fok1. A Cas9 protein may be a modified nuclease.

Wild type Cas9 and Cas9 sequences from various species may be aligned to determine corresponding homologous amino acid residues and determine and/or modify amino acid residues at, for example, D10 and H840 of SEQ ID NO: 1, allowing the generation of Cas9 variants with corresponding mutations of the homologous amino acid residues. The alignment method is known to those skilled in the art. For example, an alignment may be carried out using the NCBI Constraint-based Multiple Alignment Tool (COBALT, accessible at st-va.ncbi.nlm.nih.gov/tools/cobalt).

In alternative embodiments, the Cas protein may be from a Type-I CRISPR/Cas system. In some embodiments, the Cas protein may be a component of the Cascade complex of a Type-I CRISPR/Cas system. For example, the Cas protein may be a Cas3 protein. In some embodiments, the Cas protein may be from a Type-III CRISPR/Cas system. In some embodiments, the Cas protein may be from a Type-IV CRISPR/Cas system. In some embodiments, the Cas protein may be from a Type-V CRISPR/Cas system. In some embodiments, the Cas protein may be from a Type-VI CRISPR/Cas system. In some embodiments, the Cas protein may have an RNA cleavage activity.

Fusion Proteins

Provided herein are compositions and methods of targeted modification of genes, e.g. PCSK9, ANGPTL3, APOC3, LPA, APOB, MTP, ANGPTL4, ANGPTL8, APOA5, APOE, LDLR, IDOL, NPC1L1, ASGR1, TM6SF2, GALNT2, GCKR, LPL, MLXIPL, SORT1, TRIB1, MARC1, ABCG5, or ABCG8. In certain instances, the modification may be ex vivo or in vivo. In preferred embodiments, the targeted modification may be directed to a particular type of organ, tissue, or cells, for example, liver hepatocytes. In some embodiments, the target gene is modified genetically with a genome editing composition comprising a fusion protein. Accordingly, in some embodiments, provided herein are fusion proteins for targeted modification of genes. In some embodiments, the fusion protein comprises a target specific nuclease domain. In some embodiments, the fusion protein comprises a nucleic acid guided programmable nuclease domain. In some embodiments, the nucleic acid guided programmable nuclease may comprise at least one DNA binding domain and at least one nuclease domain. In some embodiments, the nuclease domain may be heterologous to the DNA binding domain. In some embodiments, the nuclease domain may be modified such that the nuclease domain is mutated to reduce its nuclease cleavage activity. In some embodiments, the nuclease activity is completely abolished. In some embodiments, the nuclease activity is partially reduced. In some embodiments, the modified nuclease domain may comprise a modified Cas protein domain. In certain embodiments, the modified Cas protein domain is a modified Cas9. In some embodiments, the modified Cas9 domain is a nuclease inactive Cas9 (dCas9) domain. In some embodiments, the modified dCas9 domain is a nickase domain. In some embodiments, the modified Cas9 domain contains at least one substitutions selected from D10A, N497A, R661A, Q695A, E762A, H840A, N863A, Q926A, H983A and D986A based on the *S. pyogenes* Cas9 protein. In some embodiments, the modified nuclease domain is a catalytically inactive Cpf1 domain, a catalytically inactive Cas13a domain, a catalytically inactive Cas13b domain, or a catalytically in active Cas 13c domain. In some embodiments, the modified nuclease domain is a catalytically inactive CasX, CasY, Cpf1, C2c1, C2c2, C2c3, and Argonaute protein domain.

In some embodiments, a fusion protein as described herein comprises one or more functional domains besides the nuclease domain. At least one protein domain may be located at the N-terminus, the C-terminus, or in an internal location of the fusion protein. In some embodiments, two or more heterologous protein domains are at one or more locations on the fusion protein. Non-limiting examples of functional domains include a repressor domain, an activator domain, a methyltransferase domain, a de-methylase domain. In some embodiments, the functional domain comprises a base-editing enzyme domain. In some embodiments, the functional domain is a cytidine deaminase domain. For example, the cytidine deaminase may deaminate a specific cytidine to uracil, resulting in a U-G mismatch which is subsequently resolved via cellular repair mechanisms to form a U-A base pair, and subsequently a T-A base pair, thereby creating a C-to-T substitution. Cytidine deaminase domain and cytidine-deaminase fusion protein sequences are known to those skilled in the art, as described in Komor et al., Science Advances 2017, 3(8): eaao4774; Komor et al., Nature 2016, 533: 420-424. In some embodiments, the functional domain is an adenine deaminase domain. For example, the adenine deaminase domain may deaminate an adenosine to generate inosine, which can base pair with cytidine and subsequently be corrected by the cellular repair mechanisms to guanine, thereby converting A into G. Exemplary adenosine deaminase fusion proteins as described in Gaudelli et al., Nature 2017 551(7681): 464-471, the entirety of which is incorporated herein by reference.

In some embodiments, a fusion protein as described herein comprises a nuclear localization signal (NLS). In some embodiments, the fusion protein may comprise 2, 3, 4, or 5 NLSs. In some embodiments, the fusion protein may comprise 1-10 NLS(s). The NLS sequence may be fused at the N terminus and/or the C terminus of the fusion protein. In some embodiments, the NLS may be a monopartite sequence, such as, e.g., the SV40 NLS, PKKKRKV (SEQ ID NO: 3) or PKKKRRV (SEQ ID NO:4). In some embodiments, the NLS may be a bipartite sequence, such as, e.g., the NLS of nucleoplasmin, KRPAATKKAGQAKKKK (SEQ ID NO:5). In some embodiments, the NLS may be genetically modified from its wild-type counterpart. In a preferred embodiment, the fusion protein comprises the sequence of ABE7.10 (SEQ ID NO: 6).

In some embodiments, the fusion protein can further comprise a tag domain. In some embodiments, the tag domain may comprise a fluorescent tag, a purification tag, an epitope tags, or a reporter gene tag. In some embodiments, the tag domain may comprise a fluorescent protein domain. Non-limiting examples of suitable fluorescent proteins include green fluorescent proteins (e.g., GFP, GFP-2, tagGFP, turboGFP, sfGFP, EGFP, Emerald, Azami Green, Monomeric Azami Green, CopGFP, AceGFP, ZsGreenl), yellow fluorescent proteins (e.g., YFP, EYFP, Citrine, Venus, YPet, PhiYFP, ZsYellowl), blue fluorescent proteins (e.g., EBFP, EBFP2, Azurite, mKalamal, GFPuv, Sapphire, T-sapphire), cyan fluorescent proteins (e.g., ECFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRasberry, mStrawberry, Jred), and orange fluorescent proteins (mOrange, mKO, Kusabira-Orange, Monomeric Kusabira-Orange, mTangerine, tdTomato) or any other suitable fluorescent protein. In some embodiments, the tag domain may comprise a purification tag and/or an epitope tag. Non-limiting exemplary tags include glutathione-S-transferase (GST), chitin binding protein (CBP), maltose binding protein (MBP), thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His (SEQ ID NO: 114), biotin carboxyl carrier protein (BCCP), and calmodulin. In some embodiments, the tag domain may comprise a reporter gene domain. Non-limiting exemplary reporter genes include glutathione-S-transferase (GST), horseradish peroxidase (HRP), chloramphenicol acetyltransferase (CAT), beta-galactosidase, beta-glucuronidase, luciferase, or fluorescent proteins.

In additional embodiments, the nuclease in the nuclease systems may comprise one or more programmable nucleases other than a Cas protein. For example, the nuclease may be chosen from a meganuclease (e.g., homing endonucleases), ZFN, TALEN, and megaTAL.

Naturally-occurring meganucleases may recognize and cleave double-stranded DNA sequences of about 12 to 40 base pairs, and are commonly grouped into five families. In some embodiments, the meganuclease may be chosen from the LAGLIDADG family, the GIY-YIG family, the HNH family, the His-Cys box family, and the PD-(D/E)XK family. In some embodiments, the DNA binding domain of the meganuclease may be engineered to recognize and bind to a sequence other than its cognate target sequence. In some embodiments, the DNA binding domain of the meganuclease may be fused to a heterologous nuclease domain. In some embodiments, the meganuclease, such as a homing endonuclease, may be fused to TAL modules to create a hybrid protein, such as a "megaTAL" protein. The megaTAL protein may have improved DNA targeting specificity by recognizing the target sequences of both the DNA binding domain of the meganuclease and the TAL modules.

ZFNs are fusion proteins comprising a zinc-finger DNA binding domain ("zinc fingers" or "ZFs") and a nuclease domain. Each naturally-occurring ZF may bind to three consecutive base pairs (a DNA triplet), and ZF repeats are combined to recognize a DNA target sequence and provide sufficient affinity. Thus, engineered ZF repeats may be combined to recognize longer DNA sequences, such as, e.g., 9-, 12-, 15-, or 18-bp, etc. In some embodiments, the ZFN may comprise ZFs fused to a nuclease domain from a restriction endonuclease. For example, the restriction endonuclease may be FokI. In some embodiments, the nuclease domain may comprise a dimerization domain, such as when the nuclease dimerizes to be active, and a pair of ZFNs comprising the ZF repeats and the nuclease domain may be designed for targeting a target sequence, which comprises two half target sequences recognized by each ZF repeats on opposite strands of the DNA molecule, with an interconnecting sequence in between (which is sometimes called a spacer in the literature). For example, the interconnecting sequence may be 5 to 7 bp in length. When both ZFNs of the pair bind, the nuclease domain may dimerize and introduce a DSB within the interconnecting sequence. In some embodiments, the dimerization domain of the nuclease domain may comprise a knob-into-hole motif to promote dimerization. For example, the ZFN may comprise a knob-into-hole motif in the dimerization domain of FokI.

The DNA binding domain of TALENs usually comprises a variable number of 34 or 35 amino acid repeats ("modules" or "TAL modules"), with each module binding to a single DNA base pair, A, T, G, or C. Adjacent residues at positions 12 and 13 (the "repeat-variable di-residue" or RVD) of each module specify the single DNA base pair that the module binds to. Though modules used to recognize G may also have affinity for A, TALENs benefit from a simple code of recognition-one module for each of the 4 bases-which greatly simplifies the customization of a DNA-binding domain recognizing a specific target sequence. In some embodiments, the TALEN may comprise a nuclease domain from a restriction endonuclease. For example, the restriction endonuclease may be FokI. In some embodiments, the nuclease domain may dimerize to be active, and a pair of TALENS may be designed for targeting a target sequence, which comprises two half target sequences recognized by each DNA binding domain on opposite strands of the DNA molecule, with an interconnecting sequence in between. For example, each half target sequence may be in the range of 10 to 20 bp, and the interconnecting sequence may be 12 to 19 bp in length. When both TALENs of the pair bind, the nuclease domain may dimerize and introduce a DSB within the interconnecting sequence. In some embodiments, the dimerization domain of the nuclease domain may comprise a knob-into-hole motif to promote dimerization. For example, the TALEN may comprise a knob-into-hole motif in the dimerization domain of FokI.

Certain embodiments of the disclosure also provide nucleic acids encoding the nuclease system described herein provided on a vector. In some embodiments, the nucleic acid may be a DNA molecule. In other embodiments, the nucleic acid may be an RNA molecule. In some embodiments, the nucleic acid encoding the nuclease may be an mRNA molecule.

In some embodiments, the nucleic acid encoding the nuclease may be codon optimized for efficient expression in one or more eukaryotic cell types. In some embodiments, the nucleic acid encoding the nuclease may be codon optimized for efficient expression in one or more mammalian cells. In some embodiments, the nucleic acid encoding the nuclease may be codon optimized for efficient expression in human cells. Methods of codon optimization including codon usage tables and codon optimization algorithms are available in the art.

Guide Polynucleotides

In some embodiments of the present disclosure, a CRISPR/Cas nuclease system includes at least one guide polynucleotide, for example, a guide RNA. In some embodiments, the guide RNA and the Cas protein may form a ribonucleoprotein (RNP), e.g., a CRISPR/Cas complex. The guide RNA may guide the Cas protein to a target sequence on a target nucleic acid molecule, where the guide RNA hybridizes with and the Cas protein cleaves the target sequence. In some embodiments, the CRISPR/Cas complex may be a Cpf1/guide RNA complex. In some embodiments, the CRISPR complex may be a Type-II CRISPR/Cas9 complex. In some embodiments, the Cas protein may be a Cas9 protein. In some embodiments, the CRISPR/Cas9 complex may be a Cas9/guide RNA complex.

A guide nucleic acid (e.g., guide RNA) can bind to a Cas protein and target the Cas protein to a specific location within a target polynucleotide. A guide nucleic acid can comprise a nucleic acid-targeting segment and a Cas protein binding segment.

A guide nucleic acid can refer to a nucleic acid that can hybridize to another nucleic acid, for example, the target polynucleotide in the genome of a cell. A guide nucleic acid can be RNA, for example, a guide RNA. A guide nucleic acid can be DNA. A guide nucleic acid can comprise DNA and RNA. A guide nucleic acid can be single stranded. A guide nucleic acid can be double-stranded. A guide nucleic acid can comprise a nucleotide analog. A guide nucleic acid can comprise a modified nucleotide. The guide nucleic acid can be programmed or designed to bind to a sequence of nucleic acid site-specifically.

A guide nucleic acid can comprise one or more modifications to provide the nucleic acid with a new or enhanced feature. A guide nucleic acid can comprise a nucleic acid affinity tag. A guide nucleic acid can comprise synthetic nucleotide, synthetic nucleotide analog, nucleotide derivatives, and/or modified nucleotides.

The guide nucleic acid can comprise a nucleic acid-targeting region (e.g., a spacer region), for example, at or near the 5' end or 3' end, that is complementary to a protospacer sequence in a target polynucleotide. The spacer of a guide nucleic acid can interact with a protospacer in a sequence-specific manner via hybridization (base pairing). The protospacer sequence can be located 5' or 3' of protospacer adjacent motif (PAM) in the target polynucleotide. The nucleotide sequence of a spacer region can vary and determines the location within the target nucleic acid with which the guide nucleic acid can interact. The spacer region of a guide nucleic acid can be designed or modified to hybridize to any desired sequence within a target nucleic acid.

A guide nucleic acid can comprise two separate nucleic acid molecules, which can be referred to as a double guide nucleic acid. A guide nucleic acid can comprise a single nucleic acid molecule, which can be referred to as a single guide nucleic acid (e.g., sgRNA). In some embodiments, the guide nucleic acid is a single guide nucleic acid comprising a fused CRISPR RNA (crRNA) and a transactivating crRNA (tracrRNA). In some embodiments, the guide nucleic acid is a single guide nucleic acid comprising a crRNA. In some embodiments, the guide nucleic acid is a single guide nucleic acid comprising a crRNA but lacking a tracRNA. In some embodiments, the guide nucleic acid is a double guide nucleic acid comprising non-fused crRNA and tracrRNA. An exemplary double guide nucleic acid can comprise a crRNA-like molecule and a tracrRNA-like molecule. An exemplary single guide nucleic acid can comprise a crRNA-like molecule. An exemplary single guide nucleic acid can comprise a fused crRNA-like and tracrRNA-like molecules.

A crRNA can comprise the nucleic acid-targeting segment (e.g., spacer region) of the guide nucleic acid and a stretch of nucleotides that can form one half of a double-stranded duplex of the Cas protein-binding segment of the guide nucleic acid.

A tracrRNA can comprise a stretch of nucleotides that forms the other half of the double-stranded duplex of the Cas protein-binding segment of the gRNA. A stretch of nucleotides of a crRNA can be complementary to and hybridize with a stretch of nucleotides of a tracrRNA to form the double-stranded duplex of the Cas protein-binding domain of the guide nucleic acid.

The crRNA and tracrRNA can hybridize to form a guide nucleic acid. The crRNA can also provide a single-stranded nucleic acid targeting segment (e.g., a spacer region) that hybridizes to a target nucleic acid recognition sequence (e.g., protospacer). The sequence of a crRNA, including spacer region, or tracrRNA molecule can be designed to be specific to the species in which the guide nucleic acid is to be used.

A guide RNA for a CRISPR/Cas9 system typically comprises a CRISPR RNA (crRNA) and a tracr RNA (tracr). A guide RNA for a CRISPR/Cpf1 system typically comprises a crRNA. In some embodiments, the crRNA may comprise a targeting sequence that is complementary to and hybridizes with the target sequence on the target nucleic acid molecule. The crRNA may also comprise a sequence that is complementary to and hybridizes with a portion of the tracrRNA. In some embodiments, the crRNA may parallel the structure of a naturally occurring crRNA transcribed from a CRISPR locus of a bacteria, where the targeting sequence acts as the spacer of the CRISPR/Cas9 system.

The guide RNA may target any sequence of interest via the targeting sequence of the crRNA. In some embodiments, the degree of complementarity between the targeting sequence of the guide RNA and the target sequence on the target nucleic acid molecule may be about 60%, 65%, 70%, 75%, 80%, 85%, 90%, 95%, 97%, 98%, 99%, or 100%. In some embodiments, the targeting sequence of the guide RNA and the target sequence on the target nucleic acid molecule may be 100% complementary. In other embodiments, the targeting sequence of the guide RNA and the target sequence on the target nucleic acid molecule may contain at least one mismatch. For example, the targeting sequence of the guide RNA and the target sequence on the target nucleic acid molecule may contain 1, 2, 3, 4, 5, 6, 7, 8, 9, or 10 mismatches. In some embodiments, the targeting sequence of the guide RNA and the target sequence on the target nucleic acid molecule may contain 1-6 mismatches. In some embodiments, the targeting sequence of the guide RNA and the target sequence on the target nucleic acid molecule may contain 5 or 6 mismatches.

The length of the targeting sequence may depend on the CRISPR/Cas9 system and components used. For example, different Cas9 proteins from different bacterial species have varying optimal targeting sequence lengths. Accordingly, the targeting sequence may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the targeting sequence may comprise 18-30 nucleotides in length. In some embodiments, the targeting sequence may comprise 19-24 nucleotides in length. In some embodiments, the targeting sequence may comprise 20 nucleotides in length.

The crRNA and the tracr may comprise any sequence with sufficient complementarity to promote the formation of a functional CRISPR/Cas9 complex. In some embodiments, the complementary sequence between the crRNA and the tracr may comprise all or a portion of the sequence (also called a "tag" or "handle") of a naturally-occurring crRNA that is complementary to the tracr RNA in the same CRISPR/Cas9 system. In some embodiments, the complementary sequence may comprise all or a portion of a repeat sequence from a naturally-occurring CRISPR/Cas9 system. In some embodiments, the complementary sequence may comprise a truncated or modified tag or handle sequence. In some embodiments, the degree of complementarity between the tracr RNA and the portion of the complementary portion that hybridizes with the tracr RNA along the length of the shorter of the two sequences may be about 40%, 50%, 60%, 70%, 80%, or higher, but lower than 100%. In some embodiments, the tracr RNA and the portion that hybridizes with the tracr RNA are not 100% complementary along the length of the shorter of the two sequences because of the presence of one or more bulge structures on the tracr and/or wobble base pairing. The length of the tracr RNA complementary portion to tracr may depend on the CRISPR/Cas9 system or the tracr RNA used. For example, the complementary portion may comprise 10-50 nucleotides, or more than 50 nucleotides in length. In some embodiments, the complementary portion may comprise 15-40 nucleotides in length. In other embodiments, the complementary portion may comprise 20-30 nucleotides in length. In yet other embodiments, the complementary portion may comprise 22 nucleotides in length. When a dual guide RNA is used, for example, the length of the complementary portion may have no upper limit.

In some embodiments, the tracr RNA may comprise all or a portion of a wild-type tracr RNA sequence from a naturally-occurring CRISPR/Cas9 system. In some embodiments, the tracr RNA may comprise a truncated or modified variant of the wild-type tracr RNA. The length of the tracr RNA may depend on the CRISPR/Cas9 system used. In some embodiments, the tracr RNA may comprise 5, 6, 7, 8, 9, 10, 11, 12, 13, 14, 15, 16, 17, 18, 19, 20, 25, 30, 40, 50, 60, 70, 80, 90, 100, or more than 100 nucleotides in length. In certain embodiments, the tracr is at least 26 nucleotides in length. In additional embodiments, the tracr is at least 40 nucleotides in length. In some embodiments, the tracr RNA may comprise certain secondary structures, such as, e.g., one or more hairpins or stem-loop structures, or one or more bulge structures.

In some embodiments, the guide RNA may comprise two RNA molecules and is referred to herein as a "dual guide RNA" or "dgRNA". In some embodiments, the dgRNA may comprise a first RNA molecule comprising a crRNA, and a second RNA molecule comprising a tracr RNA. The first and second RNA molecules may form a RNA duplex via the base pairing between the flagpole on the crRNA and the tracr RNA.

In some embodiments, the guide RNA may comprise a single RNA molecule and is referred to herein as a "single guide RNA" or "sgRNA". In some embodiments, the sgRNA may comprise a crRNA covalently linked to a tracr RNA. In some embodiments, the crRNA and the tracr RNA may be covalently linked via a linker. In some embodiments, the single-molecule guide RNA may comprise a stem-loop structure via the base pairing between the flagpole on the crRNA and the tracr RNA.

Certain embodiments of the disclosure also provide nucleic acids, e.g., vectors, encoding the guide RNA described herein. In some embodiments, the nucleic acid may be a DNA molecule. In other embodiments, the nucleic acid may be an RNA molecule. In some embodiments, the nucleic acid may comprise a nucleotide sequence encoding a crRNA. In some embodiments, the nucleotide sequence encoding the crRNA comprises a targeting sequence flanked by all or a portion of a repeat sequence from a naturally-occurring CRISPR/Cas system. In some embodiments, the nucleic acid may comprise a nucleotide sequence encoding a tracr RNA. In some embodiments, the crRNA and the tracr RNA may be encoded by two separate nucleic acids. In some embodiments, the crRNA and the tracr RNA may be encoded by a single nucleic acid. In some embodiments, the crRNA and the tracr RNA may be encoded by opposite strands of a single nucleic acid. In other embodiments, the crRNA and the tracr RNA may be encoded by the same strand of a single nucleic acid.

In certain embodiments, more than one guide RNA can be used with a CRISPR/Cas nuclease system. Each guide RNA may contain a different targeting sequence, such that the CRISPR/Cas system cleaves more than one target sequence. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA may be the same or different.

The methods of selecting guide RNAs for efficient targeting with high specificity and low off-target effect are known to those skilled in the art. For programmable base-editing, [selection of a genomic sequence containing a target sequence may be as described in Komor et al, Nature, 533, 420-424 (2016) is incorporated herein by reference. The guide RNA sequence and PAM preference define the genomic target sequence(s) of programmable nuclease domains (e.g. Cas9, dCas9, Cas9n, Cpf1, NgAgo domains). Methods of reducing off-target binding as described in Hsu et al (Nature biotechnology, 2013, 31(9):827-832), Fusi et al (bioRxiv 021568; doi: http://dx.doi.org/10.1101/021568), Chari et al (Nature Methods, 2015, 12(9):823-6), Doench et al (Nature Biotechnology, 2014, 32(12): 1262-7), Wang et al (Science, 2014, 343(6166): 80-4), Moreno-Mateos et al (Nature Methods, 2015, 12(10):982-8), Housden et al (Science Signaling, 2015, 8(393):rs9), Haeussler et al, (Genome Biol. 2016; 17: 148) are incorporated herein by reference. The potential for the formation of bulges between the guide RNA and the target DNA and other parameters that may influence target sequence binding may also be considered as described in Bae et al (Bioinformatics, 2014, 30, 1473-5) Housden et al (Science Signaling, 2015, 8(393):rs9), and Farboud et al (Genetics, 2015, 199(4):959-71) are also incorporated herein by reference.

RNA Modification

Provided herein are modified RNA molecules suitable for targeted ex vivo and in vivo delivery systems. A modified RNA molecule may comprise two or more linked ribonucleic acid subunits. Non-limiting exemplary modified RNAs include CRISPR guide RNA, short interfering RNA (siRNA), microRNA (miRNA), short hairpin RNA (shRNA), small nuclear RNA (snRNA), messenger RNA (mRNA), precursor mRNA (pre-mRNA), antisense RNA (asRNA), and heteronuclear RNA (hnRNA). Modified RNAs as described herein encompass both the RNA sequence and any structural embodiment thereof, e.g. single stranded, double stranded, triple stranded, circular, helical, hairpin, stem loop, buldge, etc. A modified RNA may comprise a length of at least about 3, 4, 5, 6, 7, 8, 9, 10, 20, 30, 40, 50, 100, 200, 300, 400, or 500 bases. A modified RNA may comprise a length of at least about 1 kilobase (kb), 2 kb, 3 kb, 4 kb, 5 kb, 10 kb, 20 kb, 50 kb, or more. In some embodiments, the modified RNA is a CRISPR guide RNA (gRNA). A gRNA may be a single guide RNA or a dual guide RNA. In some embodiments, the modified RNA is a mRNA. In some embodiments, a mRNA can be isolated from a cell or a tissue. In some embodiments, a mRNA can be transcribed from a DNA. In some embodiments, a mRNA can be chemically synthesized.

In certain embodiments, modified RNA molecules provided herein are resistant to degradation by RNases or other exonucleases. In certain embodiments, modified RNA molecules provided herein are stabilized to prevent degradation by endonucleases. In some embodiments, modified RNA molecules provided herein are suitable for in vivo delivery and induces less cellular immune receptor activation (e.g. TLR, RIG-I) as compared to unmodified RNA. RNA modifications as described in Diebold (2008) Adv Drug Deliv Rev. April 29; 60(7):813-23) and Sorrentino (1998) Cell Mol Life Sci. August; 54(8):785-94, the entirety of both are incorporated herein by reference.

In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable with the compounds described herein. The unmodified or natural nucleobases can be modified or replaced to provide oligonucleotides having improved properties. For example, nuclease resistant oligonucleotides can be prepared with these bases or with synthetic and natural nucleobases (e.g., inosine, xanthine, hypoxanthine, nubularine, isoguanisine, or tubercidine) and any one of the oligomer modifications described herein. Alternatively, substituted or modified analogs of any of the above bases and "universal bases" can be employed. When a natural base is replaced by a non-natural and/or universal base, the nucleotide is said to comprise a modified nucleobase and/or a nucleobase modification herein. Modified nucleobase and/or nucleobase modifications also include natural, non-natural and universal bases, which comprise conjugated moieties, e.g. a ligand described herein. Preferred conjugate moieties for conjugation with nucleobases include cationic amino groups which can be conjugated to the nucleobase via an appropriate alkyl, alkenyl or a linker with an amide linkage.

As used herein, "unmodified" or "natural" nucleobases include the purine bases adenine (A) and guanine (G), and the pyrimidine bases thymine (T), cytosine (C) and uracil (U). Exemplary modified nucleobases include, but are not limited to, other synthetic and natural nucleobases such as inosine, xanthine, hypoxanthine, nubularine, isoguanisine, tubercidine, 2-(halo)adenine, 2-(alkyl)adenine, 2-(propyl)adenine, 2-(amino)adenine, 2-(aminoalkyll)adenine, 2-(aminopropyl)adenine, 2-(methylthio)-N6-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, N6-(isopentyl)adenine, N6-(methyl)adenine, N6,N6-(dimethyl)adenine, 2-(alkyl)guanine, 2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, N4-(acetyl)cytosine, 3-(3-amino-3-carboxypropyl)uracil, 2-(thio)uracil, 5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl)uracil, 5-(guanidiniumalkyl)uracil, 5-(1,3-diazole-1-alkyl)uracil, 5-(cyanoalkyl)uracil, 5-(dialkylaminoalkyl)uracil, 5-(dimethylaminoalkyl)uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil,N-(methyl)uracil, 5-uracil (i.e., pseudouracil), 2-(thio)pseudouracil,4-(thio)pseudouracil,2,4-(dithio)psuedouracil,5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio)pseudouracil, 5-(methyl)-2,4-(dithio)pseudouracil, 1-methylpseudouracil (N1-methylpseudouracil), 1-substituted pseudouracil, 1-substituted 2-(thio)-pseudouracil, 1-substituted 4-(thio)pseudouracil, 1-substituted 2,4-(dithio) pseudouracil, 1-(aminocarbonylethylenyl)-pseudouracil, 1-(aminocarbonylethylenyl)-2-(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylaminocarbonylethylenyl)-2-(thio)-pseudouracil, 1-(aminoalkylaminocarbonylethylenyl)-4-(thio)pseudouracil, 1-(aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted-1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, N2-substituted purines, N6-substituted purines, 06-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ori/zo-substituted-6-phenyl-pyrrolo-pyrimidin-2-on-3-yl, bis-ori/zo-substituted-6-phenyl-pyrrolo-pyrimidin-2-on-3-yl, para-(aminoalkylhy droxy)-6-phenyl-pyrrolo-pyrimidin-2-on-3-yl, ori/zo-(aminoalkylhydroxy)-6-phenyl-pyrrolo-pyrimidin-2-on-3-yl, bis-ori/zo-(aminoalkylhy droxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Alternatively, substituted or modified analogs of any of the above bases and "universal bases" can be employed. A universal nucleobase is any nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, 4-fluoro-6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4, 5-trimethylphenyl, 4-methylinolyl, 4,6-dimethylindolyl, phenyl, napthalenyl, anthracenyl, phenanthracenyl, pyrenyl, stilbenyl, tetracenyl, pentacenyl, and structural derivatives thereof (see for example, Loakes, 2001, Nucleic Acids Research, 29, 2437-2447, incorporated herein by reference in its entirety). Further nucleobases include those disclosed in U.S. Pat. No. 3,687,808; those disclosed in International Application No. PCT U.S. Ser. No. 09/038,425, filed Mar. 26, 2009; those disclosed in the Concise Encyclopedia Of Polymer Science And Engineering, pages 858-859, Kroschwitz, J. I, ed. John Wiley & Sons, 1990; those disclosed by English et al, Angewandte Chemie, International Edition, 1991, 30, 613; those disclosed in Modified Nucleosides in Biochemistry, Biotechnology and Medicine, Herdewijin, P. Ed. Wiley-VCH, 2008; and those disclosed by Sanghvi, Y. S., Chapter 15, dsRNA Research and Applications, pages 289-302, Crooke, S. T. and Lebleu, B., Eds., CRC Press, 1993. Contents of all of the above are herein incorporated by reference.

In some embodiments, modified RNAs as described herein are modified to attach a delivery and/or targeting moiety such as GalNAc. Suitably, GalNAc can be attached to the 3'-end, 5'-end of the RNA, or both. In some embodiments, GalNAc is attached to the 3'-end. In some embodiments, the modified RNAs show improvements relative to their unmodified equivalents. Such improvements can relate to improved specificity (such that, for example, off-target effects are reduced or a lower concentration of gRNA is required), improved stability (e.g. resistance to enzymes such as nucleases), improved functionality or decreased immunogenicity or immunostimulatory properties. In some embodiments, the modified RNAs show efficient transfection into cells and/or improved properties allowing it to be delivered and maintained in an organism, tissue, body fluid or cell such that the RNA, e.g. a guide RNA, functionality can take place. Methods for measuring these improved properties compared to their unmodified equivalents are known to those skilled in the art and include those methods described herein. Accordingly in some embodiments, provided herein is a modified RNA that has increased stability compared to the unmodified equivalent. By un-modified equivalent is meant a RNA, e.g. a guide RNA which targets the same specific gene sequence and interacts with the same Cas9 or CRISPR nuclease and comprises natural nucleotides. Increased stability includes increased stability or resistance to enzymes such as nucleases which may be present in cells, tissues or body fluids and which may otherwise contribute to degradation of the RNA such that is has decreased functionality. In certain embodiments, increased stability includes increased serum stability. In some embodiments, provided herein is a modified guide RNA that has increased CRISPR activity compared to the un-modified equivalent. Methods for measuring CRISPR activity are described herein. In some embodiments, provided herein is a modified guide RNA that has decreased immunostimulatory activity compared to the un-modified equivalent. Methods for measuring immunostimulation are described herein.

Provided herein are modified mRNA molecules for targeted delivery. For example, a mRNA that encodes a CRISPR enzyme, e.g. a Cas9, Cas12b, or a base editor (BE) may be modified for specific tissue targeting. The mRNA may be modified at least one nucleotide at the 2' position and/or backbone modification. In some embodiments, the nucleotides in a mRNA can include modification of the thioates. In some embodiments, a mRNA can include modification of one or more of 2'-OMe, 2'-F, N-1-methyl-psuedouridine, 5-methyluridine 5-methoxyuridine, and 5-ethoxyuridine.

In certain embodiments, mRNA sequences provided herein comprise a fully modified or partially modified mRNA. In some embodiments, a mRNA comprises chemical modifications in a fragment, or multiple fragments of the entire length. Non-limiting exemplary modifications and modification patterns of the nucleotides of a mRNA, or segments thereof, are shown in Table 2 and Table 3.

Provided herein are modified guide RNAs for use with CRISPR/Cas system where the guide RNA may be modified by a chemical modification of at least one nucleotide at the 2' position and/or backbone modification. The backbone modification can include modification of the thioates. In certain embodiments, the nucleotides that are modified are selected from a group of nucleotides which interact with the Cas amino acids in the Cas protein to effect binding of the guide RNA to Cas. In certain embodiments, the modification can comprise that the 2'-OH on the nucleotide is replaced with at least one of H, —OR, —R, —O—$C_1$-$C_6$-alkylene-OR, —O—$C_1$-$C_6$-alkylene-OH, halo, —SH, —SR, —NH$_2$, —NHR, —N(R)$_2$, —$C_1$-$C_6$-alkylene-NH$_2$, —$C_1$-$C_6$-alkylene-NHR, —$C_1$-$C_6$-alkylene-N(R)$_2$, or CN, wherein each R is independently $C_1$-$C_6$ alkyl, $C_2$-$C_6$ alkenyl, or $C_2$-$C_6$ alkynyl and halo is F, $C_1$, Br or I. In some instances, the modifications are 2'-O-methyl and/or 2'-F. In some embodiments, the modification comprises one or more of 2'-F, phosphorothioate internucleotide linkage modification, acyclic nucleotides, LNA, HNA, CeNA, 2'-methoxyethyl, 2'-O-methyl, 2'-O-allyl, 2'-C-allyl, 2'-deoxy, 2'-O—N-methylacetamido (2'-O-NMA), a 2'-O-dimethylaminoethoxyethyl (2'-O-DMAEOE), 2'-O-aminopropyl (2'-O-AP), and 2'-ara-F modification. In some embodiments, the modification comprises 2'-MOE. In some embodiments, the modification comprises phosphorothioate internucleotide linkage modification. In some embodiments, the modification comprises 4-O-alkyl ribosugars such as 4'-methoxy and 4'-ethoxy modifications.

Suitably, the modified guide RNA can be applied with the *S. pyogenes* CRISPR/Cas9 system, or any other CRISPR/Cas systems such as those in *Staphylococcus aureus* or *Staphylococcus haemolyticus*. The modification, or similar modification patterns, can also be made to guide RNAs for Cpf1 from Lachnospiraceae bacterium ND2006 or Cpf1 from *Acidominococcus* species BV3L6.

In certain embodiments, guide RNA sequences comprise a fully modified single guide RNA. In some embodiments, a guide RNA comprises chemical modifications in the tracr RNA portion. Non-limiting exemplary modifications and modification patterns of the nucleotides of a guide RNA according to the disclosure are shown in Table 2 and Table 3.

Modified guide RNAs as described herein may be used in complex with CRISPR/Cas system or CRISPR/Cas enzymes to effect alteration in a target gene or DNA sequence. The CRISPR/Cas enzymes may comprise CRISPR nucleases, such as Cas9, Cpf1, C2c1, C2c2, or C2c3. In some embodiments, the CRISPR/Cas enzyme may comprise CRISPR nucleases with modified or reduced nuclease activity, such as a nuclease inactive Cas9 or Cpf1. For example, mutations may be introduced into one or both nuclease subdomains of a Cas9 enzyme to generate a Cas9 nickase or a nuclease inactive Cas9. Exemplary inactivating mutations in Cas9 include alterations at positions D10, E762, H840, N854, N863, or D986 of SEQ ID NO: 1. For example, a D10A mutation in the RuvC subdomain and an H840A mutation in the HNH subdomain of Cas9 renders the Cas9 nuclease inactive. A D10A mutation in the RuvC subdomain or a H840A in the HNH subdomain of Cas9 generates a Cas9 nickase. Additional amino acid substitutions in Cas9 are discussed in WO15/89354, which is incorporated herein in its entirety.

The modified guide RNAs share sequence identity with, or is capable of hybridize to, a target nucleotide such as a target gene or a target DNA sequence. In some embodiments, modified guide RNA has at least 100%, 99%, 98%, 96%, 95%, 90%, 85%, 80%, 75%, or 70% correspondence or identity to a target nucleotide of a gene or target DNA.

The nucleotides as described herein can be synthetic or chemically modified. For example, guide RNAs provided herein can be synthetic or chemically modified guide RNAs. The nucleotides in the guide RNA that are modified may be those corresponding to one or more nucleotides in the binding region of the guide RNA with Cas9 and/or the nucleotides in the binding region of the guide RNA with the target DNA. Remaining unmodified nucleotides of the guide RNA may be those required to be identified for minimal binding of Cas9 to the 2'-OH location on the bases. In some embodiments, the nucleotides may be modified at the 2' position of the sugar moiety of the nucleotide. In some embodiments, the 2'-OH group of the sugar moiety is replaced by a group selected from H, OR, R, halo, SH, SR, H2, NHR, N(R)$_2$ or CN, wherein R is $C_1$-$C_6$ alkyl, alkenyl or alkynyl and halo is F, Cl, Br or I. Other modifications may include, inverted (deoxy) abasics, amino, fluoro, chloro, bromo, CN, CF, methoxy, imidazole, carboxylate, thioate, CI to CIO lower alkyl, substituted lower alkyl, alkaryl or aralkyl, heterozycloalkyl; heterozycloalkaryl; aminoalkylamino; polyalkylamino or substituted silyl. Methods for making RNAs with specific sequences and modifications are known by those skilled in the art, for example, in Dellinger et al. (2011), J. Am. Chem. Soc, 133, 11540; U.S. Pat. No. 8,202,983; Kumar et al., (2007), J. Am. Chem. Soc, 129, 6859-64; WO2013176844, the entirety of which are incorporated herein by reference.

In some embodiments, polynucleotides or oligonucleotides as provided herein may be synthetic. For example, guide RNAs maybe chemically synthesized guide RNAs. Synthetic RNA production yield is based on sequences and modifications. 2'-O— methyl modifications have been shown to increase coupling efficacy or efficiency during RNA synthesis and therefore increase yield of chemically synthesized RNA. Furthermore, nucleotides may be modified by phosphorothioates. Phosphothioate (phosphorothioate)(PS) bonds substitute a sulphur atom for a non-bridging oxygen in the phosphate backbone of an oligonucleotide. Accordingly, exemplary nucleotides of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, a-LNA having an a-L-ribo configuration (a diastereomer of LNA), 2'-amino-LNA having a 2'-amino functionalization, and 2'-amino-a-LNA having a 2'-amino functionalization) or hybrids thereof.

Conjugates for Targeted Delivery

Provided herein are conjugates suitable for targeted delivery of agents, such as mRNA, guide RNA, miRNA, siRNA, DNA, peptides, or other micro or macro molecules. A conjugate can contain one or more aptamers, ligands, or moieties for targeted delivery ex vivo or in vivo. In some embodiments, a conjugate comprises a targeting moiety (or ligand), a linker, and an active agent (or payload) that is connected to the targeting moiety. An active agent can be a therapeutic agent, a prophylactic agent, or a diagnostic/prognostic agent. An active agent may have a capability of manipulating a physiological function (e.g., gene expression) in a subject. An active agent maybe a guide RNA, a mRNA, a miRNA, a siRNA, a DNA, or a peptide. The active agent may be connected with the targeting moiety via a linker, via a non-covalent linkage, via nucleobase paring, or any combination thereof. In some embodiments, the conjugate may be a conjugate between a single active agent and a single targeting moiety with the formula (I): X—Y—Z, wherein X is the targeting moiety; Y is a linker; and Z is the guide RNA. In certain embodiments, one targeting ligand can be conjugated to two or more active agents, wherein the conjugate has the formula: X—(Y—Z)n. For example, the conjugate may comprise a guide RNA and a mRNA. In certain embodiments, one active agent can be linked to two or more targeting ligands wherein the conjugate has the formula: (X—Y)n-Z. In other embodiments, one or more targeting moieties may be connected to one or more active pay loads wherein the conjugate formula may be (X—Y—Z)n. In various combinations, the formula of the conjugates maybe, for example, X—Y—Z—Y—X, (X—Y—Z)n-Y—Z, or X—Y—(X—Y—Z)$_n$, wherein X is a targeting moiety; Y is a linker; Z is an active agent, e.g. a guide RNA. The number of each moiety in the conjugate may vary dependent on types of agents, sizes of the conjugate, delivery targets, particles used to packaging the conjugate, other active agents (e.g., immunologic adjuvants) and routes of administration. Each occurrence of X, Y, and Z can be the same or different, e.g. the conjugate can contain more than one type of targeting moiety, more than one type of linker, and/or more than one type of active agent, n is an integer equal to or greater than 1. In some embodiments, n is an integer between 1 and 50, or between 2 and 20, or between 5 and 40. In some embodiments, n may be an integer of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49 or 50.

In some embodiments, an active agent, e.g., a guide RNA may be delivered to cells and tissues using viral, polymeric and liposomal formulations, cell-penetrating peptides, aptamers, ligands, or conjugates and antibody approaches. A moiety or ligand may direct guide RNAs to particular organ, tissue, or cell, for example, a liver hepatocyte, and may be referred to as a targeting moiety. In some embodiments, targeting moieties modify one or more properties of the attached molecule (e.g., a mRNA or a guide RNA), including but not limited to pharmacodynamic, pharmacokinetic, binding, absorption, cellular distribution, cellular uptake, charge and clearance.

Exemplary moieties that can be attached to a herein described active agent include, but are not limited to, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, dyes, lipid moieties such as a cholesterol moiety (Letsinger et al., Proc. Natl. Acad. Sci. USA, 1989, 86, 6553); cholic acid (Manoharan et al, Bioorg. Med. Chem. Lett., 1994, 4, 1053); a thioether, e.g., hexyl-S-tritylthiol (Manoharan et al, Ann. NY. Acad. Sci., 1992, 660, 306; Manoharan et al, Bioorg. Med. Chem. Let., 1993, 3, 2765); a thiocholesterol (Oberhauser et al., Nucl. Acids Res., 1992, 20, 533); an aliphatic chain, e.g., dodecandiol or undecyl residues (Saison-Behmoaras et al, EMBO J., 1991, 10, 111; Kabanov et al, FEBS Lett., 1990, 259, 327; Svinarchuk et al, Biochimie, 1993, 75, 49); a phospholipid, e.g., di-hexadecyl-rac-glycerol or triethylammonium-1,2-di-O-hexadecyl-rac-glycero-3-H-phosphonate (Manoharan et al, Tetrahedron Lett., 1995, 36, 3651; Shea et al, Nucl. Acids Res., 1990, 18, 3777); a polyamine or a polyethylene glycol chain (Manoharan et al., Nucleosides & Nucleotides, 1995, 14, 969); adamantane acetic acid (Manoharan et al., Tetrahedron Lett., 1995, 36, 3651); a palmityl moiety (Mishra et al, Biochim. Biophys. Acta, 1995, 1264, 229); or an octadecylamine or hexylamino-carbonyl-oxycholesterol moiety (Crooke et al, J. Pharmacol. Exp. Ther., 1996, 277, 923), all references incorporated herein in their entirety. Targeting moieties may include naturally occurring molecules, or recombinant or synthetic molecules, including, but not limited to, GalNAc or derivative thereof (e.g., a dimer, trimer, or tetramer of GalNAc or derivative thereof), polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG, e.g., PEG-2K, PEG-5K, PEG-10K, PEG-12K, PEG-15K, PEG-20K, PEG-40K), MPEG, [MPEG]2, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g, steroids, bile acids, cholesterol, cholic acid, adamantane acetic acid, 1-pyrene butyric acid, dihydrotestosterone, 1,3-Bis-0(hexadecyl)glycerol, geranyloxyhexyl group, hexadecylglycerol, borneol, menthol, 1,3-propanediol, heptadecyl group, palmitic acid, myristic acid,03-(oleoyl)litho-cholic acid, 03-(oleoyl)cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, natural or recombinant low density lipoprotein (LDL), natural or recombinant high-density lipoprotein (HDL), and a cell-permeation agent (e.g., a helical cell-permeation agent), peptide and peptidomimetic ligands, including those having naturally occurring or modified peptides, e.g., D or L peptides; a, 3, or 7 peptides; N-methyl peptides; azapeptides; peptides having one or more amide, i.e., peptide, linkages replaced with one or more urea, thiourea, carbamate, or sulfonyl urea linkages; or cyclic peptides; amphipathic peptides including, but not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, H2A peptides, *Xenopus* peptides, esculentinis-1, and caerins. A peptidomimetic (also referred to herein as an oligopeptidomimetic) is a molecule capable of folding into a defined three-dimensional structure similar to a natural peptide. The peptide or peptidomimetic ligand or moiety can be about 5-50 amino acids long, e.g., about 5, 10, 15, 20, 25, 30, 35, 40, 45, or 50 amino acids long. In some embodiments, the targeting moiety may be other peptides such as somatostatin, octeotide, LHRH (luteinizing hormone releasing hormone), epidermal growth factor receptor (EGFR) binding peptide, aptide or bipodal peptide, RGD-containing peptides, a protein scaffold such as a fibronectin domain, a single domain antibody, a stable scFv, or other homing peptides. As non-limiting examples, a protein or peptide based targeting moiety may be a protein such as thrombospondin, tumor necrosis factors (TNF), annexin V, an interferon, angiostatin, endostatin, cytokine, transferrin, GM-CSF (granulocyte-macrophage colony-stimulating factor), or growth factors such as vascular endothelial growth factor (VEGF), hepatocyte growth factor (HGF), (platelet-derived growth factor (PDGF), basic fibroblast growth factor (bFGF), and epidermal growth factor (EGF). In some embodiments, the targeting moiety maybe an antibody, an antibody fragment, RGD peptide, folic acid or prostate specific membrane antigen (PSMA). In some embodiments, the protein scaffold may be an antibody-derived protein scaffold. Non-limiting examples include single domain antibody (dAbs), nanobody, single-chain variable fragment (scFv), antigen-binding fragment (Fab), Avibody, minibody, CH2D domain, Fcab, and bispecific T-cell engager (BiTE) molecules. In some embodiments, scFv is a stable scFv, wherein the scFv has hyperstable properties. In some embodiments, the nanobody may be derived from the single variable domain (VHH) of camelidae antibody.

In some embodiments, a targeting moiety recognizes or binds a target cell, a marker, or a molecule that is present exclusively or predominantly on the surface of particular cells. For example, a targeting moiety may bind a tumor antigen and direct the activating agent, e.g. a guide RNA-Cas complex to a malignant cell. In some embodiments, the targeting moiety recognizes an intra-cellular protein. In some embodiments, a targeting moiety directs a conjugate to specific tissues, cells, or locations in a cell. The targeting moiety can direct the conjugate in culture or in a whole organism, or both. In each case, the targeting moiety may bind to a receptor that is present on the surface of or within the targeted cell(s), wherein the targeting moiety binds to the receptor with an effective specificity, affinity and avidity. In other embodiments the targeting moiety targets the conjugate to a specific tissue such as the liver, kidney, lung or pancreas. In other cases, targeting moieties can direct the conjugate to cells of the reticular endothelial or lymphatic system, or to professional phagocytic cells such as macrophages or eosinophils. In some embodiments, the targeting moiety may recognize a RTK receptor, an EGF receptor, a serine or threonine kinase, G-protein coupled receptor, methyl CpG binding protein, cell surface glycoprotein, cancer stem cell antigen or marker, carbonic anhydrase, cytolytic T lymphocyte antigen, DNA methyltransferase, an ectoenzyme, a glycosylphosphatidylinositol-anchored co-receptor, a glypican-related integral membrane proteoglycan, a heat shock protein, a hypoxia induced protein, a multi drug resistant transporter, a Tumor-associated macrophage marker, a tumor associated carbohydrate antigen, a TNF receptor family member, a transmembrane protein, a tumor necrosis factor receptor superfamily member, a tumour differentiation antigen, a zinc dependent metallo-exopeptidase, a zinc transporter, a sodium-dependent transmembrane transport protein, a member of the SIGLEC family of lectins, or a matrix metalloproteinase.

In some embodiments, a herein described conjugate, e.g., a guide RNA conjugate, comprise at least one N-Acetyl-Galactosamine (GalNAc), N—Ac-Glucosamine (GluNAc), or mannose (e.g., mannose-6-phosphate). In some embodiments, a targeting moiety comprise at least one N-Acetyl-Galactosamine (GalNAc), N—Ac-Glucosamine (GluNAc), or mannose (e.g., mannose-6-phosphate).

In some embodiments, a herein described conjugate comprises one or more targeting moieties that comprise N-acetylgalactosamine (GalNAc) or GalNAc derivatives. Such a conjugate is also referred to herein as a GalNAc conjugate. In some embodiments, the conjugate targets a RNA to a particular cell, e.g., a liver cell, e.g., a hepatocyte. In some embodiments, the GalNAc derivatives can be attached via a linker, e.g., a bivalent or trivalent branched linker.

In some embodiments, a herein described conjugate is a carbohydrate conjugate. In some embodiments, a carbohydrate conjugate comprises a monosaccharide. In some embodiments, the monosaccharide is an N-acetylgalactosamine (GalNAc). GalNAc and GalNAc derivatives are capable of binding Asialoglycoprotein receptor (ASGPR), also known as Ashwell-Morell receptor, a lectin predominantly expressed on liver hepatocytes.

GalNAc conjugates are described, for example, in U.S. Pat. No. 8,106,022, the entire content of which is hereby incorporated herein by reference. In some embodiments, the GalNAc conjugate serves as a ligand that targets the guide RNA to particular cells. In some embodiments, the GalNAc conjugate targets the guide RNA to liver cells, e.g., by serving as a ligand for the asialoglycoprotein receptor of liver cells (e.g., hepatocytes). In some embodiments, the carbohydrate conjugate comprises one or more GalNAc derivatives. The GalNAc derivatives may be attached via a linker, e.g., a bivalent or trivalent branched linker. In some embodiments the GalNAc conjugate is conjugated to the 3' end of the sense strand. In some embodiments, the GalNAc ligand is conjugated to the active agent (e.g., to the 3' end of guide RNA) via a linker, e.g., a linker as described herein. In some other embodiments, the GalNAc ligand is conjugated to the active agent (e.g., to the 5' end of guide RNA) via a linker, e.g., a linker as described herein.

In some embodiments, the GalNAc ligand may be conjugated to a shortmer oligonucleotide via a linker and spacer, wherein the shorter oligonucleotide conjugate is complementary to a segment of an RNA. The RNA encompasses all length, structure, and forms of RNA molecules, including, for example, a mRNA of interest and guide RNA of interest. In some embodiments, a shortmer-GalNAc conjugate and a RNA constitute a pharmaceutical composition. For example, a shortmer GalNAc-conjugated oligonucleotide and a RNA, e.g. a coupling sequence, together may constitute a pharmaceutical composition via W—CH-bonding of complementary nucleotides. The shortmer oligonucleotide conjugate may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the coupling sequence may comprise 15-40 nucleotides in length. In some embodiments, the coupling sequence may comprise 19-30 nucleotides in length. In some embodiments, the coupling sequence may comprise 20-24 nucleotides in length.

In some embodiments, provided herein are pharmaceutical compositions comprising one or more GalNAc conjugated shortmer oligonucleotides and one or more RNAs. In some embodiments, a single GalNAc conjugated shortmer oligonucleotide, e.g., a GalNAc conjugated RNA, may be complementary to multiple oligonucleotide segments within a RNA. For example, the single GalNAc conjugated shortmer may comprise a coupling sequence complementary to multiple segments within a RNA. In some embodiments, multiple GalNAc ligand conjugated shortmer oligonucleotides that are complementary to multiple oligonucleotide segments within an RNA may constitute a pharmaceutical composition.

In certain embodiments, the targeting moiety of a herein described conjugate comprises a ligand having a structure shown in Table 1 below.

TABLE 1
Non-limiting examples of targeting moiety structures.
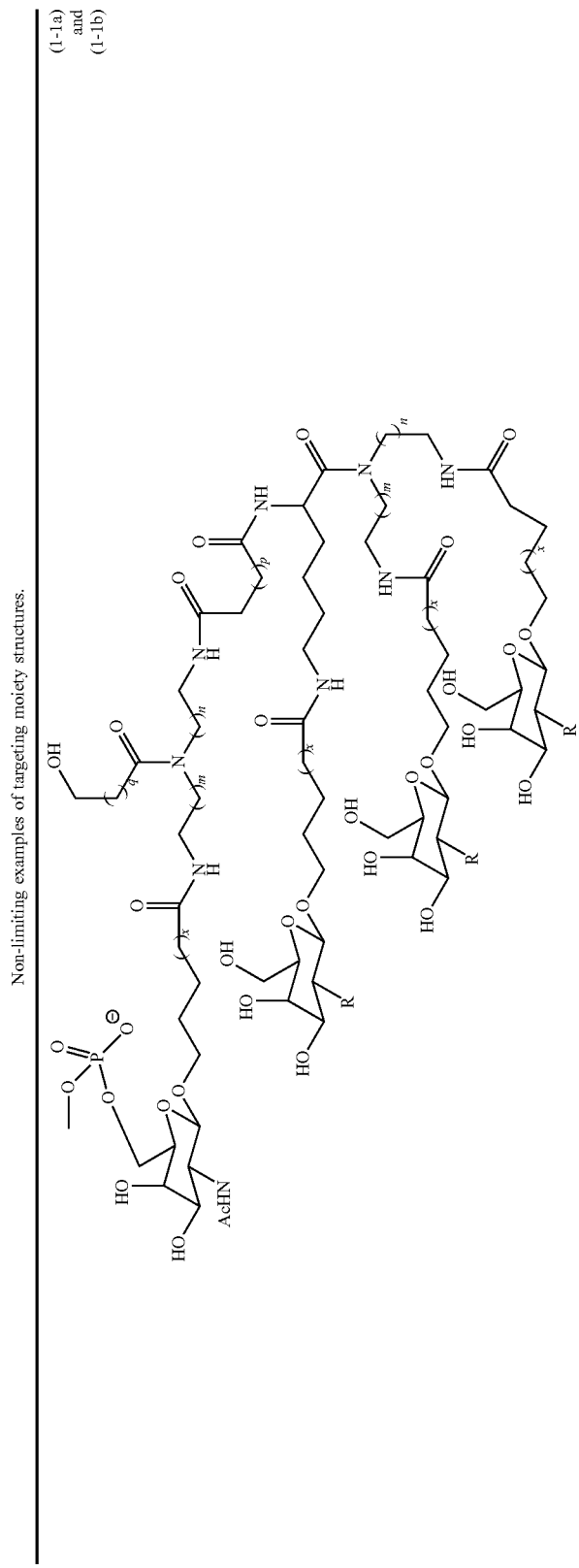
(1-1a) and (1-1b)

TABLE 1-continued
Non-limiting examples of targeting moiety structures.
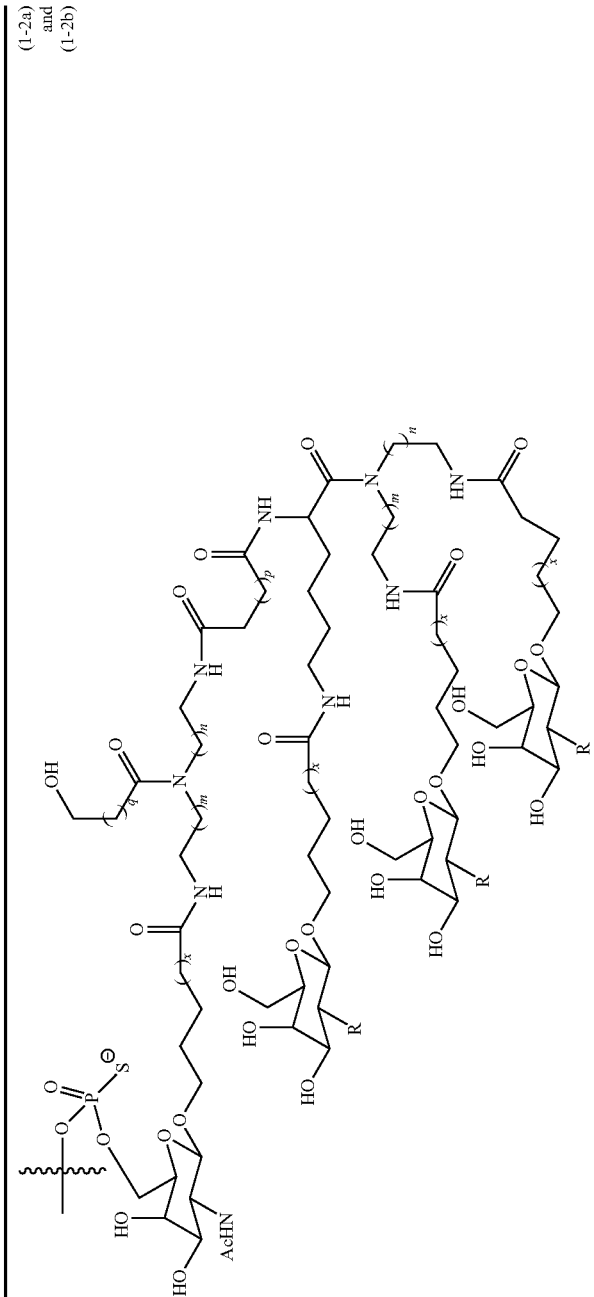
(1-2a) and (1-2b)

TABLE 1-continued
Non-limiting examples of targeting moiety structures.
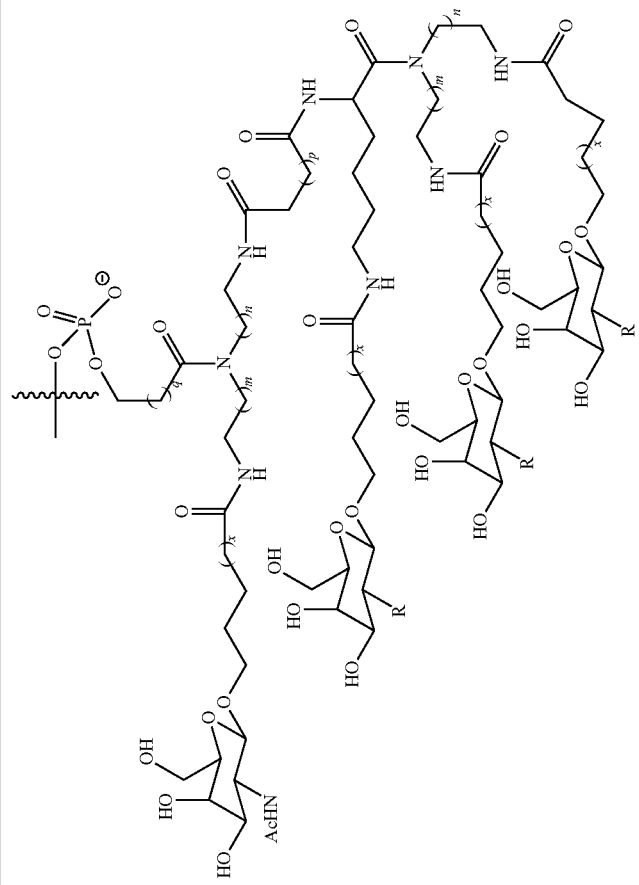
(1-3a) and (1-3b)

TABLE 1-continued
Non-limiting examples of targeting moiety structures.
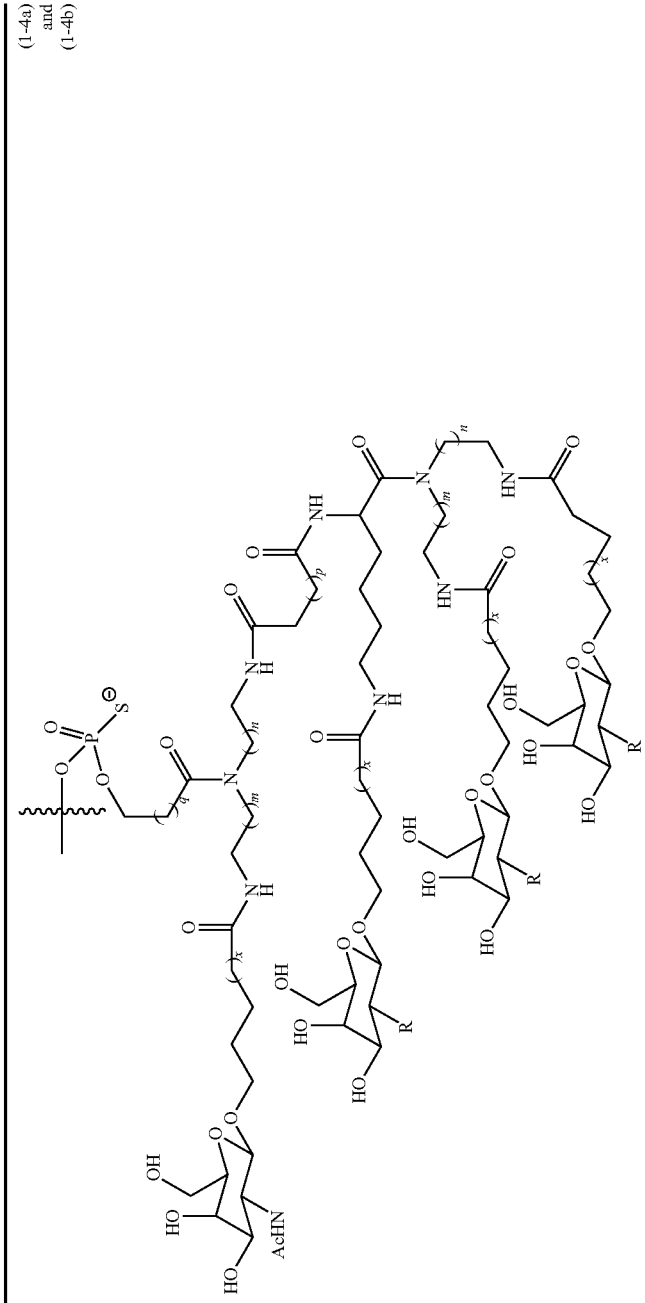
(1-4a) and (1-4b)

TABLE 1-continued
Non-limiting examples of targeting moiety structures.
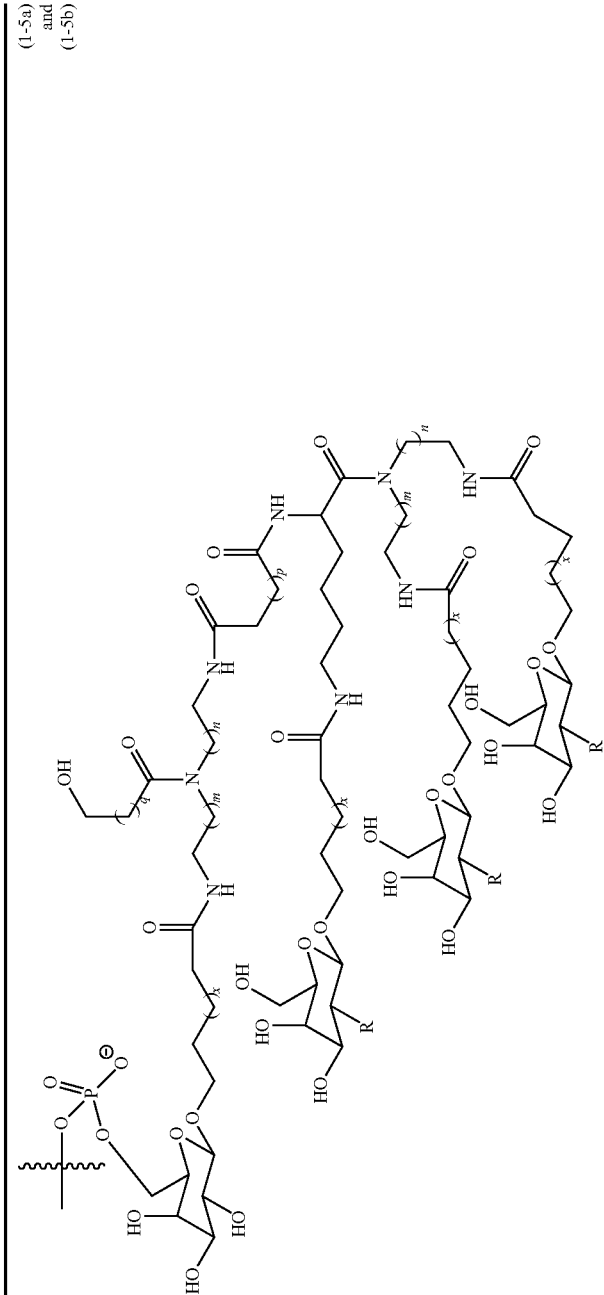
(1-5a) and (1-5b)

TABLE 1-continued
Non-limiting examples of targeting moiety structures.
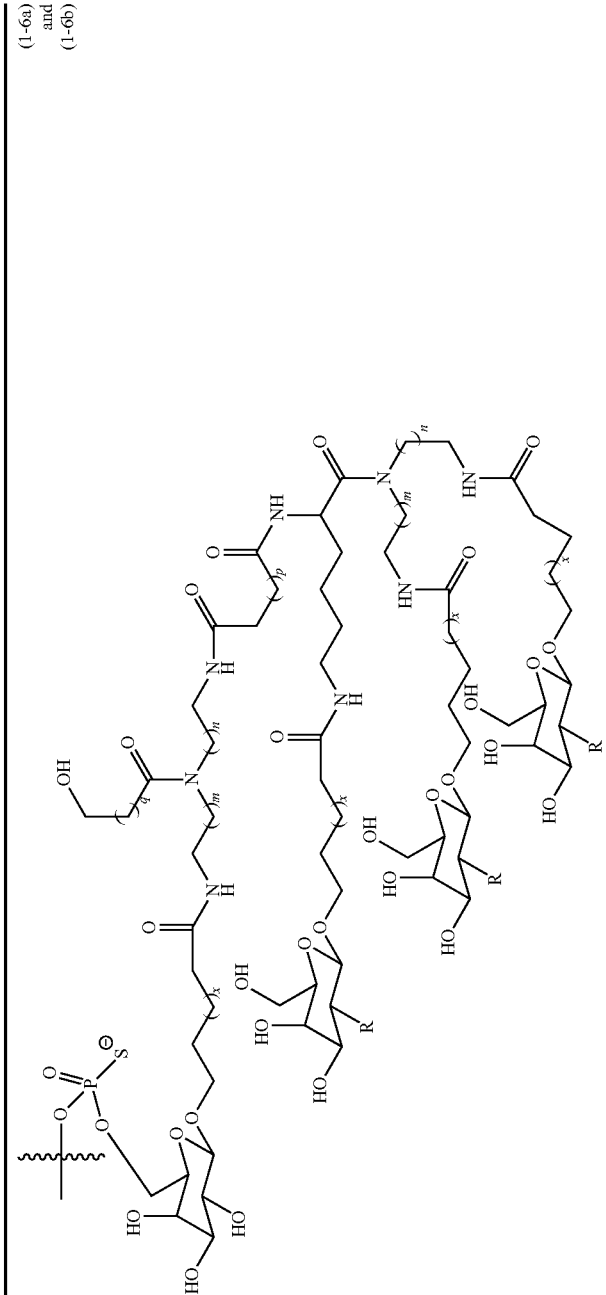
(1-6a) and (1-6b)

TABLE 1-continued
Non-limiting examples of targeting moiety structures.
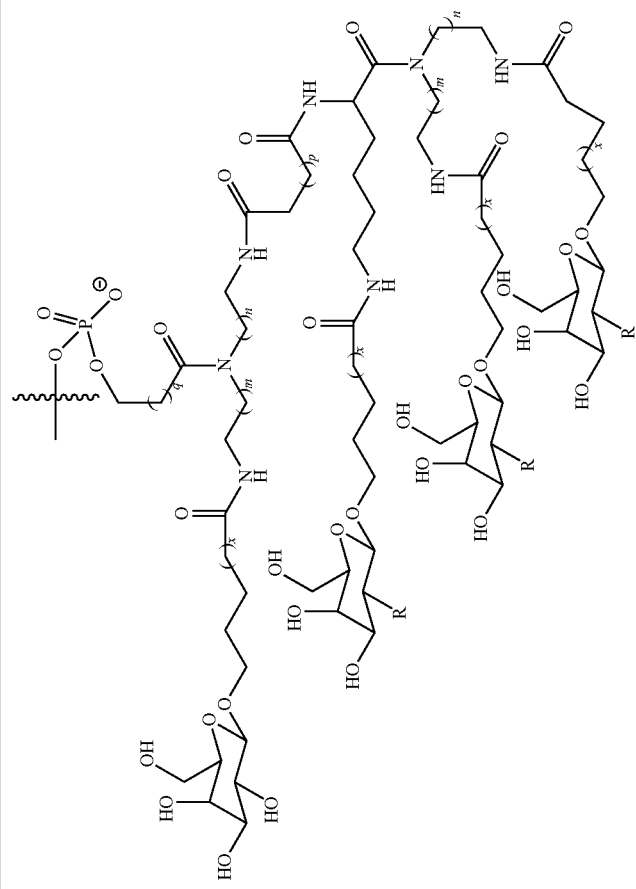
(1-7a) and (1-7b)

TABLE 1-continued
Non-limiting examples of targeting moiety structures.
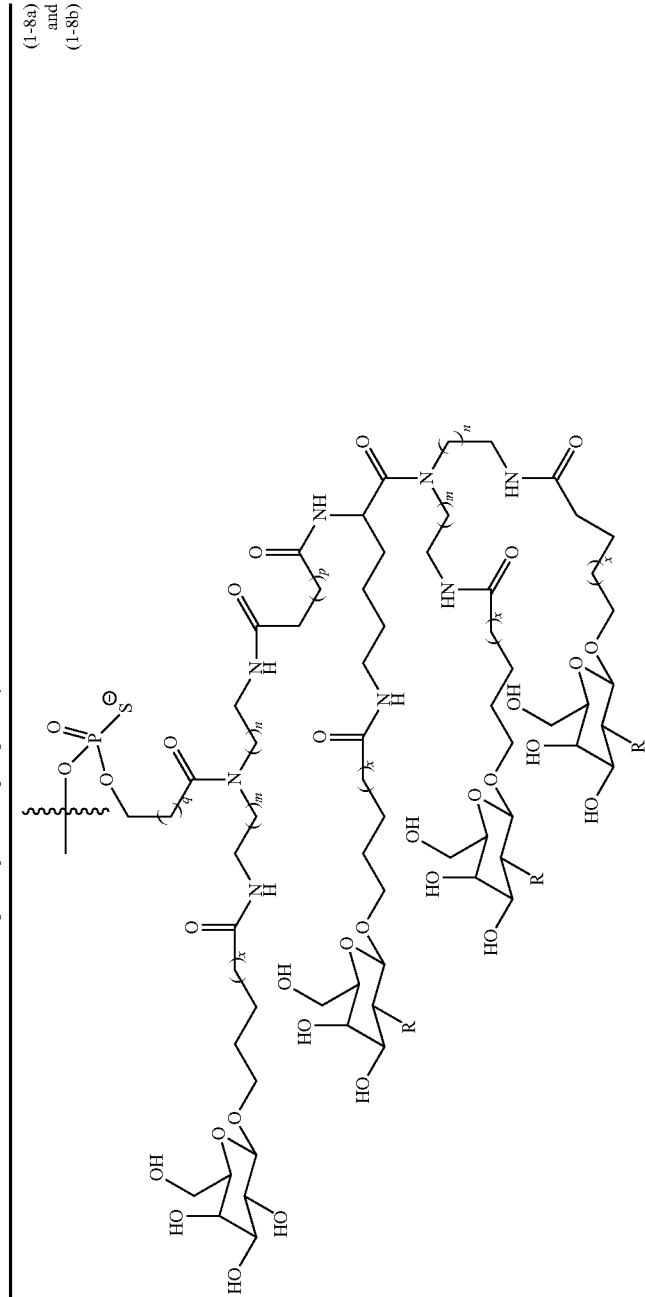
(1-8a) and (1-8b)
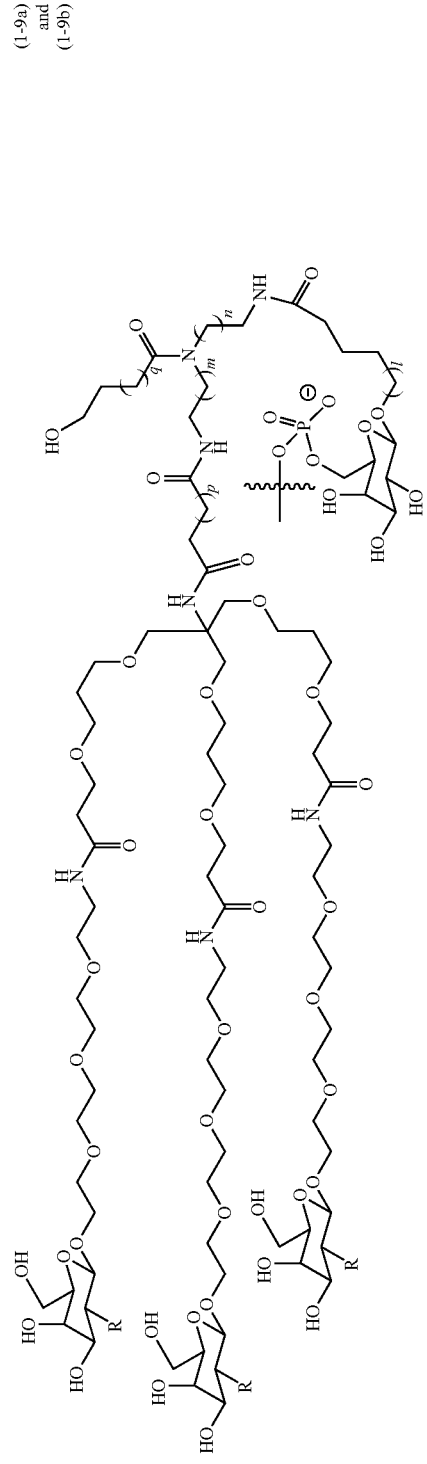
(1-9a) and (1-9b)

TABLE 1-continued
Non-limiting examples of targeting moiety structures.
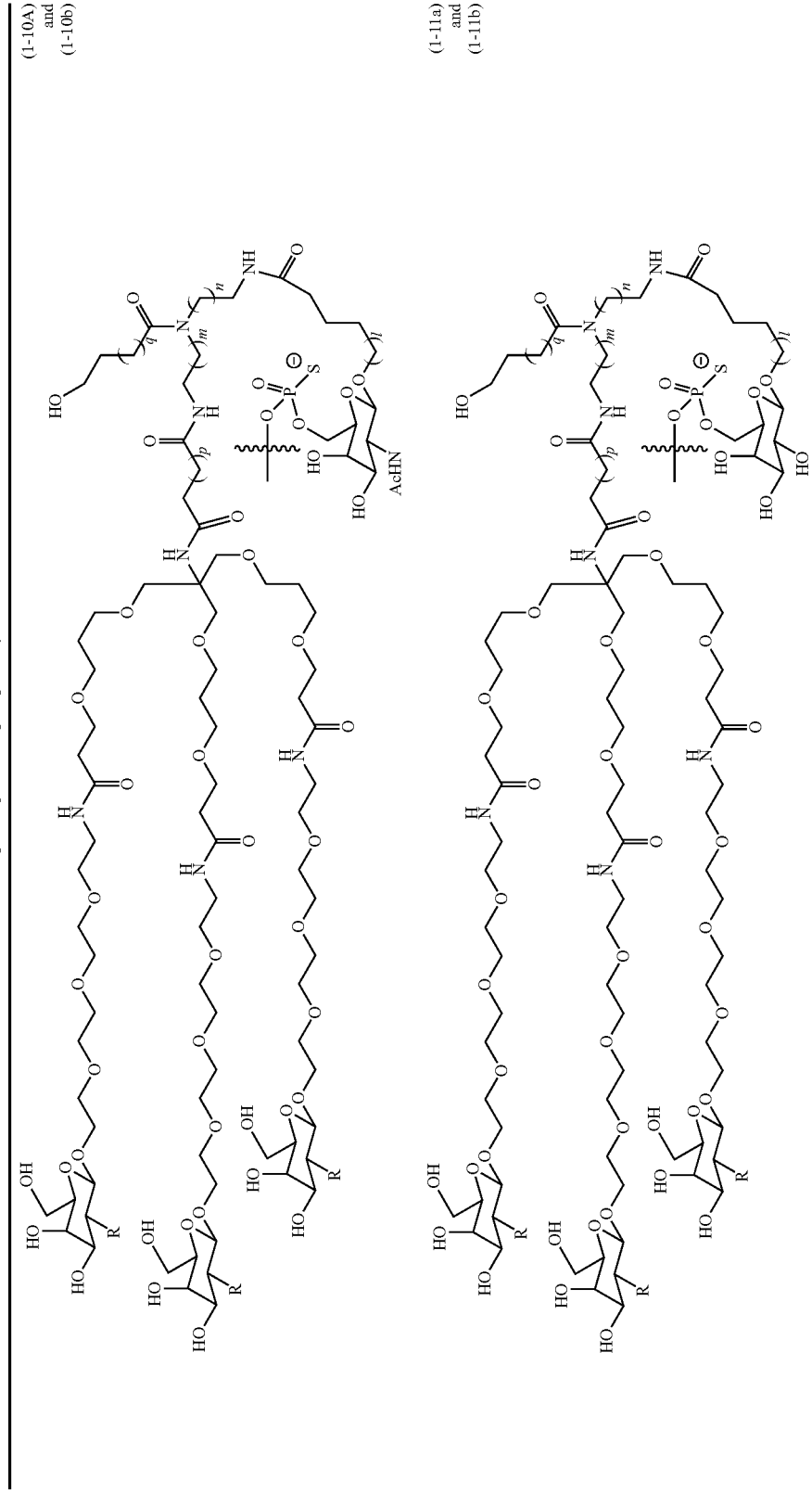
(1-10A) and (1-10b)
(1-11a) and (1-11b)

TABLE 1-continued
Non-limiting examples of targeting moiety structures.
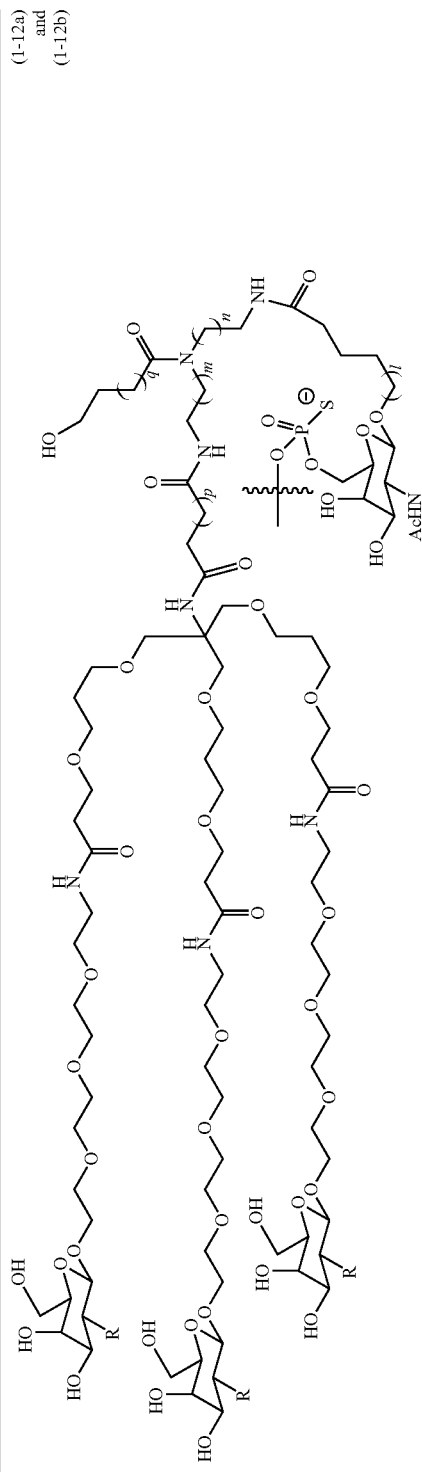
(1-12a) and (1-12b)
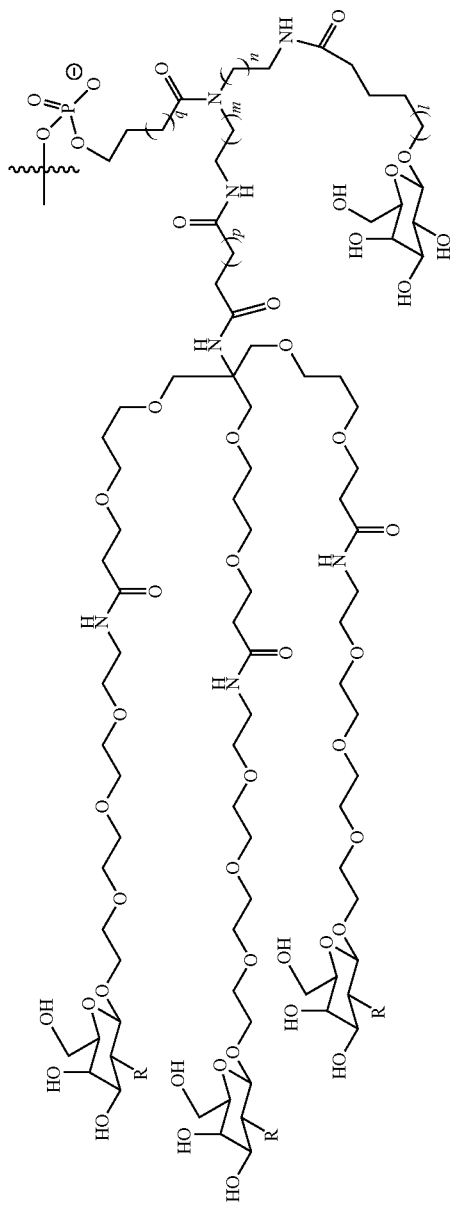
(1-13a) and (1-13b)

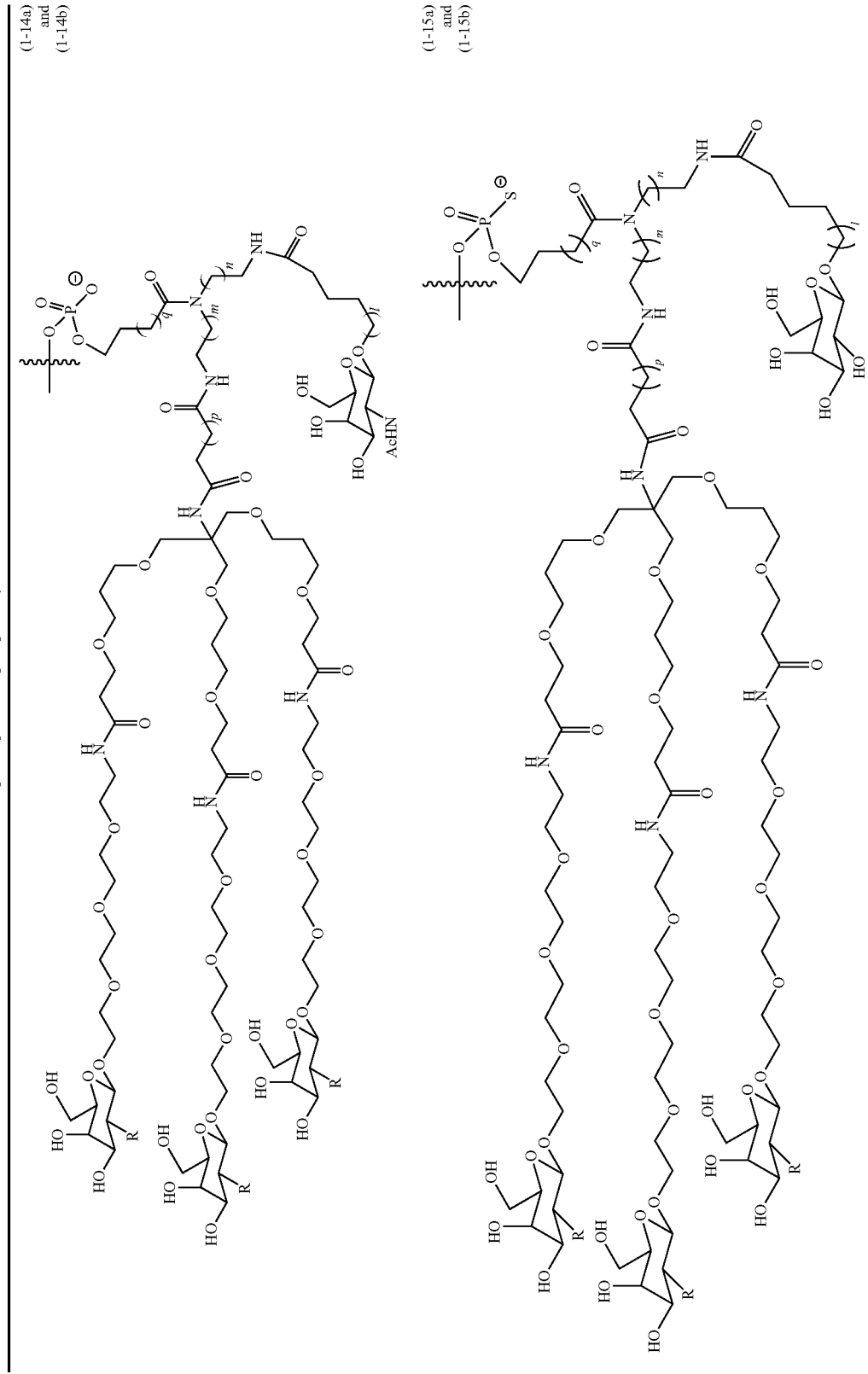

TABLE 1-continued
Non-limiting examples of targeting moiety structures.
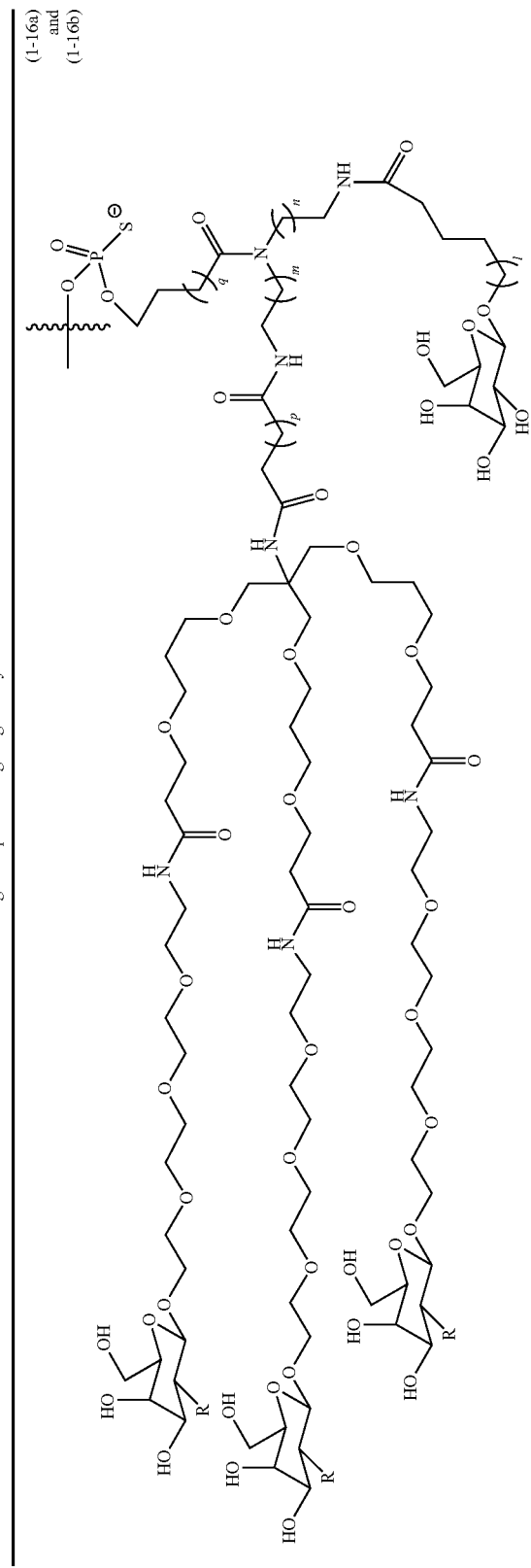
(1-16a) and (1-16b)

TABLE 1-continued
Non-limiting examples of targeting moiety structures.
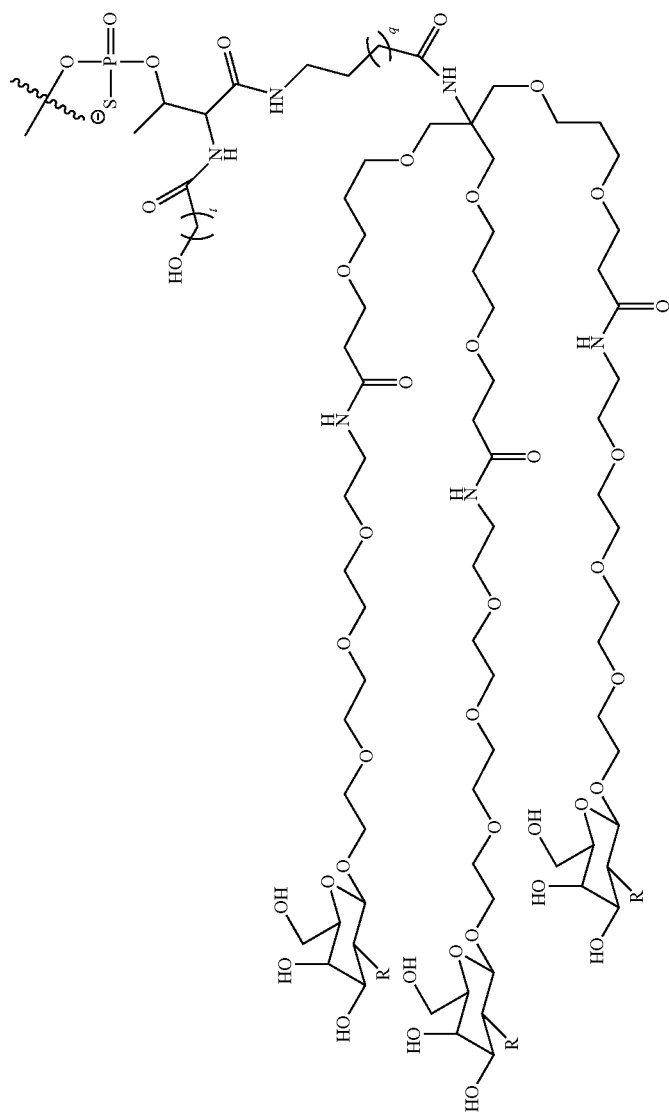
(1-17)

TABLE 1-continued
Non-limiting examples of targeting moiety structures.
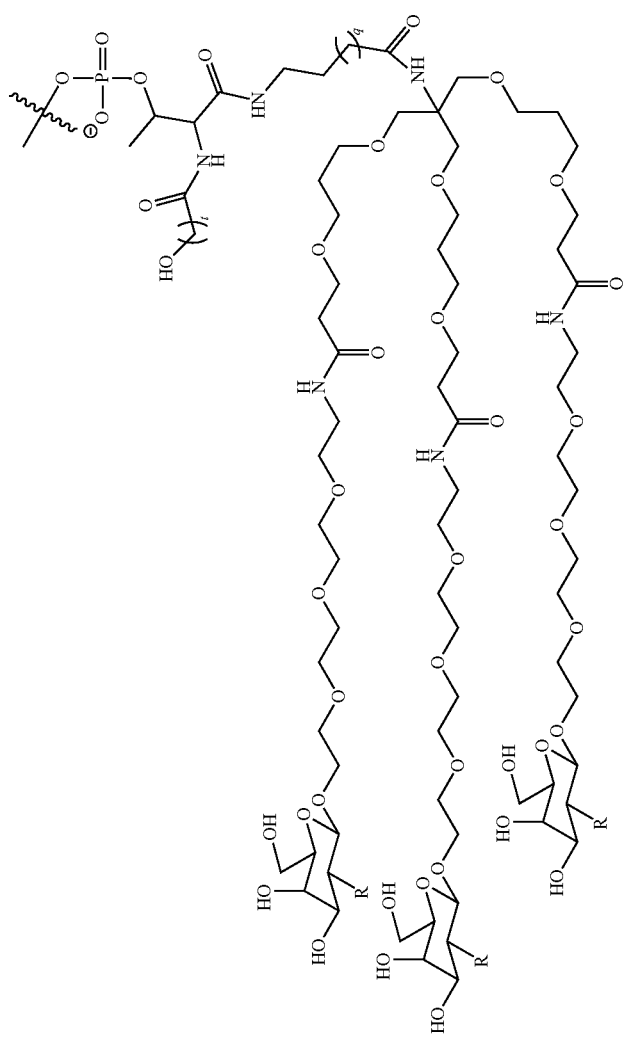
(1-18)

TABLE 1-continued
Non-limiting examples of targeting moiety structures.
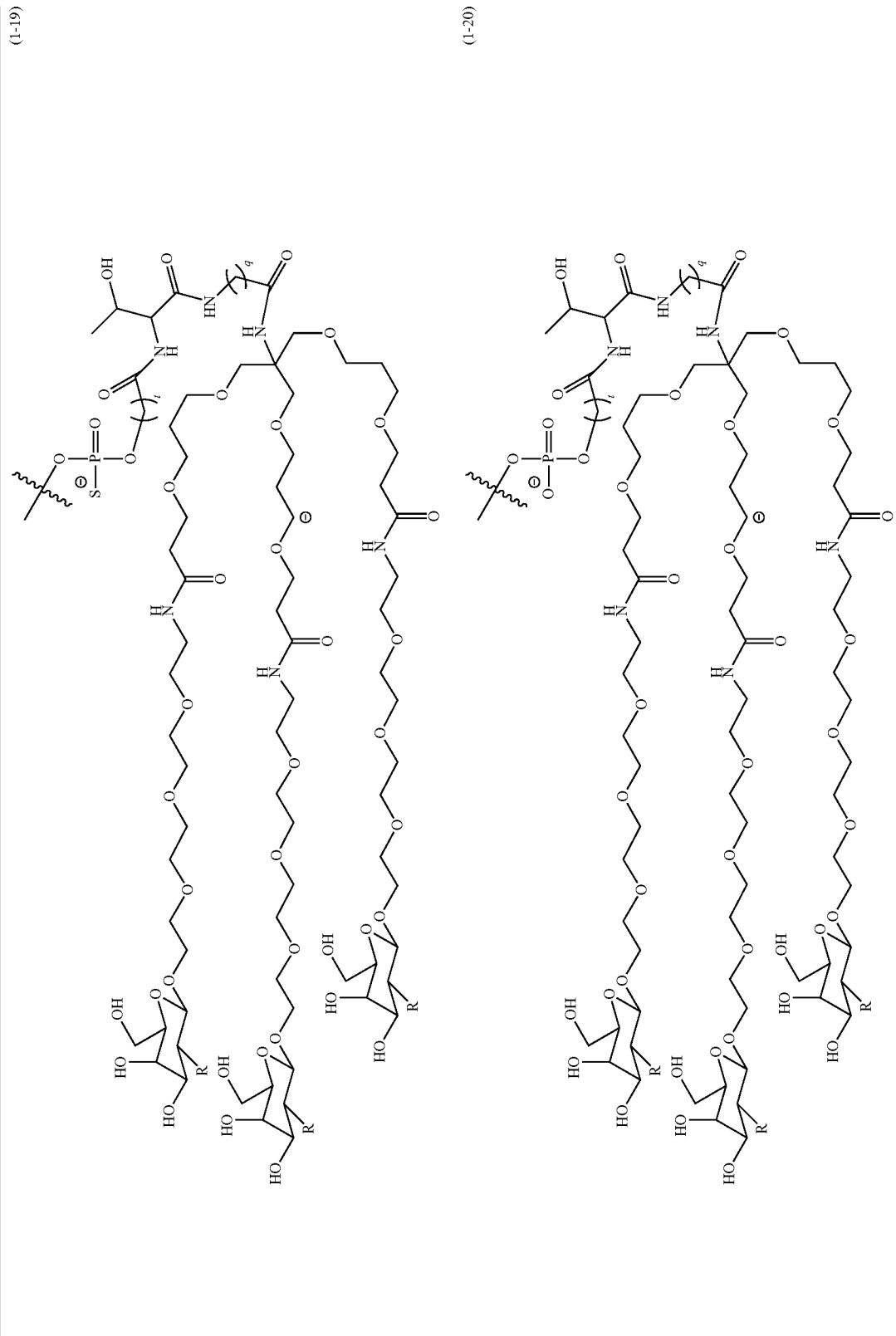

TABLE 1-continued
Non-limiting examples of targeting moiety structures.
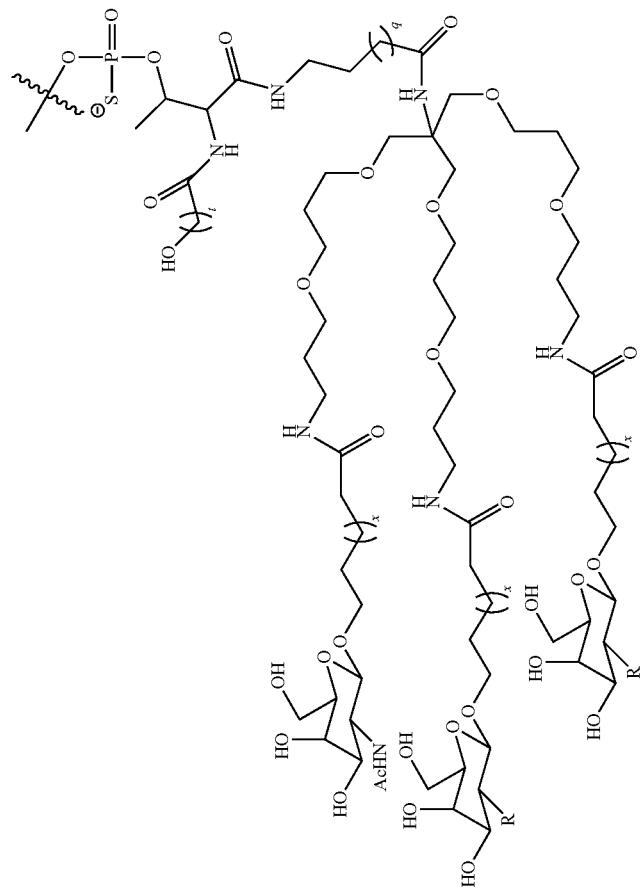
(1-21a) and (1-21b)

TABLE 1-continued
Non-limiting examples of targeting moiety structures.
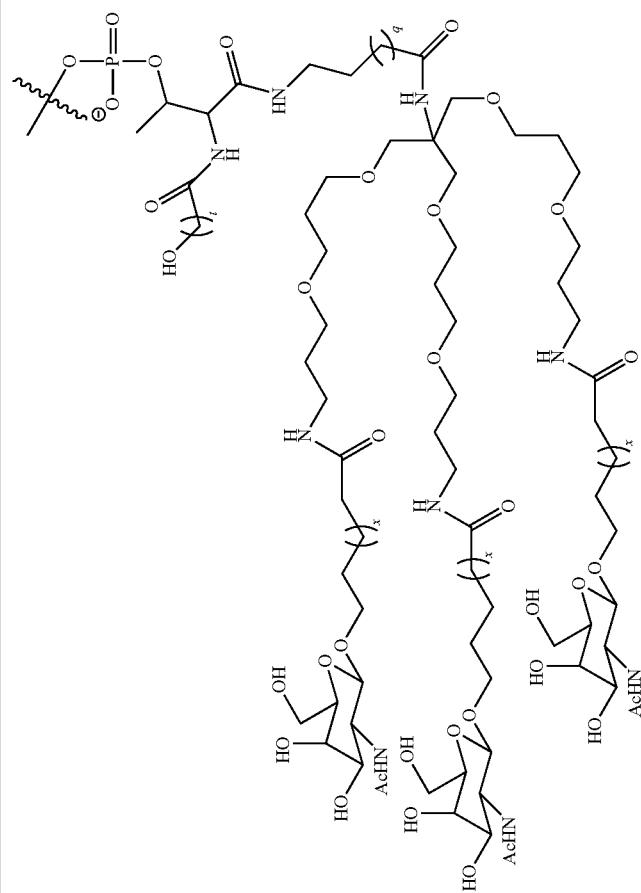
(1-22a) and (1-22b)

TABLE 1-continued
Non-limiting examples of targeting moiety structures.
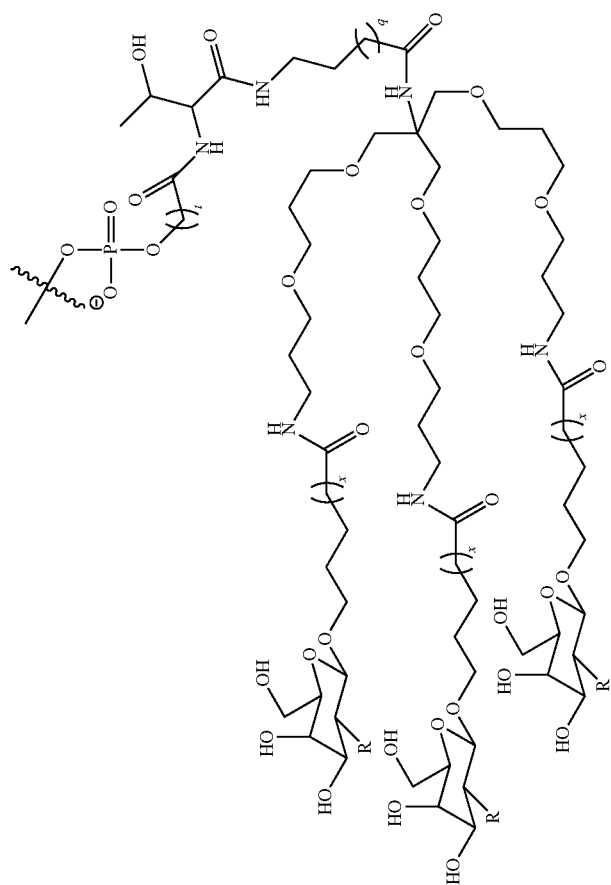
(1-23a) and (1-23b)

TABLE 1-continued
Non-limiting examples of targeting moiety structures.
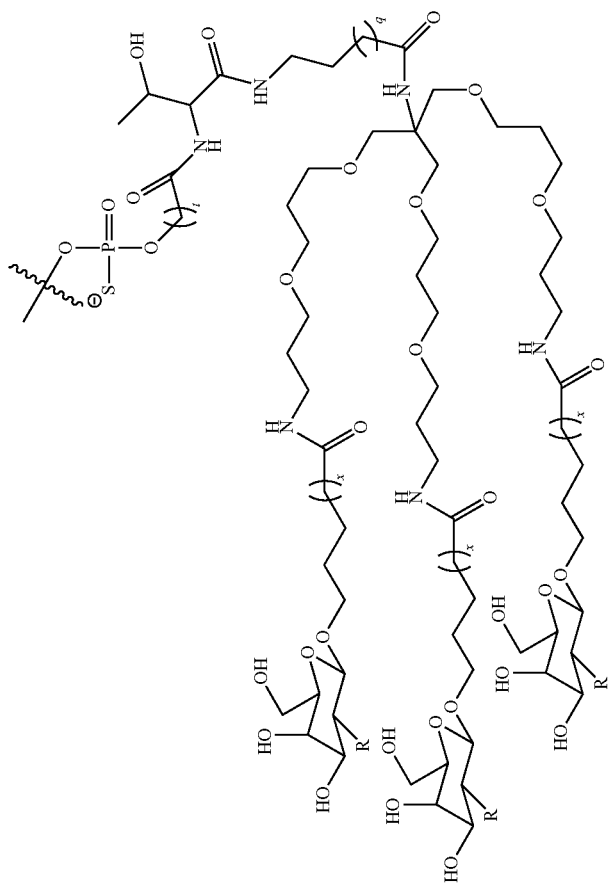
(1-24a) and (1-24b)

TABLE 1-continued
Non-limiting examples of targeting moiety structures.
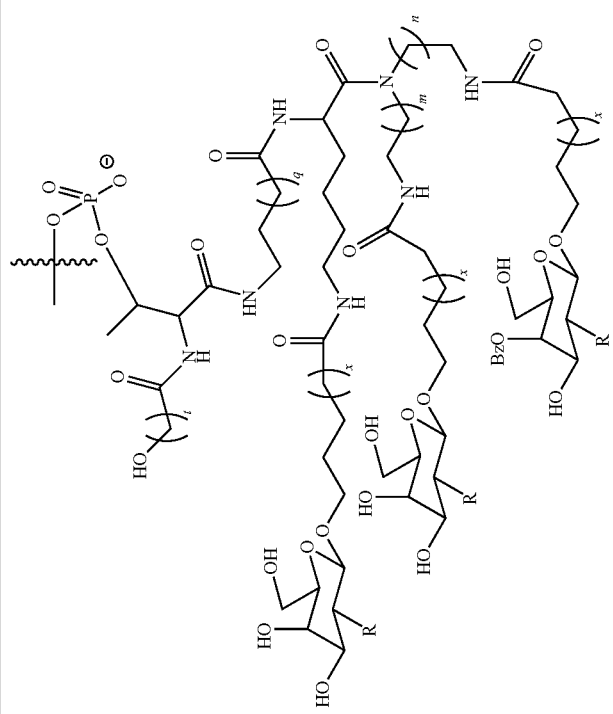
(1-25a) and (1-25b)

TABLE 1-continued
Non-limiting examples of targeting moiety structures.
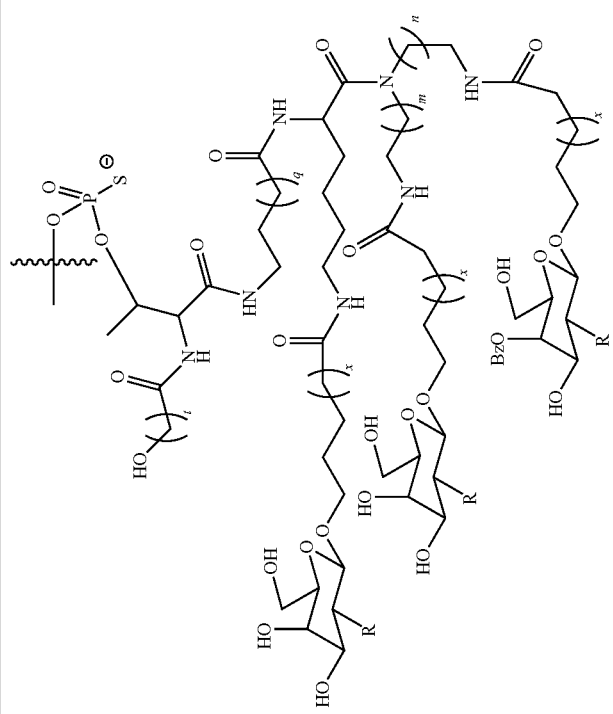
(1-26A) and (1-26b)

TABLE 1-continued
Non-limiting examples of targeting moiety structures.
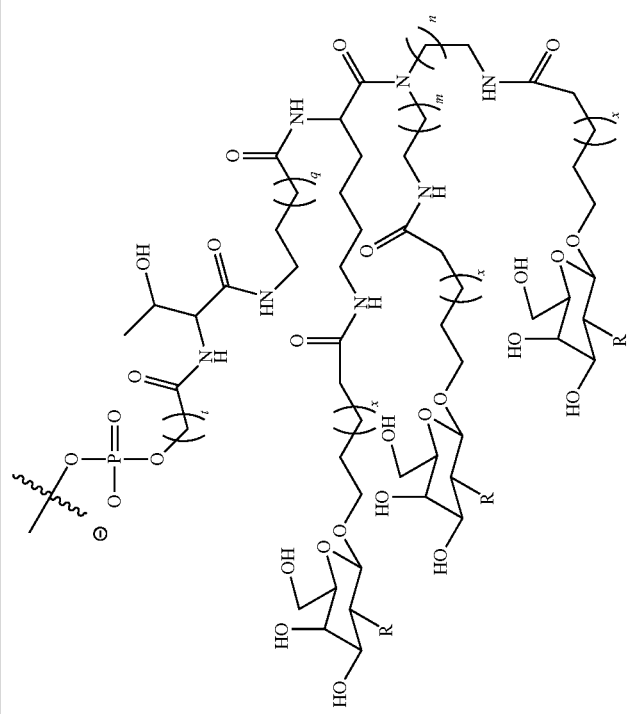
(1-27a) and (1-27b)

TABLE 1-continued
Non-limiting examples of targeting moiety structures.
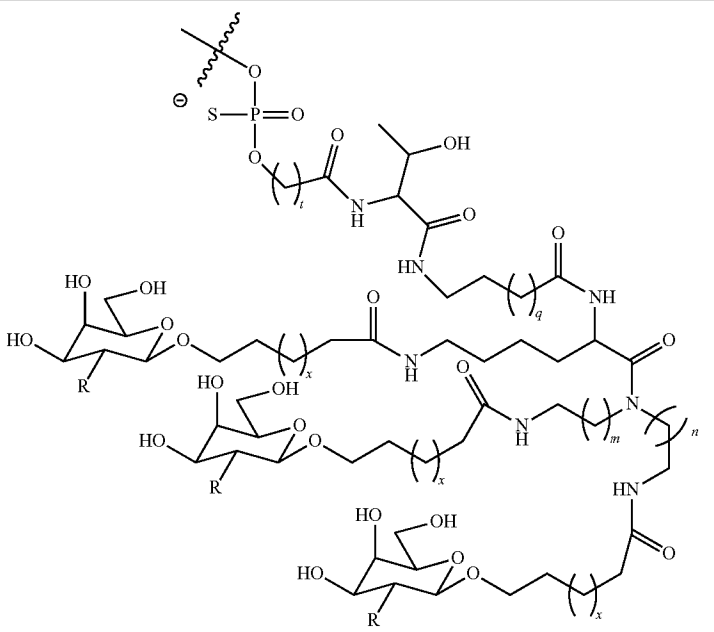
(1-28a) and (1-28b)

As shown in Table 1, each of t, n, p, q and m is independently 0, or an integer from 1 to 30. In some embodiments, each oft, n, p, q and m of Table 1 is independently 0, 1, 2, 3, 4, 5, 6, 7, 8, 9, 10, 11, 12, 14, 13, 15, 16, 17, 18, 19, or 20. In some embodiments, each of t, n, p, q and m of Table 1 is independently 0, 1, 2, 3, 4, or 5. In some embodiments, each of t, n, p, q and m of Table 1 is independently 0, 1, 2, or 3. In some embodiments, each of t, n, p, q and m of Table 1 is independently 1 or 2. Accordingly, it should be understood that it is contemplated herein that in some embodiments of compounds of Table 1, t is 0 to 10. In some embodiments, t is 1 to 5. In some embodiments, t is 10 to 20. In some embodiments, t is 1 or 2. In some embodiments, t is 1. In some embodiments, t is 2. In some embodiments of compounds of Table 1, m is 0 to 10. In some embodiments, m is 1 to 5. In some embodiments, m is 10 to 20. In some embodiments, m is 1 or 2. In some embodiments, m is 1. In some embodiments, m is 2. In some embodiments of compounds of Table 1, n is 0 to 10. In some embodiments, n is 1 to 5. In some embodiments, n is 10 to 20. In some embodiments, n is 1 or 2. In some embodiments, n is 1. In some embodiments, n is 2. In some embodiments of compounds of Table 1, p is 0 to 10. In some embodiments, p is 1 to 5. In some embodiments, p is 10 to 20. In some embodiments, p is 1 or 2. In some embodiments, p is 1. In some embodiments, p is 2. In some embodiments of compounds of Table 1, q is 0 to 10. In some embodiments, q is 1 to 5. In some embodiments, q is 10 to 20. In some embodiments, q is 1 or 2. In some embodiments, q is 1. In some embodiments, q is 2. In some embodiments, each R is OH or $NHC(O)CH_3$ or combination thereof. In some embodiments, x is 0 or an integer from 1-5 in compound (1-1a), (1-2a), (1-3a), (1-4a), (1-5a), (1-6a), (1-7a), (1-8a), (1-9a), (1-10a), (1-11a)), (1-12a), (1-16a), (1-21a), (1-22a), (1-23a), (1-24a), (1-25a) and (1-26a) of Table 1. In some embodiments, x is 0 or an integer from 1-5 in compound (1-1b), (1-2b), (1-3b), (1-4b), (1-5b), (1-6b), (1-7b), (1-8b), (1-9b), (1-10b), (1-11b)), (1-12b), (1-16b), (1-21b), (1-22b), (1-23b), (1-24b), (1-25b) and (1-26b) of Table 1. In some embodiments, x is 1. In some embodiments, x is 2. In some embodiments, x is 0. In some embodiments, x is 3. In some embodiments, x is 4. In some embodiments, x is 5.

Targeting moieties can be conjugated to nucleobases, sugar moieties, or internucleosidic linkages of a nucleic acid, e.g. a guide RNA or mRNA. Conjugation to purine nucleobases or derivatives thereof can occur at any position including, endocyclic and exocyclic atoms. In some embodiments, the 2-, 6-, 7-, or 8-positions of a purine nucleobase are attached to a moiety. Conjugation to pyrimidine nucleobases or derivatives thereof can also occur at any position. In some embodiments, the 2-, 5-, and 6-positions of a pyrimidine nucleobase can be substituted with a moiety. When a moiety is conjugated to a nucleobase, the preferred position is one that does not interfere with hybridization, i.e., does not interfere with the hydrogen bonding interactions needed for base pairing.

Conjugation to sugar moieties of nucleosides can occur at any carbon atom. Example carbon atoms of a sugar moiety that can be attached to a conjugate moiety include the 2',3', and 5' carbon atoms. The gamma-position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

There are numerous methods for preparing conjugates of oligonucleotides. Generally, an oligonucleotide is attached to a conjugate moiety by contacting a reactive group (e.g., OH, SH, amine, carboxyl, aldehyde, and the like) on the oligonucleotide with a reactive group on the conjugate moiety. In some embodiments, one reactive group is electrophilic and the other is nucleophilic. For example, an electrophilic group can be a carbonyl-containing functionality and a nucleophilic group can be an amine or thiol. Methods for conjugation of nucleic acids and related oligomeric compounds with and without linking groups are well described in the literature such as, for example, in Manoharan in Antisense Research and Applications, Crooke and LeBleu, eds., CRC Press, Boca Raton, Fla., 1993, Chapter 17, which is incorporated herein by reference in its entirety.

A targeting moiety can be attached to an active agent or therapeutic nucleic acid described herein, such as a guide RNA, via RNA-RNA or RNA-DNA base pairing and hybridization. Not intended to be bound by any theories, a targeting moiety can comprise a coupling sequence that is capable of recognizing or binding an active agent, e.g., a guide RNA or a mRNA. In some embodiments, a targeting moiety comprises a coupling sequence capable of hybridizing to a 5' portion, a 3' portion, or a middle portion of a guide RNA. A guide RNA that hybridizes with a coupling sequence may comprise an extension. For example, the coupling sequence may be able to hybridize with the extension sequence of the guide RNA, thereby directing the guide RNA to desired in vivo, ex vivo, intercellular or intracellular locations, while the guide RNA functionality such as interaction with CRISPR enzyme or binding with target sequence(s) is not affected. In some embodiments, the guide RNA comprises an extension that includes a polynucleotide tail. In some embodiments, the guide nucleic acid comprises a poly(A) tail, a poly(U) tail, or a poly(T) tail capable of hybridizing with a poly(U) tail, a poly(A) tail, or a poly(A) tail of the coupling sequence respectively. In some embodiments, the guide nucleic acid may be a guide RNA that comprises the sequence of (A)n or (U)n. In some embodiments, the guide nucleic acid may comprise DNA and may comprise the sequence of (A)n or (T)n. In some embodiments, the coupling sequence may comprise the sequence of (A)n (SEQ ID NO: 115), (U)n (SEQ ID NO: 116) or (T)n (SEQ ID NO: 117). As instantly used, n may be any integer between 1 and 200.

A coupling sequence may share sequence identity or complementarity with a nucleic acid active agent, or a portion thereof. In some embodiments, a coupling sequence may share at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% of identity with a guide RNA described herein, or a portion of such guide RNA. In some embodiments, a coupling sequence may share at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% of identity with the complementary sequence of a guide RNA described herein, or the complementary of a portion of such guide RNA. In some embodiments, the coupling sequence may comprise identity or complementarity with at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100 contiguous nucleobases of the guide RNA or a complementary thereof.

In some embodiments, a targeting moiety may comprise or be associated with a coupling sequence that is chemically modified. In some embodiments, the coupling sequence comprises an extension that hybridizes with a therapeutic nucleic acid, e.g. a guide RNA, or a portion thereof. In some embodiments, the extension of the coupling sequence may be chemically modified. In some embodiments, the therapeutic nucleic acid, e.g. a guide RNA, may comprise an extension. In some embodiments, the extension of the guide RNA may be chemically modified. Non-limiting examples of guide RNA extensions and complementary or substantially complementary coupling sequence extensions are shown below in Table 2.

TABLE 2

Exemplary RNA GalNAc conjugate single chemical entity coupling sequences.

| RNA-GalNAc Conjugate No. | RNA-GalNAc conjugate single chemical entity coupling sequences | SEQ ID No |
|---|---|---|
| 2-1 | 5'-RNA-AAAAAAAAAAAA<br>3'-ususuuuuuuuuuus(GalNAc)-5' | 7<br>8 |
| 2-2 | 5'-RNA-AAAAAAAAAAAA<br>3'-(GalNAc)uuuuuuuuuususu | 9<br>10 |
| 2-3 | 5'-RNA-AAAAAAAAAAAA<br>3'-(GalNAc)ususuuuuuuuuuu(GalNAc) | 11<br>12 |
| 2-4 | 5'-RNA-AAAAAAAAAAAAAAAAAAAAAAA<br>3'-ususuuuuuuuuuuuuuuuuuuuus(GalNAc)-5' | 13<br>14 |
| 2-5 | 5'-RNA-AAAAAAAAAAAAAAAAAAAAAAA<br>3'-(GalNAc)uuuuuuuuuuuuuuuuuuuususu | 15<br>16 |
| 2-6 | 5'-RNA-AAAAAAAAAAAAAAAAAAAAAAA<br>3'-(GalNAc)uuuuuuuuuuuuuuuuuuuuuus(GalNAc)-5' | 17<br>18 |
| 2-7 | 5'-RNA-AAAAAAAAAAAA<br>3'-usUsuUuUuUuUuUus(GalNAc)-5' | 19<br>20 |
| 2-8 | 5'-RNA-AAAAAAAAAAAA<br>3'-(GalNAc)uUuUuUuUuUusUsu | 21<br>22 |
| 2-9 | 5'-RNA-AAAAAAAAAAAA<br>3'-(GalNAc)usUsuUuUuUuUuUu(GalNAc) | 23<br>24 |
| 2-10 | 5'-RNA-AAAAAAAAAAAAAAAAAAAAAAA<br>3'-usUsuUuUuUuUuUuUuUuUuUuus(GalNAc)-5' | 25<br>26 |
| 2-11 | 5'-RNA-AAAAAAAAAAAAAAAAAAAAAAA<br>3'-(GalNAc)uUuUuUuUuUuUuUuUuUUsusu | 27<br>28 |
| 2-12 | 5'-RNA-AAAAAAAAAAAAAAAAAAAAAAA<br>3'-(GalNAc)uUuUuUuUuUuUuUuUuUuUuus(GalNAc)-5' | 29<br>30 |
| 2-13 | 5'-RNA-AAAAAAAAAAAA<br>3'-UsUsUUUUUUUUUUUs(GalNAc)-5' | 31<br>32 |
| 2-14 | 5'-RNA-AAAAAAAAAAAA<br>3'-(GalNAc)UUUUUUUUUUUsUsU | 33<br>34 |
| 2-15 | 5'-RNA-AAAAAAAAAAAA<br>3'-(GalNAc)UsUsUUUUUUUUUUU(GalNAc) | 35<br>36 |
| 2-16 | 5'-RNA-AAAAAAAAAAAAAAAAAAAAAAA<br>3'-UsUsUUUUUUUUUUUUUUUUUUUUs(GalNAc) | 37<br>38 |
| 2-17 | 5'-RNA-AAAAAAAAAAAAAAAAAAAAAAA<br>3'-(GalNAc)UUUUUUUUUUUUUUUUUUUUUsUsU | 39<br>40 |

TABLE 2-continued

Exemplary RNA GalNAc conjugate single chemical entity coupling sequences.

| RNA-GalNAc Conjugate No. | RNA-GalNAc conjugate single chemical entity coupling sequences | SEQ ID No |
|---|---|---|
| 2-18 | 5'-RNA-AAAAAAAAAAAAAAAAAAAAAAAA<br>3'-(GalNAc)UUUUUUUUUUUUUUUUUUUUUUs(GalNAc)-5' | 41<br>42 |
| 2-19 | 5'-RNA-AAAAAAAAAAA A<br>3'-usTsuTuTuTuTuTus(GalNAc)-5' | 43<br>44 |
| 2-20 | 5'-RNA-AAAAAAAAAAA A<br>3'-(GalNAc)uTuTuTuTuTusTsu | 45<br>46 |
| 2-21 | 5'-RNA-AAAAAAAAAAAA<br>3'-(GalNAc)usTsuTuTuTuTuTu(GalNAc) | 47<br>48 |
| 2-22 | 5'-RNA-AAAAAAAAAAAAAAAAAAAAA<br>3'-usTsuTuTuTuTuTuTuTuTuus(GalNAc)-5' | 49<br>50 |
| 2-23 | 5'-RNA-AAAAAAAAAAAAAAAAAAAAA<br>3'-(GalNAc)uTuTuTuTuTuTuTuTuTsusu | 51<br>52 |
| 2-24 | 5'-RNA-AAAAAAAAAAAAAAAAAAAAA<br>3'-(GalNAc)uTuTuTuTuTuTuTuTuus(GalNAc)-5' | 53<br>54 |
| 2-25 | 5'-RNA-AAAAAAAAAAAA<br>3'-TsTsTTTTTTTTTTTs(GalNAc)-5' | 55<br>56 |
| 2-26 | 5'-RNA-AAAAAAAAAAAA<br>3'-(GalNAc)TTTTTTTTTTusTsT | 57<br>58 |
| 2-27 | 5'-RNA-AAAAAAAAAAAA<br>3'-(GalNAc)TsTsTTTTTTTTTT(GalNAc) | 59<br>60 |
| 2-28 | 5'-RNA-AAAAAAAAAAAAAAAAAAAAAA<br>3'-TsTsTTTTTTTTTTTTTTTTTTTs(GalNAc)-5' | 61<br>62 |
| 2-29 | 5'-RNA-AAAAAAAAAAAAAAAAAAAAAA<br>3'-(GalNAc)TTTTTTTTTTTTTTTTTTTsTsT | 63<br>64 |
| 2-30 | 5'-RNA-AAAAAAAAAAAAAAAAAAAAAA<br>3'-(GalNAc)TTTTTTTTTTTTTTTTTTTTs(GalNAc)-5' | 65<br>66 |

As used in Table 2, uppercase A, C, G and U refer to ribonucleotides bearing nucleobases adenine, cytosine, guanidine and uracil, respectively; lowercase a, c, g and u refer to modified (e.g., 2'-OMe or 2'-MOE) ribonucleotides bearing nucleobases adenine, cytosine, guanidine and uracil, respectively; letter "T" refers to thymdine or deoxythymidine; and letter "s" refers to a phosphorus-containing linkage (such as a phosphorothioate (PS) linkage, a phosphodiester linkage, or a phosphorodithioate linkage). As used in Table 2, "(GalNAc)" refers to a targeting moiety such as one comprising a GalNAc or a derivative thereof. As used in Table 2, "(GalNAc)" also encompasses a targeting moiety that comprises multiple GalNAc structures or derivatives thereof such as a dimer, trimer, a tetramer of GalNAc or derivatives thereof, including the GalNAc structures described in Table 1. In some embodiments, "s" represents a phosphorothioate (PS) linkages. As disclosed herein, the nucleotide sequences and modification patterns encompass all length, structure, and type of RNAs or fragments thereof, CRISPR guide RNAs, e.g. sgRNAs, dual guide RNAs, or mRNAs. For example, nucleotide sequences and modification patterns as described in Table 2 above may indicate RNA sequences and modification patterns in a single guide RNA, a dual guide RNA, a nuclease mRNA, or any fragment or segment thereof.

Non-limiting examples of guide RNAs conjugated to receptor targeting moeity and coupling sequences compris-ing a targeting moiety are provided in Table 3 below. The (GalNAc) conjugate moiety is covalently conjugated to the 3' and/or 5' end of the guide RNA and/or covalently conjugated to the 3' and/or 5' end of the guide RNA with additional nucleotide spacer(s) between the ligand and guide RNA. The guide RNA conjugates 3-1 and 3-2 (Table 3) are representative examples of direct conjugation of the GalNAc ligand to the guide RNA. The guide RNA conjugates 3-10 to 3-21 where the GalNAc ligand is conjugated to the 3'/5'-terminal of the additional 3' and/or 5' nucleotide spacers. Guide RNA strand is extended to 3'-end or to the 5'-end or both ends with desired number of nucleotides. (GalNAc) is conjugated to the 3'-end, 5'-end or both ends of oligonucleotide that is (are) complementary to the extended nucleotides on the guide RNA strand to form complementary duplex leading to a single chemical entity. The conjugate designs 3-3 to 3-8 are constructed from extended nucleotide spacers and the spacer complementary strand carrying a GalNAc ligand. As used in Table 3, uppercase A, C, G and U refer to ribonucleotides bearing nucleobases adenine, cytosine, guanidine and uracil, respectively; lowercase a, c, g and u refer to modified (e.g., 2'-OMe or 2'-MOE) ribonucleotides bearing nucleobases adenine, cytosine, guanidine and uracil, respectively; letter "T" refers to thymdine or deoxythymidine; and letter "s" refers to a phosphate linkage (such as a phosphorothioate (PS) linkage, a phosphodiester linkage, or a phosphorodithioate linkage). In some embodiments, "s" represents a PS linkages. As used in Table 3, "(GalNAc)" refers to a targeting moiety such as one comprising a GalNAc or a derivative thereof. As used in Table 3, "(GalNAc)" also encompasses a targeting moiety that comprises multiple GalNAc structures or derivatives thereof such as a dimer, trimer, a tetramer of GalNAc or derivatives thereof.

TABLE 3

Guide RNA GalNAc conjugate designs

| Conjugate No. | SEQ ID No | RNA GalNAc conjugate designs |
|---|---|---|
| 3-1 | 67 | 5'-gsgscsUGAUGAG GCCGCACAUG GUUUUAGAgc uagaaauagc AAGUUAAAAU AAGGCUAGUC CGUUAUCAac uugaaaaagu ggcaccgagu cggugcuususus-(GalNAc3)-3' |
| 3-2 | 68 | 5'-gsgscsUsGAUsGAG GCCGCsACsAUG GUUUUsAGAgc usagaaausagc AAGUUsAAAAUs AAGGCUsAGUC CGUUsAUCsAac uusgaaaaagus ggcaccgagu cggugcuuusus-(GalNAc3)-3' |
| 3-3 | 69 | 5'-gsgscsUGAUGAG GCCGCACAUG GUUUUAGAgc uagaaauagc AAGUUAAAAU AAGGCUAGUC CGUUAUCAac uugaaaaagu ggcaccgagu cggugcusususuuuccuuuguuuuugsc3' |
| | 71 | 3'gsgsaaacaaaaacgs(GalNAc) |
| 3-4 | 70 | 5'-cscuuuuuuuguugsgscsUGAUGAG GCCGCACAUG GUUUUAGAgc uagaaauagc AAGUUAAAAU AAGGCUAGUC CGUUAUCAac uugaaaaagu ggcaccgagu cggugcusususu 3'gsgsaaacaaaaacgs(GalNAc)     3'gsgsaaacaaaaacgs(GalNAc) (SEQ ID NO 71)                            (SEQ ID NO 72) |
| 3-5 | 73 | 5'-cscuuuguuuuugcuuggscsUGAUGAG GCCGCACAUG GUUUUAGAgc uagaaauagc AAGUUAAAAU AAGGCUAGUC CGUUAUCAac uugaaaaagu ggcaccgagu cggugcusususuuuccuuuguuuuugsc-3' 3'gsgsaaacaaaaacgs(GalNAc)     3'gsgsaaacaaaaacgs(GalNAc) (SEQ ID NO 74)                            (SEQ ID NO 75) |
| 3-6 | 76 | 5'-gsgscsUGAUGAG GCCGCACAUG GUUUUAGAgc uagaaauagc AAGUUAAAAU AAGGCUAGUC CGUUAUCAac uugaaaaagu ggcaccgagu cggugcusususuTTTccuuuguuuuugsc3' |
| | 77 | 3'gsgsaaacaaaaacgs(GalNAc) |
| 3-7 | 78 | 5'-cscuuuguuuuugcTTTgsgscsUGAUGAG GCCGCACAUG GUUUUAGAgc uagaaauagc AAGUUAAAAU AAGGCUAGUC CGUUAUCAac uugaaaaagu ggcaccgagu cggugcusususu |
| | 79 | 3'gsgsaaacaaaaacgs(GalNAc) |
| 3-8 | 80 | 5'-cscuuuguuuuugcTTTgsgscsUGAUGAG GCCGCACAUG GUUUUAGAgc uagaaauagc AAGUUAAAAU AAGGCUAGUC CGUUAUCAac uugaaaaagu ggcaccgagu cggugcusususuTTTccuuuguuuuugsc-3' 3'gsgsaaacaaaaacgs(GalNAc)     3'gsgsaaacaaaaacgs(GalNAc) (SEQ ID NO 81)                            (SEQ ID NO 82) |
| 3-9 | 83 | 5'-(GalNAc)uuugsgscsUGAUGAG GCCGCACAUG GUUUUAGAgc uagaaauagc AAGUUAAAAU AAGGCUAGUC CGUUAUCAac uugaaaaagu ggcaccgagu cggugcuususus-(GalNAc3)-3' |
| 3-10 | 84 | 5'-(GalNAc)uuugsgscsUsGAUsGAG GCCGCsACsAUG GUUUUsAGAgc usagaaausagc AAGUUsAAAAUs AAGGCUSAGUC CGUUsAUCsAac uusgaaaaagus ggcaccgagu cggugcuuusus-(GalNAc3)-3' |
| 3-11 | 85 | 5'-(GalNAc)uuugsgscsUGAUGAG GCCGCACAUG GUUUUAGAgc uagaaauagc AAGUUAAAAU AAGGCUAGUC CGUUAUCAac uugaaaaagu ggcaccgagu cggugcusususu-3' |
| 3-12 | 86 | 5'-(GalNAc)uuugsgscsUsGAUsGAG GCCGCsACsAUG GUUUUsAGAgc usagaaausagc AAGUUsAAAAUs AAGGCUSAGUC CGUUsAUCsAac uusgaaaaagus ggcaccgagu cggugcuuusus-3' |
| 3-13 | 87 | 5'-(GalNAc)TTTgsgscsUGAUGAG GCCGCACAUG GUUUUAGAgc uagaaauagc AAGUUAAAAU AAGGCUAGUC CGUUAUCAac uugaaaaagu ggcaccgagu cggugcuususus-(GalNAc3)-3' |
| 3-14 | 88 | 5'-(GalNAc)TTTgsgscsUsGAUsGAG GCCGCsACsAUG GUUUUsAGAgc usagaaausagc AAGUUsAAAAUs AAGGCUSAGUC CGUUsAUCsAac uusgaaaaagus ggcaccgagu cggugcuuusus-(GalNAc3)-3' |

TABLE 3-continued

Guide RNA GalNAc conjugate designs

| Conjugate No. | SEQ ID No | RNA GalNAc conjugate designs |
|---|---|---|
| 3-15 | 89 | 5'-(GalNAc)TTTgsgscsUGAUGAG GCCGCACAUG GUUUUAGAgc uagaaauagc AAGUUAAAAU AAGGCUAGUC CGUUAUCAac uugaaaaagu ggcaccgagu cggugcusususu-3' |
| 3-16 | 90 | 5'-(GalNAc)TTTgsgscsUsGAUsGAG GCCGCsACsAUG GUUUUsAGAgc usagaaausagc AAGUUsAAAAUs AAGGCUSAGUC CGUUsAUCsAac uusgaaaaagus ggcaccgagu cggugcuususus-3' |
| 3-17 | 91 | 5'-gsgscsUGAUGAG GCCGCACAUG GUUUUAGAgc uagaaauagc AAGUUAAAAU AAGGCUAGUC CGUUAUCAac uugaaaaagu ggcaccgagu cggugcuususususTTTs(GalNAc3)-3' |
| 3-18 | 92 | 5'-gsgscsUsGAUsGAG GCCGCsACsAUG GUUUUsAGAgc usagaaausagc AAGUUsAAAAUs AAGGCUSAGUC CGUUsAUCsAac uusgaaaaagus ggcaccgagu cggugcuuususTTTs-(GalNAc3)-3' |
| 3-19 | 93 | 5'-gsgscsUGAUGAG GCCGCACAUG GUUUUAGAgc uagaaauagc AAGUUAAAAU AAGGCUAGUC CGUUAUCAac uugaaaaagu ggcaccgagu cggugcuusususssususuUUUs(GalNAc3)-3' |
| 3-20 | 94 | 5'-gsgscsUsGAUsGAG GCCGCsACsAUG GUUUUsAGAgc usagaaausagc AAGUUsAAAAUs AAGGCUSAGUC CGUUsAUCsAac uusgaaaaagus ggcaccgagu cggugcuuusussususuUUUs-(GalNAc3)-3' |
| 3-21 | 95 | 5'-gsgscsUGAUGAG GCCGCACAUG GUUUUAGAgc uagaaauagc AAGUUAAAAU AAGGCUAGUC CGUUAUCAac uugaaaaagu ggcaccgagu cggugcuususussususuuuus(GalNAc3)-3' |
| 3-22 | 96 | 5'-aaaaaaaaaaaaaaaaaTTTgsgscsUGAUGAG GCCGCACAUG GUUUUAGAgc uagaaauagc AAGUUAAAAU AAGGCUAGUC CGUUAUCAac uugaaaaagu ggcaccgagu cggugcusususuTTTaaaaaaaaaaaaaaaa-3' |
|  | 97 | 3'-ususuuuuuuuuuuuuuus(GalNAc)-3'   3'-ususuuuuuuuuuuuuuu(GalNAc)-5' |
| 3-23 | 98 | 5'-gsgscsUGAUGAG GCCGCACAUG GUUUUAGAgc uagaaauagc AAGUUAAAAU AAGGCUAGUC CGUUAUCAac uugaaaaagu ggcaccgagu cggugcusususuaaaaaaaaaaaaaaaaaa-3' |
|  | 99 | 3'-ususuuuuuuuuuuuuuuu(GalNAc)-3' |
| 3-24 | 100 | 5'-gsgscsUGAUGAG GCCGCACAUG GUUUUAGAgc uagaaauagc AAGUUAAAAU AAGGCUAGUC CGUUAUCAac uugaaaaagu ggcaccgagu cggugcusususuAAAAAAAAAAAAAAAAAAAA-3' |
|  | 101 | 3'-ususuuuuuuuuuuuuuuus(GalNAc)-5' |
| 3-25 | 102 | 5'-gsgscsUGAUGAG GCCGCACAUG GUUUUAGAgc uagaaauagc AAGUUAAAAU AAGGCUAGUC CGUUAUCAac uugaaaaagu ggcaccgagu cggugcusususuAAAAAAAAAAAAAAAAAAAA-3' |
|  | 103 | 3'-ususuuuuuuuuuuuuuuuuus(GalNAc)-5' |

As disclosed herein, the nucleotide sequences and modification patterns encompass all length, structure, and type of RNAs or fragments thereof, CRISPR guide RNAs, e.g. sgRNAs, dual guide RNAs, or mRNAs. For example, nucleotide sequences and modification patterns as described in Table 3 above may indicate RNA sequences and modification patterns in a single guide RNA, a dual guide RNA, a nuclease mRNA, or any fragment or segment thereof.

A targeting moiety can be attached to a nucleic acid described herein via a carrier. The carriers may include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier monomer into the backbone, e.g., the phosphate, or modified phosphate, e.g., sulfur containing, backbone, of an oligonucleotide. A "tethering attachment point" (TAP) in refers to an atom of the carrier monomer, e.g., a carbon atom or a heteroatom (distinct from an atom which provides a backbone attachment point), that connects a selected moiety. The selected moiety can be, e.g., a carbohydrate, e.g. monosaccharide, disaccharide, trisaccharide, tetrasaccharide, oligosaccharide and polysaccharide. Optionally, the selected moiety is connected by an intervening tether to the carrier monomer. Thus, the carrier will often include a functional group, e.g., an amino group, or generally, provide a bond, that is suitable for incorporation or tethering of another chemical entity, e.g., a ligand to the constituent atom. Representative U.S. patents that teach the preparation of conjugates of nucleic acids include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873;

5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; contents of which are herein incorporated in their entireties by reference.

A targeting moiety can be attached to an active agent, e.g. a guide RNA, via a linker. A linker may be bound to one or more active agents and a targeting moiety ligand to form a conjugate, wherein the conjugate releases at least one active agent, e.g. a guide RNA or guide RNA-Cas complex, upon delivery to a target cell. The linker may be attached to the targeting moiety and the active agent by functional groups independently selected from an ester bond, disulfide, amide, acylhydrazone, ether, carbamate, carbonate, and urea. Alternatively the linker can be attached to either the targeting moiety or the active agent by a non-cleavable group such as provided by the conjugation between a thiol and a maleimide, an azide and an alkyne. In some embodiments, a targeting moiety comprises one or more linkers. In some embodiments, one or more linkers as described herein connect a portion of the targeting moiety to a different portion of the targeting moiety. For example, a targeting moiety can comprise 2, 3, 4, 5 or more GalNAc structures or derivatives thereof that are connected by one or more linkers. In some embodiments, two or more GalNAc structures or derivatives thereof in a targeting moiety are connected by one or more non-cleavable linkers. In some embodiments, a herein described conjugate comprises an active agent that is directly connected to a sugar moiety of the targeting moiety.

The linkers can each independently comprises one or more functional groups selected from the group consisting of ethylene glycol, propylene glycol, amide, ester, ether, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl. In some embodiments, a linker independently comprises phosphate, phosphorothioate, amide, ether, oxime, hydrazine or carbamate. As contemplated herein it should be understood that, in some embodiments, a targeting conjugate of Formula (V), (VI), (VIa) or (VIb) comprises a linker described herein. For example, any of the groups R and $L^1$-$L^{12}$ can comprise one or more linkers.

In some embodiments, the linker can independently comprise a $C_1$-$C_{10}$ straight chain alkyl, $C_1$-$C_{10}$ straight chain O-alkyl, $C_1$-$C_{10}$ straight chain substituted alkyl, $C_1$-$C_{10}$ straight chain substituted O-alkyl, $C_4$-$C_{13}$ branched chain alkyl, $C_4$-$C_{13}$ branched chain O-alkyl, $C_2$-$C_{12}$ straight chain alkenyl, $C_2$-$C_{12}$ straight chain O-alkenyl, aralkyl, $C_3$-$C_{12}$ straight chain substituted alkenyl, $C_3$-$C_{12}$ straight chain substituted O-alkenyl, polyethylene glycol, polylactic acid, polygly colic acid, poly(lactide-co-glycolide), polycarprolactone, polycyanoacrylate, ketone, aryl, heterocyclic, succinic ester, amino acid, aromatic group, ether, crown ether, urea, thiourea, amide, purine, pyrimidine, bypiridine, indole derivative acting as a cross linker, chelator, aldehyde, ketone, bisamine, bis alcohol, heterocyclic ring structure, azirine, disulfide, thioether, hydrazone and combinations thereof. For example, the linker can be a $C_3$ straight chain alkyl or a ketone. The alkyl chain of the linker can be substituted with one or more substituents or heteroatoms. In some embodiments, the alkyl chain of the linker may optionally be interrupted by one or more atoms or groups selected from —O—, —C(═O)—, —NR, —O—C(═O)—NR—, —S—, —S—S—.

In some embodiments, the linker may be cleavable and is cleaved to release the active agent. The cleavable functionality may be hydrolyzed in vivo or may be designed to be hydrolyzed enzymatically, for example by Cathepsin B. A "cleavable" linker, as used herein, refers to any linker which can be cleaved physically or chemically. Examples for physical cleavage may be cleavage by light, radioactive emission or heat, while examples for chemical cleavage include cleavage by re-dox-reactions, hydrolysis, pH-dependent cleavage.

Linkers may comprise a direct bond or an atom such as oxygen or sulfur, a unit such as $NR^1$, C(O), C(O)NH, SO, SO2, SO2NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO2, N(R'), C(O), substituted or unsubstituted aryl, substituted or unsubstituted heteroaryl, substituted or unsubstituted heterocyclic; where R' is hydrogen, acyl, aliphatic or substituted aliphatic. In one embodiment, the linker is between 1-24 atoms, preferably 4-24 atoms, preferably 6-18 atoms, more preferably 8-18 atoms, and most preferably 8-16 atoms.

In one embodiment, the linker is —[(P-Q"-R)q-X—(P'Q'"—R')q']q"-T-, wherein P, R, T, P', R' and T are each independently for each occurrence absent, CO, NH, O, S, OC(O), NHC(O), CH2, CH2NH, CH2O; NHCH(Ra)C(O), —C(O)—CH(Ra)—NH—, CH═N—O,

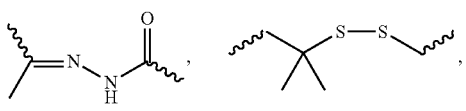

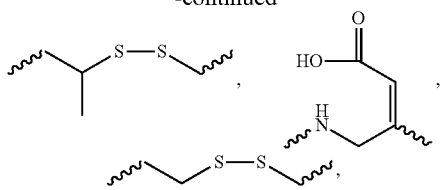

or heterocyclyl; Q" and Q'" are each independently for each occurrence absent, (CH2)n-, C(R1)(R2)(CH2)n-, (CH2)n-, —C(R1)(R2)-, —(CH2CH2O)mCH2CH2-, or —(CH2CH2O)mCH2CH2NH—; X is absent or a cleavable linking group; Ra is H or an amino acid side chain; R1 and R2 are each independently for each occurrence H, CH3, OH, SH or N(RN)2; RN is independently for each occurrence H, methyl, ethyl, propyl, isopropyl, butyl or benzyl; q, q' and q" are each independently for each occurrence 0-20 and wherein the repeating unit can be the same or different; n is independently for each occurrence 1-20; and m is independently for each occurrence 0-50.

In one embodiment, the linker comprises at least one cleavable linking group. In certain embodiments, the linker is a branched linker. The branchpoint of the branched linker may be at least trivalent, but may be a tetravalent, pentavalent or hexavalent atom, or a group presenting such multiple valencies. In certain embodiments, the branchpoint is, N, N(O) C, —O—C, —S—C, —SS—C, —C(O)N(O)—C, —OC(O)N(O)—C, —N(O)C(O)—C, or —N(O)C(O)O—C; wherein Q is independently for each occurrence H or optionally substituted alkyl. In other embodiment, the branchpoint is glycerol or glycerol derivative.

In one embodiment, a linker may be cleaved by an enzyme. As a non-limiting example, the linker may be a polypeptide moiety, e.g. AA in WO2010093395 to Govindan, the content of which is incorporated herein by reference in its entirety; that is cleavable by intracellular peptidase. Govindan teaches AA in the linker may be a di, tri, or tetrapeptide such as Ala-Leu, Leu-Ala-Leu, and Ala-Leu-Ala-Leu. In another example, the cleavable linker may be a branched peptide. The branched peptide linker may comprise two or more amino acid moieties that provide an enzyme cleavage site. Any branched peptide linker disclosed in WO 1998019705 to Dubowchik, the content of which is incorporated herein by reference in its entirety, may be used as a linker in the conjugate of the present disclosure. As another example, the linker may comprise a lysosomally cleavable polypeptide disclosed in U.S. Pat. No. 8,877,901 to Govindan et al., the content of which is incorporated herein by reference in its entirety. As another example, the linker may comprise a protein peptide sequence which is selectively enzymatically cleavable by tumor associated proteases, such as any Y and Z structures disclosed in U.S. Pat. No. 6,214,345 to Firestone et al, the content of which is incorporated herein by reference in its entirety.

In some embodiments, a linker may comprise a cleavable linking group. A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum). Cleavable linking groups may be susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular RNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

In some embodiments, a linker may comprise a phosphate based cleavable linking group. Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups (i.e., phosphorus-containing linkages or phosphorus-containing linkers) are —P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. In some embodiments, phosphate-based linking groups are OP(O)(OH) O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—S—. In some embodiments, a phosphate-based linker is O—P(O)(OH)—O—.

In some embodiments, a linker may comprise an acid cleavable linking group. Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

In some embodiments, a linker may comprise a ester based linking group. Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

In some embodiments, a linker may comprise a peptide based linking group. Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

In some embodiments, a herein described conjugate comprises a structure of Formula (I),

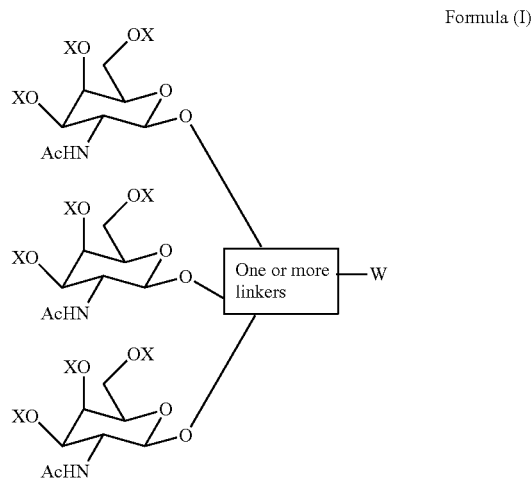

Formula (I)

wherein each X is independently H or a protecting group, and W represents an active agent or a coupling sequence. The one or more linkers of Formula (I) can each independently comprises a linker as described in this disclosure. In some embodiments, each of the protecting group of Formula (I) is independently selected from: 4-acetoxy-2,2-dimethylbutanoyl (ADMB), 3-(2-Hydroxyphenyl)-3,3-dimethylpropanoate (DMBPP), 3-(2-hydroxy-4,6-dimethylphenyl)-3,3-dimethylpropanoate groups (TMBPP), methylsulfonylethoxycarbonyl (Msc), 2,2-dimethyltrimethylene (DMTM) phosphate, 2-pyridylmethyl, ethyl mandelate, (phenylthiomethyl)benzyl, pentafluoropropionyl (PFP), benzoyl (Bz), acetyl (Ac), bacillosamine (Bac), benzyl (Bn), 1-benzenesulfinylpiperidine (BSP), tert-butoxycarbonyl (Boc), benzylidene acetal, propargyl, naphthylpropargyl, carbonate, dichloroacetyl, tert-butylsilylene, tetraisopropyldisiloxanylidene (TIPDS), methoxybenzyl (PMB), xylylene, and p-methoxyphenyl (MP). Exemplary protecting groups are further disclosed in Guo et al., Molecules 2010, 15, 7235-7265, which is hereby incorporated by reference in its entirety. In some embodiments, X is H. In some embodiments, each X is independently selected from H and Bz. In some embodiments of Formula (I), W is an active agent. In some embodiments, W is a nucleic acid. In some embodiments, W is a gRNA. In some embodiments, W is a single-stranded, double-stranded, partially double-stranded or hairpin stem-loop nucleic acid. In some embodiments of Formula (I), W is a coupling sequence. In some embodiments, W comprises an RNA or DNA sequence. W can comprise one or more modified DNA or RNA bases. The nucleobases can comprise any chemical modifications as described herein. In some embodiments, the nucleobases include a 2'-OH or 2'-OMe modification. For example, W may comprise one or more 2'-OMe modified adenine, cytosine, guanidine and uracil, referred to as (a) (c), (g), or (u). In some embodiments, a modified RNA, e.g. a gRNA or mRNA, includes at least 1, 2, 3, 4, 5, 6, 7, 8, 9, 10, 11, 12, 13, 14, 15, 20, 25, 30, 35, 40, 50 or more modified nucleobases. In some embodiments, a modified RNA comprises one or more modified nucleobases near the 5' end, near the 3' end, or in the middle of the sequence. The modified nucleobases within a modified RNA may or may not be contiguous. In some embodiments, a modified RNA comprises one or more 2'-OMe modifications scattered along the length of the sequence. In some embodiments, a modified RNA comprises one or more 2'OH modifications scattered along the length of the sequence. In some embodiments, a modified RNA comprises alternating 2'-OH and 2'OMe modifications. In some embodiments, W comprises (A)n, (T)n, (U)n, (a)n, or (u)n, wherein n is an integer no less than 3, wherein a is 2'-O-methyladenosine (2'-OMe A), and wherein u is 2'-O-methyluridine (2'-OMe-U). In some embodiments, W comprises (u)n, wherein n is an integer from 3 to 50 (SEQ ID NO: 118). In some embodiments, W comprises (u)n, wherein n is an integer from 3 to 20 (SEQ ID NO: 119) or 3 to 15 (SEQ ID NO: 120). In some embodiments, W comprises one or more nucleotide sequences that are complementary to a coupling sequence. In some embodiments, W comprises one or more guanines or cytidines. In some embodiments, W comprises at least 1, 2, 3, 4, 5, 6, 7, 8, 9, 10, 11, 12, 13, 14, 15, 20, 25, 30, 35, 40, 50 or more guanines or cytidines. In some embodiments, the one or more guanines or cytidines are complementary to one or more cytindines or guanines in a coupling sequence. In some embodiments, the guanines or cytidines are at the terminals of W or the coupling sequence. Not intended to be bound by any theory, it is contemplated that the guaninies-cytidine pairing forms "GC locks" or "CG locks" that would increase binding affinity. The guanines and/or cytidines in W or a coupling sequence may or may not be contiguous and may comprise any one of the chemical modifications as described herein, e.g. a 2'-OMe or 2'-OH modification.

In some embodiments, a conjugate of Formula (I) comprises a structure of Formula (Ia),

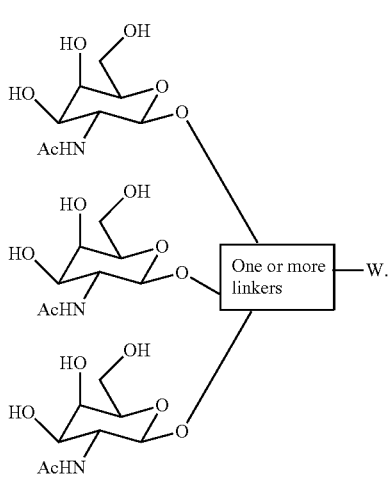

Formula (Ia)

In some embodiments, a conjugate of Formula (I) comprises a structure of Formula (Ib),

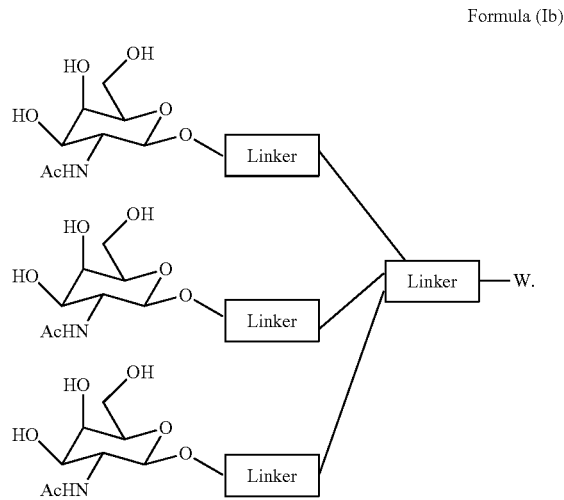

Formula (Ib)

In some embodiments, a herein described conjugate comprises a structure of Formula (II),

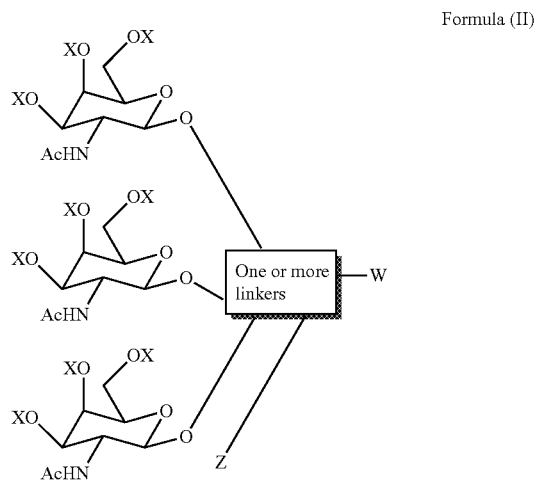

Formula (II)

wherein each X is independently H or a protecting group, Z is modified or unmodified $C_5$ or $C_6$ monosaccharide, and W represents an active agent or a coupling sequence. The one or more linkers of Formula (II) can each independently comprises a linker as described in this disclosure. In some embodiments, each of the protecting group of Formula (II) is independently selected from: 4-acetoxy-2,2-dimethylbutanoyl (ADMB), 3-(2-Hydroxyphenyl)-3,3-dimethylpropanoate (DMBPP), 3-(2-hydroxy-4,6-dimethylphenyl)-3,3-dimethylpropanoate groups (TMBPP), methylsulfonylethoxycarbonyl (Msc), 2,2-dimethyltrimethylene (DMTM) phosphate, 2-pyridylmethyl, ethyl mandelate, (phenylthiomethyl)benzyl, pentafluoropropionyl (PFP), benzoyl (Bz), acetyl (Ac), bacillosamine (Bac), benzyl (Bn), 1-benzenesulfinylpiperidine (BSP), tert-butoxycarbonyl (Boc), benzylidene acetal, propargyl, naphthylpropargyl, carbonate, dichloroacetyl, tert-butylsilylene, tetraisopropyl-disiloxanylidene (TIPDS), methoxybenzyl (PMB), xylylene, and p-methoxyphenyl (MP). In some embodiments, X is H.

In some embodiments, each X is independently selected from H and Bz. In some embodiments of Formula (II), Z is galactose or mannose. In some embodiments of Formula (II), Z is GalNAc. In some embodiments of Formula (II), W is an active agent. In some embodiments, W is a nucleic acid. In some embodiments, W is a gRNA. In some embodiments, W is a single-stranded, double-stranded, partially double-stranded or hairpin stem-loop nucleic acid. In some embodiments of Formula (II), W is a coupling sequence. In some embodiments, W comprises an RNA or DNA sequence. In some embodiments, W comprises (A)n, (T)n, (U)n, (a)n, or (u)n, wherein n is an integer no less than 3, wherein a is 2'-O-methyladenosine (2'-OMe A), and wherein u is 2'-O-methyluridine (2'-OMe-U). In some embodiments, W comprises (u)n, wherein n is an integer from 3 to 50 (SEQ ID NO: 118). In some embodiments, W comprises (u)n, wherein n is an integer from 3 to 20 (SEQ ID NO: 119) or 3 to 15 (SEQ ID NO: 120).

In some embodiments, a conjugate of Formula (II) comprises a structure of Formula (IIa),

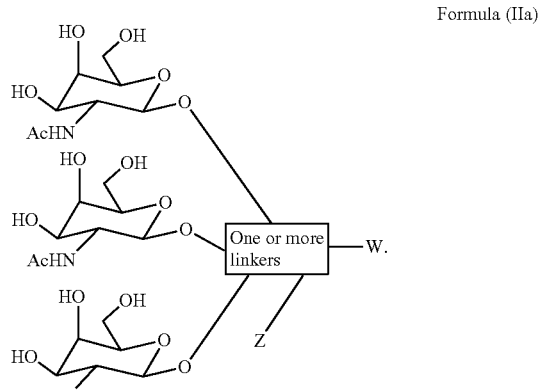

Formula (IIa)

In some embodiments, a conjugate of Formula (II) comprises a structure of Formula (IIb),

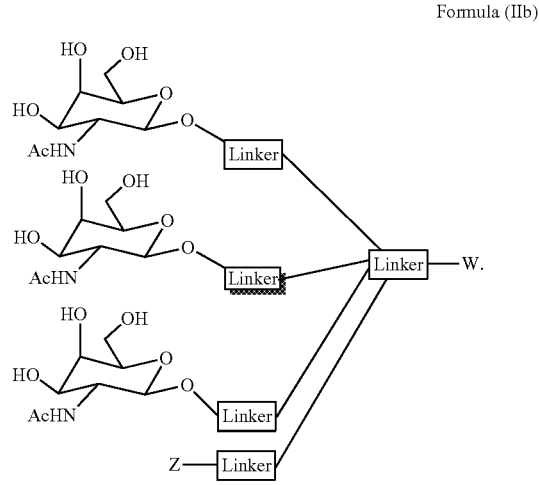

Formula (IIb)

In some embodiments, a conjugate of Formula (II) comprises a structure of Formula (IIc),

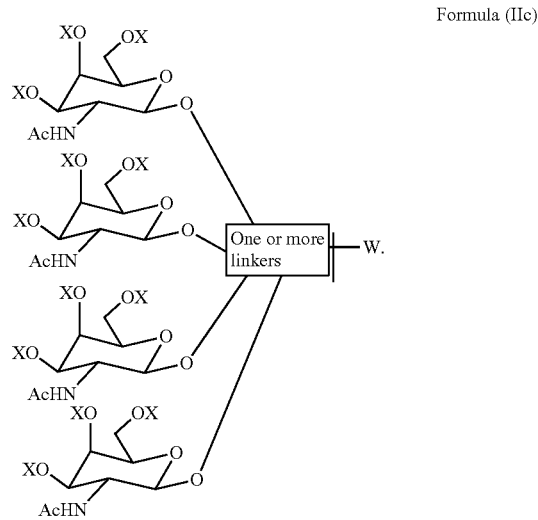

Formula (IIc)

In some embodiments, a herein described conjugate comprises a structure of Formula (III),

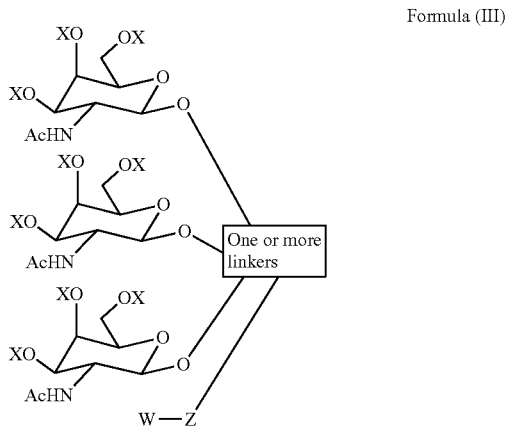

Formula (III)

wherein each X is independently H or a protecting group, Z is modified or unmodified $C_5$ or $C_6$ monosaccharide, and W represents an active agent or a coupling sequence. The one or more linkers of Formula (III) can each independently comprises a linker as described in this disclosure. In some embodiments, each of the protecting group of Formula (III) is independently selected from: 4-acetoxy-2,2-dimethylbutanoyl (ADMB), 3-(2-Hydroxyphenyl)-3,3-dimethylpropanoate (DMBPP), 3-(2-hydroxy-4,6-dimethylphenyl)-3,3-dimethylpropanoate groups (TMBPP), methylsulfonylethoxycarbonyl (Msc), 2,2-dimethyltrimethylene (DMTM) phosphate, 2-pyridylmethyl, ethyl mandelate, (phenylthiomethyl)benzyl, pentafluoropropionyl (PFP), benzoyl (Bz), acetyl (Ac), bacillosamine (Bac), benzyl (Bn), 1-benzenesulfinylpiperidine (BSP), tert-butoxycarbonyl (Boc), benzylidene acetal, propargyl, naphthylpropargyl, carbonate, dichloroacetyl, tert-butylsilylene, tetraisopropyldisiloxanylidene (TIPDS), methoxybenzyl (PMB), xylylene, and p-methoxyphenyl (MP). In some embodiments, X is H. In some embodiments, each X is independently selected from H and Bz. In some embodiments of Formula (III), Z is galactose or mannose. In some embodiments of Formula (III), Z is GalNAc. In some embodiments of Formula (III), W is an active agent. In some embodiments, W is a nucleic acid. In some embodiments, W is a gRNA. In some embodiments, W is a single-stranded, double-stranded, partially double-stranded or hairpin stem-loop nucleic acid. In some embodiments of Formula (III), W is a coupling sequence. In some embodiments, W comprises an RNA or DNA sequence. In some embodiments, W comprises (A)n, (T)n, (U)n, (a)n, or (u)n, wherein n is an integer no less than 3, wherein a is 2'-O-methyladenosine (2'-OMe A), and wherein u is 2'-O-methyluridine (2'-OMe-U). In some embodiments, W comprises (u)n, wherein n is an integer from 3 to 50 (SEQ ID NO: 118). In some embodiments, W comprises (u)n, wherein n is an integer from 3 to 20 (SEQ ID NO: 119) or 3 to 15 (SEQ ID NO: 120).

In some embodiments, a conjugate of Formula (III) comprises a structure of Formula (IIIa),

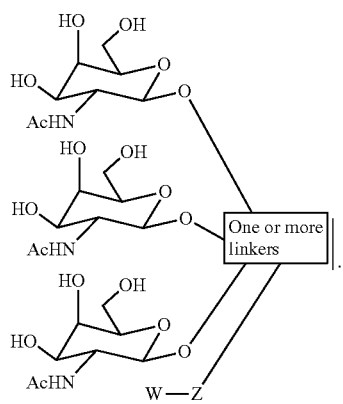

Formula (IIIa)

In some embodiments, a conjugate of Formula (III) comprises a structure of Formula (IIIb),

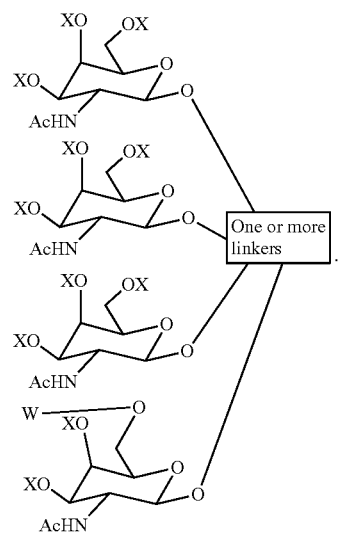

Formula (IIIb)

In some embodiments, a conjugate of Formula (III) comprises a structure of Formula (IIIc),

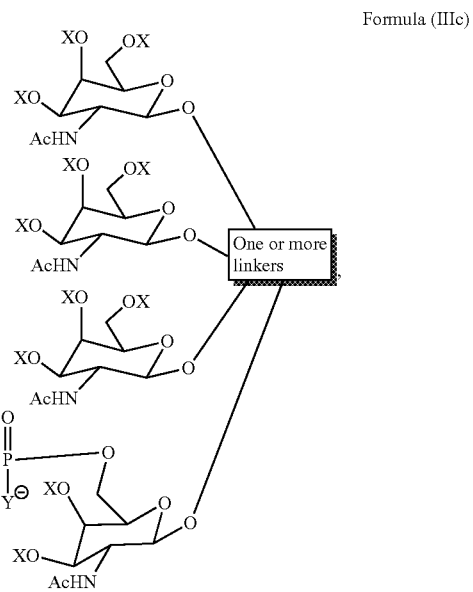

Formula (IIIc)

wherein Y is O or S.

In some embodiments, a conjugate of Formula (III) comprises a structure of Formula (IIId),

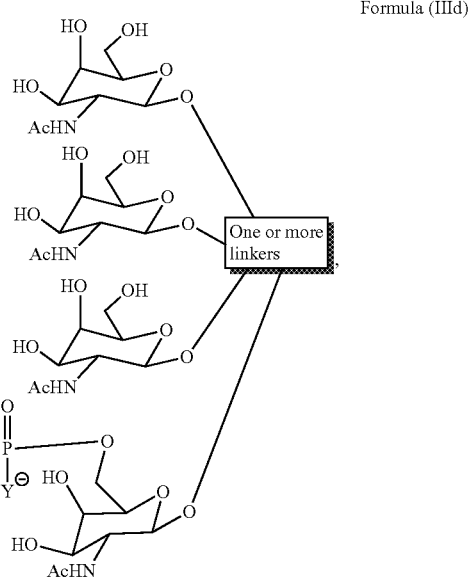

Formula (IIId)

wherein Y is O or S.

In some embodiments, a conjugate of Formula (III) comprises a structure of Formula (IIIe),

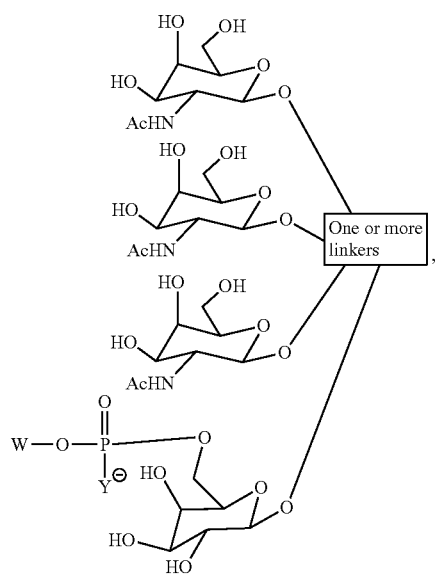

Formula (IIIe)

wherein Y is O or S.

In some embodiments, a herein described conjugate comprises a structure of Formula (IV),

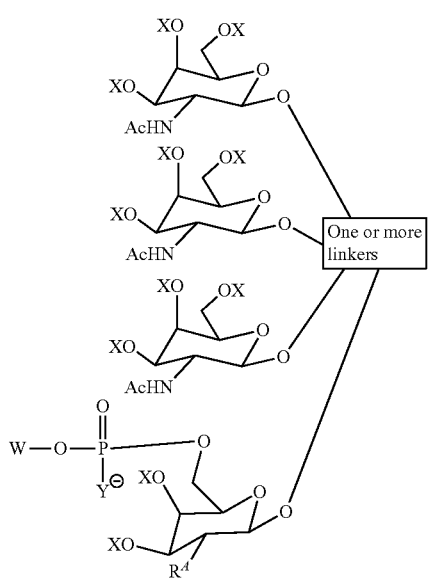

Formula (IV)

wherein each X is independently H or a protecting group, $R^A$ is —OX or —NHAc, Y is O or S, and W represents an active agent or a coupling sequence. The one or more linkers of Formula (IV) can each independently comprises a linker as described in this disclosure. In some embodiments, each of the protecting group of Formula (IV) is independently selected from: 4-acetoxy-2,2-dimethylbutanoyl (ADMB), 3-(2-Hydroxyphenyl)-3,3-dimethylpropanoate (DMBPP), 3-(2-hydroxy-4,6-dimethylphenyl)-3,3-dimethylpropanoate groups (TMBPP), methylsulfonylethoxycarbonyl (Msc), 2,2-dimethyltrimethylene (DMTM) phosphate, 2-pyridylmethyl, ethyl mandelate, (phenylthiomethyl)benzyl, pentafluoropropionyl (PFP), benzoyl (Bz), acetyl (Ac), bacillosamine (Bac), benzyl (Bn), 1-benzenesulfinylpiperidine (BSP), tert-butoxycarbonyl (Boc), benzylidene acetal, propargyl, naphthylpropargyl, carbonate, dichloroacetyl, tert-butylsilylene, tetraisopropyldisiloxanylidene (TIPDS), methoxybenzyl (PMB), xylylene, and p-methoxyphenyl (MP). In some embodiments, X is H. In some embodiments, each X is independently selected from H and Bz. In some embodiments, $R^A$ is —OX. In some embodiments, $R^A$ is —OH. In some embodiments, $R^A$ is —NHAc. In some embodiments of Formula (IV), W is an active agent. In some embodiments, W is a nucleic acid. In some embodiments, W is a gRNA. In some embodiments, W is a single-stranded, double-stranded, partially double-stranded or hairpin stem-loop nucleic acid. In some embodiments of Formula (IV), W is a coupling sequence. In some embodiments, W comprises an RNA or DNA sequence. In some embodiments, W comprises (A)n, (T)n, (U)n, (a)n, or (u)n, wherein n is an integer no less than 3, wherein a is 2'-O-methyladenosine (2'-OMe A), and wherein u is 2'-O-methyluridine (2'-OMe-U). In some embodiments, W comprises (u)n, wherein n is an integer from 3 to 50 (SEQ ID NO: 118). In some embodiments, W comprises (u)n, wherein n is an integer from 3 to 20 (SEQ ID NO: 119) or 3 to 15 (SEQ ID NO: 120).

In some embodiments, a conjugate of Formula (IV) comprises a structure of 1-1, 1-2, 1-5, 1-6, 1-9, 1-10, 1-11, or 1-12 as shown in Table 1.

In some embodiments of Formula (I), Formula (Ia), Formula (II), Formula (IIa), Formula (IIc), Formula (III), Formula (IIIa), Formula (IIIb), Formula (IIIc), Formula (IIId), Formula (IIIe), or Formula (IV), wherein the "one or more linkers" referenced in the box of the foregoing formulas comprises a structure selected from the group consisting of:

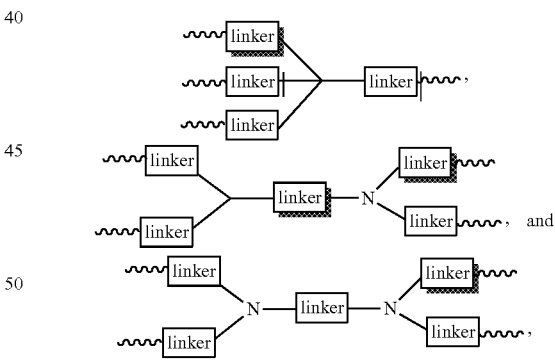

wherein each linker is independent. In some embodiments of Formula (I), Formula (Ia), Formula (Ib), Formula (II), Formula (IIa), Formula (IIb), Formula (IIc), Formula (III), Formula (IIIa), Formula (IIIb), Formula (IIIc), Formula (IIId), Formula (IIIe), or Formula (IV), wherein each of the linkers independently has a structure of -$(L^1)_{k1}$-$(L^2)_{k2}$-$(L^3)_{k3}$-$(L^4)_{k4}$-, wherein each of k1, k2, k3, and k4 is independently 0, 1 or 2, and each of the $L^1$, $L^2$, $L^3$ and $L^4$ is independently selected from oxo, ester, amide, amino, $C_1$-$C_3$ alkylene, and —$(CH_2$—$CH_2$—$O)_{1-3}$—. In some embodiments, the sum of k1, k2, k3, and k4 is an integer larger than or equal to 1. In some embodiments, the sum of k1, k2, k3, and k4 is an integer larger than or equal to 2. As one of ordinary skill in the art would recognize "N" references nitrogen and "~~~" implies an attachment point.

In some embodiments of Formula (I), Formula (Ia), Formula (Ib), Formula (II), Formula (IIa), Formula (IIb), Formula (IIc), Formula (III), Formula (IIIa), Formula (IIIb), Formula (IIIc), Formula (IIId), Formula (IIIe), or Formula (IV), wherein each of the linkers independently has a structure of -(L¹)$_{k1}$-(L²)k-(L³)$_{k3}$-(L⁴)$_{k4}$-, wherein each of k1, k2, k3, and k4 is independently 0, 1 or 2, and each of the L¹, L², L³ and L⁴ is independently selected from —O—, —S—, S(=O)$_{1-2}$—, —C(=O)—, —C(=S)—, —NR$^L$—, —OC (=O)—, —C(=O)O—, —OC(=O)O—, —C(=O) NR$^L$—, —OC(=O)NR$^L$—, —NR$^L$C(=O)—, —NR$^L$C (=O) NR$^L$—, —P(=O)R$^L$—, —NR$^L$S(=$_0$)(=NR$^L$)—, —NR$^L$S(=O)$_2$—, —S(=O)$_2$NR$^L$—, —N=N—, —(CH$_2$—CH$_2$—O)$_{1-6}$—, linear or branched C$_1$-6 alkylene, linear or branched C$_{2-6}$ alkenylene, linear or branched C$_{2-6}$ alkynylene, C$_3$-C$_8$ cycloalkylene, C$_2$-C$_7$ heterocycloalkylene, C$_6$-C$_{10}$ arylene, and C$_5$-C$_9$ heteroarylene, wherein the alkylene, alkenylene, alkynylene, cycloalkylene, cycloalkylene, arylene, or heteroarylene is substituted or unsubstituted, and wherein each R$^L$ is independently H, D, cyano, halogen, substituted or unsubstituted C$_1$-C$_6$ alkyl, —CD$_3$, —OCH$_3$, —OCD$_3$, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl. In some embodiments, each R$^L$ is independently H, substituted or unsubstituted C$_1$-C$_6$ alkyl, —OCH$_3$, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, or substituted or unsubstituted C$_2$-C$_7$ heterocycloalkyl.

In some embodiments of Formula (I), Formula (Ia), Formula (Ib), Formula (II), Formula (IIa), Formula (IIb), Formula (IIc), Formula (III), Formula (IIIa), Formula (IIIb), Formula (IIIc), Formula (IIId), Formula (IIIe), or Formula (IV), each of the linkers independently comprises a structure selected from:

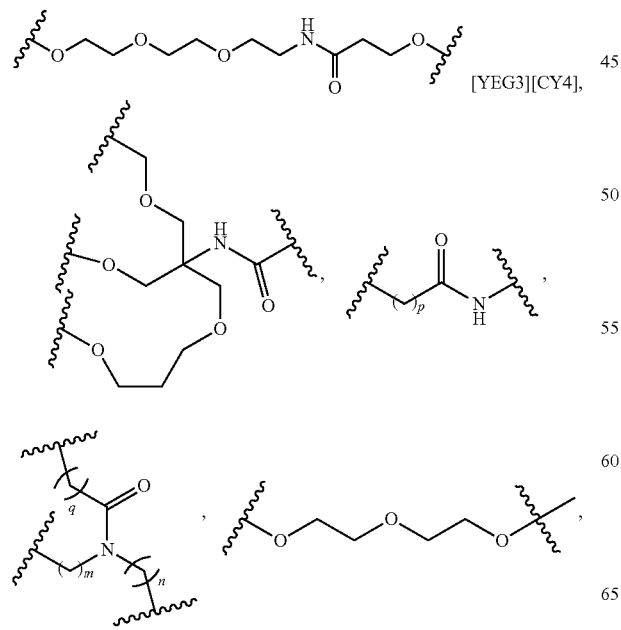
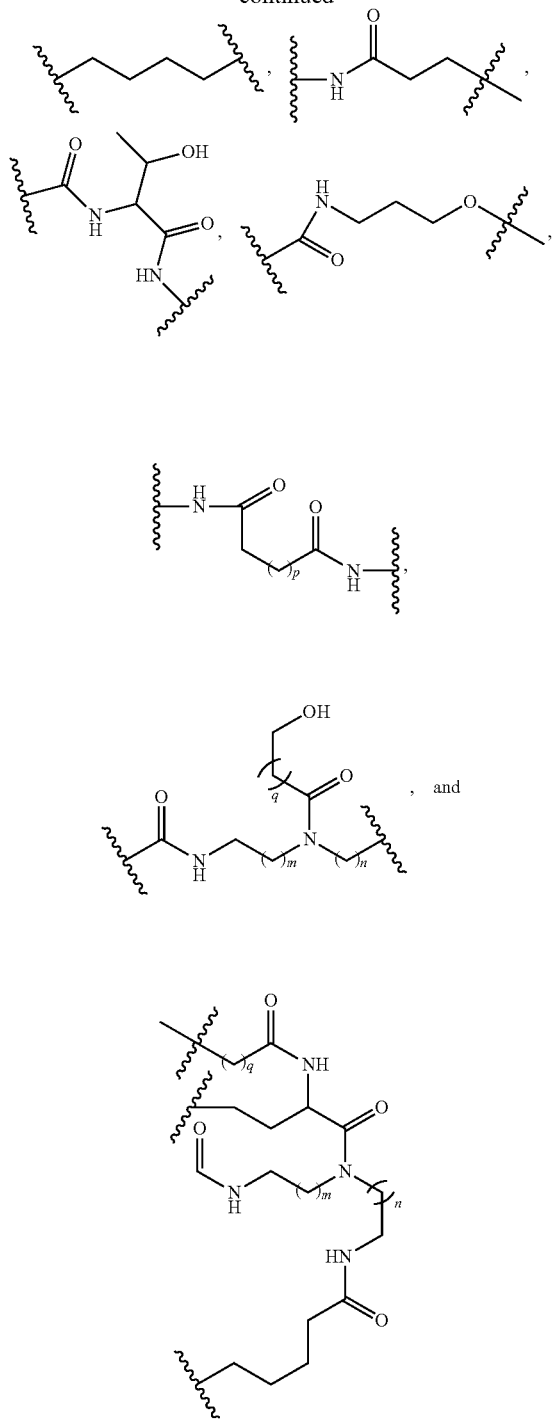

wherein each of the p, q, m, and n is independently 0, 1, 2, 3, 4, 5, 6, 7, 8, 9, 10, 11, 12, 14, 13, 15, 16, 17, 18, 19, or 20. In some embodiments, each of the p, q, m, and n is independently 0, 1, 2, 3, 4, or 5.

In some embodiments of Formula (I), Formula (Ia), Formula (Ib), Formula (II), Formula (IIa), Formula (IIb), Formula (IIc), Formula (III), Formula (IIIa), Formula (IIIb), Formula (IIIc), Formula (IIId), Formula (IIIe), or Formula (IV), wherein the "one or more linkers" referenced in the box of the foregoing formulas comprises a structure that is

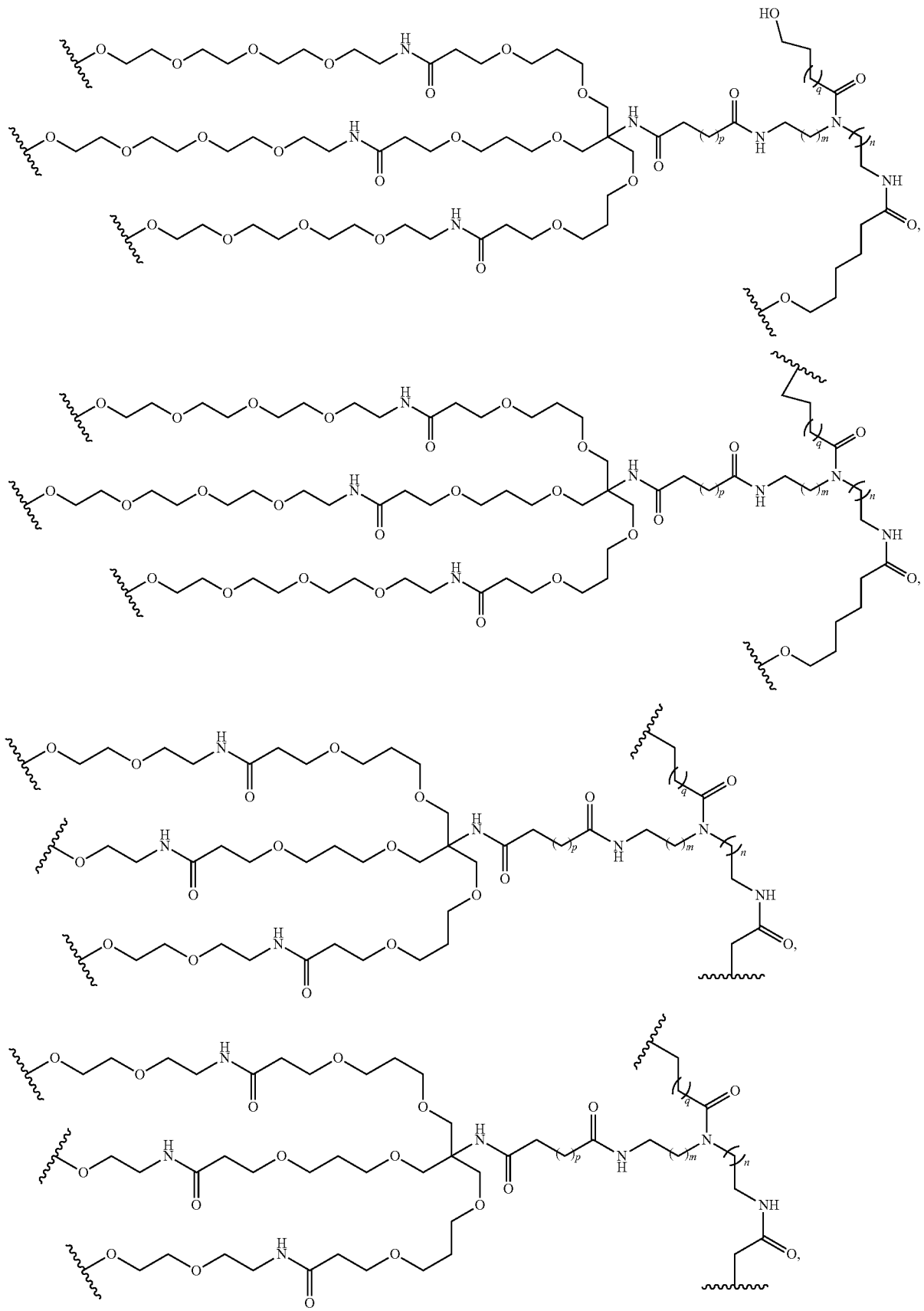

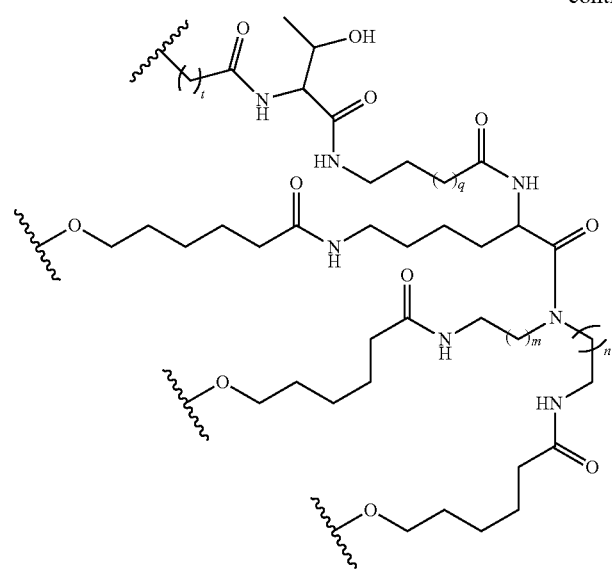
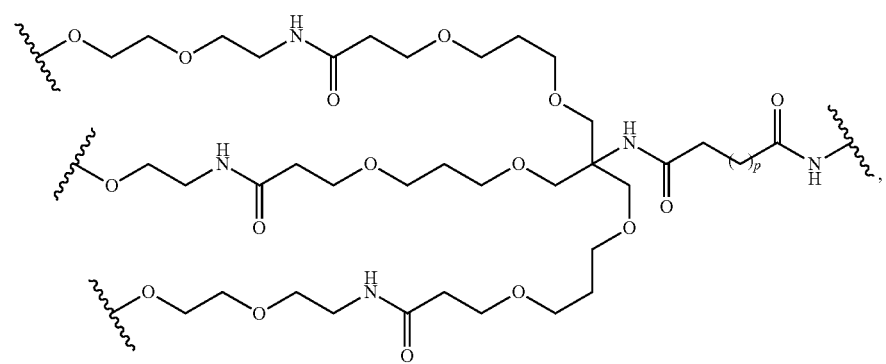
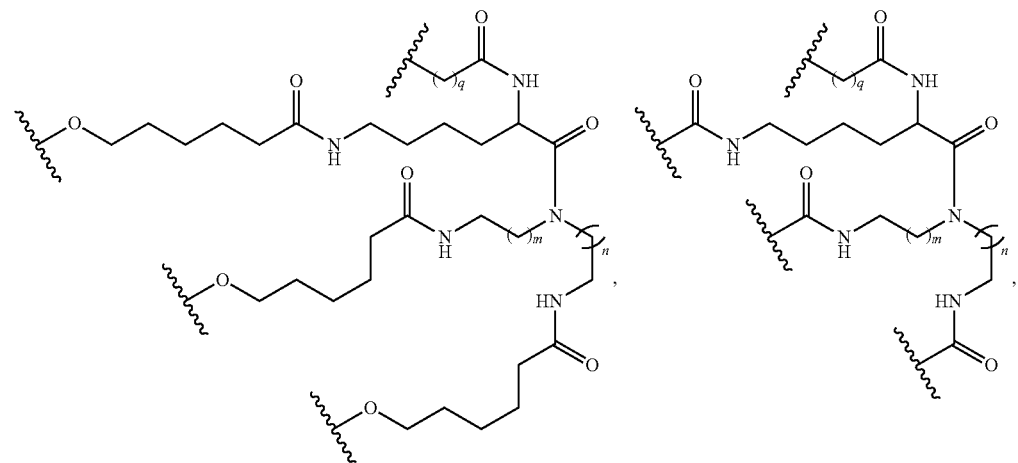

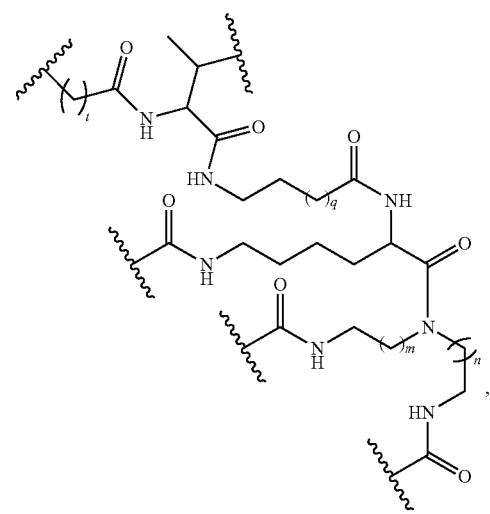
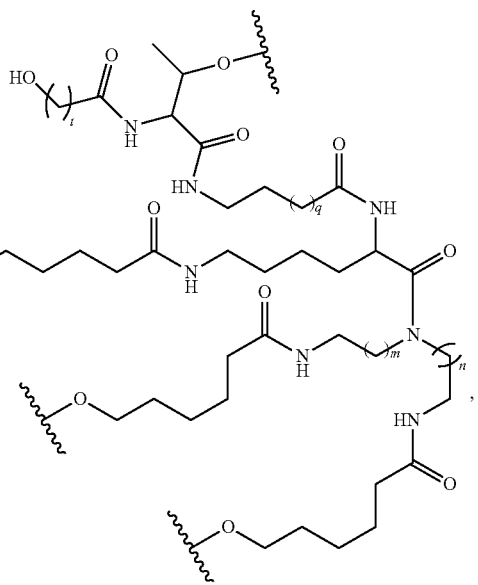
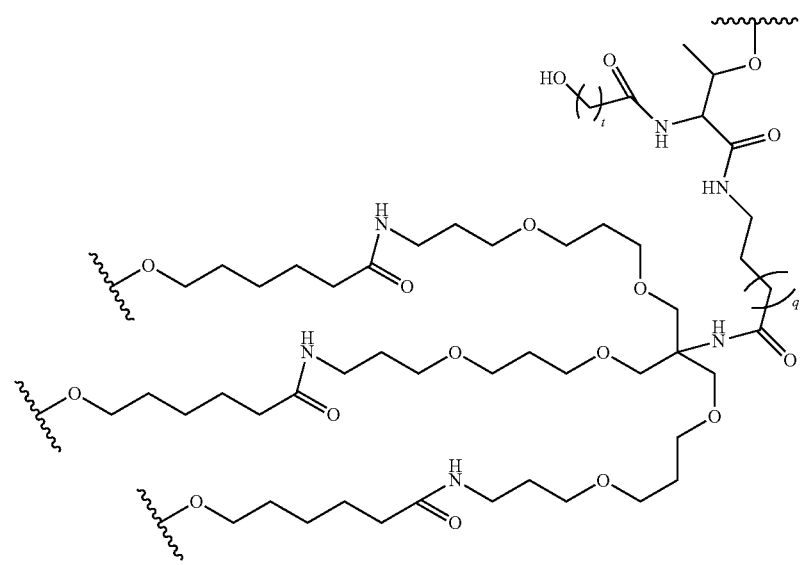
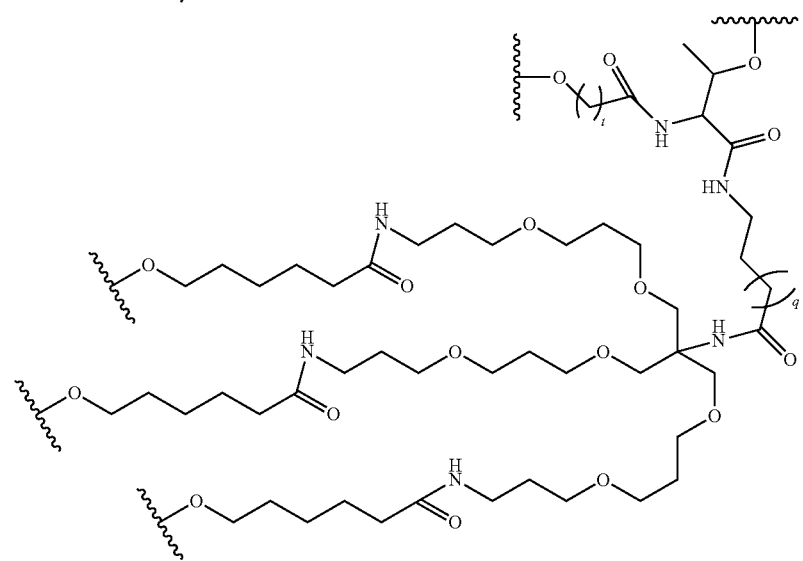

-continued
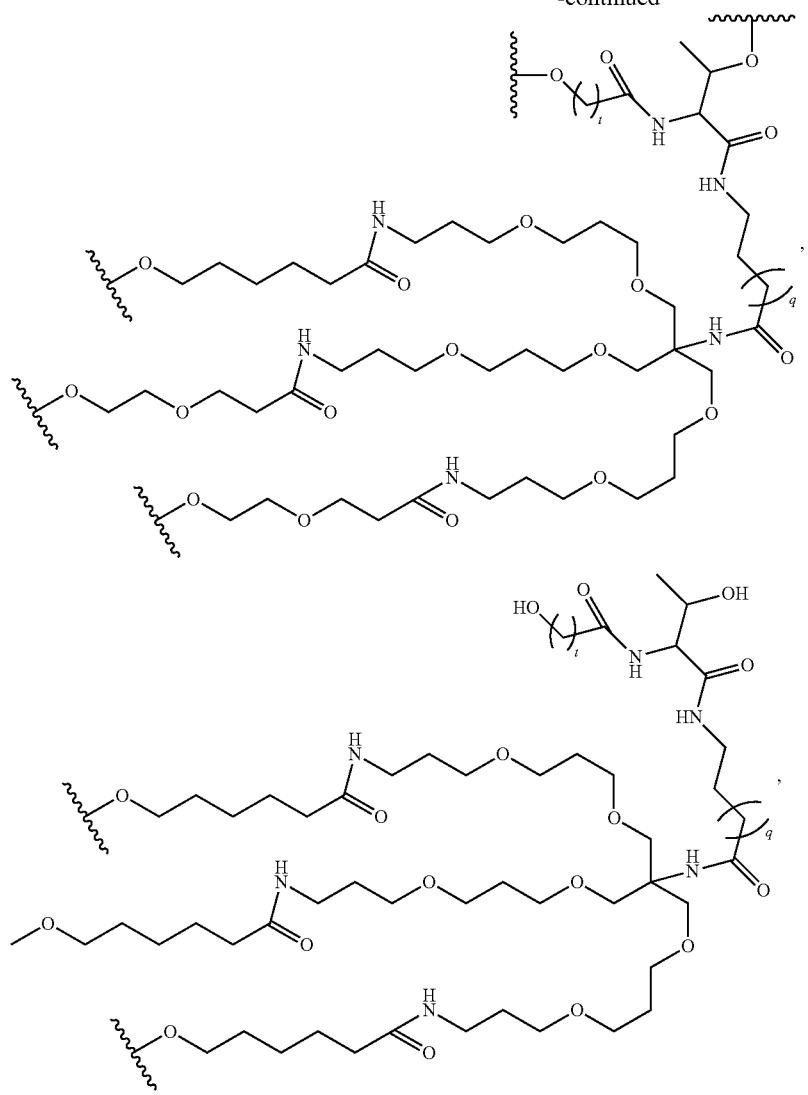
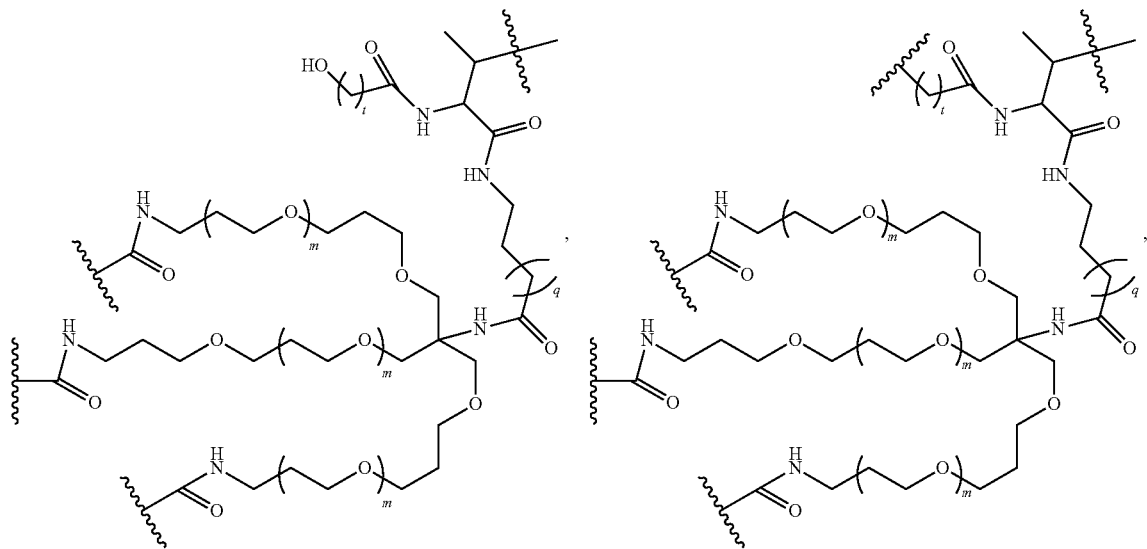

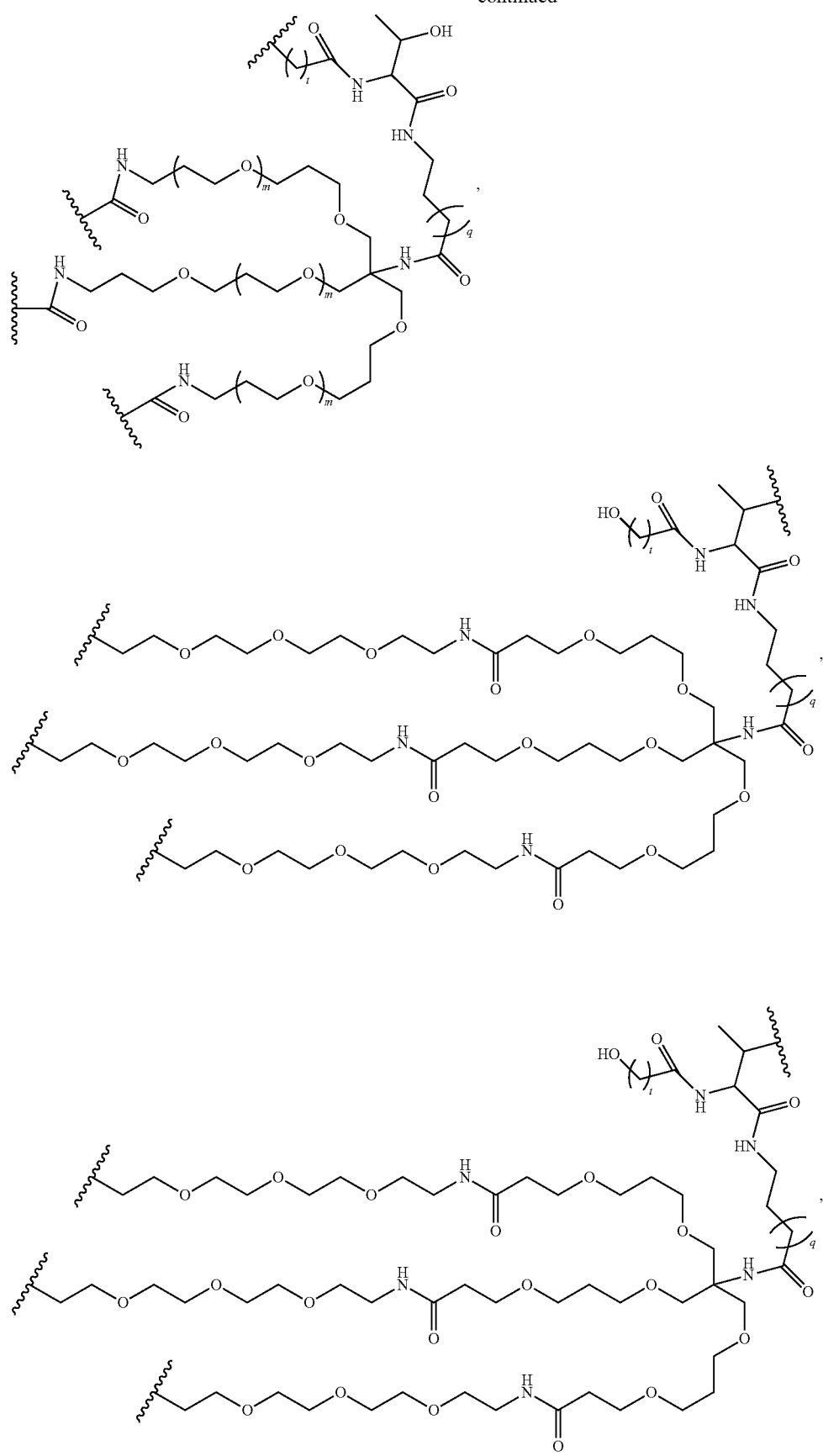

-continued

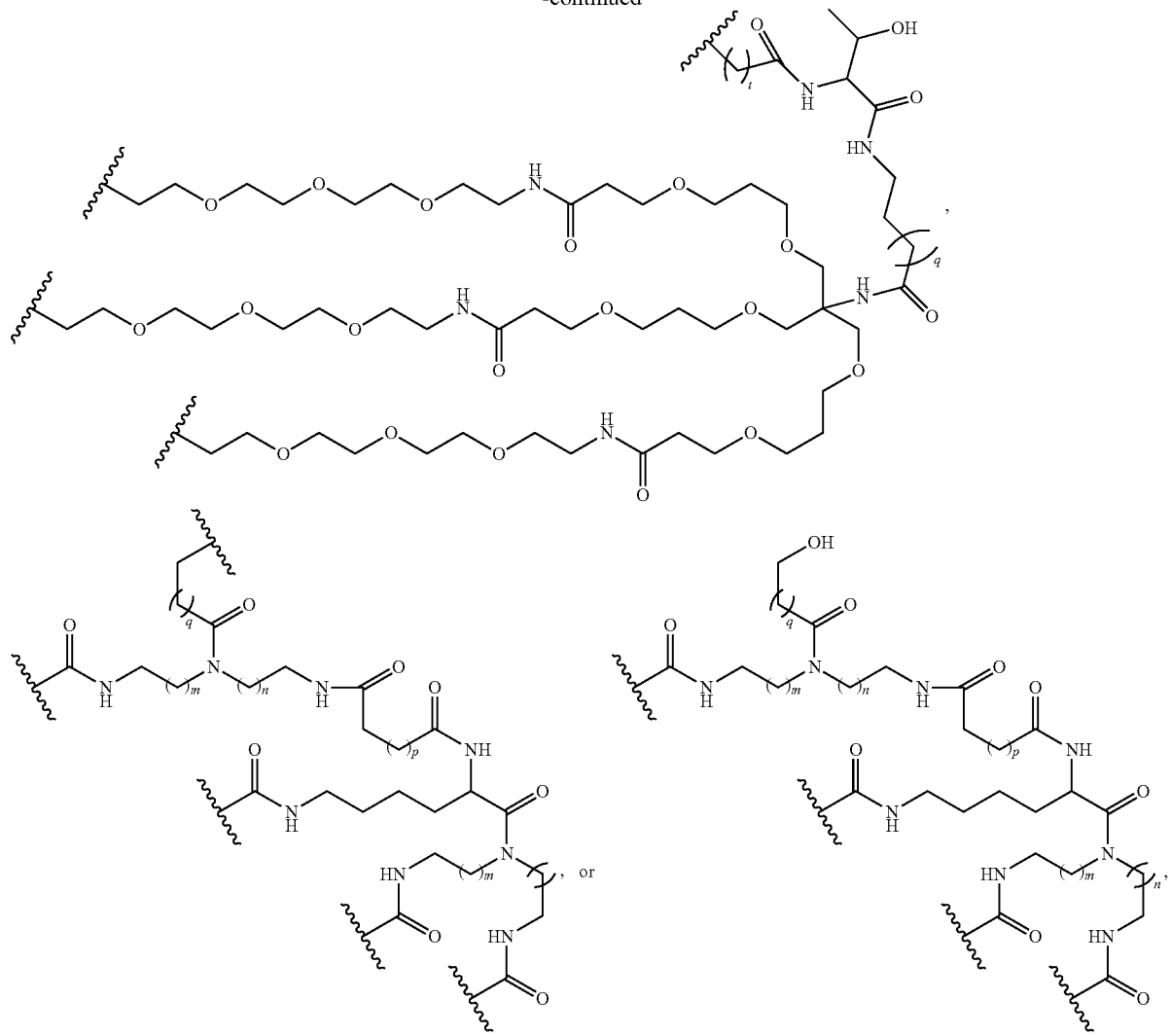

wherein each of the p, q, m, and n is independently 0, 1, 2, 3, 4, 5, 6, 7, 8, 9, 10, 11, 12, 14, 13, 15, 16, 17, 18, 19, or 20. In some embodiments, each of the p, q, m, and n is independently 0, 1, 2, 3, 4, or 5.

In some embodiments of Formula (I), Formula (Ia), Formula (Ib), Formula (II), Formula (IIa), Formula (IIb), Formula (IIc), Formula (III), Formula (IIIa), Formula (IIIb), Formula (IIIc), Formula (IIId), Formula (IIIe), or Formula (IV), W comprises one or more modified DNA or RNA bases. The nucleobases can comprise any chemical modifications as described herein. In some embodiments, the nucleobases include a 2'-OH or 2'-OMe modification. For example, W may comprise one or more 2'-OMe modified adenine, cytosine, guanidine and uracil, referred to as (a) (c), (g), or (u). In some embodiments, a modified RNA, e.g. a gRNA or mRNA, includes at least 1, 2, 3, 4, 5, 6, 7, 8, 9, 10, 11, 12, 13, 14, 15, 20, 25, 30, 35, 40, 50 or more modified nucleobases. In some embodiments, a modified RNA comprises one or more modified nucleobases near the 5' end, near the 3' end, or in the middle of the sequence. The modified nucleobases within a modified RNA may or may not be contiguous. In some embodiments, a modified RNA comprises one or more 2'-OMe modifications scattered along the length of the sequence. In some embodiments, a modified RNA comprises one or more 2'OH modifications scattered along the length of the sequence. In some embodiments, a modified RNA comprises alternating 2'-OH and 2'OMe modifications. In some embodiments, W comprises (A)n, (T)n, (U)n, (a)n, or (u)n, wherein n is an integer no less than 3, wherein a is 2'-O-methyladenosine (2'-OMe A), and wherein u is 2'-O-methyluridine (2'-OMe-U). In some embodiments, W comprises (u)n, wherein n is an integer from 3 to 50 (SEQ ID NO: 118). In some embodiments, W comprises (u)n, wherein n is an integer from 3 to 20 (SEQ ID NO: 119) or 3 to 15 (SEQ ID NO: 120). In some embodiments, W comprises one or more nucleotide sequences that are complementary to a coupling sequence. In some embodiments, W comprises one or more guanines or cytidines. In some embodiments, W comprises at least 1, 2, 3, 4, 5, 6, 7, 8, 9, 10, 11, 12, 13, 14, 15, 20, 25, 30, 35, 40, 50 or more guanines or cytidines. In some embodiments, the one or more guanines or cytidines are complementary to one or more cytidines or guanines in a coupling sequence. In some embodiments, the guanines or cytidines are at the terminals of W or the coupling sequence. Not intended to be bound by any theory, it is contemplated that the guaninies-cytidine pairing forms "GC locks" or "CG locks" that would increase binding affinity. The guanines and/or cytidines in W or a coupling sequence may or may not be contiguous and may comprise any one of the chemical modifications as described herein, e.g. a 2'-OMe or 2'-OH modification.

Receptor Targeting Conjugates

The key to fulfilling of nucleic acid-based therapy is the safe and efficacious delivery of payload to specific cell types and tissues. Lipid nanoparticles (LNPs) represent the most advanced non-viral drug delivery technological platforms in the present time. LNPs are physically able to pass through blood vessels and reach hepatocytes [*Am. J. Pathol.* 2010, 176, 14-21]. It has also been revealed that apolipoprotein E (ApoE) proteins bind to the LNPs post PEG-lipid diffusion from the LNP surface with a near neutral charge in the blood stream, and function as an endogenous ligand against hepatocytes, which express the low-density lipoprotein receptor (LDLr) [*Mol. Ther.,* 2010, 18, 1357-1364.]. It is accordingly envisioned that two key factors that control the efficient hepatic delivery of LNP are: 1) effective PEG-lipid shedding from LNP surface in blood serum and 2) ApoE binding to the LNP. The above endogenous ApoE-mediated LDLr-dependent LNP delivery route is not an effective path to achieve LNP-based hepatic gene delivery for the LDLr deficient patient population.

In one aspect, described herein are LNPs comprising receptor targeting conjugates. In some aspects, described herein are receptor targeting conjugates. The LNPs with targeting conjugates are constituted to have the receptor targeting moiety on the surface or periphery of the particle. In one aspect low mol % of the receptor targeting conjugate is used while constituting the targeting LNP to achieve low surface density of the targeting moiety on the surface/periphery of the particle. In another aspect, high mol % of the receptor targeting conjugate is used while constituting the targeting LNP to achieve high surface density of the targeting moiety on the surface/periphery of the particle. In another aspect, desired mol % of the receptor targeting conjugate is used to achieve a range of surface density of the targeting moiety on the surface/periphery of the particle. In some embodiments, the receptor targeting conjugate comprises a targeting moiety (or ligand), a linker, and a lipophilic moiety that is connected to the targeting moiety. In some embodiments, the receptor targeting moiety (or ligand) targets a lectin receptor. In some embodiments, the lectin receptor is asialoglycoprotein receptor (ASGPR). In some embodiments the receptor targeting moiety is GalNAc or a derivative GalNAc that targets ASGPR. In one aspect the receptor targeting conjugate comprises of one GalNAc moiety or derivative thereof. In another aspect, the receptor targeting conjugate comprises of two GalNAc moieties or derivative thereof. In another aspect, the receptor targeting conjugate comprises of three GalNAc moieties or derivate thereof. In another aspect, the receptor targeting conjugate is lipophilic. In some embodiments, the receptor targeting conjugate comprises one or more GalNAc moieties and one or more lipid moieties, i.e., GalNAc-Lipid. In some embodiments, the receptor targeting conjugate is a GalNAc-Lipid.

The current disclosure provides tissue specific efficient LNP delivery to hepatocytes in an LDLr independent manner. The developed by the present disclosure trivalent GalNAc-moieties are attached to hydrophobic glycerol-based dialkyl lipids chain, sterol (cholesterol, for e.g.) and hydrophobic a-tocopherol through different PEG-spacers. These GalNAc conjugated lipids are then formulated with various excipients to yield LNPs that carry low to high surface density of the custom-designed GalNAc ligands to target the asialoglycoprotein receptor (ASGPR), which is highly expressed on the surface of hepatocytes.

The ligand on the surface of the engineered LNPs facilitates ASGPR-mediated tissue-specific uptake into hepatocytes. Different GalNAc-LNPs are constituted to circumvent ApoE biding and to enable GalNAc-ASGPR interaction to facilitate clathrin-mediated uptake into hepatocytes. Modulating PEG-shedding kinetics and modulating net surface charge density of GalNAc-LNP particles by using PEG-lipids described herein in combination with GalNAc-lipids with varying PEG-tethers yield GalNAc-LNPs that lack endogenous ApoE-binding characteristics to deliver particles that carry RNA-payloads specifically to hepatocytes of LDLR-deficient preclinical animal models at safe and efficacious dose. Dose-optimization in pre-clinical animal models further advance lead GalNAc-LNP (or LNPs) to clinical development to treat LDLR-deficient patient population to elicit genome-editing at therapeutically viable safe and efficacious dose.

Accordingly, in one aspect, disclosed herein is a receptor targeting conjugate, comprising a compound of Formula (V):

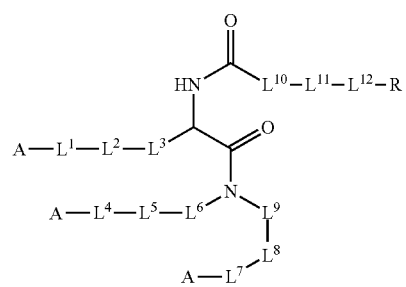

Formula (V)

wherein, a plurality of the A groups collectively comprise a receptor targeting ligand;

each of $L^1$, $L^2$, $L^3$, $L^4$, $L^5$, $L^6$, $L^7$, $L^8$, $L^9$, $L^{10}$ and $L^{12}$ is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, —N(OR$^1$)—, —O[(P=O)O—]O— or —O[(P=O)S—]O— or a bond;

$L^{11}$ is substituted or unsubstituted —(CH$_2$CH$_2$O)$_n$—, substituted or unsubstituted —(OCH$_2$CH$_2$)$_n$—, substituted or unsubstituted —(CH$_2$)$_n$—, or a bond;

each $R^1$ is independently H or substituted or unsubstituted $C_1$-$C_6$alkyl;

R is a lipid, nucleic acid, amino acid, protein, or lipid nanoparticle;

m is an integer selected from 1 to 10; and n is an integer selected from 1 to 200.

In some embodiments, a receptor targeting conjugate comprises a compound of Formula (V):

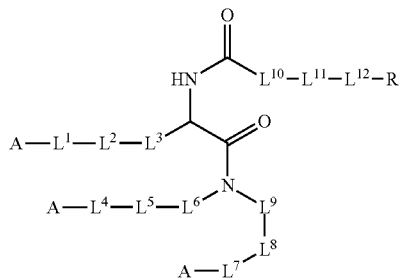

Formula (V)

wherein,
a plurality of the A groups collectively comprise a receptor targeting ligand;
each of $L^1$, $L^2$, $L^3$, $L^4$, $L^5$, $L^6$, $L^7$, $L^8$, $L^9$, $L^{10}$ and $L^{12}$ is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, or —N(OR$^1$)—;
$L^{11}$ is substituted or unsubstituted —(CH$_2$CH$_2$O)$_n$—, or substituted or unsubstituted —(OCH$_2$CH$_2$)$_n$—;
each $R^1$ is independently H or substituted or unsubstituted $C_1$-$C_6$alkyl;
R is a lipid, nucleic acid, amino acid, protein, or lipid nanoparticle;
m is an integer selected from 1 to 10; and
n is an integer selected from 1 to 200.

In some embodiments, $L^{11}$ is —(CH$_2$CH$_2$O)$_n$— or —(OCH$_2$CH$_2$)$_n$—.

In some embodiments of a compound of Formula (V), A binds to a lectin. In some embodiment, the lectin is an asialoglycoprotein receptor (ASGPR). In some embodiments, A comprises one or more N-acetylgalactosamine (GalNAc) or GalNAc derivatives.

In some embodiments of a compound of Formula (V), A is N-acetylgalactosamine (GalNAc) or a derivative thereof. In some embodiments, A is GalNAc. In some embodiments, A is or comprises galactose.

In some embodiments of a compound of Formula (V), each $L^1$, $L^4$, and $L^7$ is independently substituted or unsubstituted $C_1$-$C_{12}$ alkylene. In some embodiments of a compound of Formula (V), each $L^1$, $L^4$, and $L^7$ is independently substituted or unsubstituted $C_2$-$C_6$ alkylene. In some embodiments of a compound of Formula (V), each $L^1$, $L^4$, and $L^7$ is $C_4$ alkylene.

In some embodiments of a compound of Formula (V), each $L^2$, $L^5$, and $L^8$ is independently —C(=O)NR$^1$—, —NR$^1$C(=O)—, —OC(=O)NR$^1$—, —NR$^1$C(=O)O—, —NR$^1$C(=O)NR$^1$—, or —C(=O)NR$^1$C(=O)—. In some embodiments of a compound of Formula (V), each $L^2$, $L^5$, and $L^8$ is independently —C(=O)NR$^1$— or —NR$^1$C(=O)—. In some embodiments of a compound of Formula (V), each $L^2$, $L^5$, and $L^8$ is —C(=O)NH—.

In some embodiments of a compound of Formula (V), each $L^3$, $L^6$, and $L^9$ is independently substituted or unsubstituted $C_1$-$C_{12}$ alkylene. In some embodiments of a compound of Formula (V), each $L^3$ is substituted or unsubstituted $C_2$-$C_6$ alkylene. In some embodiments of a compound of Formula (V), $L^3$ is $C_4$ alkylene. In some embodiments of a compound of Formula (V), each $L^6$ and $L^9$ is independently substituted or unsubstituted $C_2$-$C_{10}$ alkylene. In some embodiments of a compound of Formula (V), each $L^6$ and $L^9$ is independently substituted or unsubstituted $C_2$-$C_6$ alkylene. In some embodiments of a compound of Formula (V), each $L^6$ and $L^9$ is $C_3$ alkylene.

In some embodiments of a compound of Formula (V), $R^1$ is H. In some embodiments, $R^1$ is substituted or unsubstituted $C_1$-$C_6$alkyl. In some embodiments, $R^1$ is methyl.

In another aspect, disclosed herein is a receptor targeting conjugate, comprising a compound of Formula (VI):

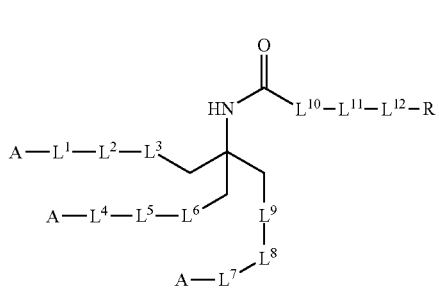

Formula (VI)

wherein,
a plurality of the A groups collectively comprise a receptor targeting ligand;
each of $L^1$, $L^2$, $L^3$, $L^4$, $L^5$, $L^6$, $L^7$, $L^8$, $L^9$, $L^{10}$ and $L^{12}$ is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, —N(OR$^1$)—, —O[(P=O)O—]O—, —O[(P=O)S—]O—, or a bond;
$L^{11}$ is substituted or unsubstituted —(CH$_2$CH$_2$O)$_n$—, substituted or unsubstituted —(OCH$_2$CH$_2$)$_n$—, substituted or unsubstituted —(CH$_2$)$_n$—, or a bond;
each $R^1$ is independently H or substituted or unsubstituted $C_1$-$C_6$alkyl;
R is a lipid, nucleic acid, amino acid, protein, or lipid nanoparticle;
m is an integer selected from 1 to 10; and
n is an integer selected from 1 to 200.

In some embodiments, disclosed herein is a receptor targeting conjugate, comprising a compound of Formula (VI):

Formula (VI)

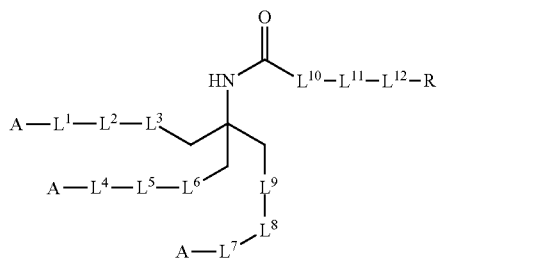

wherein,
a plurality of the A groups collectively comprise a receptor targeting ligand;
each of $L^1$, $L^2$, $L^3$, $L^4$, $L^5$, $L^6$, $L^7$, $L^8$, $L^9$, $L^{10}$ and $L^{12}$ is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —$(CH_2CH_2O)_m$—, —$(OCH_2CH_2)_m$—, —O—, —S—, —S(=O)—, —S(=O)_2—, —S(=O)(=NR^1)—, —C(=O)—, —C(=N—OR^1)—, —C(=O)O—, —OC(=O)—, —C(=O)C(=O)—, —C(=O)NR^1—, —NR^1C(=O)—, —OC(=O)NR^1—, —NR^1C(=O)O—, —NR^1C(=O)NR^1—, —C(=O)NR^1C(=O)—, —S(=O)_2NR^1—, —NR^1S(=O)_2—, —NR^1—, or —N(OR^1)—; $L^{11}$ is substituted or unsubstituted —$(CH_2CH_2O)_n$— or substituted or unsubstituted —$(OCH_2CH_2)_n$—;
each $R^1$ is independently H or substituted or unsubstituted $C_1$-$C_6$alkyl;
R is a lipid, nucleic acid, amino acid, protein, or lipid nanoparticle;
m is an integer selected from 1 to 10; and
n is an integer selected from 1 to 200.

In some embodiments, $L^{11}$ is —$(CH_2CH_2O)_n$— or —$(OCH_2CH_2)_n$—.

In some embodiments of a compound of Formula (VI), A binds to a lectin. In some embodiment, the lectin is an asialoglycoprotein receptor (ASGPR). In some embodiments, A comprises one or more N-acetylgalactosamine (GalNAc) or GalNAc derivatives.

In some embodiments of a compound of Formula (VI), A is N-acetylgalactosamine (GalNAc) or a derivative thereof. In some embodiments, A is GalNAc.

In some embodiments of a compound of Formula (VI), each $L^1$, $L^4$, and $L^7$ is independently substituted or unsubstituted $C_1$-$C_{12}$ alkylene or substituted or unsubstituted $C_1$-$C_{12}$ heteroalkylene.

In some embodiments of a compound of Formula (VI), each $L^1$, $L^4$, and $L^7$ is independently substituted or unsubstituted $C_1$-$C_{12}$ heteroalkylene.

In some embodiments of a compound of Formula (VI), each $L^1$, $L^4$, and $L^7$ is independently substituted or unsubstituted $C_1$-$C_{12}$ heteroalkylene comprising 1-10 O atoms.

In some embodiments of a compound of Formula (VI), each $L^1$, $L^4$, and $L^7$ is independently —$(CH_2CH_2O)_{p1}$—$(CH_2)_{q1}$—; wherein p1 is 1-8; and q1 is 1-6.

In some embodiments of a compound of Formula (VI), each $L^1$, $L^4$, and $L^7$ is —$(CH_2CH_2O)_3$—$(CH_2)_2$—.

In some embodiments of a compound of Formula (VI), each $L^1$, $L^4$, and $L^7$ is independently substituted or unsubstituted $C_1$-$C_{12}$ alkylene.

In some embodiments of a compound of Formula (VI), each $L^1$, $L^4$, and $L^7$ is independently substituted or unsubstituted $C_2$-$C_6$ alkylene.

In some embodiments of a compound of Formula (VI), each $L^1$, $L^4$, and $L^7$ is $C_4$ alkylene.

In some embodiments of a compound of Formula (VI), each $L^2$, $L^5$, and $L^8$ is independently —C(=O)NR^1—, —NR^1C(=O)—, —OC(=O)NR^1—, —NR^1C(=O)O—, —NR^1C(=O)NR^1—, or —C(=O)NR^1C(=O)—.

In some embodiments of a compound of Formula (VI), each $L^2$, $L^5$, and $L^8$ is independently —C(=O)NR^1— or —NR^1C(=O)—.

In some embodiments of a compound of Formula (VI), each $L^2$, $L^5$, and $L^8$ is —NHC(=O)—.

In some embodiments of a compound of Formula (VI), each $L^2$, $L^5$, and $L^8$ is —C(=O)NH—.

In some embodiments of a compound of Formula (VI), each $L^3$, $L^6$, and $L^9$ is independently substituted or unsubstituted $C_1$-$C_{12}$ heteroalkylene.

In some embodiments of a compound of Formula (VI), each $L^3$, $L^6$, and $L^9$ is independently substituted or unsubstituted $C_1$-$C_{12}$ heteroalkylene comprising 1-10 O atoms.

In some embodiments of a compound of Formula (VI), each $L^3$, $L^6$, and $L^9$ is independently —$(CH_2CH_2O)_{p2}$—$(CH_2CH_2CH_2O)_{q2}$—; wherein p2 is 1-8; and q2 is 1-6. In some embodiments, p2 is 1. In some embodiments, p2 is 2. In some embodiments, p2 is 3. In some embodiments, p2 is 4. In some embodiments, p2 is 5. In some embodiments, p2 is 6. In some embodiments, p2 is 7. In some embodiments, p2 is 8. In some embodiments, q2 is 1. In some embodiments, q2 is 2. In some embodiments, q2 is 3. In some embodiments, q2 is 4. In some embodiments, q2 is 5. In some embodiments, q2 is 6.

In some embodiments of a compound of Formula (VI), each $L^3$, $L^6$, and $L^9$ is —$(CH_2CH_2O)$—$(CH_2CH_2CH_2O)$—.

In some embodiments of a compound of Formula (VI), each $L^3$, $L^6$, and $L^9$ is independently —$(CH_2CH_2CH_2O)_{q3}$—; wherein q3 is 1-8. In some embodiments, q3 is 1. In some embodiments, q3 is 2. In some embodiments, q3 is 3. In some embodiments, q3 is 4. In some embodiments, q3 is 5. In some embodiments, q3 is 6. In some embodiments, q3 is 7. In some embodiments, q3 is 8.

In some embodiments of a compound of Formula (VI), each $L^3$, $L^6$, and $L^9$ is —$(CH_2CH_2CH_2O)_2$—.

In some embodiments, a compound of Formula (VI) has a structure of Formula (VIa):

Formula (VIa)

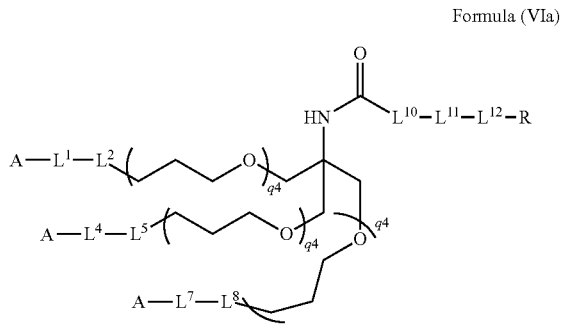

wherein
each q4 is 1-10.

In some embodiments of a compound of Formula (VIb), q4 is 1-8. In some embodiments, q4 is 1-4. In some embodiments, q4 is 1-3. In some embodiments, q4 is 1. In some embodiments, q4 is 2. In some embodiments, q4 is 3. In some embodiments, q4 is 4. In some embodiments, q4 is 5.

In some embodiments of a compound of Formula (V) or Formula (VI), $L^{10}$ is substituted or unsubstituted $C_1$-$C_{12}$ alkylene. In some embodiments, $L^{10}$ is substituted or unsubstituted $C_1$-$C_4$ alkylene. In some embodiments, $L^{10}$ is $C_2$ alkylene.

In some embodiments, a compound of Formula (VI) has a structure of Formula (VIb):

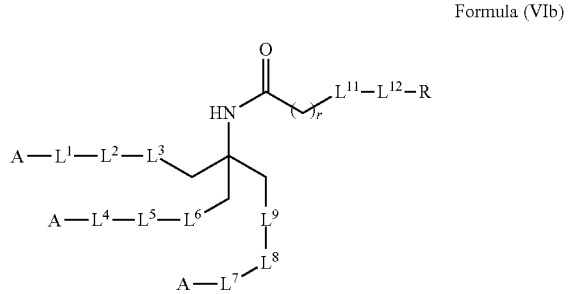

Formula (VIb)

wherein,
r is 1-4.

In some embodiments of a compound of Formula (VIb), r is 1, 2, or 3. In some embodiments, r is 1 or 2. In some embodiments, r is 2 or 3. In some embodiments, r is 1. In some embodiments, r is 2. In some embodiments, r is 3. In some embodiments, r is 4.

In some embodiments of a compound of Formula (V), Formula (VI), Formula (VIa), or Formula (VIb), $L^{11}$ is —(OCH$_2$CH$_2$)$_n$—. In some embodiments, n is 1-100. In some embodiments, n is 2-50. In some embodiments, n is 10-50. In some embodiments, n is 20-50. In some embodiments, n is 30-50. In some embodiments, n is 40-50. In some embodiments, n is 2, 12, 37, or 45. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 19. In some embodiments, n is 20. In some embodiments, n is 21. In some embodiments, n is 22. In some embodiments, n is 23. In some embodiments, n is 24. In some embodiments, n is 25. In some embodiments, n is 26. In some embodiments, n is 27. In some embodiments, n is 28. In some embodiments, n is 29. In some embodiments, n is 30. In some embodiments, n is 31. In some embodiments, n is 32. In some embodiments, n is 33. In some embodiments, n is 34. In some embodiments, n is 35. In some embodiments, n is 36. In some embodiments, n is 37. In some embodiments, n is 38. In some embodiments, n is 39. In some embodiments, n is 40. In some embodiments, n is 41. In some embodiments, n is 42. In some embodiments, n is 43. In some embodiments, n is 44. In some embodiments, n is 45. In some embodiments, n is 46. In some embodiments, n is 47. In some embodiments, n is 48. In some embodiments, n is 49. In some embodiments, n is 50. In some embodiments, n is at least 1. In some embodiments, n is at least 2. In some embodiments, n is at least 3. In some embodiments, n is at least 4. In some embodiments, n is at least 5. In some embodiments, n is at least 6. In some embodiments, n is at least 7. In some embodiments, n is at least 8. In some embodiments, n is at least 9. In some embodiments, n is at least 10. In some embodiments, n is at least 11. In some embodiments, n is at least 12. In some embodiments, n is at least 13. In some embodiments, n is at least 14. In some embodiments, n is at least 15. In some embodiments, n is at least 16. In some embodiments, n is at least 17. In some embodiments, n is at least 18. In some embodiments, n is at least 19. In some embodiments, n is at least 20. In some embodiments, n is at least 21. In some embodiments, n is at least 22. In some embodiments, n is at least 23. In some embodiments, n is at least 24. In some embodiments, n is at least 25. In some embodiments, n is at least 26. In some embodiments, n is at least 27. In some embodiments, n is at least 28. In some embodiments, n is at least 29. In some embodiments, n is at least 30. In some embodiments, n is at least 31. In some embodiments, n is at least 32. In some embodiments, n is at least 33. In some embodiments, n is at least 34. In some embodiments, n is at least 35. In some embodiments, n is at least 36. In some embodiments, n is at least 37. In some embodiments, n is at least 38. In some embodiments, n is at least 39. In some embodiments, n is at least 40. In some embodiments, n is at least 41. In some embodiments, n is at least 42. In some embodiments, n is at least 43. In some embodiments, n is at least 44. In some embodiments, n is at least 45. In some embodiments, n is at least 46. In some embodiments, n is at least 47. In some embodiments, n is at least 48. In some embodiments, n is at least 49. In some embodiments, n is at most 2. In some embodiments, n is at most 3. In some embodiments, n is at most 4. In some embodiments, n is at most 5. In some embodiments, n is at most 6. In some embodiments, n is at most 7. In some embodiments, n is at most 8. In some embodiments, n is at most 9. In some embodiments, n is at most 10. In some embodiments, n is at most 11. In some embodiments, n is at most 12. In some embodiments, n is at most 13. In some embodiments, n is at most 14. In some embodiments, n is at most 15. In some embodiments, n is at most 16. In some embodiments, n is at most 17. In some embodiments, n is at most 18. In some embodiments, n is at most 19. In some embodiments, n is at most 20. In some embodiments, n is at most 21. In some embodiments, n is at most 22. In some embodiments, n is at most 23. In some embodiments, n is at most 24. In some embodiments, n is at most 25. In some embodiments, n is at most 26. In some embodiments, n is at most 27. In some embodiments, n is at most 28. In some embodiments, n is at most 29. In some embodiments, n is at most 30. In some embodiments, n is at most 31. In some embodiments, n is at most 32. In some embodiments, n is at most 33. In some embodiments, n is at most 34. In some embodiments, n is at most 35. In some embodiments, n is at most 36. In some embodiments, n is at most 37. In some embodiments, n is at most 38. In some embodiments, n is at most 39. In some embodiments, n is at most 40. In some embodiments, n is at most 41. In some embodiments, n is at most 42. In some embodiments, n is at most 43. In some embodiments, n is at most 44. In some embodiments, n is at most 45. In some embodiments, n is at most 46. In some embodiments, n is at most 47. In some embodiments, n is at most 48. In some embodiments, n is at most 49. In some embodiments, n is at most 50.

In some embodiments of a compound of Formula (V), Formula (VI), Formula (VIa), or Formula (VIb), $L^{12}$ is —O—, —C(=O)O—, —C(=O)NR$^1$—, —NR$^1$C(=O)—, or —NR$^1$C(=O)O—. In some embodiments, $L^{12}$ is —C(=O)O— or —NR$^1$C(=O)O—. In some embodiments, $L^{12}$ is —C(=O)O—. In some embodiments, $L^{12}$ is —NHC(=O)O—. In some embodiments, $L^{12}$ is —NHC(=O)—.

In some embodiments of a compound of Formula (VI), Formula (VIa), or Formula (VIb), $R^1$ is H. In some embodiments, $R^1$ is substituted or unsubstituted $C_1$-$C_6$alkyl. In some embodiments, $R^1$ is methyl.

In accordance with the foregoing referenced formulas, in some embodiments of a compound of Formula (V) or (VI), $L^1$ is substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, —N(OR$^1$)—, —O[(P=O)O—]O—, —O[(P=O)S—]O—, or a bond. In some embodiments, $L^1$ is substituted or unsubstituted $C_1$-$C_{12}$ alkylene. In some embodiments, $L^1$ is substituted or unsubstituted $C_1$-$C_{12}$ heteroalkylene. In some embodiments, $L^1$ is substituted or unsubstituted $C_2$-$C_{12}$ alkenylene. In some embodiments, $L^1$ is substituted or unsubstituted $C_2$-$C_{12}$ alkynylene. In some embodiments, $L^1$ is —(CH$_2$CH$_2$O)$_m$— or —(OCH$_2$CH$_2$)$_m$—. In some embodiments, $L^1$ is —O—. In some embodiments, $L^1$ is —S—. In some embodiments, $L^1$ is —S(=O)—. In some embodiments, $L^1$ is —S(=O)$_2$—. In some embodiments, $L^1$ is —S(=O)(=NR$^1$)—. In some embodiments, $L^1$ is —C(=O)—. In some embodiments, $L^1$ is —C(=N—OR$^1$)—. In some embodiments, $L^1$ is —C(=O)O—. In some embodiments, $L^1$ is OC(=O)—. In some embodiments, $L^1$ is —C(=O)C(=O)—. In some embodiments, $L^1$ is —C(=O)NR$^1$—. In some embodiments, $L^1$ is —NR$^1$C(=O)—. In some embodiments, $L^1$ is —OC(=O)NR$^1$—. In some embodiments, $L^1$ is —NR$^1$C(=O)O—. In some embodiments, $L^1$ is —NR$^1$C(=O)NR$^1$—. In some embodiments, $L^1$ is —C(=O)NR$^1$C(=O)—. In some embodiments, $L^1$ is —S(=O)$_2$NR$^1$—. In some embodiments, $L^1$ is —NR$^1$S(=O)$_2$—. In some embodiments, $L^1$ is —NR$^1$—. In some embodiments, $L^1$ is —N(OR$^1$)—. In some embodiments, $L^1$ is —O[(P=O)O—]O—. In some embodiments, $L^1$ is —O[(P=O)S—]O—. In some embodiments, $L^1$ is a bond.

In accordance with the foregoing referenced formulas, in some embodiments of a compound of Formula (V) or (VI), $L^2$ is substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, —N(OR$^1$)—, —O[(P=O)O—]O—, —O[(P=O)S—]O—, or a bond. In some embodiments, $L^2$ is substituted or unsubstituted $C_1$-$C_{12}$ alkylene. In some embodiments, $L^2$ is substituted or unsubstituted $C_1$-$C_{12}$ heteroalkylene. In some embodiments, $L^2$ is substituted or unsubstituted $C_2$-$C_{12}$ alkenylene. In some embodiments, $L^2$ is substituted or unsubstituted $C_2$-$C_{12}$ alkynylene. In some embodiments, $L^2$ is —(CH$_2$CH$_2$O)$_m$— or —(OCH$_2$CH$_2$)$_m$—. In some embodiments, $L^2$ is —O—. In some embodiments, $L^2$ is —S—. In some embodiments, $L^2$ is —S(=O)—. In some embodiments, $L^2$ is —S(=O)$_2$—. In some embodiments, $L^2$ is —S(=O)(=NR$^1$)—. In some embodiments, $L^2$ is —C(=O)—. In some embodiments, $L^2$ is —C(=N—OR$^1$)—. In some embodiments, $L^2$ is —C(=O)O—. In some embodiments, $L^2$ is OC(=O)—. In some embodiments, $L^2$ is —C(=O)C(=O)—. In some embodiments, $L^2$ is —C(=O)NR$^1$—. In some embodiments, $L^2$ is —NR$^1$C(=O)—. In some embodiments, $L^2$ is —NRHC(=O)—. In some embodiments, $L^2$ is —OC(=O)NR$^1$—. In some embodiments, $L^2$ is —NR$^1$C(=O)O—. In some embodiments, $L^2$ is —NR$^1$C(=O)NR$^1$—. In some embodiments, $L^2$ is —C(=O)NR$^1$C(=O)—. In some embodiments, $L^2$ is —S(=O)$_2$NR$^1$—. In some embodiments, $L^2$ is —NR$^1$S(=O)$_2$—. In some embodiments, $L^2$ is —NR$^1$—. In some embodiments, $L^2$ is —N(OR$^1$)—. In some embodiments, $L^2$ is —O[(P=O)O—]O—. In some embodiments, $L^2$ is —O[(P=O)S—]O—. In some embodiments, $L^2$ is a bond.

In accordance with the foregoing referenced formulas, in some embodiments of a compound of Formula (V) or (VI), $L^3$ is substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, —N(OR$^1$)—, —O[(P=O)O—]O—, —O[(P=O)S—]O—, or a bond. In some embodiments, $L^3$ is substituted or unsubstituted $C_1$-$C_{12}$ alkylene. In some embodiments, $L^3$ is an unsubstituted $C_{3-4}$ alkylene. In some embodiments, $L^3$ is an unsubstituted $C_1$-4 alkylene. In some embodiments, $L^3$ is substituted or unsubstituted $C_1$-$C_{12}$ heteroalkylene. In some embodiments, $L^3$ is substituted or unsubstituted $C_2$-$C_{12}$ alkenylene. In some embodiments, $L^3$ is substituted or unsubstituted $C_2$-$C_{12}$ alkynylene. In some embodiments, $L^3$ is —(CH$_2$CH$_2$O)$_m$— or —(OCH$_2$CH$_2$)$_m$—. In some embodiments, $L^3$ is —O—. In some embodiments, $L^3$ is —S—. In some embodiments, $L^3$ is —S(=O)—. In some embodiments, $L^3$ is —S(=O)$_2$—. In some embodiments, $L^3$ is —S(=O)(=NR$^1$)—. In some embodiments, $L^3$ is —C(=O)—. In some embodiments, $L^3$ is —C(=N—OR$^1$)—. In some embodiments, $L^3$ is —C(=O)O—. In some embodiments, $L^3$ is OC(=O)—. In some embodiments, $L^3$ is —C(=O)C(=O)—. In some embodiments, $L^3$ is —C(=O)NR$^1$—. In some embodiments, $L^3$ is —NR$^1$C(=O)—. In some embodiments, $L^3$ is —OC(=O)NR$^1$—. In some embodiments, $L^3$ is —NR$^1$C(=O)O—. In some embodiments, $L^3$ is —NR$^1$C(=O)NR$^1$—. In some embodiments, $L^3$ is —C(=O)NR$^1$C(=O)—. In some embodiments, $L^3$ is —S(=O)$_2$NR$^1$—. In some embodiments, $L^3$ is —NR$^1$S(=O)$_2$—. In some embodiments, $L^3$ is —NR$^1$—. In some embodiments, $L^3$ is —N(OR$^1$)—. In some embodiments, $L^3$ is —O[(P=O)O—]O—. In some embodiments, $L^3$ is —O[(P=O)S—]O—. In some embodiments, $L^3$ is a bond.

In accordance with the foregoing referenced formulas, in some embodiments of a compound of Formula (V) or (VI), $L^4$ is substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —$(CH_2CH_2O)_m$—, —$(OCH_2CH_2)_m$—, —O—, —S—, —S(=O)—, —S(=O)_2—, —S(=O)(=NR^1)—, —C(=O)—, —C(=N—OR^1)—, —C(=O)O—, —OC(=O)—, —C(=O)C(=O)—, —C(=O)NR^1—, —NR^1C(=O)—, —OC(=O)NR^1—, —NR^1C(=O)O—, —NR^1C(=O)NR^1—, —C(=O)NR^1C(=O)—, —S(=O)_2NR^1—, —NR^1S(=O)_2—, —NR^1—, —N(OR^1)—, —O[(P=O)O—]O—, —O[(P=O)S—]O—, or a bond. In some embodiments, $L^4$ is substituted or unsubstituted $C_1$-$C_{12}$ alkylene. In some embodiments, $L^4$ is an unsubstituted $C_4$ alkylene. In some embodiments, $L^4$ is substituted or unsubstituted $C_1$-$C_{12}$ heteroalkylene. In some embodiments, $L^4$ is substituted or unsubstituted $C_2$-$C_{12}$ alkenylene. In some embodiments, $L^4$ is substituted or unsubstituted $C_2$-$C_{12}$ alkynylene. In some embodiments, $L^4$ is —$(CH_2CH_2O)_m$— or —$(OCH_2CH_2)_m$—. In some embodiments, $L^4$ is —O—. In some embodiments, $L^4$ is —S—. In some embodiments, $L^4$ is —S(=O)—. In some embodiments, $L^4$ is —S(=O)_2—. In some embodiments, $L^4$ is —S(=O)(=NR^1)—. In some embodiments, $L^4$ is —C(=O)—. In some embodiments, $L^4$ is —C(=N—OR^1)—. In some embodiments, $L^4$ is —C(=O)O—. In some embodiments, $L^4$ is OC(=O)—. In some embodiments, $L^4$ is —C(=O)C(=O)—. In some embodiments, $L^4$ is —C(=O)NR^1—. In some embodiments, $L^4$ is —NR^1C(=O)—. In some embodiments, $L^4$ is —OC(=O)NR^1—. In some embodiments, $L^4$ is —NR^1C(=O)O—. In some embodiments, $L^4$ is —NR^1C(=O)NR^1—. In some embodiments, $L^4$ is —C(=O)NR^1C(=O)—. In some embodiments, $L^4$ is —S(=O)_2NR^1—. In some embodiments, $L^4$ is —NR^1S(=O)_2—. In some embodiments, $L^4$ is —NR^1—. In some embodiments, $L^4$ is —N(OR^1)—. In some embodiments, $L^4$ is —O[(P=O)O—]O—. In some embodiments, $L^4$ is —O[(P=O)S—]O—. In some embodiments, $L^4$ is a bond.

In accordance with the foregoing referenced formulas, in some embodiments of a compound of Formula (V) or (VI), $L^5$ is substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —$(CH_2CH_2O)_m$—, —$(OCH_2CH_2)_m$—, —O—, —S—, —S(=O)—, —S(=O)_2—, —S(=O)(=NR^1)—, —C(=O)—, —C(=N—OR^1)—, —C(=O)O—, —OC(=O)—, —C(=O)C(=O)—, —C(=O)NR^1—, —NR^1C(=O)—, —OC(=O)NR^1—, —NR^1C(=O)O—, —NR^1C(=O)NR^1—, —C(=O)NR^1C(=O)—, —S(=O)_2NR^1—, —NR^1S(=O)_2—, —NR^1—, —N(OR^1)—, —O[(P=O)O—]O—, —O[(P=O)S—]O—, or a bond. In some embodiments, $L^5$ is substituted or unsubstituted $C_1$-$C_{12}$ alkylene. In some embodiments, $L^5$ is substituted or unsubstituted $C_1$-$C_{12}$ heteroalkylene. In some embodiments, $L^5$ is substituted or unsubstituted $C_2$-$C_{12}$ alkenylene. In some embodiments, $L^5$ is substituted or unsubstituted $C_2$-$C_{12}$ alkynylene. In some embodiments, $L^5$ is —$(CH_2CH_2O)_m$— or —$(OCH_2CH_2)_m$—. In some embodiments, $L^5$ is —O—. In some embodiments, $L^5$ is —S—. In some embodiments, $L^5$ is —S(=O)—. In some embodiments, $L^5$ is —S(=O)_2—. In some embodiments, $L^5$ is —S(=O)(=NR^1)—. In some embodiments, $L^5$ is —C(=O)—. In some embodiments, $L^5$ is —C(=N—OR^1)—. In some embodiments, $L^5$ is —C(=O)O—. In some embodiments, $L^5$ is OC(=O)—. In some embodiments, $L^5$ is —C(=O)C(=O)—. In some embodiments, $L^5$ is —C(=O)NR^1—. In some embodiments, $L^5$ is —NR^1C(=O)—. In some embodiments, $L^2$ is —NRHC(=O)—. In some embodiments, $L^5$ is —OC(=O)NR^1—. In some embodiments, $L^5$ is —NR^1C(=O)O—. In some embodiments, $L^5$ is —NR^1C(=O)NR^1—. In some embodiments, $L^5$ is —C(=O)NR^1C(=O)—. In some embodiments, $L^5$ is —S(=O)_2NR^1—. In some embodiments, $L^5$ is —NR^1S(=O)_2—. In some embodiments, $L^5$ is —NR^1—. In some embodiments, $L^5$ is —N(OR^1)—. In some embodiments, $L^5$ is —O[(P=O)O—]O—. In some embodiments, $L^5$ is —O[(P=O)S—]O—. In some embodiments, $L^5$ is a bond.

In accordance with the foregoing referenced formulas, in some embodiments of a compound of Formula (V) or (VI), $L^6$ is substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —$(CH_2CH_2O)_m$—, —$(OCH_2CH_2)_m$—, —O—, —S—, —S(=O)—, —S(=O)_2—, —S(=O)(=NR^1)—, —C(=O)—, —C(=N—OR^1)—, —C(=O)O—, —OC(=O)—, —C(=O)C(=O)—, —C(=O)NR^1—, —NR^1C(=O)—, —OC(=O)NR^1—, —NR^1C(=O)O—, —NR^1C(=O)NR^1—, —C(=O)NR^1C(=O)—, —S(=O)_2NR^1—, —NR^1S(=O)_2—, —NR^1—, —N(OR^1)—, —O[(P=O)O—]O—, —O[(P=O)S—]O—, or a bond. In some embodiments, $L^6$ is substituted or unsubstituted $C_1$-$C_{12}$ alkylene. In some embodiments, $L^6$ is an unsubstituted $C_3$-4 alkylene. In some embodiments, $L^6$ is an unsubstituted $C_1$-4 alkylene. In some embodiments, $L^6$ is substituted or unsubstituted $C_1$-$C_{12}$ heteroalkylene. In some embodiments, $L^6$ is substituted or unsubstituted $C_2$-$C_{12}$ alkenylene. In some embodiments, $L^6$ is substituted or unsubstituted $C_2$-$C_{12}$ alkynylene. In some embodiments, $L^6$ is —$(CH_2CH_2O)_m$— or —$(OCH_2CH_2)_m$—. In some embodiments, $L^6$ is —O—. In some embodiments, $L^6$ is —S—. In some embodiments, $L^6$ is —S(=O)—. In some embodiments, $L^6$ is —S(=O)_2—. In some embodiments, $L^6$ is —S(=O)(=NR^1)—. In some embodiments, $L^6$ is —C(=O)—. In some embodiments, $L^6$ is —C(=N—OR^1)—. In some embodiments, $L^6$ is —C(=O)O—. In some embodiments, $L^6$ is OC(=O)—. In some embodiments, $L^6$ is —C(=O)C(=O)—. In some embodiments, $L^6$ is —C(=O)NR^1—. In some embodiments, $L^6$ is —NR^1C(=O)—. In some embodiments, $L^6$ is —OC(=O)NR^1—. In some embodiments, $L^6$ is —NR^1C(=O)O—. In some embodiments, $L^6$ is —NR^1C(=O)NR^1—. In some embodiments, $L^6$ is —C(=O)NR^1C(=O)—. In some embodiments, $L^6$ is —S(=O)_2NR^1—. In some embodiments, $L^6$ is —NR^1S(=O)_2—. In some embodiments, $L^6$ is —NR^1—. In some embodiments, $L^6$ is —N(OR^1)—. In some embodiments, $L^6$ is —O[(P=O)O—]O—. In some embodiments, $L^6$ is —O[(P=O)S—]O—. In some embodiments, $L^6$ is a bond.

In accordance with the foregoing referenced formulas, in some embodiments of a compound of Formula (V) or (VI), $L^7$ is substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —$(CH_2CH_2O)_m$—, —$(OCH_2CH_2)_m$—, —O—, —S—, —S(=O)—, —S(=O)_2—, —S(=O)(=NR^1)—, —C(=O)—, —C(=N—OR^1)—, —C(=O)O—, —OC(=O)—, —C(=O)C(=O)—, —C(=O)NR^1—, —NR^1C(=O)—, —OC(=O)NR^1—, —NR^1C(=O)O—, —NR^1C(=O)NR^1—, —C(=O)NR^1C(=O)—, —S(=O)_2NR^1—, —NR^1S(=O)_2—, —NR^1—, —N(OR^1)—, —O[(P=O)O—]O—, —O[(P=O)S—]O—, or a bond. In some embodiments, $L^7$ is substituted or unsubstituted $C_1$-$C_{12}$ alkylene. In some embodiments, $L^7$ is an unsubstituted $C_4$ alkylene. In some embodiments, $L^7$ is substituted or unsubstituted $C_1$-$C_{12}$ heteroalkylene. In some embodiments, $L^7$ is substituted or unsubstituted $C_2$-$C_{12}$ alkenylene. In some embodiments, $L^7$ is substituted or unsubstituted $C_2$-$C_{12}$ alkynylene. In some embodiments, $L^7$ is —$(CH_2CH_2O)_m$— or —$(OCH_2CH_2)_m$—. In some embodiments, $L^7$ is —O—. In some embodiments, $L^7$ is —S—. In some embodiments, $L^7$ is —S(=O)—. In some embodiments, $L^7$ is —S(=O)$_2$—. In some embodiments, $L^7$ is —S(=O)(=NR$^1$)—. In some embodiments, $L^7$ is —C(=O)—. In some embodiments, $L^7$ is —C(=N—OR$^1$)—. In some embodiments, $L^7$ is —C(=O)O—. In some embodiments, $L^7$ is OC(=O)—. In some embodiments, $L^7$ is —C(=O)C(=O)—. In some embodiments, $L^7$ is —C(=O)NR$^1$—. In some embodiments, $L^7$ is —NR$^1$C(=O)—. In some embodiments, $L^7$ is —OC(=O)NR$^1$—. In some embodiments, $L^7$ is —NR$^1$C(=O)O—. In some embodiments, $L^7$ is —NR$^1$C(=O)NR$^1$—. In some embodiments, $L^7$ is —C(=O)NR$^1$C(=O)—. In some embodiments, $L^7$ is —S(=O)$_2$NR$^1$—. In some embodiments, $L^7$ is —NR$^1$S(=O)$_2$—. In some embodiments, $L^7$ is —NR$^1$—. In some embodiments, $L^7$ is —N(OR$^1$)—. In some embodiments, $L^7$ is —O[(P=O)O—]O—. In some embodiments, $L^7$ is —O[(P=O)S—]O—. In some embodiments, $L^7$ is a bond.

In accordance with the foregoing referenced formulas, in some embodiments of a compound of Formula (V) or (VI), $L^7$ is substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —$(CH_2CH_2O)_m$—, —$(OCH_2CH_2)_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, —N(OR$^1$)—, —O[(P=O)O—]O—, —O[(P=O)S—]O— or a bond. In some embodiments, $L^8$ is substituted or unsubstituted $C_1$-$C_{12}$ alkylene. In some embodiments, $L^8$ is substituted or unsubstituted $C_1$-$C_{12}$ heteroalkylene. In some embodiments, $L^8$ is substituted or unsubstituted $C_2$-$C_{12}$ alkenylene. In some embodiments, $L^8$ is substituted or unsubstituted $C_2$-$C_{12}$ alkynylene. In some embodiments, $L^8$ is —$(CH_2CH_2O)_m$— or —$(OCH_2CH_2)_m$—. In some embodiments, $L^8$ is —O—. In some embodiments, $L^8$ is —S—. In some embodiments, $L^8$ is —S(=O)—. In some embodiments, $L^8$ is —S(=O)$_2$—. In some embodiments, $L^8$ is —S(=O)(=NR$^1$)—. In some embodiments, $L^8$ is —C(=O)—. In some embodiments, $L^8$ is —C(=N—OR$^1$)—. In some embodiments, $L^8$ is —C(=O)O—. In some embodiments, $L^8$ is OC(=O)—. In some embodiments, $L^8$ is —C(=O)C(=O)—. In some embodiments, $L^8$ is —C(=O)NR$^1$—. In some embodiments, $L^8$ is —NR$^1$C(=O)—. In some embodiments, $L^8$ is —OC(=O)NR$^1$—. In some embodiments, $L^8$ is —NR$^1$C(=O)O—. In some embodiments, $L^2$ is —NRHC(=O)—. In some embodiments, $L^8$ is —NR$^1$C(=O)NR$^1$—. In some embodiments, $L^8$ is —C(=O)NR$^1$C(=O)—. In some embodiments, $L^8$ is —S(=O)$_2$NR$^1$—. In some embodiments, $L^8$ is —NR$^1$S(=O)$_2$—. In some embodiments, $L^8$ is —NR$^1$—. In some embodiments, $L^8$ is —N(OR$^1$)—. In some embodiments, $L^8$ is —O[(P=O)O—]O—. In some embodiments, $L^8$ is —O[(P=O)S—]O—. In some embodiments, $L^8$ is a bond.

In accordance with the foregoing referenced formulas, in some embodiments of a compound of Formula (V) or (VI), $L^9$ is substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —$(CH_2CH_2O)_m$—, —$(OCH_2CH_2)_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, —N(OR$^1$)—, —O[(P=O)O—]O—, —O[(P=O)S—]O—, or a bond. In some embodiments, $L^9$ is substituted or unsubstituted $C_1$-$C_{12}$ alkylene. In some embodiments, $L^9$ is an unsubstituted $C_3$-4 alkylene. In some embodiments, $L^9$ is an unsubstituted $C_1$-4 alkylene. In some embodiments, $L^9$ is substituted or unsubstituted $C_1$-$C_{12}$ heteroalkylene. In some embodiments, $L^9$ is substituted or unsubstituted $C_2$-$C_{12}$ alkenylene. In some embodiments, $L^9$ is substituted or unsubstituted $C_2$-$C_{12}$ alkynylene. In some embodiments, $L^9$ is —$(CH_2CH_2O)_m$— or —$(OCH_2CH_2)_m$—. In some embodiments, $L^9$ is —O—. In some embodiments, $L^9$ is —S—. In some embodiments, $L^9$ is —S(=O)—. In some embodiments, $L^9$ is —S(=O)$_2$—. In some embodiments, $L^9$ is —S(=O)(=NR$^1$)—. In some embodiments, $L^9$ is —C(=O)—. In some embodiments, $L^9$ is —C(=N—OR$^1$)—. In some embodiments, $L^9$ is —C(=O)O—. In some embodiments, $L^9$ is OC(=O)—. In some embodiments, $L^9$ is —C(=O)C(=O)—. In some embodiments, $L^9$ is —C(=O)NR$^1$—. In some embodiments, $L^9$ is —NR$^1$C(=O)—. In some embodiments, $L^9$ is —OC(=O)NR$^1$—. In some embodiments, $L^9$ is —NR$^1$C(=O)O—. In some embodiments, $L^9$ is —NR$^1$C(=O)NR$^1$—. In some embodiments, $L^9$ is —C(=O)NR$^1$C(=O)—. In some embodiments, $L^9$ is —S(=O)$_2$NR$^1$—. In some embodiments, $L^9$ is —NR$^1$S(=O)$_2$—. In some embodiments, $L^9$ is —NR$^1$—. In some embodiments, $L^9$ is —N(OR$^1$)—. In some embodiments, $L^9$ is —O[(P=O)O—]O—. In some embodiments, $L^9$ is —O[(P=O)S—]O—. In some embodiments, $L^9$ is a bond.

In accordance with the foregoing referenced formulas, in some embodiments of a compound of Formula (V) or (VI), $L^{10}$ is substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —$(CH_2CH_2O)_m$—, —$(OCH_2CH_2)_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, —N(OR$^1$)—, —O[(P=O)O—]O—, —O[(P=O)S—]O—, or a bond. In some embodiments, $L^{10}$ is substituted or unsubstituted $C_1$-$C_{12}$ alkylene. In some embodiments, $L^{10}$ is substituted or unsubstituted $C_1$-$C_{12}$ heteroalkylene. In some embodiments, $L^{10}$ is substituted or unsubstituted $C_2$-$C_{12}$ alkenylene. In some embodiments, $L^{10}$ is substituted or unsubstituted $C_2$-$C_{12}$ alkynylene. In some embodiments, $L^{10}$ is —$(CH_2CH_2O)_m$— or —$(OCH_2CH_2)_m$—. In some embodiments, $L^{10}$ is —O—. In some embodiments, $L^{10}$ is —S—. In some embodiments, $L^{10}$ is —S(=O)—. In some embodiments, $L^{10}$ is —S(=O)$_2$—. In some embodiments, $L^{10}$ is —S(=O)(=NR$^1$)—. In some embodiments, $L^{10}$ is —C(=O)—. In some embodiments, $L^{10}$ is —C(=N—OR$^1$)—. In some embodiments, $L^{10}$ is —C(=O)O—. In some embodiments, $L^{10}$ is OC(=O)—. In some embodiments, $L^{10}$ is —C(=O)C(=O)—. In some embodiments, $L^{10}$ is —C(=O)NR$^1$—. In some embodiments, $L^{10}$ is —NR$^1$C(=O)—. In some embodiments, $L^{10}$ is —OC(=O)NR$^1$—. In some embodiments, $L^{10}$ is —NR$^1$C(=O)O—. In some embodiments, $L^{10}$ is —NR$^1$C(=O)NR$^1$—. In some embodiments, $L^{10}$ is —C(=O)NR$^1$C(=O)—. In some embodiments, $L^{10}$ is —S(=O)$_2$NR$^1$—. In some embodiments, $L^{10}$ is —NR$^1$S(=O)$_2$—. In some embodiments, $L^{10}$ is —NR$^1$—. In some embodiments, $L^{10}$ is —N(OR$^1$)—. In some embodiments, $L^{10}$ is —O[(P=O)O—]O—. In some embodiments, $L^{10}$ is —O[(P=O)S—]O—. In some embodiments, $L^{10}$ is substituted or unsubstituted C$_1$-C$_6$ alkylene. In some embodiments, $L^{10}$ is substituted or unsubstituted C$_1$-C$_3$ alkylene. In some embodiments, $L^{10}$ is substituted or unsubstituted C$_2$-C$_3$ alkylene. In some embodiments, $L^{10}$ is —CH$_2$CH$_2$—. In some embodiments, $L^{10}$ is a bond.

In accordance with the foregoing referenced formulas, in some embodiments of a compound of Formula (V) or (VI), $L^{11}$ is substituted or unsubstituted —(CH$_2$CH$_2$O)$_n$—, substituted or unsubstituted —(OCH$_2$CH$_2$)$_n$—, substituted or unsubstituted —(CH$_2$)$_n$—, or bond. In some embodiments, $L^{11}$ is substituted or unsubstituted —(CH$_2$CH$_2$O)$_n$—. In some embodiments, $L^{11}$ is substituted or unsubstituted —(OCH$_2$CH$_2$)$_n$—. In some embodiments, $L^{11}$ is substituted or unsubstituted —(CH$_2$)$_n$—. In some embodiments, $L^{11}$ is a bond. In some embodiments, n is 30 to 50. In some embodiments, n is 30 to 40. In some embodiments, n is 40 to 50.

In accordance with the foregoing referenced formulas, in some embodiments of a compound of Formula (V) or (VI), $L^{12}$ is substituted or unsubstituted C$_1$-C$_{12}$ alkylene, substituted or unsubstituted C$_1$-C$_{12}$ heteroalkylene, substituted or unsubstituted C$_2$-C$_{12}$ alkenylene, substituted or unsubstituted C$_2$-C$_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, —N(OR$^1$)—, —O[(P=O)O—]O—, —O[(P=O)S—]O—, or a bond. In some embodiments, $L^{12}$ is substituted or unsubstituted C$_1$-C$_{12}$ alkylene. In some embodiments, $L^{12}$ is substituted or unsubstituted C$_1$-C$_{12}$ heteroalkylene. In some embodiments, $L^{12}$ is substituted or unsubstituted C$_2$-C$_{12}$ alkenylene. In some embodiments, $L^{12}$ is substituted or unsubstituted C$_2$-C$_{12}$ alkynylene. In some embodiments, $L^{12}$ is —(CH$_2$CH$_2$O)$_m$— or —(OCH$_2$CH$_2$)$_m$—. In some embodiments, $L^{12}$ is —O—. In some embodiments, $L^{12}$ is —S—. In some embodiments, $L^{12}$ is —S(=O)—. In some embodiments, $L^{12}$ is —S(=O)$_2$—. In some embodiments, $L^{12}$ is —S(=O)(=NR$^1$)—. In some embodiments, $L^{12}$ is —C(=O)—. In some embodiments, $L^{12}$ is —C(=N—OR$^1$)—. In some embodiments, $L^{12}$ is —C(=O)O—. In some embodiments, $L^{12}$ is OC(=O)—. In some embodiments, $L^{12}$ is —C(=O)C(=O)—. In some embodiments, $L^{12}$ is —C(=O)NR$^1$—. In some embodiments, $L^{12}$ is —NR$^1$C(=O)—. In some embodiments, $L^{12}$ is —OC(=O)NR$^1$—. In some embodiments, $L^{12}$ is —NR$^1$C(=O)O—. In some embodiments, $L^{12}$ is —NR$^1$C(=O)NR$^1$—. In some embodiments, $L^{12}$ is —C(=O)NR$^1$C(=O)—. In some embodiments, $L^{12}$ is —S(=O)$_2$NR$^1$—. In some embodiments, $L^{12}$ is —NR$^1$S(=O)$_2$—. In some embodiments, $L^{12}$ is —NR$^1$—. In some embodiments, $L^{12}$ is —N(OR$^1$)—. In some embodiments, $L^{12}$ is —O[(P=O)O—]O—. In some embodiments, $L^{12}$ is —O[(P=O)S—]O—. In some embodiments, $L^{12}$ is substituted or unsubstituted C$_1$-C$_6$ alkylene. In some embodiments, $L^{12}$ is substituted or unsubstituted C$_1$-C$_3$ alkylene. In some embodiments, $L^{12}$ is substituted or unsubstituted C$_2$-C$_3$ alkylene. In some embodiments, $L^{12}$ is —CH$_2$CH$_2$—. In some embodiments of a compound of Formula (V) or (VI), $L^{12}$ is —NR$^1$C(=O)O—. In some embodiments, $L^{12}$ is a bond. In some embodiments, $L^{12}$ is an organic molecular residue that intercalates with group R. In some embodiments, $L^{12}$ can ionically/electrostatically interact with a base pair or covalently bond with a base pair. Some non-limiting examples of an organic molecular residue that intercalates with group R can include berberine, ethidium bromide, daunomycin, thalidomide, doxorubicin (adriamycin), aflatoxin B1, amsacrine, acridines (e.g., proflavine, quinacrine, acridine orange, Pyrazoloacridine), acriflavin, amonafide, 1,10-phenanthroline, metal cations with polycyclic aromatic ligands (e.g. metals such as Rh(III); ligands such as Ir(III), dipyridine, terpyridine), bleomycin, actinomycin D, and ellipticine.

In some embodiments of a compound of Formula (V) or (VI), m is an integer selected from 1 to 10. In some embodiments, m is selected from 1 to 3. In some embodiments, m is selected from 1 to 5. In some embodiments, m is selected from 3 to 8. In some embodiments, m is selected from 2 to 5. In some embodiments, m is selected from 5 to 10. In some embodiments, m is 1, 2, 3, 4, 5, 6, 7, 8, 9 or 10. In some embodiments, m is 1. In some embodiments, m is 2. In some embodiments, m is 3.

In some embodiments of a compound of Formula (V) or (VI), n is an integer selected from 1 to 200. In some embodiments, n is selected from 1 to 20. In some embodiments, n is selected from 1 to 50. In some embodiments, n is selected from 1 to 100. In some embodiments, n is selected from 50 to 100. In some embodiments, n is selected from 25 to 50. In some embodiments, n is selected from 30 to 40. In some embodiments, n is selected from 25 to 75. In some embodiments, n is selected from 100 to 200. In some embodiments, n is selected from 50 to 150. In some embodiments, n is selected from 150 to 200.

In some embodiments of a compound of Formula (VI), Formula (VIa), or Formula (VIb), m is an integer selected from 1 to 10. In some embodiments, m is selected from 1 to 3. In some embodiments, m is selected from 1 to 5. In some embodiments, m is selected from 3 to 8. In some embodiments, m is selected from 2 to 5. In some embodiments, m is selected from 5 to 10. In some embodiments, m is 1, 2, 3, 4, 5, 6, 7, 8, 9 or 10. In some embodiments, m is 1. In some embodiments, m is 2. In some embodiments, m is 3.

In some embodiments of a compound of Formula (VI), Formula (VIa), or Formula (VIb), n is an integer selected from 1 to 200. In some embodiments, n is selected from 1 to 20. In some embodiments, n is selected from 1 to 50. In some embodiments, n is selected from 1 to 100. In some embodiments, n is selected from 50 to 100. In some embodiments, n is selected from 25 to 50. In some embodiments, n is selected from 30 to 40. In some embodiments, n is selected from 25 to 75. In some embodiments, n is selected from 100 to 200. In some embodiments, n is selected from 50 to 150. In some embodiments, n is selected from 150 to 200.

In some embodiments of a compound of Formula (V), Formula (VI), Formula (VIa), or Formula (VIb), each $R^1$ is independently H or —CH$_3$. In some embodiments, $R^1$ is H.

In some embodiments of a compound of Formula (V), Formula (VI), Formula (VIa), or Formula (VIb), R comprises one or more of fatty alcohols, fatty acids, glycerolipids, glycerophospholipids, sphingolipids, saccharolipids, polyketides, sterol lipids, and prenol lipids. In some embodiments, the R comprises one or more fatty alcohols. In some embodiments, each fatty alcohol is independently a saturated, monounsaturated, or polyunsaturated fatty alcohol. In some embodiments, the fatty alcohol comprises one or more a C$_2$-C$_{26}$ fatty alcohol. In some embodiments, the fatty alcohol comprises two or more a $C_2$-$C_{26}$ fatty alcohol. In some embodiments, each fatty alcohol is a $C_{12}$, $C_{14}$, $C_{16}$, $C_{18}$, $C_{20}$, or $C_{22}$ fatty alcohol. In some embodiments, each fatty alcohol is independently docosahexaenol, eicosapentaenol, oleyl alcohol, stearyl alcohol, (9Z,12Z)-octadeca-9,12-dien-1-yl alcohol, (Z)-docos-13-en-1-yl alcohol, docosanyl alcohol, (E)-octadec-9-en-1-yl alcohol, icosanyl alcohol, (9Z,12Z,15Z)-octadeca-9,12,15-trien-1-yl alcohol, or palmityl alcohol. In some embodiments, each fatty alcohol is a stearyl alcohol. In some embodiments, the R comprises one or more sterol lipids. In some embodiments, the R comprises one or more of vitamins. In some embodiments, each vitamin is independently a vitamin A, vitamin D, vitamin E, or vitamin K.

In some embodiments, R group provided in Formula (V), Formula (VI), Formula (VIa), or Formula (VIb) comprises a payload as described herein. In some embodiments, R group provided in Formula (V), Formula (VI), Formula (VIa), or Formula (VIb) comprises a lipid.

In some embodiments, R group provided in Formula (V), Formula (VI), Formula (VIa), or Formula (VIb) comprises a nucleic acid. In some embodiments, the nucleic acid is a single-stranded nucleic acid. In some embodiments, single-stranded nucleic acid is a DNA. In some embodiments, single-stranded nucleic acid is an RNA. In some embodiments, the nucleic acid is a double-stranded nucleic acid. In some embodiments, the double-stranded nucleic acid is a DNA. In some embodiments, the double-stranded nucleic acid is an RNA. In some embodiments, the double-stranded nucleic acid is a DNA-RNA hybrid. In some embodiments, the nucleic acid is a messenger RNA (mRNA), a microRNA, an asymmetrical interfering RNA (aiRNA), a small hairpin RNA (shRNA), or a Dicer-Substrate dsRNA. In some embodiments, the nucleic acid is an mRNA. In some embodiments, R comprises an mRNA molecule encoding a Cas nuclease, i.e., a Cas nuclease mRNA. In some embodiments, R comprises one or more guide RNAs or nucleic acids encoding guide RNAs. In some embodiments, R comprises a template nucleic acid for repair or recombination. In some embodiments, R comprises an mRNA encoding a gene editor nuclease. In some embodiments, R comprises an mRNA encoding a base editor nuclease. In some embodiments, R comprises an mRNA encoding a restriction enzyme. In some embodiments, R comprises zinc-finger nuclease or TALEN nuclease. In some embodiments, R comprises a guide RNA. In some embodiments, the gRNA hybridizes a gene selected from PCSK9, ANGPTL3, APOC3, LPA, APOB, MTP, ANGPTL4, ANGPTL8, APOA5, APOE, LDLR, IDOL, NPC1L1, ASGR1, TM6SF2, GALNT2, GCKR, LPL, MLXIPL, SORT1, TRIB1, MARC1, ABCG5, and ABCG8. In some embodiments, the gRNA hybridizes with PCSK9. In some embodiments, the gRNA hybridizes with ANGPTL3. In some embodiments, R comprises a guide RNA sequence as described herein. In some embodiments, R comprises a coupling sequence as described herein. In some embodiments, R comprises an mRNA, guide RNA, siRNA, antisense oligonucleotides, microRNA, decoy RNA, or aptamer. In some embodiments, when R is an nucleic acid, $L^{12}$ can intercalate with or bind to group R.

In some embodiments, R group provided in Formula (V), Formula (VI), Formula (VIa), or Formula (VIb) comprises an amino acid. In some embodiment, the amino acid is a natural amino acid. In some embodiment, the amino acid is an amino acid that is outside the 20 canonical amino acids. The amino acid can be modified.

In some embodiments, R group provided in Formula (V), Formula (VI), Formula (VIa), or Formula (VIb) comprises a protein. In some embodiments, the protein is an Argonaute protein. In some embodiments, the protein is a cas protein. In some embodiments, the protein is an RNP.

In some embodiments, R group provided in Formula (V), Formula (VI), Formula (VIa), or Formula (VIb) comprises a lipid nanoparticle.

It is to be understood that the linkage between $L^{12}$ and R can be a covalent bond, a hydrogen bond, intermolecular or intramolecular interaction.

In some embodiments of a compound of Formula (V), Formula (VI), Formula (VIa), or Formula (VIb), A is

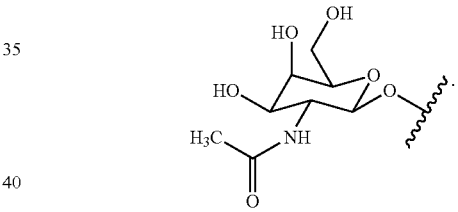

In some embodiments of a compound of Formula (V), Formula (VI), Formula (VIa), or Formula (VIb), A is galactose.

In some embodiments, receptor targeting conjugates described herein are GalNAc-conjugated lipids that have a structure given in Table 4.

TABLE 4
Exemplary GalNAc-conjugated lipids
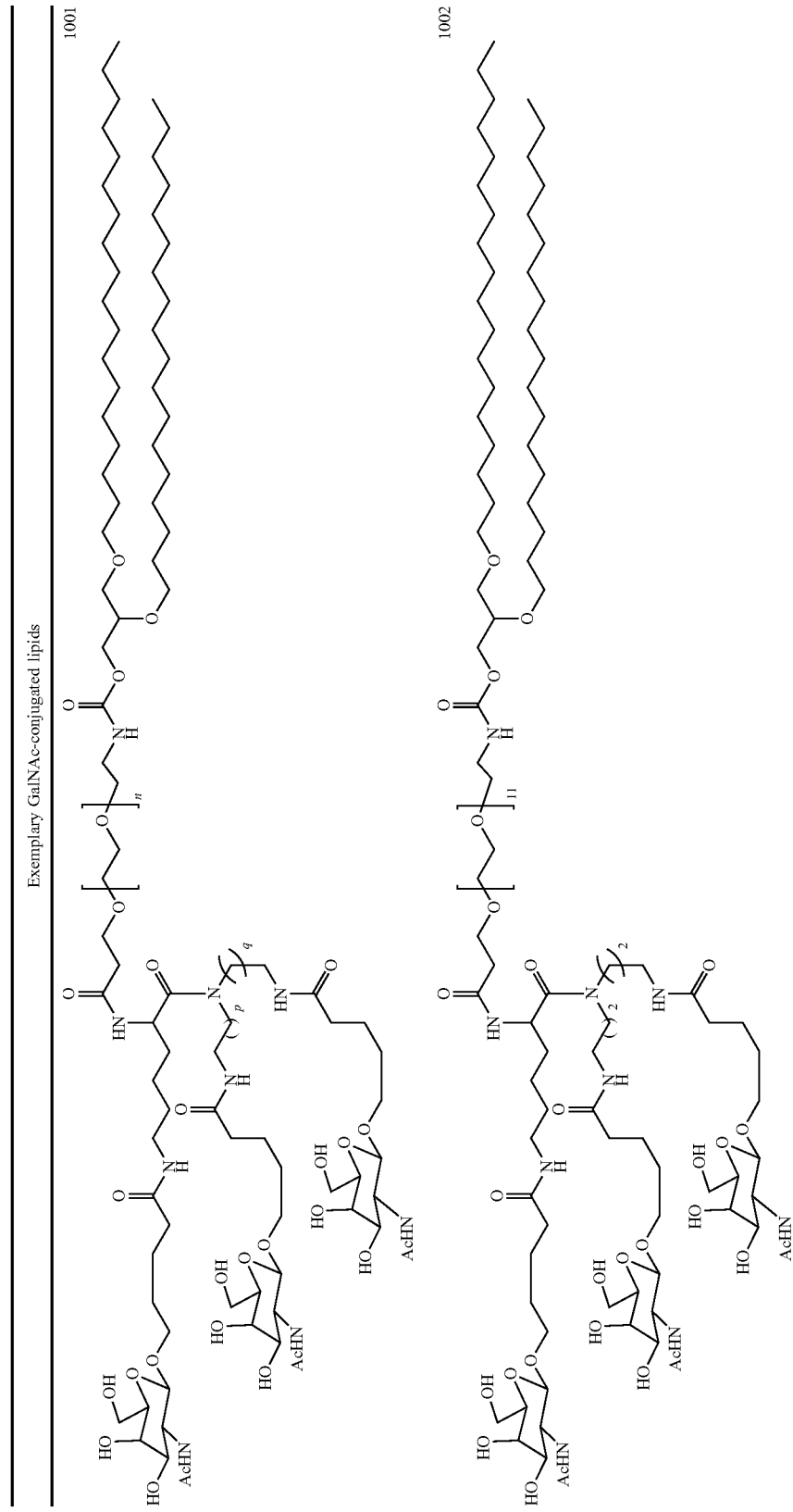

TABLE 4-continued
Exemplary GalNAc-conjugated lipids
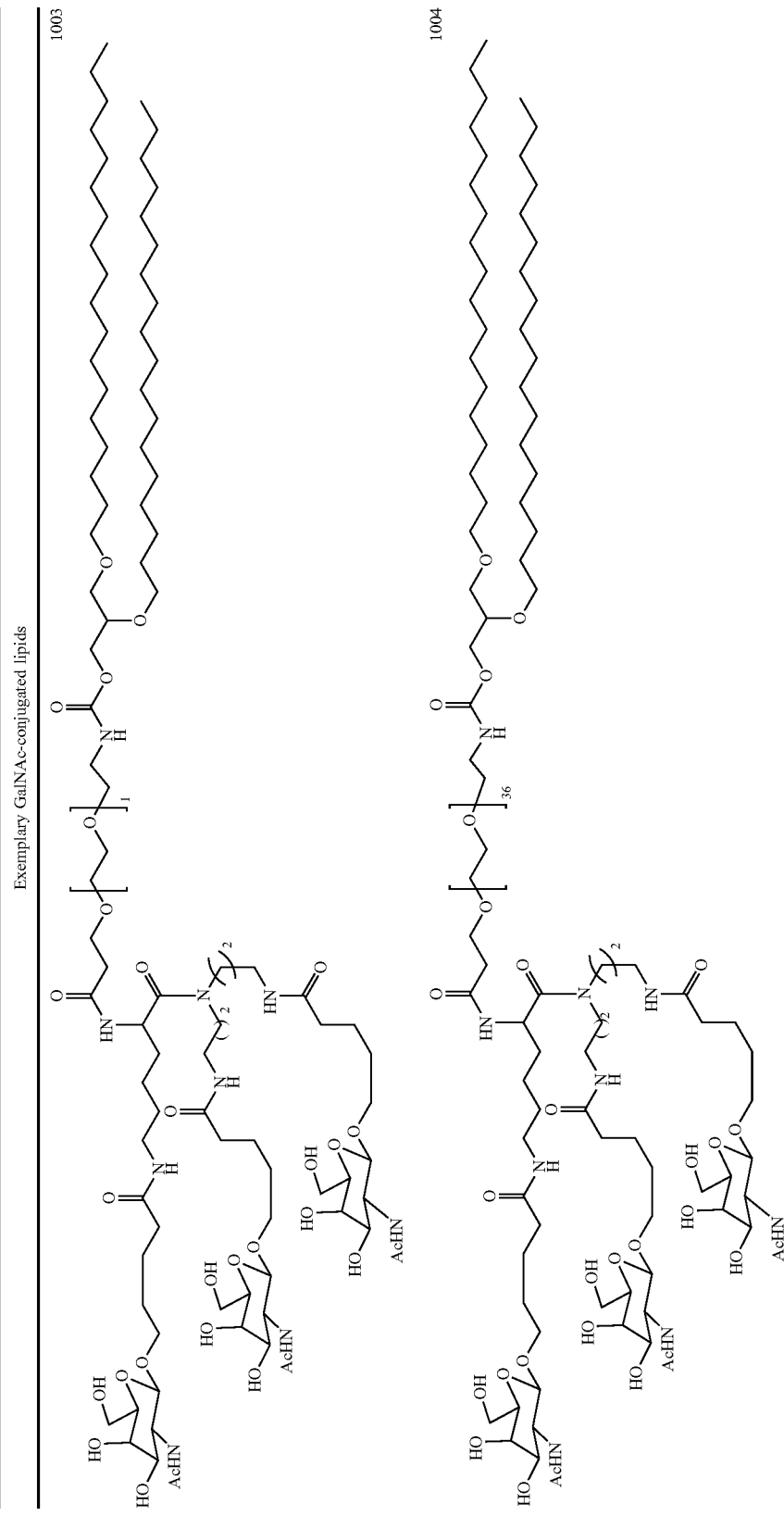

TABLE 4-continued
Exemplary GalNAc-conjugated lipids
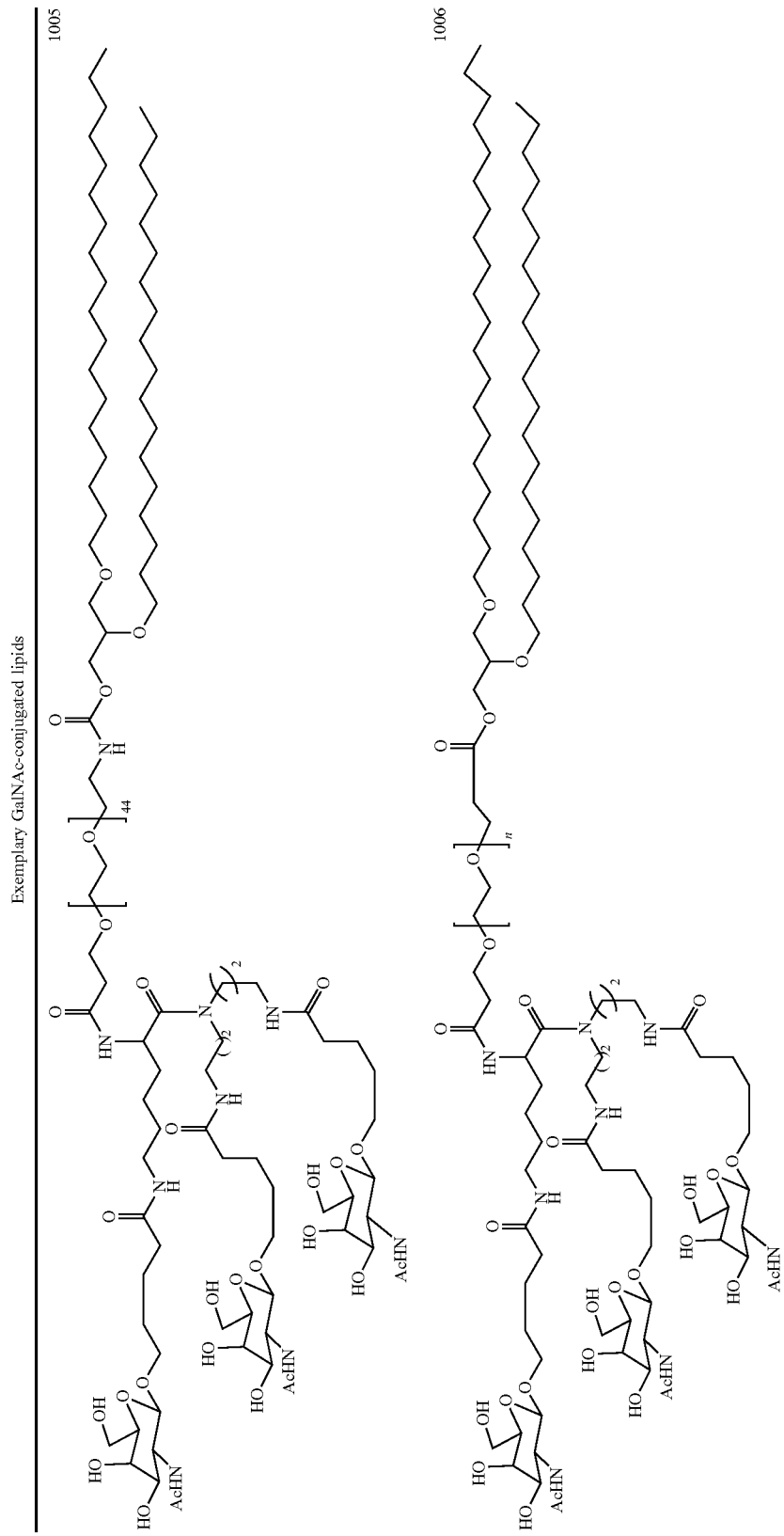

TABLE 4-continued
Exemplary GalNAc-conjugated lipids
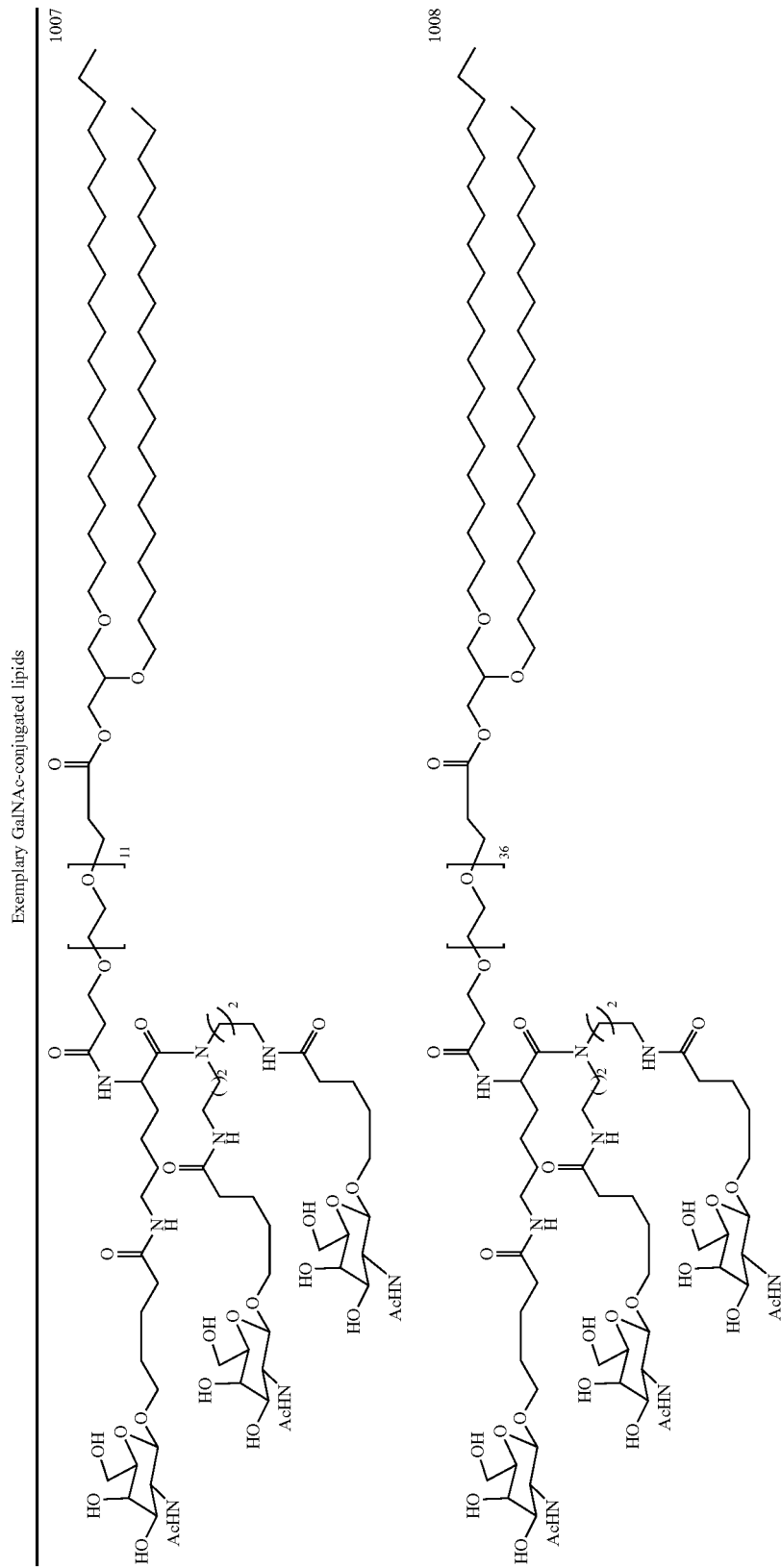

TABLE 4-continued
Exemplary GalNAc-conjugated lipids
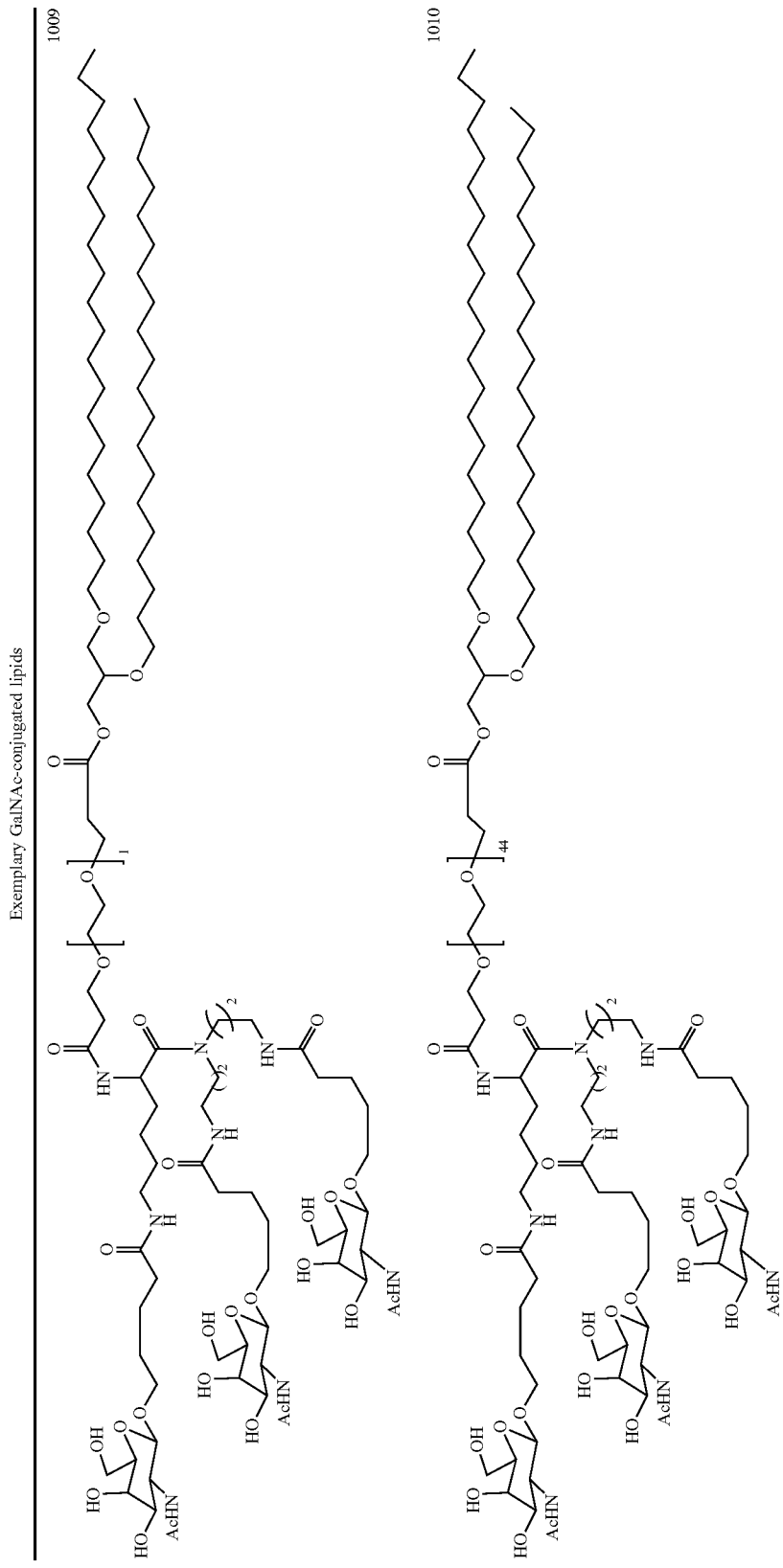

TABLE 4-continued
Exemplary GalNAc-conjugated lipids
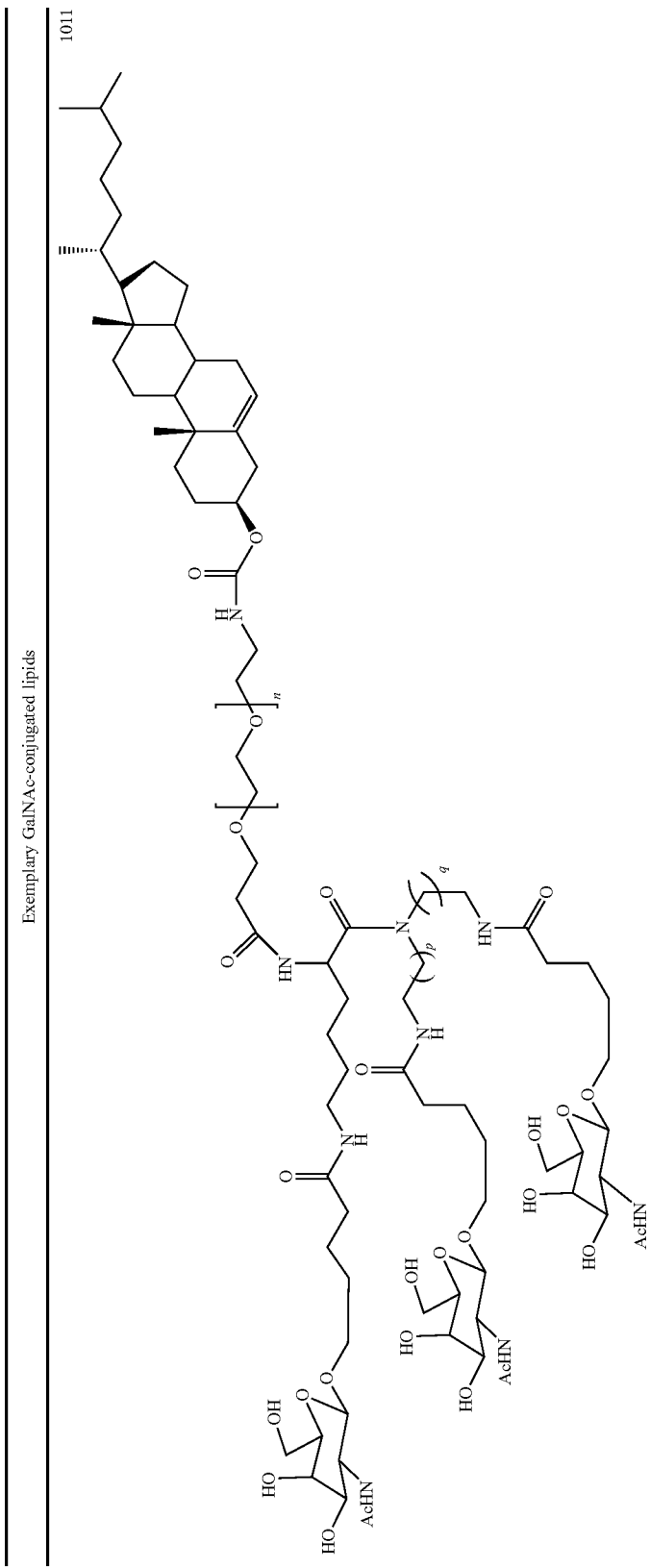
1011

TABLE 4-continued
Exemplary GalNAc-conjugated lipids
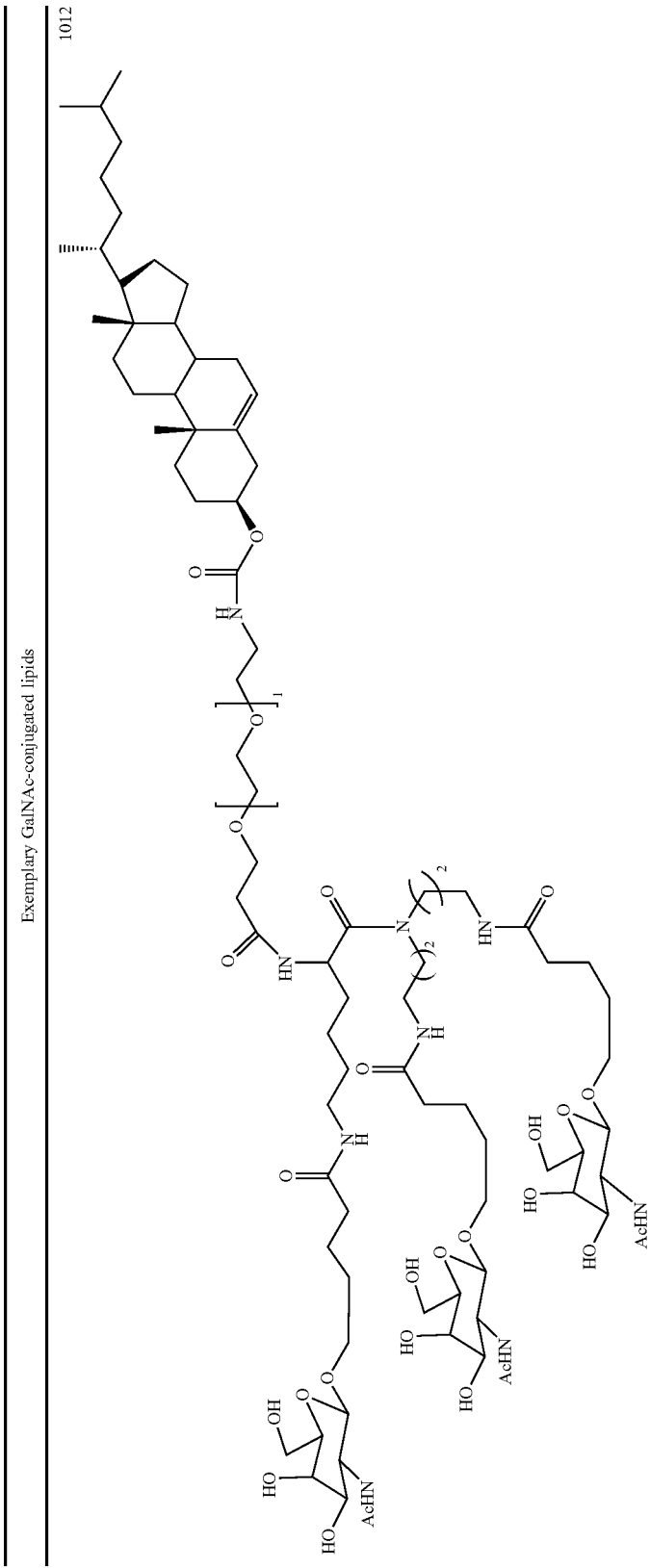
1012

TABLE 4-continued
Exemplary GalNAc-conjugated lipids
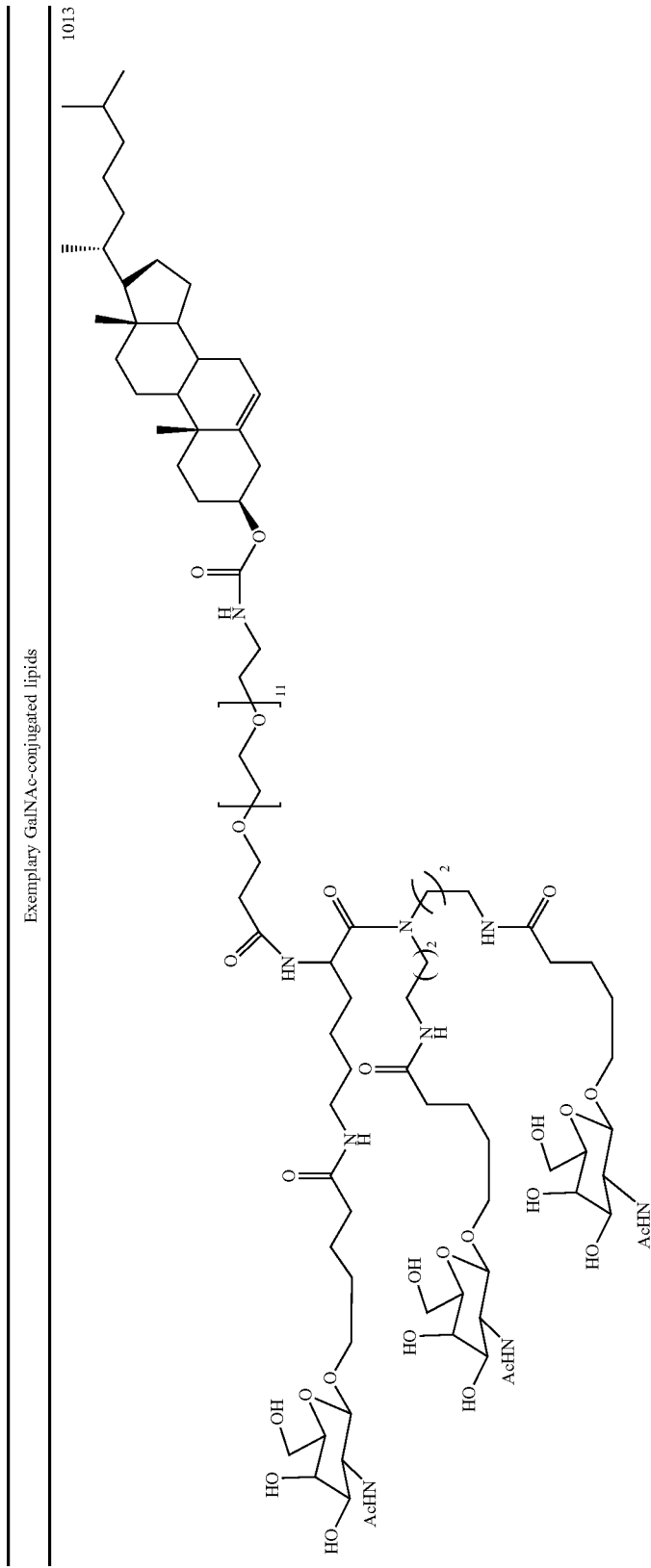
1013

TABLE 4-continued
Exemplary GalNAc-conjugated lipids
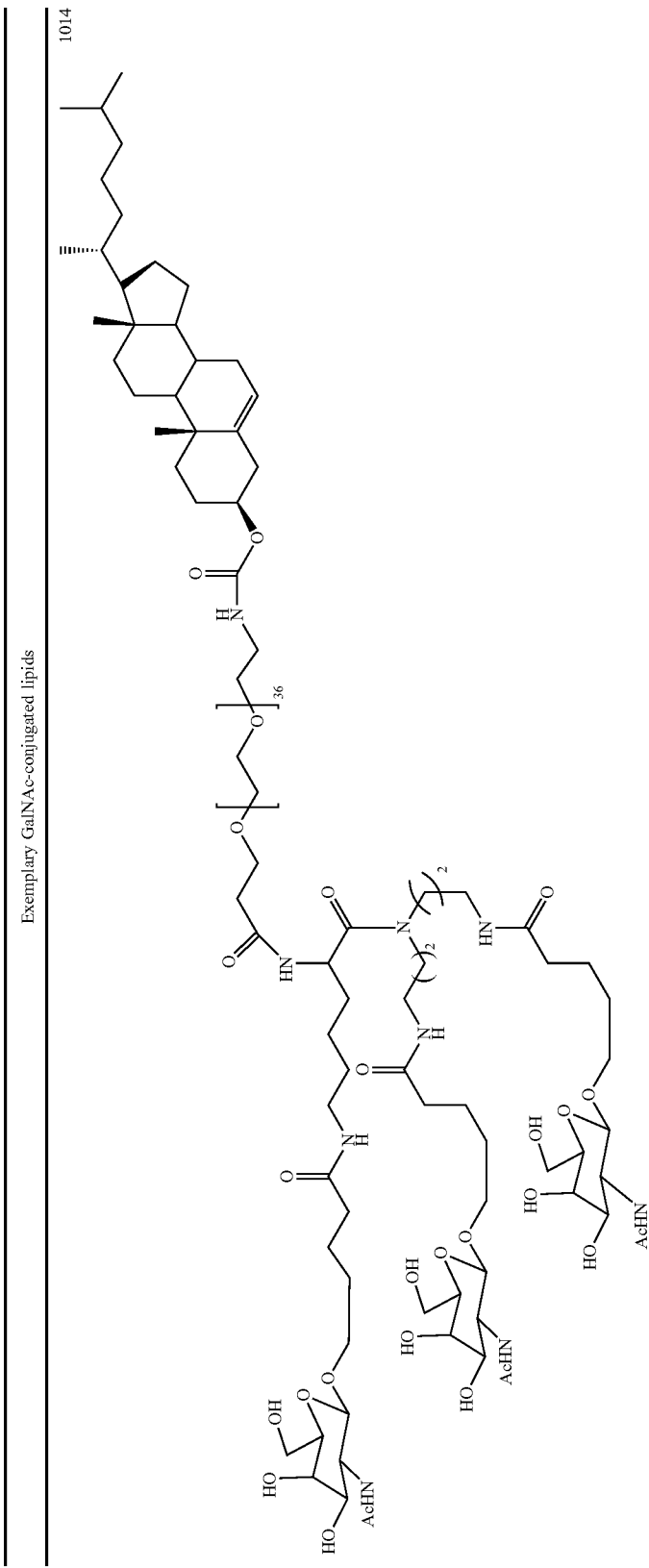
1014

TABLE 4-continued
Exemplary GalNAc-conjugated lipids
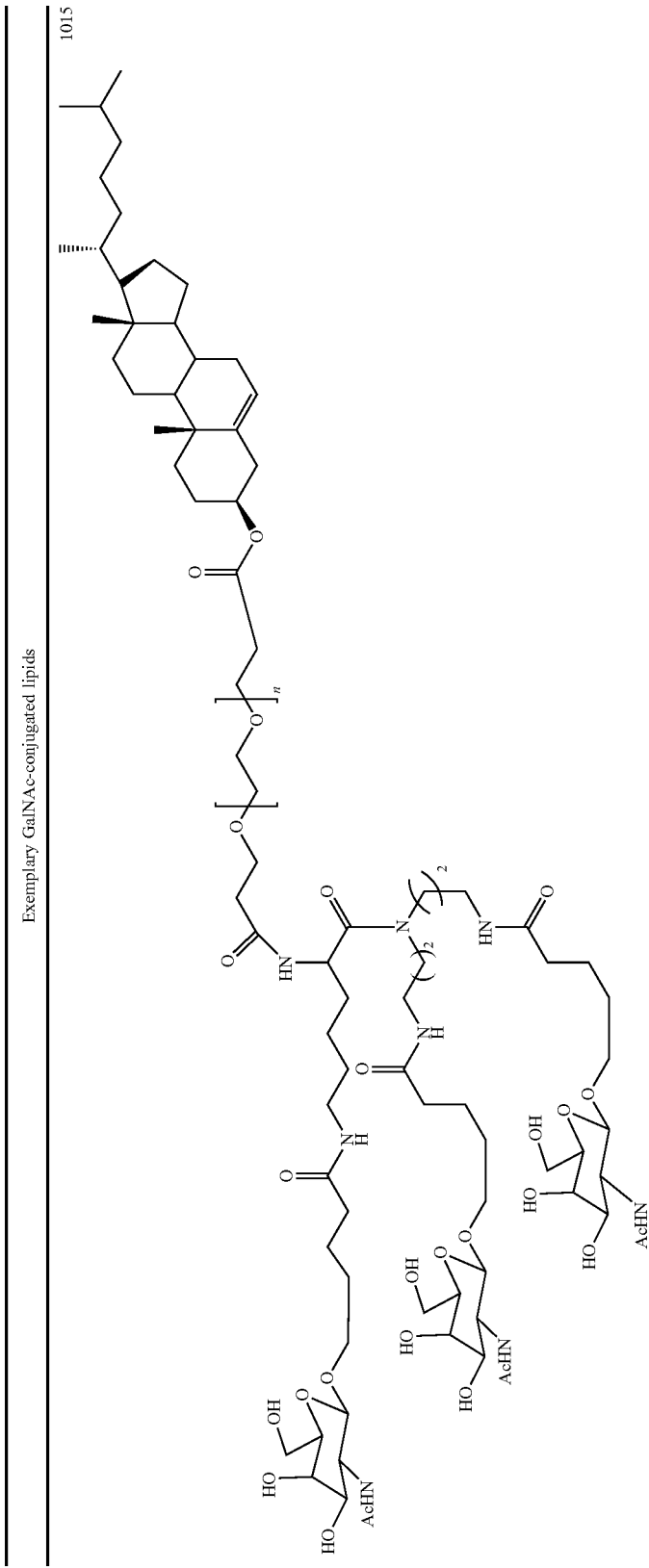
1015

TABLE 4-continued
Exemplary GalNAc-conjugated lipids
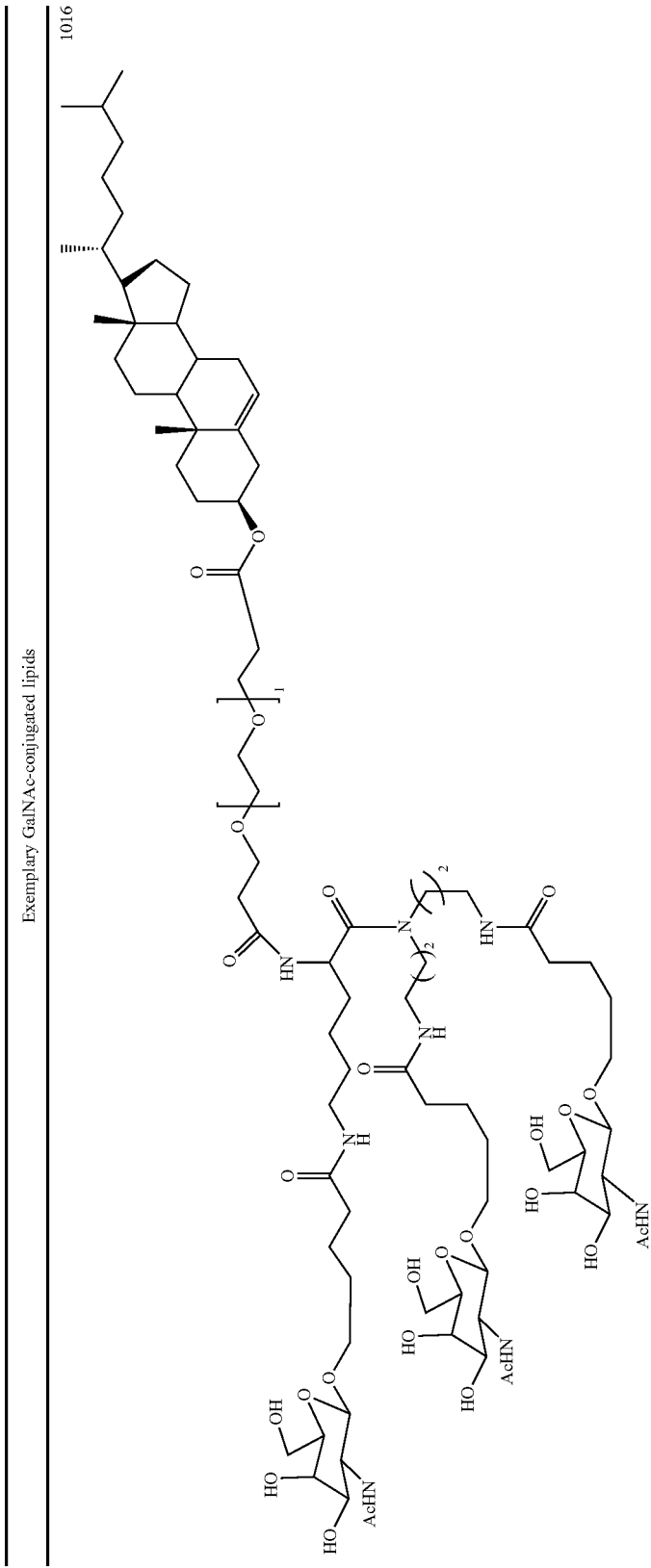
1016

TABLE 4-continued
Exemplary GalNAc-conjugated lipids
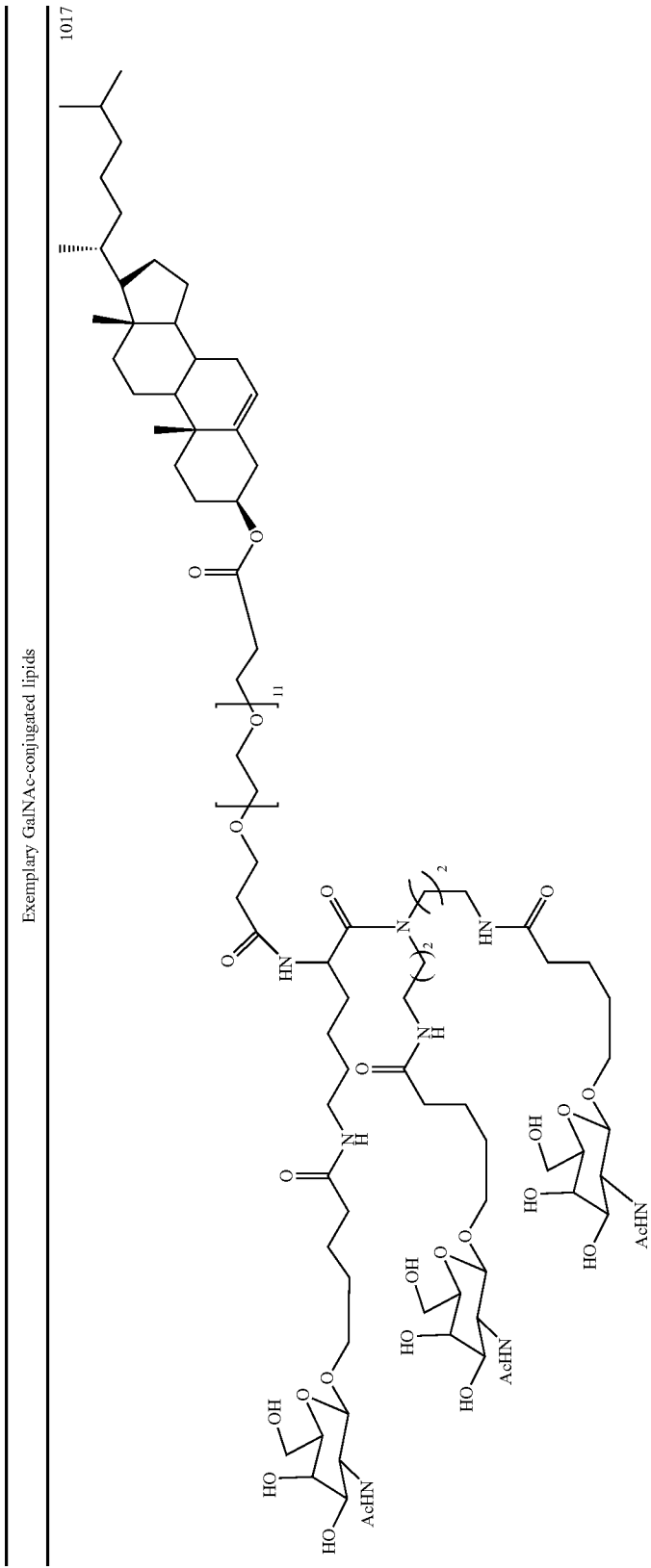
1017

TABLE 4-continued
Exemplary GalNAc-conjugated lipids
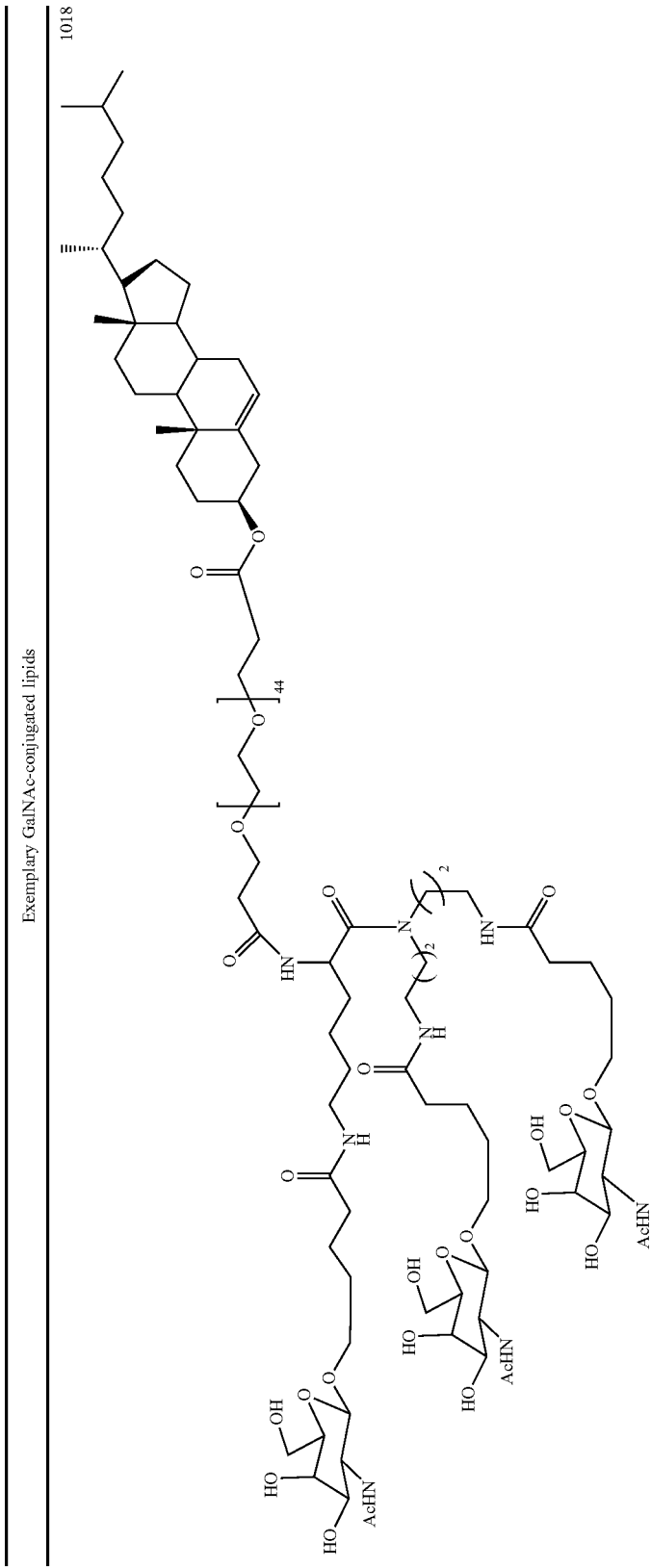
1018

TABLE 4-continued
Exemplary GalNAc-conjugated lipids
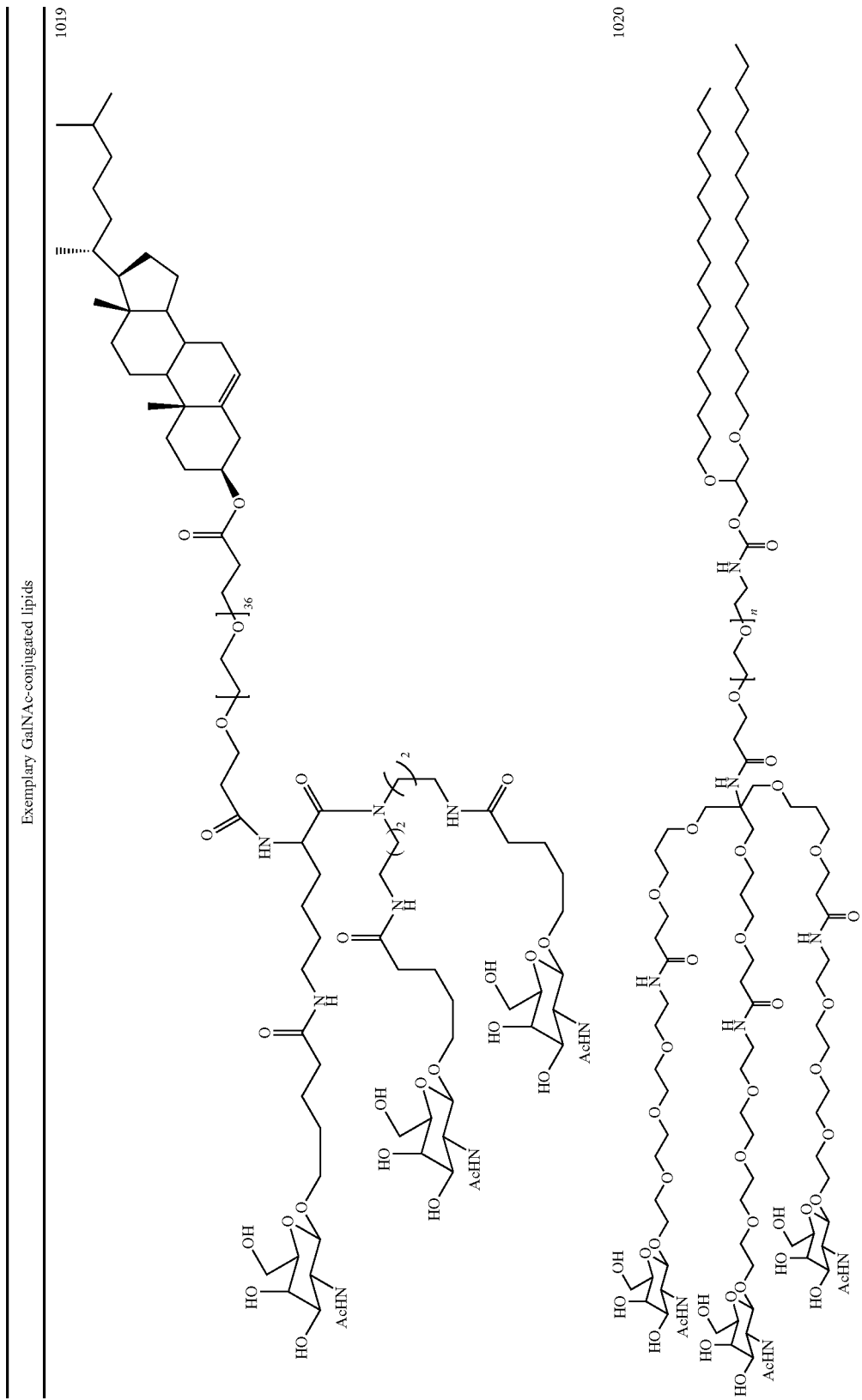

TABLE 4-continued

Exemplary GalNAc-conjugated lipids

TABLE 4-continued
Exemplary GalNAc-conjugated lipids
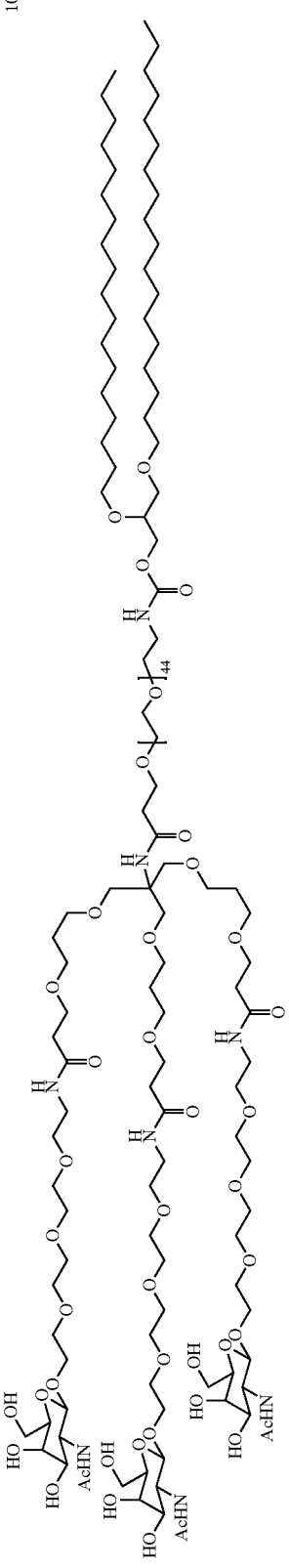

TABLE 4-continued

Exemplary GalNAc-conjugated lipids

TABLE 4-continued
Exemplary GalNAc-conjugated lipids
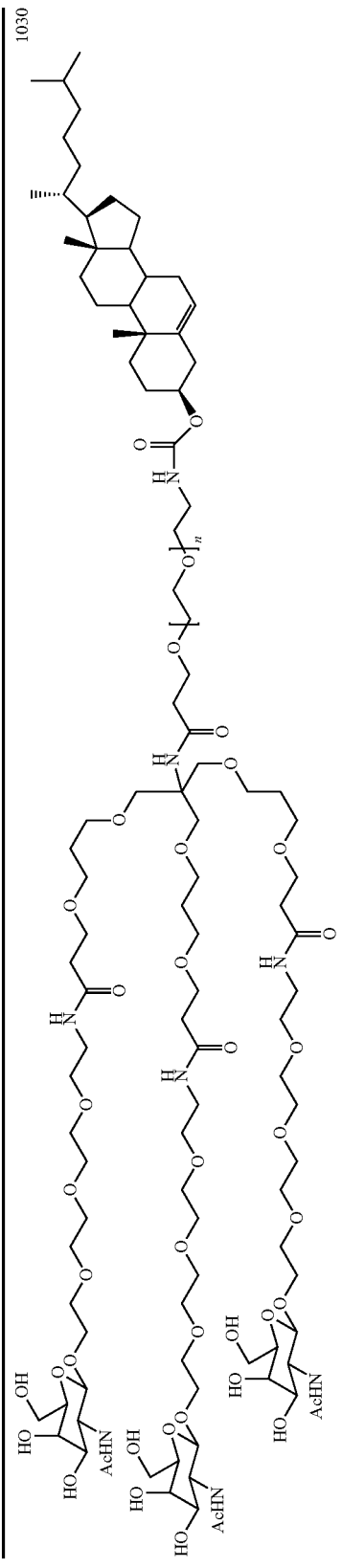
1030
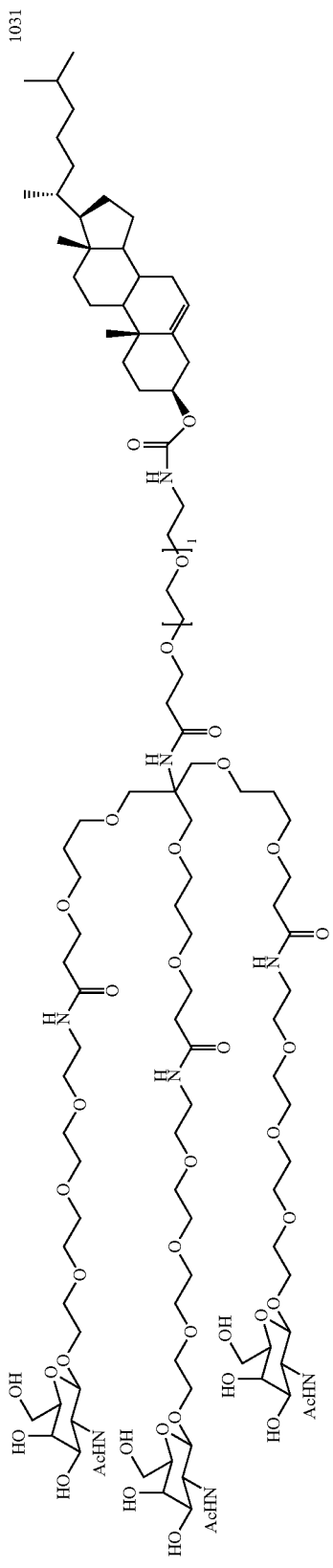
1031
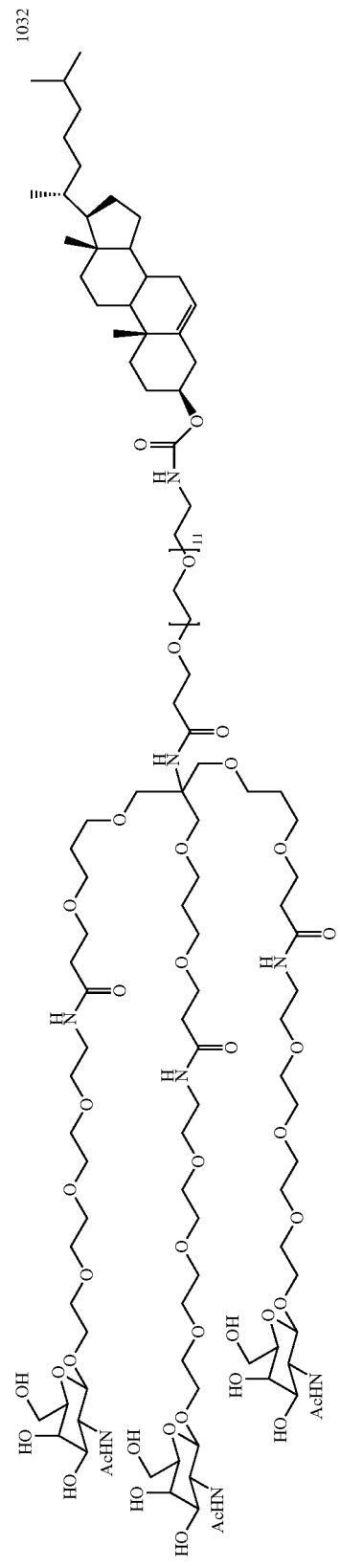
1032

TABLE 4-continued
Exemplary GalNAc-conjugated lipids
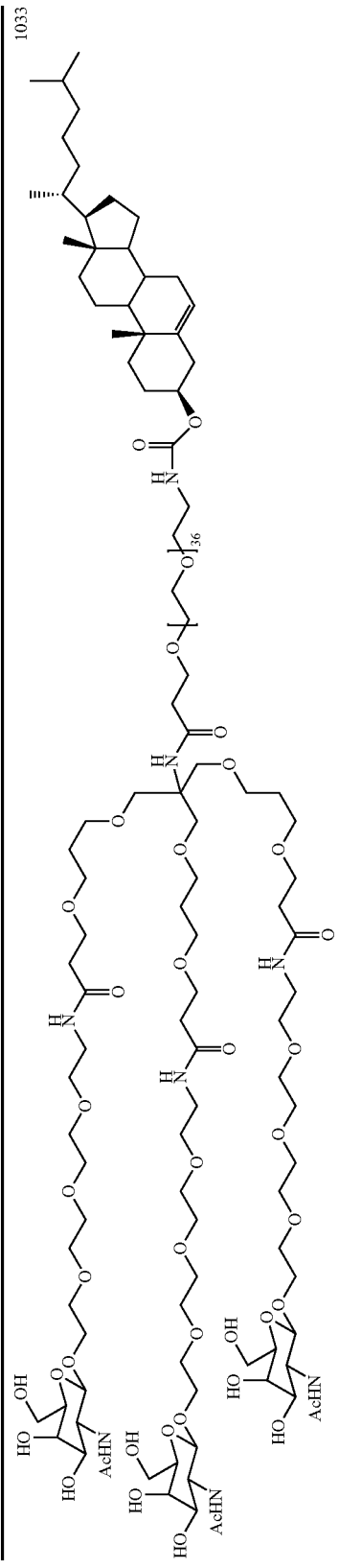
1033
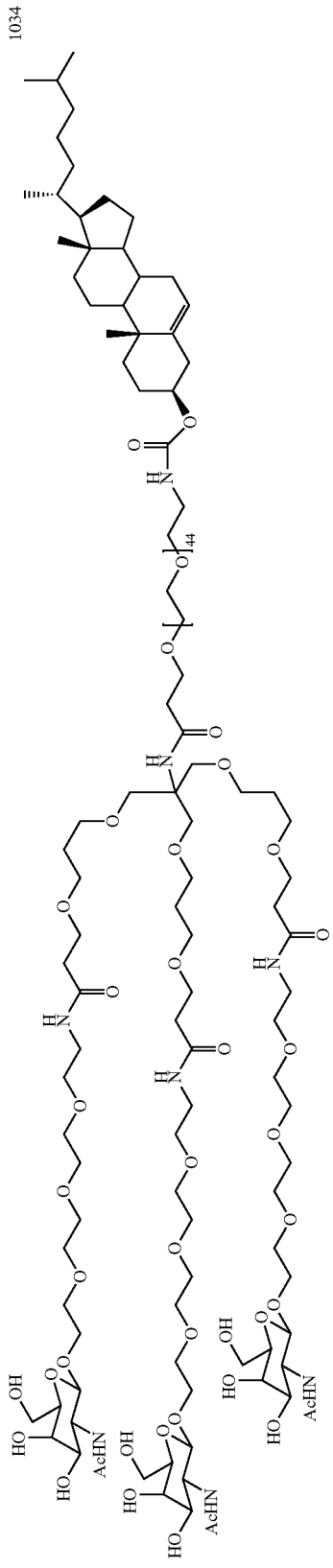
1034
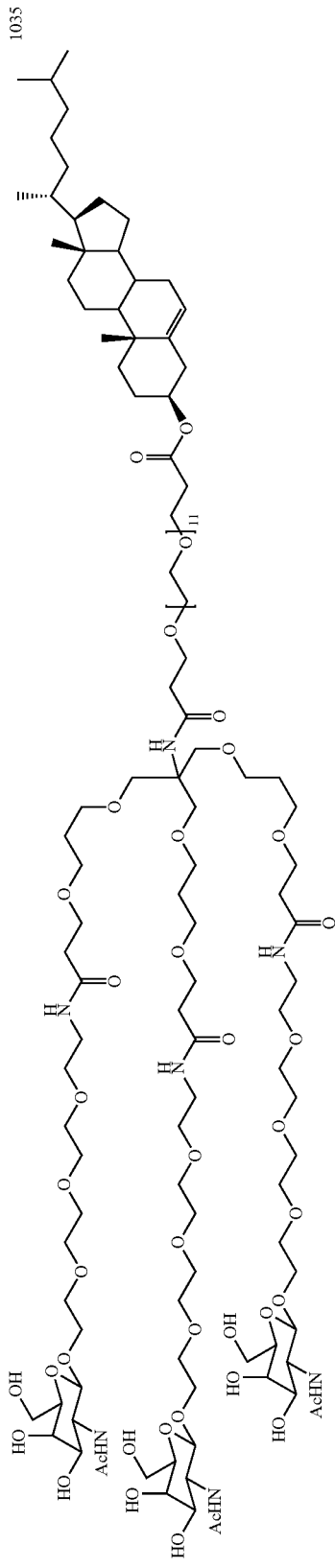
1035

TABLE 4-continued
Exemplary GalNAc-conjugated lipids
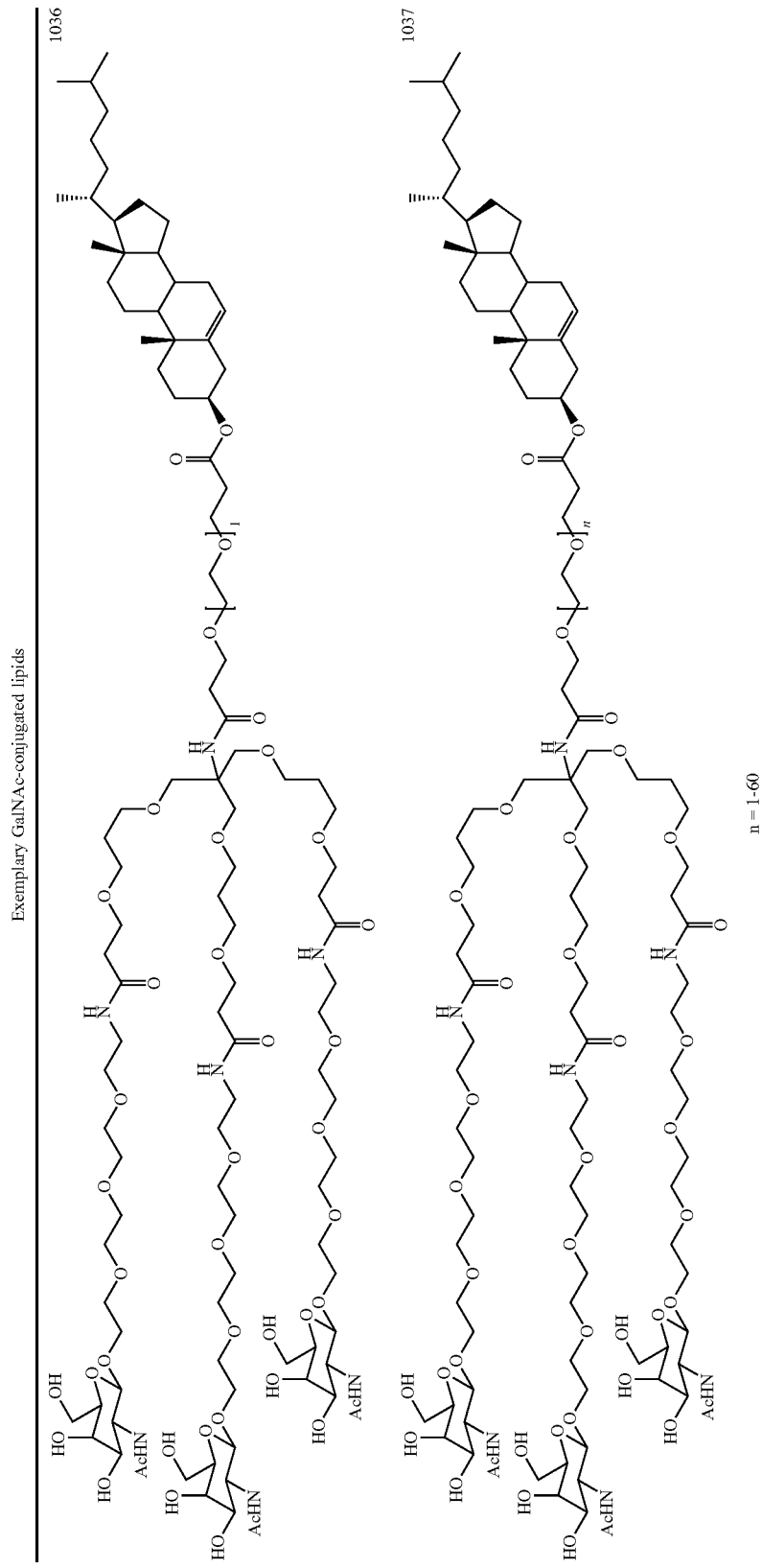
n = 1-60

TABLE 4-continued
Exemplary GalNAc-conjugated lipids
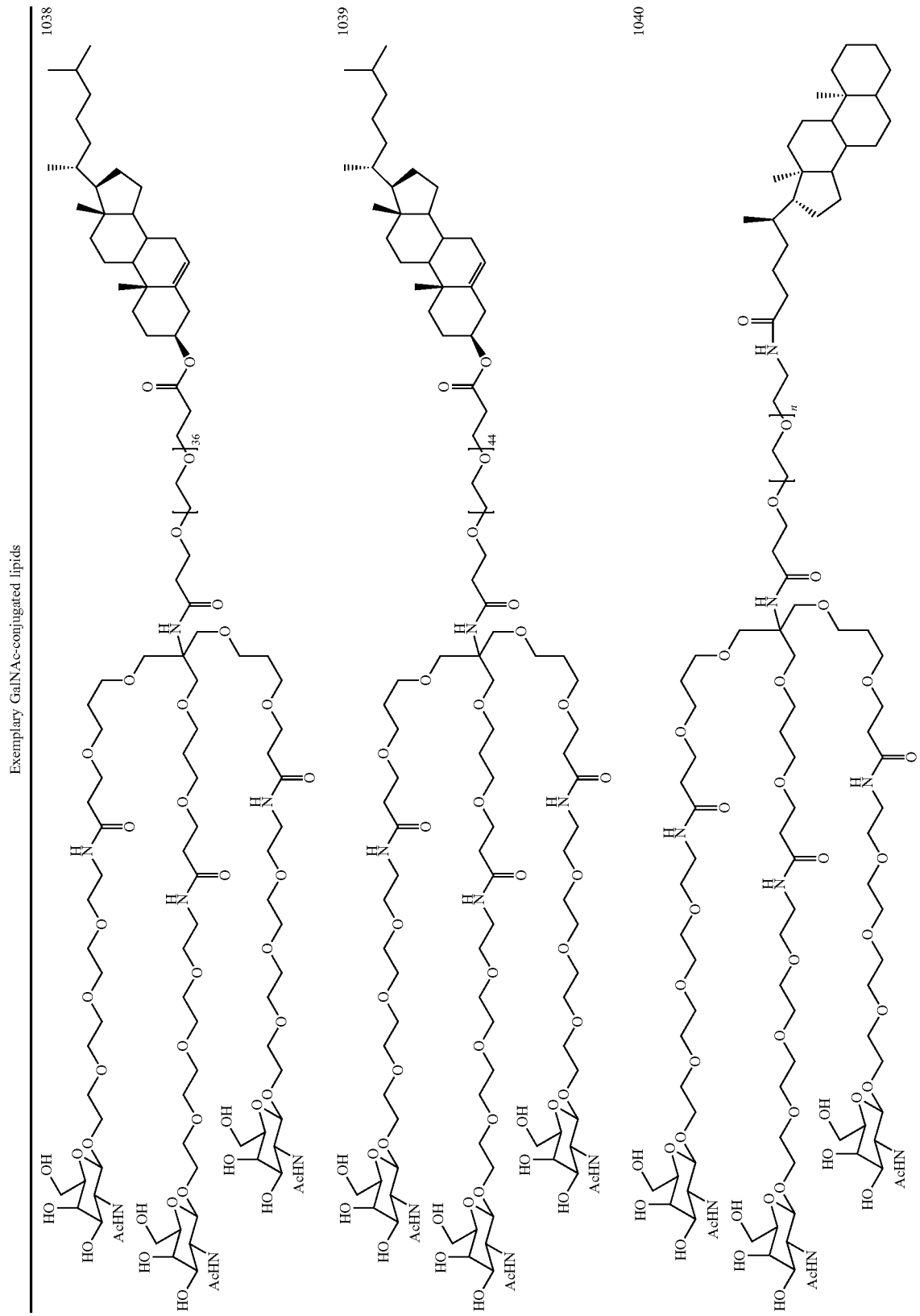

TABLE 4-continued
Exemplary GalNAc-conjugated lipids
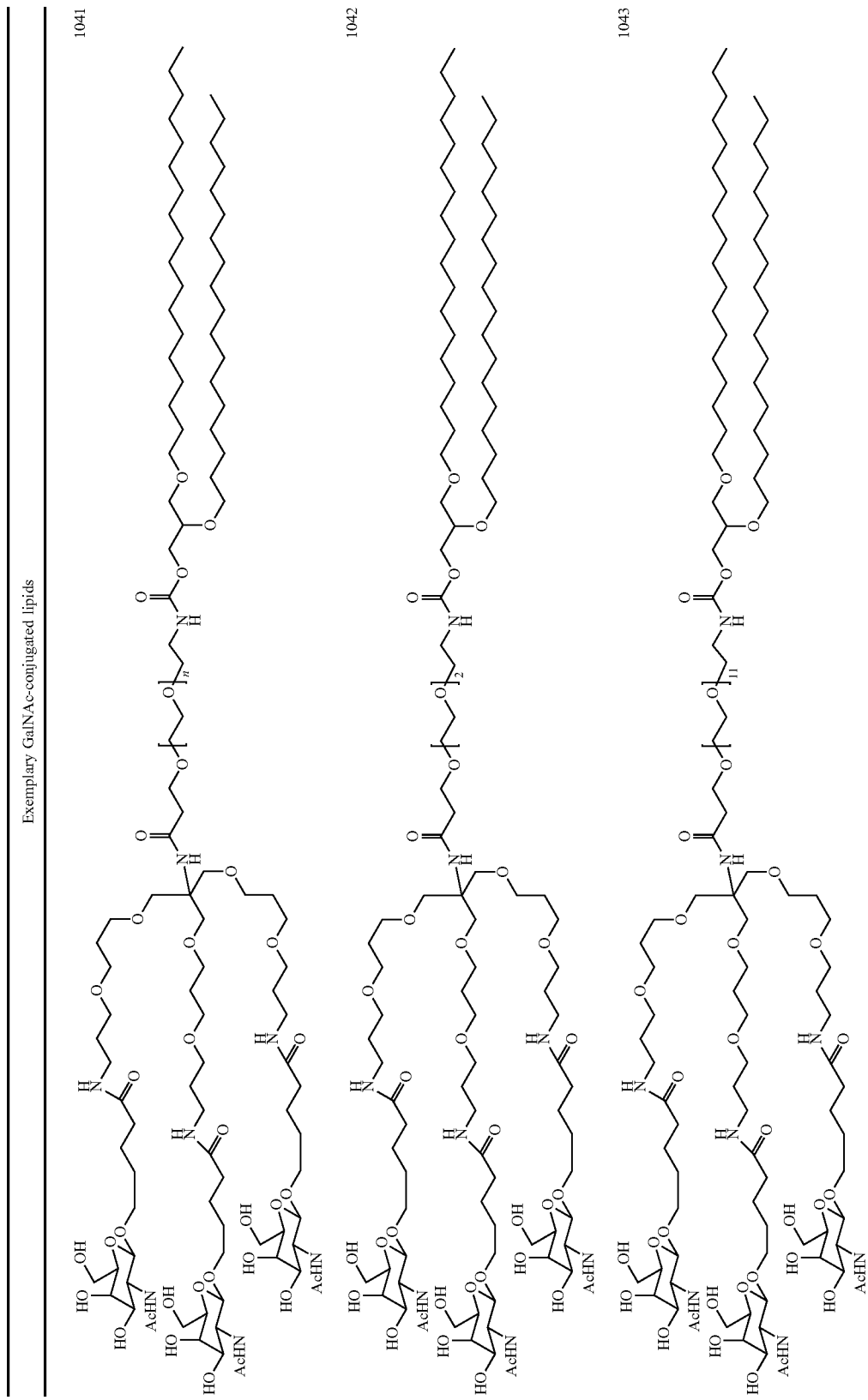

TABLE 4-continued
Exemplary GalNAc-conjugated lipids
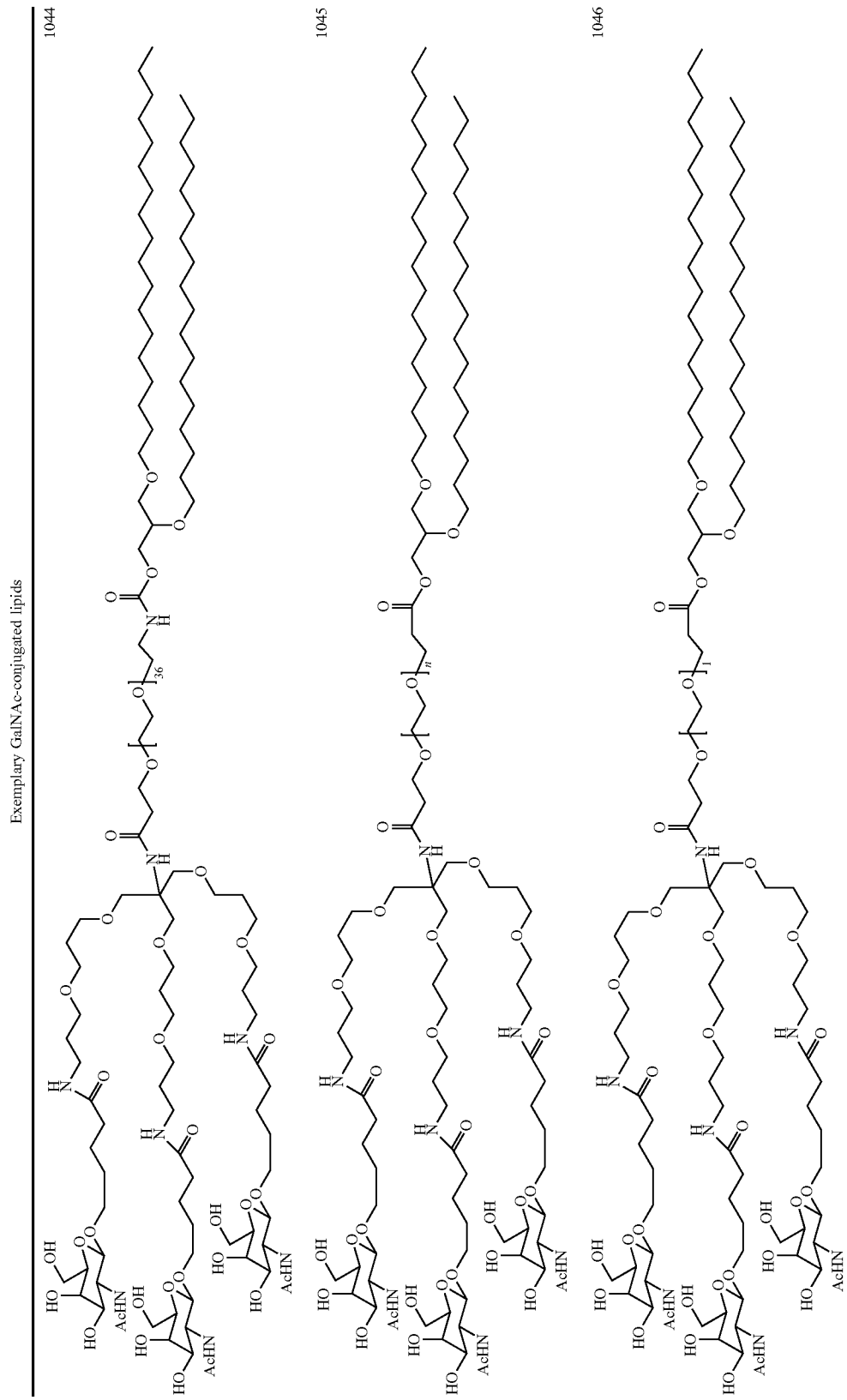

TABLE 4-continued
Exemplary GalNAc-conjugated lipids
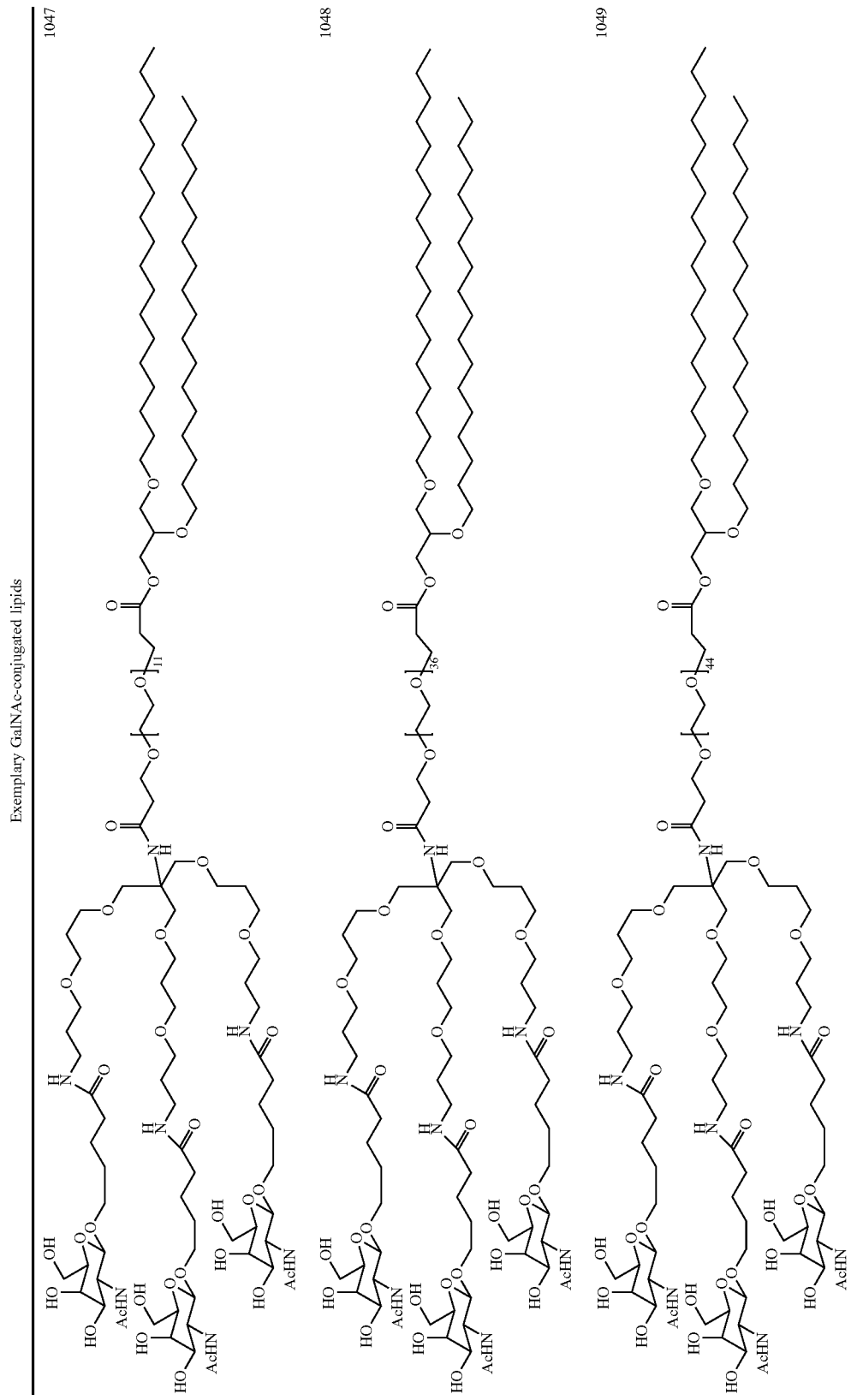

TABLE 4-continued
Exemplary GalNAc-conjugated lipids
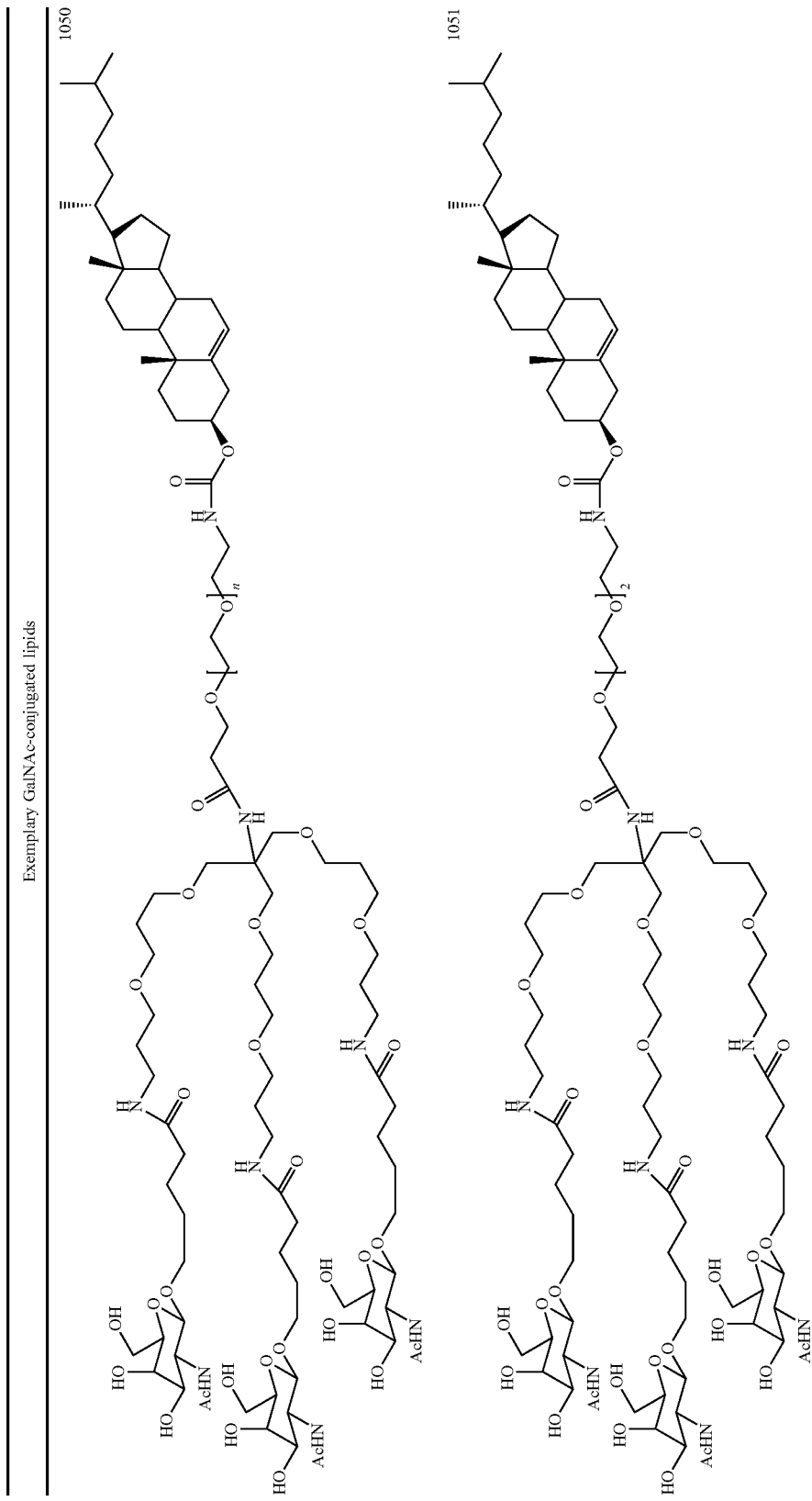

TABLE 4-continued
Exemplary GalNAc-conjugated lipids
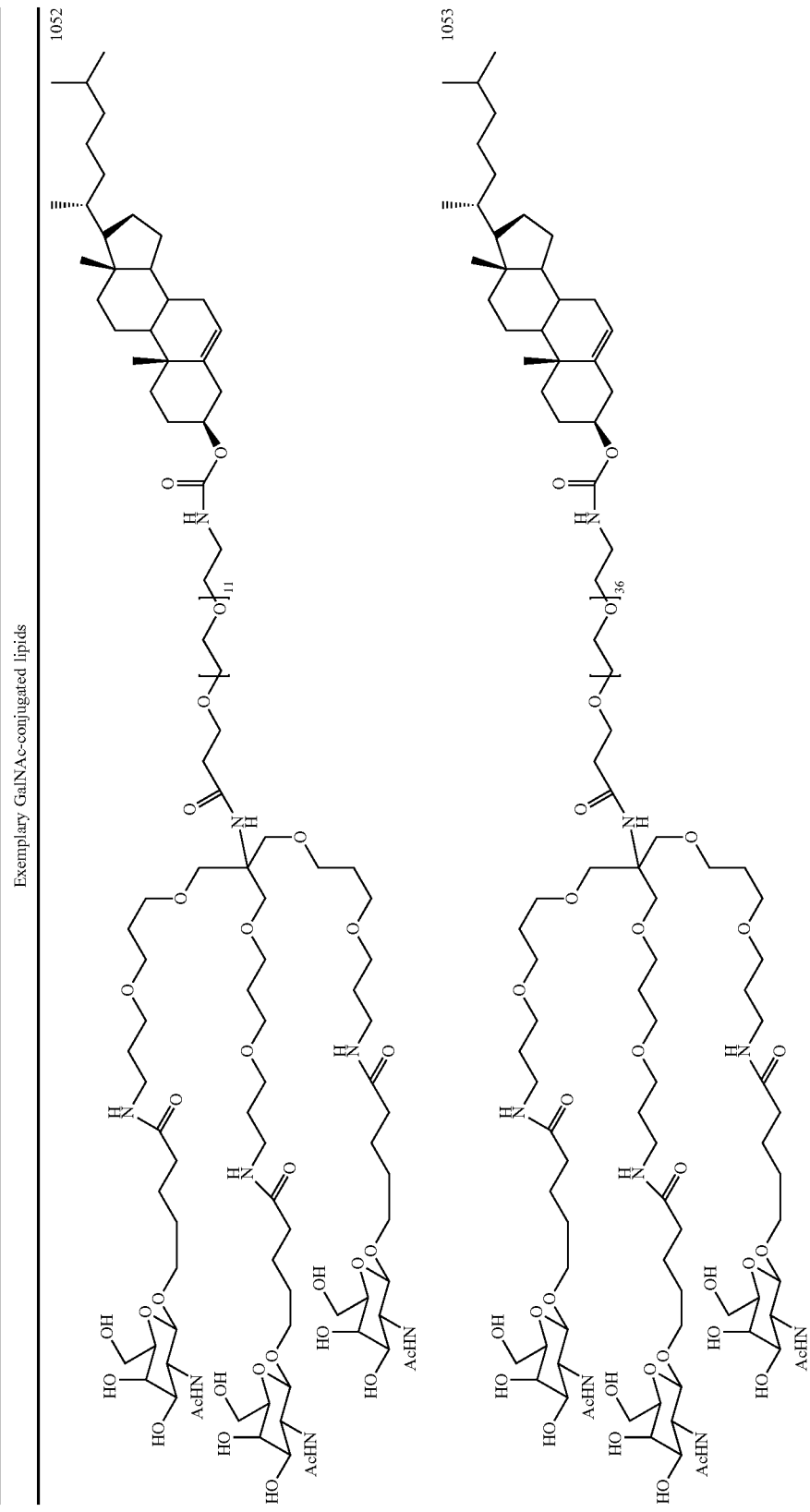

TABLE 4-continued
Exemplary GalNAc-conjugated lipids
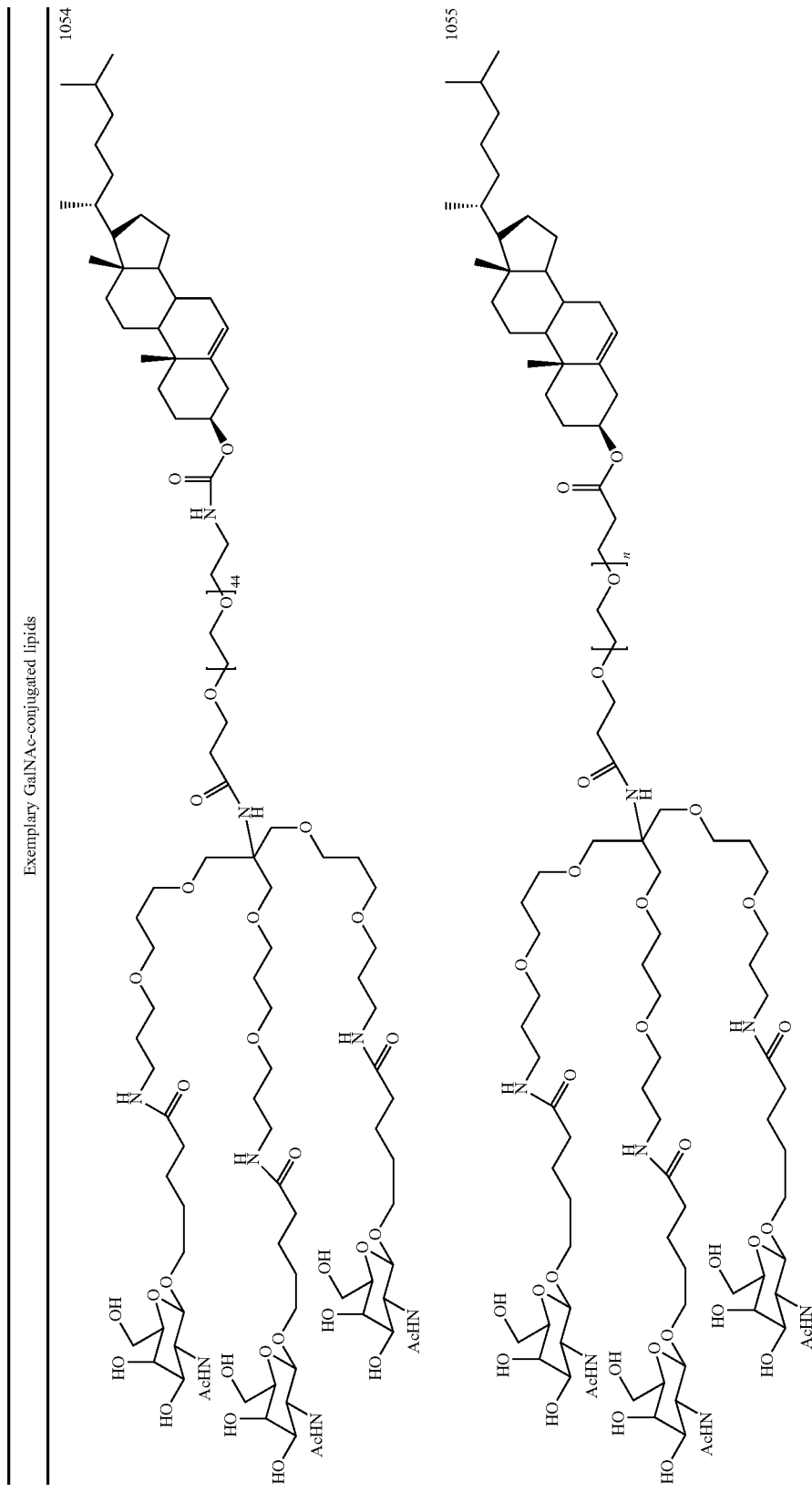

TABLE 4-continued
Exemplary GalNAc-conjugated lipids
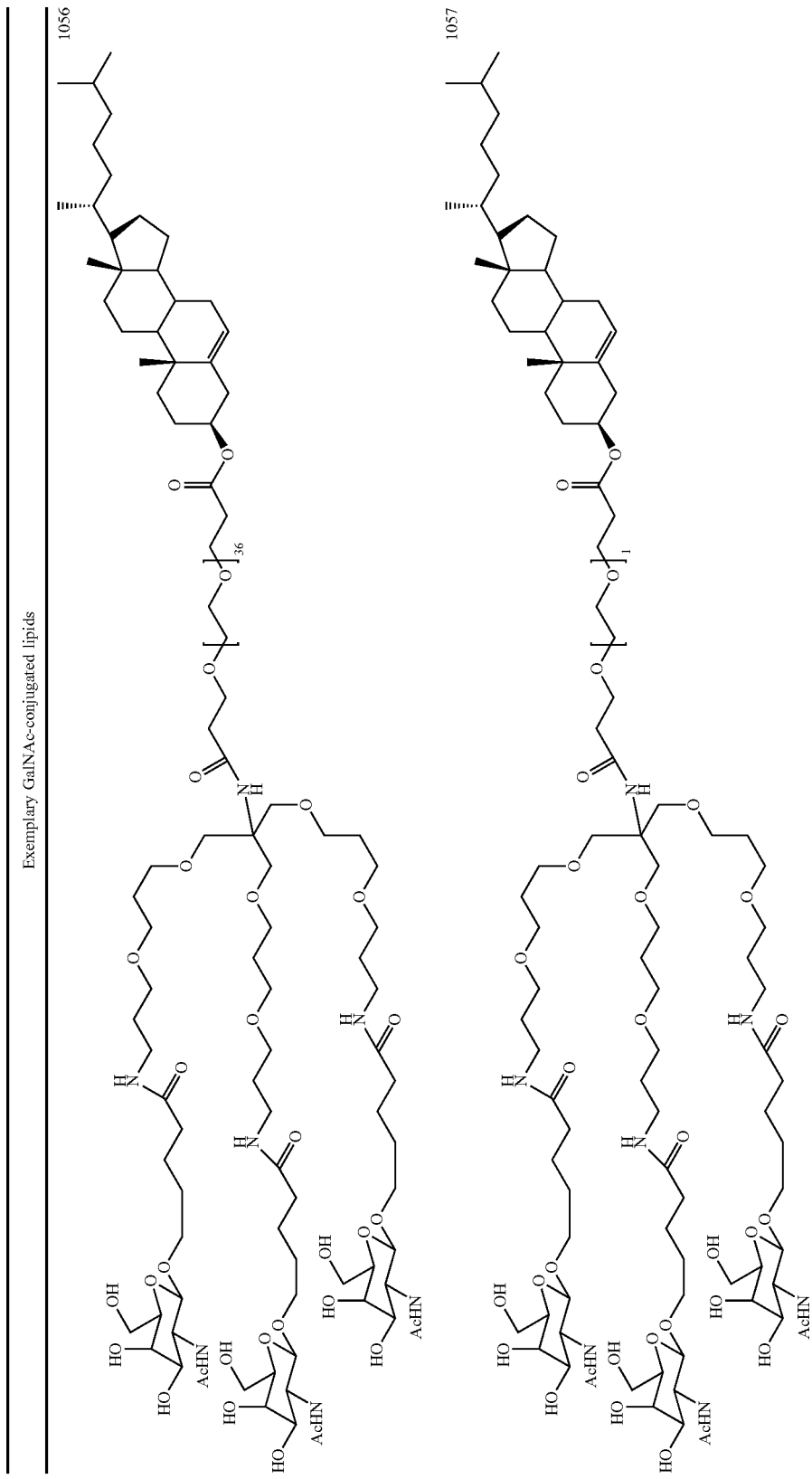

TABLE 4-continued
Exemplary GalNAc-conjugated lipids
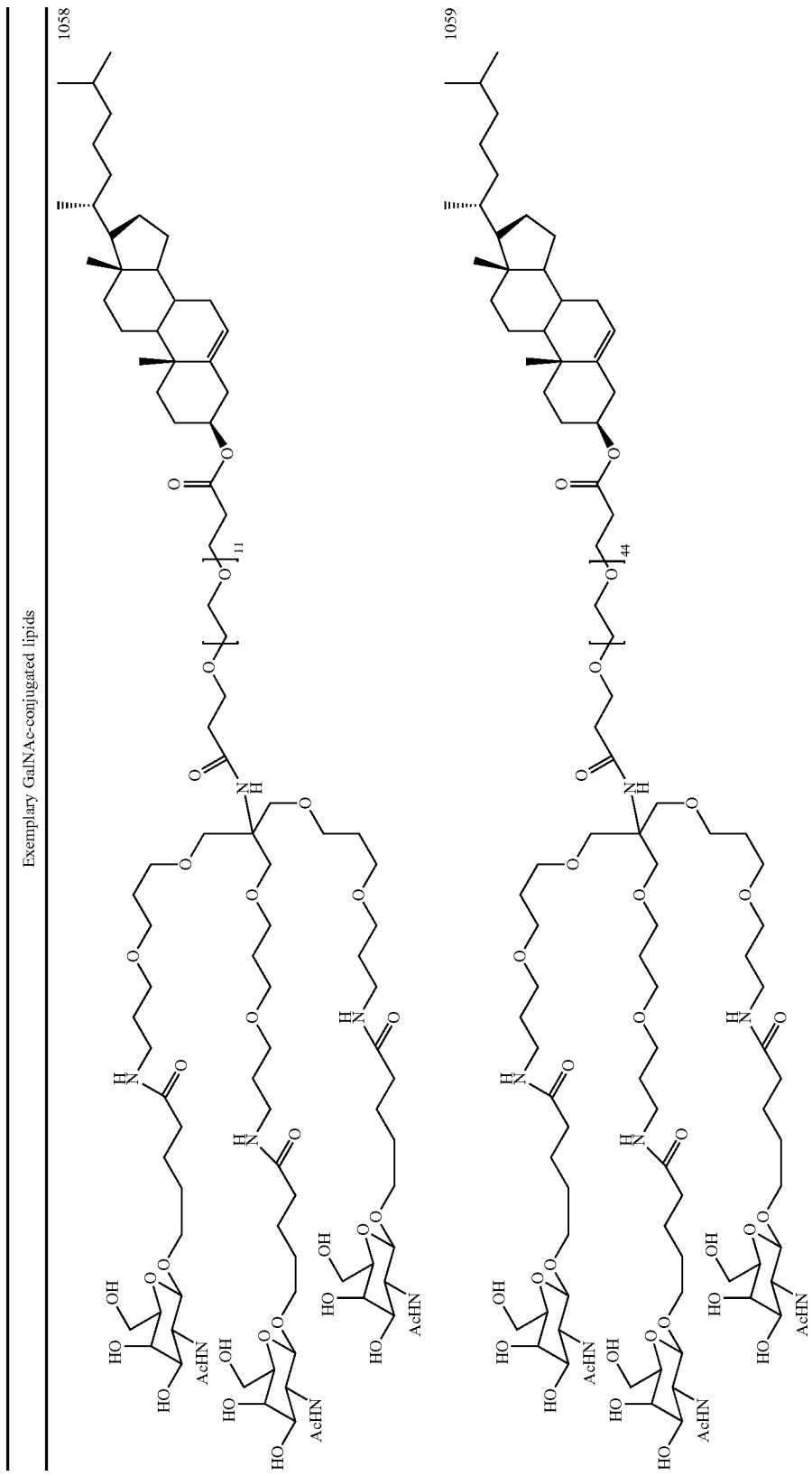

TABLE 4-continued
Exemplary GalNAc-conjugated lipids
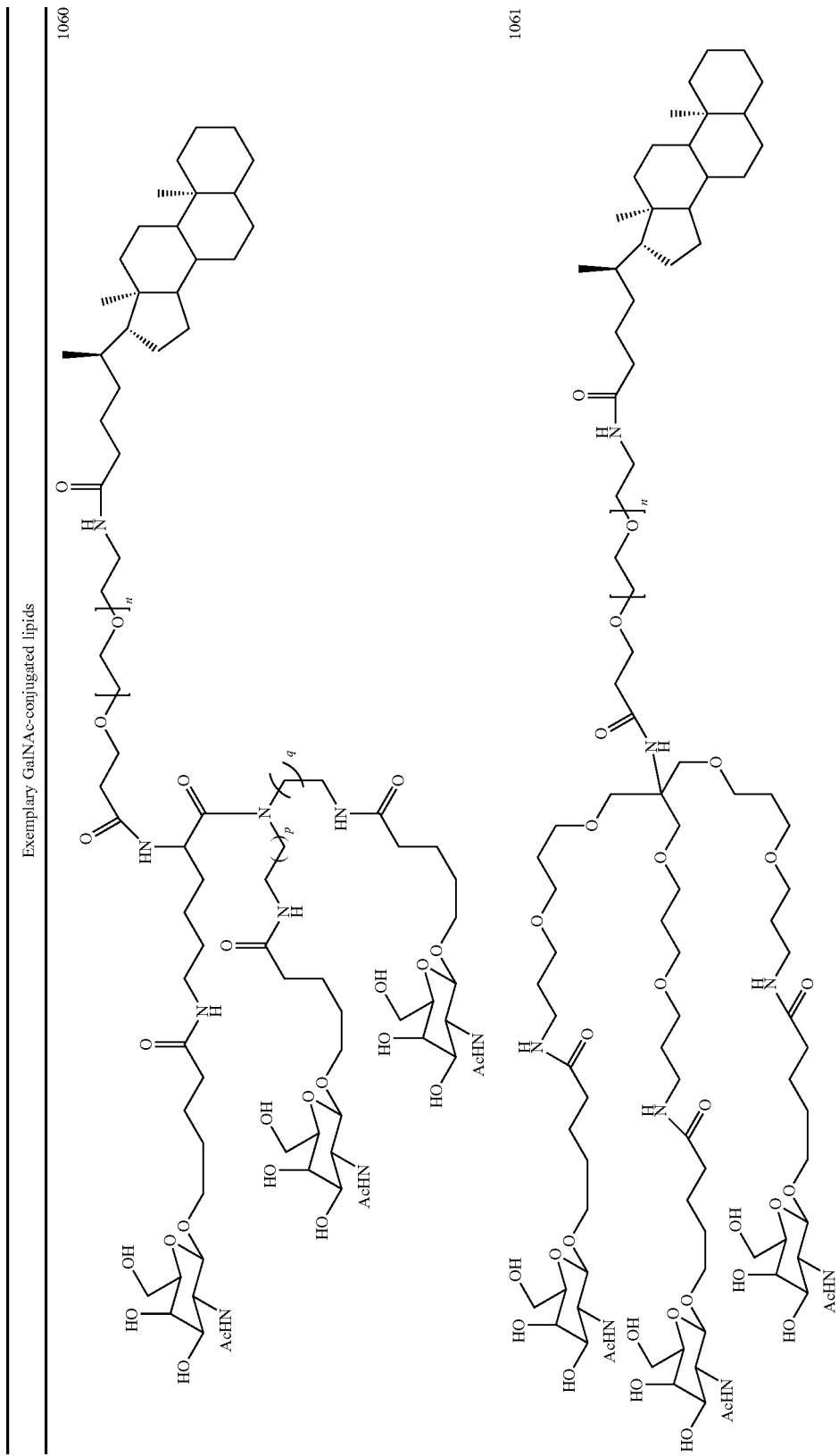

TABLE 4-continued
Exemplary GalNAc-conjugated lipids
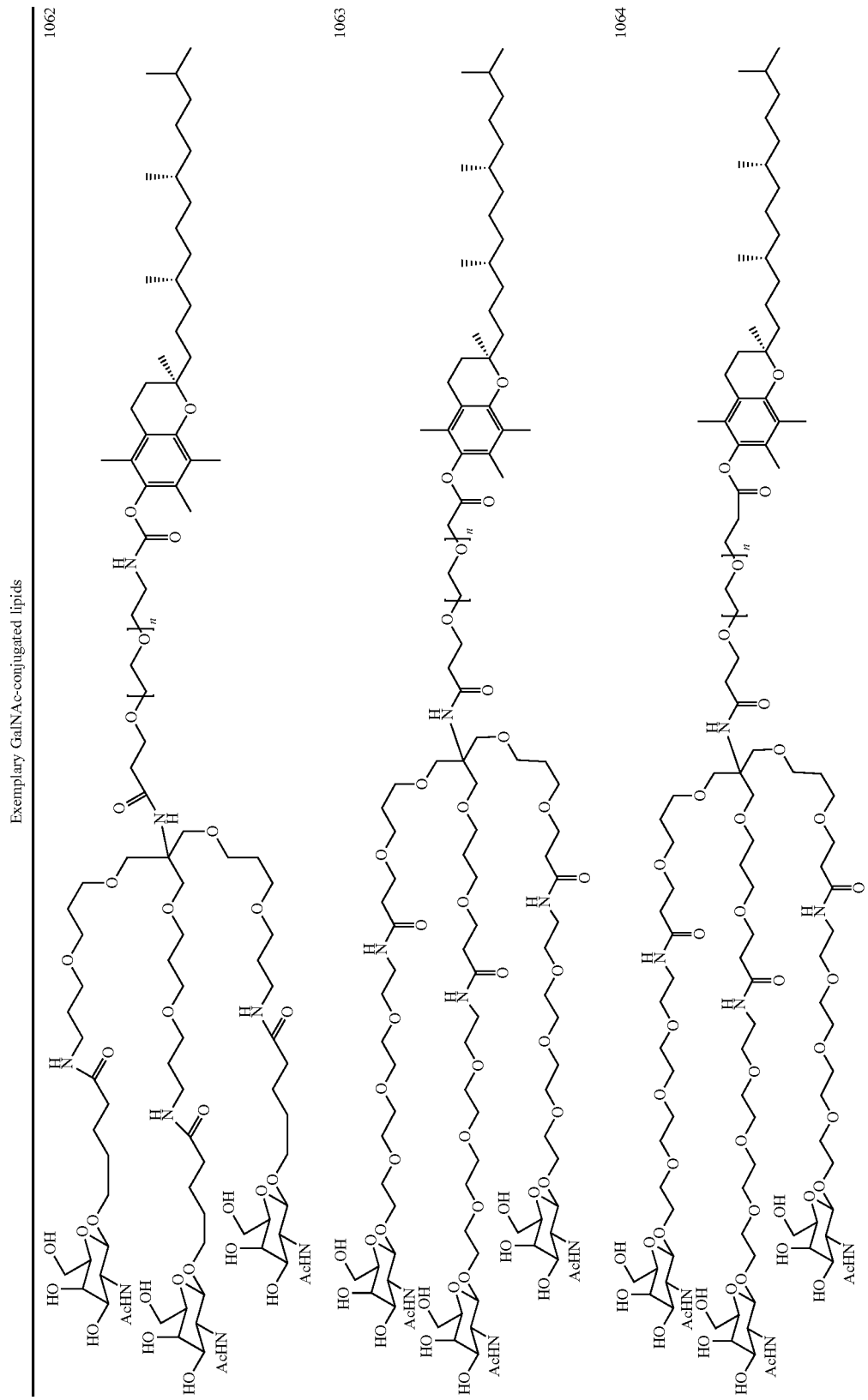

TABLE 4-continued
Exemplary GalNAc-conjugated lipids
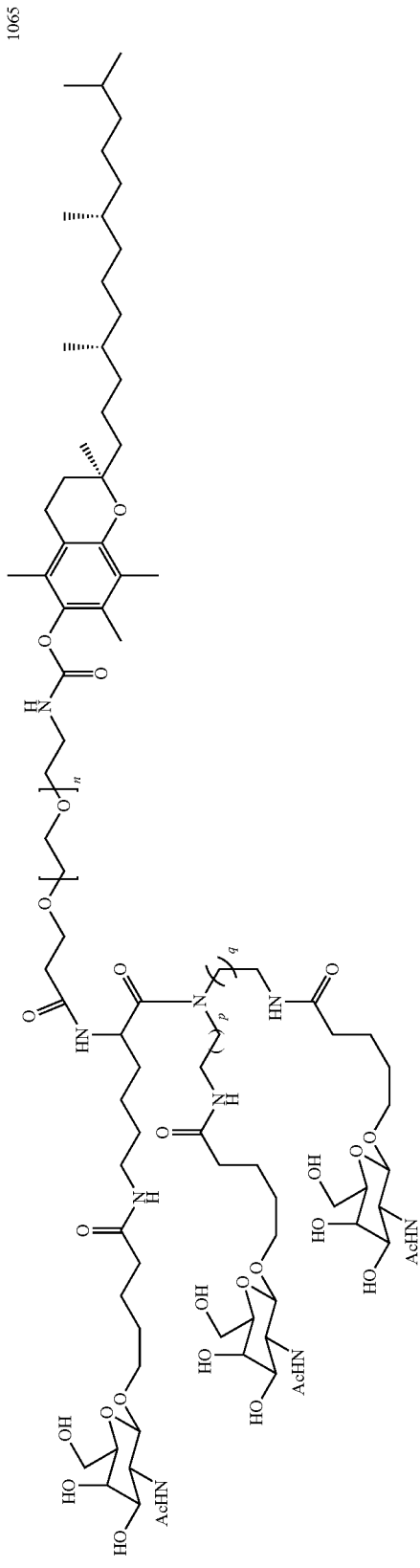
1065
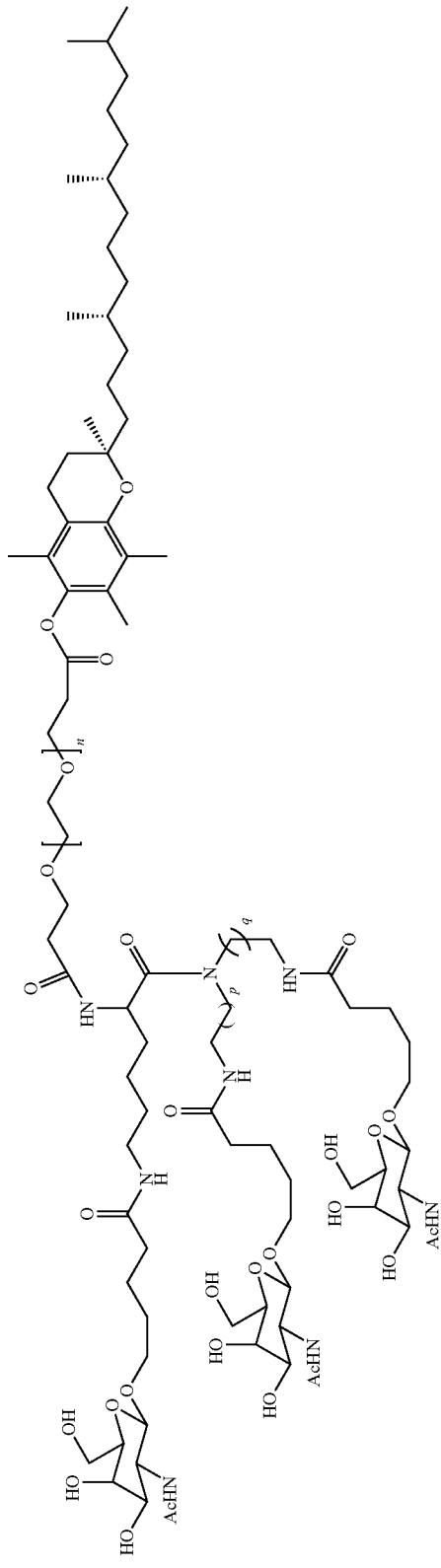
1066

TABLE 4-continued
Exemplary GalNAc-conjugated lipids
| 1067 | 1068 | 1069 |
|---|---|---|
| 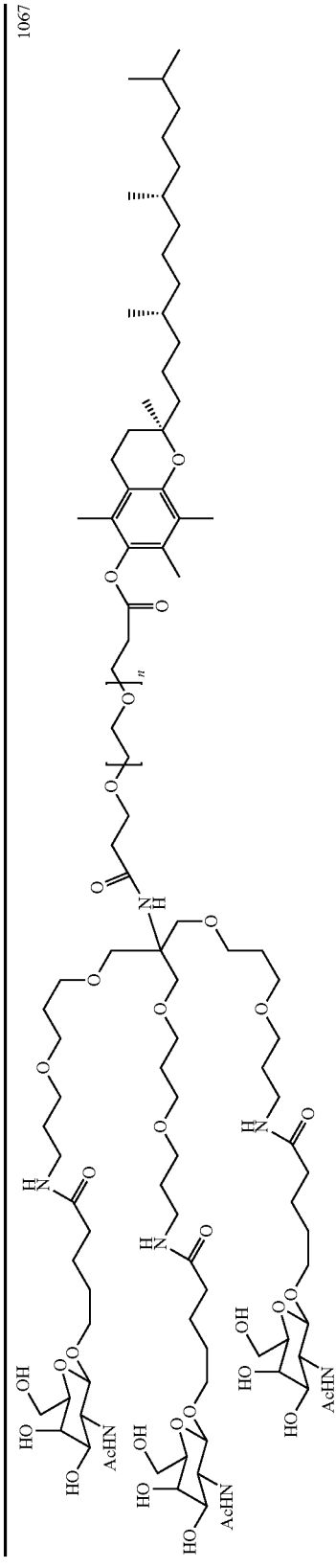 | 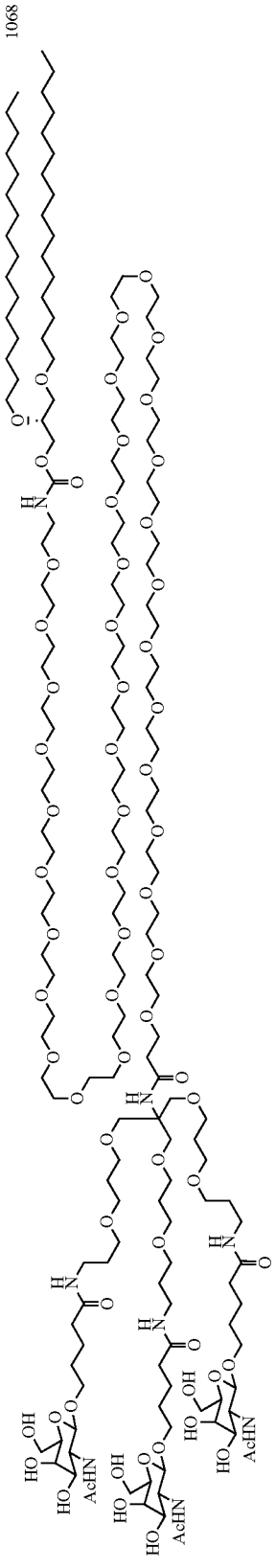 | 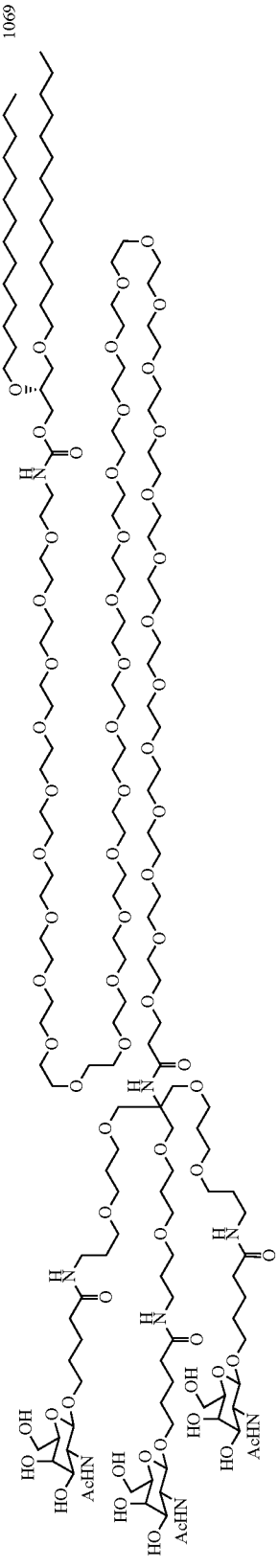 |

TABLE 4-continued
Exemplary GalNAc-conjugated lipids
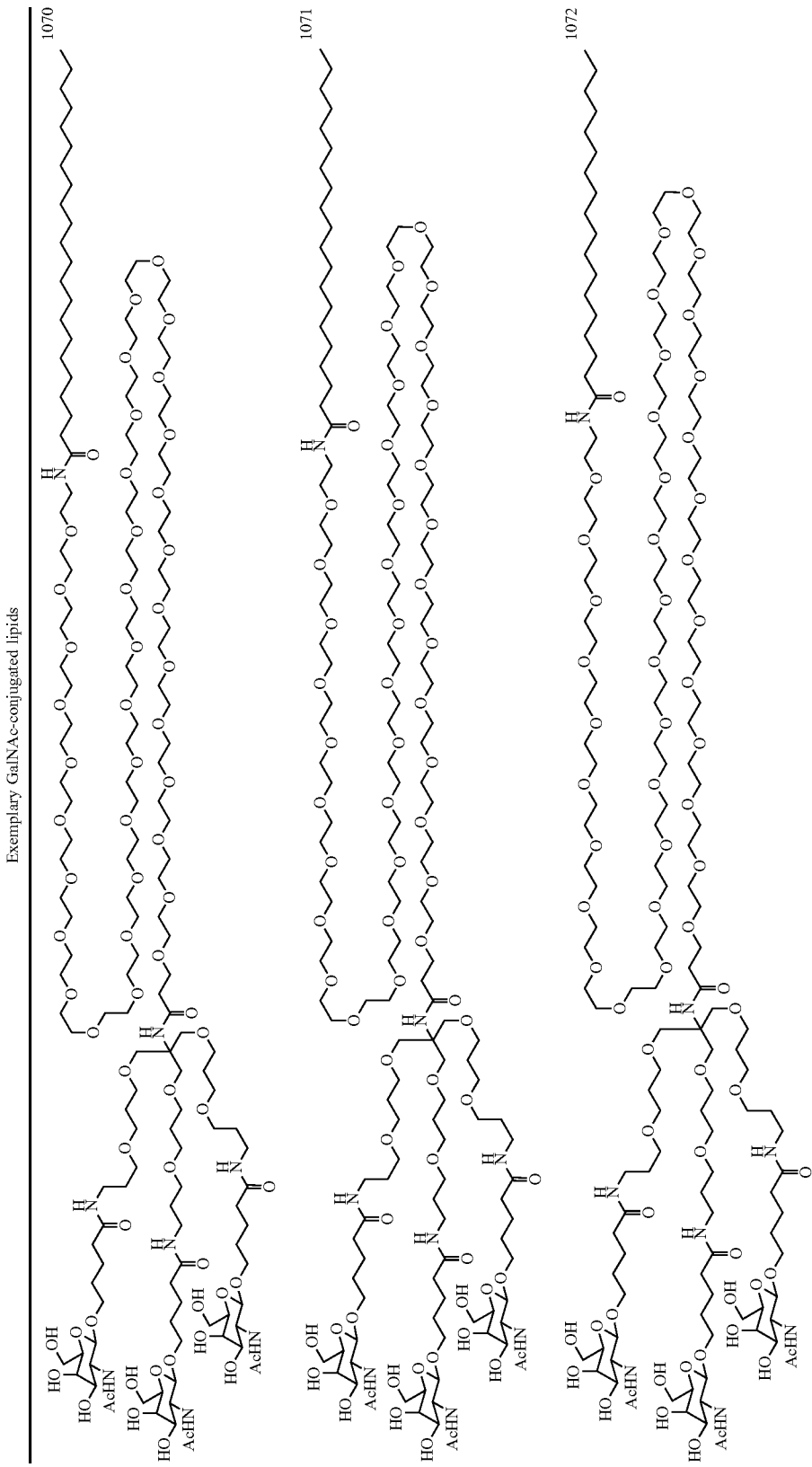

TABLE 4-continued
Exemplary GalNAc-conjugated lipids
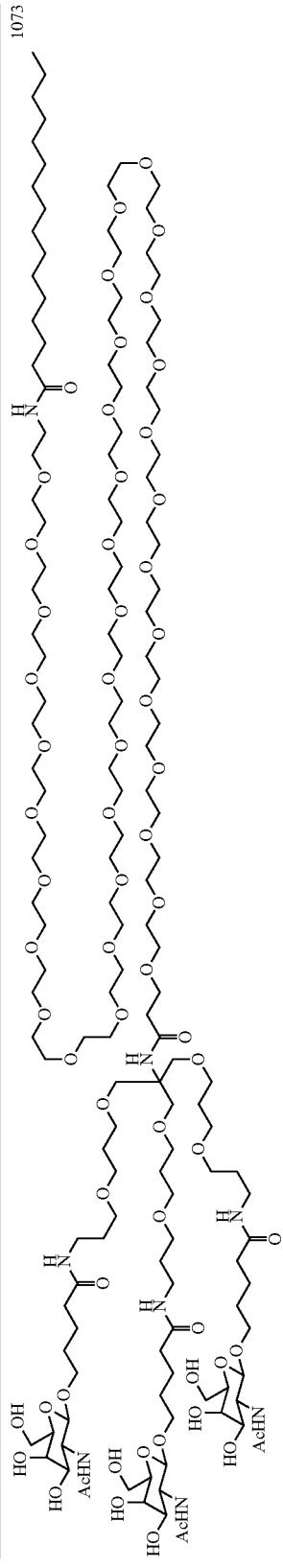
1073
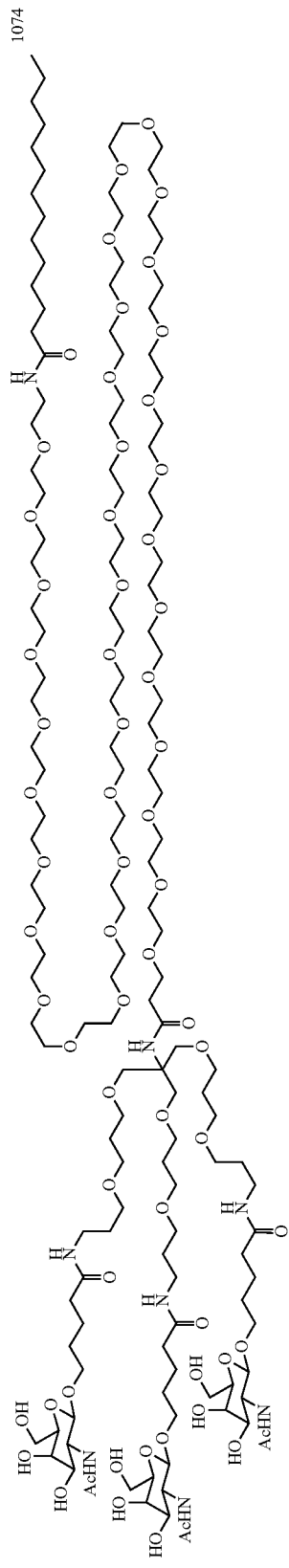
1074
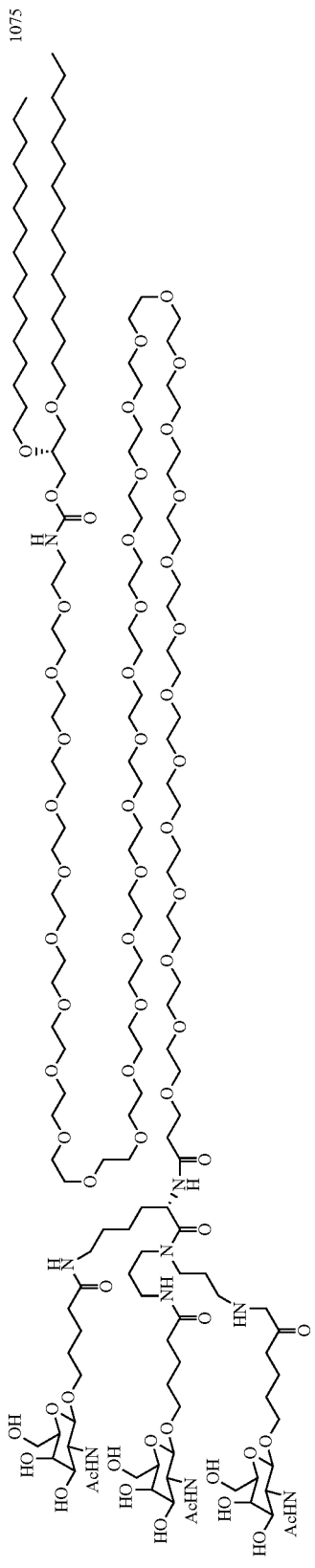
1075

TABLE 4-continued
Exemplary GalNAc-conjugated lipids
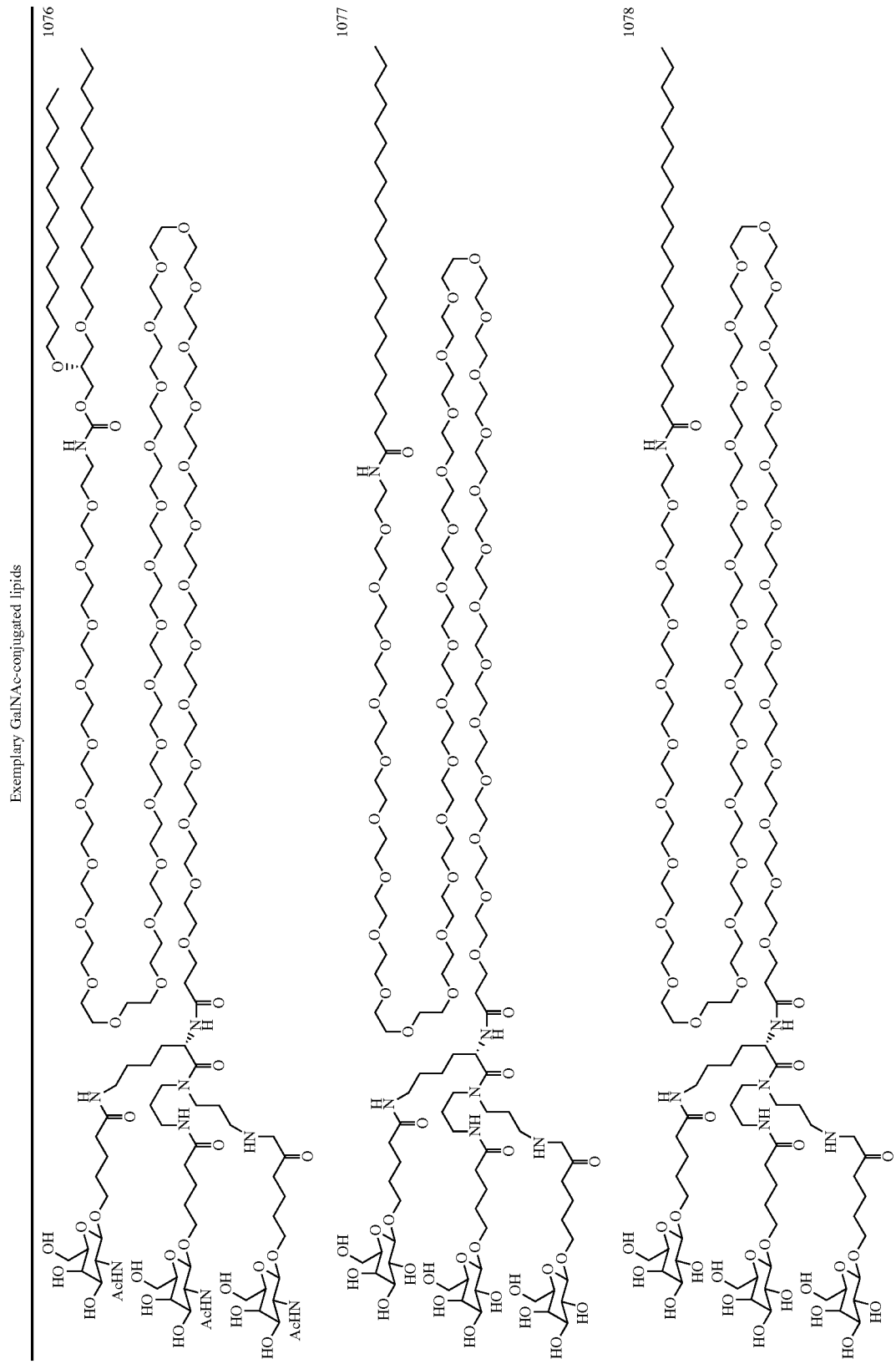

TABLE 4-continued
Exemplary GalNAc-conjugated lipids
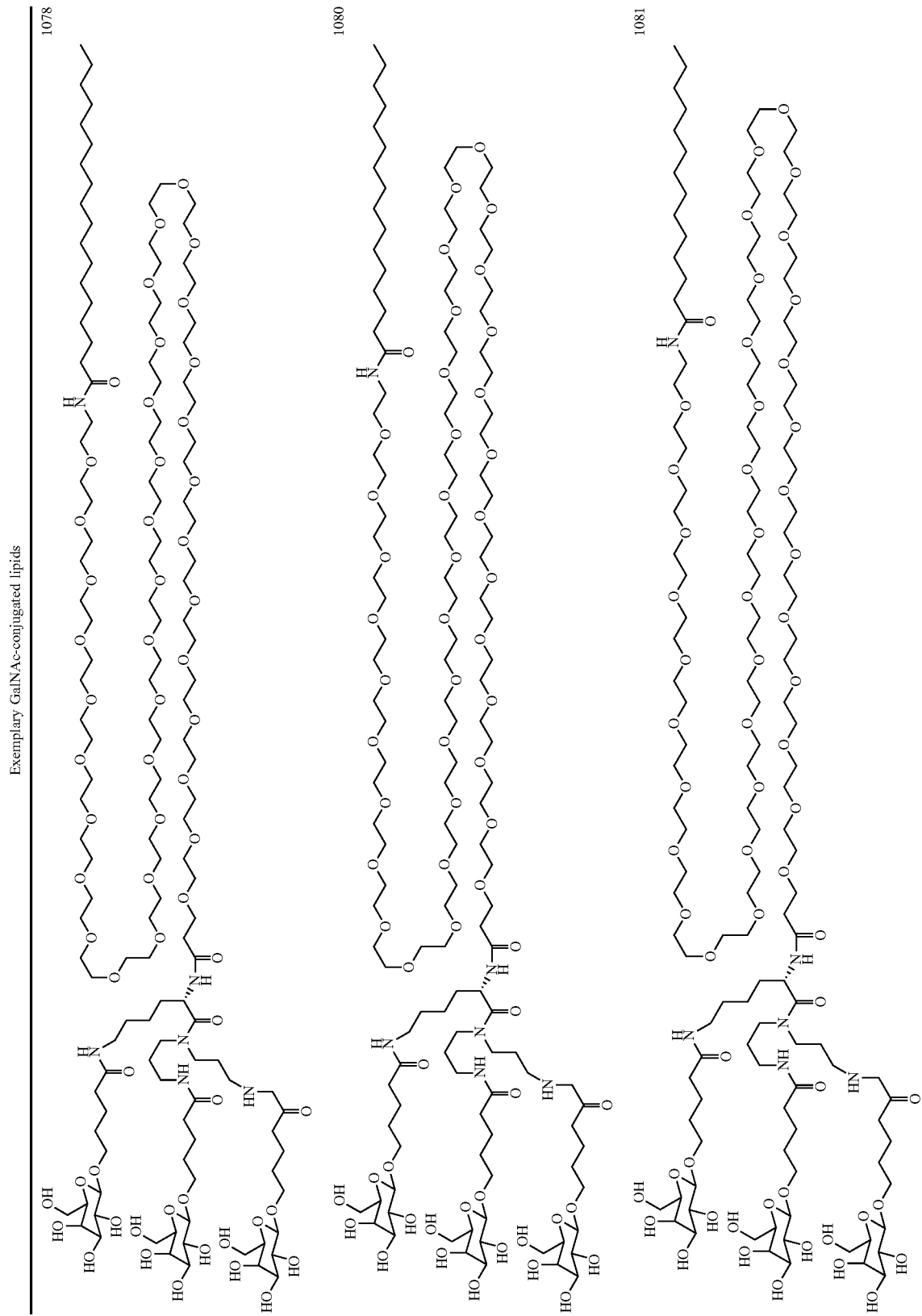

TABLE 4-continued
Exemplary GalNAc-conjugated lipids
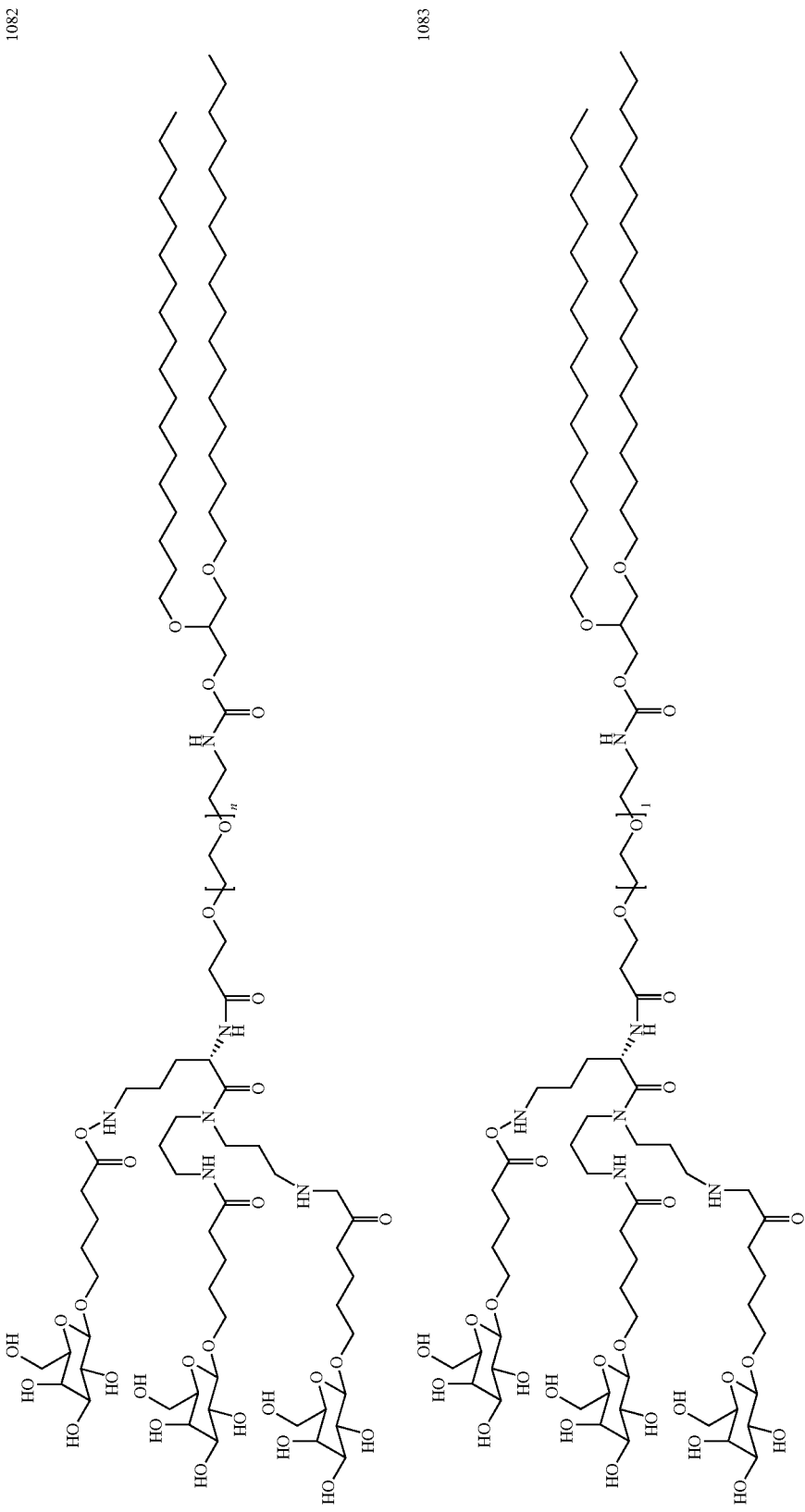
1082
1083

TABLE 4-continued
Exemplary GalNAc-conjugated lipids
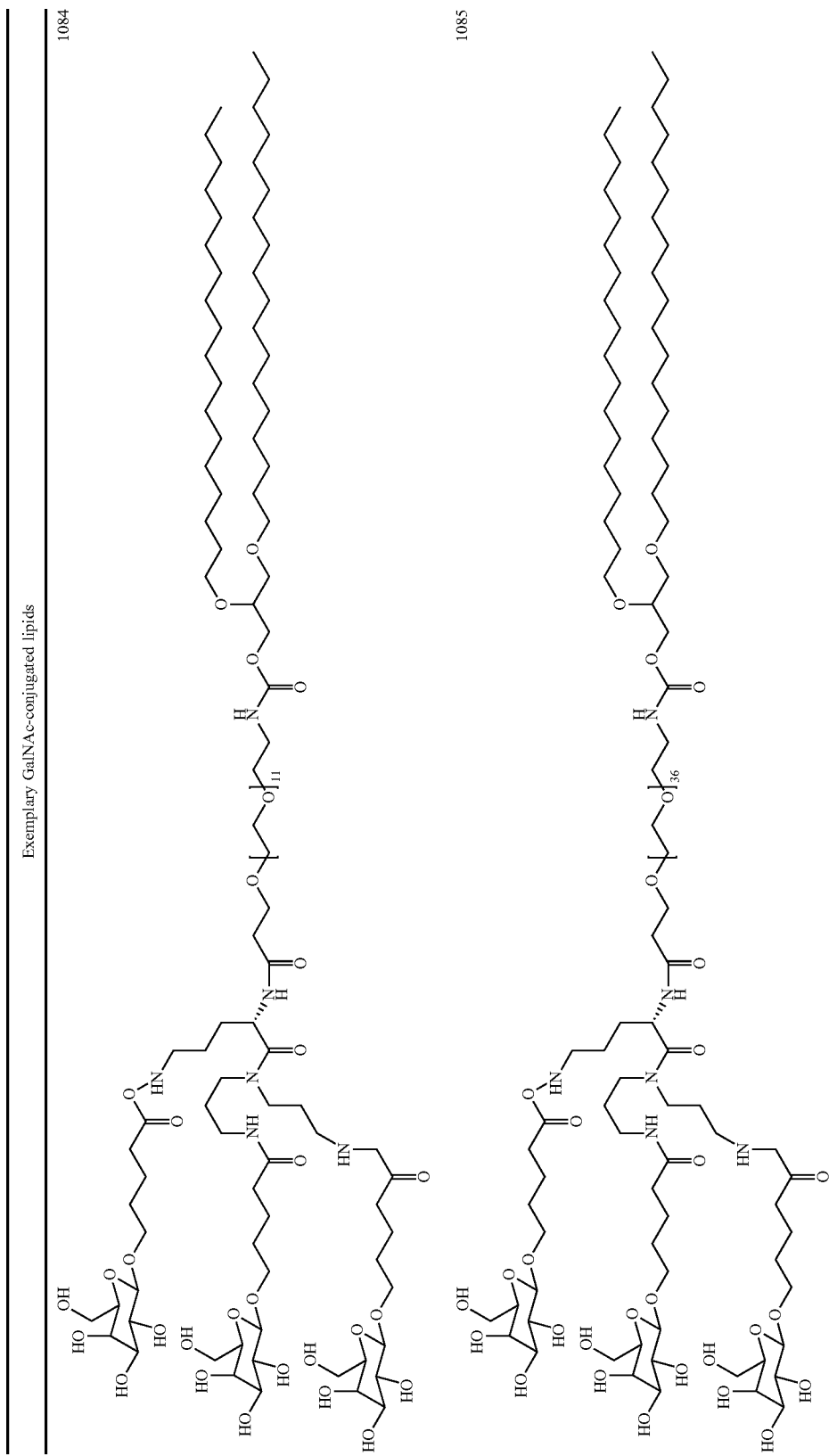

Each asymmetric carbon in Table 4 represents racemic, R and S configuration unless otherwise specified. As shown in Table 4, each of n, p, and q is independently 0, or an integer from 1 to 200. In some embodiments, each of n, p, and q of Table 4 is independently 0, or an integer from 1 to 100. In some embodiments, each of n, p, and q of Table 4 is independently 0, or an integer from 1 to 50. In some embodiments, each of n, p, and q of Table 4 is independently 0, 1, 2, 3, 4, 5, 6, 7, 8, 9, 10, 11, 12, 14, 13, 15, 16, 17, 18, 19, or 20. In some embodiments, each of n, p, and q of Table 4 is independently 0, 1, 2, 3, 4, or 5. In some embodiments, each of n, p, and q of Table 4 is independently 0, 1, 2, or 3. In some embodiments, each of n, p, and q of Table 4 is independently 1 or 2. In some embodiments, n is 1-60 and each of p and q is independently 1-9 in Table 4. In some implementations, the exemplary GalNAc-conjugated lipids ID numbers 1001, 1011, 1015, 1020, 1025, 1030, 1037, 1040, 1041, 1045, 1050, 1055, 1060, 1061, 1062, 1063, 1064, 1065, 1066, 1067, and 1082 from Table 4 have n=1, 11, 36, or 44. In some embodiments of the exemplary GalNAc-conjugated lipids of Table 4, n is 1 to 100. In some embodiments, n is 1 to 50. In some embodiments, n is 25 to 50. In some embodiments, n is 1 to 10. In some embodiments, n is 1 to 5. In some embodiments, n is 1 to 50. In some embodiments, n is 25 to 75. In some embodiments, n is 100 to 150. In some embodiments, n is 1. In some embodiments, n is 11. In some embodiments, n is 36. In some embodiments, n is 44. In some embodiments, n is 40 to 50. In some embodiments, n is 30 to 40. In some embodiments of the exemplary GalNAc-conjugated lipids of Table 4, p is 1 to 100. In some embodiments, p is 1 to 50. In some embodiments, p is 25 to 50. In some embodiments, p is 1 to 10. In some embodiments, p is 1 to 5. In some embodiments, p is 1 to 50. In some embodiments, p is 25 to 75. In some embodiments, p is 100 to 150. In some embodiments, p is 40 to 50. In some embodiments, p is 30 to 40. In some embodiments of the exemplary GalNAc-conjugated lipids of Table 4, q is 1 to 100. In some embodiments, q is 1 to 50. In some embodiments, q is 25 to 50. In some embodiments, q is 1 to 10. In some embodiments, q is 1 to 5. In some embodiments, q is 1 to 50. In some embodiments, q is 25 to 75. In some embodiments, q is 100 to 150. In some embodiments, q is 40 to 50. In some embodiments, q is 30 to 40.

Lipid Nanoparticle (LNP) Compositions

In one aspect, disclosed herein are lipid nanoparticle compositions that comprise a receptor targeting conjugate as described herein. In some embodiments, disclosed herein are lipid nanoparticle compositions that comprise (i) a payload, such as a therapeutic agent, or a target of interest and (ii) a receptor targeting conjugate as described herein. In some embodiments, disclosed herein are lipid nanoparticle compositions that comprise (i) one or more nucleic acid molecular entities (i.e., nucleic acids such as mRNA and gRNA) and (ii) a receptor targeting conjugate as described herein. In some embodiments, herein described nanoparticle compositions comprise two or more receptor targeting conjugates, which conjugates can be the same or different. In some embodiments, the one or more nucleic acid molecular entities comprise a nucleic acid described herein. In some embodiments, the one or more nucleic acid molecular entities comprise a single guide RNA (sgRNA) or guide RNA (gRNA) targeting a disease causing gene of interest produced in the hepatocytes. In some embodiments, the one or more nucleic acid molecular entities comprise an mRNA that encodes a Cas nuclease. In some embodiments, at least one of the one or more nucleic acid molecular entities comprises a chemical modification, e.g., a chemical modification as described herein. In some embodiments, the chemical modification is a 2'-F modification, a phosphorothioate internucleotide linkage modification, acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methyl-acetamido (2'-O-NMA), a 2'-O-dimethylaminoethoxyethyl (2'-O-DMAEOE), 2'-O-aminopropyl (2'-O-AP), 4'-O-methyl, or a 2'-ara-F modification. In some embodiments, the chemical modification is a 2'-O-methyl modification.

In some embodiments, the receptor targeting conjugate comprises from about 0.001 mol % to about 20 mol % of the total lipid content present in a herein described nanoparticle composition. In some embodiments, the receptor targeting conjugate comprises from about 0.01 mol % to about 1 mol % of the total lipid content present in a herein described nanoparticle composition. In some embodiments, the receptor targeting conjugate comprises from about 0.001 mol %, about 0.005 mol %, about 0.01 mol %, about 0.02 mol %, about 0.03 mol %, about 0.04 mol %, about 0.05 mol %, about 0.06 mol %, about 0.07 mol %, about 0.08 mol %, or about 0.09 mol %, to about 1 mol %, about 1.5 mol %, about 2 mol %, about 5 mol %, about 10 mol %, or about 20 mol % of the total lipid content present in a herein described nanoparticle composition. In some embodiments, the receptor targeting conjugate comprises from about 0.001 mol %, about 0.005 mol %, about 0.01 mol %, about 0.02 mol %, about 0.03 mol %, about 0.04 mol %, or about 0.05 mol %, to about 0.06 mol %, about 0.07 mol %, about 0.08 mol %, about 0.09 mol %, about 1 mol %, about 1.5 mol %, about 2 mol %, about 5 mol %, about 10 mol %, or about 20 mol % of the total lipid content present in a herein described nanoparticle composition. In some embodiments, the receptor targeting conjugate comprises about 0.01 mol %, about 0.02 mol %, about 0.03 mol %, about 0.04 mol %, about 0.05 mol %, about 0.06 mol %, about 0.07 mol %, about 0.08 mol %, about 0.09 mol %, about 0.1 mol %, about 0.2 mol %, about 0.3 mol %, about 0.4 mol %, about 0.5 mol %, about 0.6 mol %, about 0.7 mol %, about 0.8 mol %, about 0.9 mol %, about 1 mol %, about 1.1 mol %, about 1.2 mol %, about 1.3 mol %, about 1.4 mol %, about 1.5 mol %, about 1.6 mol %, about 1.7 mol %, about 1.8 mol %, about 1.9 mol %, about 2.0 mol %, about 3.0 mol %, about 4.0 mol %, or about 5.0 mol % of the total lipid content present in a herein described nanoparticle composition.

In some embodiments, an LNP described herein comprises from about 0.000001 mol % to about 30 mol % of the receptor targeting conjugate based on total lipid or total excipient content. In some embodiments, an LNP described herein comprises from about 0.0001 mol % to about 25 mol % of the receptor targeting conjugate based on total lipid or total excipient content. In some embodiments, an LNP described herein comprises from about 0.0001, 0.001, 0.005, 0.01, 0.025, 0.05, or 0.25 mol % to about 0.5, 1, 1.125, 1.25, 1.5, 1.75, 2, 5, 10, 15, 20 or 25 mol % of the receptor targeting conjugate based on total lipid or total excipient content. In some embodiments, an LNP described herein comprises from about 0.001 mol % to about 1 mol % of the receptor targeting conjugate based on total lipid or total excipient content. In some embodiments, an LNP described herein comprises from about 0.005 mol % to about 1 mol % of the receptor targeting conjugate based on total lipid or total excipient content. In some embodiments, an LNP described herein comprises from about 0.025 mol % to about 1, 1.5 or 2 mol % of the receptor targeting conjugate based on total lipid or total excipient content. In some embodiments, an LNP described herein comprises from about 0.25 mol % to about 1 mol % of the receptor targeting conjugate based on total lipid or total excipient content. In some embodiments, an LNP described herein comprises from about 0.25 mol % to about 1.5 or 2 mol % of the receptor targeting conjugate based on total lipid or total excipient content. In some embodiments, an LNP described herein comprises from about 0.05 mol % to about 1.5 or 2 mol % of the receptor targeting conjugate based on total lipid or total excipient content. In some embodiments, an LNP described herein comprises from about 0.05 mol % to about 1 mol % of the receptor targeting conjugate based on total lipid or total excipient content. In some embodiments, an LNP described herein comprises from about 0.001 mol % to about 2 mol % of the receptor targeting conjugate based on total lipid or total excipient content. In some embodiments, an LNP described herein comprises from about 0.005 mol % to about 2 mol % of the receptor targeting conjugate based on total lipid or total excipient content. In some embodiments, an LNP described herein comprises at least about 0.001, 0.005, 0.01, 0.05, 0.1, 0.25, 0.75, or 1 mol % of the receptor targeting conjugate based on total lipid or total excipient content. In some embodiments, an LNP described herein comprises at most about 0.5, 1, 2, 3, 4, 5, 6, 7, 8, 9, or 10 mol % of the receptor targeting conjugate based on total lipid or total excipient content. In some embodiments, an LNP described herein comprises at most about 1 mol % of the receptor targeting conjugate based on total lipid or total excipient content. In some embodiments, an LNP described herein comprises at most about 2 mol % of the receptor targeting conjugate based on total lipid or total excipient content.

In some embodiments, the herein described LNP compositions are sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less. The LNPs described herein can have a mean diameter of from about 1 nm to about 2500 nm, from about 10 nm to about 1500 nm, from about 20 nm to about 1000 nm, from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, or from about 70 nm to about 80 nm. The LNPs described herein can have a mean diameter of about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, or greater. The LNPs described herein can be substantially non-toxic.

Cholesterol

In some embodiments, a herein described LNP composition comprises a cholesterol or a derivative thereof. In some embodiments, the LNP composition comprises a structural lipid. The structural lipid can be selected from steroid, sterol, alkyl resoreinol, cholesterol or derivative thereof, fecosterol, sitosterol, ergosterol, campesterol, stigmasterol, brassicasterol, tomatidine, tomatine, ursolic acid, alpha-tocopherol, and a combination thereof. In some embodiments, the structural lipid is a corticosteroid such as prednisolone, dexamethasone, prednisone, and hydrocortisone. In some embodiments, the cholesterol or derivative thereof is cholesterol, 5-heptadecylresorcinol, or cholesterol hemisuccinate. In some embodiments, the cholesterol or derivative thereof is cholesterol.

In some embodiments, the cholesterol or derivative thereof is a cholesterol derivative. In some embodiments, the cholesterol derivative is a polar cholesterol analogue. In some embodiments, the polar cholesterol analogue is 5a-cholestanol, 5ß-coprostanol, cholesteryl-(2'-hydroxy)-ethyl ether, cholesteryl-(4'-hydroxy)-butyl ether, or 6-ketocholestanol. In some embodiments, the polar cholesterol analogue is cholesteryl-(4'-hydroxy)-butyl ether. In some embodiments, the cholesterol derivative is a non-polar cholesterol analogue. In some embodiments, the non-polar cholesterol analogue is 5α-cholestane, cholestenone, 5α-cholestanone, 5β-cholestanone, or cholesteryl decanoate.

In some embodiments, the cholesterol or the derivative thereof comprises from 20 mol % to 50 mol % of the total lipid present in the nanoparticle composition. In some embodiments, the cholesterol or the derivative thereof comprises about 20 mol %, about 21 mol %, about 22 mol %, about 23 mol %, about 24 mol %, about 25 mol %, about 26 mol %, about 27 mol %, about 28 mol %, about 29 mol %, about 30 mol %, about 31 mol %, about 32 mol %, about 33 mol %, about 34 mol %, about 35 mol %, about 36 mol %, about 37 mol %, about 38 mol %, about 39 mol %, about 40 mol %, about 41 mol %, about 42 mol %, about 43 mol %, about 44 mol %, about 45 mol %, about 46 mol %, about 47 mol %, about 48 mol %, or about 50 mol % of the total lipid present in the nanoparticle composition.

Phospholipid

In some embodiments, a herein described LNP composition comprises a phospholipid. In some embodiments, the phospholipid comprises a lipid selected from the group consisting of: phosphatidylcholine (PC), phosphatidylethanolamine amine, glycerophospholipid, sphingophospholipids, Guriserohosuhono, sphingolipids phosphono lipids, natural lecithins, and hydrogenated phospholipid. In some embodiments, the phospholipid comprises a phosphatidylcholine. Exemplary phosphatidylcholines include, but are not limited to, soybean phosphatidylcholine, egg yolk phosphatidylcholine (EPC), distearoylphosphatidylcholine, 1,2-distearoyl-sn-glycero-3-phosphocholine (DSPC), dipalmitoyl phosphatidylcholine, dipalmitoyl-sn-glycero-3-phosphocholine (DPPC), 2-Oleoyl-1-palmitoyl-sn-glycero-3-phosphocholine (POPC), dimyristoyl phosphatidylcholine (DMPC), and dioleoyl phosphatidylcholine (DOPC). In certain specific embodiments, the phospholipid is DSPC.

In some embodiments, the phospholipid comprises a phosphatidylethanolamine amine. In some embodiments, the phosphatidylethanolamine amine is distearoyl phosphatidylethanolamine (DSPE), dipalmitoyl phosphatidyl ethanolamine (DPPE), 1,2-dioleoyl-sn-glycero-3-phosphoethanolamine (DOPE), dimyristoyl phosphoethanolamine (DMPE), 16-0-Monome Le PE, 16-0-dimethyl PE, 18-1-trans PE, palmitoyl oleoyl-phosphatidylethanolamine (POPE), or 1-stearoyl-2-oleoyl-phosphatidyl ethanolamine (SOPE). In some embodiments, the phospholipid comprises a glycerophospholipid. In some embodiments, the glycerophospholipid is plasmalogen, phosphatidate, or phosphatidylcholine. In some embodiments, the glycerophospholipid is phosphatidylserine, phosphatidic acid, phosphatidylglycerol, phosphatidylinositol, palmitoyl oleoyl phosphatidylglycerol (POPG), or lysophosphatidylcholine. In some embodiments, the phospholipid comprises a sphingophospholipid. In some embodiments, the sphingophospholipid is sphingomyelin, ceramide phosphoethanolamine, ceramide phosphoglycerol, or ceramide phosphoglycerophosphoric acid. In some embodiments, the phospholipid comprises a natural lecithin. In some embodiments, the natural lecithin is egg yolk lecithin or soybean lecithin. In some embodiments, the phospholipid comprises a hydrogenated phospholipid. In some embodiments, the hydrogenated phospholipid is hydrogenated soybean phosphatidylcholine. In some embodiments, the phospholipid is selected from the group consisting of: phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine.

In some embodiments, the phospholipid comprises a lipid selected from: 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 2-Oleoyl-1-palmitoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin.

A phospholipid can comprise a phospholipid moiety and one or more fatty acid moieties. A phospholipid moiety can comprise phosphatidyl choline, phosphatidyl ethanolamine, phosphatidyl glycerol, phosphatidyl serine, phosphatidic acid, 2-lysophosphatidyl choline, or a sphingomyelin. A fatty acid moiety can comprise lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, or docosahexaenoic acid. In some specific embodiments, a phospholipid can be functionalized with or cross-linked to one or more alkynes, which may undergo a copper-catalyzed cycloaddition upon exposure to an azide.

In some embodiments, the LNP composition comprises a plurality of phospholipids, for example, at least 2, 3, 4, 5, or more distinct phospholipids. In some embodiments, the phospholipid comprises from 1 mol % to 20 mol % of the total lipid present in the LNP composition. In some embodiments, the phospholipid comprises from about 5 mol % to about 15 mol % of the total lipid present in the LNP composition. In some embodiments, the phospholipid comprises from about 8 mol % to about 12 mol % of the total lipid present in the LNP composition. In some embodiments, the phospholipid comprises from about 5 mol %, about 6 mol %, about 7 mol %, about 8 mol %, about 9 mol %, about 10 mol %, about 11 mol %, about 12 mol %, about 13 mol %, about 14 mol %, or about 15 mol % of the total lipid present in the LNP composition. In some embodiments, the phospholipid comprises from about 9 mol %, about 10 mol %, or about 11 mol % of the total lipid present in the LNP composition.

Stealth Lipids

In some embodiments, a herein described LNP composition comprises a stealth lipid. "Stealth lipids" can refer to lipids that alter the length of time the nanoparticles can exist in vivo (e.g., in the blood). Stealth lipids can assist in the formulation process by, for example, reducing particle aggregation and controlling particle size. Stealth lipids used herein may modulate pharmacokinetic properties of the LNP. Stealth lipids suitable for use in a lipid composition of the disclosure can include, but are not limited to, stealth lipids having a hydrophilic head group linked to a lipid moiety. Stealth lipids suitable for use in a lipid composition of the present disclosure and information about the biochemistry of such lipids can be found in Romberg et al, Pharmaceutical Research, Vol. 25, No. 1, 2008, pg. 55-71 and Hoekstra et al, Biochimica et Biophysica Acta 1660 (2004) 41-52. Additional suitable PEG lipids are disclosed, e.g., in WO 2006/007712.

In some embodiments, the stealth lipid is a PEG-lipid. In one embodiment, the hydrophilic head group of stealth lipid comprises a polymer moiety selected from polymers based on PEG (sometimes referred to as poly(ethylene oxide)), poly(oxazoline), poly(vinyl alcohol), poly(glycerol), poly (N-vinylpyrrolidone), polyaminoacids and poly N-(2-hydroxypropyl)methacrylamide]. Stealth lipids can comprise a lipid moiety. In some embodiments, the lipid moiety of the stealth lipid may be derived from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

PEG-Lipid

In some embodiments, a described LNP composition comprises a PEG-lipid. In some embodiments, the described LNP composition comprises two or more PEG-lipids. Exemplary PEG-lipids include, but are not limited to, the lipids in Table 2. Exemplary PEG-lipids also include, but are not limited to, PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, the one or more PEG-lipids can comprise PEG-c-DOMG, PEG-DMG, PEG-DLPE, PEG-DMPE, PEG-DPPC, a PEG-DSPE lipid, or a combination thereof. In some embodiments, PEG moiety is an optionally substituted linear or branched polymer of ethylene glycol or ethylene oxide. In some embodiments, the PEG moiety is substituted, e.g., by one or more alkyl, alkoxy, acyl, hydroxy, or aryl groups. In some embodiments, the PEG moiety includes PEG copolymer such as PEG-polyurethane or PEG-polypropylene (see, e.g., j. Milton Harris, Poly(ethylene glycol) chemistry: biotechnical and biomedical applications (1992)). In some embodiments, the PEG moiety does not include PEG copolymers, e.g., it may be a PEG monopolymer. Exemplary PEG-lipids include, but are not limited to, PEG-dilauroylglycerol, PEG-dimyristoylglycerol (PEG-DMG), PEG-dipalmitoylglycerol, PEG-distearoylgiycerol (PEG-DSPE), PEG-dipalmitoylglycerol, PEG-disterylglycerol, PEG-dilaurylglycamide, PEG-dimyristylglycamide, PEG-dipalmitoylglycamide, PEG-disterylglycamide, PEG-cholesterol, and PEG-DMB (3,4-Ditetradecoxylbenzyl-[omega]-methyl-poly(ethylene glycol) ether), 1,2-dimyristoyl-sn-glycero-3-phosphoethanolamine-N-[methoxy(polyethylene glycol)-2000]).

In some embodiments, a PEG-lipid is a PEG-lipid conjugate, for example, PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., WO 2010/006282), polyamide oligomers (e.g., ATTA-lipid conjugates), and mixtures thereof.

A PEG-lipid can comprise one or more ethylene glycol units, for example, at least 1, at least 2, at least 5, at least 10, at least 20, at least 30, at least 40, at least 50, at least 60, at least 70, at least 80, at least 90, at least 100, at least 120, or at least 150 ethylene glycol units. In some embodiments, a number average molecular weight of the PEG-lipids is from about 200 Da to about 5000 Da. In some embodiments, a number average molecular weight of the PEG-lipids is from about 500 Da to about 3000 Da. In some embodiments, a number average molecular weight of the PEG-lipids is from about 750 Da to about 2500 Da. In some embodiments, a number average molecular weight of the PEG-lipids is from about 750 Da to about 2500 Da. In some embodiments, a number average molecular weight of the PEG-lipids is about 500 Da, about 750 Da, about 1000 Da, about 1250 Da, about 1500 Da, about 1750 Da, or about 2000 Da. In some embodiments, a polydispersity index (PDI) of the one or more PEG-lipids is smaller than 2. In some embodiments, a PDI of the one or more PEG-lipids is at most 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. In some embodiments, a PDI of the one or more PEG-lipids is at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0.

In some embodiments, the PEG-lipid comprises from about 0.1 mol % to about 10 mol % of the total lipid present in the LNP composition. In some embodiments, the PEG-lipid comprises from about 0.1 mol % to about 6 mol % of the total lipid present in the LNP composition. In some embodiments, the PEG-lipid comprises from about 0.5 mol % to about 5 mol % of the total lipid present in the LNP composition. In some embodiments, the PEG-lipid comprises from about 1 mol % to about 3 mol % of the total lipid present in the LNP composition. In some embodiments, the PEG-lipid comprises about 2.0 mol % to about 2.5 mol % of the total lipid present in the LNP composition. In some embodiments, the PEG-lipid comprises about 1 mol %, about 1.1 mol %, about 1.2 mol %, about 1.3 mol %, about 1.4 mol %, about 1.5 mol %, about 1.6 mol %, about 1.7 mol %, about 1.8 mol %, about 1.9 mol %, about 2.0 mol %, about 2.1 mol %, about 2.2 mol %, about 2.3 mol %, about 2.4 mol %, about 2.5 mol %, about 2.6 mol %, about 2.7 mol %, about 2.8 mol %, about 2.9 mol %, or about 3.0 mol % of the total lipid present in the LNP composition.

Amino Lipid

In some embodiments, an LNP composition described herein comprises an amino lipid. In some embodiments, the LNP comprises a plurality of amino lipids. For example, the LNP composition can comprise 2, 3, 4, 5, 6, 7, 8, 9, 10, or more amino lipids. For another example, the LNP composition can comprise at least 2, at least 3, at least 4, at least 5, at least 6, at least 7, at least 9, at least 10, or at least 20 amino lipids. For yet another example, the LNP composition can comprise at most 2, at most 3, at most 4, at most 5, at most 6, at most 7, at most 9, at most 10, at most 20, or at most 30 amino lipids.

In some embodiments, an LNP composition described herein comprises one or more amino lipids. In some embodiments, the one or more amino lipids comprise from about 1 mol % to about 65 mol % of the total lipid present in the LNP composition. In some embodiments, the one or more amino lipids comprise from about 10 mol % to about 60 mol % of the total lipid present in the LNP composition. In some embodiments, the one or more amino lipids comprise from about 40 mol % to about 65 mol % of the total lipid present in the LNP composition. In some embodiments, the one or more amino lipids comprise from about 10 mol %, about 15 mol %, about 20 mol %, about 25 mol %, about 30 mol %, about 35 mol % or about 40 mol % to about 45 mol %, 50 mol %, 55 mol %, 60 mol %, or about 65 mol % of the total lipid present in the LNP composition. In some embodiments, the one or more amino lipids comprise about 40 mol %, about 41 mol %, about 42 mol %, about 43 mol %, about 44 mol %, about 45 mol %, about 46 mol %, about 47 mol %, about 48 mol %, about 49 mol %, about 50 mol %, about 51 mol %, about 52 mol %, about 53 mol %, about 54 mol %, about 55 mol %, about 56 mol %, about 57 mol %, about 58 mol %, about 59 mol %, about 60 mol %, about 61 mol %, about 62 mol %, about 63 mol %, about 64 mol %, or about 65 mol % of the total lipid present in the LNP composition. In some embodiments, the LNP composition comprises a first amino lipid and a second amino lipid. In some embodiments, the first amino lipid comprises from about 1 mol % to about 99 mol % of the total amino lipids present in the LNP composition. In some embodiments, the first amino lipid comprises from about 16.7 mol % to about 66.7 mol % of the total amino lipids present in the LNP composition. In some embodiments, the first amino lipid comprises from about 20 mol % to about 60 mol % of the total amino lipids present in the LNP composition.

In some embodiments, the amino lipid is an ionizable lipid. An ionizable lipid can comprise one or more ionizable nitrogen atoms. In some embodiments, at least one of the one or more ionizable nitrogen atoms is positively charged. In some embodiments, at least 10 mol %, 20 mol %, 30 mol %, 40 mol %, 50 mol %, 60 mol %, 70 mol %, 80 mol %, 90 mol %, 95 mol %, or 99 mol % of the ionizable nitrogen atoms in the LNP composition are positively charged. In some embodiments, the amino lipid comprises a primary amine, a secondary amine, a tertiary amine, an imine, an amide, a guanidine moiety, a histidine residue, a lysine residue, an arginine residue, or any combination thereof. In some embodiments, the amino lipid comprises a primary amine, a secondary amine, a tertiary amine, a guanidine moiety, or any combination thereof. In some embodiments, the amino lipid comprises a tertiary amine.

In some embodiments, the amino lipid is a cationic lipid. In some embodiments, the amino lipid is an ionizable lipid. In some embodiments, the amino lipid comprises one or more nitrogen atoms. In some embodiments, the amino lipid comprises one or more ionizable nitrogen atoms. Exemplary cationic and/or ionizable lipids include, but are not limited to, 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-

DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3P)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(33)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). Further examples of the amino lipids suitable for the present disclosure can be found in US 20180290965A1, WO 2017/173054A1, US 20150273068A1, WO 2015/095340A1, U.S. Pat. Nos. 9,365,610, 8,193,246, 8,192,753, 9,549,983, 8,017,804, 8,357,722, 7,799,565, and 7,745,651, all of which are hereby incorporated by reference in their entirety.

In some embodiments, an amino lipid described herein can take the form of a salt, such as a pharmaceutically acceptable salt. All pharmaceutically acceptable salts of the amino lipid are encompassed by this disclosure. As used herein, the term "amino lipid" also includes its pharmaceutically acceptable salts, and its diastereomeric, enantiomeric, and epimeric forms.

In some embodiments, an amino lipid described herein, possesses one or more stereocenters and each stereocenter exists independently in either the R or S configuration. The lipids presented herein include all diastereomeric, enantiomeric, and epimeric forms as well as the appropriate mixtures thereof. The lipids provided herein include all cis, trans, syn, anti, entgegen (E), and zusammen (Z) isomers as well as the appropriate mixtures thereof.

Payload

In one aspect, the herein described LNP compositions comprise a payload. The LNP compositions described herein can be designed to deliver a payload, such as a therapeutic agent, or a target of interest. Exemplary therapeutic agents include, but are not limited to, antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siNA), messenger ribonucleic acid (messenger RNA, mRNA), short interfering RNA (siRNA), double-stranded RNA (dsRNA), micro-RNA (miRNA), and short hairpin RNA (shRNA)molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (assymetrical interfering RNA), and siRNA with 1, 2 or more mismatches between the sense and anti-sense strand to relevant cells and/or tissues, such as in a cell culture, subject or organism. Therapeutic agents can be purified or partially purified, and can be naturally occurring or synthetic, or chemically modified. In some embodiments, the therapeutic agent is an RNAi agent, short interfering nucleic acid (siNA), short interfering RNA (siRNA), double-stranded RNA (dsRNA), micro-RNA (miRNA), or a short hairpin RNA (shRNA)molecule. In some embodiments, the therapeutic agent is an mRNA.

In some embodiments, the payload comprises one or more nucleic acid(s) (i.e., one or more nucleic acid molecular entities). In some embodiments, the nucleic acid is a single-stranded nucleic acid. In some embodiments, single-stranded nucleic acid is a DNA. In some embodiments, single-stranded nucleic acid is an RNA. In some embodiments, the nucleic acid is a double-stranded nucleic acid. In some embodiments, the double-stranded nucleic acid is a DNA. In some embodiments, the double-stranded nucleic acid is an RNA. In some embodiments, the double-stranded nucleic acid is a DNA-RNA hybrid. In some embodiments, the nucleic acid is a messenger RNA (mRNA), a microRNA, an asymmetrical interfering RNA (aiRNA), a small hairpin RNA (shRNA), or a Dicer-Substrate dsRNA.

In some embodiments, the payload comprises an mRNA. In some embodiments, the payload comprises an mRNA molecule encoding a Cas nuclease, i.e., a Cas nuclease mRNA. In some embodiments, the payload comprises one or more guide RNAs or nucleic acids encoding guide RNAs. In some embodiments, the payload comprises a template nucleic acid for repair or recombination. In some embodiments, the payload comprises an mRNA encoding a gene editor nuclease. In some embodiments, the payload comprises an mRNA encoding a base editor nuclease. In some embodiments, the payload comprises an mRNA encoding a restriction enzyme. In some embodiments, the payload comprises zinc-finger nuclease or TALEN nuclease.

In some embodiments, the mRNA payload, such as a Cas nuclease mRNA, can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. Additional modifications to improve stability, expression, and immunogenicity can also be made. The mRNA encoding a Cas nuclease can be codon optimized for expression in a particular cell type, such as a eukaryotic cell, a mammalian cell, or more specifically, a human cell. In some embodiments, the mRNA encodes a human codon optimized Cas9 nuclease or human codon optimized Cpf nuclease as the Cas nuclease. In some embodiments, the mRNA encodes a gene editor (i.e., genome editor)nuclease and is called a gene editor mRNA. In some embodiments, the gene editor is a Cas protein, such as the ones described herein. In some embodiments, the gene editor is an engineered nuclease. In some embodiments, the gene editor introduces a double stranded break in a gene of interest. In some embodiments, the gene editor introduces a double stranded break at a targeted point within a gene of interest. In some embodiments, the gene editor introduces a single stranded break in a gene of interest. In some embodiments, the gene editor is a base editor. In some embodiments, the gene editor inserts a nucleic acid sequence into a gene of interest. In some embodiments, the gene editor deletes a targeted sequence from a gene of interest. In some embodiments, the gene editor mRNA encodes Cas9 nuclease. In some embodiments, the gene editor mRNA encodes base editor nuclease. In some embodiments, the gene editor mRNA encodes a restriction enzyme. In some embodiments, the gene editor mRNA encodes zinc-finger nuclease. In some embodiments, the gene editor mRNA encodes transcription activator-like effector-based nucleases (TALEN). In some embodiments, the gene editor mRNA encodes a meganuclease. In some embodiments, the gene editor mRNA encodes an Argonaute protein. In some embodiments, the mRNA is purified. In some embodiments, the mRNA is purified using a precipitation method (e.g., LiCl precipitation, alcohol precipitation, or an equivalent method, e.g., as described herein) or a chromatography-based method (e.g., an HPLC-based method or an equivalent method).

In some embodiments, the Cas nuclease mRNA comprises a 3' or 5' untranslated region (UTR). In some embodiments, the 3' or 5' UTR can be derived from a human gene sequence. Exemplary 3' and 5' UTRs include α- and β-globin, albumin, HSD17B4, and eukaryotic elongation factor 1a. In addition, viral-derived 5' and 3' UTRs can also be used and include orthopoxvirus and cytomegalovirus UTR sequences. In certain embodiments, the mRNA includes a 5' cap, such as m7G(5')ppp(5')N. In certain embodiments, this cap can be a cap-0 where nucleotide N does not contain 2'OMe, or cap-1 where nucleotide N contains 2'OMe, or cap-2 where nucleotides N and N+1 contain 2'OMe. In some embodiments, the 5' cap can regulate nuclear export; prevent degradation by exonucleases; promote translation; and promote 5' proximal intron excision. In addition, caps can also contain a non-nucleic acid entity that acts as the binding element for eukaryotic translation initiation factor 4E, eIF4E. In certain embodiments, the mRNA includes a poly(A) tail. This tail can be about 40 to about 300 nucleotides in length. In some embodiments, the tail is about 40 to about 100 nucleotides in length. In some embodiments, the tail is about 100 to about 300 nucleotides in length. In some embodiments, the tail is about 100 to about 300 nucleotides in length. In some embodiments, the tail is about 50 to about 200 nucleotides in length. In some embodiments, the tail is about 50 to about 250 nucleotides in length. In certain embodiments, the tail is about 100, 150, or 200 nucleotides in length. The poly(A) tail can contain modifications to prevent exonuclease degradation including phosphorothioate linkages and modifications to the nucleobase. In some embodiments, the poly(A) tail contains a 3' "cap" which could include modified or non-natural nucleobases or other synthetic moieties. In some embodiments, the mRNA comprises at least one element that is capable of modifying the intracellular half-life of the RNA. The half-life of the RNA can be increased or decreased. In some embodiments, the element is capable of increasing or decreasing the stability of the RNA. In some embodiments the element may promote RNA decay. In some embodiments, the element can activate translation. In some embodiments, the element may be within the 3' UTR of the RNA. For example, the element may be an mRNA decay signal or may include a polyadenylation signal (PA).

In some embodiments, the Cas nuclease mRNA encodes a Cas protein from a CRISPR/Cas system. In some embodiments, the Cas protein comprises at least one domain that interacts with a guide RNA ("gRNA"). In some embodiments, the Cas protein is directed to a target sequence by a guide RNA. The guide RNA can interact with the Cas protein as well as the target sequence such that, it can direct binding to the target sequence. In some embodiments, the guide RNA provides the specificity for the targeted cleavage, and the Cas protein may be universal and paired with different guide RNAs to cleave different target sequences. In certain embodiments, the Cas protein may cleave single or double-stranded DNA. In certain embodiments, the Cas protein may cleave RNA. In certain embodiments, the Cas protein may nick RNA. In some embodiments, the Cas protein comprises at least one DNA binding domain and at least one nuclease domain. In some embodiments, the nuclease domain may be heterologous to the DNA binding domain. In certain embodiments, the Cas protein may be modified to reduce or eliminate nuclease activity. The Cas protein may be used to bind to and modulate the expression or activity of a DNA sequence.

In some embodiments, the CRISPR/Cas system comprises Class 1 or Class 2 system components, including ribonucleic acid protein complexes. The Class 2 Cas nuclease families of proteins are enzymes with DNA endonuclease activity, and they can be directed to cleave a desired nucleic acid target by designing an appropriate guide RNA, as described further herein. A Class 2 CRISPR/Cas system component may be from a Type-IIA, Type-IIB, Type-IIC, Type V, or Type VI system. Class 2 Cas nucleases include, for example, Cas9, Cpf1, C2c1, C2c2, and C2c3 proteins. In some embodiments, the Cas protein is from a Type-II CRISPR/Cas system, i.e., a Cas9 protein from a CRISPR/Cas9 system, or a Type-V CRISPR/Cas system, e.g., a Cpf1 protein. In some embodiments, the Cas protein is from a Class 2 CRISPR/Cas system, i.e., a single-protein Cas nuclease such as a Cas9 protein or a Cpf1 protein.

Exemplary species that the Cas9 protein or other components can be from include, but are not limited to, *Streptococcus pyogenes*, *Streptococcus thermophilus*, *Streptococcus* sp., *Staphylococcus aureus*, *Listeria innocua*, *Lactobacillus gasseri*, *Francisella novicida*, *Wolinella succinogenes*, *Sutterella wadsworthensis*, *Gamma proteobacterium*, *Neisseria meningitidis*, *Campylobacter jejuni*, *Pasteurella multocida*, *Fibrobacter succinogene*, *Rhodospirillum rubrum*, *Nocardiopsis dassonvillei*, *Streptomyces pristinaespiralis*, *Streptomyces viridochromogenes*, *Streptomyces viridochromogenes*, *Streptosporangium roseum*, *Alicyclobacillus acidocaldarius*, *Bacillus pseudomycoides*, *Bacillus selenitireducens*, *Exiguobacterium sibiricum*, *Lactobacillus delbrueckii*, *Lactobacillus salivarius*, *Lactobacillus buchneri*, *Treponema denticola*, *Microscilla marina*, *Burkholderiales bacterium*, *Polar omonas naphthalenivorans*, *Polar omonas* sp., *Crocosphaera watsonii*, *Cyanothece* sp., *Microcystis aeruginosa*, *Synechococcus* sp., *Acetohalobium arabaticum*, *Ammonifex degensii*, *Caldicelulosiruptor becscii*, *Candidatus Desulforudis*, *Clostridium botulinum*, *Clostridium difficile*, *Finegoldia magna*, *Natranaerobius thermophilus*, *Pelotomaculum thermopropionium*, *Acidithiobacillus caldus*, *Acidithiobacillus ferrooxidans*, *Allochromatium vinosum*, *Marinobacter* sp., *Nitrosococcus halophilus*, *Nitrosococcus watsoni*, *Pseudoalteromonas haloplanktis*, *Ktedonobacter racemifer*, *Methanohalobium evestigatum*, *Anabaena variabilis*, *Nodular ia spumigena*, *Nostoc* sp., *Arthrospira maxima*, *Arthrospira platensis*, *Arthrospira* sp., *Lyngbya* sp., *Microcoleus chthonoplastes*, *Oscillator ia* sp., *Petrotoga mobilis*, *Thermosipho africanus*, *Streptococcus pasteurianus*, *Neisseria cinerea*, *Campylobacter lari*, *Parvibaculum lavamentivorans*, *Coryne bacterium diphtheria*, or *Acaryochloris marina*. In some embodiments, the Cas9 protein is from *Streptococcus pyogenes*. In some embodiments, the Cas9 protein may be from *Streptococcus thermophilus*. In some embodiments, the Cas9 protein is from *Staphylococcus aureus*.

In some embodiments, the payload comprises at least one guide RNA. The guide RNA may guide the Class 2 Cas nuclease to a target sequence on a target nucleic acid molecule, where the guide RNA hybridizes with and the Cas nuclease cleaves or modulates the target sequence. In some embodiments, a guide RNA binds with and provides specificity of cleavage by a Class 2 nuclease. In some embodiments, the guide RNA and the Cas protein may form a ribonucleoprotein (RNP), e.g., a CRISPR/Cas complex. In some embodiments, the CRISPR complex may be a Type-II CRISPR/Cas9 complex. In some embodiments, the CRISPR/Cas complex may be a Type-V CRISPR/Cas complex, such as a Cpf1/guide RNA complex. In some embodiments, the Cas nuclease may be a single-protein Cas nuclease, e.g. a Cas9 protein or a Cpf 1 protein. In some embodiments, the guide RNA targets cleavage by a Cas9 protein. In some embodiments, the payload comprises two or more guide RNA molecules. In some embodiments, the two or more guide RNA molecules target the same disease-causing gene. In some embodiments, the two or more guide RNA molecules target different genes. In some specific embodiments, the two guide RNA molecules target two separate disease-causing genes of interest.

A guide RNA for a CRISPR/Cas9 nuclease system comprises a CRISPR RNA (crRNA) and a tracr RNA (tracr). In some embodiments, the crRNA may comprise a targeting sequence that is complementary to and hybridizes with the target sequence on the target nucleic acid molecule. The crRNA may also comprise a flagpole that is complementary to and hybridizes with a portion of the tracrRNA. In some embodiments, the crRNA may parallel the structure of a naturally occurring crRNA transcribed from a CRISPR locus of a bacteria, where the targeting sequence acts as the spacer of the CRISPR/Cas9 system, and the flagpole corresponds to a portion of a repeat sequence flanking the spacers on the CRISPR locus. The guide RNA may target any sequence of interest via the targeting sequence of the crRNA. In some embodiments, the degree of complementarity between the targeting sequence of the guide RNA and the target sequence on the target nucleic acid molecule is at least about 60%, 65%, 70%, 75%, 80%, 85%, 90%, 95%, 97%, 98%, 99%, or 100%. In some embodiments, the targeting sequence of the guide RNA and the target sequence on the target nucleic acid molecule may be 100% complementary. In other embodiments, the targeting sequence of the guide RNA and the target sequence on the target nucleic acid molecule may contain at least one mismatch. For example, the targeting sequence of the guide RNA and the target sequence on the target nucleic acid molecule may contain 1, 2, 3, 4, 5, 6, 7, 8, 9, or 10 mismatches. In some embodiments, the targeting sequence of the guide RNA and the target sequence on the target nucleic acid molecule may contain 1-6 mismatches.

In some embodiments, the length of the targeting sequence depends on the CRISPR/Cas system and components used. For example, different Cas proteins from different bacterial species have varying optimal targeting sequence lengths. Accordingly, the targeting sequence may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the targeting sequence comprised 18-24 nucleotides in length. In some embodiments, the targeting sequence comprises 19-21 nucleotides in length. In some embodiments, the targeting sequence comprises 20 nucleotides in length.

In some embodiments, the guide RNA is a "dual guide RNA" or "dgRNA". In some embodiments, the dgRNA comprises a first RNA molecule comprising a crRNA, and a second RNA molecule comprising a tracr RNA. The first and second RNA molecules may form a RNA duplex via the base pairing between the flagpole on the crRNA and the tracr RNA. In some embodiments, the guide RNA is a "single guide RNA" or "sgRNA". In some embodiments, the sgRNA may comprise a crRNA covalently linked to a tracr RNA. In some embodiments, the crRNA and the tracr RNA may be covalently linked via a linker. In some embodiments, the single-molecule guide RNA may comprise a stem-loop structure via the base pairing between the flagpole on the crRNA and the tracr RNA. In some embodiments, the sgRNA is a "Cas9 sgRNA" capable of mediating RNA-guided DNA cleavage by a Cas9 protein. In certain embodiments, the guide RNA comprises a crRNA and tracr RNA sufficient for forming an active complex with a Cas9 protein and mediating RNA-guided DNA cleavage. In some embodiments, the payload comprises more than one guide RNAs; each guide RNA contains a different targeting sequence, such that the CRISPR/Cas system cleaves more than one target sequence. In some embodiments, one or more guide RNAs may have the same or differing properties such as activity or stability within a CRISPR/Cas complex. Where more than one guide RNA is used, each guide RNA can be encoded on the same or on different expression cassettes. The promoters used to drive expression of the more than one guide RNA may be the same or different.

In some embodiments, the nucleic acid payload, such as RNAs, is modified. Modified nucleosides or nucleotides can be present in a guide RNA or mRNA. A guide RNA or Cas nuclease encoding mRNA comprising one or more modified nucleosides or nucleotides is called a "modified" RNA to describe the presence of one or more non-naturally and/or naturally occurring components or configurations that are used instead of or in addition to the canonical A, G, C, and U residues. In some embodiments, a modified RNA is synthesized with a non-canonical nucleoside or nucleotide. Modified nucleosides and nucleotides can include one or more of: (i) alteration, e.g., replacement, of one or both of the non-linking phosphate oxygens and/or of one or more of the linking phosphate oxygens in the phosphodiester backbone linkage (an exemplary backbone modification); (ii) alteration, e.g., replacement, of a constituent of the ribose sugar, e.g., of the 2' hydroxyl on the ribose sugar (an exemplary sugar modification); (iii) wholesale replacement of the phosphate moiety with "dephospho" linkers (an exemplary backbone modification); (iv) modification or replacement of a naturally occurring nucleobase, including with a non-canonical nucleobase (an exemplary base modification); (v) replacement or modification of the ribose-phosphate backbone (an exemplary backbone modification); (vi)modification of the 3' end or 5' end of the oligonucleotide, e.g., removal, modification or replacement of a terminal phosphate group or conjugation of a moiety, cap or linker (such 3' or 5' cap modifications may comprise a sugar and/or backbone modification); and (vii)modification or replacement of the sugar (an exemplary sugar modification).

In some embodiments, the payload can include a template nucleic acid. The template can be used to alter or insert a nucleic acid sequence at or near a target site for a Cas nuclease. In some embodiments, the template is used in homologous recombination. In some embodiments, the homologous recombination may result in the integration of the template sequence or a portion of the template sequence into the target nucleic acid molecule. In some embodiments, a single template is provided. In other embodiments, two or more templates are provided such that homologous recombination may occur at two or more target sites.

In some embodiments, the payload, such as one or more RNAs, are fully encapsulated within the lipid portion of the particle, thereby protecting the RNAs from nuclease degradation. Fully encapsulated can indicate that the RNA in the nucleic acid-lipid particle is not significantly degraded after exposure to serum or a nuclease assay that would significantly degrade free DNA or RNA. In some embodiments, the nucleic acid-lipid particle composition comprises a RNA molecule that is fully encapsulated within the lipid portion of the particles, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the RNA encapsulated therein.

In some embodiments, the payload comprises an mRNA and one or more guide RNA. In some embodiments, the mRNA encodes a gene editor nuclease and is called a gene editor mRNA. In some embodiments, the gene editor mRNA encodes Cas9 nuclease. In some embodiments, the mRNA encodes base editor nuclease. In some embodiments, the gene editor mRNA encodes zinc-finger nuclease. In some embodiments, the gene editor mRNA encodes TALEN nuclease.

Additional Compositions of the LNP

In some embodiments, an LNP composition described herein comprises one or more antioxidants. In some embodiments, the one or more antioxidants function to reduce a degradation of the cationic lipids, the payload, or both. In some embodiments, the one or more antioxidants comprise a hydrophilic antioxidant. In some embodiments, the one or more antioxidants is a chelating agent such as ethylenediaminetetraacetic acid (EDTA) and citrate. In some embodiments, the one or more antioxidants is EDTA. In some embodiments, the one or more antioxidants comprise a lipophilic antioxidant. In some embodiments, the lipophilic antioxidant comprises a vitamin E isomer or a polyphenol. In some embodiments, the one or more antioxidants are present in the LNP composition at a concentration of at least 1 mM, at least 10 mM, at least 20 mM, at least 50 mM, or at least 100 mM. In some embodiments, the one or more antioxidants are present LNP composition at a concentration of about 20 mM.

Method of Making Lipid Nanoparticles

Described in the present disclosure are innovative processes for making LNP compositions, e.g., LNPs comprising a receptor targeting conjugate such as a GalNAc-lipid.

Traditionally, LNPs comprising GalNAc-lipids are prepared by a post-addition process (i.e., Post-addition of GalNAc-lipid), which involves the addition of GalNAc-lipids into pre-formed LNPs after an incubation period, followed by buffer exchange. The traditionally used post-addition process is illustrated as Process 1 in FIG. 9.

While the traditional process of post-addition of receptor targeting conjugates such as GalNAc-lipids into pre-formed LNPs is effective in preparing nanoparticles, the innovative processes described herein (e.g., by adding GalNAc-Lipid into LNP excipients, by split addition, or by successively introducing GalNAc-lipid through a third channel/port into the inline mixing chamber) offer significant advantages over the post-addition or post-insertion of GalNAc-lipid. The said advantages include, but are not limited to, more homogenous distribution of GalNAc-lipid across lipid nanoparticles and better process control over post-insertion and downstream processing of GalNAc-LNPs. For example, in some cases, the lipid nanoparticles prepared by a process involving the addition of GalNAc-lipid into LNP excipients have better particle uniformity and/or provide better editing efficacy than corresponding lipid nanoparticles prepared by post-addition of GalNAc-lipid. In some cases, the lipid nanoparticles prepared by a process involving split addition of GalNAc-lipid have better particle uniformity and/or provide better editing efficacy than corresponding lipid nanoparticles prepared by post-addition of GalNAc-lipid. Similarly, the successive third port insertion of GalNAc-lipid into the inline mixing chamber produced better particle uniformity and/or better editing efficacy than corresponding corresponding lipid nanoparticles prepared by post-insertion of GalNAc-lipid.

Provided in the present disclosure is a method of making a formulation comprising the herein-described nanoparticles. In some embodiments, the lipid nanoparticles comprise (i) one or more nucleic acid molecular entities, (ii) one or more lipids selected from a sterol or a derivative thereof, a phospholipid, a stealth lipid, and an amino lipid, and/or (iii) a receptor targeting conjugate. Accordingly, in one aspect, described herein is a method of making a formulation comprising lipid nanoparticles that comprise (i) one or more nucleic acid molecular entities, (ii) one or more lipids selected from a sterol or a derivative thereof, a phospholipid, a stealth lipid, and an amino lipid, and (iii) a receptor targeting conjugate. In some embodiments, the receptor targeting conjugate is a GalNAc-lipid. In some embodiments, the GalNAc-lipid is selected from a compound of Table 4. In some embodiments, the GalNAc-lipid is compound 1004 in Table 4. In some embodiments, the GalNAc-lipid is compound 1053, 1014, 1043, 1002, 1044, 1004 in Table 4, or a combination thereof. In some embodiments, receptor targeting conjugate is a compound in Table 4. In some embodiments, the receptor targeting conjugate comprises one or more N-acetylgalactosamine (GalNAc) or GalNAc derivatives. In some embodiments, the receptor targeting conjugate comprises a structure of Formula (I), Formula (Ia), Formula (Ib), Formula (II), Formula (IIa), Formula (IIb), Formula (IIc), Formula (III), Formula (IIIa), Formula (IIIb), Formula (IIIc), Formula (IIId), Formula (IIIe), Formula (IV), Formula (V), Formula (VI), Formula (VIa), or Formula (VIb).

A process for making lipid nanoparticles can comprise several general steps: (i) providing an aqueous solution, such as citrate or phosphate buffer, comprising one or more nucleic acid molecular entities in a first reservoir; (ii) providing a second solution comprising one or more lipids and an organic solvent, such as an alcohol (e.g., ethanol) in a second reservoir; and (iii)mixing the aqueous solution with the second solution. The first reservoir is optionally in fluid communication with the second reservoir.

The process can optionally comprise one or more dilution steps, one or more incubation steps, one or more buffer exchange steps, one or more concentration steps, and/or one or more filtrations steps. In some embodiments, the dilution step involves dilution by adding a dilution buffer. In some embodiments, the dilution step involves dilution with aqueous buffer (e.g. citrate buffer or pure water) e.g., using a pumping apparatus (e.g. a peristaltic pump). In some embodiments, the dilution buffer is an organic solution such as alcohol. The dilution step can comprise a dilution that is 1 to 20 times of the initial volume, or any numbers or ranges therebetween. In some embodiments, the dilution step comprises a dilution that is 1 to 10 times of the initial volume. In some embodiments, the dilution step is followed by the buffer exchange step or the incubation step. In some embodiments, the dilution buffer comprises one or more lipids, such as a sterol or a derivative thereof, a phospholipid, a stealth lipid, an amino lipid, a GalNAc-lipid, or a combination thereof. In some embodiments, the dilution buffer comprises stealth lipid. In some embodiments, the stealth lipid is present in the dilution buffer at 0.01 mol % to 5 mol %. In some embodiments, the dilution buffer comprises GalNAc-lipid. In some embodiments, the GalNAc-lipid is present in the dilution buffer at 0.01 mol % to 10 mol %, or any numbers or ranges therebetween. In some embodiments, a portion of the GalNAc-lipid present in the nanoparticles is introduced through the dilution buffer.

The incubation step comprises allowing a solution from the mixing step to stand in a vessel for about 0 to about 100 hours at about room temperature and optionally protected from light. In some embodiments, the incubation step runs from 0 to 24 hours, 1 minute to 2 hours, or 1 minute to 60 minutes. In some embodiments, the incubation step runs from 1 minutes to 120 minutes. In some embodiments, the incubation step is followed by the buffer exchange step. In some embodiments, the incubation step follows the buffer exchange step.

In some embodiments, the buffer exchange step comprises a solvent exchange that results in a higher concentration of phosphate buffered saline (PBS) buffer. In some embodiments, the buffer exchange step comprises removing all or a portion of organic solvent. In some embodiments, the buffer exchange step comprises dialysis through a suitable membrane (e.g. 10,000 mwc snakeskin membrane). In some embodiments, the buffer exchange step comprises filtration such as tangential flow filtration (TFF)). In some embodiments, the buffer exchange step comprises chromatography such as using a desalting column, e.g., PD10 column. In some embodiments, the buffer exchange step comprises ultrafiltration. Ultrafiltration comprises concentration of the diluted solution followed by diafiltration, e.g., using a suitable pumping system (e.g. pumping apparatus such as a peristaltic pump or equivalent thereof) in conjunction with a suitable ultrafiltration membrane (e.g. GE Hollow fiber cartridges or equivalent).

In some embodiments, the mixing step provides a clear single phase. In some embodiments, after the mixing step, the organic solvent is removed to provide a suspension of particles, wherein the one or more nucleic acid molecular entities are encapsulated by the lipid(s). The selection of an organic solvent will typically involve consideration of solvent polarity and the ease with which the solvent can be removed at the later stages of particle formation. The organic solvent, which can serve as a solubilizing agent, can be in an amount sufficient to provide a clear single phase mixture of the one or more nucleic acid molecular entities and lipid(s). The organic solvent may be selected from one or more (e.g., two) of chloroform, dichloromethane, diethylether, cyclohexane, cyclopentane, benzene, toluene, methanol, and other aliphatic alcohols (e.g. $C_1$ to $C_8$) such as ethanol, propanol, isopropanol, butanol, tert-butanol, iso-butanol, pentanol and hexanol. The methods used to remove the organic solvent can involve diafiltration or dialysis or evaporation at reduced pressures or blowing a stream of inert gas (e.g. nitrogen or argon) across the mixture.

In other embodiments, the method further comprises adding nonlipid polycations which are useful to effect the transformation of cells using the present compositions. Examples of suitable nonlipid polycations include, but are limited to, hexadimethrine bromide (sold under the brand name POLYBRENE®, from Aldrich Chemical Co., Milwaukee, Wis., USA) or other salts of hexadimethrine. Other suitable polycations include, e.g., salts of poly-L-ornithine, poly-L-arginine, poly-L-lysine, poly-D-lysine, polyallylamine and polyethyleneimine. In certain embodiments, the formation of the lipid nanoparticles can be carried out either in a mono-phase system (e.g. a Bligh and Dyer monophase or similar mixture of aqueous and organic solvents) or in a two-phase system with suitable mixing.

The lipid nanoparticles can be formed in a mono- or a bi-phase system. In some embodiments, in a mono-phase system, the amino lipid(s) and one or more nucleic acid molecular entities are each dissolved in a volume of the mono-phase mixture. Combining the two solutions provides a single mixture in which the complexes form. In some embodiments, in a bi-phase system, the amino lipids bind to the one or more nucleic acid molecular entities (which is present in the aqueous phase), and thus increasing the solubility in organic phase.

In some embodiments, the solution of sterol(s) or derivative(s) thereof, phospholipid lipid(s) and amino lipid(s) is a solution comprising organic solvent. In some embodiments, the solution of GalNAc-lipid(s) comprises organic solvent such as ethanol. In some embodiments, the stealth lipid is prepared in an aqueous solution. In some embodiments, the stealth lipid is prepared in an organic solution. Contacting the one or more nucleic acid molecular entities with the organic solution comprising one or more lipids can be accomplished by mixing together a first solution of the one or more nucleic acid molecular entities and a second solution of the lipids.

In some embodiments, the lipid nanoparticles are prepared in an apparatus comprising a first reservoir for holding an aqueous solution and a second reservoir for holding an organic lipid solution. In some embodiments, the apparatus comprises additional reservoirs for holding an aqueous solution (such as for a portion of the one or more nucleic acid molecular entities) and/or an organic solution (such as for all or a portion of the GalNAc-lipid). The apparatus can include a pump mechanism configured to pump the aqueous and the organic lipid solutions into a mixing region or mixing chamber at substantially equal flow rates. In some embodiments, the mixing region or mixing chamber comprises a T coupling or equivalent thereof, which allows the aqueous and organic fluid streams to combine as input into the T connector and the resulting combined aqueous and organic solutions to exit out of the T connector into a collection reservoir or equivalent thereof.

In one aspect, described herein is a method of preparing a formulation comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate. In some embodiments, the method comprises (a) providing a first solution comprising at least one of the one or more nucleic acid molecular entities; (b) providing a second solution comprising at least one of the one or more lipids; (c)mixing the first solution and the second solution, thereby producing a mixture comprising nanoparticles that comprise the one or more nucleic acid molecular entities and the one or more lipids; (d) combining the receptor targeting conjugate with the one or more lipids; (e) optionally carrying out a incubating step; and (f) optionally carrying out a buffer exchange step. In some embodiments, the method comprises (a) providing a first solution comprising the one or more nucleic acid molecular entities; (b) providing a second solution comprising at least one of the one or more lipids; (c)mixing the first solution and the second solution, thereby producing a mixture comprising nanoparticles that comprise the one or more nucleic acid molecular entities and the one or more lipids; (d) combining the receptor targeting conjugate with the one or more lipids; (e) incubating the nanoparticles; and (f) optionally carrying out a buffer exchange step. In some embodiments, the method comprises providing (a) a first solution comprising the one or more nucleic acid molecular entities; (b) providing a second solution comprising at least one of the one or more lipids; (c) mixing the first solution and the second solution, thereby producing a mixture comprising nanoparticles that comprise the one or more nucleic acid molecular entities and the one or more lipids; (d) combining the receptor targeting conjugate with the one or more lipids, wherein at least a portion of the receptor targeting conjugate is combined with the one or more lipids prior to or concurrently with the mixing step; (e) optionally incubating the nanoparticles; and (f) optionally carrying out a buffer exchange step.

In some embodiments, the receptor targeting conjugate is combined with the one or more lipids after the mixing step. In some embodiments, the receptor targeting conjugate is combined with the one or more lipids prior the mixing step. In some embodiments, the receptor targeting conjugate is combined with the one or more lipids concurrently with the mixing step. In some embodiments, at least a portion of the receptor targeting conjugate is combined with the one or more lipids concurrently with the mixing step. In some embodiments, at least a portion of the receptor targeting conjugate is combined with the one or more lipids prior to the mixing step. In some embodiments, the receptor targeting conjugate is combined with the one or more lipids in the second solution. In some embodiments, the receptor targeting conjugate is combined with other components of the lipid nanoparticles after incubating step. In some embodiments, the receptor targeting conjugate is combined with other components of the lipid nanoparticles after a concentrating step. In some embodiments, the receptor targeting conjugate is combined with other components of the lipid nanoparticles after freeze-thawing the nanoparticles.

Figure 10:
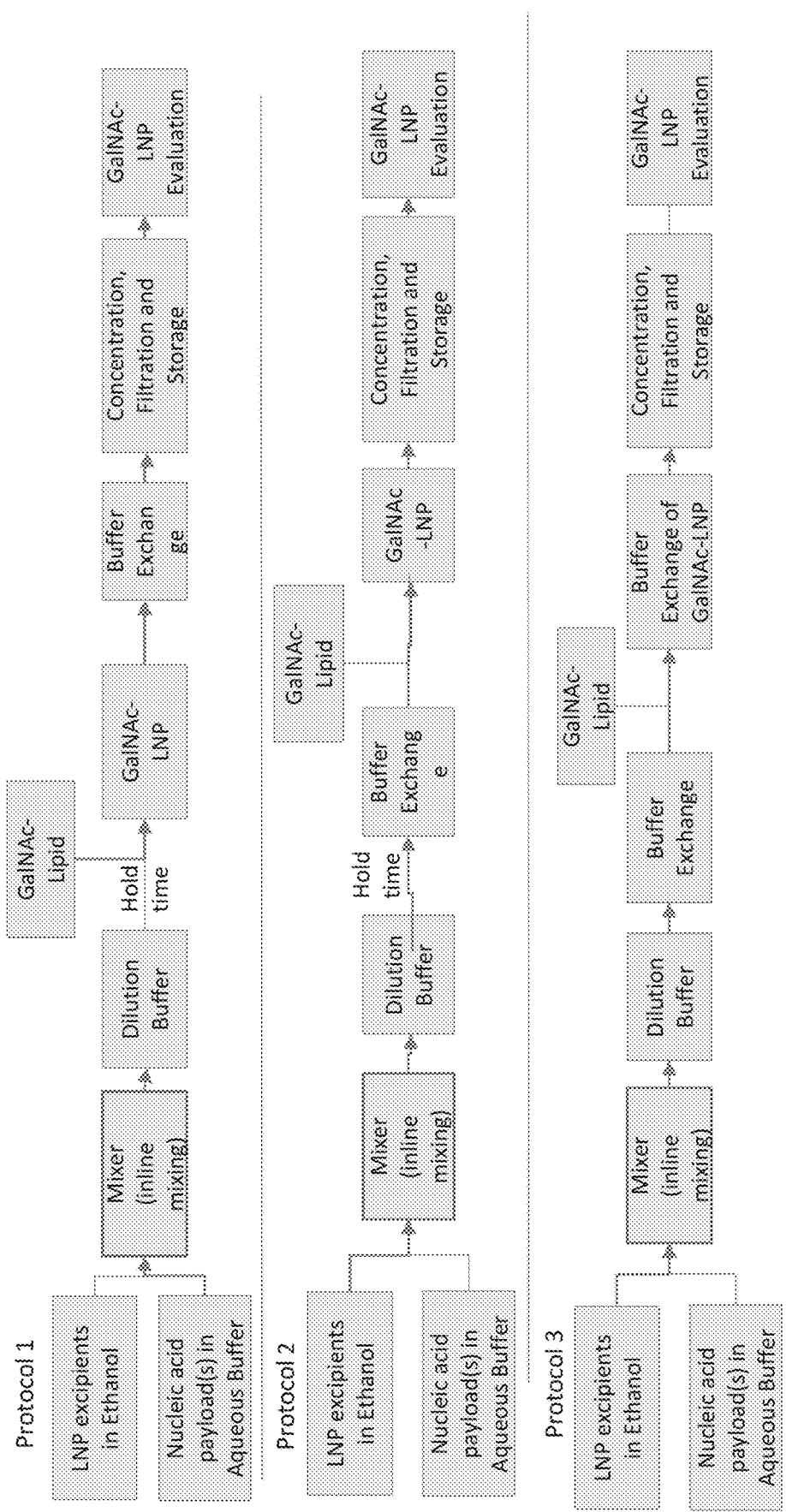
FIG. 10 illustrates three protocols for preparing lipid nanoparticles comprising post-addition of GalNAc-lipids.
Figure 11:
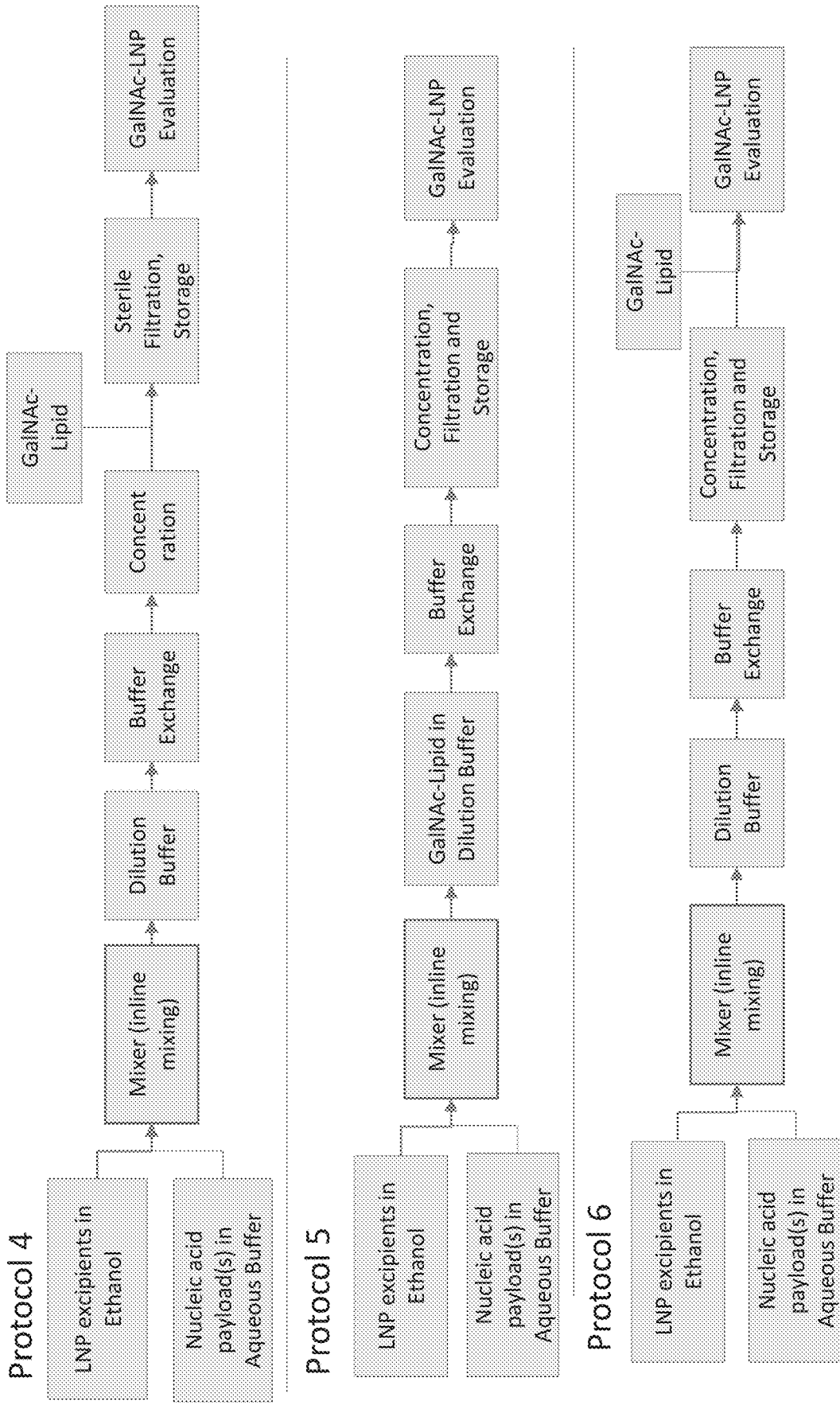
FIG. 11 illustrates three protocols for preparing lipid nanoparticles comprising post-addition of GalNAc-lipids.

A receptor targeting conjugate described herein can be partially or fully combined with other components of the lipid nanoparticles after the one or more nucleic acid molecular entities are mixed with the one or more lipids that are selected from a sterol or a derivative thereof, a phospholipid, a stealth lipid, and an amino lipid. FIGS. 10-11 illustrate 6 exemplary protocols (protocols 1-6). In some embodiments, the receptor targeting conjugate is introduced after nucleic acid molecular entities are mixed with a sterol or a derivative thereof, a phospholipid, a stealth lipid, and/or an amino lipid. In some embodiments, the receptor targeting conjugate is added in a dilution buffer. The dilution buffer can be mixed with preformed nucleic acid-lipid nanoparticles coming out of an inline mixing chamber thereby forming the nanoparticles. In some embodiments, the dilution buffer comprises at least a portion of the lipids such as stealth lipid. In some embodiments, all the receptor targeting conjugate in an LNP composition are introduced in a dilution buffer. In some embodiments, the receptor targeting conjugate is introduced to the lipid nanoparticles after an addition of a dilution buffer to the mixture and holding the diluted mixture for a period of time. In some embodiments, the holding time is between 1 and 120 minutes. In some embodiments, the holding time is between 1 and 90 minutes, between 1 and 60 minutes, or between 10 and 40 minutes. In some embodiments, the holding time is from about 25 to 35 minutes, from about 20 to 40 minutes, from about 10 to 50 minutes, or from about 5 to 60 minutes. In some embodiments, the holding time is about 10 minutes, about 15 minutes, about 20 minutes, about 25 minutes, about 30 minutes, about 35 minutes, about 40 minutes, about 45 minutes, or about 50 minutes. In some embodiments, the holding time is about 30 minutes. In some embodiments, the receptor targeting conjugate is introduced to the nanoparticles after buffer exchange. In some embodiments, the receptor targeting conjugate is introduced to the nanoparticles immediately after buffer exchange. In some embodiments, the receptor targeting conjugate is introduced to the nanoparticles after buffer exchange and concentration, but prior to storage. In some embodiments, the receptor targeting conjugate is introduced to the nanoparticles after buffer exchange, but prior to concentration and storage. In some embodiments, the receptor targeting conjugate is introduced to the nanoparticles after storage and thawing, and prior to dosing or evaluation.

Figure 12:
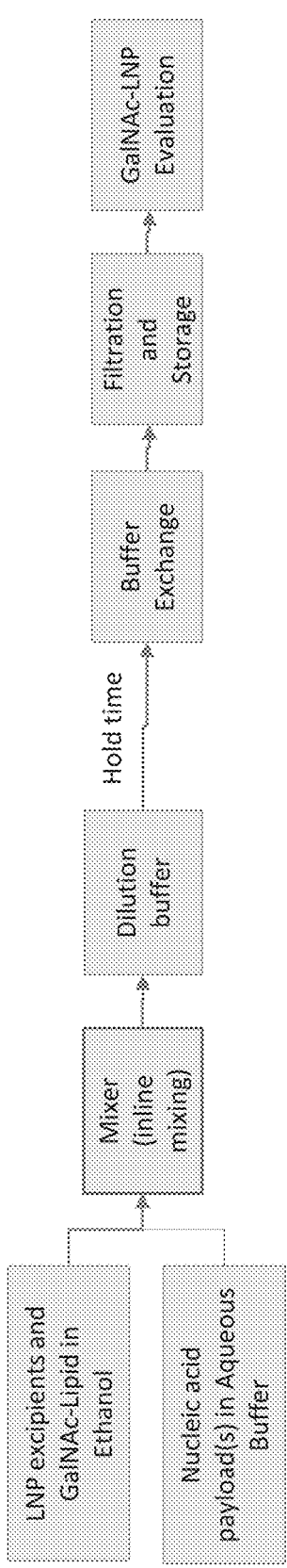
FIG. 12 illustrates three protocols for preparing lipid nanoparticles comprising addition of GalNAc-lipid into LNP excipients and split addition of GalNAc-Lipid.
Figure 12:
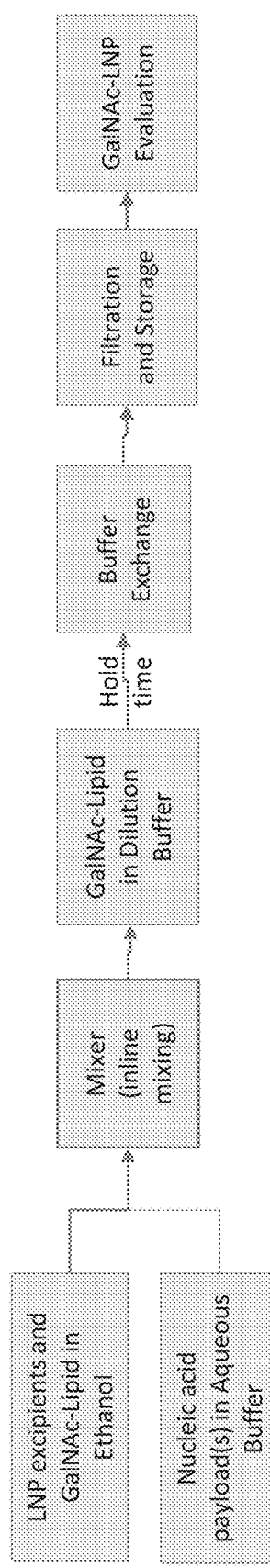
Figure 12:
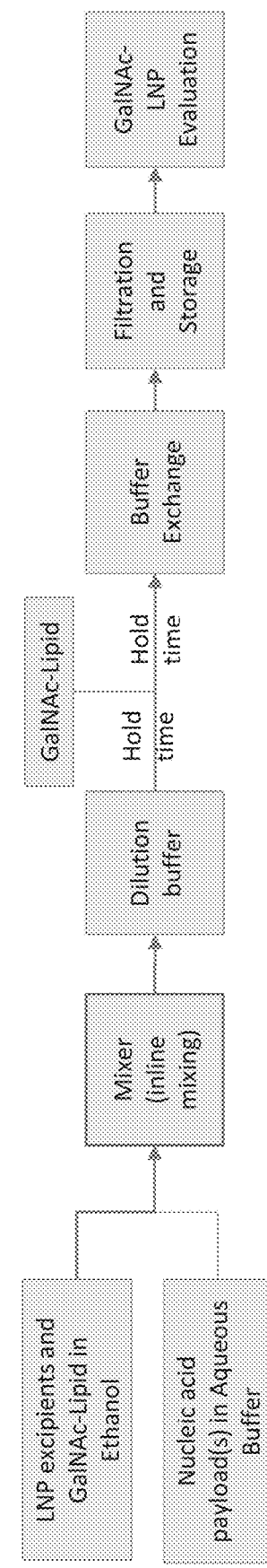
Figure 13:
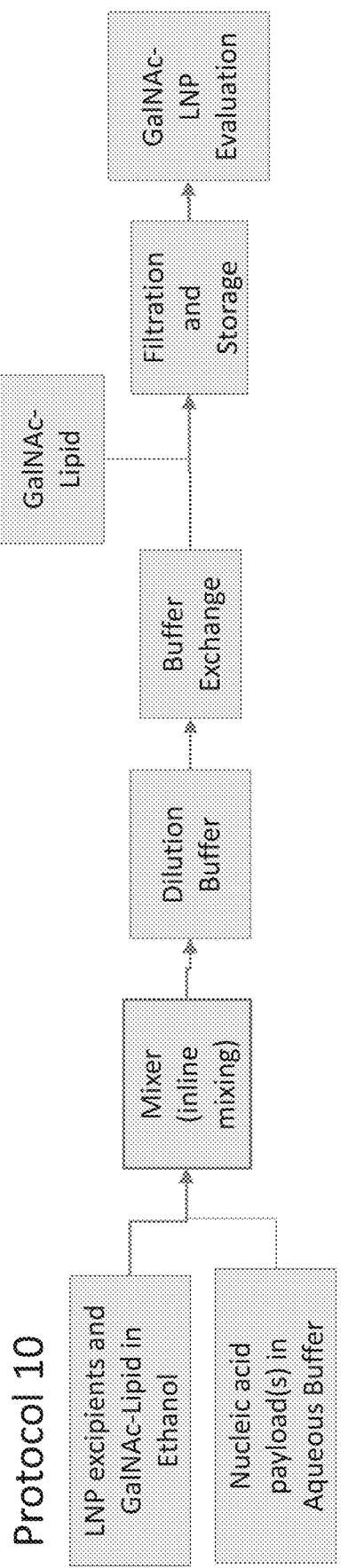
FIG. 13 illustrates two protocols for preparing lipid nanoparticles comprising addition of GalNAc-lipid into LNP excipients and split addition of GalNAc-Lipid.
Figure 13:
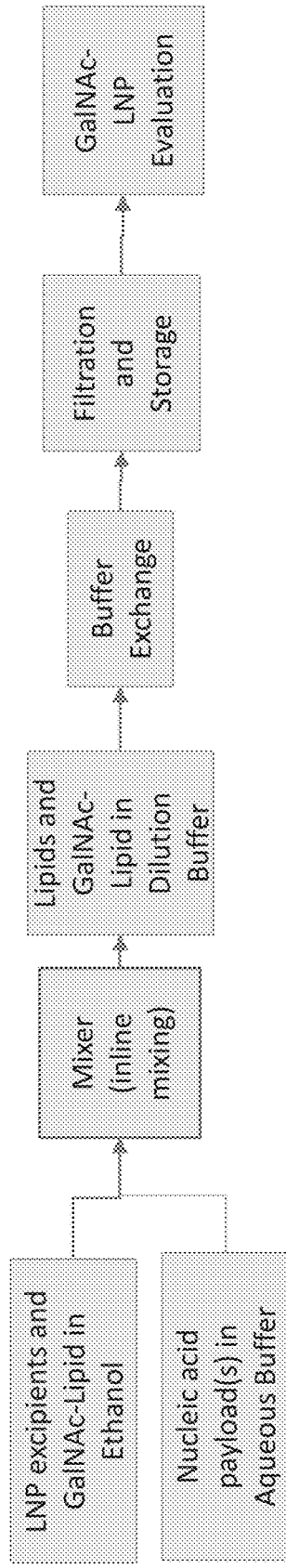

A receptor targeting conjugate described herein can be partially or fully pre-mixed with the one or more lipids that are selected from a sterol or a derivative thereof, a phospholipid, a stealth lipid, and an amino lipid, thereby being introduced to the nanoparticles simultaneously with other components of the premix (i.e., addition of GalNAc-lipid into LNP excipients). FIGS. 12-13 illustrate 5 exemplary protocols (protocols 7-11) of GalNAc-lipid addition into LNP excipients. Further exemplary protocol of addition of GalNAc-lipid into LNP excipients are illustrated as Process 4 in FIG. 9.

Figure 14:
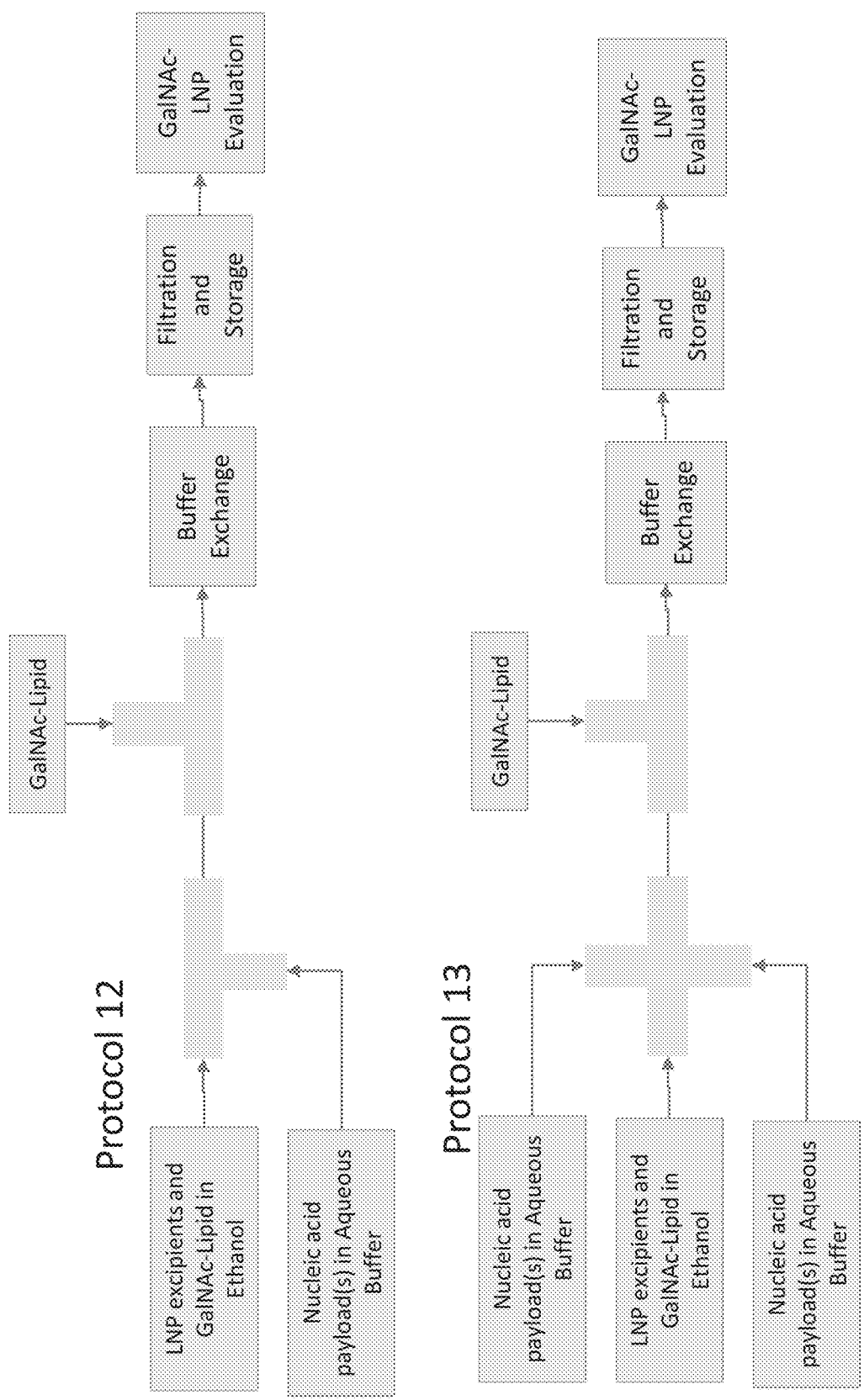
FIG. 14 illustrates two protocols for preparing lipid nanoparticles comprising cross-mixing of GalNAc-lipid.

A receptor targeting conjugate described herein can be partially or fully combined with other components of the lipid nanoparticles by inline mixing. For example, after the one or more nucleic acid molecular entities are mixed with the one or more lipids that are selected from a sterol or a derivative thereof, a phospholipid, a stealth lipid, and an amino lipid, the receptor targeting conjugate can be successively added via inline mixing through a third channel or port. The successive inline mixing can provide instantaneous mixing of the receptor targeting conjugate with the rest of components in the nanoparticles and thereby forming the target nanoparticles. In some embodiments, all or a portion of the receptor targeting conjugate is combined with other components via cross-mixing. In some embodiments, all or a portion of the receptor targeting conjugate is combined with other components via a T-shape mixer. In some embodiments, all or a portion of the receptor targeting conjugate is combined with other components via a microfluidics mixer. FIG. 14 illustrates 2 exemplary protocols (protocols 12-13) of GalNAc-lipid addition via inline mixing. Further exemplary protocol is illustrated as Process 3 in FIG. 9.

A receptor targeting conjugate described herein can be combined with other components of the lipid nanoparticles through two or more separate, independent additions (i.e., split addition of GalNAc-lipid). In some embodiments, the two or more separate additions are carried out at different steps. In some embodiments, the two or more separate additions are carried out concurrently. In some embodiments, the two or more separate additions involves different solutions. In some embodiments, a portion of the receptor targeting conjugate is combined with the one or more lipids in the second solution and a portion of the receptor targeting conjugate is combined with the one or more lipids after the mixing. In some embodiments, a portion of the receptor targeting conjugate is combined with the one or more lipids in the second solution and a portion of the receptor targeting conjugate is combined with the one or more lipids after the incubating step. In some embodiments, a portion of the receptor targeting conjugate is combined with the one or more lipids in the second solution and a portion of the receptor targeting conjugate is combined with the one or more lipids after the buffer exchange step. FIGS. 12-13 illustrate 5 exemplary protocols (protocols 7-11) of split addition of GalNAc-lipid. Further exemplary protocols of split addition of GalNAc-lipid are illustrated in FIG. 14. Similarly, other components of the LNPs can be introduced by split addition. For example, as illustrated in Protocol 13 of FIG. 14, the one or more nucleic acid molecular entities can be introduced in two separate buffer solutions. In some embodiments, the one or more nucleic acid molecular entities are introduced in 2 to 4 solutions. In some embodiments, the sterol or a derivative thereof, the phospholipid, the stealth lipid, and/or the amino lipid are independently introduced to the LNPs in 1-3 solutions, which can occur concurrently or at different times.

In some embodiments, a method of making a formulation comprising the herein-described nanoparticles comprises diluting the mixture produced by mixing the first and the second solutions by adding a dilution buffer. In some embodiments, the mixture is diluted inline. In some embodiments, the dilution buffer comprises at least a portion of the receptor targeting conjugate. In some embodiments, the dilution buffer comprises at least a portion of the stealth lipid.

In some embodiments, the first solution comprises an aqueous buffer. In some embodiments, the first solution comprises an organic solvent. In some embodiments, the first solution comprises a mixture of an aqueous buffer mixed with an organic solvent. In some embodiments, the organic solvent present in the aqueous buffer is ethanol. In some embodiments, the ethanol percentage in the aqueous buffer ranges from 0.1% to 50%, or any numbers or ranges therebetween. In some embodiments, the second solution comprises a mixture of an aqueous buffer mixed with an organic solvent. In some embodiments, the second solution comprises ethanol. In some embodiments, the second solution comprises ethanol and water. In some embodiments, the dilution buffer comprises an aqueous buffer. In some embodiments, the dilution buffer comprises an organic solvent. In some embodiments, the dilution buffer comprises ethanol and water. In some embodiments, the dilution buffer comprises 10% to 20% of ethanol in PBS buffer.

In some embodiments, a receptor targeting conjugate such as GalNAc-lipid is introduced to the nanoparticles as a solution. In some embodiments, the concentration of the receptor targeting conjugate in the solution is from about 0.1 mol % to 20 mol %, or any numbers or ranges therebetween. In some embodiments, the concentration of the receptor targeting conjugate in the solution is from about 10 mol % to about 20 mol %, from about 5 mol % to about 10 mol %, from about 0.25 mol % to about 5 mol %, from about 0.5 mol % to about 3 mol %, from about 0.5 mol % to about 2 mol %, from about 0.25 mol % to about 1 mol %, from about 0.25 mol % to about 0.5 mol %, from about 1 mol % to about 2 mol %, from about 2 mol % to about 3 mol %, or from about 0.1 mol % to about 0.5 mol %. In some embodiments, the concentration of the receptor targeting conjugate in the solution is about 0.25 mol %, about 0.5 mol %, about 0.9 mol %, about 1 mol %, about 1.5 mol %, or about 2 mol %. In some embodiments, the concentration of the receptor targeting conjugate in the solution is about 0.25 mol %.

In some embodiments, the mixing comprises laminar mixing, vortex mixing, turbulent mixing, or a combination thereof. In some embodiments, the mixing comprises cross-mixing. In some embodiments, the mixing comprises inline mixing. In some embodiments, the mixing comprises introducing at least a portion of the first solution through a first inlet channel and at least a portion of the second solution through a second inlet channel, and wherein an angle between the first inlet channel and the second inlet channel is from about 0 to 180 degrees. In some embodiments, the angle between the first inlet channel and the second inlet channel is from about 15 to 180 degrees, from about 30 to 180 degrees, from about 45 to 180 degrees, from about 60 to 180 degrees, from about 90 to 180 degrees, or any numbers or ranges therebetween. In some embodiments, the mixing comprises introducing a portion of the first solution through a third inlet channel. The mixing step can take place by any number of methods, e.g., by mechanical means such as a vortex mixer. In some embodiments, the mixing step comprises inline mixing. Exemplary mixing processes are illustrated in FIGS. 9-14. In some embodiments, the mixing step comprises cross-mixing GalNAc-lipid, as illustrated in FIG. 14. In some embodiments, the solution containing the targeting conjugate is introduced into the inline mixing chamber through a third inlet.

In some embodiments, a method of making a formulation comprising the herein-described nanoparticles comprises a filtration step. In some embodiments, a method of making a formulation comprising the herein-described nanoparticles comprises buffer exchange. In some embodiments, the buffer exchange comprises dialysis, chromatography, or tangential flow filtration (TFF).

Pharmaceutical Composition

In one aspect, disclosed herein are pharmaceutical compositions comprising one or more described LNP compositions. For example, a pharmaceutical composition can include one or more LNP compositions including one or more different payloads. In some embodiments, the pharmaceutical composition comprises two or more LNP compositions, which can be the same or different.

In one aspect, disclosed herein are pharmaceutical compositions comprising one or more described receptor targeting conjugates. In some embodiments, the pharmaceutical composition comprises two or more receptor targeting conjugates, which can be the same or different. In some embodiments, disclosed herein are pharmaceutical compositions that comprise (i) a first receptor targeting conjugate or a first nanoparticle composition, and (ii) a second receptor targeting conjugate or a second nanoparticle composition.

Pharmaceutical compositions can further include one or more pharmaceutically acceptable excipients, carrier, or accessory ingredients such as those described herein. General guidelines for the formulation and manufacture of pharmaceutical compositions and agents are available, for example, in Remington's The Science and Practice of Pharmacy, 21st Edition, A. R. Gennaro; Lippincott, Williams & Wilkins, Baltimore, Md., 2006. Excipients or carriers can include any ingredient other than the compound(s) of the disclosure, the other lipid component(s) and the payload. An excipient may impart either a functional (e.g. drug release rate controlling) and/or a nonfunctional (e.g. processing aid or diluent) characteristic to the formulations. The choice of excipient and carrier can depend on factors such as the particular mode of administration, the effect of the excipient on solubility and stability, and the nature of the dosage form. Parenteral formulations are typically aqueous or oily solutions or suspensions. Excipients or carrier such as sugars (including but not restricted to glucose, mannitol, sorbitol, etc.), salts, carbohydrates and buffering agents (preferably to a pH of from 3 to 9) can be used. In some embodiments, the LNP compositions can be formulated with a sterile non-aqueous solution or as a dried form to be used in conjunction with a suitable vehicle such as sterile, pyrogen-free water (WFI).

In some embodiments, the excipient or carrier can make up greater than 50% of the total mass or volume of a pharmaceutical composition comprising a nanoparticle composition. For example, the excipient or carrier can make up 50%, 60%, 70%, 80%, 90%, or more of a pharmaceutical composition. In some embodiments, a pharmaceutically acceptable excipient or carrier is at least 95%, at least 96%, at least 97%, at least 98%, at least 99%, or 100% pure. In some embodiments, a pharmaceutical composition can comprise between 0.1% and 100% (wt/wt) of one or more nanoparticle compositions. In certain embodiments, the nanoparticle compositions and/or pharmaceutical compositions are refrigerated or frozen for storage and/or shipment (e.g., being stored at a temperature of 4° C. or lower, such as a temperature between about −150° C. and about 0° C. or between about −80° C. and about −20° C. In some embodiments, the nanoparticle compositions and/or pharmaceutical compositions are refrigerated or frozen at about −5° C., −10° C., −15° C., −20° C., −25° C., −30° C., −40° C., −50° C., −60° C., −70° C., −80° C., −90° C., −130° C., or −150° C.

The described LNP compositions and/or pharmaceutical compositions can be administered to any patient or subject, including those patients or subjects that may benefit from a therapeutic effect provided by the delivery of the payload to one or more particular cells, tissues, organs, or systems or groups thereof. In some embodiments, the subject is a mammal such as human. In some embodiments, the subject is non-human primates or mammals, including commercially relevant mammals such as cattle, pigs, hoses, sheep, cats, dogs, mice, and/or rats.

A pharmaceutical composition including one or more nanoparticle compositions can be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure can be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., nanoparticle composition). The amount of the active ingredient is generally equal to the dosage of the active ingredient which would be administered to a subject and/or a convenient fraction of such a dosage such as, for example, one-half or one-third of such a dosage. Pharmaceutical compositions may be prepared in a variety of forms suitable for a variety of routes and methods of administration. For example, pharmaceutical compositions may be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

In some embodiments, the pharmaceutical composition comprises 1, 2, 3, 4, 5, 6, 7, 8, 9, 10 or more payloads. In some embodiments, the pharmaceutical composition comprises two distinct payloads, such guide RNA and mRNA. The guide RNA and mRNA can be located in the same LNP composition, or they can be located at separate LNP compositions. For example, a pharmaceutical composition can comprise two distinct LNP compositions, one comprising a guide RNA payload and the other comprising an mRNA payload. For another example, a pharmaceutical composition can comprise two distinct LNP compositions, one comprising a guide RNA (or mRNA) payload and the other comprising both an mRNA payload and a guide RNA payload. For yet another example, a pharmaceutical composition can comprise one LNP composition, which comprising an mRNA payload and a guide RNA payload. In some embodiments, the pharmaceutical composition comprises two or more distinct LNP compositions. In some embodiments, the two or more distinct LNP compositions are present in the pharmaceutical composition such that the mRNA molecule(s) and the guide RNA molecule(s) are at a mole or weight ratio described herein.

The gRNA and mRNA payloads can be present in the pharmaceutical composition at various molar or weight ratios. For example, the gRNA to mRNA ratio in the pharmaceutical composition can be from 0.01 to 100 by weight, and/or any value therebetween. For example, the gRNA to mRNA ratio in the pharmaceutical composition can be from 0.01 to 100 by mole, and/or any value therebetween. In some embodiments, the ratio of gRNA to mRNA in the pharmaceutical composition is from about 1 to about 50 by weight or by mole, and/or any value therebetween. In some embodiments, the ratio of gRNA to mRNA in the pharmaceutical composition is from about 0.1 to about 10 by weight or by mole, and/or any value therebetween. In some embodiments, the ratio of gRNA to mRNA in the pharmaceutical composition is from about 0.2 to about 5, from about 0.25 to about 4, from about 0.3 to about 3, or from about 0.5 to about 2 by weight. In some embodiments, the ratio of gRNA to mRNA in the pharmaceutical composition is from about 0.2 to about 5, from about 0.25 to about 4, from about 0.3 to about 3, or from about 0.5 to about 2 by mole. In some embodiments, the gRNA to mRNA ratio in the pharmaceutical composition is about 1:1, about 1:2, about 1:3, about 1:4, about 1:5, about 1:6, about 1:7, about 1:8, about 1:9, or about 1:10 by weight. In some embodiments, the gRNA to mRNA ratio in the pharmaceutical composition is about 1:1, about 1:2, about 1:3, about 1:4, about 1:5, about 1:6, about 1:7, about 1:8, about 1:9, or about 1:10 by mole. In some embodiments, the mRNA to gRNA ratio in the pharmaceutical composition is about 1:1, about 1:2, about 1:3, about 1:4, about 1:5, about 1:6, about 1:7, about 1:8, about 1:9, or about 1:10 by weight. In some embodiments, the mRNA to gRNA ratio in the pharmaceutical composition is about 1:1, about 1:2, about 1:3, about 1:4, about 1:5, about 1:6, about 1:7, about 1:8, about 1:9, or about 1:10 by mole. In some embodiments, the gRNA to mRNA ratio in the pharmaceutical composition is about 1:1 by weight. In some embodiments, the gRNA to mRNA ratio in the pharmaceutical composition is about 1:1 by mole.

In some embodiments, the gRNA in the pharmaceutical composition targets a disease-causing gene that is produced in the hepatocytes. In some embodiments, the pharmaceutical composition comprises more than one guide RNA. For example, the pharmaceutical composition can comprise 2, 3, 4, 5, or more distinct guide RNAs. In some embodiments, the pharmaceutical composition comprises two guide RNA molecules. In some embodiments, the pharmaceutical composition comprises one mRNA and two or more guide RNA molecules. In some embodiments, the two or more guide RNA molecules target the same disease-causing gene. In some embodiments, the two or more guide RNA molecules target different genes. In some specific embodiments, the two guide RNA molecules target two separate disease-causing genes of interest produced in the hepatocytes. In some embodiments, the gRNA is a sgRNA. In some embodiments, the gRNA is a dgRNA.

The LNP compositions and pharmaceutical compositions disclosed herein can be used in methods for gene editing, both in vivo and in vitro. In some embodiments, the methods comprise contacting a cell with an LNP composition or a pharmaceutical composition described herein. In some embodiments, the cell is a mammalian cell. In some embodiments, the cell is a rodent cell. In some embodiments, the cell is a human cell. In some embodiments, the cell is a liver cell. In certain embodiments, the cell is a human liver cell. In some embodiments, the liver cell is a hepatocyte. In some embodiments, the hepatocyte is a human hepatocyte. In some embodiments, the liver cell is a stem cell. In some embodiments, the human liver cell is a liver sinusoidal endothelial cell (LSEC). In some embodiments, the human liver cell is a Kupffer cell. In some embodiments, the human liver cell is a hepatic stellate cell. In some embodiments, the human liver cell is a tumor cell. In some embodiments, the human liver cell is a liver stem cell. In some embodiments, the cell comprises ApoE-binding receptors. In some embodiments, engineered cells are provided; for example an engineered cell can be derived from any one of the cell types as described herein. Such engineered cells can be produced according to the methods described herein. In some embodiments, the engineered cell resides within a tissue or organ, e.g., a liver within a subject.

Target Sequences

The present disclosure provides active agents or therapeutic agents, such as genome editing compositions, and methods and compositions for targeted delivery thereof. The therapeutic agents described herein may comprise genome editing composition directed to and modify, alter, or cleave a target sequence on a target nucleic acid molecule. For example, the active agent may comprise a nucleic acid or a nucleic acid-protein complex capable of effecting a modification to a target sequence.

The target sequence may be a DNA sequence or a RNA sequence. In some embodiments, the active agent or therapeutic agent may comprise a RNA interference factor. In some embodiments, the active agent may comprise a siRNA, shRNA, antisense oligonucleotide, microRNA, anti-microRNA or antimir, supermir, antagomir, ribozyme, triplex-forming oligonucleotide, decoy oligonucleotide, splice-switching oligonucleotide, immunostimulatory oligonucleotide, RNA activator, or a U1 adaptor. The active agent may recognize the target sequence and mediate cleavage and/or degradation of the target sequence. In some embodiments, the active or therapeutic agent may comprise a guide RNA. The guide RNA may be complexed with a nucleic acid guided programmable nuclease, such as a CRISPR enzyme, such as a Cas9, or a fusion protein thereof further comprising a functional domain. The target sequence may be recognized by the nucleic acid guided programmable nuclease domain. The target sequence may be cleaved by the nucleic acid guided programmable nuclease domain and/or modified by the functional domain, such as a deaminase domain, a methylase domain, a methyltransferase domain, an activation domain, a repressor domain, a nuclease domain, a transposase domain, or a recombinase domain. In some embodiments, a Cas9 protein may be directed by a guide RNA to a target sequence of a target nucleic acid molecule, where the guide RNA hybridizes with and the Cas protein cleaves the target sequence. In some embodiments, the target sequence may be complementary to the targeting sequence of the guide RNA. In some embodiments, the degree of complementarity between a targeting sequence of a guide RNA and its corresponding target sequence may be about 50%, 55%, 60%, 65%, 70%, 75%, 80%, 85%, 90%, 95%, 97%, 98%, 99%, or 100%. In some embodiments, the target sequence and the targeting sequence of the guide RNA may be 100% complementary. In other embodiments, the target sequence and the targeting sequence of the guide RNA may contain at least one mismatch. For example, the target sequence and the targeting sequence of the guide RNA may contain 1, 2, 3, 4, 5, 6, 7, 8, 9, or 10 mismatches. In some embodiments, the target sequence and the targeting sequence of the guide RNA may contain 1-6 mismatches. In some embodiments, the target sequence and the targeting sequence of the guide RNA may contain 5 or 6 mismatches.

The length of the target sequence may depend on the nuclease system used. For example, the target sequence for a CRISPR/Cas system may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the target sequence may comprise 18-24 nucleotides in length. In some embodiments, the target sequence may comprise 19-21 nucleotides in length. In some embodiments, the target sequence may comprise 20 nucleotides in length. When nickases are used, the target sequence may comprise a pair of target sequences recognized by a pair of nickases on opposite strands of the DNA molecule.

In some embodiments, the active or therapeutic agent may comprise a meganuclease system. the target sequence for a meganuclease may comprise 12-40 or more nucleotides in length. When ZFNs are used, the target sequence may comprise two half target sequences recognized by a pair of ZFNs on opposite strands of the DNA molecule, with an interconnecting sequence in between. In some embodiments, each half target sequence for ZFNs may independently comprise 9, 12, 15, 18, or more nucleotides in length. In some embodiments, the interconnecting sequence for ZFNs may comprise 4-20 nucleotides in length. In some embodiments, the interconnecting sequence for ZFNs may comprise 5-7 nucleotides in length.

When TALENs are used, the target sequence may similarly comprise two half target sequences recognized by a pair of TALENs on opposite strands of the DNA molecule, with an interconnecting sequence in between. In some embodiments, each half target sequence for TALENs may independently comprise 10-20 or more nucleotides in length. In some embodiments, the interconnecting sequence for TALENs may comprise 4-20 nucleotides in length. In some embodiments, the interconnecting sequence for TALENs may comprise 12-19 nucleotides in length.

In some embodiments, the target sequence may be adjacent to a protospacer adjacent motif (PAM), a short sequence recognized by a CRISPR/Cas complex. The protospacer adjacent motif, or PAM, is essential for target binding for CRISPR/Cas complexes. Typically, a PAM is a 2-6 base pair DNA sequence immediately following the DNA target sequence of the Cas nuclease. The PAM may be a 5' PAM or a 3' PAM. The exact sequence of PAM depends on the type of Cas protein. For example, a typical SpCas9 binding requires a 3'-NGG-5' PAM, also known as a canonical PAM, where the N is any one of A, G, C, or T. A SpCas9 with certain amino acid substitutions, e.g. D1 135E, R1335Q, G1218R, and/or T1337R can recognize a NGA PAM or a NGCG PAM. A SaCas9 binding requires a 3'-NNGRRT-5' PAM. A SaCas9 with certain amino substitutions, e.g., K781E, K697N, H1014R, can recognize a NNNRRT PAM.

In some embodiments, the PAM may be adjacent to or within 1, 2, 3, or 4, nucleotides of the 3' end of the target sequence. The length and the sequence of the PAM may depend on the Cas9 protein used. For example, the PAM may be selected from a consensus or a particular PAM sequence for a specific Cas9 protein or Cas9 ortholog, including those disclosed in FIG. 1 of Ran et al., Nature, 520: 186-191 (2015), which is incorporated herein by reference. In some embodiments, the PAM may comprise 2, 3, 4, 5, 6, 7, 8, 9, or 10 nucleotides in length. Non-limiting exemplary PAM sequences include NGG, NGGNG, NG, NAAAAN, NNAAAAW, NNNNACA, GNNNCNNA, and NNNNGATT (wherein N is defined as any nucleotide, and W is defined as either A or T). In some embodiments, the PAM sequence may be NGG. In some embodiments, the PAM sequence may be NGGNG. In some embodiments, the PAM sequence may be NNAAAAW. Additional evolved Cas variants and PAM sequences as described in Hu et al., Evolved Cas9 variants with broad PAM compatibility and high DNA specificity, Nature 2018 556(7699): 57-63 is incorporated herein in its entirety.

The target nucleic acid molecule may be any DNA or RNA molecule that is endogenous or exogenous to a cell. As used herein, the term "endogenous sequence" refers to a sequence that is native to the cell. The term "exogenous sequence" refers to a sequence that is not native to a cell, or a sequence whose native location in the genome of the cell is in a different location. In some embodiments, the target nucleic acid molecule may be a plasmid, a genomic DNA, or a chromosome from a cell or in the cell. In some embodiments, the target sequence of the target nucleic acid molecule may be a genomic sequence from a cell or in the cell. In some embodiments, the cell may be a prokaryotic cell. In other embodiments, the cell may be a eukaryotic cell. In some embodiments, the eukaryotic cell may be a mammalian cell. In some embodiments, the eukaryotic cell may be a rodent cell. In some embodiments, the eukaryotic cell may be a human cell. In some embodiments, the eukaryotic cell may be a liver cell. In some embodiments, the eukaryotic cell may be a hepatocyte. In some embodiments, the eukaryotic cell may be a parenchymal cell, a sinusoidal endothelial cell, a phagocytic Kupffer cell, or a stellate cell. In further embodiments, the target sequence may be a viral sequence. In yet other embodiments, the target sequence may be a synthesized sequence. In some embodiments, the target sequence may be on a eukaryotic chromosome, such as a human chromosome.

In some embodiments, the target sequence may be located in a coding sequence of a gene, an intron sequence of a gene, a transcriptional control sequence of a gene, a translational control sequence of a gene, or a non-coding sequence between genes. In some embodiments, the gene may be a protein coding gene. In other embodiments, the gene may be a non-coding RNA gene. In some embodiments, the target sequence may comprise all or a portion of a disease-associated gene. In some embodiments, the target sequence may comprise all or a portion of a gene associated with a coronary disease. In some embodiments, the target sequence may comprise at least a portion of a gene encoding an apolipoprotein. In some embodiments, the target sequence may comprise at least a portion of a gene selected from PCSK9, ANGPTL3, APOC3, LPA, APOB, MTP, ANGPTL4, ANGPTL8, APOA5, APOE, LDLR, IDOL, NPC1L1, ASGR1, TM6SF2, GALNT2, GCKR, LPL, MLXIPL, SORT1, TRIB1, MARC1, ABCG5, and ABCG8.

In some embodiments, contacting a target sequences with the genome editing composition described herein leads to a base editing event within or adjacent to the target sequence. For example, a target base (e.g. a C base) within or adjacent to a target sequence may be converted to a T base as the result of contact with the genome editing composition as disclosed in the present disclosure comprising a fusion protein comprising a nucleic acid guided nuclease domain and a deaminase domain. In some embodiments, the target base is located upstream (5' end of) of the PAM. In some embodiments, the target base is located at a position 1, 2, 3, 4, 5, 6, 7, 8, 9, 10, 11, 12, 13, 14, 15, 16, 17, 18, 19, 20, 21, 22, 23, 24, 25, 26, 28, 29, 30, 31, 32, 33, 34, 35, 36, 37, 38, 39, 40, 41, 42, 43, 44, 45, 46, 47, 48, 49, or 50 base pairs upstream (5' end of) the PAM. In some embodiments, the target base is located at a position within 13 to 17 base pairs upstream (5' end) of the PAM. In some embodiments, the target base is located at a position outside of 13 to 17 base pairs upstream (5' end) of the PAM. In some embodiments, the target base pair is located at a position 10-15 base pairs upstream (5' end) of the PAM. In some embodiments, the target base is located at a position 11-12 base pairs upstream of the PAM. In some embodiments, the target base is 11 base pairs upstream (5' end) of the PAM. In some embodiments, the target base is located in the coding region (e.g., an exon) of the target sequence, e.g. the ANGPTL3 encoding polynucleotide (e.g., the ANGPTL3 gene locus). For example, conversion of a base in the coding region of the ANGPTL3 gene locus may result in an amino acid change in the ANGPTL3 protein sequence, i.e., a mutation. In some embodiments, the mutation is a loss of function mutation. In some embodiments, a mutation may introduce a pre-mature stop codon into the coding region the target sequence, e.g. coding region of the ANGPTL3 gene. In some embodiments, a loss-of-function mutation is a naturally occurring loss-of-function mutation. In some embodiments, the mutation is located in the coding region of the PCSK9 gene, e.g. a G106R, L253F, A443T, R93C, G24D, S47F, R46H, S 153N, or H193Y mutation. In some embodiments, the loss-of-function mutation introduces a pre-mature stop codon into the coding region of the ANGPTL3 gene. In some embodiments, a loss of function mutation may be introduced into the coding region of a APOC3 gene, e.g. a R19X mutation. In some embodiments, a loss of function mutation may be introduced into a Low-Density Lipoprotein Receptor (LDL-R) protein. In some embodiments, a loss of function mutation may be introduced into a Inducible Degrader of the LDL Receptor (IDOL) protein.

In some embodiments, a target sequence is located in a non-coding region of the target sequence, e.g., in an intron or a splicing site of a target gene. In some embodiments, a target sequence is located in a splicing site and the editing of such target base causes alternative splicing of the target gene mRNA. In some embodiments, the alternative splicing leads to leading to loss-of-function mutants. In some embodiments, the alternative splicing leads to introduction of a premature stop codon or a frameshift in the target mRNA, resulting in truncated, unstable, or folding-defective polypeptides. In some embodiments, stop codons may be introduced into the coding sequence of a apolipoprotein encoding gene upstream of the normal stop codon (referred to as a "premature stop codon"). In some embodiments, stop codons may be introduced into the coding region of the target gene. Premature stop codons cause premature translation termination, in turn resulting in truncated and non-functional proteins and induces rapid degradation of the mRNA via the non-sense mediated mRNA decay pathway. See, e.g., Baker et al., Current Opinion in Cell Biology 16 (3): 293-299, 2004; Chang et al, Annual Review of Biochemistry 76: 51-74, 2007; and Behm-Ansmant et ah, Genes & Development 20 (4): 391-398, 2006, each of which is incorporated herein by reference. The genome editing composition described herein may be used to introduce multiple editing events to the target sequence. For example, the genome editing composition may comprise a nucleic acid guide programmable nuclease that induces double strand breaks, deletions, insertions, frameshift, reversions, or other alterations in the target gene. For example, the genome editing composition may comprise a nucleic acid guided programmable nuclease-deaminase fusion protein that can convert several amino acids to create a stop codon (e.g., TAA, TAG, or TGA).

In some embodiments, simultaneous introduction of mutations into more than one protein factors in the LDL-mediated cholesterol clearance pathway are provided. For example, in some embodiments, a mutation may be simultaneously introduced into one or more, preferably at least two, of ANGPTL3, PCSK9, LDLR, APOB, APOE, IDOL, and other LDL-mediated pathway involved genes. In some embodiments, a loss-of-function mutation may be simultaneously introduced into one or more, preferably at least two, of ANGPTL3, PCSK9, APOB, and another LDL-mediated pathway involved gene. In some embodiments, mutations may be simultaneously introduced into ANGPTL3, PCSK9, LDLR, and IDOL. To simultaneously introduce of loss-of-function mutations into more than one protein, multiple guide nucleotide sequences are used.

In some embodiments, the target sequence may be located in a non-genic functional site in the genome that controls aspects of chromatin organization, such as a scaffold site or locus control region. In some embodiments, the target sequence may be a genetic safe harbor site, i.e., a locus that facilitates safe genetic modification.

Templates

In some embodiments, at least one template may be provided as a substrate during the repair of the cleaved target nucleic acid molecule. In some embodiments, the template may be used in homologous recombination, such as, e.g., high-fidelity homologous recombination. In some embodiments, the homologous recombination may result in the integration of the template sequence into the target nucleic acid molecule. In some embodiments, a single template or multiple copies of the same template may be provided. In other embodiments, two or more templates may be provided such that homologous recombination may occur at two or more target sites. For example, different templates may be provided to repair a single gene in a cell, or two different genes in a cell. In some embodiments, the different templates may be provided in independent copy numbers.

In some embodiments, the template may be used in homology-directed repair, requiring DNA strand invasion at the site of the cleavage in the nucleic acid. In some embodiments, the homology-directed repair may result in the copying of the template sequence into the target nucleic acid molecule. In some embodiments, a single template or multiple copies of the same template may be provided. In other embodiments, two or more templates having different sequences may be inserted at two or more sites by homology-directed repair. For example, different templates may be provided to repair a single gene in a cell, or two different genes in a cell. In some embodiments, the different templates may be provided in independent copy numbers.

In some embodiments, the template may be incorporated into the cleaved nucleic acid as an insertion mediated by non-homologous end joining. In some embodiments, the template sequence has no similarity to the nucleic acid sequence near the cleavage site. In some embodiments, the template sequence (e.g., the coding sequence in the template) has no similarity to the nucleic acid sequence near the cleavage site. The template sequence may be flanked by target sequences that may have similar or identical sequence (s) to a target sequence near the cleavage site. In some embodiments, a single template or multiple copies of the same template may be provided. In other embodiments, two or more templates having different sequences may be inserted at two or more sites by non-homologous end joining. For example, different templates may be provided to insert a single template in a cell, or two different templates in a cell. In some embodiments, the different templates may be provided in independent copy numbers.

In some embodiments, the template sequence may correspond to an endogenous sequence of a target cell. In some embodiments, the endogenous sequence may be a genomic sequence of the cell. In some embodiments, the endogenous sequence may be a chromosomal or extrachromosomal sequence. In some embodiments, the endogenous sequence may be a plasmid sequence of the cell. In some embodiments, the template sequence may be substantially identical to a portion of the endogenous sequence in a cell at or near the cleavage site, but comprise at least one nucleotide change. In some embodiments, the repair of the cleaved target nucleic acid molecule with the template may result in a mutation comprising an insertion, deletion, or substitution of one or more nucleotides of the target nucleic acid molecule. In some embodiments, the mutation may result in one or more amino acid changes in a protein expressed from a gene comprising the target sequence. In some embodiments, the mutation may result in one or more nucleotide changes in an RNA expressed from the target gene. In some embodiments, the mutation may alter the expression level of the target gene. In some embodiments, the mutation may result in increased or decreased expression of the target gene. In some embodiments, the mutation may result in gene knockdown. In some embodiments, the mutation may result in gene knockout. In some embodiments, the repair of the cleaved target nucleic acid molecule with the template may result in replacement of an exon sequence, an intron sequence, a transcriptional control sequence, a translational control sequence, or a non-coding sequence of the target gene.

In other embodiments, the template sequence may comprise an exogenous sequence. In some embodiments, the exogenous sequence may comprise a protein or RNA coding sequence operably linked to an exogenous promoter sequence such that, upon integration of the exogenous sequence into the target nucleic acid molecule, the cell is capable of expressing the protein or RNA encoded by the integrated sequence. In other embodiments, upon integration of the exogenous sequence into the target nucleic acid molecule, the expression of the integrated sequence may be regulated by an endogenous promoter sequence. In some embodiments, the exogenous sequence may be a chromosomal or extrachromosomal sequence. In some embodiments, the exogenous sequence may provide a cDNA sequence encoding a protein or a portion of the protein. In yet other embodiments, the exogenous sequence may comprise an exon sequence, an intron sequence, a transcriptional control sequence, a translational control sequence, or a non-coding sequence. In some embodiments, the integration of the exogenous sequence may result in gene knock-in.

The template may be of any suitable length. In some embodiments, the template may comprise 10, 15, 20, 25, 50, 75, 100, 150, 200, 500, 1000, 1500, 2000, 2500, 3000, 3500, 4000, 4500, 5000, 5500, 6000, or more nucleotides in length. In some embodiments, the template may comprise a nucleotide sequence that is complementary to a portion of the target nucleic acid molecule comprising the target sequence (i.e., a "homology arm"). In some embodiments, a homology arm may comprise 10, 15, 20, 25, 50, 75, 100, 150, 200, 500, 1000, 1500, 2000, 2500, 3000 or more nucleotides in length. In some embodiments, the template may comprise a homology arm that is complementary to the sequence located upstream or downstream of the cleavage site on the target nucleic acid molecule. In some embodiments, the template may comprise a first nucleotide sequence and a second homology arm that are complementary to the sequences located upstream and downstream of the cleavage site, respectively. Where a template contains two homology arms, each arm can be the same length or different lengths, and the sequence between the homology arms can be substantially similar or identical to the target sequence between the homology arms, or be entirely unrelated. In some embodiments, the degree of complementarity between the first nucleotide sequence on the template and the sequence upstream of the cleavage site, and between the second nucleotide sequence on the template and the sequence downstream of the cleavage site, may permit homologous recombination, such as, e.g., high-fidelity homologous recombination, between the template and the target nucleic acid molecule. In some embodiments, the degree of complementarity may be about 50%, 55%, 60%, 65%, 70%, 75%, 80%, 85%, 90%, 95%, 97%, 98%, 99%, or 100%. In some embodiments, the degree of complementarity may be about 95%, 97%, 98%, 99%, or 100%. In some embodiments, the degree of complementarity may be about 98%, 99%, or 100%. In some embodiments, the degree of complementarity may be 100%. In some embodiments, for example those described herein where a template is incorporated into the cleaved nucleic acid as an insertion mediated by non-homologous end joining, the template has no homology arms. In some embodiments, a template having no homology arms comprises target sequences flanking one or both ends of the template sequence, e.g., as described herein. In some embodiments, a template having no homology arms comprises target sequences flanking both ends of the template sequence. In some embodiments, a target sequence flanking the end of the template sequence is about 10-50 nucleotides. In some embodiments, a target sequence flanking the end of the template sequence is about 10-20 nucleotides, about 15-20 nucleotides, about 20-25 nucleotides, or about 20-30 nucleotides. In some embodiments, a target sequence flanking the end of the template sequence is about 17-23 nucleotides. In some embodiments, a target sequence flanking the end of the template sequence is about 20 nucleotides.

In some embodiments, a nucleic acid molecule is expressed from the template if homologous recombination occurs between the template and the genomic sequence. In some embodiments, for example, the template does not have a promoter for expressing the nucleic acid molecule and/or the ATG transcriptional start site is removed from the coding sequence.

Delivery

Provided herein are methods and compositions for editing a nucleic acid molecule in a cell with a nuclease system and targeted delivery thereof. In some embodiments, the nucleic acid comprises a nucleic acid sequence encoding a gene. In some embodiments, the nucleic acid comprises a nucleic acid sequence encoding a gene associated with a disease or disorder.

The active agents comprising nucleic acids described herein, e.g. modified guide RNAs, may be conjugated with one or more targeting moieties for targeted delivery to desired in vivo locations. The guide RNA conjugates or guide RNA-protein complex conjugates may be introduced into the cell via any methods known in the art, such as, e.g., viral or bacteriophage infection, transfection, conjugation, protoplast fusion, lipofection, lipid particle or vesicle transduction, electroporation, calcium phosphate precipitation, polyethyleneimine (PEI)-mediated transfection, DEAE-dextran-mediated transfection, liposome-mediated transfection, e.g. transfection mediated by cationic liposomes, particle gun technology, calcium phosphate precipitation, shear-driven cell permeation, fusion to a cell-penetrating peptide followed by cell contact, microinjection, and nanoparticle-mediated delivery. In some embodiments, the nuclease system may be introduced into the cell via viral infection. In some embodiments, the nuclease system may be introduced into the cell via bacteriophage infection. Liposomes may include those formed from 1,2-dioleyloxy-N,N-dimethylaminopropane (DODMA) liposomes, DiLa2 liposomes from Marina Biotech (Bothell, WA), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and liposomes which may deliver small molecule drugs such as, but not limited to, DOXIL® (from Janssen Biotech, Inc. (Horsham, PA)).

In some embodiments, the methods and compositions provided herein may comprise introducing a vector system described herein into a cell. In some embodiments, the vector system encodes the nuclease system in whole or in part. In some embodiments, the vector system comprises one, two, three, or more vectors. In some embodiments, the introduction of the vector system into the cell may result in a stable cell line having the edited nucleic acid molecule while the vectors are lost, e.g., targeted for self-destruction. In some embodiments, the cell is a eukaryotic cell. Non-limiting examples of eukaryotic cells include yeast cells, plant cells, insect cells, cells from an invertebrate animal, cells from a vertebrate animal, mammalian cells, rodent cells, mouse cells, rat cells, and human cells. In some embodiments, the eukaryotic cell may be a mammalian cell. In some embodiments, the eukaryotic cell may be a rodent cell. In some embodiments, the eukaryotic cell may be a human cell. Similarly, the target sequence may be from any such cells or in any such cells.

In some embodiments, the polynucleotides or oligonucleotides provided herein, for example guide RNAs or mRNAs, may be formulated in a lipid vesicle which may have crosslinks between functionalized lipid bilayers, or lipid-polycation complex. The liposome formulation may be influenced by, but not limited to, the selection of the cationic lipid component, the degree of cationic lipid saturation, the nature of the PEGylation, ratio of all components and biophysical parameters such as size, or poly cationic composition. In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo. The lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), respiratory (e.g., nasal, pharyngeal, tracheal and bronchial membranes), genital (e.g., vaginal, cervical and urethral membranes). The formulations may use nanoparticles larger than 10-200 nm which are preferred for higher drug encapsulation efficiency and the ability to provide the sustained delivery of a wide array of drugs which had been thought to be too large to rapidly diffuse through mucosal barriers. The dynamic transport of nanoparticles may be measured using fluorescence recovery after photobleaching (FRAP) and high resolution multiple particle tracking (MPT). The formulations can be made for controlled release and/or targeted delivery. The lipid nanoparticle engineered to penetrate mucus may include surface altering agents such as, but not limited to, mRNA, anionic protein (e.g., bovine serum albumin), surfactants (e.g., cationic surfactants such as for example dimethyldioctadecylammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4, dornase alfa, neltenexine, erdosteine) and various DNases including rhDNase. The surface altering agent may be embedded or enmeshed in the particle's surface or disposed or dispersed (e.g., by coating, adsorption, covalent linkage, or other process) on the surface of the lipid nanoparticle.

In a further embodiment, guide RNA of the present disclosure and the CRISPR system may be formulated as a lipoplex, such as, without limitation, the ATUPLEX™ system, the DACC system, the DBTC system and other siRNA-lipoplex technology. The liposomes, lipoplexes, or lipid nanoparticles may be used to improve the efficacy of the modified guide RNAs for example by increasing cell transfection, increasing the translation of encoded protein or increasing the stability. A cell penetrating peptide may be used with the pharmaceutical formulations of the present disclosure such as a cell-penetrating peptide sequence attached to polycations that facilitates delivery to the intracellular space, e.g., HIV-derived TAT peptide, penetratins, transportans, or hCT derived cell-penetrating peptides. In another embodiment, lipid nanoparticles which target specific cell types may be used. Alternatively, the lipid nanoparticle may be encapsulated into any polymer or hydrogel known in the art which may form a gel when injected into a subject. As another non-limiting example, the lipid nanoparticle may be encapsulated into a polymer matrix which may be biodegradable. In yet another embodiment, the pharmaceutical compositions may be sustained release formulations. In a further embodiment, the sustained release formulations may be for subcutaneous delivery. Sustained release formulations may include, but are not limited to, PLGA microspheres, ethylene vinyl acetate (EVAc), poloxamer, GELSITE® (Nanotherapeutics, Inc. Alachua, FL), HYLENEX® (Halozyme Therapeutics, San Diego, CA), surgical sealants such as fibrinogen polymers (Ethicon Inc. Cornelia, GA), TISSELL® (Baxter International, Inc Deerfield, IL), PEG-based sealants, and COSEAL® (Baxter International, Inc Deerfield, IL).

In some embodiments, the nucleic acids as described herein, such as a guide RNA, may be complexed with a CRISPR enzyme. In some embodiments, a part or all of the complex may be delivered via a vector system comprising one or more vectors. In some embodiments, the vector may be a DNA vector. In other embodiments, the vector may be an RNA vector. In some embodiments, the RNA vector may be an mRNA, e.g. an mRNA that encodes a nuclease such as Cas9. In some embodiments, the vector may be circular.

In other embodiments, the vector may be linear. Non-limiting exemplary vectors include plasmids, phagemids, cosmids, artificial chromosomes, minichromosomes, transposons, viral vectors, and expression vectors. In some embodiments, the nuclease is provided by an RNA vector, e.g., as mRNA, and the template is provided by a viral vector. In some embodiments, the vector may be a viral vector. In some embodiments, the viral vector may be genetically modified from its wild-type counterpart. For example, the viral vector may comprise an insertion, deletion, or substitution of one or more nucleotides to facilitate cloning or such that one or more properties of the vector is changed. Such properties may include packaging capacity, transduction efficiency, immunogenicity, genome integration, replication, transcription, and translation. In some embodiments, a portion of the viral genome may be deleted such that the virus is capable of packaging exogenous sequences having a larger size. In some embodiments, the viral vector may have an enhanced transduction efficiency. In some embodiments, the immune response induced by the virus in a host may be reduced. In some embodiments, viral genes (such as, e.g., integrase) that promote integration of the viral sequence into a host genome may be mutated such that the virus becomes non-integrating. In some embodiments, the viral vector may be replication defective. In some embodiments, the viral vector may comprise exogenous transcriptional or translational control sequences to drive expression of coding sequences on the vector. In some embodiments, the virus may be helper-dependent. For example, the virus may need one or more helper virus to supply viral components (such as, e.g., viral proteins) required to amplify and package the vectors into viral particles. In such a case, one or more helper components, including one or more vectors encoding the viral components, may be introduced into a host cell along with the vector system described herein. In other embodiments, the virus may be helper-free. For example, the virus may be capable of amplifying and packaging the vectors without any helper virus. In some embodiments, the vector system described herein may also encode the viral components required for virus amplification and packaging.

Non-limiting exemplary viral vectors include adeno-associated virus (AAV) vector, lentivirus vectors, adenovirus vectors, herpes simplex virus (HSV-1) vectors, bacteriophage T4, baculovirus vectors, and retrovirus vectors. In some embodiments, the viral vector may be an AAV vector. In other embodiments, the viral vector may a lentivirus vector. In some embodiments, the lentivirus may be non-integrating. In some embodiments, the viral vector may be an adenovirus vector. In some embodiments, the adenovirus may be a high-cloning capacity or "gutless" adenovirus, where all coding viral regions apart from the 5' and 3' inverted terminal repeats (ITRs) and the packaging signal (Ψ) are deleted from the virus to increase its packaging capacity. In yet other embodiments, the viral vector may be an HSV-1 vector. In some embodiments, the HSV-1-based vector is helper dependent, and in other embodiments it is helper independent. For example, an amplicon vector that retains only the packaging sequence requires a helper virus with structural components for packaging, while a 30 kb-deleted HSV-1 vector that removes non-essential viral functions does not require helper virus. In additional embodiments, the viral vector may be bacteriophage T4. In some embodiments, the bacteriophage T4 may be able to package any linear or circular DNA or RNA molecules when the head of the virus is emptied. In further embodiments, the viral vector may be a baculovirus vector. In yet further embodiments, the viral vector may be a retrovirus vector. In embodiments using AAV or lentiviral vectors, which have smaller cloning capacity, it may be necessary to use more than one vector to deliver all the components of a vector system as disclosed herein. For example, one AAV vector may contain sequences encoding a Cas9 protein, while a second AAV vector may contain one or more guide sequences and one or more copies of template.

In certain embodiments, a viral vector may be modified to target a particular tissue or cell type. For example, viral surface proteins may be altered to decrease or eliminate viral protein binding to its natural cell surface receptor(s). In some embodiments, the vector may be modified for liver specific delivery. The surface proteins may also be engineered to interact with a receptor specific to a desired cell type. Viral vectors may have altered host tropism, including limited or redirected tropism. In some embodiments, the viral vector may be engineered to express or display a first binding moiety. The first binding moiety may be fused to a viral surface protein or glycoprotein, conjugated to a virus, chemically crosslinked to a virion, bound to a virus envelope, or joined to a viral vector by any other suitable method. The first binding moiety is capable of binding to a second binding moiety, which may be used to direct the virus to a desired cell type. In some embodiments, the first binding moiety is avidin, streptavidin, neutravidin, captavidin, or another biotin-binding moiety, and the second binding moiety is biotin or an analog thereof. A biotinylated targeting agent may then be bound to the avidin on the viral vector and used to direct the virus to a desired cell type. For example, a T4 vector may be engineered to display a biotin-binding moiety on one or more of its surface proteins. The cell-specificity of such a T4 vector may then be altered by binding a biotinylated antibody or ligand directed to a cell of choice. In alternate embodiments, the first and second binding moieties are hapten and an anti-hapten binding protein; digoxigenin and an anti-digoxigenin binding protein; fluorescein and an anti-fluorescein binding protein; or any other suitable first and second binding moieties that are binding partners.

In some embodiments, the vector may be capable of driving expression of one or more coding sequences in a cell. In some embodiments, the cell may be a prokaryotic cell, such as, e.g., a bacterial cell. In some embodiments, the cell may be a eukaryotic cell, such as, e.g., a yeast, plant, insect, or mammalian cell. In some embodiments, the eukaryotic cell may be a mammalian cell. In some embodiments, the eukaryotic cell may be a rodent cell. In some embodiments, the eukaryotic cell may be a human cell. Suitable promoters to drive expression in different types of cells are known in the art. In some embodiments, the promoter may be wild-type. In other embodiments, the promoter may be modified for more efficient or efficacious expression. In yet other embodiments, the promoter may be truncated yet retain its function. For example, the promoter may have a normal size or a reduced size that is suitable for proper packaging of the vector into a virus.

In some embodiments, the vector may comprise a nucleotide sequence encoding the nuclease described herein. In some embodiments, the vector system may comprise one copy of the nucleotide sequence encoding the nuclease. In other embodiments, the vector system may comprise more than one copy of the nucleotide sequence encoding the nuclease. In some embodiments, the nucleotide sequence encoding the nuclease may be operably linked to at least one transcriptional or translational control sequence. In some embodiments, the nucleotide sequence encoding the nuclease may be operably linked to at least one promoter. In some embodiments, the nucleotide sequence encoding the nuclease may be operably linked to at least one transcriptional or translational control sequence.

In some embodiments, the promoter may be constitutive, inducible, or tissue-specific. In some embodiments, the promoter may be a constitutive promoter. Non-limiting exemplary constitutive promoters include cytomegalovirus immediate early promoter (CMV), simian virus (SV40) promoter, adenovirus major late (MLP) promoter, Rous sarcoma virus (RSV) promoter, mouse mammary tumor virus (MMTV) promoter, phosphoglycerate kinase (PGK) promoter, elongation factor-alpha (EF1α) promoter, ubiquitin promoters, actin promoters, tubulin promoters, immunoglobulin promoters, a functional fragment thereof, or a combination of any of the foregoing. In some embodiments, the promoter may be a CMV promoter. In some embodiments, the promoter may be a truncated CMV promoter. In other embodiments, the promoter may be an EF1α promoter. In some embodiments, the promoter may be an inducible promoter. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech). In some embodiments, the promoter may be a tissue-specific promoter. In some embodiments, the tissue-specific promoter is exclusively or predominantly expressed in liver tissue. Non-limiting exemplary tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, Nphs1 promoter, OG-2 promoter, SP-B promoter, SYN1 promoter, and WASP promoter.

In some embodiments, the vector may encode a Cas protein or a portion of a Cas protein, such as a Cas9 protein or Cpf1 protein. The vector system may further comprise a vector comprising a nucleotide sequence encoding the guide RNA described herein. In some embodiments, the vector system may comprise one copy of the guide RNA. In other embodiments, the vector system may comprise more than one copy of the guide RNA. In embodiments with more than one guide RNA, the guide RNAs may be non-identical such that they target different target sequences, or have other different properties, such as activity or stability within the Cas9 RNP complex. In some embodiments, the nucleotide sequence encoding the guide RNA may be operably linked to at least one transcriptional or translational control sequence. In some embodiments, the nucleotide sequence encoding the guide RNA may be operably linked to at least one promoter. In some embodiments, the promoter may be recognized by RNA polymerase III (Pol III). Non-limiting examples of Pol III promoters include U6, H1 and tRNA promoters. In some embodiments, the nucleotide sequence encoding the guide RNA may be operably linked to a mouse or human U6 promoter. In other embodiments, the nucleotide sequence encoding the guide RNA may be operably linked to a mouse or human H1 promoter. In some embodiments, the nucleotide sequence encoding the guide RNA may be operably linked to a mouse or human tRNA promoter. In embodiments with more than one guide RNA, the promoters used to drive expression may be the same or different. In some embodiments, the nucleotide encoding the crRNA of the guide RNA and the nucleotide encoding the tracr RNA of the guide RNA may be provided on the same vector. In some embodiments, the nucleotide encoding the crRNA and the nucleotide encoding the tracr RNA may be driven by the same promoter. In some embodiments, the crRNA and tracr RNA may be transcribed into a single transcript. For example, the crRNA and tracr RNA may be processed from the single transcript to form a double-molecule guide RNA. Alternatively, the crRNA and tracr RNA may be transcribed into a single-molecule guide RNA. In other embodiments, the crRNA and the tracr RNA may be driven by their corresponding promoters on the same vector. In yet other embodiments, the crRNA and the tracr RNA may be encoded by different vectors.

In some embodiments, the vector system may further comprise a vector comprising the template described herein. In some embodiments, the vector system may comprise one copy of the template. In other embodiments, the vector system may comprise more than one copy of the template. In some embodiments, the vector system may comprise 2, 3, 4, 5, 6, 7, 8, 9, 10, or more copies of the template. In some embodiments, the vector system may comprise 4, 5, 6, 7, 8, or more copies of the template. In some embodiments, the vector system may comprise 5, 6, 7, or more copies of the template. In some embodiments, the vector system may comprise 6 copies of the template. The multiple copies of the template may be located on the same or different vectors. The multiple copies of the template may also be adjacent to one another, or separated by other nucleotide sequences or vector elements. In other embodiments, two or more templates may be provided such that homologous recombination may occur at two or more target sites. For example, different templates may be provided to repair a single gene in a cell, or two different genes in a cell. In some embodiments, the different templates may be provided in independent copy numbers.

A vector system may comprise 1-3 vectors. In some embodiments, the vector system may comprise one single vector. In other embodiments, the vector system may comprise two vectors. In additional embodiments, the vector system may comprise three vectors.

In some embodiments, the nucleotide sequence encoding the nuclease and the template may be located on the same or separate vectors. In some embodiments, the nucleotide sequence encoding the nuclease and the template may be located on the same vector. In some embodiments, the nucleotide sequence encoding the nuclease and the template may be located on separate vectors. The sequences may be oriented in the same or different directions and in any order on the vector.

In some embodiments, the nucleotide sequence encoding a Cas9 protein and a template may be located on the same or separate vectors. In some embodiments, all of the sequences may be located on the same vector. In some embodiments, two or more sequences may be located on the same vector. The sequences may be oriented in the same or different directions and in any order on the vector. In some embodiments, the nucleotide sequence encoding the Cas9 protein and the nucleotide sequence encoding the guide RNA may be located on the same vector. In some embodiments, the nucleotide sequence encoding the Cas9 protein and the template may be located on the same vector. In a particular embodiment, the vector system may comprise a first vector comprising the nucleotide sequence encoding the Cas9 protein, and a second vector comprising the nucleotide sequence encoding the template or multiple copies of the template.

In some embodiments, the template may be released from the vector on which it is located by the nuclease system encoded by the vector system. In some embodiments, the template may be released from the vector by a Cas9 protein provided from an mRNA. The template may comprise at least one target sequence that is recognized by the guide RNA. In some embodiments, the template may be flanked by a target sequence at the 5' and 3' ends of the template. Upon expression of Cas9 protein and delivery of the guide RNA, the guide RNA may hybridize with and the Cas9 protein may cleave the target sequence at both ends of the template such that the template is released from the vector. In additional embodiments, the template may be released from the vector by a nuclease encoded by the vector system by having a target sequence recognized by the nuclease at the 5' and 3' ends of the template. The target sequences at either end of the template may be oriented such that the PAM sequence is closer to the template. In such an orientation, fewer non-template nucleic acids remain on the ends of the template after release from the vector. In some embodiments, the target sequences flanking the template may be the same. In some embodiments, the target sequences flanking the template may be the same as the target sequence found at the cleavage site in which the template is incorporated, e.g., by HR, HDR, or non-homologous end joining. In other embodiments, the target sequences flanking the template may be different. For example, the target sequence at the 5' end of the template may be recognized by one guide RNA or nuclease, and the target sequence at the 3' end of the template may be recognized by another guide RNA or nuclease.

In some embodiments, the vector encoding the nuclease system may comprise at least one target sequence within the vector, to create a self-destroying (or "self-cleaving" or "self-inactivating") vector system to control the amount of the nuclease system to be expressed. In some embodiments, the self-destroying vector system results in a reduction in the amount of nuclease activity. In further embodiments, the self-destroying vector system results in a reduction in the amount of vector nucleic acid. In embodiments in which the system comprises Cas9, it also comprises guide RNA(s) that recognize the target sequence. In this way, the residence time and/or the level of activity of the nuclease system may be temporally controlled to avoid adverse effects associated with overexpression of the nuclease system. Such adverse effects may include, e.g., an off-target effect by the nuclease. In some embodiments, one or more target sequences may be located at any place on the vector such that, upon expression of the nuclease, the nuclease recognizes and cleaves the target sequence in the vector that contains the nuclease-encoding sequence. The one or more target sequences of the self-destroying vector may be the same. Optionally, the self-destroying vector may comprise multiple target sequences. In some embodiments, the cleavage at a target sequence may reduce the expression of at least one component of the nuclease system, such as, for example, Cas9. In some embodiments, the cleavage may reduce the expression of the nuclease transcript. For example, a target sequence may be located within the nucleotide sequence encoding the nuclease such that the cleavage results in the disruption of the coding region. In other embodiments, a target sequence may be located within a non-coding region on the vector encoding the nuclease. In some embodiments, a target sequence may be located within the promoter that drives the expression of the nuclease such that the cleavage results in the disruption of the promoter sequence. For example, the vector may contain a target sequence (and its corresponding guide RNA) that targets a Cas9 sequence. In certain embodiments, a target sequence may be located between the promoter and the nucleotide sequence encoding the nuclease such that the cleavage results in the separation of the coding sequence from its promoter. In certain embodiments, a target sequence outside the nuclease coding sequence and a target sequence within the nuclease coding sequence are included.

In some embodiments, the vector encoding a Cas9 protein may comprise at least one target sequence that is recognized by a guide RNA. In some embodiments, the target sequence may be located at any place on the vector such that, upon expression of the Cas9 protein and the guide RNA, the guide RNA hybridizes with and the Cas9 protein cleaves the target sequence in the vector encoding the Cas9 protein. In some embodiments, the cleavage at the target sequence may reduce the expression of the Cas9 protein transcript. For example, the target sequence may be located within the nucleotide sequence encoding the Cas9 protein such that the cleavage results in the disruption of the coding region. In other embodiments, the target sequence may be located within a non-coding region on the vector encoding the Cas9 protein. In some embodiments, the target sequence may be located within the promoter that drives the expression of the Cas9 protein such that the cleavage results in the disruption of the promoter sequence. In some embodiments, the target sequence may be located within the nucleotide sequence encoding the Cas9 protein such that the cleavage results in the disruption of the coding sequence. In other embodiments, the target sequence may be located between the promoter and the nucleotide sequence encoding the Cas9 protein such that the cleavage results in the separation of the coding sequence from its promoter.

The target sequences for release of the template, for vector self-destruction, and for targeting by the nuclease system in a cell may be the same or different. For example, the target sequence at the 3' end of the template may be present within the promoter driving the expression of the nuclease (e.g., the Cas9 protein) such that the release of the template simultaneously results in the disruption of the expression of the nuclease (e.g., the Cas9 protein). In some embodiments, both target sequences flanking the template, the target sequences for disrupting the expression of the nuclease (e.g., the Cas9 protein), and the target sequence in the target nucleic acid molecule in a cell may be the same sequence that is recognized by a single guide RNA or nuclease. Thus, in some embodiments, the vector system may comprise only one type of target sequence, and the nuclease system may comprise only one guide RNA. In other embodiments, these target sequences may comprise different sequences that are recognized by different guide RNAs.

In some embodiments, the vector system may comprise inducible promoters to start expression only after it is delivered to a target cell. Non-limiting exemplary inducible promoters include those inducible by heat shock, light, chemicals, peptides, metals, steroids, antibiotics, or alcohol. In some embodiments, the inducible promoter may be one that has a low basal (non-induced) expression level, such as, e.g., the Tet-On® promoter (Clontech).

In additional embodiments, the vector system may comprise tissue-specific promoters to start expression only after it is delivered into a specific tissue. Non-limiting exemplary tissue-specific promoters include albumin promoter, α-1 antitrypsin promoter, hemopexin promoter, B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, Nphs1 promoter, OG-2 promoter, SP-B promoter, SYN1 promoter, and WASP promoter. In particular embodiments, the tissue specific promoter is an albumin promoter, a α-1 antitrypsin promoter, a hepatitis B virus core promoter, or a hemopexin gene promoter. Methods of examining liver specific promoters are described in Kramer et al., Molecular Therapy 7(3): 375-385 (2003), which is incorporated herein in its entirety by reference.

In some embodiments of the present disclosure, the activity of the nuclease system may be temporally regulated by adjusting the residence time, the amount, and/or the activity of the expressed components of the nuclease system. For example, as described herein, the nuclease may be fused with a protein domain that is capable of modifying the intracellular half-life of the nuclease. In certain embodiments involving two or more vectors (e.g., a vector system in which the components described herein are encoded on two or more separate vectors), the activity of the nuclease system may be temporally regulated by controlling the timing in which the vectors are delivered. For example, in some embodiments a vector encoding the nuclease system may deliver the nuclease prior to the vector encoding the template. In other embodiments, the vector encoding the template may deliver the template prior to the vector encoding the nuclease system. In some embodiments, the vectors encoding the nuclease system and template are delivered simultaneously. In certain embodiments, the simultaneously delivered vectors temporally deliver, e.g., the nuclease, template, and/or guide RNA components. In further embodiments, the RNA (such as, e.g., the nuclease transcript) transcribed from the coding sequence on the vectors may further comprise at least one element that is capable of modifying the intracellular half-life of the RNA and/or modulating translational control. In some embodiments, the half-life of the RNA may be increased. In some embodiments, the half-life of the RNA may be decreased. In some embodiments, the element may be capable of increasing the stability of the RNA. In some embodiments, the element may be capable of decreasing the stability of the RNA. In some embodiments, the element may be within the 3' UTR of the RNA. In some embodiments, the element may include a polyadenylation signal (PA). In some embodiments, the element may include a cap, e.g., an upstream mRNA end. In some embodiments, the PA may be added to the 3' UTR of the RNA. In some embodiments, the RNA may comprise no PA such that it is subject to quicker degradation in the cell after transcription. In some embodiments, the element may include at least one AU-rich element (ARE). The AREs may be bound by ARE binding proteins (ARE-BPs) in a manner that is dependent upon tissue type, cell type, timing, cellular localization, and environment. In some embodiments the destabilizing element may promote RNA decay, affect RNA stability, or activate translation. In some embodiments, the ARE may comprise 50 to 150 nucleotides in length. In some embodiments, the ARE may comprise at least one copy of the sequence AUUUA. In some embodiments, at least one ARE may be added to the 3' UTR of the RNA. In some embodiments, the element may be a Woodchuck Hepatitis Virus (WHP) Posttranscriptional Regulatory Element (WPRE), which creates a tertiary structure to enhance expression from the transcript. In further embodiments, the element is a modified and/or truncated WPRE sequence that is capable of enhancing expression from the transcript, as described, for example in Zufferey et al., J Virol, 73(4): 2886-92 (1999) and Flajolet et al., J Virol, 72(7): 6175-80 (1998). In some embodiments, the WPRE or equivalent may be added to the 3' UTR of the RNA. In some embodiments, the element may be selected from other RNA sequence motifs that are enriched in either fast- or slow-decaying transcripts.

Embodiments of the disclosure also encompass treating a patient with the vector system described herein. In some embodiments, the method may comprise administering the vector system described herein to the patient. The method may be used as a single therapy or in combination with other therapies available in the art. In some embodiments, the patient may have a mutation (such as, e.g., insertion, deletion, substitution, chromosome translocation) in a disease-associated gene. In some embodiments, administration of the vector system may result in a mutation comprising an insertion, deletion, or substitution of one or more nucleotides of the disease-associated gene in the patient. Certain embodiments may include methods of repairing the patient's mutation in the disease-associated gene. In some embodiments, the mutation may result in one or more amino acid changes in a protein expressed from the disease-associated gene. In some embodiments, the mutation may result in one or more nucleotide changes in an RNA expressed from the disease-associated gene. In some embodiments, the mutation may alter the expression level of the disease-associated gene. In some embodiments, the mutation may result in increased or decreased expression of the gene. In some embodiments, the mutation may result in gene knockdown in the patient. In some embodiments, the administration of the vector system may result in the correction of the patient's mutation in the disease-associated gene. In some embodiments, the administration of the vector system may result in gene knockout in the patient. In some embodiments, the administration of the vector system may result in replacement of an exon sequence, an intron sequence, a transcriptional control sequence, a translational control sequence, or a non-coding sequence of the disease-associated gene.

In some embodiments, the administration of the vector system may result in integration of an exogenous sequence of the template into the patient's genomic DNA. In some embodiments, the exogenous sequence may comprise a protein or RNA coding sequence operably linked to an exogenous promoter sequence such that, upon integration of the exogenous sequence into the patient's genomic DNA, the patient is capable of expressing the protein or RNA encoded by the integrated sequence. The exogenous sequence may provide a supplemental or replacement protein coding or non-coding sequence. For example, the administration of the vector system may result in the replacement of the mutant portion of the disease-associated gene in the patient. In some embodiments, the mutant portion may include an exon of the disease-associated gene. In other embodiments, the integration of the exogenous sequence may result in the expression of the integrated sequence from an endogenous promoter sequence present on the patient's genomic DNA. For example, the administration of the vector system may result in supply of a functional gene product of the disease-associated gene to rectify the patient's mutation. In some embodiments, the administration of the vector system may result in integration of a cDNA sequence encoding a protein or a portion of the protein. In yet other embodiments, the administration of the vector system may result in integration of an exon sequence, an intron sequence, a transcriptional control sequence, a translational control sequence, or a non-coding sequence into the patient's genomic DNA. In some embodiments, the administration of the vector system may result in gene knockin in the patient.

Administration and Method of Use

Provided herein are methods and compositions for editing a target nucleic acid in a cell. Further provided herein are pharmaceutical compositions and methods for modifying the function and activity of a target gene in a cell of a subject. The genome editing compositions described herein may be administered to a subject in need thereof, in a therapeutically effective amount, to treat conditions related to high circulating cholesterol levels and/or coronary disease, e.g. hypercholesterolemia, elevated total cholesterol levels, elevated low-density lipoprotein (LDL) levels, elevated LDL-cholesterol levels, reduced high-density lipoprotein levels, liver steatosis, coronary heart disease, ischemia, stroke, peripheral vascular disease, thrombosis, type 2 diabetes, high elevated blood pressure, atherosclerosis, obesity, Alzheimer's disease, [CYS]neurodegeneration, and combinations thereof can be administered to the subject in a variety of ways, including parenterally, intravenously, intradermally, intramuscularly, colonically, rectally or intraperitoneally. In some embodiments, the pharmaceutical composition may be co-administered with pharmaceutically acceptable salt by intraperitoneal injection, intramuscular injection, subcutaneous injection, or intravenous injection of the subject. In some embodiments, the pharmaceutical composition may be directly injected to a specific tissue, such as the liver tissue. In some embodiments, the pharmaceutical compositions can be administered parenterally, intravenously, intramuscularly or orally. The oral formulations can be further coated or treated to prevent or reduce dissolution in stomach. The compositions of the present disclosure can be administered to a subject using any suitable methods known in the art. Suitable formulations for use in the present disclosure and methods of delivery are generally well known in the art. For example, the composition of the present disclosure can be formulated as pharmaceutical compositions with a pharmaceutically acceptable diluent, carrier or excipient. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

Pharmaceutical formulations described herein can be administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the pharmaceutical formulation is in the form of a tablet. In other embodiments, pharmaceutical formulations containing an composition or inhibitory agent described herein are in the form of a capsule. In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a composition or inhibitory agent described herein can be formulated for use as an aerosol, a mist or a powder. For buccal or sublingual administration, the compositions may take the form of tablets, lozenges, or gels formulated in a conventional manner. In some embodiments, a composition or inhibitory agent described herein can be prepared as transdermal dosage forms. In some embodiments, a composition or inhibitory agent described herein can be formulated into a pharmaceutical composition suitable for intramuscular, subcutaneous, or intravenous injection. In some embodiments, a composition or inhibitory agent described herein can be administered topically and can be formulated into a variety of topically administrable compositions, such as solutions, suspensions, lotions, gels, pastes, medicated sticks, balms, creams or ointments. In some embodiments, a composition or inhibitory agent described herein can be formulated in rectal compositions such as enemas, rectal gels, rectal foams, rectal aerosols, suppositories, jelly suppositories, or retention enemas.

In one aspect, disclosed herein is a method of treating a disease or condition in a mammal, the method comprising administering to a mammal a therapeutically effective amount of a herein described pharmaceutical composition. In one aspect, disclosed herein are methods for treating a disease or condition, including raising an immune response to an immunogen, in a subject. In one embodiment, the disease or condition is treatable by administering the payload. In some embodiments, the disease or condition is characterized by missing or aberrant protein or polypeptide activity. For example, an LNP composition comprising an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. A payload included in an LNP composition may also be capable of altering the rate of transcription of a given species, thereby affecting gene expression.

Diseases and/or conditions characterized by dysfunctional or aberrant protein or polypeptide activity can include, but are not limited to, rare diseases, infectious diseases (as both vaccines and therapeutics), cancer and proliferative diseases, genetic diseases (e.g., cystic fibrosis), autoimmune diseases, diabetes, neurodegenerative diseases, cardio- and reno-vascular diseases, and metabolic diseases. Multiple diseases and/or conditions may be characterized by missing (or substantially diminished such that proper protein function does not occur) protein activity. Such proteins may not be present, or they may be essentially non-functional. A specific example of a dysfunctional protein is the missense mutation variants of the cystic fibrosis transmembrane conductance regulator (CFTR) gene. In some embodiments, the present disclosure provides a method for treating such diseases and/or conditions in a subject by administering an LNP composition or pharmaceutical composition comprising an RNA payload, wherein the RNA can be an mRNA encoding a polypeptide that antagonizes or otherwise overcomes an aberrant protein activity present in the cell of the subject.

Dosage

Appropriate dosage or effective amounts for administration vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. Factors involved in dosage determination are known to those of ordinary skill in the art without additional experimentation other than routine test. It is generally preferred that a maximum dose of the individual components or combinations thereof be used, that is, the highest safe dose according to sound medical judgment. Empirical considerations, such as the half-life, generally will contribute to the determination of the dosage. For example, therapeutic agents that are compatible with the human immune system, such as polypeptides comprising regions from humanized antibodies or fully human antibodies, may be used to prolong half-life of the polypeptide and to prevent the polypeptide being attacked by the host's immune system.

Frequency of administration may be determined and adjusted over the course of therapy, and is generally, but not necessarily, based on treatment and/or suppression and/or amelioration and/or delay of a disease. Alternatively, sustained continuous release formulations of a polypeptide or a polynucleotide may be appropriate. Various formulations and devices for achieving sustained release are known in the art. In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays.

The dosing regimen can vary over time. In some embodiments, for an adult subject of normal weight, doses ranging from about 0.01 to 1000 mg/kg may be administered. In some embodiments, the dose is between 1 to 200 mg. In some embodiments, the doses may range from about 0.01 to 0.05 mg/kg, between about 0.01 to 0.1 mg/kg, between about 0.01 to 1 mg/kg, between about 0.01 to 10 mg/kg, between about 0.01 to 100 mg/kg, between 0.01 to 500 mg/kg, between about 0.1 to 1 mg/kg, between about 0.1 to 5 mg/kg, between about 0.1 to 10 mg/kg, between about 0.1 to 100 mg/kg, between about 0.1 to 500 mg/kg, between about 0.1 to 1000 mg/kg, between about 1 to 5 mg/kg, between about 1 to 10 mg/kg, between about 1 to 100 mg/kg, between about 1 to 500 mg/kg, between about 1 to 1000 mg/kg, between about 10 to 100 mg/kg, between about 10 to 500 mg/kg, between about 10 to 1000 mg/kg, or between about 100 to 1000 mg/kg. The particular dosage regimen, i.e., dose, timing and repetition, will depend on the particular subject and that subject's medical history, as well as the properties of the polypeptide or the polynucleotide (such as the half-life of the polypeptide or the polynucleotide, and other considerations well known in the art).

As will be apparent to those skilled in the art, the appropriate dosage of a therapeutic agent as described herein will depend on the specific agent (or compositions thereof) employed, the formulation and route of administration, the type and severity of the disease, whether the polypeptide or the polynucleotide is administered for preventive or therapeutic purposes, previous therapy, the subject's clinical history and response to the antagonist, and the discretion of the attending physician. Typically the clinician will administer a polypeptide until a dosage is reached that achieves the desired result.

Administration of one or more therapeutic compositions, e.g. polypeptides, polynucleotides, or RNPs, can be continuous or intermittent, depending, for example, upon the recipient's physiological condition, whether the purpose of the administration is therapeutic or prophylactic, and other factors known to skilled practitioners. The administration of a polypeptide may be essentially continuous over a preselected period of time or may be in a series of spaced dose, e.g., either before, during, or after developing a disease.

Biological Samples

A sample, e.g., a biological sample can be taken from a subject. A biological sample can comprise a plurality of biological samples. The plurality of biological samples can contain two or more biological samples; for examples, about 2-1000, 2-500, 2-250, 2-100, 2-75, 2-50, 2-25, 2-10, 10-1000, 10-500, 10-250, 10-100, 10-75, 10-50, 10-25, 25-1000, 25-500, 25-250, 25-100, 25-75, 25-50, 50-1000, 50-500, 50-250, 50-100, 50-75, 60-70, 100-1000, 100-500, 100-250, 250-1000, 250-500, 500-1000, 2, 3, 4, 5, 6, 7, 8, 9, 10, 11, 12, 13, 14, 15, 16, 17, 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, 1000, or more biological samples. The biological samples can be obtained from a plurality of subjects, giving a plurality of sets of a plurality of samples. The biological samples can be obtained from about 2 to about 1000 subjects, or more; for example, about 2-1000, 2-500, 2-250, 2-100, 2-50, 2-25, 2-20, 2-10, 10-1000, 10-500, 10-250, 10-100, 10-50, 10-25, 10-20, 15-20, 25-1000, 25-500, 25-250, 25-100, 25-50, 50-1000, 50-500, 50-250, 50-100, 100-1000, 100-500, 100-250, 250-1000, 250-500, 500-1000, or at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 68, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, or 1000 or more subjects.

The biological samples can be obtained from human subjects. The biological samples can be obtained from human subjects at different ages. The human subject can be prenatal (e.g., a fetus), a child (e.g., a neonate, an infant, a toddler, a preadolescent), an adolescent, a pubescent, or an adult (e.g., an early adult, a middle aged adult, a senior citizen). The human subject can be between about 0 months and about 120 years old, or older. The human subject can be between about 0 and about 12 months old; for example, about 1, 2, 3, 4, 5, 6, 7, 8, 9, 10, 11, or 12 months old. The human subject can be between about 0 and 12 years old; for example, between about 0 and 30 days old; between about 1 month and 12 months old; between about 1 year and 3 years old; between about 4 years and 5 years old; between about 4 years and 12 years old; about 1, 2, 3, 4, 5, 6, 7, 8, 9, 10, 11, or 12 years old. The human subject can be between about 13 years and 19 years old; for example, about 13, 14, 15, 16, 17, 18, or 19 years old. The human subject can be between about 20 and about 39 year old; for example, about 20, 21, 22, 23, 24, 25, 26, 27, 28, 29, 30, 31, 32, 33, 34, 35, 36, 37, 38, or 39 years old. The human subject can be between about 40 to about 59 years old; for example, about 40, 41, 42, 43, 44, 45, 46, 47, 48, 49, 50, 51, 52, 53, 54, 55, 56, 57, 58, or 59 years old. The human subject can be greater than 59 years old; for example, about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 years old. The human subjects can include living subjects or deceased subjects. The human subjects can include male subjects and/or female subjects.

Biological samples can be obtained from any suitable source that allows determination of expression levels of genes, e.g., from cells, tissues, bodily fluids or secretions, or a gene expression product derived therefrom (e.g., nucleic acids, such as DNA or RNA; polypeptides, such as protein or protein fragments). The nature of the biological sample can depend upon the nature of the subject. If a biological sample is from a subject that is a unicellular organism or a multicellular organism with undifferentiated tissue, the biological sample can comprise cells, such as a sample of a cell culture, an excision of the organism, or the entire organism. If a biological sample is from a multicellular organism, the biological sample can be a tissue sample, a fluid sample, or a secretion.

The biological samples can be obtained from different tissues. The term tissue is meant to include ensembles of cells that are of a common developmental origin and have similar or identical function. The term tissue is also meant to encompass organs, which can be a functional grouping and organization of cells that can have different origins. The biological sample can be obtained from any tissue.

The biological samples can be obtained from different tissue samples from one or more humans or non-human animals. Suitable tissues can include connective tissues, muscle tissues, nervous tissues, epithelial tissues or a portion or combination thereof. Suitable tissues can also include all or a portion of a lung, a heart, a blood vessel (e.g., artery, vein, capillary), a salivary gland, a esophagus, a stomach, a liver, a gallbladder, a pancreas, a colon, a rectum, an anus, a hypothalamus, a pituitary gland, a pineal gland, a thyroid, a parathyroid, an adrenal gland, a kidney, a ureter, a bladder, a urethra, a lymph node, a tonsil, an adenoid, a thymus, a spleen, skin, muscle, a brain, a spinal cord, a nerve, an ovary, a fallopian tube, a uterus, vaginal tissue, a mammary gland, a testicle, a vas deferens, a seminal vesicle, a prostate, penile tissue, a pharynx, a larynx, a trachea, a bronchi, a diaphragm, bone marrow, a hair follicle, or a combination thereof. A biological sample from a human or non-human animal can also include a bodily fluid, secretion, or excretion; for example, a biological sample can be a sample of aqueous humour, vitreous humour, bile, blood, blood serum, breast milk, cerebrospinal fluid, endolymph, perilymph, female ejaculate, amniotic fluid, gastric juice, menses, mucus, peritoneal fluid, pleural fluid, saliva, sebum, semen, sweat, tears, vaginal secretion, vomit, urine, feces, or a combination thereof. The biological sample can be from healthy tissue, diseased tissue, tissue suspected of being diseased, or a combination thereof.

In some embodiments, the biological sample is a fluid sample, for example a sample of blood, serum, sputum, urine, semen, or other biological fluid. In certain embodiments the sample is a blood sample. In some embodiments the biological sample is a tissue sample, such as a tissue sample taken to determine the presence or absence of disease in the tissue. In certain embodiments the sample is a sample of thyroid tissue.

The biological samples can be obtained from subjects in different stages of disease progression or different conditions. Different stages of disease progression or different conditions can include healthy, at the onset of primary symptom, at the onset of secondary symptom, at the onset of tertiary symptom, during the course of primary symptom, during the course of secondary symptom, during the course of tertiary symptom, at the end of the primary symptom, at the end of the secondary symptom, at the end of tertiary symptom, after the end of the primary symptom, after the end of the secondary symptom, after the end of the tertiary symptom, or a combination thereof. Different stages of disease progression can be a period of time after being diagnosed or suspected to have a disease; for example, at least about, or at least, 1, 2, 3, 4, 5, 6, 7, 8, 9, 10, 11, 12, 13, 14, 15, 16, 17, 18, 19, 20, 21, 22, 23 or 24 hours; 1, 2, 3, 4, 5, 6, 7, 8, 9, 10, 11, 12, 13, 14, 15, 16, 17, 18, 19, 20, 21, 22, 23, 24, 25, 26, 27 or 28 days; 1, 2, 3, 4, 5, 6, 7, 8, 9, 10, 11, 12, 13, 14, 15, 16, 17, 18, 19 or 20 weeks; 1, 2, 3, 4, 5, 6, 7, 8, 9, 10, 11 or 12 months; 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 years after being diagnosed or suspected to have a disease. Different stages of disease progression or different conditions can include before, during or after an action or state; for example, treatment with drugs, treatment with a surgery, treatment with a procedure, performance of a standard of care procedure, resting, sleeping, eating, fasting, walking, running, performing a cognitive task, sexual activity, thinking, jumping, urinating, relaxing, being immobilized, being emotionally traumatized, being shock, and the like.

The methods of the present disclosure provide for analysis of a biological sample from a subject or a set of subjects. The subject(s) may be, e.g., any animal (e.g., a mammal), including but not limited to humans, non-human primates, rodents, dogs, cats, pigs, fish, and the like. The present methods and compositions can apply to biological samples from humans, as described herein.

A biological sample can be obtained by methods known in the art such as the biopsy methods provided herein, swabbing, scraping, phlebotomy, or any other suitable method. The biological sample can be obtained, stored, or transported using components of a kit of the present disclosure. In some cases, multiple biological samples, such as multiple thyroid samples, can be obtained for analysis, characterization, or diagnosis according to the methods of the present disclosure. In some cases, multiple biological samples, such as one or more samples from one tissue type (e.g., thyroid) and one or more samples from another tissue type (e.g., buccal) can be obtained for diagnosis or characterization by the methods of the present disclosure. In some cases, multiple samples, such as one or more samples from one tissue type (e.g., thyroid) and one or more samples from another tissue (e.g., buccal) can be obtained at the same or different times. In some cases, the samples obtained at different times are stored and/or analyzed by different methods. For example, a sample can be obtained and analyzed by cytological analysis (e.g., using routine staining). In some cases, a further sample can be obtained from a subject based on the results of a cytological analysis. The diagnosis of a disease or condition, e.g. a coronary disease can include examination of a subject by a physician, nurse or other medical professional. The examination can be part of a routine examination, or the examination can be due to a specific complaint including, but not limited to, one of the following: pain, illness, anticipation of illness, presence of a suspicious lump or mass, a disease, or a condition. The subject may or may not be aware of the disease or condition. The medical professional can obtain a biological sample for testing. In some cases the medical professional can refer the subject to a testing center or laboratory for submission of the biological sample. The methods of obtaining provided herein include methods of biopsy including fine needle aspiration, core needle biopsy, vacuum assisted biopsy, incisional biopsy, excisional biopsy, punch biopsy, shave biopsy or skin biopsy. In some cases, the methods and compositions provided herein are applied to data only from biological samples obtained by FNA. In some cases, the methods and compositions provided herein are applied to data only from biological samples obtained by FNA or surgical biopsy. In some cases, the methods and compositions provided herein are applied to data only from biological samples obtained by surgical biopsy. A biological sample can be obtained by non-invasive methods, such methods including, but not limited to: scraping of the skin or cervix, swabbing of the cheek, saliva collection, urine collection, feces collection, collection of menses, tears, or semen. The biological sample can be obtained by an invasive procedure, such procedures including, but not limited to: biopsy, alveolar or pulmonary lavage, needle aspiration, or phlebotomy. The method of biopsy can further include incisional biopsy, excisional biopsy, punch biopsy, shave biopsy, or skin biopsy. The method of needle aspiration can further include fine needle aspiration, core needle biopsy, vacuum assisted biopsy, or large core biopsy. Multiple biological samples can be obtained by the methods herein to ensure a sufficient amount of biological material. Generic methods for obtaining biological samples are also known in the art and further described in for example Ramzy, Ibrahim *Clinical Cytopathology and Aspiration Biopsy* 2001 which is herein incorporated by reference in its entirety. The biological sample can be a fine needle aspirate of a thyroid nodule or a suspected thyroid tumor. The fine needle aspirate sampling procedure can be guided by the use of an ultrasound, X-ray, or other imaging device.

In some cases, the subject can be referred to a specialist such as an oncologist, surgeon, or endocrinologist for further diagnosis. The specialist can likewise obtain a biological sample for testing or refer the individual to a testing center or laboratory for submission of the biological sample. In any case, the biological sample can be obtained by a physician, nurse, or other medical professional such as a medical technician, endocrinologist, cytologist, phlebotomist, radiologist, or a pulmonologist. The medical professional can indicate the appropriate test or assay to perform on the sample, or the molecular profiling business of the present disclosure can consult on which assays or tests are most appropriately indicated. The molecular profiling business can bill the individual or medical or insurance provider thereof for consulting work, for sample acquisition and or storage, for materials, or for all products and services rendered.

A medical professional need not be involved in the initial diagnosis or sample acquisition. An individual can alternatively obtain a sample through the use of an over the counter kit. The kit can contain a means for obtaining said sample as described herein, a means for storing the sample for inspection, and instructions for proper use of the kit. In some cases, molecular profiling services are included in the price for purchase of the kit. In other cases, the molecular profiling services are billed separately.

A biological sample suitable for use by the molecular profiling business can be any material containing tissues, cells, nucleic acids, genes, gene fragments, expression products, gene expression products, and/or gene expression product fragments of an individual to be tested. Methods for determining sample suitability and/or adequacy are provided. The biological sample can include, but is not limited to, tissue, cells, and/or biological material from cells or derived from cells of an individual. The sample can be a heterogeneous or homogeneous population of cells or tissues. The biological sample can be obtained using any method known to the art that can provide a sample suitable for the analytical methods described herein.

Obtaining a biological sample can be aided by the use of a kit. A kit can be provided containing materials for obtaining, storing, and/or shipping biological samples. The kit can contain, for example, materials and/or instruments for the collection of the biological sample (e.g., sterile swabs, sterile cotton, disinfectant, needles, syringes, scalpels, anesthetic swabs, knives, curette blade, liquid nitrogen, etc.). The kit can contain, for example, materials and/or instruments for the storage and/or preservation of biological samples (e.g., containers; materials for temperature control such as ice, ice packs, cold packs, dry ice, liquid nitrogen; chemical preservatives or buffers such as formaldehyde, formalin, paraformaldehyde, glutaraldehyde, alcohols such as ethanol or methanol, acetone, acetic acid, HOPE fixative (Hepes-glutamic acid buffer-mediated organic solvent protection effect), heparin, saline, phosphate buffered saline, TAPS, bicine, Tris, tricine, TAPSO, HEPES, TES, MOPS, PIPES, cadodylate, SSC, MES, phosphate buffer; protease inhibitors such as aprotinin, bestatin, calpain inhibitor I and II, chymostatin, E-64, leupeptin, alpha-2-macroglobulin, pefabloc SC, pepstatin, phenylmethanesufonyl fluoride, trypsin inhibitors; DNAse inhibitors such as 2-mercaptoethanol, 2-nitro-5-thicyanobenzoic acid, calcium, EGTA, EDTA, sodium dodecyl sulfate, iodoacetate, etc.; RNAse inhibitors such as ribonuclease inhibitor protein; double-distilled water; DEPC (diethyprocarbonate) treated water, etc.). The kit can contain instructions for use. The kit can be provided as, or contain, a suitable container for shipping. The shipping container can be an insulated container. The shipping container can be self-addressed to a collection agent (e.g., laboratory, medical center, genetic testing company, etc.). The kit can be provided to a subject for home use or use by a medical professional. Alternatively, the kit can be provided directly to a medical professional.

One or more biological samples can be obtained from a given subject. In some cases, between about 1 and about 50 biological samples are obtained from the given subject; for example, about 1-50, 1-40, 1-30, 1-25, 1-20, 1-15, 1-10, 1-7, 1-5, 5-50, 5-40, 5-30, 5-25, 5-15, 5-10, 10-50, 10-40, 10-25, 10-20, 25-50, 25-40, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 biological samples can be obtained from the given subject. Multiple biological samples from the given subject can be obtained from the same source (e.g., the same tissue), e.g., multiple blood samples, or multiple tissue samples, or from multiple sources (e.g., multiple tissues). Multiple biological samples from the given subject can be obtained at the same time or at different times. Multiple biological samples from the given subject can be obtained at the same condition or different condition. Multiple biological samples from the given subject can be obtained at the same disease progression or different disease progression of the subject. If multiple biological samples are collected from the same source (e.g., the same tissue) from the particular subject, the samples can be combined into a single sample. Combining samples in this way can ensure that enough material is obtained for testing and/or analysis.

Provided herein are methods and compositions for targeted delivery of therapeutic agents such as guide RNAs or guide RNA-Cas complexes. The present inventors have surprisingly found that distinct structures of GalNAc and GalNAc derivative targeting moieties conjugated with guide RNA display high tissue specific delivery efficiency, and maintains the ability to bind and modify target DNA. Advantageously, modified guide RNAs covalently conjugated with GalNAc targeting moiety, as well as guide RNAs connected to GalNAc targeting moiety through nucleic acid base pairing and hybridization show stability and effective specific delivery to liver. The inventors show for the first time that conjugation of gRNA with distinct GalNAc moieties, either by covalent linkage or by hybridization efficiently directs the gRNA or gRNA-Cas9 complex to hepatocytes, and maintain sgRNA integrity, secondary structure stability, as well as CRISPR enzyme activity and increased CRISPR editing efficacy in vivo.

EXAMPLES

The following examples are provided to better illustrate the present disclosure and are not to be interpreted as limiting the scope of the disclosure. To the extent that specific materials are mentioned, it is merely for purposes of illustration and is not intended to limit the disclosure. One skilled in the art may develop equivalent means or reactants without the exercise of inventive capacity and without departing from the scope of the disclosure.

Example 1. Synthesis of N-Acetylgalcosamine Derived Monomers for Conjugation to Nucleic Acids/Oligonucleotides Scheme 1.
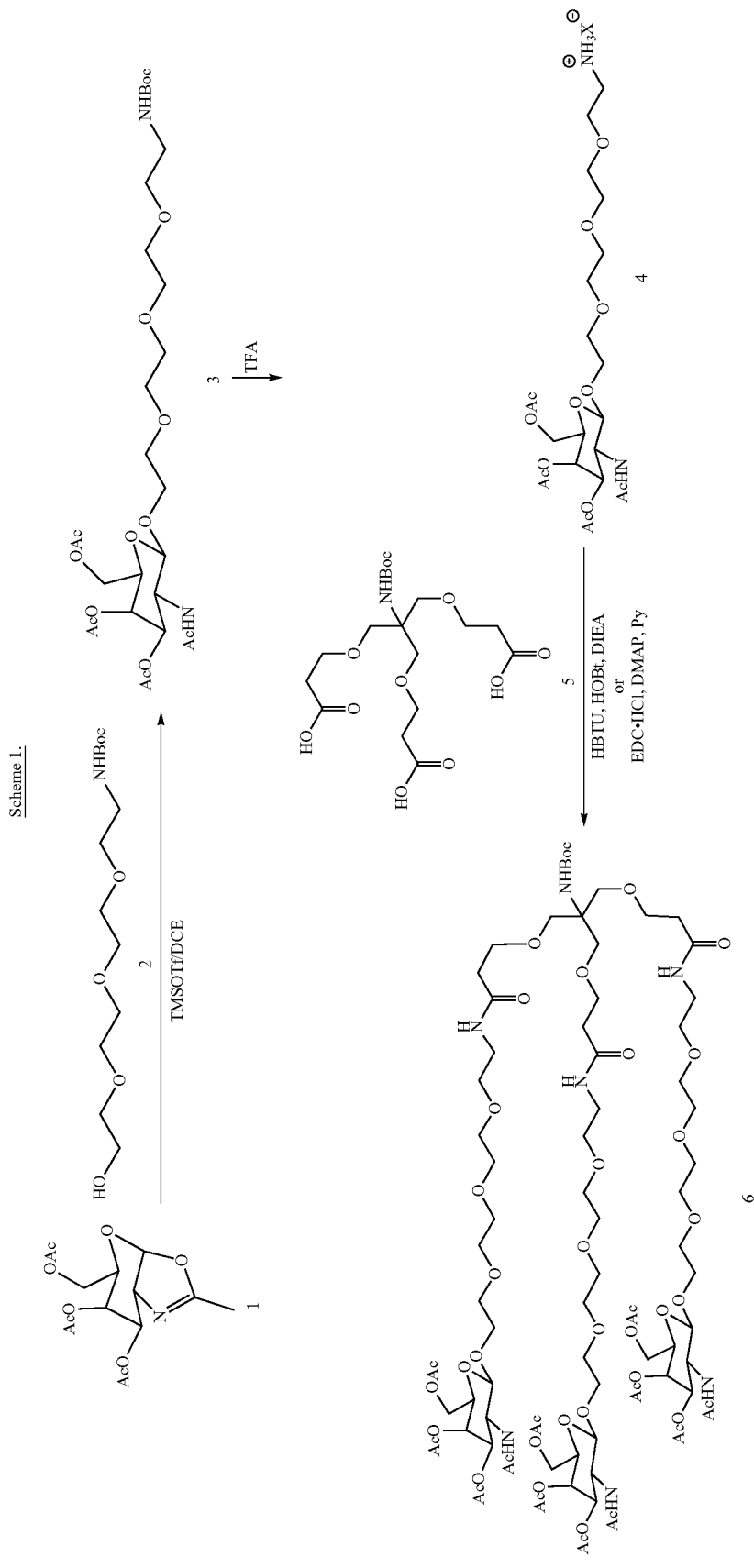

Compound 6 is prepared starting from the activated sugar 1 as reported (WO 2018/136620 A2). Compound 5 is purchased from a commercial source.
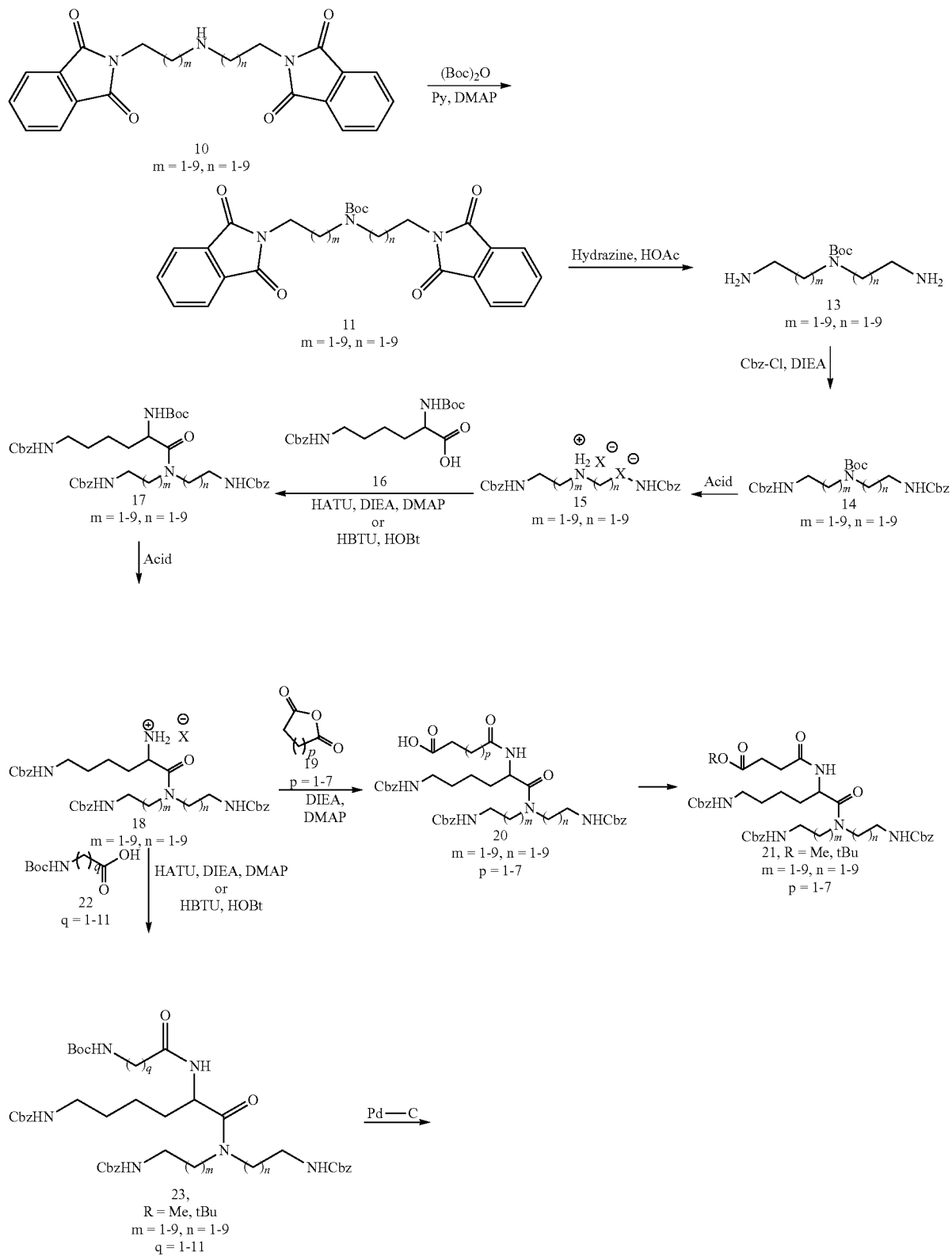
Scheme 2$^a$

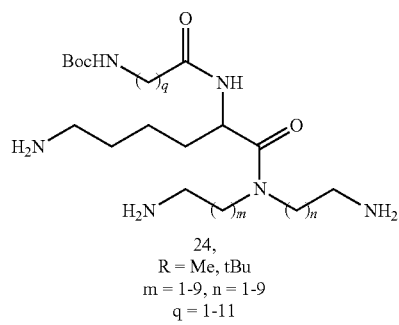
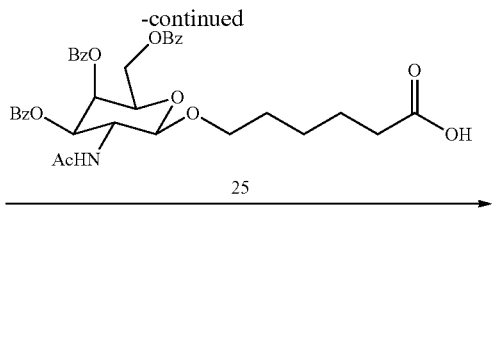

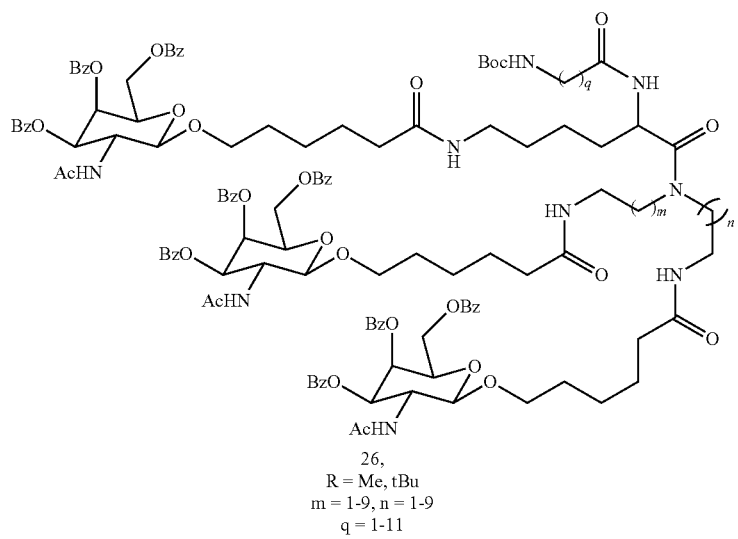

*a* Optically pure R, S and racemic versions of all the intermediates and target compounds are prepared starting from the corresponding chirally pure or racemic starting materials.

Compound 10 are purchased from commercial sources or prepared as reported in the literature (Bull. Chem. Soc. Japan (1998), 71(3), 717-721; J. Med. Chem. (2010), 53(1), 432-440, US20120114696 A1). The amine-protected R, S and racemic lysine 16 is purchased from commercial sources. The fully protected spacer 21 in optically pure and racemic forms are prepared starting from compound 10. The sugar-protected N-acetylgalactosamine (GalNAc) derivative 25 is prepared according to reported procedure (WO 2018/136620 A2). The intermediate compound 23 is prepared from compound 18 and commercially available N-Boc amino acid 22. The fully protected sugar intermediate compound 26 is prepared from compound 23 and the sugar intermediate 25.

Scheme 3*a*

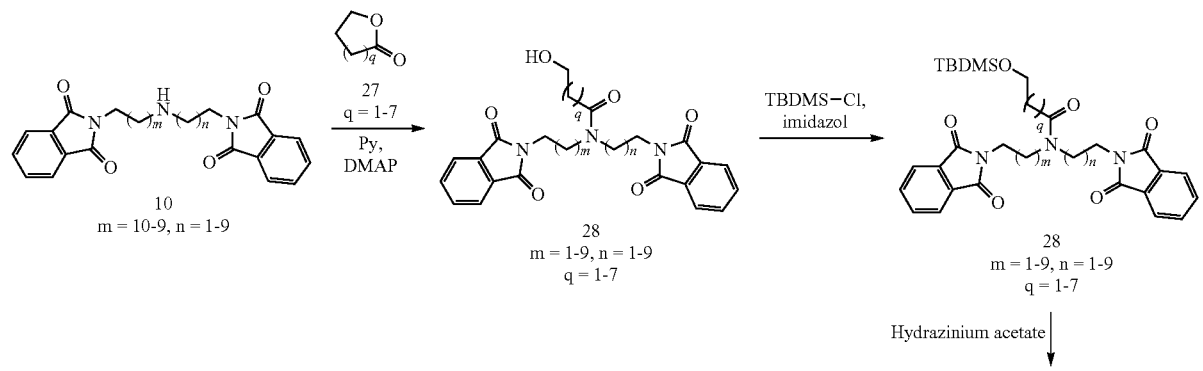

-continued
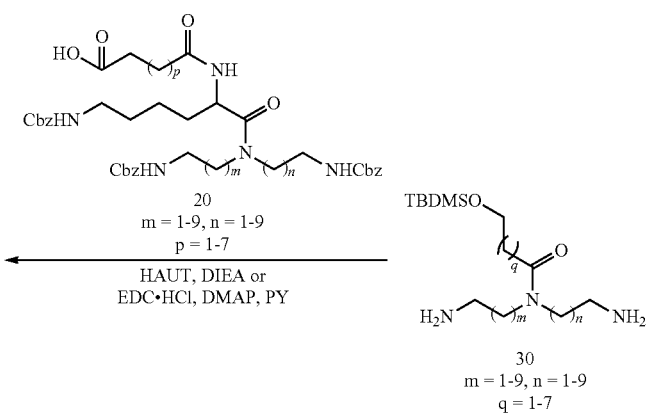
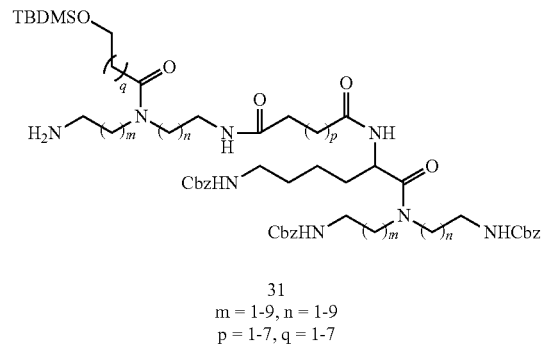
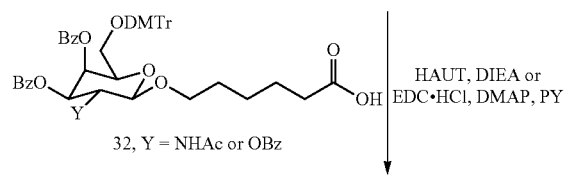
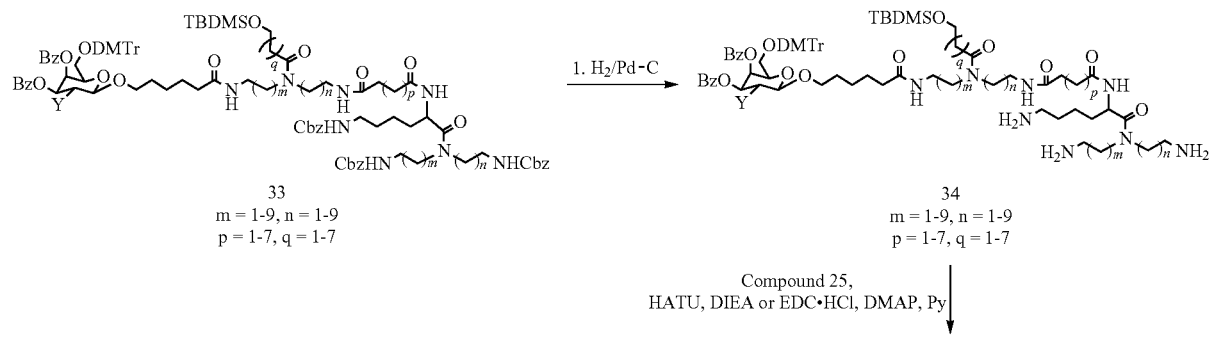
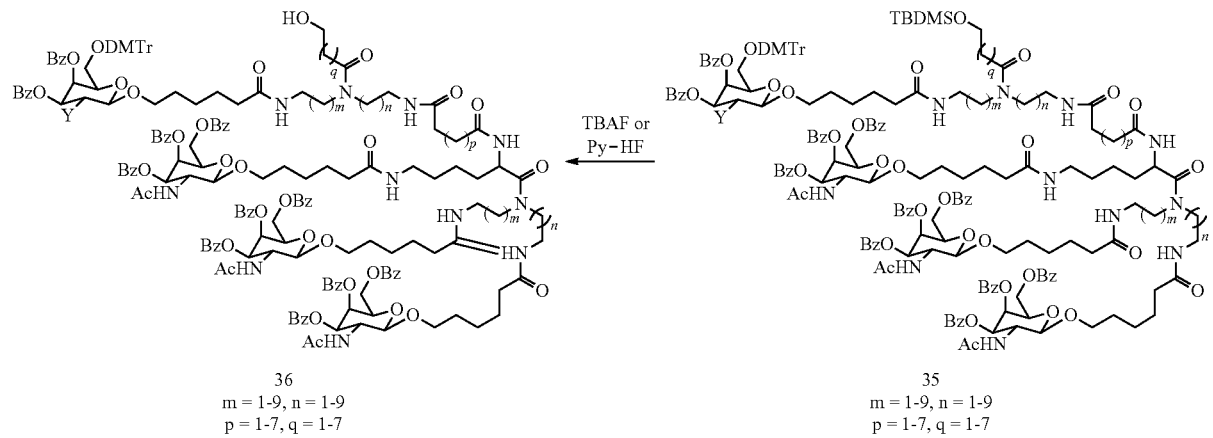

-continued

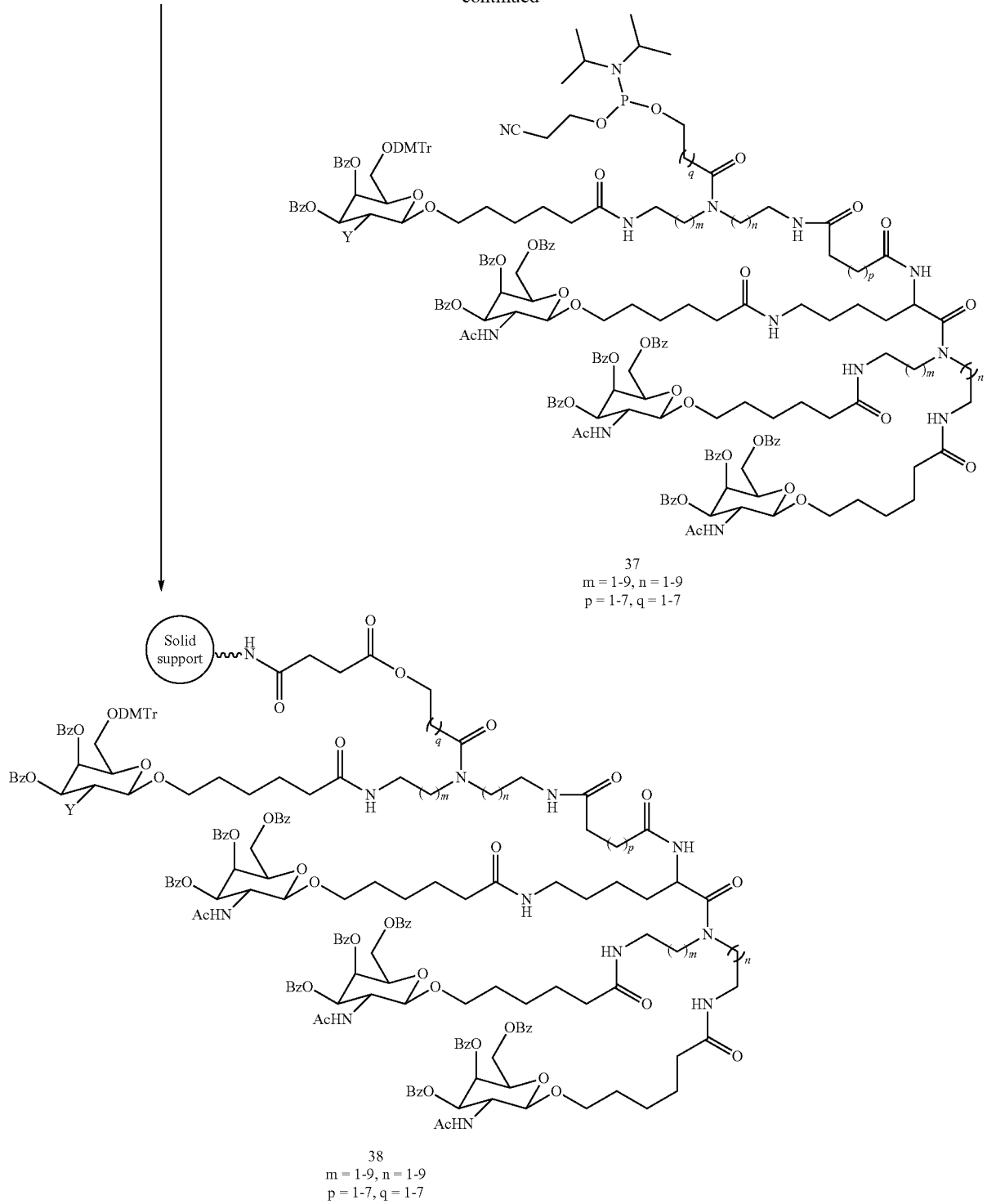

37
m = 1-9, n = 1-9
p = 1-7, q = 1-7

38
m = 1-9, n = 1-9
p = 1-7, q = 1-7

[a]Optically pure R, S and racemic versions of all the intermediates and target compounds are prepared starting from the corresponding chirally pure or racemic starting materials.

Desired lactones 27 are purchased from commercially available sources. Compound 32 is prepared from D-galactosamine as reported (WO 2018/136620 A2). The amine intermediate 31 is prepared from compound 10 and desired lactone 27. Compound 31 is then reacted with the acid 32 under peptide coupling conditions to obtain compound 33, which is then subjected to hydrogenation over Pd—C to obtain the amine intermediate 34. The amine then is coupled with the acid 25 to obtain compound 35. Treatment compound 35 with HIF-py affords compound 36. Phosphitylation of compound 36 affords the phosphoramidite 37 (WO 2018/136620 A2). Treatment of compound 36 with succinic anhydride in the presence of DMAP followed by treatment of the semi-succinate with amine-functionalized solid support under peptide coupling conditions affords the solid support 38. Unreacted amine on the support are capped by treating with acetic anhydride.

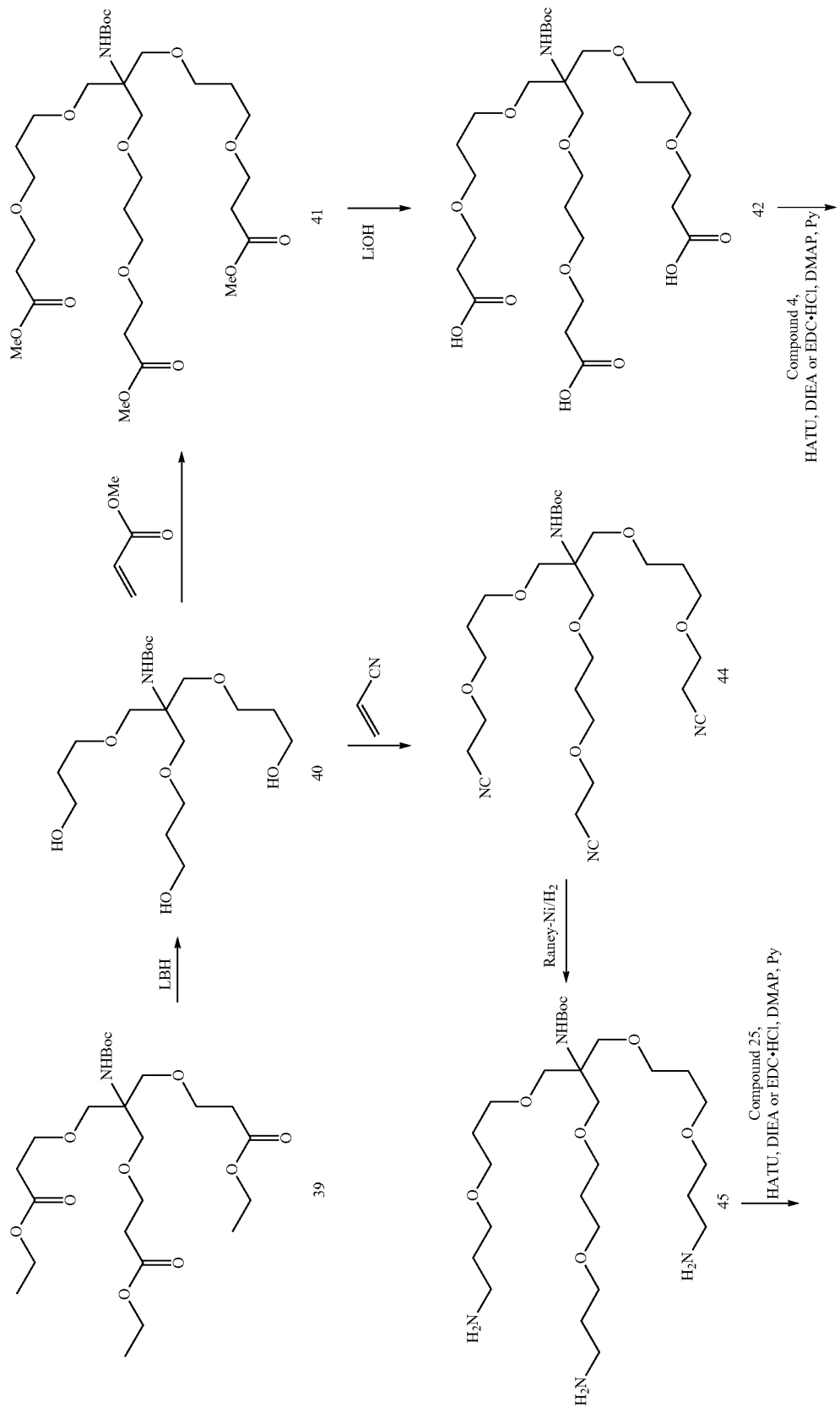

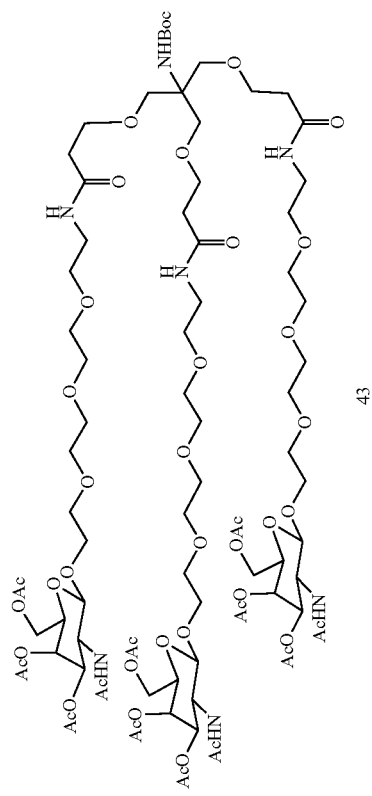
43
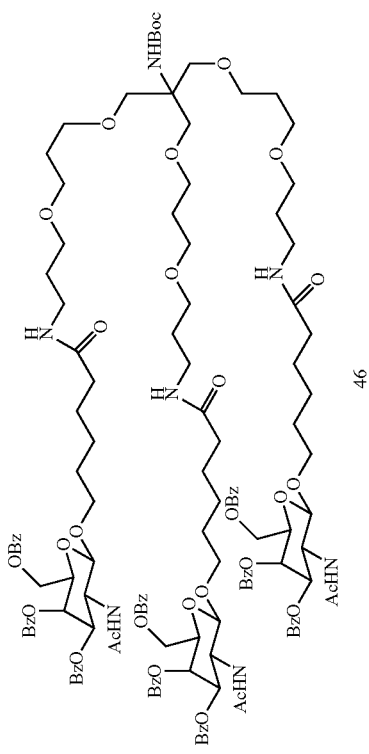
46

Compound 39, purchased from a commercial source, is treated with lithium borohydride to obtain the triol 40. Compound 40 upon treatment with methyl acrylate under Michael addition conditions affords compound 41. Hydrolysis of the triester 41 afforded the tri-acid 42, which is then coupled with the amine 4 under peptide coupling conditions to afford compound 43.

Compound 40 is treated with acrylonitrile under Michael addition conditions to obtain compound 44, which is subsequently treated with Raney-Ni under hydrogen to obtain the amine 45. The amine 45 is treated with the acid 25 under peptide coupling condition to obtain compound 46.

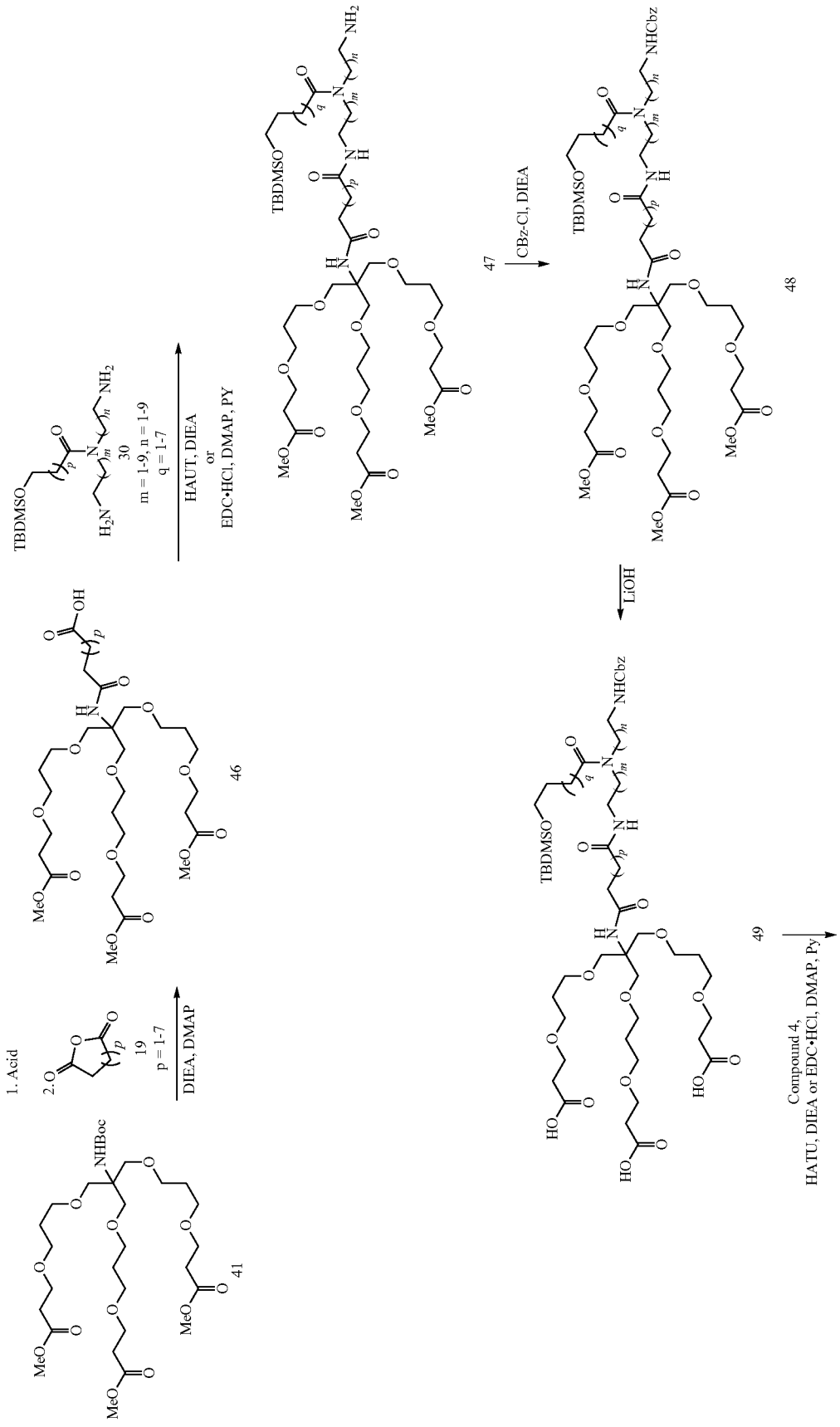

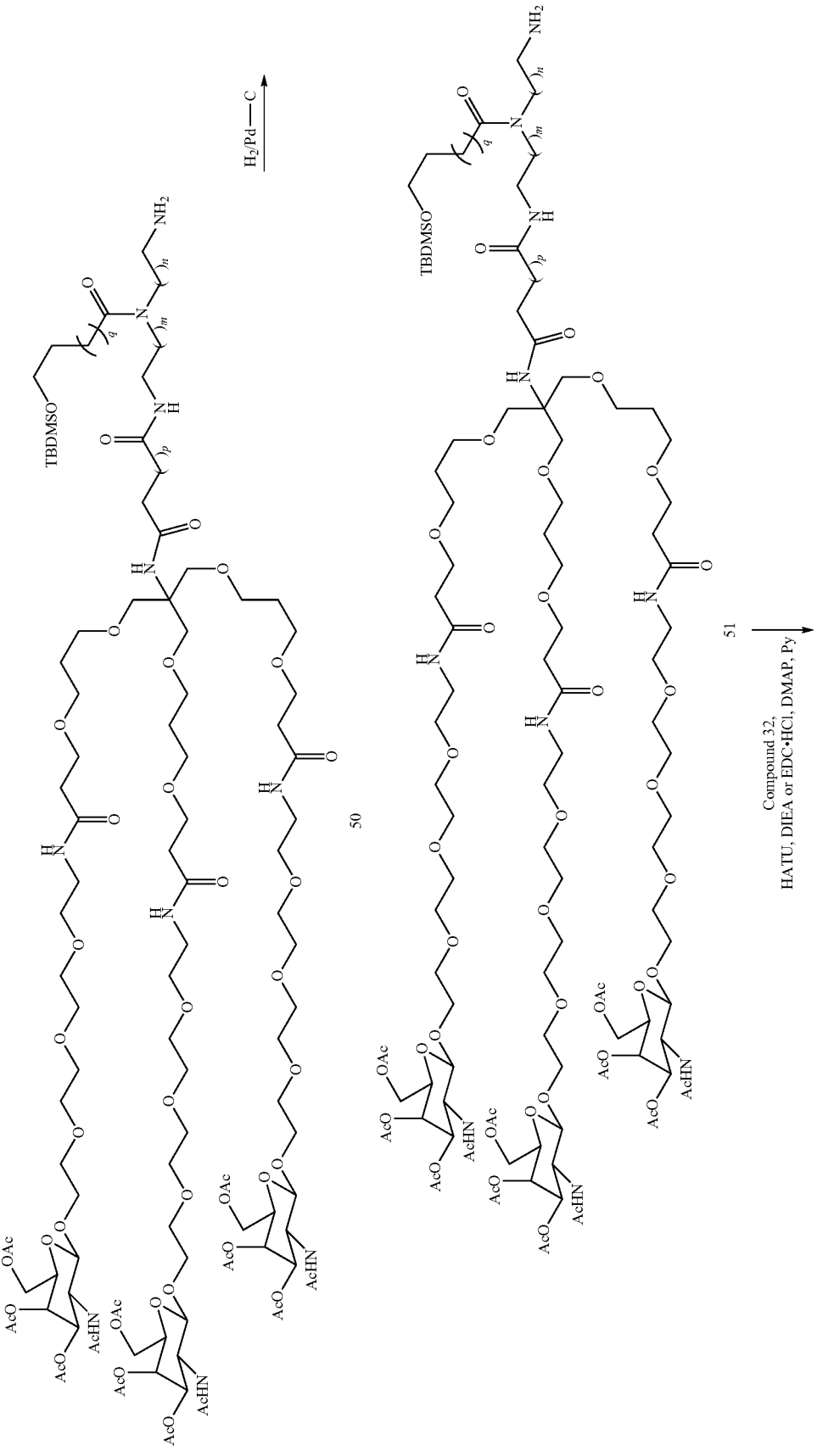

-continued
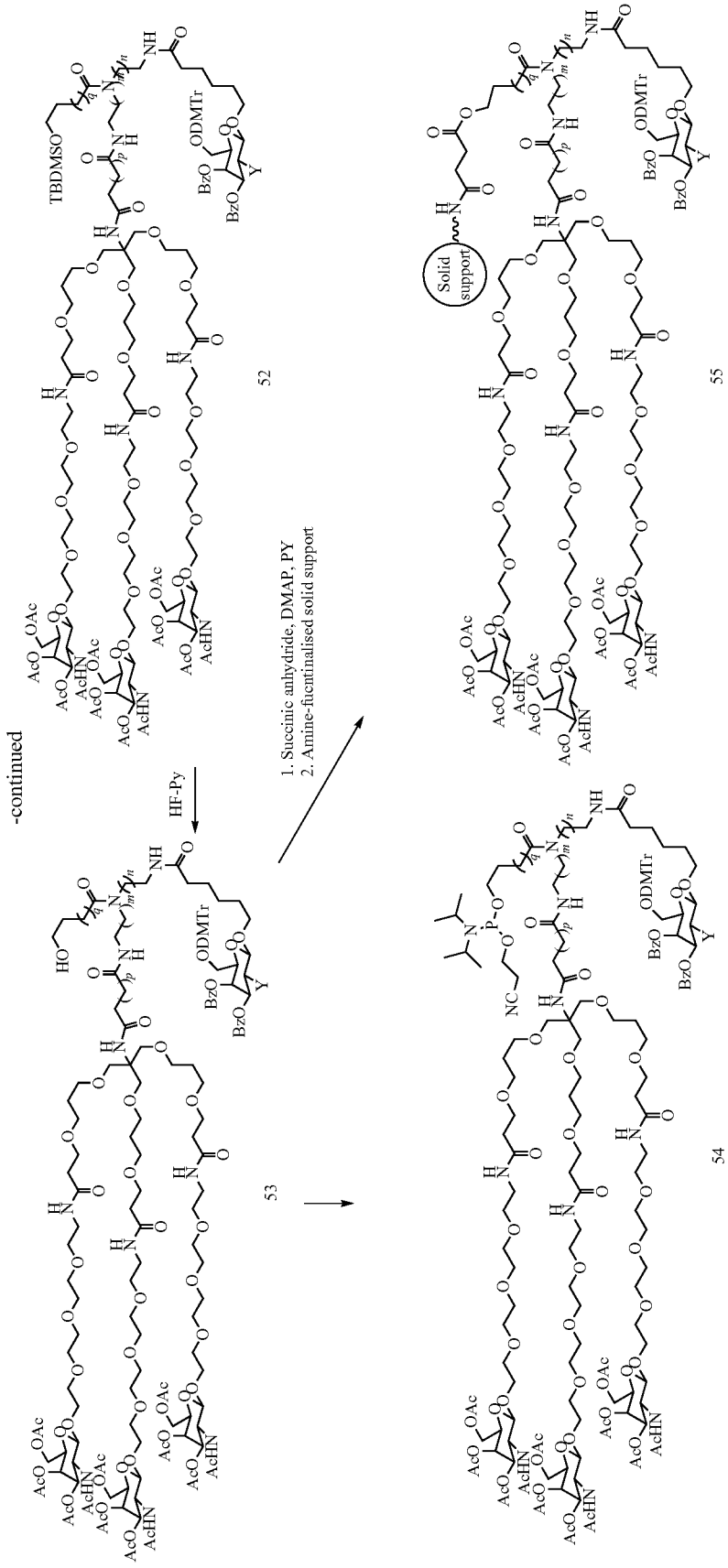

Compound 49 is prepared from compounds 41 and 30. Treatment of compound 41 with acid followed by reaction with desired anhydride 19 afforded acid 46. 1 mol equivalent of acid 46 is treated with one mol equivalent of the amine 30 under peptide coupling conditions to obtain compound 47. Treatment of the amine 47 with Cbz-Cl in the presense of base followed by treatment with LiOH affords compound 49. Reaction of compound 49 with excess amine 4 under peptide coupling condition yields compound 50. Treatment of compound 50 with hydrogen over Pd—C affords compound 51, which is then coupled with the acid 32 under peptide coupling conditions affords compound 52. Treatment of compound 52 with Py-HF yields compound 53. Phosphitylation of 53 affords the phosphoramidite 54. Treatment of 53 with succinic anhydride in the presence of base followed by treatment with amine-functionalized solid support under peptide coupling conditions yields the solid support 55. Unreacted amine on the support 55 is capped by treating with acetic anhydride in the presence of a base.

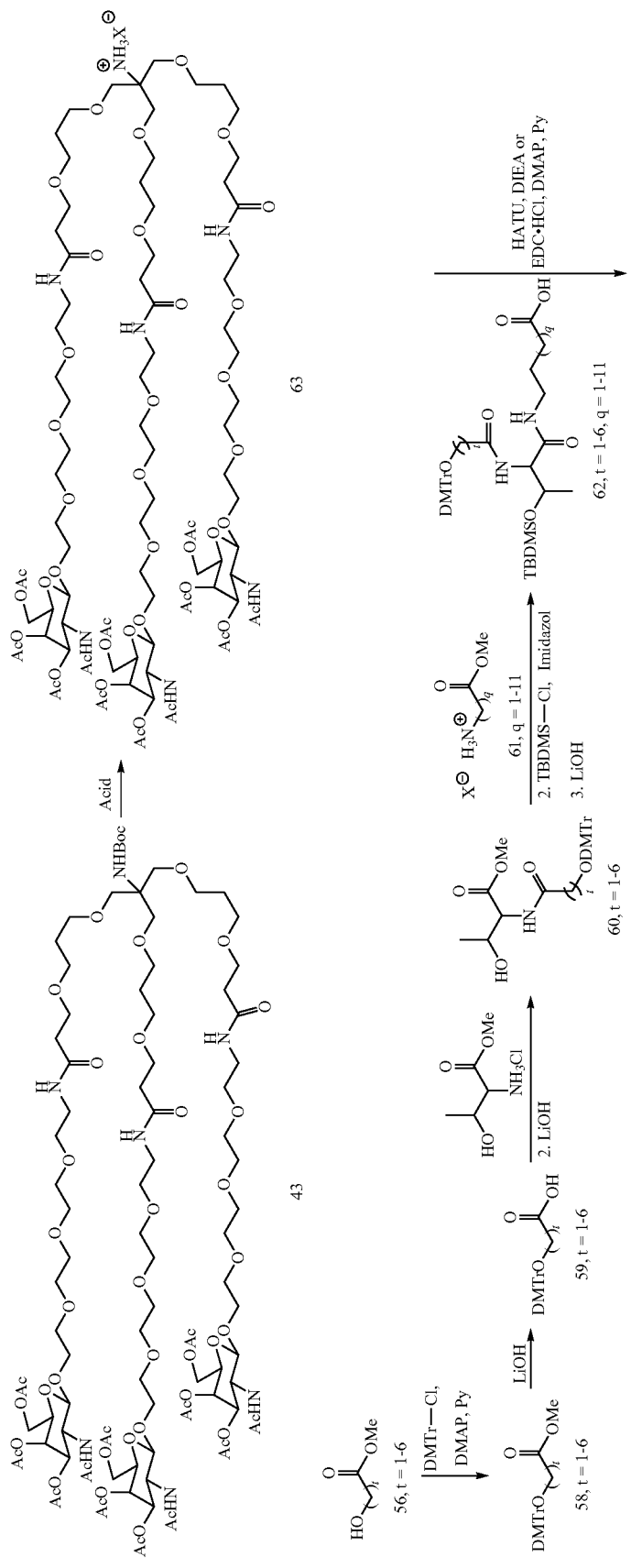
Scheme 6[a]

-continued
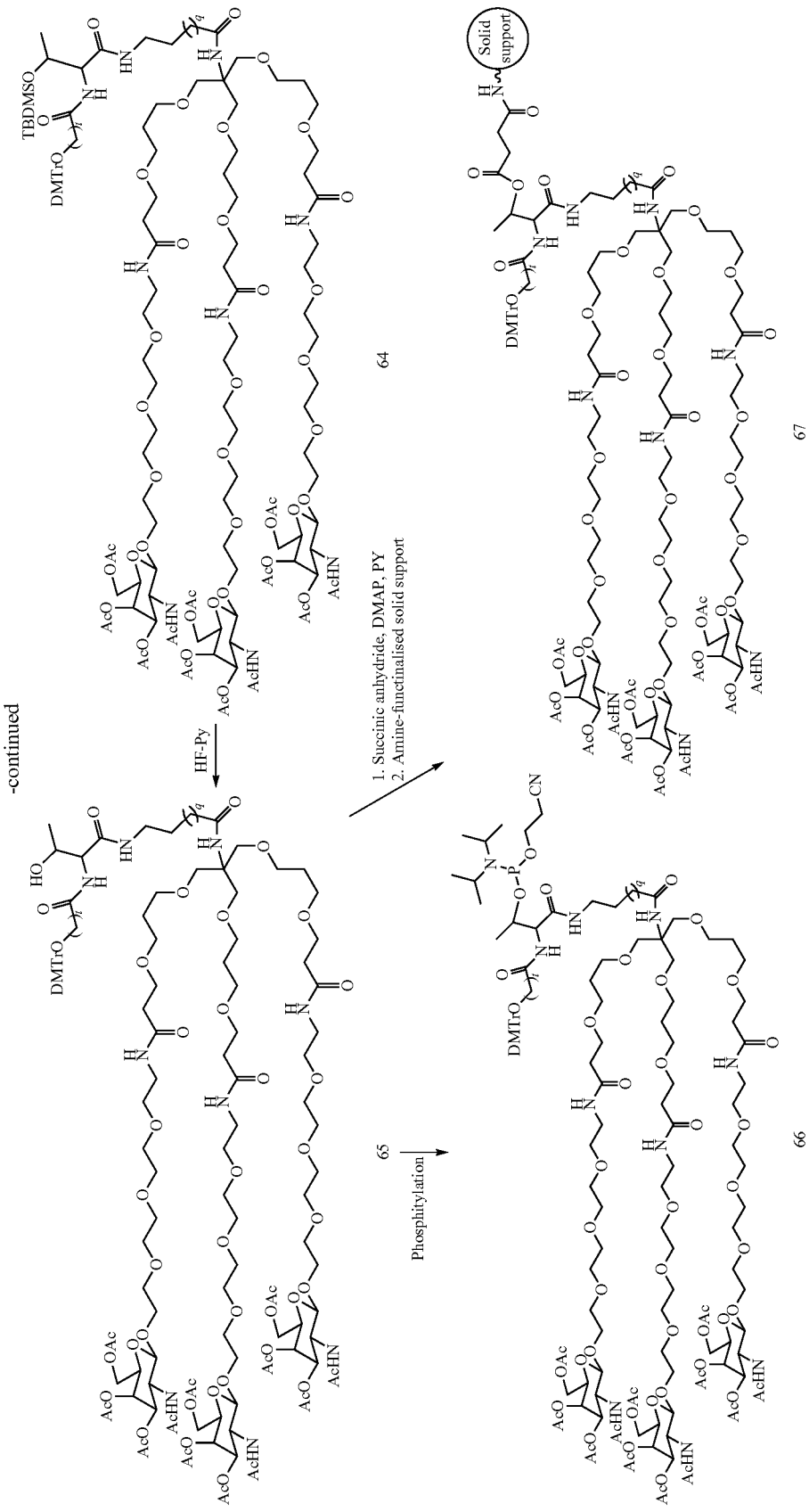

-continued
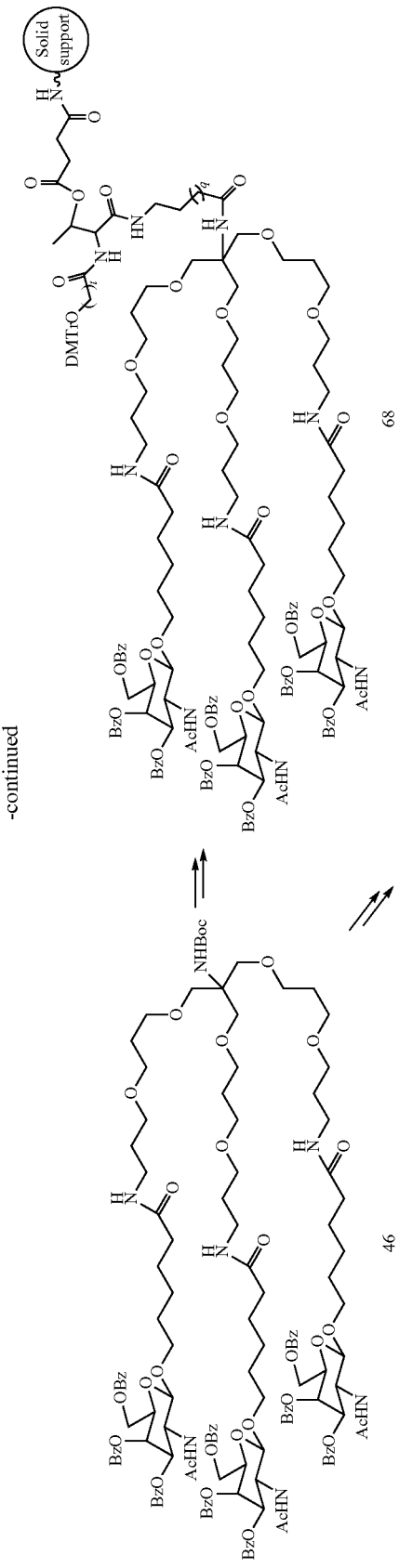
68
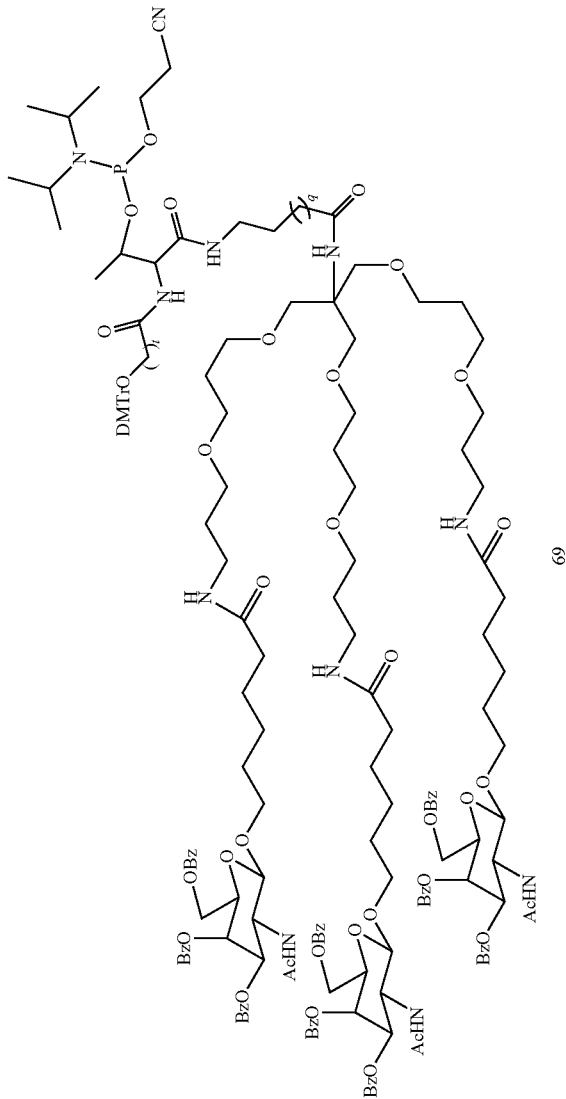
69
*Optically pure R, S and racemic versions of all the intermediates and target compounds are prepared starting from the corresponding chirally pure or racemic starting materials.

The acid 62 is prepared from commercially available methyl ester of hydroxy acid(s) 56. The hydroxyl group of the compound 56 is protected as DMTr and then the ester is hydrolyzed to obtain the acid 59. Compound 59 is reacted with hydrochloride salt of methionine methyl ester under peptide coupling conditions in the presence of base and then with LiOH in the presence of water to obtain the acid 60. The acid 60 is successively reacted with (1) the amine hydrochloride 61 under peptide coupling conditions to form the amide bond; (2) TBDMS-Cl in the presence of imidazole and (3) with LiOH in the presence of water to obtain compound 62. The amine salt 63 is prepared from compound 43. Compound 63 is then reacted with the compound 62 under peptide coupling conditions to yield compound 64. Treatment of 64 with Py-HF affords compound 65. Phosphitylation of 65 yields the phosphoramidite 66. Treatment of 65 successively with succinic anhydride in the presence of DMAP and then with amine-functionalized solid support under peptide coupling conditions yields the solid support 67. The unreacted amine on the solid support was then quenched by reacting with acetic anhydride in the presence of a base.

The phosphoramidite 68 and the solid support 69 are prepared from compound 46 and 62 as shown in the first part of Scheme 6 and as described above.

Scheme 7<sup>a</sup>

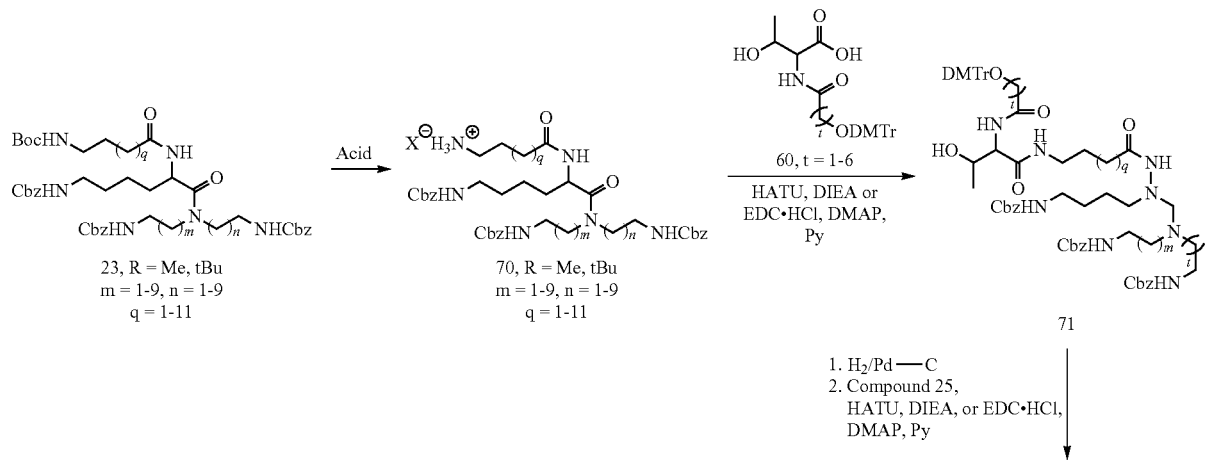

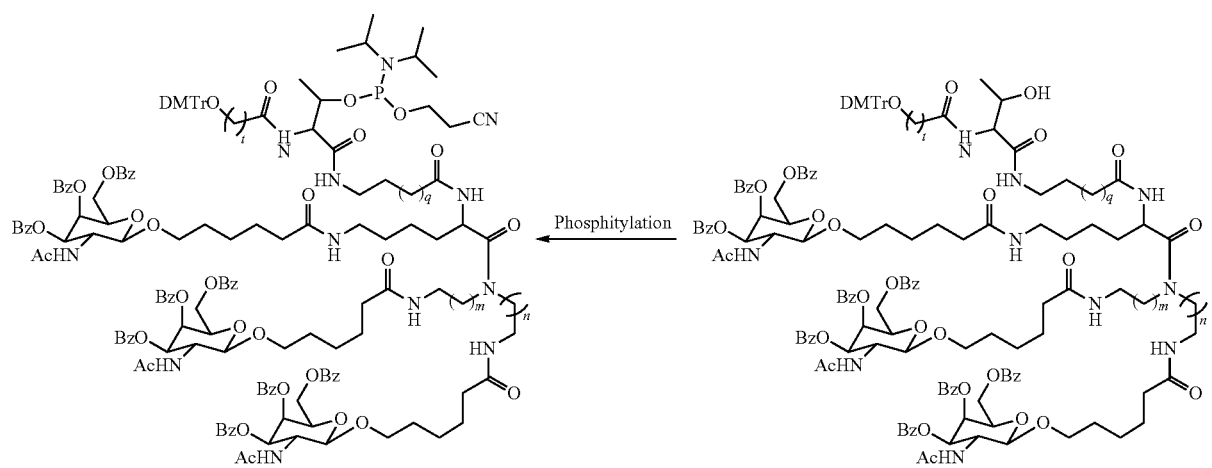

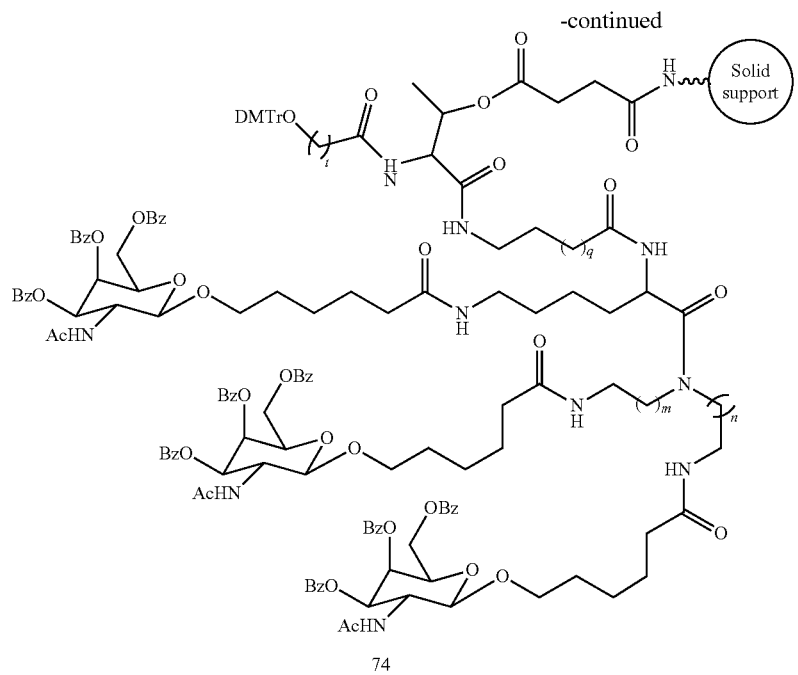

74

<sup>a</sup>Optically pure R, S and racemic versions of all the intermediates and target compounds are prepared starting from the corresponding chirally pure or racemic starting materials.

The phosphoramidite 73 and the solid support 74 are prepared from desired starting material(s)23 as shown in the Scheme 7. Treatment of 23 with acid affords compound 70. Compound 70 is then reacted with compound 60 under peptide coupling conditions to obtain compound 71. Compound 71 is hydrogenated over Pd—C at atmospheric pressure and the reacted with compound 25 under peptide coupling conditions to compound 72. Phosphitylation of compound 72 affords the phosphoramidite 73. Treatment of compound 72 with succinic anhydride in the presence of a base followed treatment with amine-functionalized solid support under peptide coupling conditions affords the solid support 74. Unreacted amine on the support obtained is quenched by reacting with acetic anhydride in the presence of a base to yield the solid support ready for nucleic acid/oligonucleotide synthesis.

Example 2. GalNAc Conjugate Synthesis

The desired nucleic acid conjugates are synthesized using the solid support and phosphoramidites described in Scheme 1-7 and in the publication Brown et al., NUCLEIC ACID THERAPEUTICS (DOI: 10.1089/nat.2019.0782) and as described in the publications: Rajeev, et al., *Chem Bio Chem* 2015, 16, 903-908, Nair et al., *J. Am. Chem. Soc.* 2014, 136, 16958-16961 and WO 2018/136620 A2.

Example 3. Targeted Delivery of mRNA to Hepatocytes In Vitro

The RNA poly(A) tail is annealed with short complementary oligonucleotides conjugated with GalNAc ligand (Table 2). The single chemical entity thus formed is incubated with ASGPR expressing, rodent, non-human primates and human primary hepatocytes, and/or hepatoma cell lines to enable ASGPR-mediated uptake into the cell to elicit expression of the corresponding protein. The expression of the protein of interest is assayed to check the efficiency of GalNAc-ASGPR mediated delivery of the mRNA. Expression of GFP and GFP-Luc mRNA are used as the probes, initially.

Example 4. Targeted Delivery of mRNA to Hepatocytes In Vivo in Rodents and Non-Human Primates The RNA poly(A) tail is annealed with short complementary oligonucleotides conjugated with GalNAc ligand (Table 2). The single chemical entity thus formed is subcutaneously or intravenously administered to enable ASGPR-mediated uptake of the RNA payload to hepatocytes to elicit protein expression in liver. Expression of the protein in the livers of treated animals are assayed at regular intervals, after administration.

Example 5. Targeted Delivery of Guide RNA to ASGPR Expressing Cell Lines In Vitro The guide RNA (gRNA) conjugated with GalNAc (Table 1) is incubated with ASGPR expressing rodent, non-human primates and human primary hepatocytes, and/or hepatoma cell lines to enable ASGPR-mediated uptake into the cell. The mRNA encoding gene editing protein is delivered to these cell lines by simple transfection using lipofectamine or equivalent transfection agents or by using AAV or AV vectors to express the protein.

The gRNA and modified gRNA is annealed with complementary short oligonucleotide conjugated with GalNAc is incubated with ASGPR expressing rodent, non-human primates and human primary hepatocytes, and HepG2 cell lines to enable ASGPR-mediated uptake into the cell. Gene editing in hepatocytes and hepatoma cells are assayed after 12 to 36 h post incubation with the gRNA.

Example 6. Gene Editing in Hepatocytes

The RNA is delivered to ASGPR expressing cell lines using AAV or AV vector and allowed it to express the ribonucleoprotein (RNP). The cell line is then incubated with GalNAc conjugated guide RNA from Table 2 or 3 or constituted from Tables 2 and 3. ASGPR-mediated delivery of the GalNAc conjugated guide RNA into the receptor expressing cells. The guide RNA after uptake into the cell form complex with the expressed RNP to elicit gene editing.

The guide RNA modified with GalNAc from Table 1 is incubated with the cell lines after certain interval namely 1, 2, 3, 4, 5, 6, 7, 8, 9, 10, 11, 12, 13, or 14 days after administering the AAV or AV vector encoding the RNA, or at a later timepoint beyond 14 days. Different concentrations of gRNA-GalNAc are evaluated at different interval post administration of the gene editor RNA AAV and or AV vector. Gene editing in hepatocytes and hepatoma cells are assayed after 12 to 36 h post incubation with the gRNA.

Example 7. RNA Encoding RNP of Interest is Administered by LNP-Mediated Delivery to Express the Protein in ASGPR Expressing Cell Lines In Vitro The guide RNA modified with GalNAc from Table 1 is incubated with the cell lines after certain interval namely 1, 2, 3, 4, 5, 6, 7, 8, 9, 10, 11, 12, 18, 24 or 36 h after administering the mRNA. Different weight and molar ratio of the mRNA to guide are also evaluated under the same experimental conditions. The highest mRNA to guide ratio is 100:1 and the lowest is 1:100. The ratio in between 100:1 and 1:100 are also evaluated. Gene editing in the livers of treated animals are assayed after 24 to 96 h post incubation with the gRNA and the results are compared with untreated controls at the same timepoints.

Example 8. Gene Editing in Liver In Vivo in Rodents and in Non-Human Primates The RNA is delivered to livers of rodent and non-human primates using AAV or AV vector and allowed it to express the ribonucleoprotein (RNP). Subcutaneous (SC) or intravenous (IV) administration of GalNAc conjugated guide RNA from Table 2 or 3, or constituted from Tables 2 and 3 enable ASGPR-mediated delivery of the GalNAc conjugated guide RNA into hepatocytes. The guide RNA after uptake into the hepatocytes form complex with the expressed RNP to form RNP-guide RNA complex to produce gene editing.

The guide RNA modified with GalNAc from Table 1 is subcutaneously or intravenously administered after certain interval namely 1, 2, 3, 4, 5, 6, 7, 8, 9, 10, 11, 12, 13, or 14 days after administering the AAV or AV vector encoding the RNA, or at a later timepoint beyond 14 days. Different concentrations of gRNA-GalNAc are evaluated at different interval post administration of the gene editor RNA AAV and or AV vector. Gene editing in the livers of treated animals are assayed after 24 to 96 h post incubation with the gRNA and the results are compared with untreated controls at the same timepoints.

Example 9. In Vivo Administration

The RNA encoding RNP of interest is administered by LNP-mediated delivery to rodents and non-human primates by IV infusion over a period ranging from 30 min to 120 min. The infusion time is determined based on the total dose and/or total dosing volume of the LNP formulation. In certain LNP dosing, the monkeys are subjected to steroid pretreatment to avoid acute infusion related reactions. The guide RNA modified with GalNAc from Table 1 in saline or equivalent diluent is administered subcutaneously to intravenously after certain interval namely 0, 1, 2, 3, 4, 5, 6, 7, 8, 9, 10, 11, 12, 18, 24 or 36 h after administering the mRNA. Different weight and molar ratio of the mRNA to guide are also evaluated under the same experimental conditions. The highest mRNA to guide ratio is 100:1 and the lowest is 1:100. The ratio in between 100:1 and 1:100 are also evaluated. Gene editing in the livers of treated animals are assayed after 24 to 96 h post incubation with the gRNA and the results are compared with untreated controls at the same timepoints.

Example 10. Targeted Delivery of Gene Editor mRNA and Guide RNA (gRNA) to Hepatocytes In Vitro ASGPR-expressing primary hepatocytes are incubated with gene-editor mRNA-GalNAc single chemical entity and guide RNA-GalNAc conjugate to produce editing of the targeted gene in hepatocytes. The gene-editor mRNA-GalNAc single chemical entity and gRNA-GalNAc conjugate are:

(1) Co-incubated at different mRNA to gRNA ratio ranging from 100:1 to 1:100 by weight and several ratios in between.

(2) The gene-editor mRNA-GalNAc single chemical entity is incubated with the cell lines first and then different ratio of the gRNA-guide from Table 2 or 3, or constituted from Tables 2 and 3 is incubated with the same cell lines at intervals namely 0, 1, 2, 3, 4, 5, 6, 7, 8, 9, 10, 11, 12, 18, 24 or 36 h after administering the mRNA. Different weight and molar ratio of the mRNA to guide are also evaluated under the same experimental conditions. The highest mRNA to guide ratio is 100:1 and the lowest is 1:100. The ratio in between 100:1 and 1:100 are also evaluated.

Gene editing in the treated cells are assayed after 24 to 36 h post incubation with the gRNA and the results are compared with untreated controls at the same timepoints.

Example 11. Targeted Delivery of Gene Editor mRNA and Guide RNA (gRNA) to Liver In Vivo in Rodents and in Non-Human Primates The gene-editor mRNA-GalNAc single chemical entity and gRNA-GalNAc conjugate to produce editing of the targeted gene in the hepatocytes. The gene-editor mRNA-GalNAc single chemical entity and gRNA-GalNAc conjugate are:

(1) Co-administered subcutaneously or intravenously at different mRNA to gRNA ratio ranging from 100:1 to 1:100 by weight and several ratios in between.

(2) The gene-editor mRNA-GalNAc single chemical entity is incubated with the cell lines first and then different ratio of the gRNA-guide from Table 2 or 3, or constituted from Tables 1 and 2 is incubated with the same cell lines at intervals namely 0, 1, 2, 3, 4, 5, 6, 7, 8, 9, 10, 11, 12, 18, 24 or 36 h after administering the mRNA. Different weight and molar ratio of the mRNA to guide are also evaluated under the same experimental conditions. The highest mRNA to guide ratio is 100:1 and the lowest is 1:100. The ratio in between 100:1 and 1:100 are also evaluated.

Example 12. RNP-gRNA Complex Preparation and Evaluation to be Incorporated

Gene editing in the livers of treated animals are assayed after 24 to 96 h post incubation with the gRNA and the results are compared with untreated controls at the same timepoints.

Example 13. In Vivo Administration of Single Chemical Entities of gRNA-GalNAc and mRNA-GalNAc and from Tables 1 and 2 to Rodents and Non-Human Primates The single chemical entity gRNA-GalNAc and mRNA-GalNAc from Tables 1 and 2 is mixed with other components of the nanoparticles prior to dosing. The gRNA and mRNA to be dosed is individually formulated into nanoparticle compositions. Alternatively, the gRNA and mRNA can be pre-mixed before the formation of nanoparticles. After mixing the mRNA and gRNA are dosed and the gene editing in the livers of treated animals are assayed as described in Example 11.

Example 14. Synthesis of N-Acetylgalcosamine-Lipid (GalNAc-Lipid) Conjugates to Constitute GalNAc-LNPs for Targeted Delivery to Hepatocytes In Vitro and In Vivo

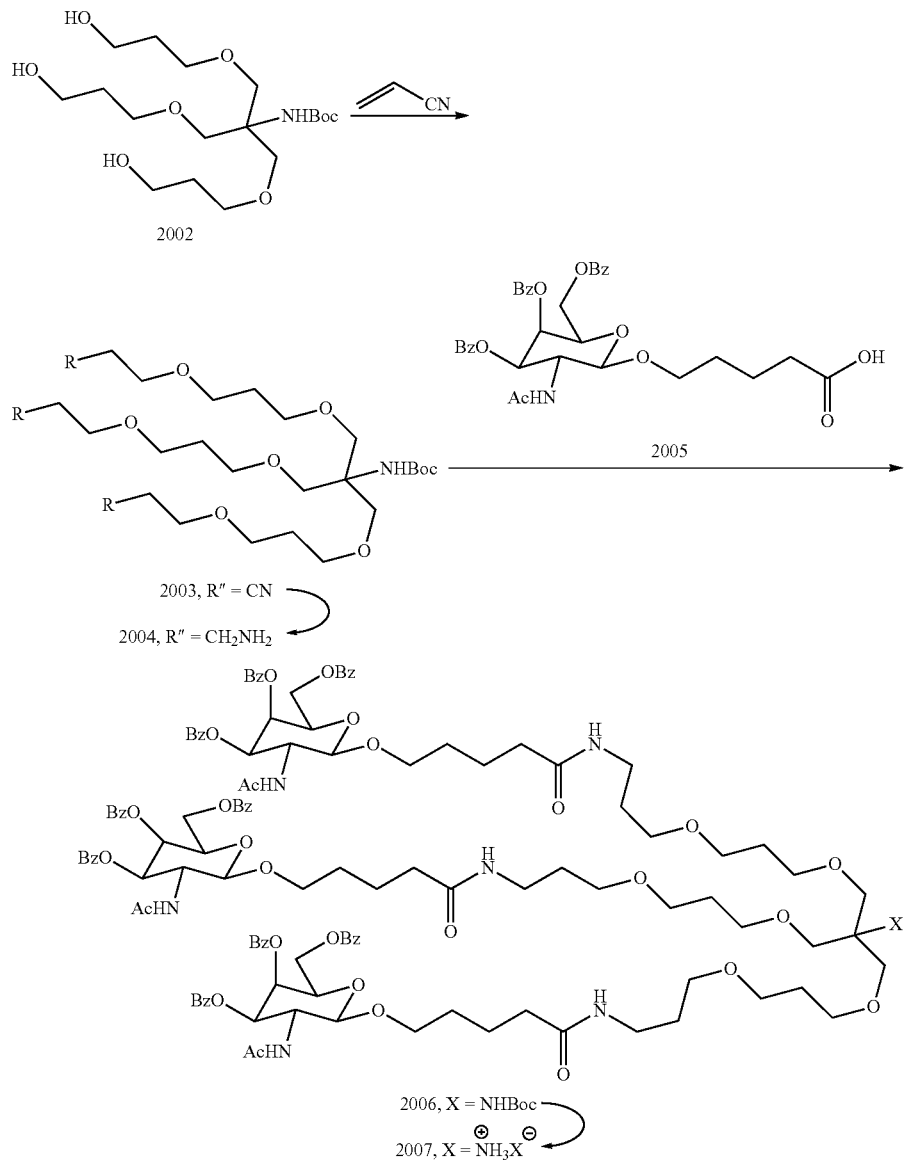

Scheme 9
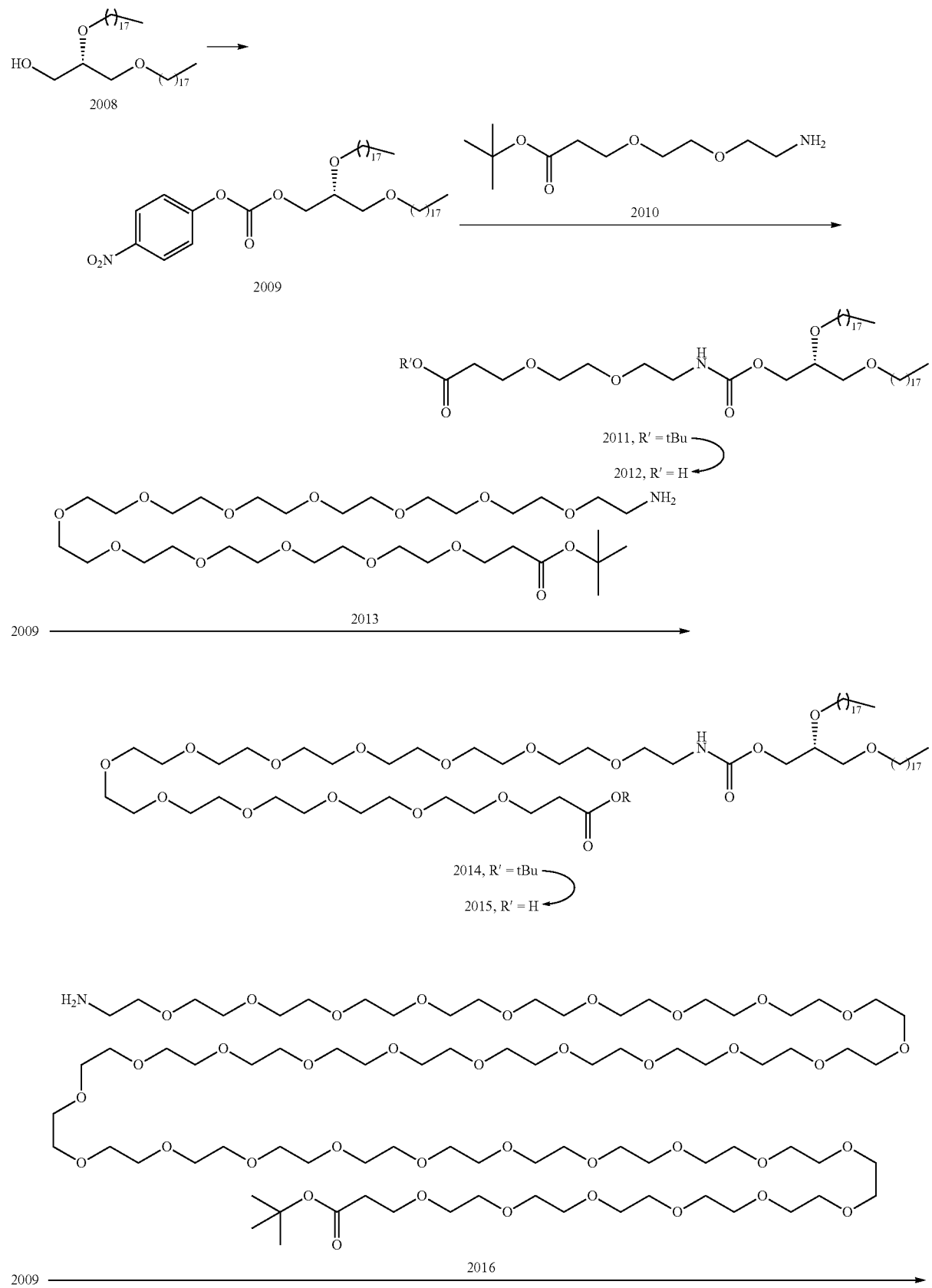

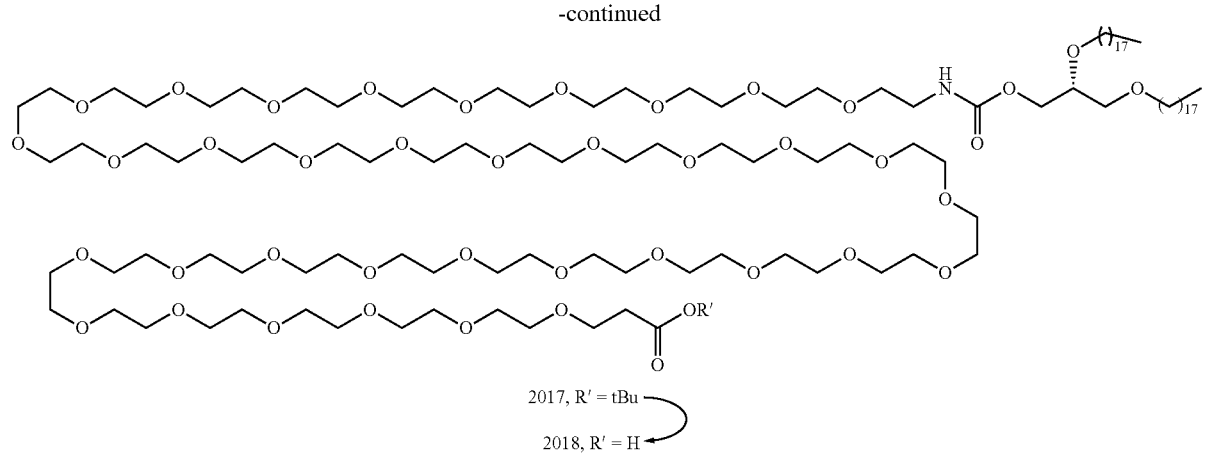
2017, R' = tBu
2018, R' = H
Scheme 10
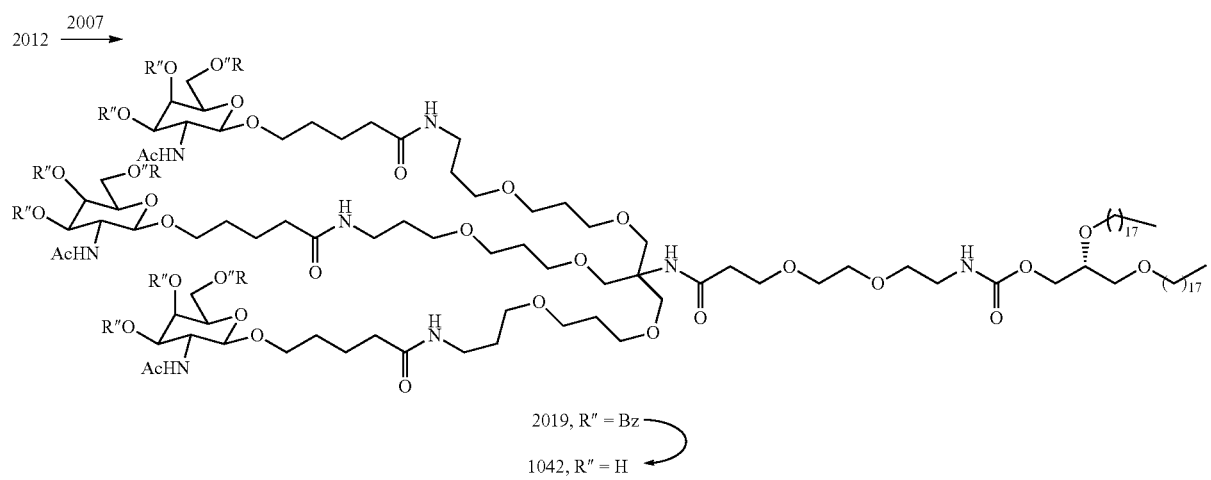
2019, R'' = Bz
1042, R'' = H
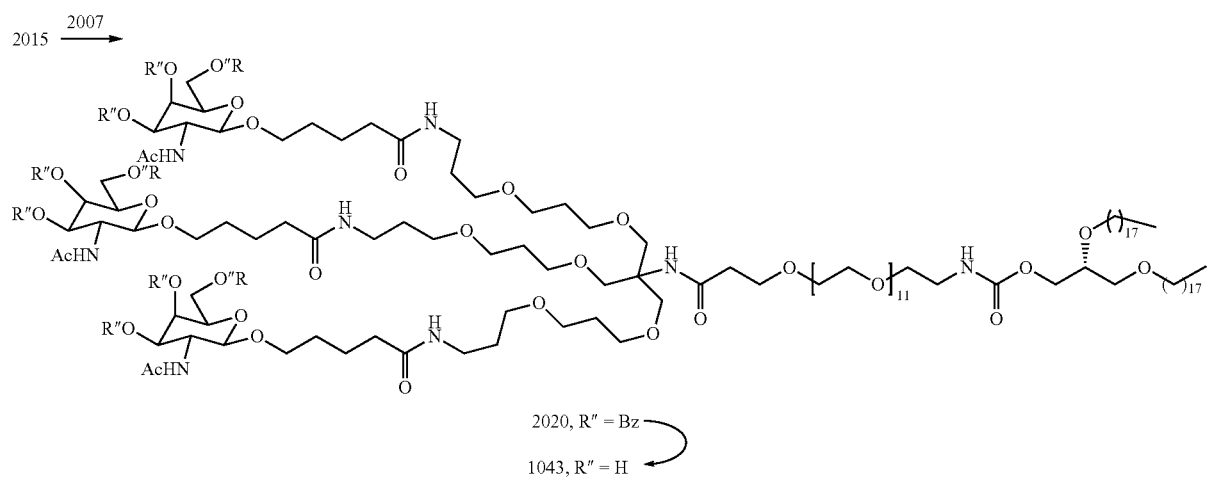
2020, R'' = Bz
1043, R'' = H

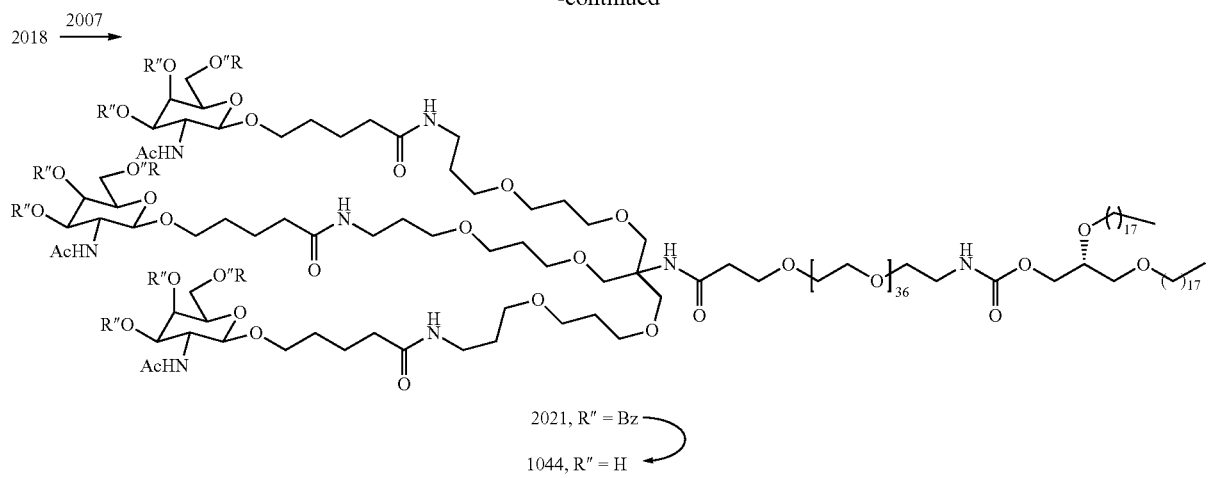
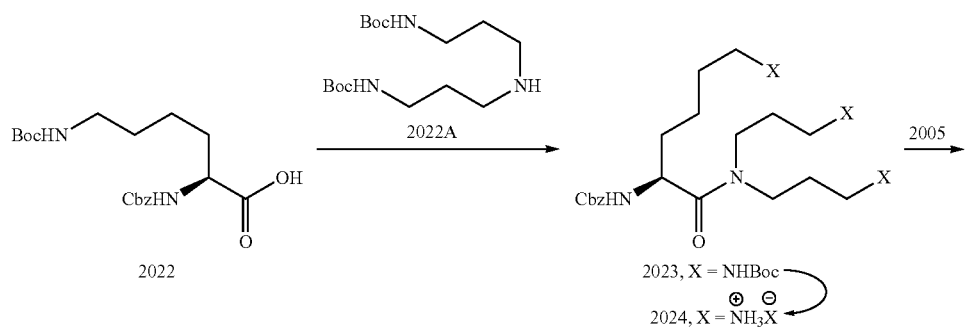
Scheme 11
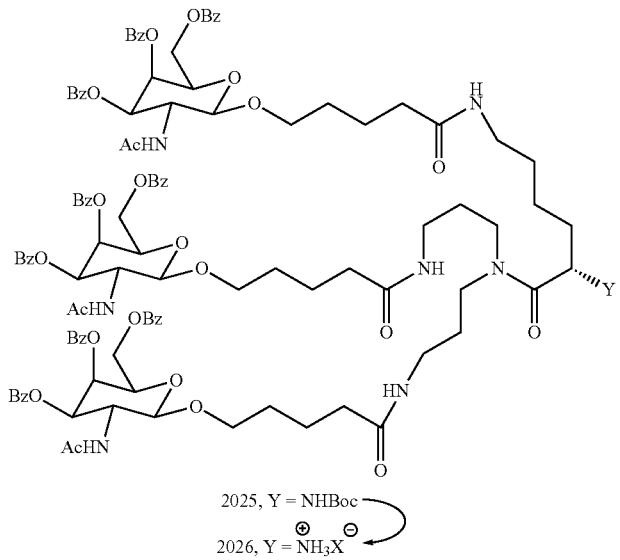

-continued
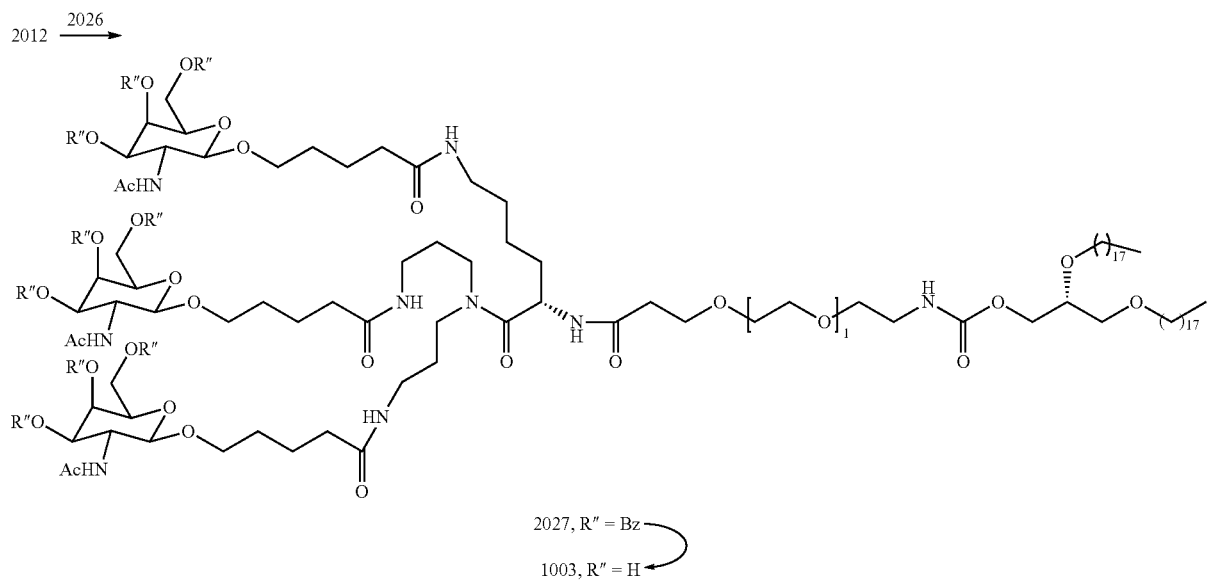
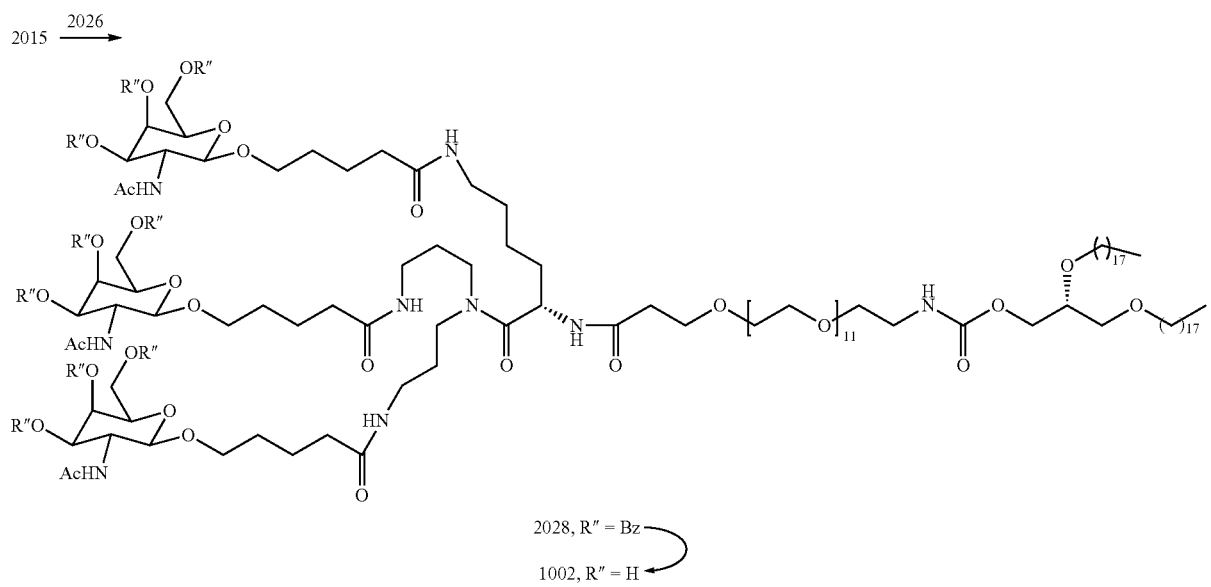

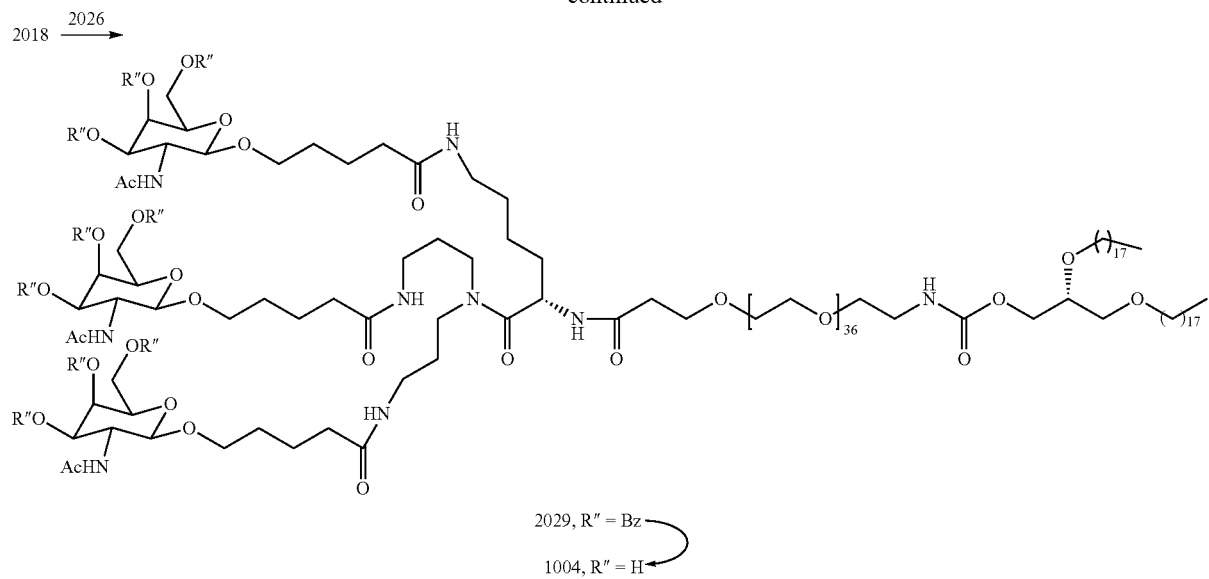
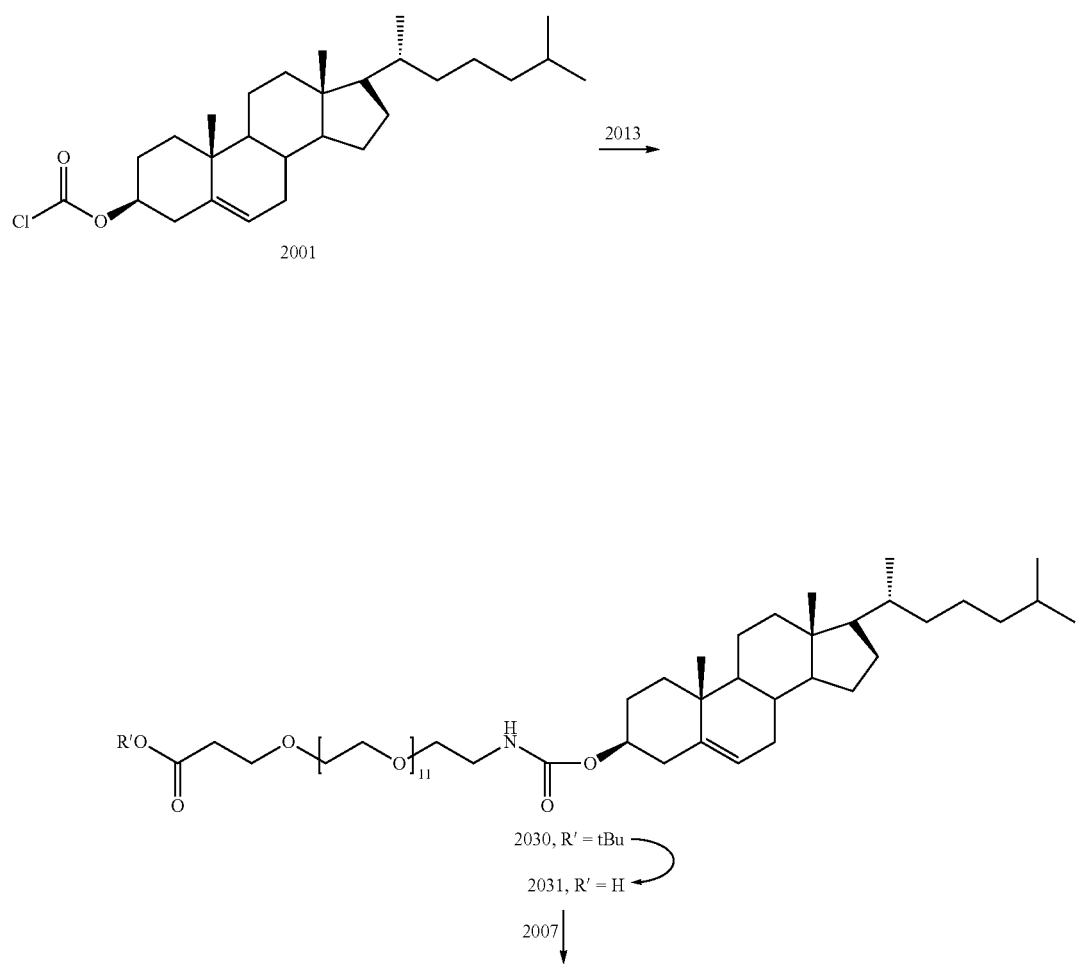
Scheme 12

341 342
-continued
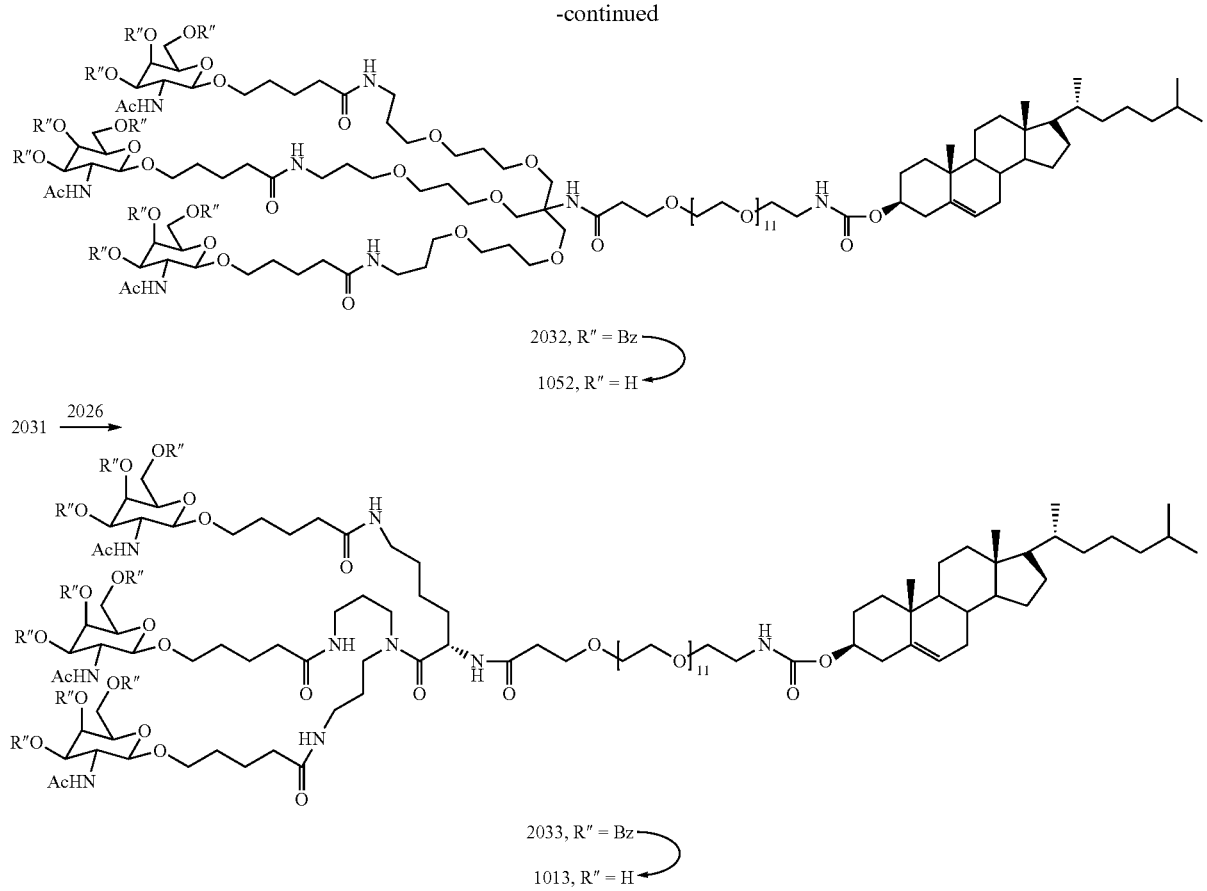
2032, R″ = Bz
1052, R″ = H
2033, R″ = Bz
1013, R″ = H
Scheme 13
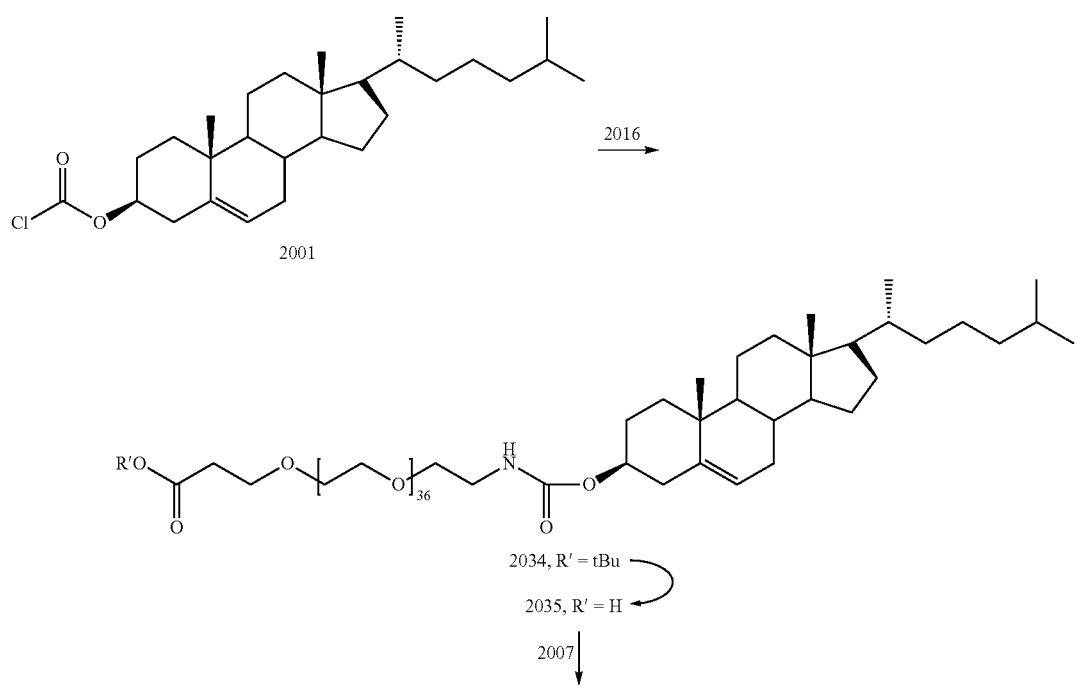
2034, R′ = tBu
2035, R′ = H
2007

343 344
-continued
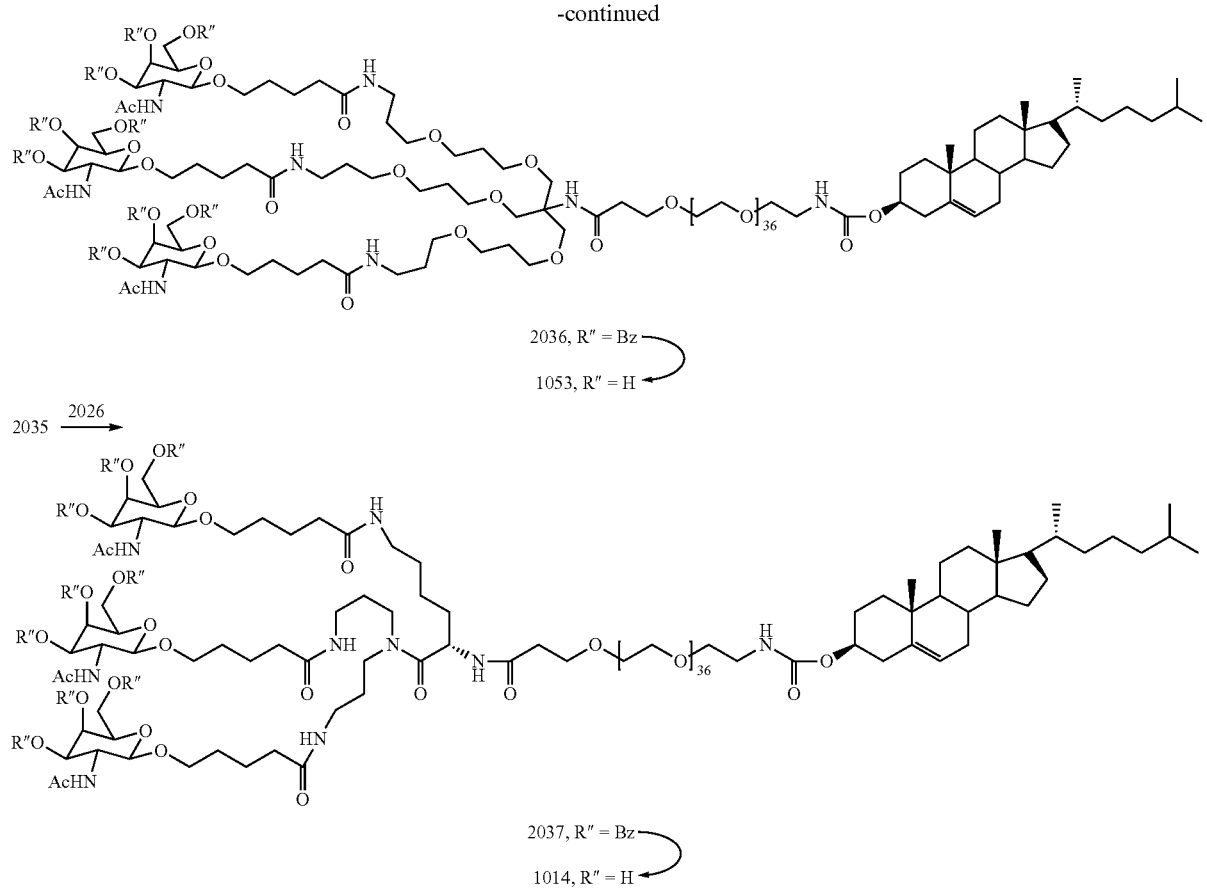
2036, R″ = Bz
1053, R″ = H
2035 →2026
2037, R″ = Bz
1014, R″ = H
Scheme 14
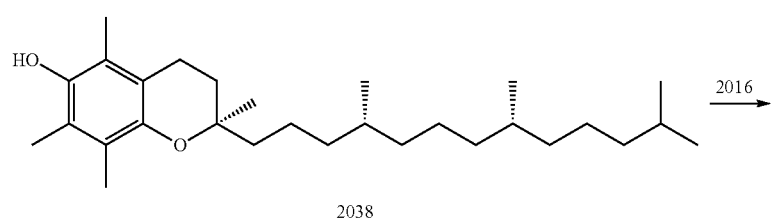
2038
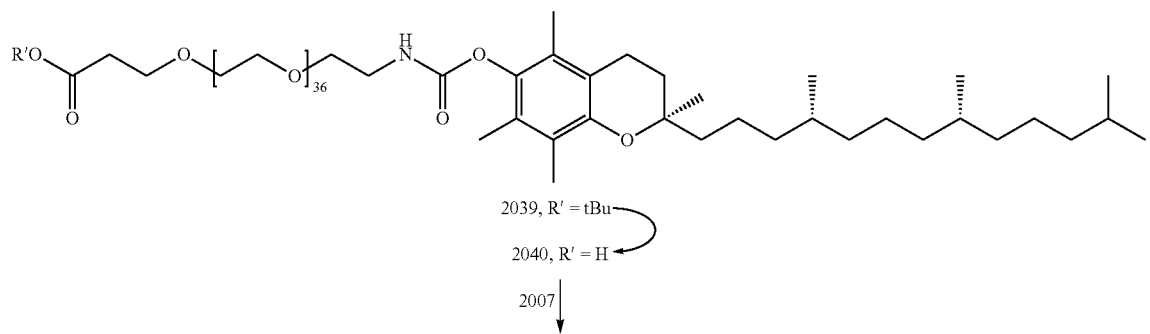
2039, R′ = tBu
2040, R′ = H
2007

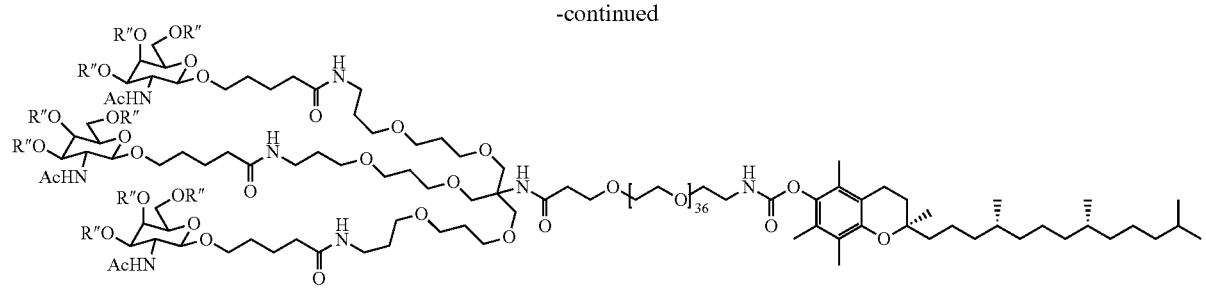
2041, R″ = Bz
1062 n = 36, R″ = H
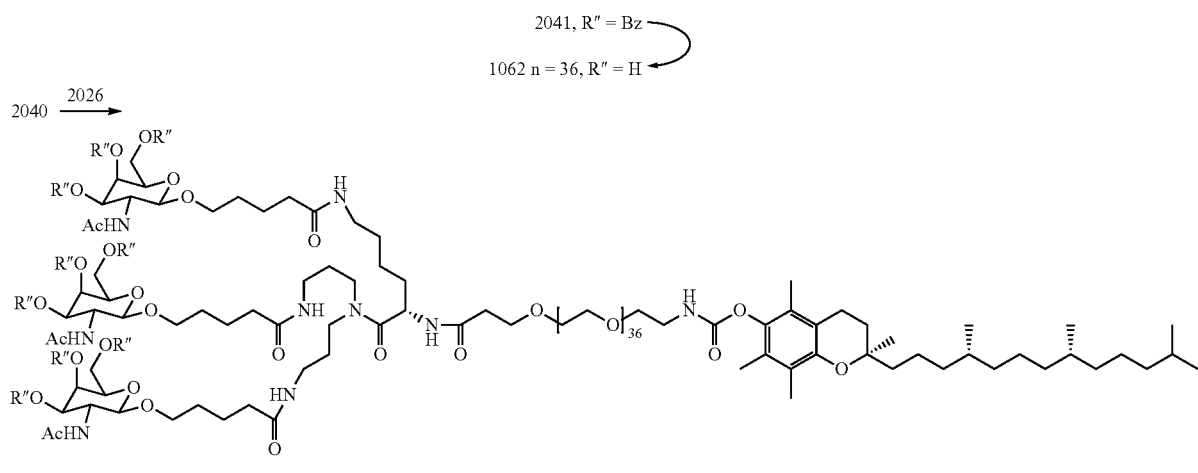
2042, R″ = Bz
1065, n = 36; p, q = 2, R″ = H
Scheme 15
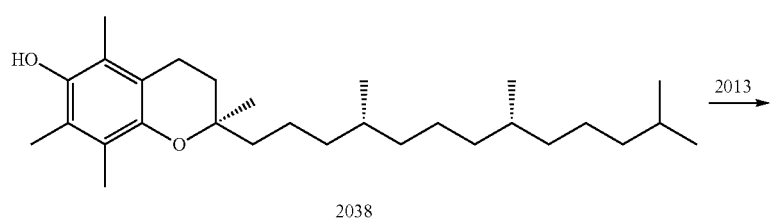
2038
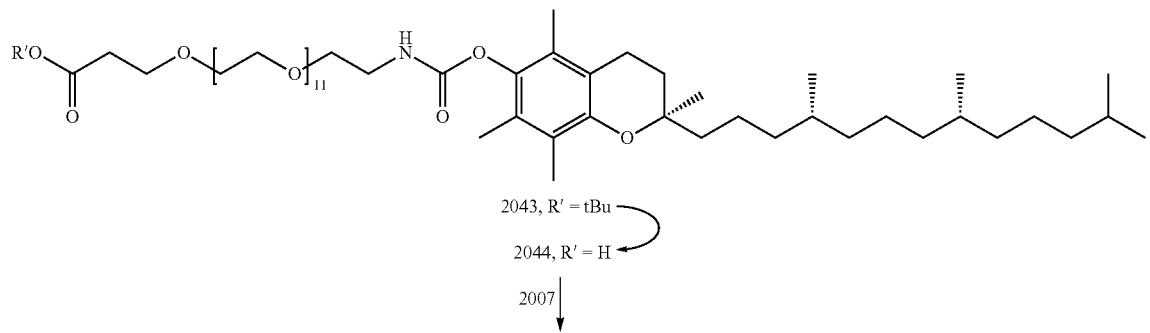
2043, R′ = tBu
2044, R′ = H 347                                  348
-continued
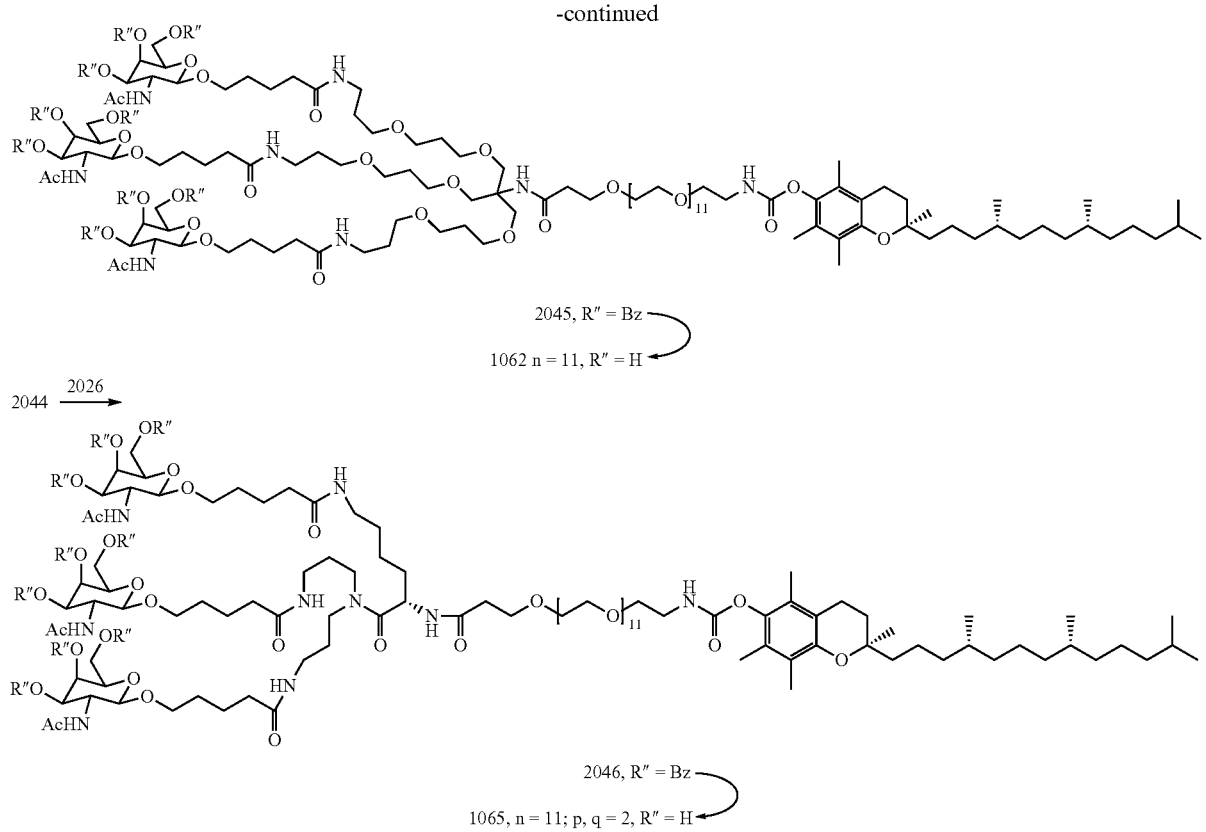
Scheme 16
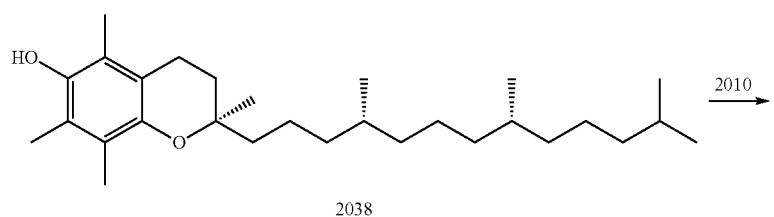
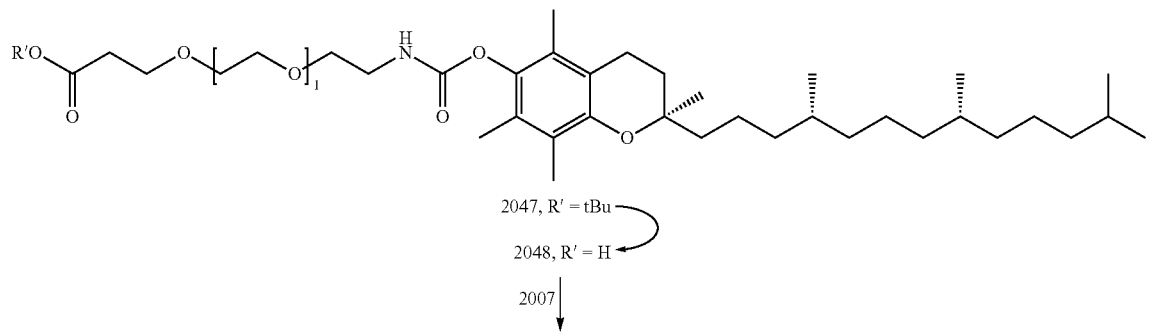

-continued
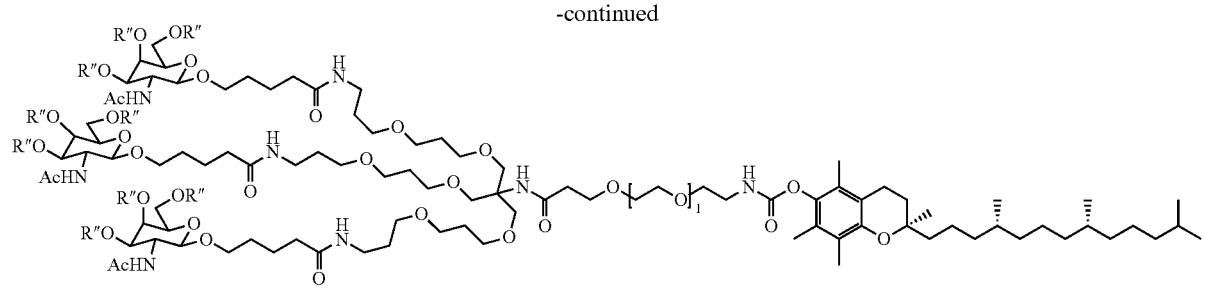
2049, R″ = Bz
1062 n = 1, R″ = H
2048 →(2026)
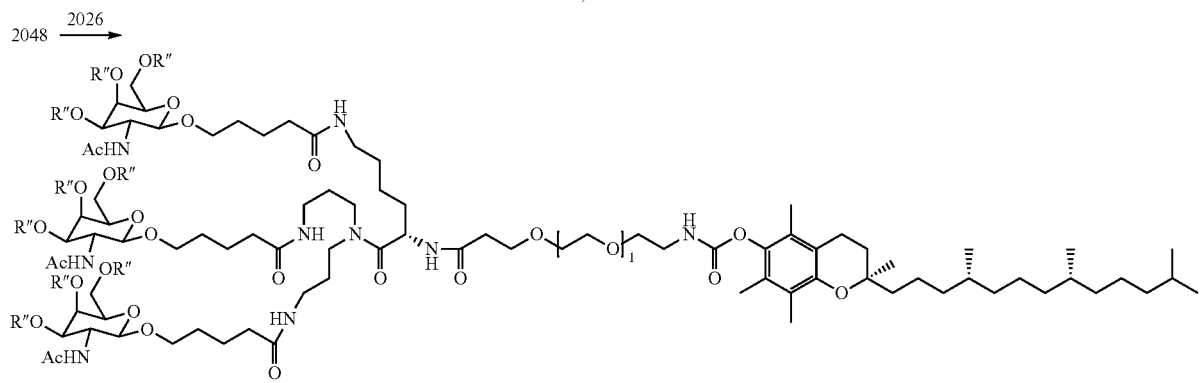
2050, R″ = Bz
1065, n = 1; p, q = 2, R″ = H
Scheme 17
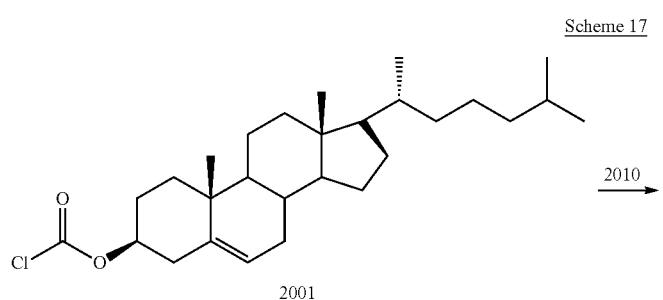
2001 →(2010)
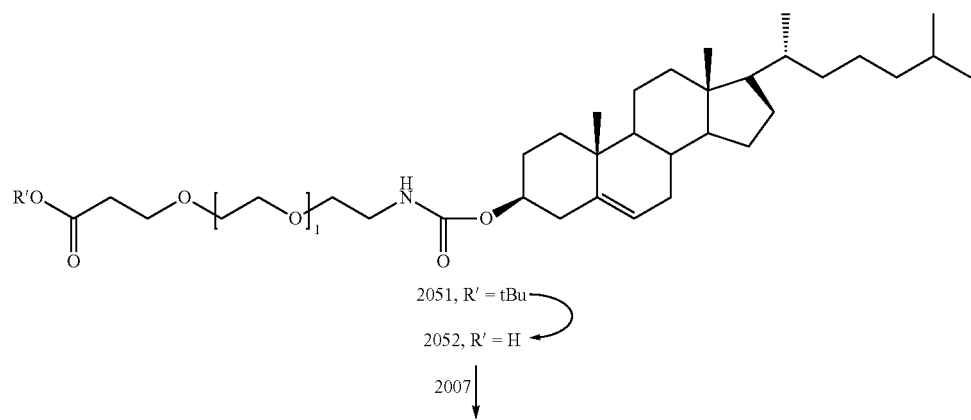
2051, R′ = tBu
2052, R′ = H
↓(2007)

351 352
-continued
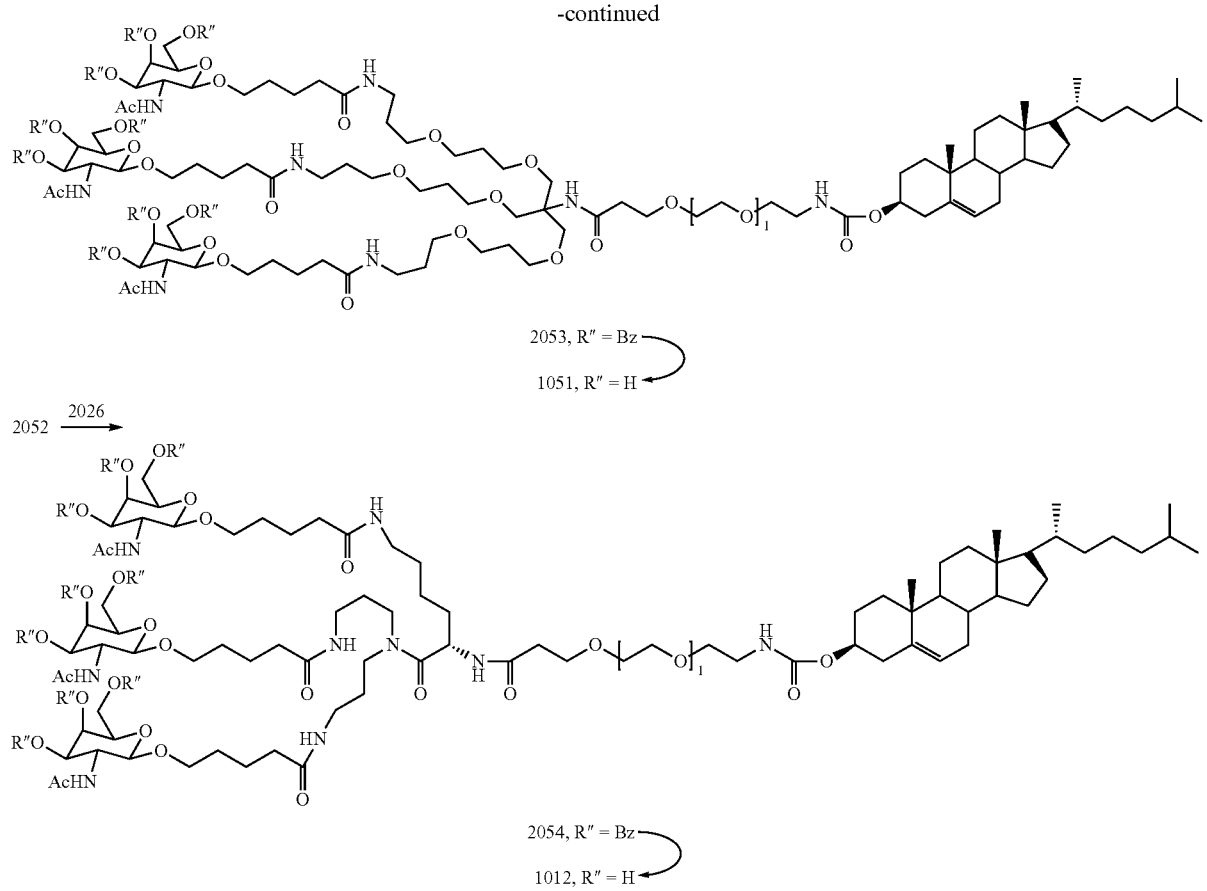
2053, R″ = Bz
1051, R″ = H
2052 →[2026]
2054, R″ = Bz
1012, R″ = H
Scheme 18
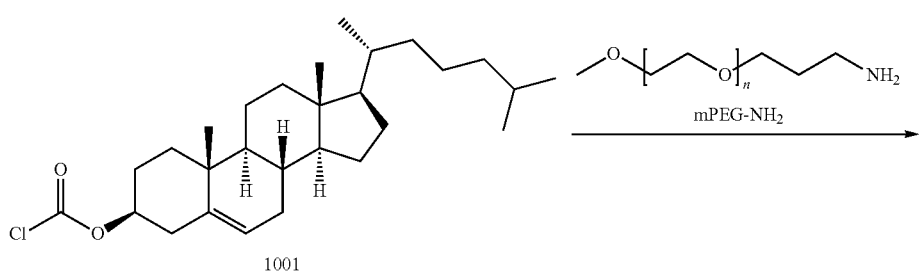
1001
mPEG-NH₂ →
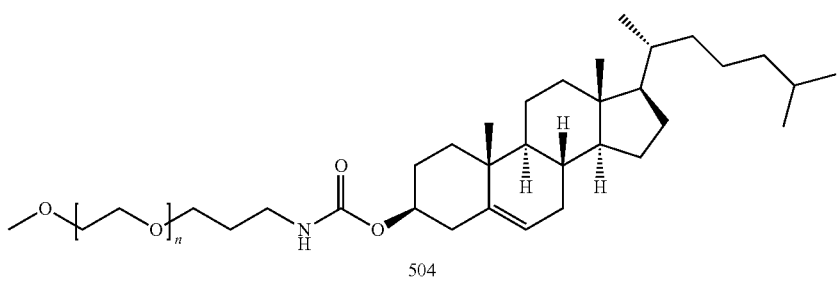
504

Example 15. Synthesis of GalNAc-Lipids 1042, 1043 and 1044

Compound 2002 was prepared according to reported procedure (Organic Lett., 2010, 12, 5262). Compound 2002 (1 mol eq), acrylonitrile (4.6 mol eq) and 5M aq. NaOH (0.166 vol) and THE (10.0 vol) stirred at ambient temperature for 48 h. The reaction mixture was concentrated and the residue was dissolved in ethyl acetate (EtOAc, 5.0 vol) and washed with water and brine. The organic layer was concentrated and purified by column chromatography using EtOAc/MeOH eluent to obtain compound 2003 as a pale yellow liquid (yield: 50%).

Compound 2003 (1 mol eq.) and Raney-Ni (200% w/w) was suspended in 1:1 25% aq. Ammonia/water (10.0 vol) and hydrogenated at 50 kg/cm³ pressure. The reaction mixture was filtered through celite and concentrated to obtain compound 2004 as pale yellow liquid (yield: 84%).

The amine 2004 (1 mol eq.), compound 2005 (J. Am. Chem. Soc. 2014, 136, 16958; 3.6 mol eq.) were stirred with EDC·HCl (4 mol eq.), HOBt (0.1 mol eq) and DIEA (10 mol eq) in DMF (10 vol) at 0° C.-RT for 16 h. The reaction mixture was slowly transferred to ice-water and top layer was decanted. Residue was dissolved in EtOAc, washed with 5% aq. citric acid followed 5% aq. $Na_2CO_3$ and brine. Organic layer was concentrated to obtain crude compound as a foamy solid. The crude thus obtained was then purified by column chromatography to obtain the desired compound 2006 (52%).

Compound 2006 (1 mol eq.) was stirred with trifluoroacetic acid (4 vol.) in dichloromethane, 0° C.-RT for 24 h. The reaction mixture was concentrated to remove volatiles; residue was co-distilled with toluene (2 vol×2). Residue was dissolved in methanol (1 vol) and n-hexane (10 vol); top layer was decanted and the residue was dissolved in dichloromethane. Evaporated solvents and volatiles in vacuo to obtain compound 2007 as a colorless paste (yield: 100%).

Compound 2008 (1 mol eq.) and 4-nitrophenyl chloroformate (4 mol eq.) were stirred in dichloromethane (10 vol) in the presence of pyridine (4 mol eq.) at ambient temperature for 4 h. The reaction mixture was evaporated in vacuo and the residue was purified column chromatography to obtain compound 2009.

Compound 2009 (1 mol eq.) was stirred with the amine 2010 (1.5 mol eq.) in dichloromethane (10 vol) in the presence of pyridine (2 mol eq. at ambient temperature overnight. The reaction mixture was diluted with water. The product was extracted into dichloromethane and concentrated to dryness. The residue was purified by column chromatography to obtain compound 2011 (yield: 81%). Treatment of 2011 (1 mol eq.) with formic acid (5 vol) in dichloromethane at ambient temperature for 6 h. Solvent and volatiles were removed in vacuo. The residue was washed with toluene twice and with diethyl ether to obtain compound 2012 (yield: 80%).

Compound 2009 (1 mol eq.) was stirred with the amine 2013 (1.5 mol eq.) in dichloromethane (10 vol) in the presence of pyridine (2 mol eq.) at ambient temperature overnight. The reaction mixture was diluted with water. The product was extracted into dichloromethane and concentrated to dryness. The residue was purified by column chromatography to obtain compound 2014 (yield: 65%). Treatment of 2014 (1 mol eq.) with formic acid (5 vol) in dichloromethane at ambient temperature for 6 h. Solvent and volatiles were removed in vacuo. The residue was washed with toluene twice and with diethyl ether to obtain compound 2015 (yield: 87%).

Compound 2009 (1 mol eq.) was stirred with the amine 2016 (1.5 mol eq.) in dichloromethane (10 vol) in the presence of pyridine (2 mol eq.) at ambient temperature overnight. The reaction mixture was diluted with water. The product was extracted into dichloromethane and concentrated to dryness. The residue was purified by column chromatography to obtain compound 2017 (yield: 51%). Treatment of 2017 (1 mol eq.) with formic acid (5 vol) in dichloromethane (2 vol) at ambient temperature for 6 h. Solvent and volatiles were removed in vacuo. The residue was washed with toluene twice and with diethyl ether to obtain compound 2018 (yield: 87%).

Compound 2007 (1 mol eq.) and compound 2015 (1.1 mol eq) were mixed with HBTU (1.2 mol eq.), HOBt (0.1 mol eq.) and DIEA (3 mol eq) in dichloromethane (10 vol) at 0° C.-RT under stirring for 2 h. The reaction mixture was washed with water and the organic layer was concentrated in vacuo. The crude product was then purified by silica gel column chromatography to obtain compound 2020 (yield: 35%). To a stirring solution of compound 2020 (0.7 g, 0.19 mmol) in ethanol (3 mL) was added aqueous ammonia (6 mL) at room temperature and the resulting reaction mixture was warmed at 40° C. for 48 h. Reaction mixture is concentrated under reduced pressure at 40° C. The residue obtained is triturated with diethyl ether (2×5 mL) and acetonitrile (3×5 mL), dried under vacuum pressure to afford 1043 as off white solid (200 mg, yield: 38.87%). $^1$H NMR (400 MHz, DMSO-$d_6$): δ 7.70-7.80 (m, 2H), 7.60 (d, J=9.2 Hz, 2H), 7.05-7.15 (m, 4H), 4.44-4.57 (m, 9H), 4.20 (d, J=8.4 Hz, 3H), 3.86-3.98 (m, 2H), 3.62-3.68 (m, 9H), 3.46-3.55 (m, 55H), 3.25-3.39 (m, 18H), 3.02-3.08 (m, 8H), 2.02 (t, J=6.8 Hz, 6H), 1.78 (s, 9H), 1.56-1.69 (m, 12H), 1.40-1.48 (m, 17H), 1.22 (s, 56H), 0.82-0.85 (m, 6H); HRMS (ESI-TOF)m/z: [M+H]$^+$ and [M+Na]$^+$ calculated for 2598.71 and 2620.7. found 2598.72 and 2620.73.

Compound 2007 (1 mol eq.) and compound 2018 (1.1 mol eq) were mixed with HBTU (1.2 mol eq.), HOBt (0.1 mol eq.) and DIEA (3 mol eq) in dichloromethane (10 vol) at 0° C.-RT under stirring for 2 h. The reaction mixture was washed with water and the organic layer was concentrated in vacuo. The crude product was then purified by silica gel column chromatography to obtain compound 2021 (yield: 30%). To a stirred solution of compound 2021 (0.8 g, 0.17 mmol) in ethanol (3 mL) was added aqueous ammonia (6 mL) at room temperature and the resulting reaction mixture was warmed at 40° C. for 48 h. Reaction mixture was concentrated under reduced pressure at 40° C. The residue obtained was triturated with diethyl ether (2×5 mL) and acetonitrile (3×5 mL), dried under vacuum pressure to afford Compound 1044 as off white solid (450 mg, yield: 70%). $^1$H NMR (400 MHz, DMSO-$d_6$): δ 7.71-7.74 (m, 1H), 7.61 (d, J=8.8 Hz, 1H), 7.10-7.14 (m, 1H), 4.52-4.62 (m, 2H), 4.46 (d, J=4.4 Hz, 1H), 4.19 (d, J=8.4 Hz, 1H), 3.86-3.98 (m, 1H), 3.61-3.68 (m, 4H), 3.46-3.55 (m, 57H), 3.27-3.42 (m, 8H), 3.0-3.15 (m, 3H), 2.0-2.03 (m, 2H), 1.78-1.81 (m, 3H), 1.65-1.69 (m, 2H), 1.56-1.59 (m, 2H), 1.38-1.49 (m, 6H), 1.15-1.25 (m, 23H), 0.81-0.85 (m, 2H); HRMS (ESI-TOF) m/z: [M+NH$_4$]$^+$ calculated for 3672.34. found 3672.37.

To a stirred solution of 2019 (850 mg, 00274 mmol) in ethanol (3 mL) was added aqueous ammonia (6 mL) at room temperature and the resulting reaction mixture was warmed at 40° C. for 48 h. Reaction mixture was concentrated under reduced pressure at 40° C. The residue obtained was triturated with diethyl ether (5×15 mL) and acetonitrile (5×10 mL), dried under vacuum pressure to afford 1042 as off white solid (400 mg, yield: 67.5%). $^1$H NMR (400 MHz, DMSO-$d_6$): δ 7.71 (t, J=5.6 Hz, 3H), 7.59 (d, J=9.2 Hz, 3H), 7.12-7.15 (m, 2H), 4.52-4.57 (m, 6H), 4.44 (d, J=4.0 Hz, 3H), 4.20 (d, J=8.4 Hz, 3H), 3.86-3.98 (m, 2H), 3.62-3.68 (m, 9H), 3.45-3.53 (m, 22H), 3.31-3.39 (m, 19H), 3.02-3.10 (m, 9H), 2.02 (t, J=7.2 Hz, 6H), 1.78 (s, 9H), 1.64-1.70 (m, 6H), 1.54-1.61 (m, 6H), 1.38-1.49 (m, 18H), 1.21 (s, 62H), 0.82-0.85 (m, 6H); HRMS (ESI-TOF)m/z: [M+H]$^+$ calculated for 2158.44. found 2158.45.

Example 16. Synthesis of GalNAc-Lipids 1002, 1003 and 1004

Compound 2022 (1 mol eq.) and compound 2022A (1 mol eq.) were stirred with EDC·HCl (1.1 mol eq.) in the presence of DIEA (2 mol eq.) and HOBt (0.1 mol eq.) in DMF at 0° C.-RT for 16 h. The reaction mixture was slowly poured into ice-water and top layer was decanted. The residue was dissolved in EtOAc and washed with 5% aq. citric acid, 5% aq. $Na_2CO_3$ followed by water and brine wash. The organic layer was concentrated to obtain compound 2023 as a foamy solid (yield: 88.7%). The crude product thus obtained could be used for the next step without further purification.

Compound 2023 (1 mol eq.) was stirred with trifluoroacetic acid (4 vol) in dichloromethane (4 vol) at 0° C.-RT for 24 h. The reaction mixture was concentrated in vacuo to remove volatiles, and the residue was co-distilled with toluene. The residue thus obtained was dissolved in methanol (1 vol) and 10 vol of n-hexane was added. Top layer was decanted and the gummy mass was dissolved in dichloromethane and evaporated to get compound 2024 as a colorless paste (yield: 94.3%).

Compound 2024 (1 mol eq.) and compound 2005 (3.6 mol eq.) were stirred with EDC·HCl (4 mol eq.) in the presence of DIEA (10 mol eq.) and HOBt (0.1 mol eq.) in DMF (10 vol) at 0° C.-RT for 16 h. The reaction mixture was slowly poured into ice-water and top layer was decanted. The residue was dissolved in EtOAc and washed with 5% aq. citric acid, 5% aq. $Na_2CO_3$ followed by water and brine wash. The organic layer was concentrated to a foamy solid, which was then purified by column chromatography to obtain compound 2025 as a foamy solid (yield: 70%).

Compound 2025 (1 mol eq.) was suspended on 105 Pd—C in THF:IPA (1:3, 10 vol) and hydrogenated at normal pressure. The reaction mixture was filtered through a celite bed. The filtrate was concentrated in vacuo to an off-white solid, which was subsequently purified by column chromatography to afford compound 2026 (yield: 58%).

Compound 2026 (1 mol eq.) and compound 2012 (1.1 mol eq.) were stirred with HBTU (1.2 mol eq.) in the presence of DIEA (3 mol eq.) and HOBt (0.1 mol eq.) in dichloromethane (10 vol) at 0° C.-RT for 2 h. The reaction mixture was washed with water and the organic layer was concentrated to get crude compound as pale brown foamy solid. Column chromatographic purification of the crude afforded compound 2027 (yield: 60.7%). To a stirred solution of 2027 (1.4 g, 0.48 mmol) in methanol (14.0 mL) was added solution of sodium methoxide (26.0 mg, 0.48 mmol) in methanol (1 mL) at 0° C.±5° C. and the resulting reaction mixture was warmed to room temperature for 2 h. Reaction mixture was diluted with DCM (5.0 mL) and acidified with resin Dowex to pH ~5 to 6. Reaction mixture was filtered through Buchner funnel and filtrate was concentrated under reduced pressure at 40° C. The residue obtained was triturated with diethyl ether (5×20 mL) and acetonitrile (5×10 mL), dried under vacuum pressure to afford 1003 as off white solid (0.5 g, yield: 52.9%). $^1$H NMR (400 MHz, DMSO-$d_6$): δ 8.11 (d, J=8 Hz, 1H), 7.83 (t, J=5.2 Hz, 1H), 7.69-7.74 (m, 2H), 7.62 (d, J=8.8 Hz, 3H), 7.18 (t, J=5.6 Hz, 1H), 4.52-4.60 (m, 1H), 4.20-4.25 (m, 3H), 3.80-4.05 (m, 19H), 3.64-3.74 (m, 1OH), 3.42-3.52 (m, 17H), 3.25-3.40 (m, 16H), 2.97-3.10 (m, 9H), 2.30-2.41 (m, 2H), 2.01-2.08 (m, 6H), 1.79 (s, 9H), 1.42-1.50 (m, 21H), 1.22 (s, 61H), 0.82-0.86 (m, 6H); HRMS (ESI-TOF)m/z: [M+H]$^+$ and [M+Na]$^+$ calculated for 1951.31 and 1973.31. found 1951.31 and 1973.29.

Compound 2026 (1 mol eq.) and compound 2015 (1.1 mol eq.) were stirred with HBTU (1.2 mol eq.) in the presence of DIEA (3 mol eq.) and HOBt (0.1 mol eq.) in dichloromethane (10 vol) at 0° C.-RT for 2 h. The reaction mixture was washed with water and the organic layer was concentrated to get crude compound as pale brown foamy solid. Column chromatographic purification of the crude afforded compound 2028 (yield: 68.7%). To a stirred solution of 2028 (1.2 g, 0.36 mmol) in ethanol (3.0 mL) was added aqueous ammonia (6.0 mL) at room temperature and the resulting reaction mixture was warmed at 40° C. for 48 h. Reaction mixture was concentrated under reduced pressure at 40° C. The residue obtained was triturated with diethyl ether (3×10 mL) and acetonitrile (4×10 mL), dried under vacuum pressure to afford compound 1002 as off white solid (470 mg, yield: 54.5%). $^1$H NMR (400 MHz, DMSO-$d_6$): δ 8.09 (d, J=8 Hz, 1H), 7.81 (t, J=5.2 Hz, 1H), 7.67-7.72 (m, 2H), 7.60 (d, J=9.2 Hz, 3H), 7.13 (t, J=5.6 Hz, 1H), 4.52-4.58 (m, 7H), 4.44 (d, J=4.0 Hz, 3H), 4.20 (d, J=8.4 Hz, 3H), 3.86-3.98 (m, 3H), 3.57-3.71 (m, 10H), 3.42-3.52 (m, 55H), 2.94-3.11 (m, 8H), 2.0-2.06 (m, 6H), 1.78 (s, 9H), 1.35-1.75 (m, 21H), 1.22 (s, 60H), 0.80-0.85 (m, 6H); HRMS (ESI-TOF)m/z: [M+H]$^+$ calculated for 2391.57. found 2391.58.

Compound 2026 (1 mol eq.) and compound 2018 (1.1 mol eq.) were stirred with HBTU (1.2 mol eq.) in the presence of DIEA (3 mol eq.) and HOBt (0.1 mol eq.) in dichloromethane (10 vol) at 0° C.-RT for 2 h. The reaction mixture was washed with water and the organic layer was concentrated to get crude compound as pale brown foamy solid. Column chromatographic purification of the crude afforded compound 2029 (yield: 68.7%). To a stirred solution of 2029 (0.55 g, 0.12 mmol) in ethanol (2.0 mL) was added aqueous ammonia (4.0 mL) at room temperature and the resulting reaction mixture was warmed at 40° C. for 48 h. Reaction mixture was concentrated under reduced pressure at 40° C. The residue obtained was triturated with diethyl ether (2×5 mL) and acetonitrile (3×5 mL), dried under vacuum pressure to afford 1004 as off white solid (230 mg, yield: 53.17%). $^1$H NMR (400 MHz, DMSO-$d_6$): δ 8.11 (d, J=10 Hz, 1H), 7.85-7.95 (m, 1H), 7.70-7.80 (m, 1H), 7.62 (d, J=11.6 Hz, 2H), 7.14 (bs, 1H), 4.47-4.57 (m, 8H), 4.21 (d, J=10.8 Hz, 2H), 3.95-4.05 (m, 3H), 3.86-3.96 (m, 3H), 3.63-3.67 (m, 13H), 3.28-3.38 (m, 30H), 2.95-3.15 (m, 1OH), 1.95-2.15 (m, 6H), 1.79 (s, 9H), 1.35-1.45 (m, 20H), 1.22 (s, 52H), 0.85-0.95 (m, 6H); HRMS (ESI-TOF)m/z: [M+H]$^+$ calculated for 3448.20. found 3448.21.

Example 17. Synthesis of GalNAc-Lipids 1013 and 1052

Cholesteryl chloroformate was reacted with compound 2013 in the presence of base in dichloromethane afforded compound 2030. Compound 2030 was treated with formic acid in THF to afford compound 2031. Compound 2031 was reacted with compound 2007 as described in Example 16 to yield compound 2032. To a stirred solution of 2032 (880 mg, 0.264 mmol) in ethanol (3 mL) was added aqueous ammonia (6 mL) at room temperature and the resulting reaction mixture was warmed at 40° C. for 48 h. Reaction mixture was concentrated under reduced pressure at 40° C. The residue obtained was triturated with diethyl ether (10×10 mL), dried under vacuum pressure to afford 1052 as off white solid (500 mg, yield: 79.5%). $^1$H NMR (400 MHz, DMSO-d$_6$): δ 7.65-7.75 (m, 1H), 7.81 (bs, 1H), 7.70-7.80 (m, 1H), 7.59-7.61 (d, J=8.4 Hz, 2H), 7.0-7.11 (bs, 3H), 5.30 (s, 1H), 4.50-4.70 (m, 6H), 4.40-4.50 (m, 3H), 4.26-4.44 (m, 3H), 3.61-3.67 (m, 8H), 3.35-3.47 (m, 45H), 2.95-3.07 (m, 8H), 1.95-2.01 (m, 6H), 1.76 (s, 13H), 1.30-1.47 (m, 26H), 1.05-1.15 (m, 8H), 0.95-1.0 (m, 4H), 0.8-0.95 (m, 8H), 0.65 (s, 3H); HRMS (ESI-TOF)m/z: [M+H]$^+$ calculated for 2374.91. found 2374.37.

To a stirred solution of 2033 (730 mg, 0.23 mmol) in ethanol (3 mL) was added aqueous ammonia (6 mL) at room temperature and the resulting reaction mixture was warmed at 40° C. for 48 h. Reaction mixture was concentrated under reduced pressure at 40° C. The residue obtained was triturated with diethyl ether (5×10 mL), dried under vacuum pressure to afford 1013 as off white solid (500 mg, yield: 97.9%). $^1$H NMR (400 MHz, DMSO-d$_6$): δ 8.08 (d, J=7.2 Hz, 1H), 7.80-7.90 (m, 1H), 7.65-7.75 (m, 2H), 7.60 (d, J=8.4 Hz, 2H), 7.0-7.11 (m, 3H), 5.30 (s, 1H), 4.51-4.55 (m, 6H), 4.44-4.45 (m, 2H), 4.17-4.27 (m, 3H), 3.62-3.70 (m, 8H), 3.37-3.60 (m, 45H), 2.95-3.15 (m, 8H), 1.95-2.10 (m, 6H), 1.76 (s, 9H), 1.25-1.75 (m, 30H), 1.05-1.20 (m, 9H), 0.80-1.0 (m, 12H), 0.45-.55 (m, 3H); HRMS (ESI-TOF)m/z: [M+H]$^+$ calculated for 2181.67. found 2182.32.

Example 18. Synthesis of GalNAc-Lipids 1014 and 1053

To a stirred solution of 2037 (0.9 g, 0.21 mmol) in ethanol (3 mL) was added aqueous ammonia (6 mL) at room temperature and the resulting reaction mixture was warmed at 40° C. for 48 h. Reaction mixture was concentrated under reduced pressure at 40° C. The residue obtained was triturated with diethyl ether (6×10 mL), dried under vacuum pressure to afford 1014 (300 mg, yield: 42.97%) as off white solid. $^1$H NMR (400 MHz, DMSO-d$_6$): δ 8.10 (d, J=8.0 Hz, 1H), 7.83 (t, J=6.8 Hz, 1H), 7.72 (q, J=5.6 Hz, 2H), 7.62 (d, J=8.4 Hz, 3H), 7.02 (t, J=5.2 Hz, 1H), 5.33 (bs, 1H), 4.53-4.59 (m, 7H), 4.46 (d, J=4.0 Hz, 3H), 4.20-4.32 (m, 4H), 3.63-3.72 (m, 11H), 3.30-3.60 (m, 157H), 2.95-3.15 (m, 9H), 2.26-2.38 (m, 3H), 2.03-2.08 (m, 6H), 1.90-2.0 (m, 2H), 1.75-1.86 (m, 13H), 1.30-1.60 (m, 31H), 0.95-1.15 (m, 13H), 0.83-0.90 (m, 1OH), 0.64 (s, 3H); HRMS (ESI-TOF) m/z: [M+H]$^+$ calculated for 3238.94. found 3238.95.

To a stirred solution of 2036 (1.2 mg, 0.264 mmol) in ethanol (6 mL) was added aqueous ammonia (12 mL) at room temperature and the resulting reaction mixture was warmed at 40° C. for 48 h. Reaction mixture was concentrated under reduced pressure at 40° C. The residue obtained was triturated with diethyl ether (12×10 mL), dried under vacuum pressure to afford 1053 as off white wax (500 mg, yield: 53.0%). $^1$H NMR (400 MHz, DMSO-d$_6$): δ 7.70-7.75 (m, 2H), 7.59 (d, J=8.8 Hz, 2H), 6.95-7.15 (m, 4H), 5.32 (bs, 1H), 4.51-4.56 (m, 2H), 4.44-4.45 (m, 1H), 4.18 (d, J=8.4 Hz, 1H), 3.61-3.67 (m, 4H), 3.34-3.67 (m, 51H), 3.29-3.34 (m, 6H), 3.03-3.05 (m, 3H), 2.0-2.04 (m, 3H), 1.88-1.96 (m, 2H), 1.76 (s, 4H), 1.65-1.75 (m, 2H), 1.55-1.65 (m, 3H), 1.30-1.50 (m, 8H), 1.0-1.20 (m, 3H), 0.90-0.93 (m, 1H), 0.86 (d, J=6.4 Hz, 1H), 0.81 (dd, J=6.4 Hz, J=1.6 Hz, 2H), 0.6 (s, 1H); HRMS (ESI-TOF)m/z: [M+H]$^+$ calculated for 3446.05. found 3446.08.

Example 19. Synthesis of GalNAc-Lipids 1062 and 1065

Compound 2038 is reacted with 4-nitrophenyl chloroformate in the presence of a base to form the corresponding 4-nitrophenyl carbonate. The carbonate thus formed is reacted with compound 2016 to yield compound 2039. Compound 2039 is treated with formic acid to obtain compound 2040. Compound 2040 is coupled to 2007 under peptide coupling conditions as described in Example 15 afforded compound 2041. Compound 2041 is treated with NaOMe followed by work-up and purification as described in Example 15/16 afforded compound 1062.

Compound 1065 is prepared from compounds 2040 and 2026 as described above.

Example 20. Synthesis of GalNAc-Lipids 1062 and 1065

Compound 2038 is reacted with 4-nitrophenyl chloroformate in the presence of a base to form the corresponding 4-nitrophenyl carbonate. The carbonate thus formed is reacted with compound 2013 in the presence of base in dichloromethane afforded compound 2043. Compound 2043 is treated with formic acid in THF to afford compound 2044. Compound 2044 is reacted with compound 2007 as described in Example 16 to yield compound 2045. Compound 2045 is treated with NaOMe and followed similar work-up and purification afforded compound 1062.

Compound 1065 is prepared from compounds 2044 and 2026 as described above. Compounds 1083, 1084 and 1085 may also be prepared from galactose in a similar manner in accordance with preparation of 1004 as described above.

Scheme 18

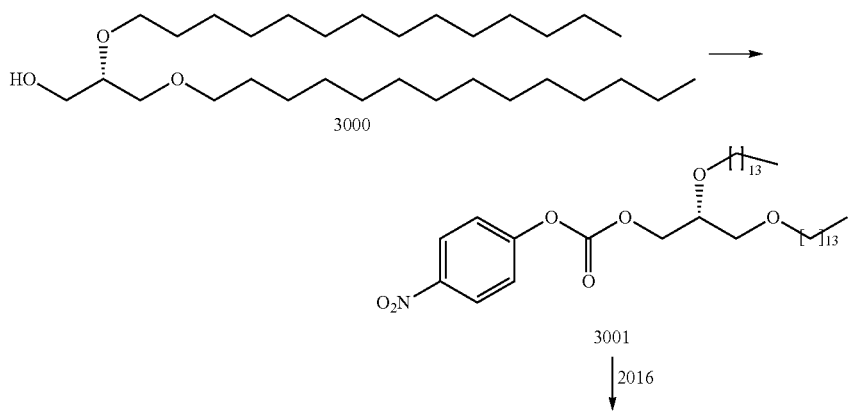

-continued
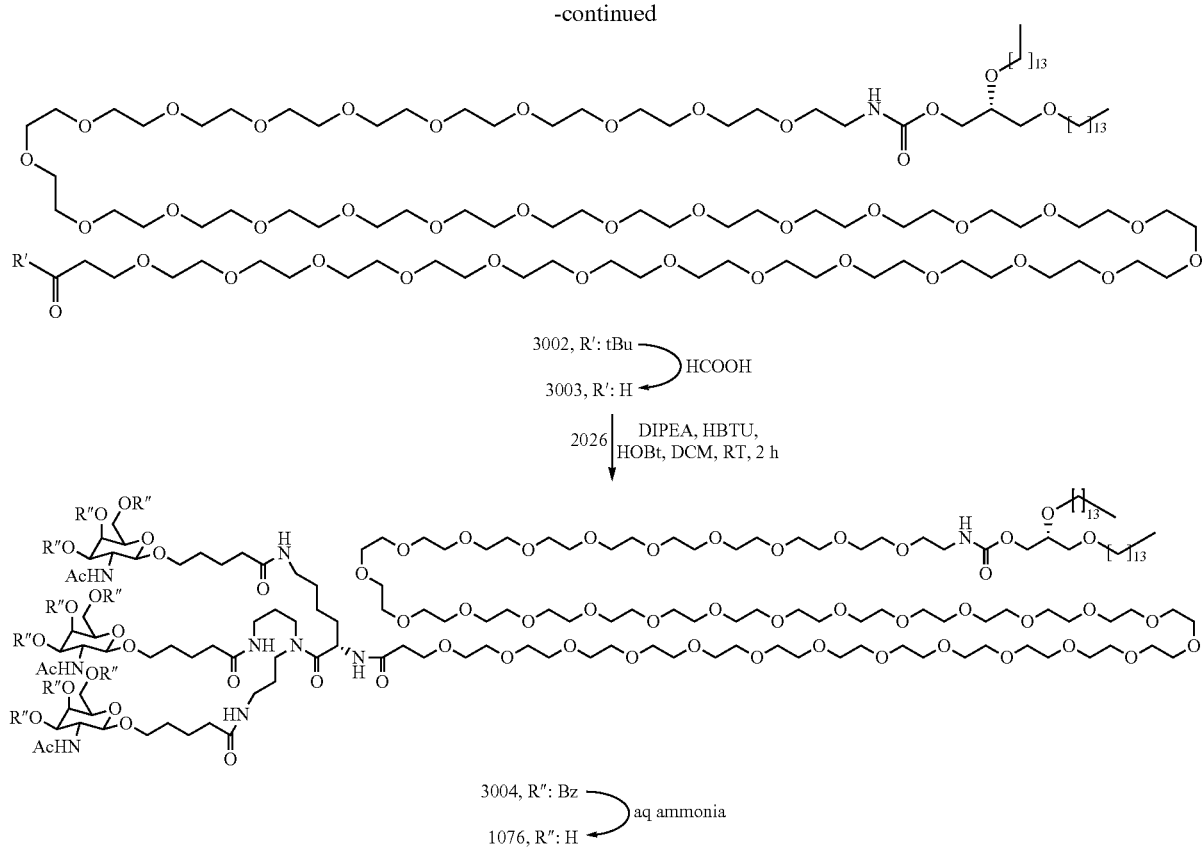
Scheme 19
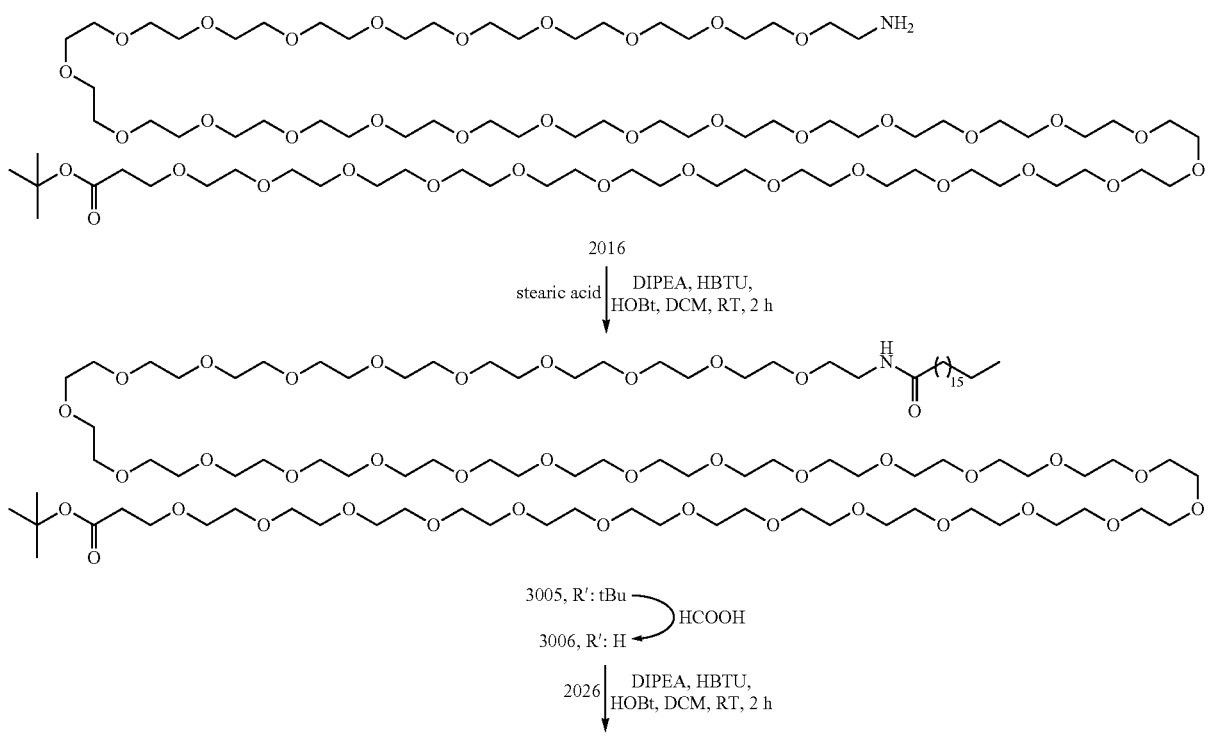

-continued

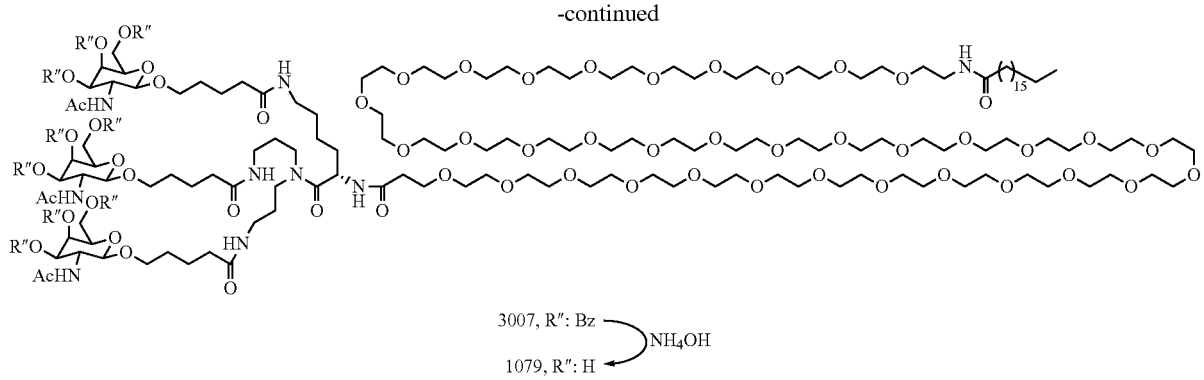

3007, R″: Bz ⎫
               ⎬ NH₄OH
1079, R″: H  ⎭

Scheme 20

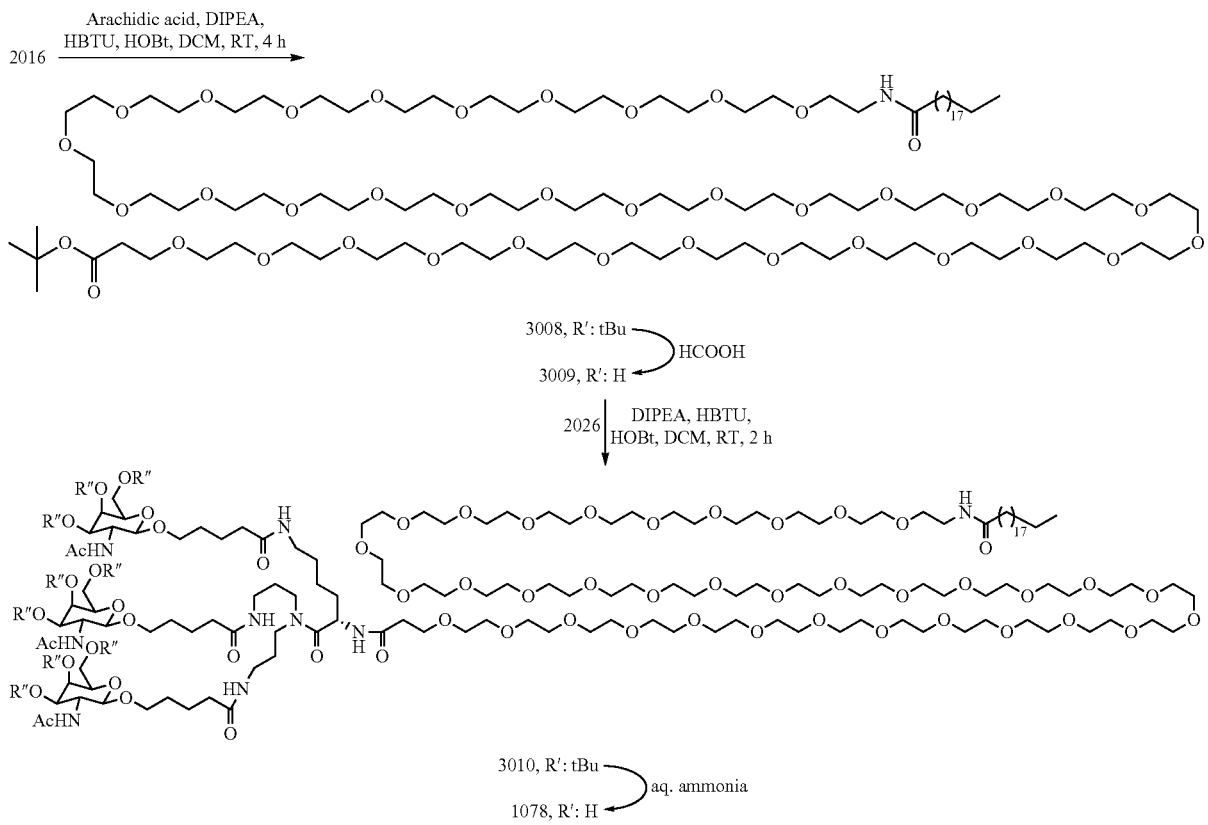

3008, R′: tBu ⎫
               ⎬ HCOOH
3009, R′: H  ⎭

2026 | DIPEA, HBTU, HOBt, DCM, RT, 2 h

3010, R′: tBu ⎫
               ⎬ aq. ammonia
1078, R′: H  ⎭

Example 20A: Exemplary synthesis of GalNAc-Lipid 1076: To a suspension of 3000 (4.6 g, 9.5 mmol) in DCM (46 mL) was added pyridine (3.0 mL) drop wise at room temperature (RT) over a period of 10 min. To the above solution, p-Nitrophenylchloroformate (7.66 g, 38.0 mmol) was added portion wise and the resulting suspension stirred at RT for 1 h. Reaction mixture was concentrated under reduced pressure and the crude mass was purified by silica gel column chromatography (CombiFlash rf) using 800 EtOAc in Hexane as eluent to yield 3001 as color less liquid (3.01 g, yield: 48.78% o). ¹H NMR (400 MHz, CDCl₃): δ 8.26-8.29 (m, 2H), 7.37-7.41 (m, 2H), 5.44-5.48 (m, 1H), 4.31-4.35 (m, 1H), 3.71-3.73 (m, 1H), 3.44-3.61 (m, 6H), 1.53-1.60 (m, 4H), 1.25-1.31 (m, 8H), 0.86-0.89 (in, 6H). To a stirred solution of 3001 (3 g, 4.6 mmol) in DCM (30 mL) was added pyridine (0.74 mL) and 2016 (11.98 g, 6.9 mol) at RT. The reaction was continued for 12 h at RT and the reaction mixture was concentrated under reduced and the crude compound was purified by neutral alumina column chromatography (CombiFlash rf) using 80% o EtOAc in Hexane as eluent to afford 3002 as off white solid (5.35 g, yield: 51.890%). ¹H NMR (400 MHz, DMSO-d₆): δ 7.13 (t, J=5.6 Hz, 1H), 3.86-3.99 (m, 2H), 3.47-3.57 (m, 4H), 3.30-3.49 (m, 146H), 3.07-3.11 (m, 2H), 2.39-2.49 (m, 2H), 1.45-1.55 (m, 4H), 1.45 (s, 9H), 1.20-1.45 (m, 43H), 0.75-0.85 (in, 6H).

Formic acid (35.0 mL) was added to a stirred solution of 3002 (5.0 g, 2.2 mmol) in DCM (10 mL) at ice cold temperature and the resulting reaction was stirred at RT for 6 h. The reaction mixture was concentrated to remove formic acid and co-distilled with toluene under reduced pressure to get the desired 3003 as off-white solid (4.28 g, yield: 89.1%). 3003 was used as is in the next step. $^{1}$H NMR (400 MHz, CDCl$_3$): δ 5.27 (bs, 1H), 4.06-4.20 (m, 4H), 3.75-3.85 (m, 3H), 3.50-3.70 (m, 144H), 3.30-3.50 (m, 6H), 2.59 (t, J=6 Hz, 2H), 1.53-1.56 (m, 4H), 1.20-1.30 (m, 45H), 0.80-0.90 (m, 6H). To a stirred solution of 3003 (3.32 g, 1.5 mmol) in DCM (32.0 mL) was added HOBt (0.02 g, 0.15 mmol) and HBTU (0.71 g, 1.8 mmol) at ice cold temperature followed by the addition of DIPEA (0.78 mL, 4.5 mmol). A solution of 2026 (3.2 g, 1.5 mmol) in DCM (15.0 mL) was added to above reaction at RT and the resulting reaction mixture was stirred for 1 h at RT. Water (30.0 mL) was added to the reaction mixture and extracted with DCM (2×30.0 mL). The combined organic layers washed with saturated aqueous sodium bicarbonate solution (50.0 mL) followed by brine (50.0 mL), dried over anhydrous sodium sulfate. The organic layer was filtered and filtrate was evaporated under reduced pressure. The crude was purified by silica gel column chromatography (CombiFlash rf) using 10% MeOH in DCM as eluent to afford 3004 (2.9 g, yield: 45.24%) as grey semisolid. $^{1}$H NMR (400 MHz, DMSO-d$_6$): δ 7.97-8.13 (m, 4H), 7.88-7.92 (m, 12H), 7.83 (t, J=4.8 Hz, 1H), 7.66-7.73 (m, 11H), 7.62 (t, J=7.2 Hz, 3H), 7.53-7.58 (m, 9H), 7.47 (t, J=7.6 Hz, 6H), 7.37 (t, J=8 Hz, 6H), 7.15 (t, J=6 Hz, 1H), 5.73-5.75 (m, 3H), 5.35 (dd, J=10.8 Hz, J=2.8 Hz, 3H), 4.71 (d, J=8.4 Hz, 3H), 4.45-4.57 (m, 1H), 4.41-4.45 (m, 6H), 4.22-4.35 (m, 6H), 3.30-4.0 (m, 12H), 3.08-3.20 (m, 9H), 2.03-2.07 (m, 1.68 (s, 11H), 1.42-1.49 (m, 22H), 1.21-1.30 (m, 48H), 0.80-0.90 (m, 6H).

Aqueous ammonia (16.8 mL) was added to a stirred solution of 3004 (2.8 g, 0.69 mmol) in ethanol (8.4 mL) at RT and the resulting reaction mixture was stirred at 40° C. for 48 h. Reaction mixture was concentrated under reduced pressure. The resultant residue was triturated with diethyl ether (10×50 mL) and the residue was dried under vacuum pressure to afford 1076 as pale yellow solid (1.85 g, yield: 80.43%). $^{1}$H NMR (400 MHz, DMSO-d$_6$): δ 8.11 (d, J=5.6 Hz, 1H), 7.81-7.84 (m, 1H), 7.69-7.74 (m, 2H), 7.61 (d, J=8.8 Hz, 3H), 7.14 (t, J=5.6 Hz, 1H), 4.54-4.59 (m, 7H), 4.46-4.47 (m, 3H), 4.20 (d, J=8.4 Hz, 3H), 3.86-3.99 (m, 2H), 3.62-3.68 (m, 1OH), 3.30-3.50 (m, 159H), 2.96-3.11 (m, 11H), 2.0-2.07 (m, 7H), 1.78 (s, 9H), 1.41-1.47 (m, 26H), 1.18-1.22 (m, 54H), 0.80-0.85 (m, 8H); HRMS (ESI-TOF)m/z: [M+H]$^+$ calculated for 3336.08. found 3336.0.

Example 20B: Exemplary Synthesis of 1079 (Scheme 19)

To a stirred solution of stearic acid (0.43 g, 1.51 mmol) in DCM (8.6 mL) was added HOBt (0.02 g, 0.15 mmol) at RT. To this reaction mixture was added HBTU (0.72 g, 1.81 mmol) at ice cold temperature followed by addition of DIPEA (0.78 mL, 4.53 mmol). A solution of 2016 (2.61 g, 1.51 mmol) in DCM (2.1 mL, 5 vol) was added at ice cold temperature to the above reaction mixture and the resulting mixture was stirred for 4 h at RT. Water (30.0 mL) was added to reaction and extracted with DCM (2×30 mL). The combined organic layers was washed with brine (30.0 mL), dried over anhydrous sodium sulfate, and filtered. The filtrate was evaporated under reduced pressure and the crude was purified by silica gel column chromatography (CombiFlash rf) using 10% MeOH in DCM as eluent to afford 3005 as off white solid (2.31 g, Yield: 76.74%). $^{1}$H NMR (400 MHz, CDCl$_3$): δ 6.30-6.40 (bs, 1H), 3.38-3.72 (m, 151H), 2.68 (bs, 3H), 2.49 (t, J=8.8 Hz, 2H), 2.19 (t, J=9.6 Hz, 2H), 1.61-1.64 (m, 4H), 1.45 (s, 9H), 1.20-1.45 (m, 29H), 0.80-0.85 (m, 3H).

Formic acid (14.7 mL) was added to a stirred solution of 3005 (2.1 g, 1.0 mmol) in DCM (10.5 mL) at ice cold temperature. The resulting reaction mixture was stirred at room temperature for 12 h. The reaction mixture was concentrated to remove formic acid and co-distilled with toluene (3×) under reduced pressure. The residue was triturated with diethyl ether (21.0 mL), filtered and resultant residue was dried under vacuum pressure to obtain 3006 as off-white solid (1.81 g, yield: 88.72%). $^{1}$H NMR (400 MHz, CDCl$_3$): δ 6.25 (bs, 1H), 3.54-3.81 (m, 144H), 3.42-3.47 (m, 3H), 2.59 (t, J=6.4 Hz, 2H), 2.17 (t, J=7.6 Hz, 2H), 1.40-1.63 (m, 4H), 1.20-1.45 (m, 27H), 0.80-0.85 (m, 3H).

To a stirred solution of 3006 (0.58 g, 0.29 mmol) in DCM (8.0 mL) was added HOBt (0.038 g, 0.028 mmol) at RT. To this reaction mixture was added HBTU (0.13 g, 0.34 mmol) at ice cold temperature followed by DIPEA (0.14 mL, 0.85 mmol). A solution of 2026 (0.6 g, 0.28 mmol) in DCM (3.0 mL) was added at ice cold temperature to above and the resulting reaction mixture was stirred for 2 h at RT. To the reaction mixture was added water (25 mL) and extracted with DCM (2×20 mL). The combined organic layer was washed with brine (30 mL), dried over anhydrous sodium sulphate, and filtered. The filtrate was evaporated under reduced pressure and crude was purified by silica gel column chromatography (CombiFlash rf) using 10% MeOH in DCM as eluent to afford 3007 as grey semisolid (0.76 g, yield: 66.66%). $^{1}$H NMR (400 MHz, DMSO-d$_6$): δ 8.74 (bs, 1H), 8.11 (d, J=8 Hz, 1H), 7.99 (d, J=9.2 Hz, 3H), 7.88-7.92 (m, 13H), 7.78-7.85 (m, 2H), 7.66-7.74 (m, 11H), 7.62 (t, J=7.2 Hz, 3H), 7.52-7.58 (m, 9H), 7.47 (t, J=8 Hz, 6H), 7.39 (t, J=8 Hz, 6H), 5.73-5.75 (m, 3H), 5.35 (dd, J=14 Hz, J=3.2 Hz, 3H), 4.72 (d, J=8.4 Hz, 3H), 4.50-4.57 (m, 1H), 4.41-4.45 (m, 6H), 4.24-4.33 (m, 6H), 3.76-3.79 (m, 3H), 3.43-3.61 (m, 175H), 3.32-3.38 (m, 3H), 3.08-3.16 (m, 8H), 2.90-3.0 (m, 5H), 2.0-2.07 (m, 8H), 1.68 (s, 12H), 1.40-1.49 (m, 21H), 1.21-1.27 (m, 62H), 0.80-0.90 (m, 3H).

To a stirred solution of 3007 (0.75 g, 0.69 mmol) in ethanol (2.2 mL) was added aqueous ammonia (4.5 mL) at RT and the resulting reaction was continued at 40° C. for 48 h. Reaction mixture was concentrated under reduced pressure and the crude was triturated with diethyl ether (5×20 mL). The solid residue after filtration was dried under reduced pressure to afford 1079 as off white solid (0.35 g, yield: 60.8%). $^{1}$H NMR (400 MHz, DMSO-d$_6$): δ 8.11 (d, J=7.6 Hz, 1H), 7.80-7.85 (m, 2H), 7.70-7.75 (m, 2H), 7.63 (d, J=8.4 Hz, 3H)), 4.47-4.59 (m, 9H), 4.20 (d, J=8 Hz, 3H), 3.62-3.68 (m, 12H), 3.49 (s, 141H), 2.97-3.16 (m, 11H), 2.0-2.03 (m, 8H), 1.78 (s, 9H), 1.42-1.47 (m, 19H), 1.21 (s, 29H), 0.80-0.855 (m, 3H); HRMS (ESI-TOF) m/z: [M+H]$^+$ calculated for 3091.87. found 3092.75.

Example 20C: Exemplary Synthesis of 1078 (Scheme 20)

To a stirred solution of arachidic acid (0.46 g, 1.40 mmol) in DCM (10.0 mL)) was added HOBt (0.018 g, 0.14 mmol) at RT. To this reaction mixture was added HBTU (0.67 g, 1.68 mmol) at ice cold temperature followed by DIPEA (0.76 mL, 4.20 mmol). A solution of 2016 (2.54 g, 1.40 mmol) in DCM (5 mL) was added at ice cold temperature and the resulting reaction mixture was stirred for 4 h at RT. To the reaction mixture was added water (30.0 mL) and extracted with DCM (2×30 mL). The combined organic layer was washed with brine (30.0 mL), dried over anhydrous sodium sulphate and filtered. Filtrate was evaporated under reduced pressure and obtained crude was purified by silica gel column chromatography using 10% MeOH in DCM as eluent to afford 3008 as off white solid (2.52 g, yield: 89.04%). $^1$H NMR (400 MHz, CDCl$_3$): δ 6.38 (bs, 1H), 3.38-3.72 (m, 132H), 2.47-2.57 (m, 4H), 2.19 (t, J=9.6 Hz, 1H), 1.61-1.64 (m, 1H), 1.43 (s, 9H), 1.20-1.24 (m, 29H), 0.80-0.85 (m, 3H).

Formic acid (16.1 mL) was added to a stirred solution of 3008 (2.3 g, 1.10 mmol) at ice cold temperature in DCM (11.5 mL) and the resulting reaction mixture was stirred for 12 h at room temperature. The reaction mixture was concentrated to remove formic acid and co-distilled with toluene (3×) under reduced pressure and obtained residue was triturated with diethyl ether (23 mL), filtered and the residue was dried under high vacuum to yield 3009 as off-white solid (2.11 g, yield: 94.6%). $^1$H NMR (400 MHz, CDCl$_3$): δ 6.29 (bs, 1H), 5.03 (bs, 3H), 3.54-3.82 (m, 146H), 3.44-3.46 (m, 3H), 2.59 (t, J=6 Hz, 2H), 2.18 (t, J=7.6 Hz, 2H), 1.59-1.63 (m, 2H), 1.25-1.35 (s, 32H), 0.80-0.85 (m, 3H).

To a stirred solution of 3009 (0.59 g, 0.29 mmol) in DCM (6 mL) was added HOBt (0.038 g, 0.028 mmol) at room temperature. To this reaction mixture was added HBTU (0.135 g, 0.34 mmol) at ice cold temperature followed by DIPEA (0.14 mL, 0.85 mmol). A solution of 2026 (0.6 g, 0.28 mmol) in DCM (3 mL) was added and the resulting reaction mixture was stirred for 2 h at RT. To the reaction mixture was added water (25 mL) and extracted with DCM (2×20 mL). The combined organic layers were washed with brine (30.0 mL), dried over anhydrous sodium sulphate, and filtered. Filtrate was evaporated under reduced pressure and crude was purified by silica gel column chromatography (CombiFlash rf) using 10% MeOH in DCM as eluent to afford 3010 as grey semisolid (0.91 g, yield: 79.13%). $^1$H NMR (400 MHz, DMSO-d$_6$): δ 8.11 (d, J=7.6 Hz, 1H), 7.97 (d, J=9.2 Hz, 3H), 7.90 (t, J=7.2 Hz, 12H), 7.78-7.82 (m, 2H), 7.66-7.70 (m, 11H), 7.62-7.64 (m, 3H), 7.53-7.60 (m, 9H), 7.47 (t, J=8 Hz, 6H), 7.37 (t, J=7.6 Hz, 6H), 5.73-5.74 (m, 4H), 5.35 (dd, J=11.2 Hz, J=2.8 Hz, 3H), 4.72 (d, J=8.4 Hz, 3H), 4.50-4.57 (m, 1H), 4.41-4.47 (m, 6H), 4.24-4.36 (m, 6H), 3.76-3.79 (m, 3H), 3.43-3.49 (m, 151H), 3.35-3.38 (m, 3H), 2.96-3.18 (m, 1OH), 2.30-2.35 (m, 1H), 2.0-2.06 (m, 8H), 1.68 (s, 12H), 1.44-1.49 (m, 20H), 1.21-1.26 (m, 44H), 0.81-0.85 (m, 3H).

To a stirred solution of 3010 (0.87 g, 0.21 mmol) in ethanol (2.6 mL) was added aqueous ammonia (5.2 mL) at room temperature and the resulting reaction mixture was continued at 40° C. for 48 h. Purification was performed as described in 1079 synthesis to afford 1078 as off white solid (0.45 g, yield: 67.25%). $^1$H NMR (400 MHz, DMSO-d$_6$): δ 8.10-8.12 (m, 1H), 7.80-7.85 (m, 2H), 7.70-7.75 (m, 2H), 7.63 (d, J=7.6 Hz, 3H)), 4.50-4.60 (m, 9H), 4.20 (d, J=8 Hz, 3H), 3.63-3.68 (m, 12H), 3.49 (s, 162H), 2.97-3.16 (m, 17H), 2.0-2.03 (m, 9H), 1.78 (s, 9H), 1.42-1.47 (m, 24H), 1.21 (s, 36H), 0.80-0.85 (m, 3H); HRMS (ESI-TOF)m/z: [M+H]$^+$ calculated for 3119.91. found 3120.8.

Example 21. Synthesis of mPEG2000-Cholesterol 504 mPEG-2000-NH$_2$ (1 mol eq.) was stirred with cholesteryl chloroformate (1001, 1 mol eq.) in the presence of pyridine (3 mol eq.) in dichloromethane at ambient temperature for 18 h. The reaction mixture was washed with water; solvents and volatiles were evaporated in vacuo. The crude mixture was subjected to silica gel column chromatographic purification to obtain the desired compound 504 (yield: 22%). ELSD-HPLC 990%; average mol. Wt. 2329. found: 2330.56. $^1$H NMR (400 MHz, DMSO, d$_6$): δ ppm 7.01-6.98 (t, 1H), 5.35 (bs, 1H), 4.41-4.21 (m, 1H), 3.85-3.64 (m, 1H), 3.68-3.35 (in, 194H), 3.23 (s, 3H), 3.18-2.95 (m, 2H), 2.42-2.15 (m, 2H), 2.00-1.96 (in, 2H), 1.95-1.76 (m, 3H), 1.75-0.32 (m, 36H), 0.23-0.15 (s, 3H).

Example 22. Guide RNA (gRNA) and mRNA for LNP Evaluation

The guide RNAs (gRNA) shown in Table were synthesized under solid phase oligonucleotide synthesis and deprotection conditions using controlled pore glass support and commercially available phosphoramidite monomers and oligonucleotide synthesis reagents (Methods in Molecular Biology, 1993, 20, 81-114; ACS Chem. Biol. 2015, 10, 1181-1187, incorporated herein by reference in its entirety). The deprotected guide RNAs were purified by HPLC and the integrity of each guide RNA was confirmed by mass spectrometric analysis. The observed mass of each guide RNA was conformed to calculated mass.

TABLE 5

Single guide RNA (gRNA) used in the studies described in Examples 2-25

| Target* | gRNA | Protospacer SEQ ID No | Protospacer (5'-3') | gRNA sequence (5'-3')# | gRNA SEQ ID NO |
|---|---|---|---|---|---|
| PCSK9 | GA055 | 104 | CAGGTTCCAT GGGATGCTCT | csasgsGUUCCAUGGGAUGCUCUgUUUUAGagcu agaaauagcaaGUUaAaAuAaggcuaGUccGUUAuc AAcuugaaaaagugGcaccgagucggugcusususu | 121 |
| PCSK9 | GA010 | 105 | GGCTGATGA GGCCGCACAT G | gsgscsUGAUGAGGCCGCACAUGGUUUUAGagcu agaaauagcAAGUUAAAAUAAGGCUAGUCCGUU AUCAacuugaaaaaguggcaccgagucggugcusususu | 122 |
| PCSK9 | GA255 | 106 | CCCATACC TTGGAGCA ACGG | cscscsAUACCUUGGAGCAACGGgUUUUA GagcuaGaaauagcaaGUUaAaAuAaggcUaGUC cGUUAucAAcuuGaaaaaguGgcaccgAgUCggu gcusususu | 123 |
| PCSK9 | GA256 | 107 | CCCATACC TTGGAGCA ACGG | cscscsAUACCUUGGAGCAACGGgUUUUA GagcuagaaauagcaaGUUaAaAuAaggcuaGUcc GUUAucAAcuugaaaaagugGcaccgagucggugcus ususu | 123 |

TABLE 5-continued

Single guide RNA (gRNA) used in the studies described in Examples 2-25

| Target* | gRNA | Protospacer SEQ ID No | Protospacer (5'-3') | gRNA sequence (5'-3')# | gRNA SEQ ID NO |
|---|---|---|---|---|---|
| PCSK9 | GA257 | 108 | CCCATACC TTGGAGCA ACGG | cscscsAUACCUUGGAGCAACGGgUUUUA GagcuaGaaauagcaaGUUaAaAuAaggcuaGUcc GUUAucAAcuuGaaaaagugGcaccgagucggugcu sususu | 123 |
| PCSK9 | GA292 | 109 | CCCATACC TTGGAGCA ACGG | cscscsAUACUUGGAGCAACGGGUUUUAG AGCUAGAAAUAGCAAGUUAAAAUAAG GCUAGUCCGUUAUCAACUUGAAAAAG UGGCACCGAGUCGGUGCUsususu | 124 |
| PCSK9 | GA097 | 110 | CCCGCACC TTGGCGCA GCGG | cscscsGCACCUUGGCGCAGCGGgUUUUA GagcuagaaauagcaaGUUaAaAuAaggcuaGUcc GUUAucAAcuugaaaaagugGcaccgagucggugcus ususu | 125 |
| ANGPTL3 | GA258 | 111 | GAGATACC TGAGTAAC TTTC | gsasgsAUACCUGAGUAACUUUCgUUUUA GagcuaGaaauagcaaGUUaAaAuAaggCUaGUC cGUUAucAAcuuGaaaaaguGgcaccgAgUCggu gcusususu | 126 |
| ANGPTL3 | GA259 | 112 | GAGATACC TGAGTAAC TTTC | gsasgsAUACCUGAGUAACUUUCgUUUUA GagcuagaaauagcaaGUUaAaAuAaggcuaGUcc GUUAucAAcuugaaaaagugGcaccgagucggugcus ususu | 126 |
| ANGPTL3 | GA260 | 113 | GAGATACC TGAGTAAC TTTC | gsasgsAUACCUGAGUAACUUUCgUUUUA GagcuaGaaauagcaaGUUaAaAuAaggcuaGUcc GUUAucAAcuuGaaaaagugGcaccgagucggugcu sususu | 126 |

*The gRNAs were designed to target mouse, rat, monkey and human PCSK9 and ANGPTL3 genes. # uppercase and lowercase letters in the guide RNA sequence indicate nucleotides carrying 2'-ribo (2'-OH) and 2'-O-methyl (2'-OMe) ribosugar moiety, respectively, and the letter 's' indicates phosphorothioate (PS) linkage.

mRNA Encoding SpCas9, CBE, and ABE Proteins mRNA for SpCas9, CBE, and ABE were produced by different methods well known in the art. One of such methods used herein was in vitro transcription (IVT) using T7 polymerase or additional RNA polymerase variants. Typically, IVT of mRNA uses a linearized DNA template that comprises a T7 polymerase promoter, mRNA coding sequence (CDS), 3' and 5' untranslated regions (UTRs), poly A tail, and additional replication and transcription regulatory elements. Prior to IVT, the DNA template was in the form of a plasmid, PCR product, or additional double-stranded DNA construct. A typical IVT reaction includes T7 polymerase, DNA template, RNase inhibitor, cap analog, inorganic pyrophosphatase, and naturally occurring ribonucleotides (rNTPs) such as GTP, ATP, CTP, UTP, or substitutions of natural rNTPs with modified rNTPs such as pseudouridine, N1-methylpseudouridine, 5-methyl cytidine, 5-methoxyuridine, N6-methyl adenosine, and N4-acetylcytidine. The cap analog was a dinucleotide or trinucleotide cap structure with the first initiating nucleotide containing standard 2'-hydroxyl group, 2'-O-methyl group, or additional 2'chemical modification. Cap analog also was added after the IVT reaction using a vaccinia capping enzyme. After IVT, in some cases DNase is added to the transcription mixture to remove DNA template; alternatively, residual DNA was removed by ion exchange column chromatography. Purification and concentration of mRNA were performed with ion exchange chromatography, affinity chromatography, precipitation, ion-pairing reverse-phase chromatography, enzymatic reactions, size exclusion chromatography, and/or tangential flow filtration. Similar IVT and purification process were used to produce mRNA encoding SpCas9, CBE, and ABE; in all cases the DNA template, reaction conditions, and purification parameters were optimized for the specific gene of interest. In some examples, capped and polyadenylated mRNA were obtained from commercially sources (TriLink, for e.g.).

Example 23. Preparation of Lipid Nanoparticles (LNPs)

The LNPs used as reference in these studies are prepared according to published procedures and are constituted from published LNP excipients and genome editor mRNAs (Miller et al., Angew. Chem. Int. Ed. 2017, 56, 1059-1063; Yin et al., Nature Biotechnology 2016, 34, 328-333) and guide RNAs (Chadwick et al., Arterioscler. Thromb. Vasc. Biol. 2017, 37, 1741-1747; Rossidis et al., Nat. Med. 2018, 24, 1513-1518. doi:10.1038/s41591-018-0184-6; Ding et al., Circ Res. 2014, 115, 488-492). The gRNA payload is selected from Table 5 and mRNA payloads used for constituting these LNPs are prepared as described in Example 22 or may be purchased commercially from third parties, for example, such as TriLink BioTechnologies. The reference LNP A1 (Table 6) is constituted from the published lipid 501 (Table 6), cholesterol, DSPC and PEG-lipid from Table 7 as described in the literature (Angew. Chem. Int. Ed. 2012, 51, 8529-8533). Similarly, the benchmark LNPs B1 and $C_1$ are constituted from lipids 502 (WO 2015/095340 A1) and 503 (Molecular Therapy 2018, 26, 1509-1519) respectively in combination with cholesterol, DSPC and PEG-DMG (506 and 507, Table 7) as summarized in Table 6. The reported genome editor nuclease mRNA and guide RNAs are used as payload for constituting the reference LNPs. In one approach the LNP formulations A1, B1 and C₁ are made by co-formulating mRNA and guide RNA. In this co-formulation method mRNA to guide RNA ratio is varied from 10:1 to 1:10, that result in a series of LNPs for in vitro and in vivo gene editing evaluation. In the second approach: guide RNA and mRNA are formulated separately using same lipid ratios as in Table 6 and then pre-formulated LNPs with guide and mRNA are mixed together at various ratios to obtain a new series of LNPs for gene editing evaluation.

TABLE 6

Exemplary lipid compositions of LNPs A1, B1 and C1

| LNP Formulation | Lipid | Excipients, % mol | | | |
|---|---|---|---|---|---|
| | | Lipid | Cholesterol | DSPC | PEG-DMG |
| A1 | 501 | 50 | 38.5 | 10 | 1.5 |
| B1 | 502 | 45 | 44 | 9 | 2 |
| C1 | 503 | 50 | 38.5 | 9 | 1.5 |

TABLE 7

Lipids and PEG-Lipids excipients used for LNP preparations

| Compound number | Structure |
|---|---|
| 501 | 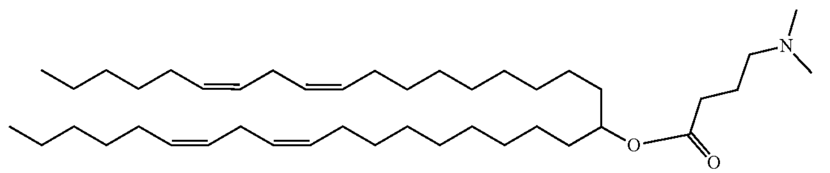 [SMILES: CCCCC/C=C\C/C=C\CCCCCCCCC(CCCCCCCC/C=C\C/C=C\CCCCC)OC(=O)CCCN(C)C] |
| 502 | 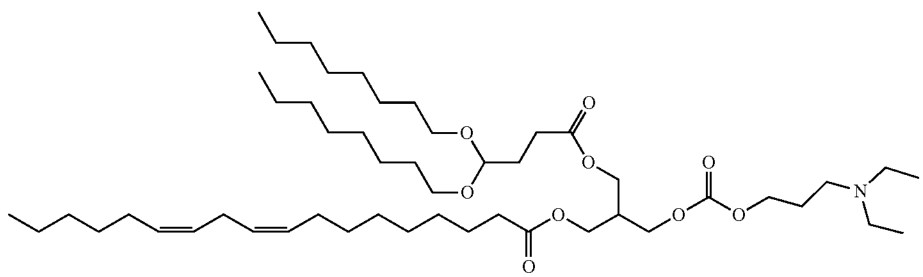 [SMILES: CCCCC/C=C\C/C=C\CCCCCCCC(=O)OCC(COC(=O)CCC(OCCCCCCCC)OCCCCCCCC)COC(=O)OCCCN(CC)CC] |
| 503 | 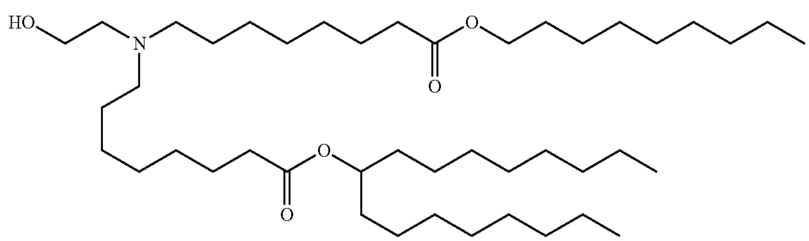 [SMILES: CCCCCCCCCOC(=O)CCCCCCCN(CCO)CCCCCCCC(=O)OC(CCCCCCCC)CCCCCCCC] |
| 504 | n = 42-46 |
| 505 | 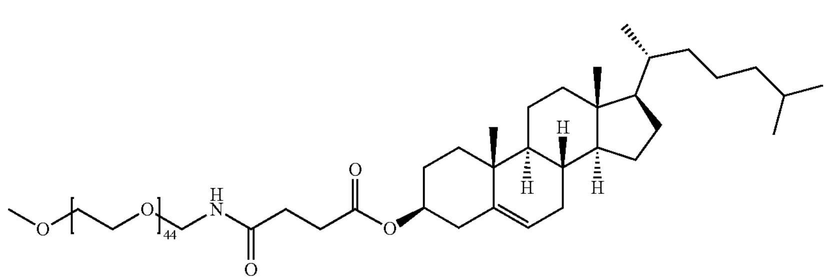 |

TABLE 7-continued

Lipids and PEG-Lipids excipients used for LNP preparations

| Compound number | Structure |
|---|---|
| 506 | [chemical structure: distearylglycerol carbamate-PEG, (R) stereochemistry, 44 PEG units] |
| 507 | [chemical structure: distearylglycerol diester-PEG, 44 PEG units] |
| 508 | [chemical structure: distearylglycerol carbamate-PEG, (R) stereochemistry, 44 PEG units] |

Example 24. Preparation of Hepatocyte Targeting LNPs

Example 24-A

LNPs from Example 23 were reconstituted successively with GalNAc-lipid 1002 and 1004 (Table 4) to obtain the desired hepatocyte targeted GalNAc-LNPs. A series of GalNAc-LNPs were generated by successively co-formulating 1002 or 1004 using the composition described in Table 6 at different mol % (0.01 to 5 mol %) of each targeting lipids. Another set of LNPs were yielded when 1002 and 1004 was successively added at various mol % (0.01 to 5 mol %) to preformulated LNPs from Table 6 for in vitro and in vivo gene editing. Hepatocyte targeting GalNAc-Lipid (1002 or 1004) was added during the formulation as described in Tables 8-13.

All LNPs prepared were stored either at 2-8° C. or −80° C. (Tables 6, 8-13). Following formulation, LNPs were buffer exchanged and concentrated. LNPs were buffer exchanged into buffers of varying ionic strengths from 0 to 200 mM. In some cases, the buffer exchange was carried out by PD-10 column, in others it was dialysis, and in other instances Tangential Flow Filtration (TFF) was used. In some cases, TFF was used to concentrate the LNPs, and in other instances an amicon centrifugation concentration column was used. LNPs were exchanged into and concentrated in the final formulation buffer at pH 7 or 8. Cryoprotectant was added such that the final concentration of cryoprotectant in the final formulation buffer is 0-500 mM. LNPs were without cryoprotectant were then stored at 2-8° C., and with cryoprotect were frozen first and stored at −80° C.

Example 24-B

The targeting lipids of Example 24-A is then successively replaced with targeting lipids 1042, 1043 and 1044 (Table 4), where the presentation of the ligand is different than those of 1002, 1003 and 1004. The lipid chain and tethers separating the ligand moieties are kept the same in both series of targeting lipids. The same number of formulations with different ratio of payloads (guide RNA and mRNA) and individual formulation of guide RNA and mRNA are also prepared as described in Example 23 for evaluation. The guide RNA used for each individual formulation is selected from Table 5. The mRNA can be Trilink mRNA, MS004, or MA004, or any other mRNA.

The targeting lipids of Example 24-A is then successively replaced with targeting lipids 1012, 1014, 1051 and 1053 (Table 4), where the distearylglycerol moiety is replaced with a cholesterol moiety. The same number of formulations with different ratio of payloads (guide RNA and mRNA) and individual formulation of guide RNA and mRNA are also prepared as described in Example 23 for evaluation. The guide RNA used for each individual formulation is selected from Table 5. The mRNA can be Trilink mRNA, MS004, or MA004, or any other mRNA.

The targeting lipids of Example 24-A are replaced with targeting lipids 1062 and 1065 to generate new targeting LNPs for evaluation. In the new formulations thus obtained the distearylglycerol moiety is replaced with a tocopherol moiety.

The targeting lipids of Example 24-A are replaced with targeting lipids 1003 to generate new targeting LNPs for evaluation.

Example 25. GalNAc-Lipid Post-Addition Processes with LNPs

Certain LNPs compositions of Tables 6, 8, 9-12 and 7 were formulated and allowed to rest for a range of 1 minute to 120 minutes. The stealth lipid was included in the initial lipid mixture and/or in the dilution buffer at a mol % of 0-5 in some instances. In some instances, GalNAc-Lipid 1004, among others, was added in an ethanol/aqueous solution at a mol % of 0.01-10 following LNP formulation. It was added in the range of 1 minutes to 120 minutes following LNP formulation and allowed to interact with the LNPs in ethanol/aqueous buffer for 1 minute to 120 minutes before buffer exchange into formulation buffer. In some cases, the buffer exchange was carried out by PD-10 column, in others it was dialysis, and in other instances TFF was used. In some cases, TFF was used to concentrate the LNPs, and in other cases an amicon centrifugation concentration column was used.

Post addition of GalNAc-Lipid to LNPs is described in Tables 8-13. Data is shown therein.

TABLE 8

Exemplary lipid compositions

| LNP Formulation | Lipid of Table 6, % mol | Receptor targeting conjugate y of Formula (V) or (VI) (e.g., compound of Table 4), % mol | Cholesterol, % mol | Neutral lipid (e.g., DSPC) % mol | Stealth Lipid (e.g., PEG-DMG) % mol |
|---|---|---|---|---|---|
| 7-1 | 50 | 0 | 38.5 | 10 | 1.5 |
| 7-2 | 45 | 0 | 44 | 9 | 2 |
| 7-3 | 50 | 0 | 38.5 | 9 | 1.5 |
| 7-4 | 49.99 | 0.01 | 38.5 | 10 | 1.5 |
| 7-5 | 44.99 | 0.01 | 44 | 9 | 2 |
| 7-6 | 49.99 | 0.01 | 38.5 | 9 | 1.5 |
| 7-7 | 49.9 | 0.1 | 38.5 | 10 | 1.5 |
| 7-8 | 44.9 | 0.1 | 44 | 9 | 2 |
| 7-9 | 49.9 | 0.1 | 38.5 | 9 | 1.5 |
| 7-10 | 49 | 1 | 38.5 | 10 | 1.5 |
| 7-11 | 44 | 1 | 44 | 9 | 2 |
| 7-12 | 49 | 1 | 38.5 | 9 | 1.5 |
| 7-13 | 45 | 5 | 38.5 | 10 | 1.5 |
| 7-14 | 40 | 5 | 44 | 9 | 2 |
| 7-15 | 45 | 5 | 38.5 | 9 | 1.5 |
| 7-16 | 47.1 | 0.5 | 46.1 | 4.7 | 2.1 |
| 7-17-1[1] | 47.1 | 0 | 46.1 | 4.7 | 2.1 |

[1] 7-17-1 was made with GA055 PCSK9 guide RNA and MS004 Cas9 mRNA

TABLE 9

Example of GalNAc-LNP formulation parameters and characteristics using 1004 as GalNAc-lipid. 1004 was added to the LNP post formulation. LNP composition (mol %):iLipid (502)/DSPC/Cholesterol/PEG—DMG (507) = 47.1:4.7:46.1:2.1.

| LNP ID | Cargo types | GalNAc-Lipid 1004 mol % | Addition of 1004 | Dilution buffer | Buffer exchange process | Storage condition (° C.) |
|---|---|---|---|---|---|---|
| 7-16 | GA055 + MS004 | 0.5 | Post LNP formulation | 16% ethanol in PBS | Dialysis to PBS | 2-8 |
| 7-16-A | GA259 + MA002 | | | 16% ethanol in PBS | Dialysis to PBS | 2-8 |
| 7-16-B | GA259 + MA002 | | | 5% ethanol in PBS | Dialysis to PBS | 2-8 |
| 7-16-C | GA259 + MA002 | | | Diluted to 5% ethanol in PBS | Dialysis to PBS | 2-8 |
| 7-16-D | GA259 + MA002 | | | 16% ethanol in water | Dialysis to PBS | 2-8 |
| 7-16-E | GA257 + MA004 | | | 16% ethanol in water | Dialysis to 50 mM Tris | −80 |
| 7-16-F | GA055 + MS004 | | | 5% ethanol in PBS | TFF to 50 mM Tris | −80 |
| 7-16-G | GA055 + MS004 | | | 16% ethanol in PBS | Dialysis to 50 mM Tris | 2-8 |
| 7-16-H | GA257 + MA004 | | | 16% ethanol in PBS | PD 10 to PBS | 2-8 |
| 7-16-I | GA257 + MA004 | | | 16% ethanol in PBS | TFF to 50 mM Tris | −80 |
| 7-16-J | GA055 + MS004 | | | 16% ethanol in PBS | Dialysis to 50 mM Tris | −80 |
| 7-16-K | GA257 + MA004 | | | 16% ethanol in water | TFF to 50 mM Tris | −80 |
| 7-16-L | GA097 + MA004 | 0.5 | | 16% ethanol in water | TFF to 50 mM Tris | −80 |
| 7-16-M | GA097 + MA004 | 1 | | 16% ethanol in PBS | TFF to 50 mM Tris | −80 |
| 7-16-N | GA256 + MA004 | 0.5 | | 16% ethanol in PBS | Dialysis to PBS | 2-8 |
| 7-16-O* | GA256 + MA004 | 0.5 | | 16% ethanol in PBS | Dialysis to PBS | 2-8 |
| 7-16-P* | GA256 + MA004 | 0.5 | In Dilution buffer | 16% ethanol in PBS | Dialysis to PBS | 2-8 |

*the LNP composition (mol %) is iLipid (502)/DSPC/Cholesterol/PEG-DMG (507) = 55:4.7:38.2:2.1. The ratios stated herein are based on the ratio of the LNP components before the addition of GalNAc lipid. Upon the inclusion of the GalNAc lipid, the composition shifts slightly.

TABLE 10

Example of GalNAc-LNP formulation parameters and characteristics using 1004 as GalNAc-lipid. 1004 was added to the LNP post formulation. LNP composition (mol %):iLipid (502)/DSPC/Cholesterol/PEG—DMG (507) = 47.1:4.7:46.1:2.1. 7-19 and 7-20 carried MA002 (ABE mRNA) and GA259 (ANGPTL3 guide RNA) at 1:1 ratio. 7-22 contained MA004 ABE mRNA and GA256 (PCSK9 guide RNA) at 1:1 ratio. All other stated GalNAc-LNPs were carrying MS004 (SpCas9 mRNA) and GA055 (PCSK9 gRNA) at 1:1 ratio.

| LNP ID | mol % of 1004 | Addition of 1004 | Dilution buffer | Buffer exchange | Storage (° C.) | Average diameter (nm) | PDI | RNA entrapment (%) |
|---|---|---|---|---|---|---|---|---|
| 7-17-A | 2 | Post LNP formulation | PBS | Dialyzed to PBS | 4-8 | 84.4 | 0.0641 | 97.06 |
| 7-18 | 1 | | PBS | | 4-8 | 77.13 | 0.15 | 96.55 |
| 7-16 | 0.5 | | PBS | | 4-8 | 77.5 | 0.002 | 97.3 |
| 7-19 | 0.25 | | PBS | | 4-8 | 76.3 | 0.02 | 98.5 |
| 7-20 | 0.05 | | PBS | | 4-8 | 77.04 | 0.08 | 98.74 |
| 7-21 | 0.5 | Added after buffer exchange to LNP and then buffer exchanged to PBS | PBS | PD10 | 4-8 | 93.5 | 0.03 | — |
| 7-22 | 0.5 | Added to the final thawed LNP | | | −80 | 88.5 | 0.07 | 92.2 |
| 7-23 | 0.5 | Added to the thawed final LNP | | | 4-8 | 91.87 | 0.01 | — |
| 7-24 | 0.5 | Collected in buffer containing 1004 | PBS | Dialyzed to PBS | 4-8 | 81.5 | 0.0778 | 97.0 |
| 7-25 | 0.5 | Collected in water containing 1004 | water | Dialyzed to PBS | 4-8 | 83 | 0.12 | — |

TABLE 11

Example of GalNAc-LNP formulation parameters and characteristics using 1004 as GalNAc-lipid. 1004 was added to the LNP at various stages of the formulation process. LNP composition (mol %):iLipid (502)/DSPC/Cholesterol (=47.1:4.7:46.1) remained unchanged during all the examples. All the GalNAc-LNPs were carrying MS004 (SpCas9 mRNA) and GA055 (PCSK9 gRNA) at 1:1 ratio, except 7-39, 7-40, and 7-41 which were gRNA GA256 and mRNA MA004 at 1:1 ratio; formulation 7-26 contains GA257 gRNA and mRNA MA004; formulation 7-29 contains GA259 gRNA and mRNA MA002

| LNP-ID | 507 (mol %) | 1004 in lipid excipient stream (mol %) | 1004 in Dilution buffer# (mol %) | Average LNP particle diameter (nm) | PDI | RNA entrapment (%) |
|---|---|---|---|---|---|---|
| 7-26 | 0 | 2.1 | 0 | 80.9 | 0.04 | 85 |
| 7-27 | 0 | 1.5 | 0 | 124 | 0.01 | — |
| 7-28 | 0 | 1 | 0 | 139 | 0.04 | — |
| 7-29 | 2.1 | 0.5 | 0 | 73.5 | 0.02 | 99.0 |
| 7-30 | 2.1 | 0.25 | 0.25 | 103 | 0.04 | — |
| 7-31 | 1.6 | 0.25 | 0 | 93.4 | 0.074 | 96.85 |
| 7-32 | 1.1 | 0.51 | 0 | 98.5 | 0.051 | 96.46 |
| 7-33 | 0 | 0.91 | 0 | 102 | 0.053 | 96.81 |
| 7-33-A* | 2.1 | 0.5 | — | 85.2 | 0.0521 | 95.5 |
| 7-39 | 1.1 | 1.0 | 0 | 85.7 | 0.0382 | 94.3 |
| 7-40 | 0 | 1.5 | 0 | 118 | 0.049 | 93.6 |
| 7-41 | 2.1 | 0.25 | 0.25 post addition | 73.1 | 0.00619 | 97 |

Figure 9:
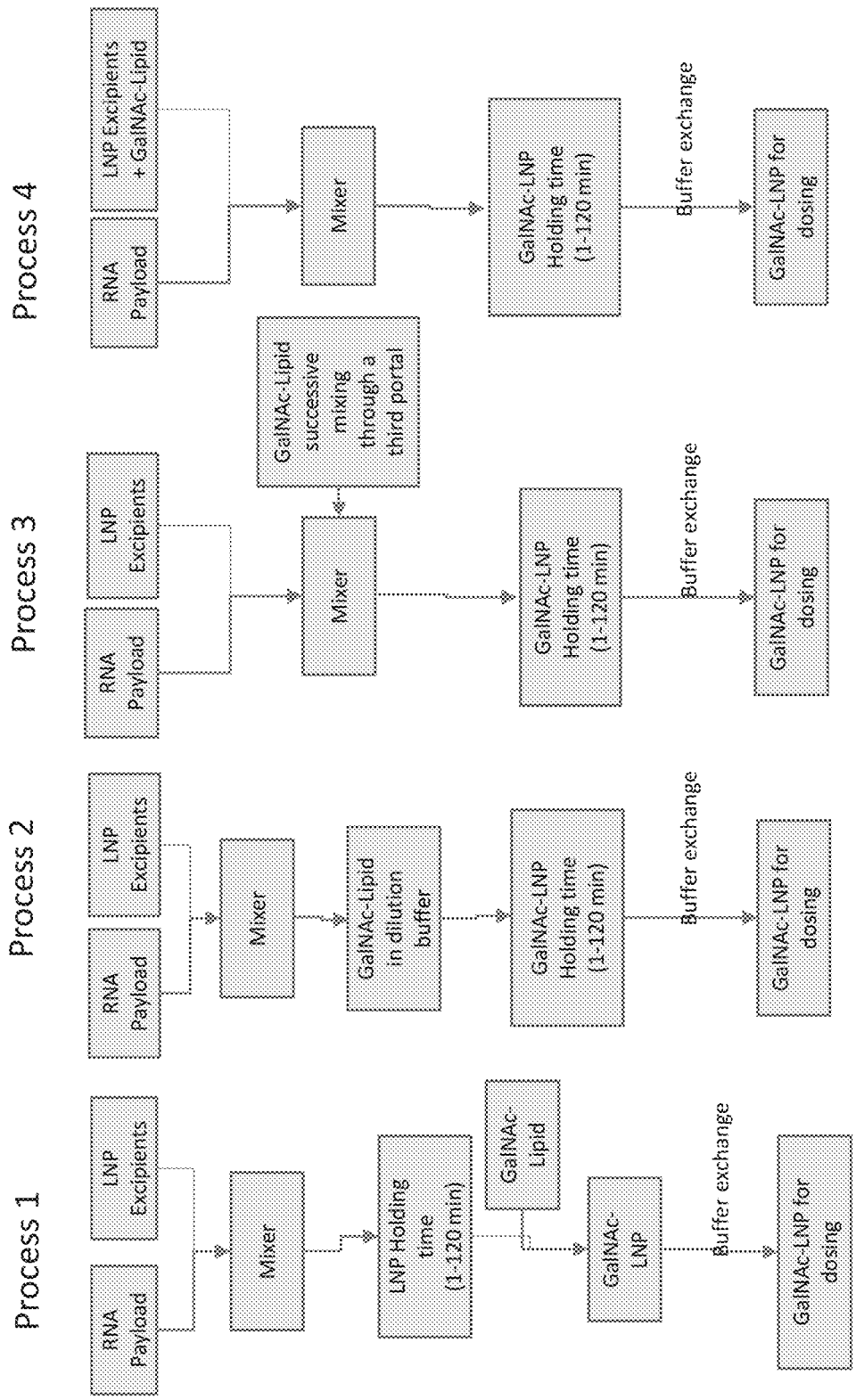
FIG. 9 illustrates four general processes of introducing GalNAc-lipids into lipid nanoparticles.

Dilution buffer is 16.5% ethanol in PBS.
*GalNAc-Lipid 1004 was added using a third port mixing, as reflected in Process 3 of FIG. 9.

TABLE 12

Example of GalNAc-LNP formulation parameters and characteristics using various GalNAc-lipids. LNPs 7-34 and 7-35 were made following the method of LNP 7-16 (Table 9) whereas 7-36 and 7-37 were made following method as described to make 7-16-D (Table 9). LNP composition (mol %): iLipid (502)/DSPC/Cholesterol/PEG—DMG (507) = 47.1/4.7/46.1/2.1. All the GalNAc-LNPs carried GA259 (gRNA) and MA004 (mRNA) at 1:1 ratio, except 7-38A was gRNA GA256 and mRNA MA004

| LNP ID | GalNAc-lipid | mol % | GalNAc-lipid addition | Average diameter (nm) | PDI | RNA entrapment (%) |
|---|---|---|---|---|---|---|
| 7-34 | 1053 | 0.5 | Post LNP formulation | 76.2 | 0.13 | 98.37 |
| 7-35 | 1014 | 0.5 | | 73.5 | 0.1 | 99.1 |
| 7-36 | 1043 | 0.5 | | 79 | 0.1 | 97.06 |
| 7-37 | 1002 | 0.5 | | 80.55 | 0.17 | 98.07 |
| 7-38-A | 1044 | 0.5 | | 74.1 | 0.036 | 96 |

Evaluation of LNP Components Using HPLC

Figure 1B:
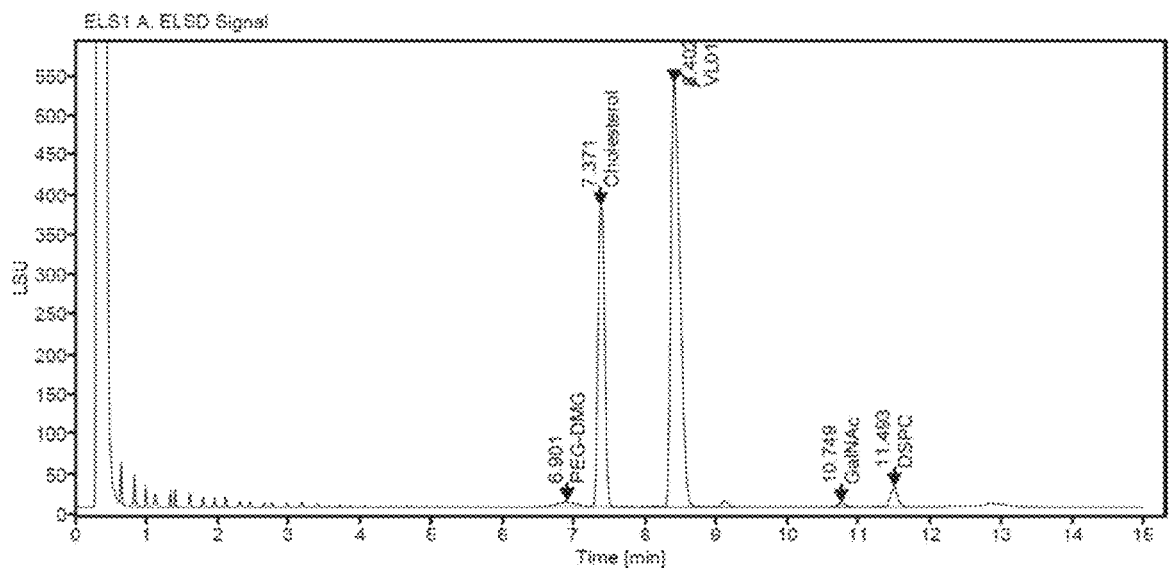

The lipid composition of the LNP was characterized by HPLC methods as seen in FIG. 1A-FIG. 1B. The HPLC methods used were an ion-pairing reverse phase high performance liquid chromatography with evaporative light scattering detection (IP-RPLC-HPLC-ELSD) to quantify the % of each lipid in a given sample. Each lipid component was calibrated against a standard curve with sample detection above the limit of quantitation (S/N≥10). FIG. 1A-FIG. 1B display the HPLC chromatogram demonstrating GalNAc-lipid incorporation: (FIG. 1A) reference LNP with no GalNAc-Lipid present and (FIG. 1B) LNP constituted with GalNAc-Lipid. The HPLC peak at retention time (RT)6.721 min labeled as PEG-DMG is PEG-Lipid 507 and the peak at RT 8.176 min labeled as VL01 is the amino lipid 502 in FIG. 1A. The HPLC peak at RT 6.901 min labeled as PEG-DMG is PEG-Lipid 507, the peak at RT 8.402 labeled as VL01 is the amino lipid 502 and the HPLC peak at RT 10.749 min labeled as GalNAc is 1004 in FIG. 1B.

Example 26. LNPs Constituted with PEG-DSG (508)

The PEG-lipid excipients used in Examples 23, 24 and 25 are replaced with PEG-DSG (508, Table 7) to obtain targeting and non-targeting LNPs for further evaluation and to compare delivery efficiency and gene editing in vitro and in vivo under LNP-mediated delivery/uptake conditions.

Example 27. LNPs Constituted with PEG-Cholesterol (504)

The PEG-DSG used for constituting LNPs in Example 26 is replaced with PEG-Cholesterol (504 and 505, Table 7) to obtain targeting and non-targeting LNPs for further evaluation and to compare delivery efficiency and gene editing in vitro and in vivo under LNP-mediated delivery/uptake conditions.

Example 28. LNPs Constituted with Single mRNA Payload

The payloads in Examples 23-27 are replaced with a single mRNA payload (Molecular Therapy 2018, 26, 1509-1519) to evaluate mRNA expression in vitro and in vivo under LNP-mediated delivery/uptake conditions.

Example 29. LNPs Constituted with Single siRNA Payloads

The payload in Examples 23-28 are replaced with an siRNA to evaluated RNAi-mediated gene silencing. The siRNA used for evaluation is the reported FVII siRNA under LNP-mediated delivery/uptake conditions (Jayaraman et al, Angew. Chem. Int. Ed. 2012, 51, 8529-8533).

Example 30. LNPs Constituted with Antisense Oligonucleotide Payloads

The payload in Examples 23-28 is replaced with antisense oligonucleotide to evaluated antisense effect in vitro and in vivo under LNP-mediated delivery/uptake conditions (Prakash et al., ACS Chemical Biology, 2013, 8(7), 1402-1406).

Example 31. LNPs Constituted with Antimir/Antagomir Payloads

The payload in Examples 23-28 is replaced with a miRNA for miRNA activity evaluation in vitro and in vivo under LNP-mediated delivery/uptake conditions (Zhang et al., J. Controlled Release 2013, 168, 251-261; Kruetzfeldt et al., Nature 2005, 438, 685-689).

Example 32. LNPs Constituted with microRNA Payload

The payload in Example 26 is replaced with a miRNA for microRNA activity evaluation in vitro and in vivo under LNP-mediated delivery/uptake conditions (Wang et al., J. Control Release 2013, 28, 690-8).

Example 33. In Vitro Evaluation of LNPs

Gene editing activity of the LNPs obtained from Examples 23-27 are evaluated in hepatocytes (rodent, monkey and human) as described in Finn et al., Cell Reports 2018, 22, 2227-2235.

Editing efficiency of LNPs these LNPS are tested in the presence and in the absence of serum in the media.

In addition, LNPs obtained Examples 23-27 are tested in the above cell lines under serum-free conditions and in the presence or absence of recombinant human ApoE (Akinc et al, Mol Ther. 2010, 18, 1357-64).

Gene editing activity of all these LNPs are also evaluated in ASGPR, LDLr and ApoE knockout hepatocytes (human, monkey and rodent) under all conditions described above.

Example 34. Evaluation of GalNAc-LNP Binding to ASGPR

ASGPR biding of all ASGPR targeting LNPs obtained from Examples 23-31 is measured as described in Mol Ther. 2010, 18, 1357-64.

Example 35. GalNAc-Lipid Inclusion after LNP Formation

The LNPs were formulated and allowed to rest for a range of 1 min to 120 min. The stealth lipid was included in the initial lipid mixture and/or in the dilution buffer at a mol % of 0-5 in some instances. The LNPs were buffer exchanged and concentrated, in some cases using TFF to concentrate, and in other cases an amicon centrifugation concentration column was used. In some instances, the buffer exchange was carried out by PD-10 column, in others it was dialysis, and in other instances TFF was used. GalNAc-Lipid 1004 was/is then added in an ethanol/aqueous solution at a mol % of 0.01-10, in the range of 1 to 120 minutes following LNP concentration, and allowed to interact with the LNPs.

In another formulation approach, LNPs are formulated and allowed to rest for a range of 1 minute to 120 minutes. The stealth lipid may be included in the initial lipid mixture and/or in the dilution buffer at a mol % of 0-5 in some instances. The LNPs are diluted in dilution buffer in a range of 1 to 1000% of the initial volume. GalNAc-Lipid 1004 is then added in an ethanol/aqueous solution at a mol % of 0.01-10, in the range of 1 minute to 120 minutes following LNP formulation, and allowed to interact with the LNPs in ethanol/aqueous buffer for 1 minute to 120 minutes before buffer exchange into final formulation buffer at a pH 7 or 8.

The LNPs are formulated as described above and buffer exchanged into final formulation buffer. The stealth lipid was included in the initial lipid mixture and/or in the dilution buffer at a mol % of 0-5 in some instances. GalNAc-Lipid 1004 in solution is then added at a mol % in a range of 0.01-10, allowed to interact for a range of 1 to 120 minutes, and then the solution is buffer exchanged into the final formulation buffer.

In other embodiments, the LNPs are formulated as described above and buffer exchanged into the final formulation buffer. The stealth lipid was included in the initial lipid mixture and/or in the dilution buffer at a mol % of 0-5 in some instances. GalNAc-Lipid 1004 in solution is then added at a mol % in a range of 0.01-10, allowed to interact for a range of 1 to 120 minutes.

In some embodiments, the LNPs are collected post-formulation directly into a dilution buffer containing GalNAc-Lipid 1004 in solution at a mol % in the range of 0.01-10. The stealth lipid may be included in the initial lipid mixture and/or in the dilution buffer at a mol % of 0-5 in some instances. The GalNAc-Lipid 1004 incorporates into the LNPs in solution and the solution is buffer exchanged into the final formulation buffer following a period of 1 to 120 minutes.

LNPs were/are also formulated and buffer exchanged into the final formulation buffer. Cryoprotectant is then added to the LNPs thus formed to store at −80° C. as described in Example 24. The LNPs devoid of cryoprotectant are stored at 2-8° C. and the final formulation that contains the cryoprotectant are stored at −80° C. The frozen LNPs are then thawed at room temperature. GalNAc-Lipid 1004 in an ethanol/aqueous solution is then added to the thawed LNPs at a mol % of 0.01-10. In some instances, the LNPs are then buffer exchanged into the final formulation buffer. In other instances, they are not buffer exchanged following GalNAc-Lipid addition.

In some instances, buffer exchange was performed through a PD-10 desalting column (column packed with Sephadex to separate high from low molecular weight compounds by desalting and buffer exchange), dialysis, or Tangential Flow Filtration (TFF). In some instances, the LNPs are stored at 2-8° C. or −80° C. following GalNAc-Lipid addition and buffer exchange.

GalNAc-LNPs are then constituted by replacing the GalNAc-Lipid 1004 with other GalNAc-Lipids from Table 4.

Example 36. GalNAc-Lipid Inclusion in Pre-Formulation Lipid Mixture to Obtain GalNAc-LNP The exemplary GalNAc-Lipid 1004 from Table 4 was included in the initial lipid mixture (including but not limited to: ionizable lipid, stealth lipid, helper lipid, etc.) at a mol % of 0.01-10, pre-formulation of LNPs. The stealth lipid was included at a mol % of 0-5 in some instances. LNPs were formulated and buffer exchanged in a range of 1 minute to 1 day following formulation and were stored as described in Example 24.

The exemplary GalNAc-Lipid 1004 from Table 4, in some instances, is included in the initial lipid mixture (including but not limited to: ionizable lipid, stealth lipid, helper lipid, etc.) at a mol % of 0.01-10, pre-formulation of LNPs. The stealth lipid was included at a mol % of 0-5 in some instances. The LNPs were formulated and collected directly into a solution containing 0.01-10 mol % of GalNAc-Lipid 1004. The LNPs are allowed to rest for 1 to 120 min before being buffer exchanged into final formulation buffer for storing at 2-8° C. and/or for storing at −80° C., as described in Example 24.

GalNAc-Lipid 1004, in some instances, was included in the initial lipid mixture (including but not limited to: ionizable lipid, stealth lipid, helper lipid, etc.) at a mol % of 0.01-10, pre-formulation of LNPs. The stealth lipid was included at a mol % of 0-5 in some instances. The LNPs were formulated and allowed to rest for 1 min to 120 min. GalNAc-Lipid in an ethanol/aqueous solution was/is then added to the LNPs at a mol % of 0.01-10 and the mixture is allowed to rest for a further 1 min to 120 min. The LNPs are then buffer exchanged into final formulation buffer for storing at 2-8° C. and/or for storing at −80° C., as described in Example 24.

GalNAc-Lipid 1004, in some instances, is included in the initial mixture of lipids (including but not limited to: ionizable lipid, stealth lipid, helper lipid, etc.) at a mol % of 0.01-10, pre-formulation of LNPs. The stealth lipid may be included at a mol % of 0-5 in some instances. The LNPs are formulated and then buffer exchanged into storage buffer for storing at 2-8° C. and/or for storing at −80° C., as described in Example 24, and stored at 2-8° C. and/or −80° C. The LNPs are then thawed at room temperature. GalNAc-Lipid 1004 in an ethanol/aqueous solution is then added to the LNPs at a mol % of 0.01-10, and the mixture is allowed to rest for a further 1 min to 120 min.

LNPs were stored as described in Example 24. In some instances, buffer exchange is/was performed through a PD-10 column, dialysis, or Tangential Flow Filtration (TFF). In some instances, the LNPs are/were stored at 2-8° C. or −80° C. following GalNAc-Lipid addition and appropriate buffer exchange depending on the desired storage conditions.

GalNAc-LNPs are then constituted by replacing the GalNAc-Lipid 1004 with other GalNAc-Lipids from Table 4.

Example 37. In Line Dilution of LNPs with GalNAc to Constitute GalNAc-LNP

GalNAc-LNPs were formulated using an in-line (third channel) dilution method. One channel/line is the lipid mixture (including but not limited to: ionizable lipid, stealth lipid, helper lipid, etc.). The other channel/line contains cargo in an aqueous solution (including but not limited to: guide RNA and mRNA). The third channel/line contains the desired GalNAc-Lipid 1004 in an ethanol/aqueous solution such that the final mol % in the LNPs is in the range of 0.01-10. The LNPs were allowed to rest for 1 min to 120 min before being buffer exchanged into the final formulation buffer and stored as described in Example 24.

In other instances, GalNAc-LNPs are formulated using an in-line (third channel) dilution method. One channel/line is the lipid mixture (including but not limited to: ionizable lipid, stealth lipid, helper lipid, etc.). The other channel/line contains cargo in an aqueous solution (including but not limited to: guide RNA and mRNA). The third channel/line contains the desired GalNAc-Lipid 1004 in an ethanol/aqueous solution such that the final mol % in the LNPs is in the range of 0.01-10%. LNPs are then collected directly into a solution containing 0.01-10 mol % of the same GalNAc-Lipid. The LNPs are allowed to rest for 1 min to 120 min before being buffer exchanged into the final formulation buffer for storing at 2-8° C. and/or for storing at −80° C., as described in Example 24.

In other instances, LNPs are formulated using an in-line (third channel) dilution method. One channel/line is the lipid mixture (including but not limited to: ionizable lipid, stealth lipid, helper lipid, etc.). The other channel/line contains cargo in an aqueous solution (including but not limited to: guide RNA and mRNA). The third channel/line contains the desired GalNAc-Lipid from Table 4 in an ethanol/aqueous solution such that the final mol % in the LNPs is in the range of 0.01-10. The LNPs are formulated and allowed to rest for 1 min to 120 min. GalNAc-Lipid 1004 in an ethanol/aqueous solution is then added to the LNPs at a mol % of 0.01-10 and the mixture is allowed to rest for a further 1 to 120 min. The LNPs are then buffer exchanged into the final formulation buffer for storing at 2-8° C. and/or for storing at −80° C., as described in Example 24.

LNPs were/are stored as described in Example 24. In some instances, buffer exchange is/was performed through using a PD-10 column, by dialysis, or by Tangential Flow Filtration (TFF). In some instances, the LNPs are stored at 2-8° C. or −80° C. following GalNAc-Lipid addition and appropriate storage buffer exchange.

GalNAc-LNPs are then constituted by replacing the GalNAc-Lipid 1004 with other GalNAc-Lipids from Table 4.

Example 38. In Vivo Gene Editing Evaluation of LNPs

Gene editing activity of a number of formulated LNPs from Examples 23-27 were evaluated in wild-type, and LDLr and ApoE knockout rodent models and in non-human primates.

Mice were treated in accordance with institutional ethical guidelines of animal care, handling, and termination. Mice were kept in a pathogen-free facility, with free access to standard chow and water. Mice were dosed with test articles or PBS as a vehicle by retro-orbital route according to their bodyweight. Relevant tissues were collected post dosed fifth or sixth day. Genomic DNA was extracted, and percent editing of target sequence was evaluated by next-generation sequencing to determine editing efficiency and the results are depicted in FIGS. 3-8.

Figure 2:
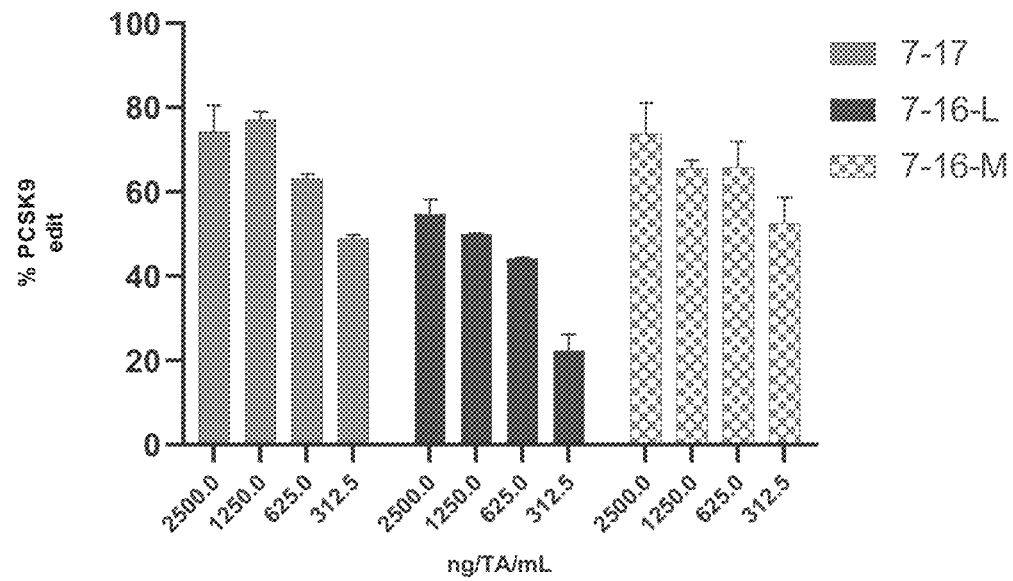
FIG. 2 illustrates in vitro PCSK9 gene editing efficiency in primary human hepatocytes of LNP formulations in compositions herein.

FIG. 2. illustrates PCSK9 editing efficiency in primary human hepatocytes in vitro following transfection with 7-17, 7-16-L, and 7-16-M for three days before harvesting for NGS analysis as described in Example 33. LNPs were dosed in a dose response ranging from 312.5 ng/mL LNPs concentration to 2500 ng/mL LNPs concentration.

Figure 3:
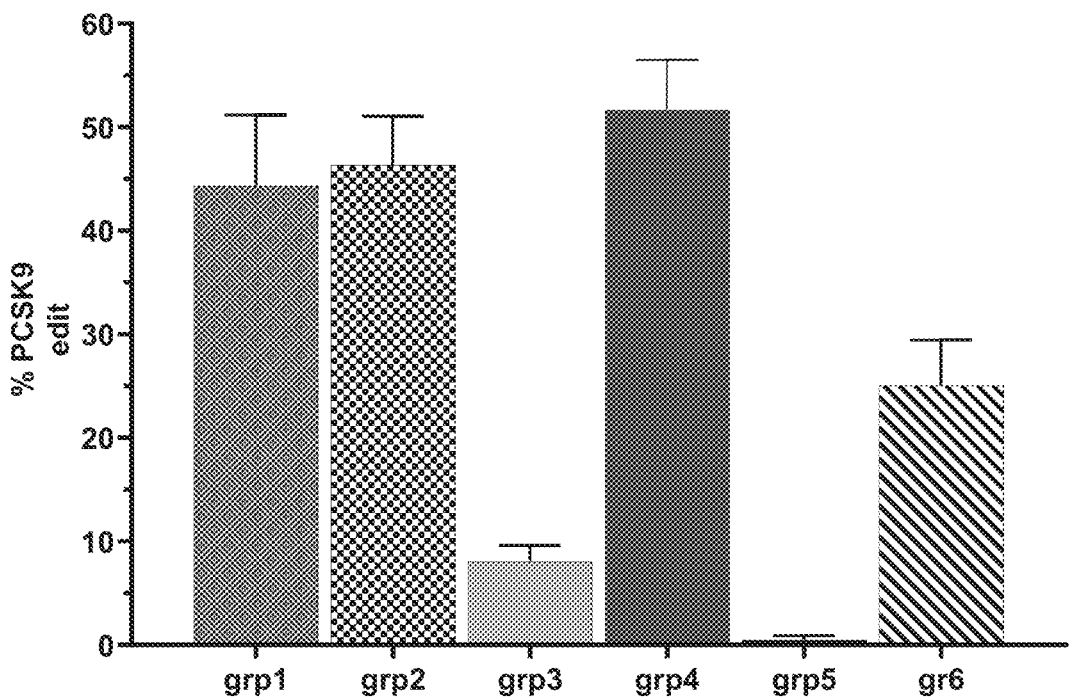
FIG. 3 illustrates PCSK9 gene editing in wild type, LDLr −/−, and ApoE −/− mice liver, after retro-orbital administration of LNPs compositions here within, carrying SpCas9 mRNA and PCSK9 gRNA at 1:1 ratio.

FIG. 3 illustrates PCSK9 gene editing in wild type (grp1 and 2), LDLR knockout (LDLR−/−, grp 3 and 4) and ApoE knockout (ApoE −/−, grp 5 and 6)mice (n=5) liver at 1 mg/kg dose, after retro-orbital administration of LNPs 7-17-1 and 7-16 carrying SpCas9 mRNA (MS004) and PCSK9 gRNA (GA055) at 1:1 ratio. 7-17-1 is the reference LNP and 7-16 is the GalNAc-LNP with 1004 as GalNAc-Lipid. grp 1, 3 and 5 were treated with 7-17-1, and grp 2, 4 and 6 were treated with 7-16. LNP IDs are given in Table 8 and 9. The reference LNP 7-17-1 that lacks the GalNAc-Lipid produced low or very poor editing in LDLR−/− and ApoE−/− mice.

Figure 4:
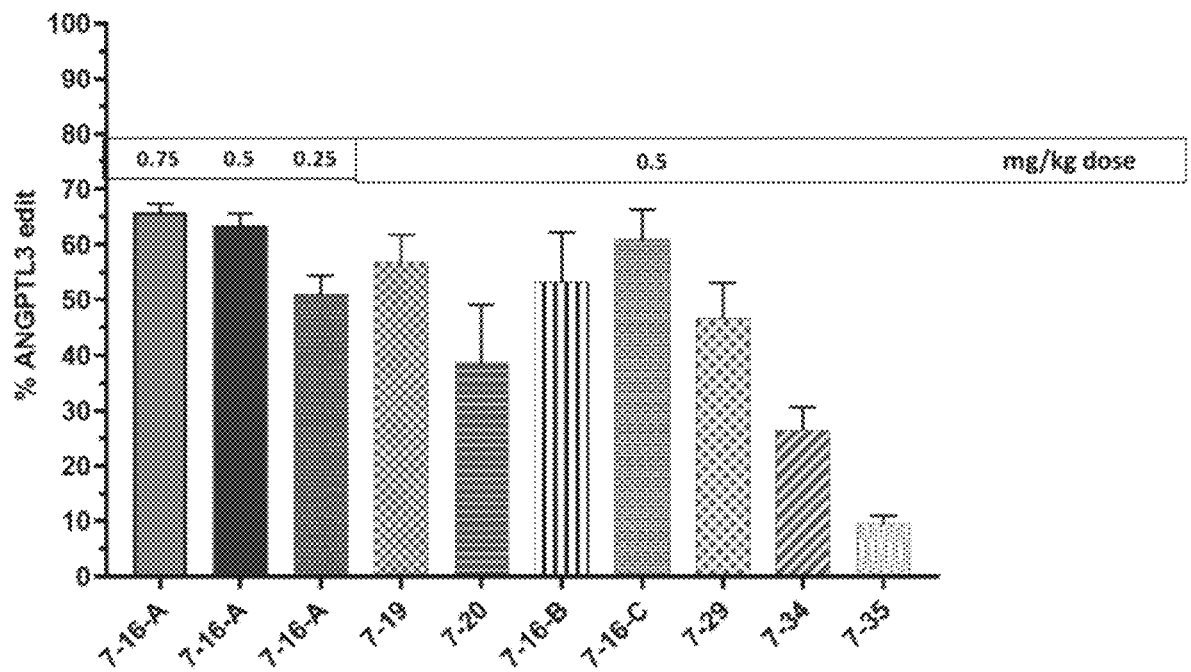
FIG. 4 illustrates ANGPTL3 gene editing in LDLr −/− mice liver after retro-orbital administration of LNPs compositions herein carrying ABE mRNA and ANGPTL3 gRNA at 1:1 ratio.

FIG. 4 illustrates gene editing in LDLR−/− mice liver after retro-orbital administration of GalNAc-LNPs compositions herein carrying ABE mRNA MA002 and gRNA GA259 at 1:1 ratio. 7-16-A, 7-16-B and 7-16-C were prepared as described in Table 9 with ANGPTL3 guide GA259 and ABE mRNA MA002; 7-19 and 7-20 were prepared as described in Table 10 with ANGPTL3 guide GA259 and ABE mRNA MA002; 7-29 was prepared as described in Table 11 with ANGPTL3 guide GA259 and ABE mRNA MA002; and 7-34 and 7-35 were prepared as described in Table 12 with ANGPTL3 guide GA259 and ABE mRNA MA002. The data highlights the dose response of 7-16-A as well as the effect of formulation process of GalNAc-LNPs (7-16-B, 7-16-C, 7-29) on hepatic gene editing activity. 7-19 and 7-20 illustrates the effect of GalNAc-Lipid (1004)mol % titration on hepatic gene editing in vivo. 7-34 and 7-35 (Table 4) have cholesterol as a lipid anchor. The editing data of 7-29 and 7-35 conclude that the lipid anchor impacts in vivo efficacy of GalNAc-LNP.

Figure 5:
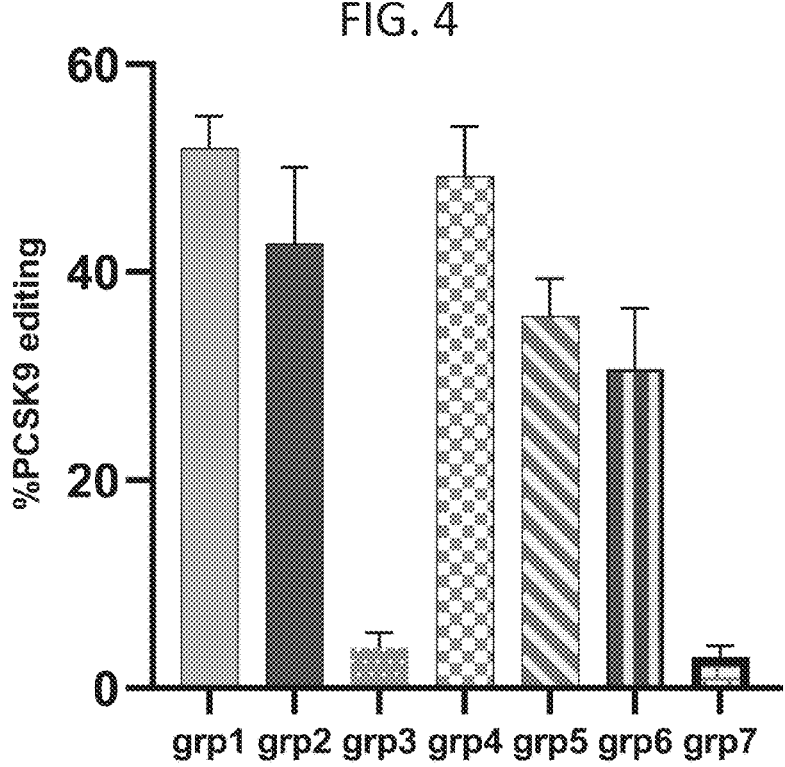
FIG. 5 illustrates PCSK9 gene editing in wild type and LDLr −/− mice liver after retro-orbital administration of LNPs carrying ABE mRNA and PCSK9 gRNA at 1:1 ratio.

FIG. 5 illustrates the PCSK9 gene editing in wild type (grp1, 2 and 3) and LDLR−/− (grp 4, 5, 6 and 7)mice (n=5) liver after retro-orbital administration of LNPs carrying ABE mRNA (MA004) and PCSK9 gRNA (GA257) at 1:1 ratio. 7-16-I was administered to grp 1, 4, and 5; grps 2 and 6 were treated with 7-16-H at 0.25 mg/mL total RNA dose; 7-26 was administered to groups 3 and 7 at 0.25 mg/mL. Grp 1, 2, 4, and 6 were dosed at 0.25 mg/kg; and grp 5 was dosed at 0.125 mg/kg. LNP IDs and formulation information are given in Table 9 and Table 11. Formulation 7-16-H and 7-16-I compared editing efficiency of the same formulation when buffer exchanged by PD-10 column and stored at 2-8° C., and buffer exchange via TFF and stored at −80° C. respectively. In formulation 7-26 (grp3 wild-type; grp7 LDLR−/− at 0.25 mg/kg) the PEG-Lipid 507 was completely replaced with GalNAc-Lipid 1004. Grp 1 (7-16-I), grp 2 (7-16-H), grp 4 (7-16-I) and grp 6 (7-16-H) illustrate the effect of buffer exchange conditions of same GalNAc-LNPs lipid composition (Table 9) on hepatic gene editing in WT and LDLR−/− mice respectively. Grps 4 and 5 were treated with formulation 7-16-I at 0.25 and 0.125 mg/kg dose respectively to show the dose response effect on hepatic gene activity in LDLR−/− mice.

Figure 6:
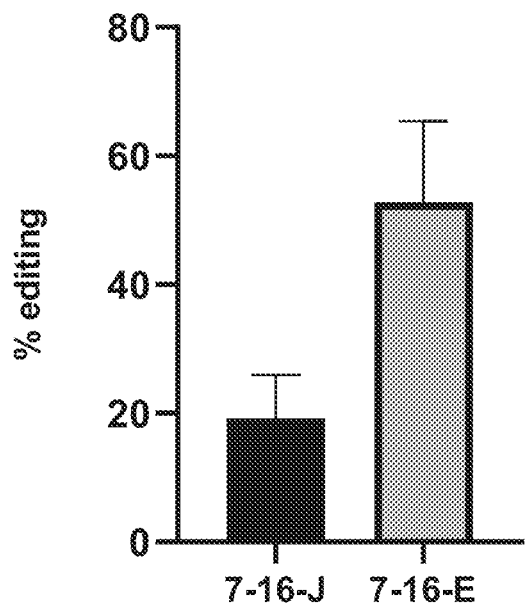
FIG. 6 illustrates PCSK9 gene editing in wild type female mice hepatocytes after retro-orbital administration of LNPs compositions herein.

FIG. 6 illustrates PCSK9 gene editing in wild type female mice (n=5) hepatocytes after retro-orbital administration of LNPs 7-16-J and 7-16-E (Table 9). 7-16-J was constituted with SpCas9 mRNA (MS004) and PCSK9 gRNA (GA055) and 7-16-E with ABE mRNA (MA004) and PCSK9 (GA257) gRNA at 1:1 ratio. 7-16-J and 7-16-E were dosed at 0.25 mg/kg and at 0.5 mg/kg, respectively.

Figure 7:
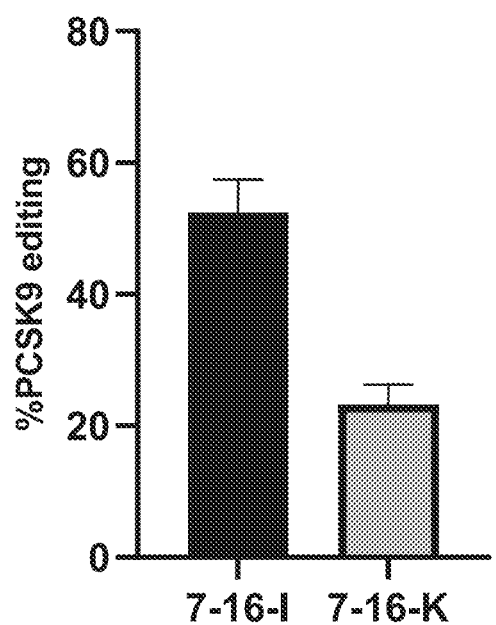
FIG. 7 illustrates PCSK9 gene editing in wild type female mice hepatocytes after retro-orbital administration of LNPs compositions herein.

FIG. 7 illustrates the PCSK9 gene editing in wild type female mice (n=5) hepatocytes after retro-orbital administration of LNPs 7-16-I and 7-16-K at 0.25 mg/kg. Both LNPs contain ABE mRNA MA004 and PCSK9 gRNA GA257. Both formulations contain same excipient and 1004 mol %. For the preparation of 7-16-I and 7-16-K the LNPs after inline mixing were collected in PBS containing 16% ethanol and water containing 16% ethanol, respectively. LNP IDs and formulation information are given in Table 9.

Figure 8:
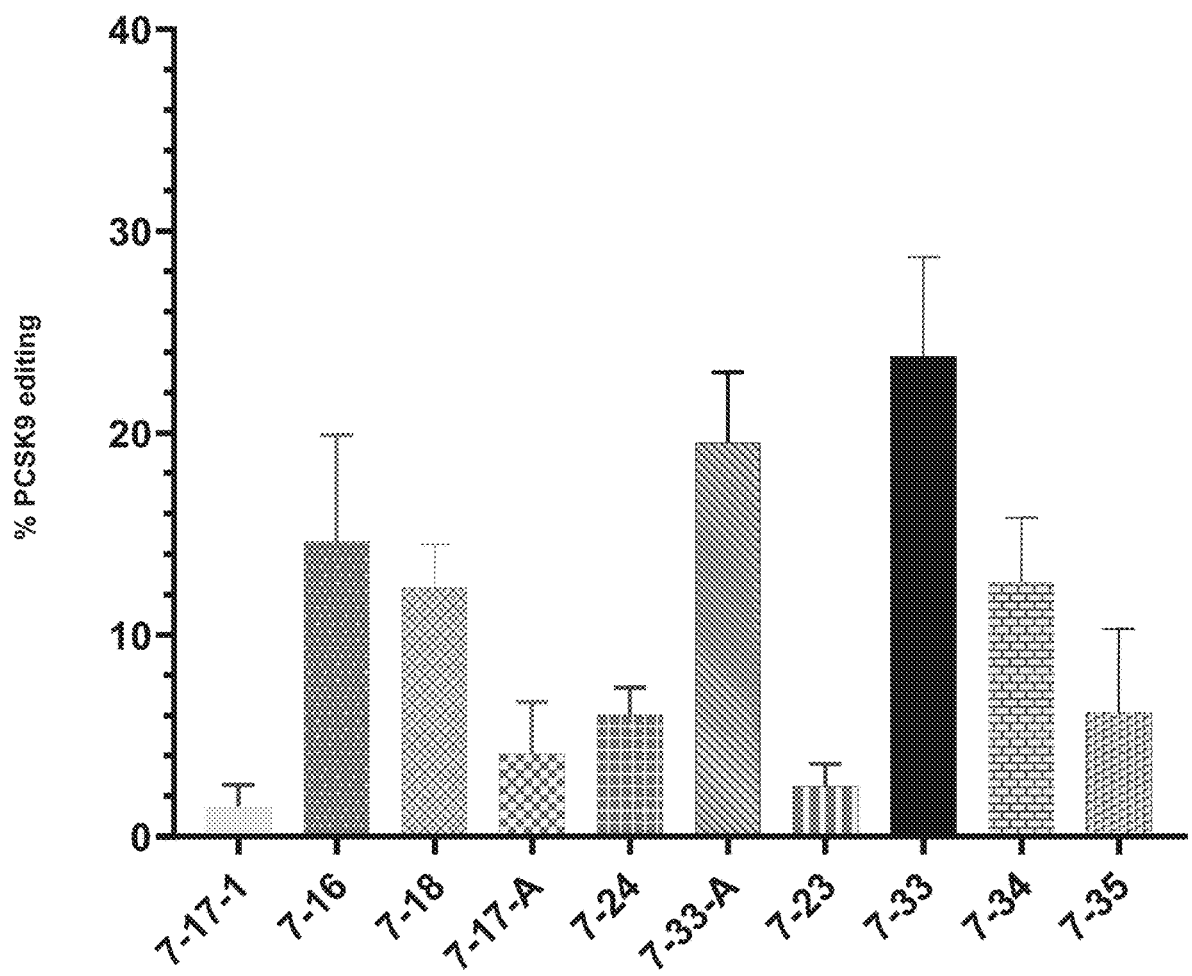
FIG. 8 illustrates PCSK9 editing in LDLR−/− female mice hepatocytes after retro-orbital administration of LNPs compositions herein carrying Cas9 mRNA and gRNA.

FIG. 8 illustrates PCSK9 editing in LDLR−/− female mice (n=5) hepatocytes after retro-orbital administration of LNPs carrying Cas9 mRNA and gRNA at 0.5 mg/kg dose. 7-17-1 (Table 8), 7-16 (Table 9), 7-18 (Table 10), 7-17-A (Table 10), 7-24 (Table 10), 7-33-A (Table 11), 7-23 (Table 10) and 7-33 (Table 11) constituted with spCas9 mRNA and gRNA. 7-17-1 (Table 8), 7-16 (table 9), 7-18 (Table 10) and 7-17-A (Table 10) shows the effect of GalNAc-Lipid (1004) mol % (0, 0.5, 1.0 and 2.0 mol %, respectively) titration on gene editing activity in LDLR−/− mice hepatocytes. All three formulation were prepared by following Process 1 in FIG. 9. The effect of various formulation processes on gene editing potency is being tested by 7-24, 7-33-A, 7-23 and 7-33 GalNAc-LNPs. Formulation 7-17-1 is the control LNP that lacks the GalNAc-Lipid 1004. 7-24 contains 0.5 mol % of 1004 where the GalNAc-Lipid was added to the collection buffer (Process 2, FIG. 9). 7-33-A was prepared by introducing the GalNAc-Lipid 1004 through third port/inline mixing into the mixing chamber (Process 3, FIG. 9). 7-23 the GalNAc-Lipid was added to pre-formed LNP stored at −80° C., after thawing prior to retro-orbital administration to the mice. 7-33 was prepared by premixing GalNAc-Lipid 1004 with other lipid excipients (Process 4, FIG. 9). 7-34 and 7-35 (Table 12) were constituted with ABE mRNA and ANGPTL3 gRNA at 1:1 ratio where the GalNAc-Lipid 1004 was replaced with 1053 and 1014 respectively (post insertion 0.5 mol %), and demonstrates that GalNAc-LNP containing 1004 is capable of being a more efficacious design.

Figure 15:
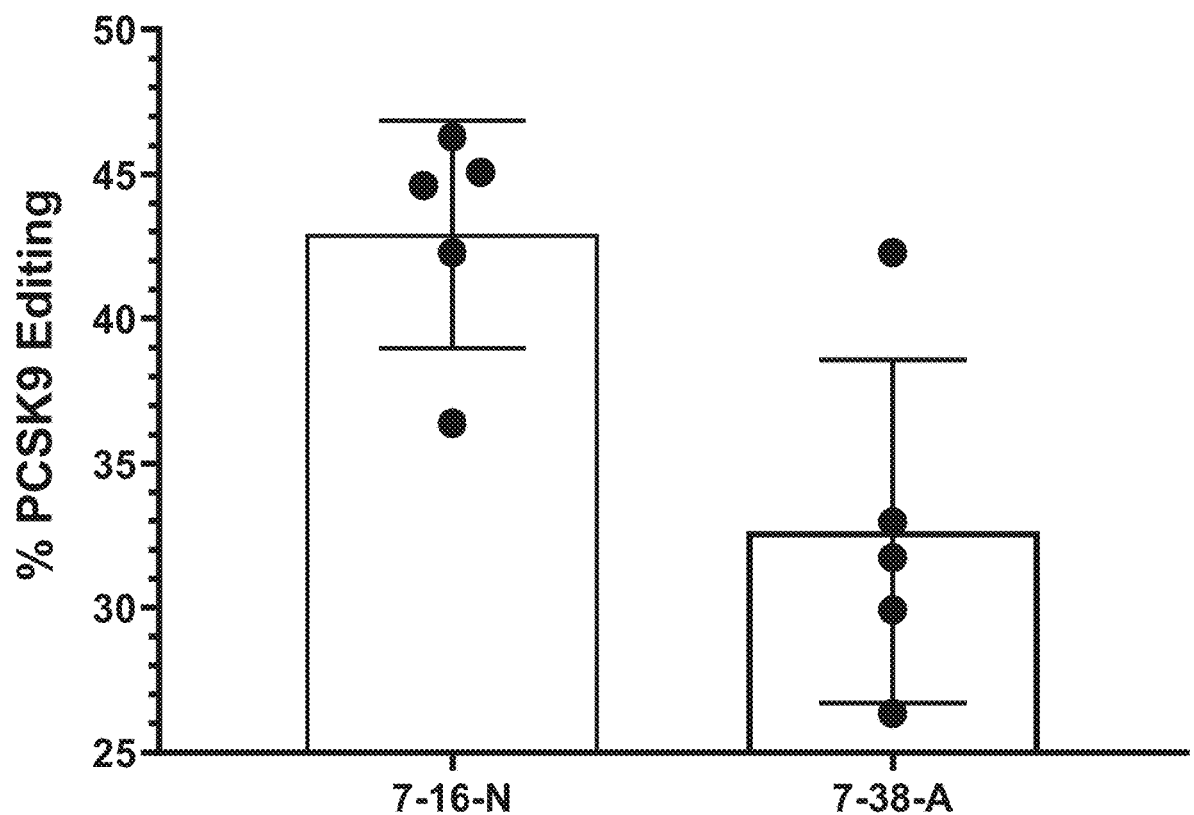
FIG. 15 illustrates PCSK9 editing in LDLR−/− female mice hepatocytes after retro-orbital administration of LNP compositions herein carrying PCSK9 ABE mRNA and guide RNA in a 1:1 ratio.

FIG. 15 illustrates the PCSK9 gene editing in LDLR−/− female mice (n=5) hepatocytes after retro-orbital administration of LNPs 7-16-N and 7-38-A at 0.25 mg/kg. 7-16-N includes 1004 and is described in Table 9, and 7-38-A includes 1044 and is described in Table 12. 7-16-N and 7-38-A contain PCSK9 guide RNA GA256 and ABE mRNA MA004. 1004 shows higher efficacy for the same method of formulation as compared to 1044. They were both made according to Process 1 in FIG. 9 and Protocol 1 in FIG. 10.

LNPs were also dosed to cynomolgus non-human primates at 1 mg/kg dose. LNPs were given via IV infusion over 1 hour. LNPs were prepared with LNP IDs given in Table 5 and/or 7, according to GalNAc-Lipid addition methods described in Examples 24, and shown in Table 13. LNPs had previously been stored at −80° C. as described in Example 24. LNP 7-17 served as control, while LNPs 7-16-L and 7-16-M had GalNAc-Lipid 1004 in the formulation. Primates were sacrificed on Day 1 or Day 14 following dosing. The end points included but were not limited to: LDL-c levels in blood, % editing of target gene in liver hepatocytes, PCSK9 protein levels in blood, ANGPTL3 protein levels in blood, among other lipid parameters.

These formulations were then incubated with human and monkey primary hepatocytes as described in Example 33 and the results are summarized in FIG. 2. FIG. 2 illustrates in vitro PCSK9 gene editing efficiency in primary human hepatocytes of LNP formulations 7-17, 7-16-L and 7-16-M.

TABLE 13

LNPs were prepared as described in Examples 23 and 24, and were stored at −80° C. as described in Example 24. They were then tested in non-human primates. LNPs were administered via IV infusion at 1 mg/kg dose

| LNP-ID | gRNA+ mRNA | No. of Animals | mol % GalNAc-Lipid 1004 | Average LNP size (nm) | PDI | Dose (mg/kg) | RNA entrapment (%) | Dose Volume (mL/kg) | Dose Route/ Regimen |
|---|---|---|---|---|---|---|---|---|---|
| 7-17 | MA004 + GA097 | 5 | 0 | 91 | 0.05 | 1 | 96.2 | 6 | IV inf., 1 h D0 |
| 7-16-L | MA004 + GA097 | 5 | 0.5 | 73.1 | 0.06 | 1 | 97.1 | 6 | IV inf., 1 h D0 |
| 7-16-M | MA004 + GA097 | 3 | 1 | 79 | 0.09 | 1 | 96.5 | 6 | IV inf., 1 h D0 |

Genomic DNA Isolation

Genomic DNA was isolated from approximately 20 μL of whole mouse liver lysate using a bead-based extraction kit, MagMAX-96 DNA Multi-Sample Kit (Thermo-Fisher Scientific) on the KingFisher Flex automated extraction instrument (Thermo-Fisher Scientific) according to the manufacturer's protocols. Mouse whole liver was lysed using the FastPrep-24 system (MP Bio) according the to manufacturer's protocol. Livers were loaded into 2 mL lysing matrix tubes (MP Bio) with 0.5 mL of PBS. Extracted genomic DNA was stored at 4° C. until further use or at −80° C. for long term storage.

Next Generation Sequencing (NGS) and Analysis of Editing Efficiency

Next generation sequencing (NGS), or deep sequencing, was performed on the region of interest to determine the extent of gene editing. Samples were prepared using the Nextera XT DNA library preparation kit (Illumina) according to the manufacturer's protocol. Briefly, two rounds of PCR were performed first to amplify the region of interest and second to add DNA sequences required for deep sequencing and sample identification to the initial product. The final amplicon was sequenced on the Illumina MiSeq instrument according to the manufacturer's protocol. Paired-end reads were analyzed with the CRISPResso2 pipeline (see Clement, K., Rees, H., Canver, M. C. et al. CRISPResso2 provides accurate and rapid genome editing sequence analysis. Nat Biotechnol 37, 224-226 (2019). Briefly, low-quality reads were filtered out, adapter sequences were trimmed from the reads, and the paired-end reads were merged and aligned to the amplicon sequence. The editing percentage was calculated as the number of reads supporting an insertion or a deletion, over the total number of aligned reads. For Cas9, the editing percentage was calculated as the number of reads supporting an insertion or a deletion, over the total number of aligned reads.

Example 39. GalNAc-LNPs Constituted from GalNAc-Lipid 1076

The desired GalNAc-LNPs are constituted by replacing GalNAc-Lipid of Examples 25-38 with GalNAc-Lipid 1076.

Example 40. GalNAc-LNPs Constituted from GalNAc-Lipid 1079

The desired GalNAc-LNPs are constituted by replacing GalNAc-Lipid of Examples 25-38 with GalNAc-Lipid 1079.

FIGS. 9-14 as previously noted are illustrations of representative manufacturing processes for GalNAc-LNPs disclosed herein. Illustrated in FIG. 9 are Processes 1-4. Process 1 depicts a method of preparation of GalNAc-LNPs, aspects of which are described more completely in Sato, et al J. Controlled Release, 2017, 266, 216-225. Process 2 illustrates a method for the creation of LNPs, whereby nucleic acids in an aqueous buffer are sent into a mixer through one (or more) channels and lipid components (including but not limited to: amino lipid, helper lipid, structural lipid/sterol, and stealth lipid) are sent into the mixer through a separate one or more channels. It is to be understood that the two streams of the RNA payload and LNP excipients are entering the mixer through separate channels and mixing inside the mixer; they do not contact each other before entering the mixer. The transiently formed LNP in the mixing chamber is then collected in dilution buffer containing GalNAc-Lipid at the desired mol %. The GalNAc-LNPs then enter holding time before proceeding through buffer exchange. Process 3 illustrates an in-line mixing method for the preparation of GalNAc-LNPs, whereby nucleic acids in an aqueous buffer are sent into an in-line mixer through one (or more) channels and lipid components (including but not limited to: amino lipid, helper lipid, structural lipid, and stealth lipid) are sent into the mixer through a separate one or more channels. It is to be understood that the two streams of the RNA payload and LNP excipients are entering the mixer through separate channels and mixing inside the mixer; they do not contact each other before entering the mixer. In some instances, the mixer is a T mixer, in other instances, it is a cross mixer. The solution then travels through a very short distance of tubing to immediately and successively enter another in-line mixer, where the output of the first mixer is in-line mixed with dilution buffer containing GalNAc-Lipid, such that a final desired mol % target compared to the other lipids is achieved. The distance between the two mixers is very short and so the two successive mixing events may be understood as to be almost instantaneous. The GalNAc-LNPs then enter a hold time before proceeding to buffer exchange. Process 4 illustrates a method for the preparation of GalNAc-LNPs, whereby nucleic acids in an aqueous buffer are sent into an in-line mixer through one (or more) channels and lipid components (including but not limited to: amino lipid, helper lipid, structural lipid, stealth lipid, and at least a portion or the desired mol % of the GalNAc-Lipid) are sent into the mixer through a separate one or more channels. It is to be understood that the two streams of the RNA payload and LNP excipients are entering the mixer through separate channels and mixing inside the mixer; they do not contact each other before entering the mixer. The GalNAc-LNPs then are mixed with dilution buffer, and proceed to hold time and buffer exchange. In Process 4, the GalNAc-Lipid is included either entirely or at least partially in the stream containing the lipid excipients that enters the mixer. The remainder of the GalNAc-Lipid (such that a desired target final mol % as compared to other lipids is achieved), if any, may then be included through a successive in-line mixer as described in Process 3, or may be added at a later point in the process.

As illustrated in FIGS. 10-14, specific protocols may be employed with each of the foregoing processes that further detail specific aspects of those processes. FIG. 10 illustrates Protocols 1-3 that can be used in connection with the processes of FIG. 9 to generate GalNAc-LNPs, whereby nucleic acids in an aqueous buffer are/were sent into a mixer through one (or more) channels and lipid components (including but not limited to: amino lipid, helper lipid, structural or sterol lipid, and stealth lipid) are/were sent into the mixer through a separate one or more channels. It is to be understood that the two streams of the RNA payload and LNP excipients are/were entering the mixer through separate channels and mixing inside the mixer; they do not contact each other before entering the mixer. The mixed solution then exits the mixer. Protocols 1, 2, and 3 are versions of Process 1 that differ only in at what stage the GalNAc-Lipid is added via post-addition.

FIG. 11 illustrates Protocols 4-6 that can be used in connection with the processes of FIG. 9 to generate GalNAc-LNPs, whereby nucleic acids in an aqueous buffer are sent into a mixer through one (or more) channels and lipid components (including but not limited to: amino lipid, helper lipid, structural or sterol lipid, and stealth lipid) are sent into the mixer through a separate one or more channels. It is to be understood that the two streams of the RNA payload and LNP excipients are entering the mixer through separate channels and mixing inside the mixer; they do not contact each other before entering the mixer. The mixed solution then exits the mixer. Protocol 4 is a version of Process 1 in FIG. 9 where GalNAc-Lipid is added after concentration. Protocol 5 utilizes Process 2 in FIG. 9, where GalNAc-Lipid is contained in the static dilution buffer in the collection vessel. Protocol 6 utilizes Process 1 where GalNAc-Lipid is added after concentration, filtration, and storage.

FIG. 12 illustrates Protocols 7-9 that can be used in connection with the processes of FIG. 9 to generate GalNAc-LNPs, whereby nucleic acids in an aqueous buffer are sent into a mixer through one (or more) channels and lipid components (including but not limited to: amino lipid, helper lipid, structural or sterol lipid, stealth lipid, and at least a portion of the GalNAc-Lipid) are sent into the mixer through a separate one or more channels. It is to be understood that the two streams of the RNA payload and LNP excipients are entering the mixer through separate channels and mixing inside the mixer; they do not contact each other before entering the mixer. The mixed solution then exits the mixer. The diagram indicates that the stream exiting the mixture enters into dilution buffer. This is understood to mean the stream either contacts a static dilution buffer in a collection vessel or enters a very short length of tubing that conveys the stream into a successive in-line mixer in which the stream from the first mixer is in-line mixed with dilution buffer in this successive mixer. Protocol 7 utilizes Process 4 from FIG. 9 to generate GalNAc-LNPs. Here, GalNAc-Lipid is entirely included in the mix of other lipids entering the mixer. The separate nucleic acid aqueous stream and lipid stream mix inside the mixer before exiting and contacting dilution buffer in one of the ways described above. Protocol 8 utilizes a version of Process 4 from FIG. 9 to generate GalNAc-LNPs. Here, GalNAc-Lipid is included in the mix of other lipids entering the mixer, as well as in the dilution buffer, which may be included in the protocol in either of the two ways described above. Protocol 9 utilizes a version of Process 4 from FIG. 9 to generate GalNAc-LNPs. Here, GalNAc-Lipid is included in the mix of other lipids entering the mixer, and is added to the GalNAc-LNPs at a later point in the process—in this case after dilution buffer is introduced to the GalNAc-LNPs in either way as described above and they complete a hold time, before completing another hold time following GalNAc-Lipid addition and being buffer exchanged.

FIG. 13 illustrates Protocols 10 and 11 that can be used in connection with the processes of FIG. 9 to generate GalNAc-LNPs, whereby nucleic acids in an aqueous buffer are sent into a mixer through one (or more) channels and lipid components (including but not limited to: amino lipid, helper lipid, structural or sterol lipid, stealth lipid, and at least a portion of the GalNAc-Lipid) are sent into the mixer through a separate one or more channels. It is to be understood that the two streams of the RNA payload and LNP excipients are entering the mixer through separate channels and mixing inside the mixer; they do not contact each other before entering the mixer. The mixed solution then exits the mixer. The diagram indicates that the stream exiting the mixture enters into dilution buffer. This is understood to mean the stream either contacts a static dilution buffer in a collection vessel or enters a very short length of tubing that conveys the stream into a successive in-line mixer in which the stream from the first mixer is in-line mixed with dilution buffer in this successive mixer. Protocol 10 utilizes a version of Process 4 from FIG. 9 to generate GalNAc-LNPs. Here, GalNAc-Lipid is included in the mix of other lipids entering the mixer, and is added to the GalNAc-LNPs at a later point in the process—in this case after buffer exchange. Protocol 11 utilizes a version of Process 4 from FIG. 9 to generate GalNAc-LNPs. Here, GalNAc-Lipid is included in the mix of other lipids entering the mixer, and is also present, possibly with none or a portion of other lipid components, in the dilution buffer. The dilution buffer is understood to contact GalNAc-LNPs in either of the ways described above.

FIG. 14 illustrates Protocols 12 and 13 that can be used in connection with the processes of FIG. 9 to generate GalNAc-LNPs, whereby nucleic acids in an aqueous buffer are sent into a mixer through one (or more) channels and lipid components (including but not limited to: amino lipid, helper lipid, structural or sterol lipid, stealth lipid, and at least a portion of the GalNAc-Lipid) are sent into the mixer through a separate one or more channels. It is to be understood that the two streams of the RNA payload and LNP excipients are entering the mixer through separate channels and mixing inside the mixer; they do not contact each other before entering the mixer. The mixed solution then exits the mixer and enters a very short length of tubing that conveys the stream into a successive in-line mixer in which the stream from the first mixer is in-line mixed with dilution buffer that contains GalNAc-Lipid in this successive mixer. Protocol 12 utilizes Process 3 in FIG. 9 to generate GalNAc-LNPs. Here, some or none of the GalNAc-Lipid is included in the stream with the other lipids that enters the first T mixer. It is to be understood that the protocol depicted in Protocol 12 can be carried out with or without GalNAc-Lipid in the stream with the other lipids that enters the first mixer. The stream that exits the first T mixer is then conveyed via a very short length of tubing into another successive T mixer, where it is mixed with dilution buffer containing GalNAc-Lipid. Protocol 13 utilizes Process 3 in FIG. 9 to generate GalNAc-LNPs. Here, some or none of the GalNAc-Lipid is included in the stream with the other lipids that enters the first cross mixer. It is to be understood that the protocol depicted in Protocol 13 can be carried out with or without GalNAc-Lipid in the stream with the other lipids that enters the first mixer. The stream that exits the first cross mixer is then conveyed via a very short length of tubing into a successive T mixer, where it is in-line mixed with dilution buffer containing GalNAc-Lipid.

Example 41. Preparation of Exemplary RNA GalNAc Conjugate

The RNA-GalNAc conjugate 2-1, for example, is prepared by the hybridization of a 13-mer oligo(2'—O-methoxyuridine) with a covalently conjugated GalNAc ligand at the 5'-end of the sequence (SEQ ID No 8) to the poly(A) tail at the 3'-end of the RNA (SEQ ID No 7, Table 2). In conjugate 2-2 the GalNAc ligand is covalently linked to the 3'-end of the oligo(2'—O-methoxyuridine) (SEQ ID No 10) that hybridizes with the poly(A) of the RNA (SEQ ID No 8). In RNA-GalNAc conjugate 2-3, the poly(A) tail of SEQ ID No 11 is hybridized with a oligo(2'—O-methoxyuridine) (SEQ ID No 12) carrying the GalNAc ligand at both end of the oligonucleotide. For the preparation of the RNA-GalNAc conjugates 2-4, 2-5 and 2-6, the oligo(2'—O-methoxyuridine) length is increased to 24-mer. The RNA-GalNAc conjugates 2-7 to 2-30 are prepared by partially or completely substituting 2'-O-methoxyuridine (u) either with uridine (U) or thymidine (T) as described in the Table 2. The GalNAc conjugated oligonucleotides 8-10 and 12-36 are prepared using the GalNAc ligand monomers 37 and 38 (Scheme 3, for example) under solid phase oligonucleotide synthesis and deprotection as described in J. Am. Chem. Soc. 2014, 136, 16958-16961.

All patents and publications mentioned in this specification are herein incorporated by reference to the same extent as if each independent patent and publication was specifically and individually indicated to be incorporated by reference.

Other Embodiments

From the foregoing description, it will be apparent that variations and modifications may be made to the disclosure described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment, any portion of the embodiment, or in combination with any other embodiments or any portion thereof.

As is set forth herein, it will be appreciated that the disclosure comprises specific embodiments and examples of targeting moiety structures, GalNac conjugate coupling sequences, guide RNA Galnac conjugate designs, GalNac conjugates structures including linkers and other components thereof, GalNac conjugated lipids, gRNA designs and modifications thereto, lipid compositions, lipid excipient formulations, lipid nanoparticle compositions with and without active agent payloads including but no limited to RNA, lipid nanoparticles comprised of GalNac-lipids that act as ligands to facilitate transfection and efficacy of active agents in receptor deficient cells and mammals; and specific examples and embodiments describing the synthesis, manufacture, use, and efficacy of the foregoing individually and in combination including as pharmaceutical compositions for treating disease and for in vivo and in vitro delivery of active agents to mammalian cells under conditions where there is an absence of ApoE and/or to such mammalian cells that are deficient in LDL receptors.

While specific examples and numerous embodiments have been provided to illustrate aspects and combinations of aspects of the foregoing, it should be appreciated and understood that any aspect, or combination thereof, of an exemplary or disclosed embodiment may be excluded therefrom to constitute another embodiment without limitation and that it is contemplated that any such embodiment can constitute a separate and independent claim. Similarly, it should be appreciated and understood that any aspect or combination of aspects of one or more embodiments may also be included or combined with any aspect or combination of aspects of one or more embodiments and that it is contemplated herein that all such combinations thereof fall within the scope of this disclosure and can be presented as separate and independent claims without limitation. Accordingly, it should be appreciated that any feature presented in one claim may be included in another claim; any feature presented in one claim may be removed from the claim to constitute a claim without that feature; and any feature presented in one claim may be combined with any feature in another claim, each of which is contemplated herein. The following enumerated clauses are further illustrative examples of aspects and combination of aspects of the foregoing embodiments and examples:

1. A receptor targeting conjugate, comprising a compound of Formula (V):

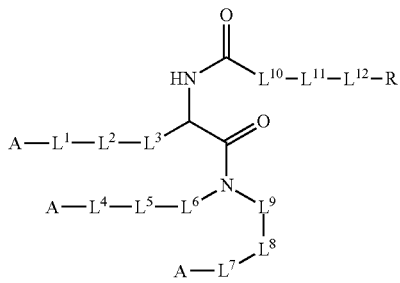

Formula (V)

wherein,
A is a receptor targeting moiety;
each $L^1$, $L^2$, $L^3$, $L^4$, $L^5$, $L^6$, $L^7$, $L^8$, $L^9$, $L^{10}$, and $L^{12}$, is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, or —N(OR$^1$)—;
$L^{11}$ is —(CH$_2$CH$_2$O)$_n$— or —(OCH$_2$CH$_2$)$_n$—;
each $R^1$ is independently H or substituted or unsubstituted $C_1$-$C_6$alkyl;
R is a lipophilic organic residue;
m is an integer selected from 1 to 10; and
n is an integer selected from 1 to 200.

2. The receptor targeting conjugate of clause 1, wherein each $L^1$, $L^4$, and $L^7$ is independently substituted or unsubstituted $C_1$-$C_{12}$ alkylene.
3. The receptor targeting conjugate of clause 2, wherein each $L^1$, $L^4$, and $L^7$ is independently substituted or unsubstituted $C_2$-$C_6$ alkylene.
4. The receptor targeting conjugate of clause 2, wherein each $L^1$, $L^4$, and $L^7$ is $C_4$ alkylene.
5. The receptor targeting conjugate of any one of clauses 1-4, wherein each $L^2$, $L^5$, and $L^8$ is independently —C(=O)NR$^1$—, —NR$^1$C(=O)—, —OC(=O)NR$^1$—, —NR$^1$C(=O)O—, —NR$^1$C(=O)NR$^1$—, or —C(=O)NR$^1$C(=O)—.
6. The receptor targeting conjugate of any one of clauses 1-5, wherein each $L^2$, $L^5$, and $L^8$ is independently —C(=O)NR$^1$— or —NR$^1$C(=O)—.
7. The receptor targeting conjugate of clause 6, wherein each $L^2$, $L^5$, and $L^8$ is —C(=O)NH—.
8. The receptor targeting conjugate of any one of clauses 1-7, wherein each $L^3$, $L^6$, and $L^9$ is independently substituted or unsubstituted $C_1$-$C_{12}$ alkylene.
9. The receptor targeting conjugate of clause 8, wherein each $L^3$ is substituted or unsubstituted $C_2$-$C_6$ alkylene.
10. The receptor targeting conjugate of clause 8, wherein $L^3$ is $C_4$ alkylene.
11. The receptor targeting conjugate of any one of clauses 1-10, wherein each $L^6$ and $L^9$ is independently substituted or unsubstituted $C_2$-$C_{10}$ alkylene.
12. The receptor targeting conjugate of clause 11, wherein each $L^6$ and $L^9$ is independently substituted or unsubstituted $C_2$-$C_6$ alkylene.
13. The receptor targeting conjugate of clause 11, wherein each $L^6$ and $L^9$ is $C_3$ alkylene.
14. A receptor targeting conjugate, comprising a compound of Formula (VI):

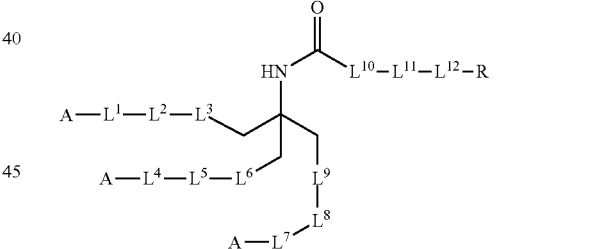

Formula (VI)

wherein,
A is a receptor targeting moiety;
each $L^1$, $L^2$, $L^3$, $L^4$, $L^5$, $L^6$, $L^7$, $L^8$, $L^9$, $L^{10}$, and $L^{12}$, is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, or —N(OR$^1$)—;
$L^{11}$ is —(CH$_2$CH$_2$O)$_n$— or —(OCH$_2$CH$_2$)$_n$—;
each $R^1$ is independently H or substituted or unsubstituted $C_1$-$C_6$alkyl;

R is a lipophilic organic residue;
m is an integer selected from 1 to 10; and
n is an integer selected from 1 to 200.

15. The receptor targeting conjugate of clause 14, wherein each $L^1$, $L^4$, and $L^7$ is independently substituted or unsubstituted $C_1$-$C_{12}$ alkylene or substituted or unsubstituted $C_1$-$C_{12}$ heteroalkylene.

16. The receptor targeting conjugate of clause 14 or 15, wherein each $L^1$, $L^4$, and $L^7$ is independently substituted or unsubstituted $C_1$-$C_{12}$ heteroalkylene.

17. The receptor targeting conjugate of clause 16, wherein each $L^1$, $L^4$, and $L^7$ is independently substituted or unsubstituted $C_1$-$C_{12}$ heteroalkylene comprising 1-10 O atoms.

18. The receptor targeting conjugate of clause 17, wherein each $L^1$, $L^4$, and $L^7$ is independently —$(CH_2CH_2O)_{p1}$—$(CH_2)_{q1}$—; wherein p1 is 1-8; and q1 is 1-6.

19. The receptor targeting conjugate of clause 18, wherein each $L^1$, $L^4$, and $L^7$ is —$(CH_2CH_2O)_3$—$(CH_2)_2$—.

20. The receptor targeting conjugate of clause 14 or 15, wherein each $L^1$, $L^4$, and $L^7$ is independently substituted or unsubstituted $C_1$-$C_{12}$ alkylene.

21. The receptor targeting conjugate of clause 20, wherein each $L^1$, $L^4$, and $L^7$ is independently substituted or unsubstituted $C_2$-$C_6$ alkylene.

22. The receptor targeting conjugate of clause 21, wherein each $L^1$, $L^4$, and $L^7$ is $C_4$ alkylene.

23. The receptor targeting conjugate of any one of clauses 14-22, wherein each $L^2$, $L^5$, and $L^8$ is independently —C(=O)NR$^1$—, —NR$^1$C(=O)—, —OC(=O)NR$^1$—, —NR$^1$C(=O)O—, —NR$^1$C(=O)NR$^1$—, or —C(=O)NR$^1$C(=O)—.

24. The receptor targeting conjugate of clause 23, wherein each $L^2$, $L^5$, and $L^8$ is independently —C(=O)NR$^1$— or —NR$^1$C(=O)—.

25. The receptor targeting conjugate of clause 24, wherein each $L^2$, $L^5$, and $L^8$ is —NHC(=O)—.

26. The receptor targeting conjugate of clause 24, wherein each $L^2$, $L^5$, and $L^8$ is —C(=O)NH—.

27. The receptor targeting conjugate of any one of clauses 14-26, wherein each $L^3$, $L^6$, and $L^9$ is independently substituted or unsubstituted $C_1$-$C_{12}$ heteroalkylene.

28. The receptor targeting conjugate of clause 27, wherein each $L^3$, $L^6$, and $L^9$ is independently substituted or unsubstituted $C_1$-$C_{12}$ heteroalkylene comprising 1-10 O atoms.

29. The receptor targeting conjugate of clause 27 or 28, wherein each $L^3$, $L^6$, and $L^9$ is independently —$(CH_2CH_2O)_{p2}$—$(CH_2CH_2CH_2O)_{q2}$—; wherein p2 is 1-8; and q2 is 1-6.

30. The receptor targeting conjugate of clause 29, wherein each $L^3$, $L^6$, and $L^9$ is —$(CH_2CH_2O)$—$(CH_2CH_2CH_2O)$—.

31. The receptor targeting conjugate of any one of clauses 14-26, wherein each $L^3$, $L^6$, and $L^9$ is independently —$(CH_2CH_2CH_2O)_{q3}$—; wherein q3 is 1-8.

32. The receptor targeting conjugate of clause 31, wherein each $L^3$, $L^6$, and $L^9$ is —$(CH_2CH_2CH_2O)_2$—.

33. The receptor targeting conjugate of any one of clauses 1-32, wherein $L^{10}$ is substituted or unsubstituted $C_1$-$C_{12}$ alkylene.

34. The receptor targeting conjugate of clause 33, wherein $L^{10}$ is substituted or unsubstituted $C_1$-$C_4$ alkylene.

35. The receptor targeting conjugate of clause 34, wherein $L^{10}$ is $C_2$ alkylene.

36. The receptor targeting conjugate of any one of clauses 1-35, wherein $L^{11}$ is —$(OCH_2CH_2)_n$—.

37. The receptor targeting conjugate of clause 36, wherein n is 1-100.

38. The receptor targeting conjugate of clause 37, wherein n is 2-50.

39. The receptor targeting conjugate of clause 38, wherein n is 2, 12, 37, or 45.

40. The receptor targeting conjugate of any one of clauses 1-39, wherein $L^{12}$ is —O—, —C(=O)O—, —C(=O)NR$^1$—, —NR$^1$C(=O)—, or —NR$^1$C(=O)O—.

41. The receptor targeting conjugate of clause 40, wherein $L^{12}$ is —C(=O)O— or —NR$^1$C(=O)O—.

42. The receptor targeting conjugate of clause 40, wherein $L^{12}$ is —C(=O)O—.

43. The receptor targeting conjugate of clause 40, wherein $L^{12}$ is —NHC(=O)O—.

44. The receptor targeting conjugate of clause 40, wherein $L^{12}$ is —NHC(=O)—.

45. The receptor targeting conjugate of any one of clauses 1-44, wherein A binds to a lectin.

46. The receptor targeting conjugate of clause 45, wherein the lectin is an asialoglycoprotein receptor (ASGPR).

47. The receptor targeting conjugate of any one of clauses 1-44, wherein A is N-acetylgalactosamine (GalNAc) or a derivative thereof.

48. The receptor targeting conjugate of any one of clauses 1-44, wherein A is

49. The receptor targeting conjugate of any one of clauses 1-48, wherein each $R^1$ is independently H or —$CH_3$.

50. The receptor targeting conjugate of any one of clauses 1-49, wherein each $R^1$ is H.

51. The receptor targeting conjugate of any one of clauses 1-50, wherein the lipophilic organic residue comprises one or more of fatty alcohols, fatty acids, glycerolipids, glycerophospholipids, sphingolipids, saccharolipids, polyketides, sterol lipids, and prenol lipids.

52. The receptor targeting conjugate of any one of clauses 1-51, wherein the lipophilic organic residue comprises one or more fatty alcohols.

53. The receptor targeting conjugate of clause 52, wherein each fatty alcohol is independently a saturated, monounsaturated, or polyunsaturated fatty alcohol.

54. The receptor targeting conjugate of clause 52 or 53, wherein the fatty alcohol comprises one or more a $C_2$-$C_{26}$ fatty alcohol.

55. The receptor targeting conjugate of any one of clauses 52-54, wherein the fatty alcohol comprises two or more a $C_2$-$C_{26}$ fatty alcohol.

56. The receptor targeting conjugate of any one of clauses 52-54, wherein each fatty alcohol is a $C_{12}$, $C_{14}$, $C_{16}$, $C_{18}$, $C_{20}$, or $C_{22}$ fatty alcohol.

57. The receptor targeting conjugate of any one of clauses 52-54, wherein each fatty alcohol is independently docosahexaenol, eicosapentaenol, oleyl alcohol, stearyl alcohol, (9Z,12Z)-octadeca-9,12-dien-1-yl alcohol, (Z)-docos-13-en-1-yl alcohol, docosanyl alcohol, (E)-octadec-9-en-1-yl alcohol, icosanyl alcohol, (9Z,12Z,15Z)-octadeca-9,12,15-trien-1-yl alcohol, or palmityl alcohol.

58. The receptor targeting conjugate of any one of clauses 52-54, wherein each fatty alcohol is a stearyl alcohol.

59. The receptor targeting conjugate of any one of clauses 1-50, wherein the lipophilic organic residue comprises one or more sterol lipids.

60. The receptor targeting conjugate of any one of clauses 1-49, wherein the lipophilic organic residue comprises one or more of vitamins.

61. The receptor targeting conjugate of any one of clauses 1-49 or 60, wherein each vitamin is independently a vitamin A, vitamin D, vitamin E, or vitamin K.

62. A receptor targeting conjugate, comprising a compound from Table 4.

63. A nanoparticle composition comprising:
   a. one or more nucleic acid molecular entities; and
   b. a receptor targeting conjugate of any one of the preceding clauses.

64. The nanoparticle composition of clause 63, wherein the receptor targeting conjugate comprises from about 0.001 mol % to about 20 mol % of the total lipid content present in the nanoparticle composition.

65. The nanoparticle composition of clause 63, wherein the receptor targeting conjugate comprises from about 0.01 mol % to about 1 mol % of the total lipid content present in the nanoparticle composition.

66. The nanoparticle composition of any one of clauses 63 to 65, further comprising a sterol or a derivative thereof, comprising from 10 mol % to 70 mol % of the total lipid content present in the nanoparticle composition.

67. The nanoparticle composition of clause 66, wherein the sterol or the derivative thereof is cholesterol or a cholesterol derivative.

68. The nanoparticle composition of clause 67, wherein the cholesterol or the cholesterol derivative comprises from 20 mol % to 50 mol % of the total lipid content present in the nanoparticle composition.

69. The nanoparticle composition of any one of clauses 63 to 68, further comprising a phospholipid, comprising from 1 mol % to 20 mol % of the total lipid content present in the nanoparticle composition.

70. The nanoparticle composition of clause 69, wherein the phospholipid comprises from about 5 mol % to about 15 mol % of the total lipid content present in said nanoparticle composition.

71. The nanoparticle composition of clause 69 or 70, wherein the phospholipid is selected from 1,2-distearoyl-sn-glycero-3-phosphocholine (DSPC), 1,2-dipalmitoyl-sn-glycero-3-phosphocholine (DPPC), 1,2-dimyristoyl-sn-glycero-phosphocholine (DMPC), 2-oleoyl-1-palmitoyl-sn-glycero-3-phosphocholine (POPC), 1,2-dioleoyl-sn-glycero-3-phosphoethanolamine (DOPE), and sphingomyelin.

72. The nanoparticle composition of clause 69 or 70, wherein the phospholipid is DSPC.

73. The nanoparticle composition of any one of clauses 63 to 72, further comprising a stealth lipid, comprising from 0.1 mol % to 6 mol % of the total lipid content present in the nanoparticle composition.

74. The nanoparticle composition of clause 73, wherein the stealth lipid comprises about 2.0 mol % to about 2.5 mol % of the total lipid content present in said nanoparticle composition.

75. The nanoparticle composition of clause 73 or 74, wherein the stealth lipid is a PEG-lipid that has a number average molecular weight of from about 200 Da to about 5000 Da.

76. The nanoparticle composition of any one of clauses 63 to 75, further comprising an amino lipid, comprising from about 10 mol % to about 60 mol % of the total lipid content present in the nanoparticle composition.

77. The nanoparticle composition of any one of clauses 63 to 76, wherein the nanoparticle composition comprises an antioxidant.

78. The nanoparticle composition of clause 77, wherein the antioxidant comprises ethylenediaminetetraacetic acid (EDTA).

79. The nanoparticle composition of any one of clauses 63 to 78, wherein the one or more nucleic acid molecular entities comprise a single guide RNA (sgRNA) or guide RNA (gRNA) targeting a disease causing gene of interest produced in the hepatocytes.

80. The nanoparticle composition of any one of clauses 63 to 78, wherein the one or more nucleic acid molecular entities comprise an mRNA that encodes a Cas nuclease.

81. The nanoparticle composition of any one of clauses 63 to 80, wherein at least one of the one or more nucleic acid molecular entities comprises a chemical modification.

82. The nanoparticle composition of clause 81, wherein the chemical modification is a 2'-F modification, a phosphorothioate internucleotide linkage modification, acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), 4'-O-methyl, or a 2'-ara-F modification.

83. The nanoparticle composition of clause 81, wherein the chemical modification is a 2'-O-methyl modification.

84. A pharmaceutical composition comprising the receptor targeting conjugate of clauses 1 to 62 or a nanoparticle composition of any one of clauses 63 to 83, and an excipient or carrier.

85. The pharmaceutical composition of clause 84, wherein the pharmaceutical composition comprises an mRNA encoding a gene editor nuclease.

86. The pharmaceutical composition of clause 84 or 85, wherein the pharmaceutical composition comprises one or more guide RNA molecules.

87. The pharmaceutical composition of clause 84 or 85, wherein said pharmaceutical composition comprises two or more guide RNA molecules.

88. The pharmaceutical composition of clause 87, wherein said two or more guide RNA molecules target two or more genes of interest.

89. The pharmaceutical composition of any one of clauses 84 to 88, wherein the mRNA encodes Cas9 nuclease.

90. The pharmaceutical composition of any one of clauses 84 to 88, wherein the mRNA encodes a base editor nuclease.

91. The pharmaceutical composition of any one of clauses 86 to 90, wherein the mRNA and the one or more guide RNA molecules are present in the same nanoparticle composition.

92. The pharmaceutical composition of any one of clauses 86 to 90, wherein the mRNA and the one or more guide RNA molecules are present in different nanoparticle compositions.

93. The pharmaceutical composition of any one of clauses 86 to 92, wherein a ratio of the gRNA molecules to the mRNA in the pharmaceutical composition is from about 0.01 to about 100 by weight or by mole.

94. The pharmaceutical composition of clause 93, wherein a ratio of said gRNA molecules to said mRNA in said pharmaceutical composition is about 50:1, about 40:1, about 30:1, about 20:1, about 18:1, about 16:1, about 14:1, about 12:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 by weight or by mole.

95. A pharmaceutical composition comprising:
   a. a first receptor targeting conjugate of any one of clauses 1-62 or a first nanoparticle composition of any one of clauses 63-83, and
   b. a second receptor targeting conjugate of any one of clauses 1-62 or a second nanoparticle composition of any one of clauses 63-83.

96. The pharmaceutical composition of clause 95, wherein said first nanoparticle composition comprises a gene editor mRNA.

97. The pharmaceutical composition of clause 95 or 96, wherein said second nanoparticle composition comprises one or more guide RNA molecules.

98. The pharmaceutical composition of any one of clauses 95 to 97, wherein a ratio of guide RNA molecules to mRNA in said pharmaceutical composition is about 50:1, about 40:1, about 30:1, about 20:1, about 18:1, about 16:1, about 14:1, about 12:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 by weight or by mole.

99. A method of delivering a nucleic acid to a cell, the method comprising contacting the cell with a nanoparticle composition of any one of clauses 63-83 or a pharmaceutical composition of any one of clauses 84-98, whereby the nucleic acid is delivered to said cell.

100. The method of clause 99, wherein said cell is contacted in vivo, ex vivo, or in intro.

101. A method of producing a polypeptide of interest in a cell, the method comprising contacting said cell with a nanoparticle composition of any one of clauses 63-83 or a pharmaceutical composition of any one of clauses 84-98, whereby the nucleic acid is capable of being translated in said cell to produce the polypeptide.

102. A method of treating a disease or condition in a subject, the method comprising administering to the subject a therapeutically effective amount of a pharmaceutical composition of any one of clauses 84-98.

103. The method of clause 102, wherein the disease or condition is a coronary disease.

104. The method of clause 102 or 103, wherein the subject is low-density lipoprotein receptor (LDLR)-deficient.

105. A method of delivering a nucleic acid molecular entity to the liver of a subject, comprising administering to the subject a pharmaceutical composition of any one of clauses 84 to 98, thereby delivering the nucleic acid molecular entity.

106. A nucleotide conjugate comprising:
   (a) a nucleic acid, and
   (b) a targeting moiety connected to the nucleic acid in (a), wherein the targeting moiety comprises a structure of Table 1.

107. The nucleotide conjugate of clause 106, wherein the targeting moiety further comprises a coupling sequence that hybridizes with the nucleic acid in (a).

108. A nucleotide conjugate comprising:
   (a) a nucleic acid, and
   (b) a targeting moiety connected to the nucleic acid in (a), wherein the targeting moiety comprises a coupling sequence that hybridizes with the nucleic acid in (a).

109. The nucleotide conjugate of any one of clauses 106-108, wherein the nucleic acid comprises a single stranded, double stranded, a partially double stranded, or a hairpin stem-loop nucleic acid, and wherein the targeting moiety is a receptor targeting moiety.

110. The nucleotide conjugate of any one of clauses 106-109, wherein the targeting moiety binds to a lectin.

111. The nucleotide conjugate of clause 110, wherein the lectin is an asialoglycoprotein receptor (ASGPR).

112. The nucleotide conjugate of clause 111, wherein the targeting moiety comprises one or more N-acetylgalactosamine (GalNAc) or GalNAc derivatives.

113. The nucleotide conjugate of any one of clauses 106-112, wherein the targeting moiety comprises a spacer.

114. The nucleotide conjugate of clause 113, wherein the spacer comprises polyethylene glycol, substituted or unsubstituted $C_1$-$C_{12}$ alkylene, or both, wherein the polyethylene glycol has from 1 to 5 repeating units.

115. The nucleotide conjugate of any one of clauses 106-114, wherein the targeting moiety is linked to one or more strands of the nucleic acid through one or more linkers.

116. The nucleotide conjugate of any one of clauses 108-115, wherein the targeting moiety comprises a structure of Table 1.

117. The nucleotide conjugate of any one of clauses 107-116, wherein the coupling sequence hybridizes with the nucleic acid in (a).

118. The nucleotide conjugate of clause 117, wherein the coupling sequence hybridizes with an extension in the nucleic acid in (a).

119. The nucleotide conjugate of any one of clauses 106-118, wherein the targeting moiety is attached to the 5' end of the nucleic acid sequence, the 3' end of the nucleic acid sequence, or the middle of the nucleic acid sequence.

120. The nucleotide conjugate of any one of clauses 106-119, wherein the targeting moiety comprises at least two GalNAcs or GalNAc derivatives.

121. The nucleotide conjugate of any one of clauses 106-120, wherein the targeting moiety comprises at least three GalNAcs or GalNAc derivatives.

122. The nucleotide conjugate of any one of clauses 114-121, wherein the GalNAcs or GalNAc derivatives are connected to the nucleic acid in (a) via a linker in the targeting moiety, via hybridization of the coupling sequence in the targeting moiety that hybridizes with the nucleic acid in (a), or via a combination thereof.

123. The nucleotide conjugate of any one of clauses 107-122, wherein the targeting moiety comprises at least two coupling sequences that hybridize with the nucleic acid in (a).

124. The nucleotide conjugate of clause 123, wherein the at least two coupling sequences are identical.

125. The nucleotide conjugate of clause 123, wherein the at least two coupling sequences are different.

126. The nucleotide conjugate of any one of clauses 106-125, further comprising a second targeting moiety.

127. The nucleotide conjugate of clause 126, wherein the second targeting moiety binds to an asialoglycoprotein receptor (ASGPR).

128. The nucleotide conjugate of clause 127, wherein the second targeting moiety is linked to one or more strands the nucleic acid through a spacer and/or through one or more linkers.

129. The nucleotide conjugate of clause 128, wherein the second targeting moiety comprises a GalNAc or GalNAc derivative.

130. The nucleotide conjugate of clause 129, wherein the second targeting moiety comprises at least three GalNAcs or GalNAc derivatives.

131. The nucleotide conjugate of clause 129 or 130, wherein the GalNAc or GalNAc derivatives are connected to the nucleic acid in (a) via a linker in the targeting moiety, via hybridization of the coupling sequence in the targeting moiety that hybridizes with the nucleic acid in (a), or via a combination thereof.

132. The nucleotide conjugate of any one of clauses 126-131, wherein the second targeting moiety comprises a structure of Table 1.

133. The nucleotide conjugate of any one of clauses 126-132, wherein the second targeting moiety comprises a coupling sequence that hybridizes with the nucleic acid.

134. The nucleotide conjugate of any one of clauses 126-133, wherein the second targeting moiety is attached to the 5' end of the nucleic acid, the 3' end of the nucleic acid, or the middle of the nucleic acid.

135. The nucleotide conjugate of any one of clauses 106-134, wherein the nucleic acid in (a) comprises RNA or DNA.

136. The nucleotide conjugate of any one of clauses 107-135, wherein the coupling sequence comprises RNA, DNA, chemically modified RNA, chemically modified DNA, or a hybrid of DNA and RNA.

137. The nucleotide conjugate of any one of clauses 107-136, wherein the coupling sequence comprises one or more of (a), (c), (g), (u), (A)n, (T)n, (U)n, (a)n, or (u)n, wherein n is an integer no less than 3, wherein a is 2'-O-methyladenosine (2'-OMe A), wherein c is 2'-O-methylacytidine (2'-OMe-C), wherein g is 2'-O-methylacytidine guanine (2'-OMe-G), and wherein u is 2'-O-methyluridine (2'-OMe-U).

138. The nucleotide conjugate of any one of clauses 107-137, wherein the coupling sequence comprises one or more of (a), (c), (g), (u), (A)n, (T)n, (U)n, (a)n, or (u)n, wherein n is an integer no less than 3, wherein a is 2'-O-methyladenosine (2'-OMe A), wherein c is 2'-O-methylacytidine (2'-OMe-C), wherein g is 2'-O-methylacytidine guanine (2'-OMe-G), and wherein u is 2'-O-methyluridine (2'-OMe-U).

139. The nucleotide conjugate of clause 137 or 138, wherein the (a), (c), (g), or (u) is scattered along the nucleic acid or the coupling sequence.

140. The nucleotide conjugate of any one of clauses 137-139, wherein the nucleic acid and the coupling sequence comprise one or more G-C base pairing within a hybridization duplex wherein the coupling sequence hybridizes with the nucleic acid and wherein said one or more G-C base pairing increases stability of the hybridization duplex.

141. The nucleotide conjugate of any one of clauses 115-140, wherein the linker comprises a covalent linker.

142. The nucleotide conjugate of any one of clauses 115-140, wherein the linker comprises a non-covalent linker.

143. The nucleotide conjugate of any one of clauses 115-142, wherein the linker comprises a monovalent linker, a bivalent linker, a trivalent linker, or a combination thereof.

144. The nucleotide conjugate of any one of clauses 115-143, wherein the linker comprises a biocleavable linker.

145. The nucleotide conjugate of any one of clauses 115-143, wherein the linker comprises a non-biocleavable linker.

146. The nucleotide conjugate of clause 142, wherein the linker comprises a phosphate, phosphorothioate, amide, ether, oxime, hydrazine or carbamate.

147. The nucleotide conjugate of clause 146, wherein the linker is a phosphate or phosphorothioate.

148. The nucleotide conjugate of any one of clauses 106-147, wherein the nucleic acid in (a) comprises a chemical modification.

149. The nucleotide conjugate of clause 148, wherein the nucleic acid in (a) comprises a 2'-F modification, a phosphorothioate internucleotide linkage modification, acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), 4'-O-methyl, or a 2'-ara-F modification.

150. The nucleotide conjugate of clause 149, wherein the nucleic acid comprises a 2'-O-methyl modification.

151. The nucleotide conjugate of clause 149, wherein the nucleic acid comprises a phosphorothioate internucleotide linkage modification.

152. The nucleotide conjugate of any one of clauses 106-151, wherein the nucleic acid is capable of hybridizing with a target sequence within a target gene of a genome.

153. The nucleotide conjugate of clause 152, wherein the nucleic acid comprises a mRNA, siRNA, shRNA, antisense oligonucleotide, microRNA, anti-microRNA or antimir, supermir, antagomir, ribozyme, triplex-forming oligonucleotide, decoy oligonucleotide, splice-switching oligonucleotide, immunostimulatory oligonucleotide, RNA activator, U1 adaptor, guide RNA, or any combinations thereof.

154. The nucleotide conjugate of clause 153, wherein the nucleic acid encodes a protein.

155. The nucleotide conjugate of clause 154, wherein the nucleic acid is a CRISPR enzyme.

156. The nucleotide conjugate of clause 153, wherein the nucleic acid is a guide RNA capable of forming a complex with a CRISPR enzyme.

157. The nucleotide conjugate of clause 156 wherein the guide RNA is a single guide RNA or a dual guide RNA.

158. The nucleotide conjugate of clause 157, wherein the CRISPR enzyme is selected from the group consisting of Cas9, Cpf1, CasX, CasY, C2c1, C2c3, and base editor fusion protein.

159. The nucleotide conjugate of any one of clauses 158, wherein the nucleic acid further comprises a mRNA encoding the CRISPR enzyme.

160. The nucleotide conjugate of clause 159, wherein the CRISPR enzyme results in an alteration in the target sequence.

161. The nucleotide conjugate of any one of clauses 152-160, wherein the target gene is involved in a lipid metabolism pathway.

162. the nucleotide conjugate of clause 161, wherein the target gene is selected from the group consisting of PCSK9, ANGPTL3, APOC3, LPA, APOB, MTP, ANGPTL4, ANGPTL8, APOA5, APOE, LDLR, IDOL, NPC1L1, ASGR1, TM6SF2, GALNT2, GCKR, LPL, MLXIPL, SORT1, TRIB1, MARC1, ABCG5, and ABCG8

163. A particle comprising the nucleotide conjugate and the CRISPR enzyme of any one of clauses 155-162.

164. The particle of clause 163, wherein the particle is a lipid nanoparticle, a liposome, an inorganic nanoparticle, or an RNP.

165. A cell comprising the nucleotide conjugate of any one of clauses 106-162.

166. The cell of clause 165, wherein the cell is a prokaryotic cell, a eukaryotic cell, a vertebrate cell, a mouse cell, a non-human primate cell, or a human cell.

167. A pharmaceutical composition comprising the nucleotide conjugate of any one of clauses 106-162, the particle of clause 163 or 164, or the cell of clause 165 or 166.

168. The pharmaceutical composition of clause 167, further comprising a pharmaceutically acceptable adjuvant, diluent, carrier, preservative, excipient, buffer, stabilizer, or a combination thereof.

169. The pharmaceutical composition of clause 168, wherein the carrier comprises solvents, dispersion media, dispersion or suspension aids, surface active agents, isotonic agents, thickening or emulsifying agents, preservatives, lipids, lipidoids, polymers, lipoplexes, core-shell nanoparticles, hyaluronidase, nanoparticle mimics, or combinations thereof.

170. A kit comprising the nucleotide conjugate of any one of clauses 106-162.

171. A method for reducing the risk of coronary disease in a subject in need thereof, comprising administering to the subject an effective amount of the nucleotide conjugate of any one of clauses 106-162.

172. A method for reducing the risk of coronary disease in a subject in need thereof, comprising administering to the subject an effective amount of a pharmaceutical composition, said pharmaceutical composition comprising
  (a) a nucleic acid, and
  (b) a targeting moiety connected to the nucleic acid in (a), wherein the targeting moiety comprises a structure of Table 1.

173. A method of delivering a nucleic acid to the liver of a subject, comprising administering to the subject said nucleic acid connected to a targeting moiety, wherein the targeting moiety comprises a structure of Table 1.

174. The method of clause 172 or 173, wherein the targeting moiety further comprises a coupling sequence that hybridizes with the nucleic acid in (a).

175. A method for reducing the risk of coronary disease in a subject in need thereof, comprising administering to the subject an effective amount of a pharmaceutical composition, said pharmaceutical composition comprising
  (a) a nucleic acid, and
  (b) a targeting moiety connected to the nucleic acid in (a), wherein the targeting moiety comprises a coupling sequence that hybridizes with the nucleic acid in (a).

176. A method of delivering a nucleic acid to the liver of a subject, comprising administering to the subject said nucleic acid connected to a targeting moiety, wherein the targeting moiety comprises a coupling sequence that hybridizes with the nucleic acid.

177. The method of any one of the clauses 172-176, wherein the nucleic acid comprises a single stranded, double stranded, a partially double stranded, or a hairpin stem-loop nucleic acid, and wherein the targeting moiety is a receptor targeting moiety.

178. The method of any one of clauses 172-177, wherein the targeting moiety binds to a lectin.

179. The method of clause 178, wherein the lectin is an asialoglycoprotein receptor (ASGPR).

180. The method of any one of clauses 172-179, wherein the targeting moiety comprises one or more N-acetylgalactosamine (GalNAc) or GalNAc derivatives.

181. The method of clause 180, wherein the targeting moiety comprises at least three GalNAc or GalNAc derivatives.

182. The method of any one of clauses 172-181, wherein the nucleic acid comprises (i) a guide RNA and a nuclease mRNA or (ii) a guide RNA complexed in a nuclease RNP, and wherein the guide RNA is capable of directing the nuclease to a target sequence in a target gene.

183. The method of clause 182, wherein the guide RNA comprises a single guide RNA or a dual guide RNA.

184. The method of clause 183, wherein the nuclease is a CRISPR enzyme.

185. The method of clause 184, wherein the CRISPR enzyme selected from the group consisting of Cas9, Cpf1, CasX, CasY, C2c1, C2c3, and base editor fusion protein.

186. The method of clause 185, wherein the CRISPR enzyme results in an alteration in the target sequence.

187. The method of any one of clauses 182-186, wherein the administration results in reduced expression of the target gene in the liver of the subject.

188. The method of clause 186 or 187, wherein expression of the target gene in the liver of the subject is reduced by at least 1%, at least 5%, at least 10%, at least 20%, at least 30%, at least 40%, at least 50%, at least 60%, at least 70%, at least 80%, at least 85%, at least 90%, at least 95%, at least 96%, at least 97%, at least 98%, at least 99%, or greater than 99.99% as compared to a control tissue of the subject.

189. The method of any one of clauses 182-188, wherein the target gene is associated with a coronary disease.

190. The method of clause 189, wherein the target gene is selected from the group consisting of PCSK9, ANGPTL3, APOC3, LPA, APOB, MTP, ANGPTL4, ANGPTL8, APOA5, APOE, LDLR, IDOL, NPC1L1, ASGR1, TM6SF2, GALNT2, GCKR, LPL, MLXIPL, SORT1, TRIB1, MARC1, ABCG5, and ABCG8.

191. The method of any one of clauses 182-190, wherein the guide RNA comprises a sequence selected from the group consisting of SEQ ID NOs 1-23.

192. The method of any one of clauses 174-191, wherein the coupling sequence comprises RNA, DNA, chemically modified RNA, chemically modified DNA, or a hybrid of DNA and RNA.

193. The method of any one of clauses 174-192, wherein the coupling sequence comprises (A)n, (T)n, (U)n, (a)n, or (u)n, wherein n is an integer no less than 3, wherein a is 2'-O-methyladenosine (2'-OMe A), and wherein u is 2'-O-methyluridine (2'-OMe-U).

194. The method of any one of clauses 172-193, wherein the nucleic acid in (a) comprises (A)n, (T)n, (U)n, (a)n, or (u)n, wherein n is an integer no less than 3, wherein a is 2'-O-methyladenosine, and wherein u is 2'-O-methyluridine.

195. The method of any one of clauses 172-194, wherein the targeting moiety is linked to the nucleic acid in (a) via a linker in the targeting moiety, via hybridization of the coupling sequence in the targeting moiety that hybridizes with the nucleic acid in (a), or via a combination thereof.

196. The method of clauses 195, wherein the linker comprises a covalent linker.

197. The method of clause 196, wherein the linker comprises a phosphate, phosphorothioate, amide, ether, oxime, hydrazine or carbamate.

198. The method of clause 197, wherein the linker is a phosphate or phosphorothioate.

199. The method of any one of 172-198, wherein the nucleic acid in (a) comprises a chemical modification.

200. The method of clause 199, wherein the nucleic acid in (a) comprises a 2'-F modification, a phosphorothioate internucleotide linkage modification, acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), a 2'-O-dimethylaminoethoxyethyl (2'-O-DMAEOE), 2'-O-aminopropyl (2'-O-AP), or a 2'-ara-F modification.

201. The method of clause 200, wherein the nucleic acid comprises a 2'-O-methyl modification.

202. The method of clause 201, wherein the nucleic acid comprises a phosphorothioate internucleotide linkage modification.

203. The method of any one of clauses 172-202, where in the level of the nucleic acid in the liver of the subject is at least 1.5, at least 2, at least 2.5, at least 3, at least 5, at least 10, at least 15, at least 20, at least 30, at least 40, at least 50 folds higher as compared to other tissues of the subject at least 1 hours, 2 hours, 6 hours, 12 hours, 24 hours, 2 days, 1 week, 2 weeks, 3 weeks, 6 weeks, or 8 weeks post delivery.

204. The method of clause any one of clauses 175-203, wherein the effective amount is about 1 mg/kg to about 10 mg/kg.

205. The method of clause 175-204, wherein the administration results in reduced blood triglycerides and/or reduced low-density lipo-protein cholesterol in the subject in need thereof.

206. The method of any one of clauses 175-205, wherein the administration is performed intravenously, intrathecally, intramuscularly, intraventricularly, intracerebrally, intracerebellarly, intracerebroventricularly, intraparenchymally, subcutaneously, or a combination thereof.

207. A method for reducing the risk of coronary disease in a subject in need thereof, the method comprising administering to the subject a pharmaceutical composition comprising
   (a) (i) a single guide RNA and a nuclease mRNA, (ii) a dual guide RNA and a nuclease mRNA, (iii) a single guide RNA and an RNP, or (iv) a dual guide RNAs and an RNP; and
   (b) a asialoglycoprotein receptor (ASGPR) targeting moiety connected to the nucleic acid in (a),
   wherein the single guide RNA or the dual guide RNA comprises 4 or more 2'-O-methyl modifications and 2 or more phosphorothioate internucleotide linkages, wherein the targeting moiety comprises a structure of Table 1, and wherein the guide RNA hybridizes with a PCSK9 gene.

208. A method for reducing the risk of coronary disease in a subject in need thereof, the method comprising administering to the subject a pharmaceutical composition comprising
   (a) (i) a single guide RNA and a nuclease mRNA, (ii) a dual guide RNA and a nuclease mRNA, (iii) a single guide RNA and an RNP, or (iv) a dual guide RNAs and an RNP; and
   (b) a targeting moiety connected to the nucleic acid in (a),
   wherein the single guide RNA or the dual guide RNA comprises 4 or more 2'-O-methyl modifications and two or more phosphorothioate internucleotide linkages, wherein the targeting moiety comprises a coupling sequence that hybridizes with the single guide RNA in (a), and wherein the guide RNA hybridizes with a PCSK9 gene.

209. The method of clause 207 or 208, wherein the nuclease mRNA and/or the single guide RNA comprises at least one chemical modification.

210. The method of clause 209, wherein the chemical modification is selected from the group consisting of a 2'-F modification, phosphorothioate internucleotide linkage modification, acyclic nucleotides, LNA, HNA, CeNA, 2'-methoxyethyl, 2'-O-methyl, 2'-O-allyl, 2'-C-allyl, 2'-deoxy, 2'-fluoro, 2'-O—N-methylacetamido (2'-O-NMA), 2'-O-dimethylaminoethoxyethyl (2'-O-DMAEOE), 2'-O-aminopropyl (2'-O-AP), 4'-O-methyl, and a 2'-ara-F modification.

211. The method of clause 210, wherein administrating of the nucleic acid conjugate results in a reduced level of immune response as compared to a control nucleic acid conjugate without said chemical modification.

212. A nucleotide conjugate comprising a structure of Formula (IV)

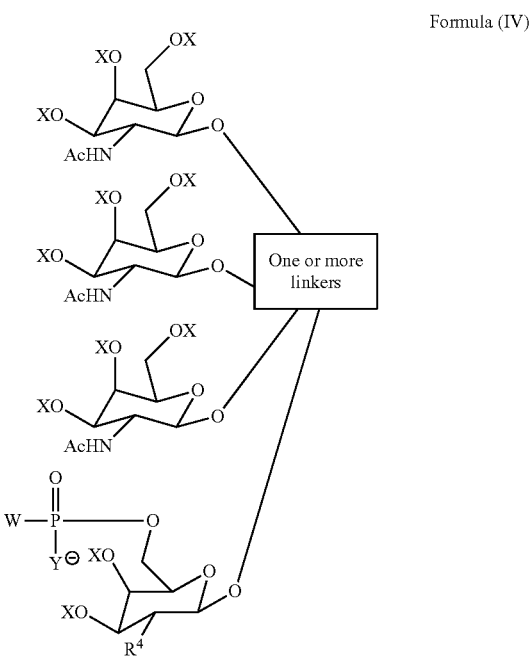

Formula (IV)

wherein each X is independently H or a protecting group, RA is —OX or —NHAc, Y is O or S, and W represents
   (a) (i) a single guide RNA and a nuclease mRNA, (ii) a dual guide RNA and a nuclease mRNA, (iii) a single guide RNA and an RNP, or (iv) a dual guide RNAs and an RNP; or
   (b) a coupling sequence.

213. The nucleotide conjugate of clause 212, wherein the one or more linkers comprise a structure selected from the group consisting of.

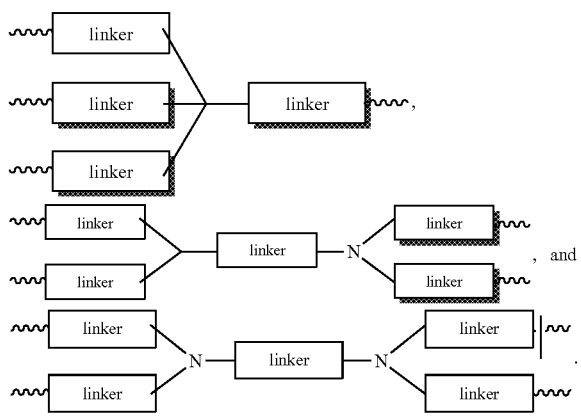

214. The nucleotide conjugate of clause 212 or 213, wherein each of the linkers independently has a structure of -$(L')_{k1}$-$(L^2)_k$-$(L^3)_{k3}$-$(L^4)_{k4}$-, wherein each of k1, k2, k3, and k4 is independently 0, 1 or 2, and each of the $L^1$, $L^2$, $L^3$ and $L^4$ is independently selected from —O—, —S—, S(=O)$_{1-2}$—, —C(=O)—, —C(=S)—, —NR$^L$—, —OC(O)—, —C(=O)O—, —OC(=O)O—, —C(=O)NR$^L$—, —OC(=O)NR$^L$—, —NR$^L$C(=O)—, —NR$^L$C(=O)NR$^L$—, —P(=O)R$^L$—, —NR$^L$S(=O)(=NR$^L$)—, —NR$^L$S(=O)$_2$—, —S(=O)$_2$NR$^L$—, —N=N—, —(CH$_2$—CH$_2$—O)$_{1-6}$—, linear or branched C$_{1-6}$ alkylene, linear or branched C$_{2-6}$ alkenylene, linear or branched C$_{2-6}$ alkynylene, C$_3$-C$_8$ cycloalkylene, C$_2$-C$_7$ heterocycloalkylene, C$_6$-C$_{10}$ arylene, and C$_5$-C$_9$ heteroarylene, wherein the alkylene, alkenylene, alkynylene, cycloalkylene, cycloalkylene, arylene, or heteroarylene is substituted or unsubstituted, and wherein each R$^L$ is independently H, D, cyano, halogen, substituted or unsubstituted C$_1$-C$_6$ alkyl, —CD$_3$, —OCH$_3$, —OCD$_3$, substituted or unsubstituted C$_1$-C$_6$ haloalkyl, substituted or unsubstituted C$_1$-C$_6$ heteroalkyl, substituted or unsubstituted C$_3$-C$_5$ cycloalkyl, substituted or unsubstituted C$_2$-C$_7$ heterocycloalkyl, substituted or unsubstituted aryl, or substituted or unsubstituted heteroaryl. In some embodiments, each R$^L$ is independently H, substituted or unsubstituted C$_1$-C$_6$ alkyl, —OCH$_3$, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, or substituted or unsubstituted C$_2$-C$_7$ heterocycloalkyl.

215. The nucleotide conjugate of any one of clauses 212 to 214, wherein the sum of k1, k2, k3, and k4 is 1, 2, or 3.

216. A method of preparing a formulation comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, the method comprising:
  a. providing a first solution comprising the one or more nucleic acid molecular entities;
  b. providing a second solution comprising at least one of the one or more lipids;
  c. mixing the first solution and the second solution, thereby producing a mixture comprising nanoparticles that comprise the one or more nucleic acid molecular entities and the one or more lipids;
  d. mixing the receptor targeting conjugate with the nanoparticles produced in step (c);
  e. incubating the nanoparticles; and
  f. optionally carrying out a buffer exchange process.

217. The method of clause 216, wherein the receptor targeting conjugate is combined with the one or more lipids after the mixing step in (c).

218. The method of clause 216, wherein the receptor targeting conjugate is added in a dilution buffer, and wherein the dilution buffer is mixed with preformed nucleic acid-lipid nanoparticles coming out of an inline mixing chamber thereby forming the nanoparticles.

219. The method of clause 216, wherein the receptor targeting conjugate is introduced after an addition of a dilution buffer to the mixture and holding the diluted mixture for a period of time.

220. The method of clause 219, wherein the holding time is between 1 and 120 minutes.

221. The method of clause 219, wherein the holding time is between 1 and 90 minutes, between 1 and 60 minutes, or between 10 and 40 minutes.

222. The method of clause 219, wherein the holding time is about 30 minutes.

223. The method of clause 216, wherein the receptor targeting conjugate is introduced to the nanoparticles after buffer exchange.

224. The method of clause 216, wherein the receptor targeting conjugate is introduced to the nanoparticles after buffer exchange and concentration, but prior to storage.

225. The method of clause 216, wherein the receptor targeting conjugate is introduced to the nanoparticles after storage and thawing, and prior to dosing or evaluation.

226. A method of preparing a formulation comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, the method comprising:
  a. providing a first solution comprising the one or more nucleic acid molecular entities;
  b. providing a second solution comprising at least one of the one or more lipids;
  c. inline mixing of the first solution and the second solution, thereby producing a mixture comprising nanoparticles that comprise the one or more nucleic acid molecular entities and the one or more lipids;
  d. inline mixing of the receptor targeting conjugate to the mixture of step (c), thereby producing a mixture comprising nanoparticles that comprise the one or more nucleic acid molecular entities, the one or more lipids, and the receptor targeting conjugate;
  e. diluting the mixture of step (d) by adding a dilution buffer; and
  f. optionally carrying out a buffer exchange process.

227. The method of clause 226, wherein the inline mixing of step (c) and the inline mixing of step (d) are performed successively.

228. A method of preparing a formulation comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, the method comprising:
  a. providing a first solution comprising the one or more nucleic acid molecular entities;
  b. providing a second solution comprising (i) at least one of the one or more lipids and (ii) at least a portion of the receptor targeting conjugate;
  c. mixing the first solution and the second solution, thereby producing a mixture comprising nanoparticles;
  d. optionally incubating the nanoparticles; and
  e. optionally carrying out a buffer exchange process.

229. The method of clause 228, wherein the second solution comprises all the receptor targeting conjugate.

230. A method of preparing a formulation comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, the method comprising:
  a. providing a first solution comprising the one or more nucleic acid molecular entities;
  b. providing a second solution comprising at least one of the one or more lipids;
  c. mixing the first solution and the second solution, thereby producing a mixture comprising nanoparticles that comprise the one or more nucleic acid molecular entities and the one or more lipids;
  d. combining the receptor targeting conjugate with the one or more lipids, wherein at least a portion of the receptor targeting conjugate is combined with the one or more lipids prior to or concurrently with the mixing step;

e. optionally incubating the nanoparticles; and f. optionally carrying out a buffer exchange process.

231. The method of clause 230, wherein at least a portion of the receptor targeting conjugate is combined with the one or more lipids concurrently with the mixing step.

232. The method of clause 230, wherein at least a portion of the receptor targeting conjugate is combined with the one or more lipids prior to the mixing step.

233. The method of clause 232, wherein the receptor targeting conjugate is combined with the one or more lipids in the second solution.

234. The method of clause 228 or 230, wherein a portion of the receptor targeting conjugate is combined with the one or more lipids in the second solution and a portion of the receptor targeting conjugate is combined with the one or more lipids after the mixing.

235. The method of clause 228 or 230, wherein a portion of the receptor targeting conjugate is combined with the one or more lipids in the second solution and a portion of the receptor targeting conjugate is combined with the one or more lipids after the incubating step.

236. The method of clause 228 or 230, wherein a portion of the receptor targeting conjugate is combined with the one or more lipids in the second solution and a portion of the receptor targeting conjugate is combined with the one or more lipids after the buffer exchange step.

237. The method of any one of clauses 228 or 230, further comprising diluting the mixture produced by mixing the first and the second solutions by adding a dilution buffer.

238. The method of clause 237, wherein the mixture is diluted inline.

239. The method of clause 237 or 238, wherein the dilution buffer comprises at least a portion of the receptor targeting conjugate.

240. The method of any one of clauses 237 to 239, wherein the dilution buffer comprises at least a portion of the stealth lipid.

241. The method of any one of clauses 216 to 240, wherein the first solution comprises an aqueous buffer.

242. The method of any one of clauses 216 to 241, wherein the second solution comprises ethanol.

243. The method of any one of clauses 216 or 228 to 242, wherein the mixing comprises laminar mixing, vortex mixing, turbulent mixing, or a combination thereof.

244. The method of any one of clauses 216 or 228 to 242, wherein the mixing comprises cross-mixing.

245. The method of any one of clauses 216 or 228 to 242, wherein the mixing comprises inline mixing.

246. The method of any one of clauses 216 to 242, wherein the mixing comprises introducing at least a portion of the first solution through a first inlet channel and at least a portion of the second solution through a second inlet channel, and wherein an angle between the first inlet channel and the second inlet channel is from about 15 to 180 degrees.

247. The method of clause 246, wherein the mixing comprises introducing a portion of the first solution through a third inlet channel.

248. The method of any one of clauses 216 to 247, wherein the buffer exchange comprises dialysis, chromatography, or tangential flow filtration (TFF).

249. The method of any one of clauses 216 to 248, further comprising a filtration step.

250. The method of any one of clauses 216 to 249, wherein the receptor targeting conjugate comprises one or more N-acetylgalactosamine (GalNAc) or GalNAc derivatives.

251. The method of clause 250, wherein the receptor targeting conjugate is selected from Table 4.

252. The method of any one of clauses 216 to 249, wherein the receptor targeting conjugate is described in any one of clauses 1 to 62.

253. The method of any one of clauses 216 to 249, wherein the nanoparticles comprise a first nanoparticle composition of any one of clauses 63-83

254. The method of any one of clauses 216 to 249, wherein the formulation is a pharmaceutical composition of any one of clauses 84 to 98.

255. A pharmaceutical composition comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, wherein the formulation is prepared by a method of any one of clauses 216 to 253.

256. A pharmaceutical composition comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, wherein the formulation is prepared by a method comprising:

a. providing a first solution comprising the one or more nucleic acid molecular entities;

b. providing a second solution comprising at least one of the one or more lipids;

c. mixing the first solution and the second solution, thereby producing a mixture comprising nanoparticles that comprise the one or more nucleic acid molecular entities and the one or more lipids;

d. mixing the receptor targeting conjugate with the nanoparticles produced in step (c);

e. incubating the nanoparticles; and f. optionally carrying out a buffer exchange process.

257. A pharmaceutical composition comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, wherein the formulation is prepared by a method comprising:

a. providing a first solution comprising the one or more nucleic acid molecular entities;

b. providing a second solution comprising at least one of the one or more lipids;

c. mixing the first solution and the second solution, thereby producing a mixture comprising nanoparticles that comprise the one or more nucleic acid molecular entities and the one or more lipids;

d. combining the receptor targeting conjugate with the one or more lipids, wherein at least a portion of the receptor targeting conjugate is combined with the one or more lipids prior to or concurrently with the mixing step;

e. optionally incubating the nanoparticles; and f. optionally carrying out a buffer exchange process.

258. A pharmaceutical composition comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, wherein the formulation is prepared by a method comprising:

a. providing a first solution comprising the one or more nucleic acid molecular entities;

b. providing a second solution comprising at least one of the one or more lipids;

c. inline mixing of the first solution and the second solution, thereby producing a mixture comprising nanoparticles that comprise the one or more nucleic acid molecular entities and the one or more lipids;

d. inline mixing of the receptor targeting conjugate to the mixture of step (c), thereby producing a mixture comprising nanoparticles that comprise the one or more nucleic acid molecular entities, the one or more lipids, and the receptor targeting conjugate;

e. diluting the mixture of step (d) by adding a dilution buffer; and f. optionally carrying out a buffer exchange process.

259. A pharmaceutical composition comprising nanoparticles, wherein the nanoparticles comprise (i) one or more nucleic acid molecular entities, (ii) one or more lipids selected from a sterol or a derivative thereof, a phospholipid, a stealth lipid, and an amino lipid, and (iii) a receptor targeting conjugate, wherein the formulation is prepared by a method comprising:

a. providing a first solution comprising the one or more nucleic acid molecular entities;

b. providing a second solution comprising (i) at least one of the one or more lipids and (ii) at least a portion of the receptor targeting conjugate;

c. mixing the first solution and the second solution, thereby producing a mixture comprising nanoparticles;

d. optionally incubating the nanoparticles; and e. optionally carrying out a buffer exchange process.

260. A subject as referenced in any one of the clauses above, wherein the subject has heterozygous familial hypercholesterolemia (HeFH), homozygous familial hypercholesterolemia (HoFH) or clinical atherosclerotic cardiovascular disease (ASCVD).

261. A subject as referenced in any one of the clauses above, wherein the subject is at high risk of cardiovascular events and require additional lowering of low-density lipoprotein cholesterol (LDL-C) despite maximally tolerated lipid-lowering therapy.

262. A lipid nanoparticle composition comprising:

a. one or more nucleic acid molecular entities; and b. a receptor targeting conjugate as referenced in any one of the clauses above.

263. The lipid nanoparticle composition of clause 262, wherein the receptor targeting conjugate comprises from about 0.001 mol % to about 20 mol % of the total lipid content.

264. The lipid nanoparticle composition of clause 262, wherein the receptor targeting conjugate comprises from about 0.005 mol % to about 2 mol % of the total lipid content.

265. The lipid nanoparticle composition of clause 262, wherein the receptor targeting conjugate comprises from about 0.01 mol % to about 1.0 mol % of the total lipid content present.

266. The lipid nanoparticle composition of clause 262, wherein the nanoparticle composition further comprising amino lipid, sterol or its derivative thereof, phospholipid and PEG-Lipid 267. The lipid nanoparticle composition of clause 266, wherein the amino lipid is constituted from 1 or more amino lipids and the total amino lipids comprises to about 10 mol % to about 70 mol % of the total lipid content.

268. The lipid nanoparticle composition of clause 266, wherein the amino lipid comprises about 40 mol % to about 55 mol % of the total lipid content.

269. The lipid nanoparticle composition of clause 266, wherein the amino lipid comprises about 45 mol % to about 50 mol % of the total lipid content.

270. The lipid nanoparticle composition of clause 266, wherein the sterol or its derivative thereof comprises to about 10 mol % to about 70 mol % of the total lipid content.

271. The lipid nanoparticle of composition of clause 270, wherein the sterol or its derivative thereof is chlesterol.

272. The lipid nanoparticle composition of clause 266, wherein the phospholipid comprises to about 5 mol % to about 15 mol % of the total lipid content.

273. The lipid nanoparticle composition of clause 266, wherein the phospholipid is 1,2-distearoyl-sn-glycero-3-phosphocholine (DSPC).

274. The lipid nanoparticle composition of clause 266, wherein the stealth lipid comprises about 0 mol % to about 6 mol % of the total lipid content present in said nanoparticle composition.

275. The lipid nanoparticle composition of clause 266, wherein the stealth lipid is a PEG-lipid that has a number average molecular weight of from about 200 Da to about 5000 Da.

276. The lipid nanoparticle composition of clause 275, wherein the PEG-lipid has a number average molecular weight of from about 1500 Da to about 3000 Da.

277. The lipid nanoparticle composition of clause 276, comprising:

a. about 0.001 mol % to about 20 mol % of the receptor targeting conjugate of any one of the preceding clauses;

b. about 10 mol % to about 70 mol % of one or more amino lipids;

c. about 10 mol % to about 70 mol % of a sterol;

d. about 3 mol % to about 15 mol % of a phospholipid; and e. about 0.1 mol % to about 6 mol % of a stealth lipid.

278. The lipid nanoparticle composition of clause 277, wherein a. the targeting conjugate is selected from Table 4 and comprises 0.001 mol % to about 4 mol % of the total lipid content;

b. the amino lipid comprises about 20 mol % to 70 mol % of the total lipid content;

c. the sterol is cholesterol and it comprises about 20 mol % to about 60 mol % of the total lipid content;

d. the phospholipid is 1,2-distearoyl-sn-glycero-3-phosphocholine (DSPC) and comprises about 5 mol % to about 15 mol % of the total lipid content; and e. the stealth lipid is a PEG-lipid with a number average molecular weight of from about 200 Da to about 5000 Da and comprises about 0 mol % to about 5 mol %.

279. The lipid nanoparticle composition of clause 277, wherein a. the targeting conjugate is selected from Table 4 and comprises 0.001 mol % to about 2 mol % of the total lipid content;

b. the amino lipid comprises about 40 mol % to 70 mol % of the total lipid content;

c. the sterol is cholesterol and it comprises about 20 mol % to about 60 mol % of the total lipid content; and d. the phospholipid is 1,2-distearoyl-sn-glycero-3-phosphocholine (DSPC) and comprises about 5 mol % to about 15 mol % of the total lipid content.

280. A receptor targeting conjugate, comprising a compound of Formula (V):

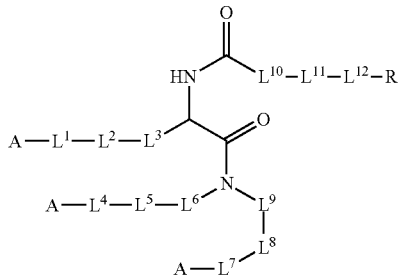

Formula (V)

wherein,
a plurality of the A groups collectively comprising a receptor targeting ligand;
each of $L^1$, $L^2$, $L^3$, $L^4$, $L^5$, $L^6$, $L^7$, $L^8$, $L^9$, $L^{10}$ and $L^{12}$ is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —$(CH_2CH_2O)_m$—, —$(OCH_2CH_2)_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, or —N(OR$^1$)—;
$L^{11}$ is substituted or unsubstituted —$(CH_2CH_2O)_n$— or substituted or unsubstituted —$(OCH_2CH_2)_n$—;
each $R^1$ is independently H or substituted or unsubstituted $C_1$-$C_6$ alkyl;
R comprises or is a lipid, nucleic acid, amino acid, protein, or lipid nanoparticle;
m is an integer selected from 1 to 10; and
n is an integer selected from 1 to 200.

281. The receptor targeting conjugate of clause 280, wherein
a. the plurality of the A groups comprises a lectin receptor targeting ligand;
b. each of $L^1$, $L^3$, $L^4$, and $L^7$ comprises —$(CH_2)_4$—;
c. each of $L^2$, $L^5$, and $L^8$ comprises —C(=O)NH—;
d. each of $L^6$ and $L^9$ comprises —$(CH_2)_3$—;
e. $L^{10}$ is —$(CH_2)_{1-3}$—, —$CH_2CH_2O$— or —$CH_2O$—;
f. $L^{11}$ is —$(CH_2CH_2O)_n$— or —$(OCH_2CH_2)_n$—, where n is an integer selected from 1 to 50;
g. $L^{12}$ is —NH(CO)O—; and
h. R is selected from the group consisting of dialkylglycerol, diacylglycerol, sterol, n-alkyl comprising $C_{10}$-$C_{30}$ carbon atoms, branched alkyl comprising $C_{10}$-$C_{30}$ carbon atoms or tocopherol.

282. The receptor targeting conjugate of clause 281, wherein the n is 1-3, 9-15, 33-39 or 41-49.

283. The receptor targeting conjugate of clause 281, wherein the lectin receptor is asialoglycoprotein receptor (ASGPR) and the plurality of the A groups comprise N-acetylgalactosamine, galactose or combination thereof.

284. The receptor targeting conjugate of clause 280, wherein each of the A groups is N-acetylgalactosamine

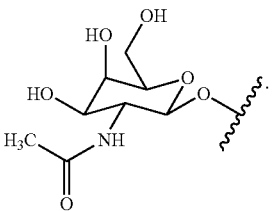 [SMILES: *OC1OC(CO)C(O)C(O)C1NC(C)=O]

285. The receptor targeting conjugate of clause 280, wherein the receptor targeting conjugate is a conjugate selected from 1001-1019, 1060, 1065, 1066 and 1075-1085 in Table 4.

286. The receptor targeting conjugate of clause 280, wherein the receptor targeting conjugate is

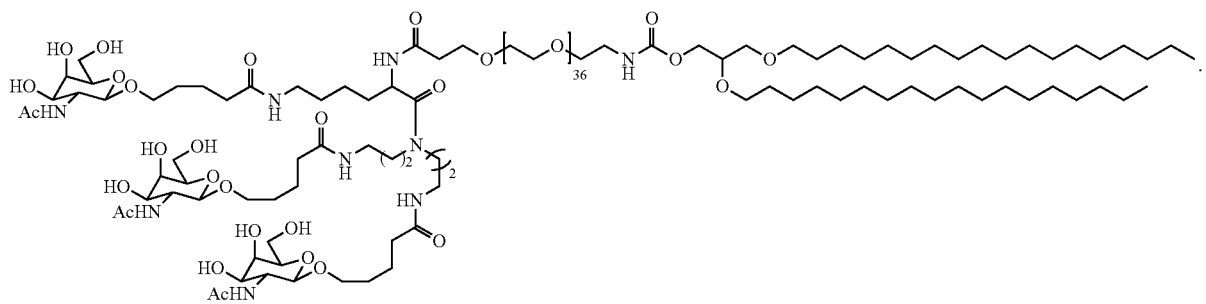

1004

287. The receptor targeting conjugate of clause 280, wherein the R comprises one or more of fatty alcohols, fatty acids, glycerolipids, glycerophospholipids, sphingolipids, saccharolipids, polyketides, or sterols or derivatives thereof.

288. The receptor targeting conjugate of clause 280, wherein the R is a lipid nanoparticle that comprises one or more mRNA encoding one or more gene editor nuclease(s) or base editors and one or more guide RNAs.

289. A method for reducing the risk of coronary disease in a subject in need thereof, the method comprising administering to the subject a lipid nanoparticle encapsulating a payload comprising one or more pharmaceutically active agents, wherein the lipid nanoparticle further comprises a receptor targeting conjugate of Formula (V):

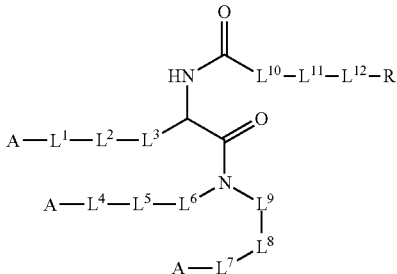

Formula (V)

wherein,
a plurality of the A groups collectively comprising a receptor targeting ligand;
each of $L^1$, $L^2$, $L^3$, $L^4$, $L^5$, $L^6$, $L^7$, $L^8$, $L^9$, $L^{10}$ and $L^{12}$ is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O)(=NR$^1$)—, —C(=O)—, —C(=N—OR$^1$)—, —C(=O)O—, —OC(=O)—, —C(=O)C(=O)—, —C(=O)NR$^1$—, —NR$^1$C(=O)—, —OC(=O)NR$^1$—, —NR$^1$C(=O)O—, —NR$^1$C(=O)NR$^1$—, —C(=O)NR$^1$C(=O)—, —S(=O)$_2$NR$^1$—, —NR$^1$S(=O)$_2$—, —NR$^1$—, or —N(OR$^1$)—;
$L^{11}$ is substituted or unsubstituted —(CH$_2$CH$_2$O)$_n$— or substituted or unsubstituted —(OCH$_2$CH$_2$)$_n$—;
each $R^1$ is independently H or substituted or unsubstituted $C_1$-$C_6$ alkyl;
R comprises or is a lipid;
m is an integer selected from 1 to 10; and
n is an integer selected from 1 to 200.

290. The method of clause 289, wherein
a. the plurality of A groups comprises a lectin receptor targeting ligand;
b. each of $L^1$, $L^3$, $L^4$, and $L^7$ comprises —(CH$_2$)$_4$—;
c. each of $L^2$, $L^5$, and $L^8$ comprises —C(=O)NH—;
d. each of $L^6$ and $L^9$ comprises —(CH$_2$)$_3$—;
e. $L^{10}$ is —(CH$_2$)$_{1-3}$—, —CH$_2$CH$_2$O— or —CH$_2$O—;
f. $L^{11}$ is —(CH$_2$CH$_2$O)$_n$— or —(OCH$_2$CH$_2$)$_n$—, where n is an integer selected from 1 to 50;
g. $L^{12}$ is —NH(CO)O—; and
h. R is selected from the group consisting of dialkylglycerol, diacylglycerol, sterol, n-alkyl comprising $C_{10}$-$C_{30}$ carbon atoms, branched alkyl comprising $C_{10}$-$C_{30}$ carbon atoms or tocopherol.

291. The method of clause 289, wherein the receptor targeting conjugate is a conjugate selected from 1001-1019, 1060, 1065, 1066 and 1075-1085 in Table 4.

292. The method of clause 289, wherein the receptor targeting conjugate is conjugate 1004 in Table 4.

293. The method of clause 292, wherein the lipid nanoparticle comprising the receptor targeting conjugate provides an improved delivery in LDLr deficient mammal as determined by percent editing of at least 50% higher than a corresponding lipid nanoparticle without the receptor targeting conjugate.

294. The method of clause 292, wherein the lipid nanoparticle comprising the receptor targeting conjugate provides an improved delivery in a mammal that lacks ApoE as determined by percent editing of at least 50% higher than a corresponding lipid nanoparticle without the receptor targeting conjugate.

295. The method of clause 289, wherein the one or more active agents comprise an mRNA encoding a gene editor nuclease or a base editor and one or more guide RNAs.

296. The method of clause 295, wherein the mRNA is an adenosine base editor and the one or more guide RNAs are complementary to (i) a segment of PCSK9 gene, (ii) a segment of ANGPTL3 gene, or both (i) and (ii).

297. The method of clause 295, wherein at least one of the one or more guide RNAs is selected from guide RNA sequences of SEQ ID NOs: 121-126 of Table 5.

298. The method of clause 289, wherein the receptor targeting conjugate comprises from about 0.001 mol % to about 0.5 mol % of the total excipients in the lipid nanoparticle.

299. A method of preparing a formulation comprising GalNAc-lipid nanoparticles, wherein the nanoparticles comprise (i) one or more nucleic acid active agents, (ii) lipid excipients comprising sterol or a derivative thereof, a phospholipid, a stealth lipid, and an amino lipid, and (iii) a GalNAc-lipid receptor targeting conjugate, the method comprising:
a. providing a first solution comprising the one or more nucleic acid active agents in aqueous buffer;
b. providing a second solution comprising (i) the lipid excipient and (ii) at least a portion of the receptor targeting conjugate in a water-miscible organic solvent such as ethanol;
c. mixing the first solution and the second solution;
d. incubating a mixture of the first and second solutions to form GalNAc-lipid nanoparticles; and
e. optionally carrying out one or more dilution, buffer exchange, concentration, filtration, and GalNAc-lipid nanoparticle evaluation processes.

300. The method of clause 299, wherein the GalNAc-lipid receptor targeting conjugate is selected from the structures identified in Table 4.

301. The method of clause 299, wherein the mixing is performed by an inline mixing apparatus having a first mixing chamber that includes a first port that separately introduces the first solution to the first mixing chamber and a second port that separately and simultaneously introduces the second solution into the first mixing chamber.

302. The method of clause 301, further comprising adding a second portion of the receptor targeting conjugate after the first solution and the second solution are mixed, wherein the addition of the second portion of the receptor targeting conjugate is pre-dissolved in a water miscible organic solvent and combined with an aqueous solution to form an aqueous dilution buffer that is mixed with the previously mixed first and second solutions in a second mixing chamber conjoined with and downstream from the first mixing chamber of the inline mixing apparatus prior to incubation.

303. The method of clause 302, further comprising a buffer exchange process after the second portion of the receptor targeting conjugate is added.

304. A method of preparing a formulation comprising GalNAc-lipid nanoparticles, wherein the nanoparticles comprise (i) one or more nucleic acid molecular entities, (ii) lipid excipient comprising one or more sterols or a derivative thereof, a phospholipids, a stealth lipids, or an amino lipids, and (iii) one or more GalNAc-lipid receptor targeting conjugates, the method comprising:
 a. providing a first solution comprising the one or more nucleic acid molecular entities in an aqueous buffer;
 b. providing a second solution comprising at least one of the one or more lipid excipients in a water-miscible organic solvent;
 c. providing a third solution comprising at least a portion of the receptor targeting conjugate;
 d. mixing the first solution, the second solution, and the third solution in one or more mixing chambers wherein each solution is introduced separately via an inlet port to the one or more mixing chambers;
 e. incubating a mixture of the first, second and third solutions to form GalNAc-lipid nanoparticles; and
 f. optionally carrying out one or more dilution, a buffer exchange, concentration, filtration, and GalNAc-lipid nanoparticle evaluation processes.

305. The method of clause 304, wherein the first solution comprises an aqueous buffer, and wherein the second solution and the third solution are each independently prepared from a water-miscible alcohol.

306. The method of clause 304, wherein the first solution, the second solution, and the third solution are introduced to a mixer simultaneously.

307. The method of clause 304, wherein the first solution, the second solution, and the third solution are introduced to a mixer sequentially prior to incubation.

308. The method of clause 304, wherein the first solution, the second solution, and the third solution are combined in an in-line mixer apparatus having a first mixing chamber conjoined to a second downstream mixing chamber, wherein the first and second solutions are pre-mixed in the first mixing chamber and immediately flow into a second mixing chamber and wherein the third solution is mixed with the first and second solution in the second mixing chamber; and wherein the third solution may optionally comprise a targeting conjugate and/or lipid excipients pre-dissolved in a water-miscible organic solvent mixed in or diluted with an aqueous dilution buffer.

309. The method of clause 304, wherein the water-miscible organic solvent is ethanol.

310. A targeting moiety or receptor targeting conjugate as referenced in any one of the foregoing clauses, wherein the targeting moiety or receptor targeting conjugate has a structure represented in Table 1.

311. A GalNAc conjugate as referenced in any one of the foregoing clauses, wherein the GalNAc conjugate comprises a sequence shown in Table 2 or Table 3.

312. A receptor targeting conjugate as referenced in any one of the foregoing clauses, wherein the receptor targeting conjugate comprises a structure of Table 4.

313. A guide RNA as referenced in any one of the foregoing clauses, wherein the guide RNA comprises a sequence shown in Table 5.

314. A lipid excipient as referenced in any one of the foregoing clauses, wherein the lipid excipient comprises a structure of Table 6 or Table 7.

315. A lipid nanoparticle as referenced in any one of the foregoing clauses, wherein the lipid nanoparticle comprises a composition of Table 8, Table 9, Table 10, Table 11, Table 12, or Table 13.

It will also be appreciated from reviewing the present disclosure, that it is contemplated that the one or more aspects or features presented in one set of clauses may also be included in other clauses or in combination with the one or more aspects or features in other clauses.

What is claimed is:

1. A compound of Formula (V), or a stereoisomer or a salt thereof,

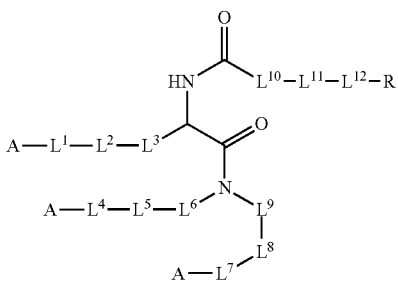

Formula (V)

wherein, each of $L^1$, $L^2$, $L^3$, $L^4$, $L^5$, $L^6$, $L^7$, $L^8$, $L^9$, $L^{10}$ and $L^{12}$ is independently substituted or unsubstituted $C_1$-$C_{12}$ alkylene, substituted or unsubstituted $C_1$-$C_{12}$ heteroalkylene, substituted or unsubstituted $C_2$-$C_{12}$ alkenylene, substituted or unsubstituted $C_2$-$C_{12}$ alkynylene, —(CH$_2$CH$_2$O)$_m$—, —(OCH$_2$CH$_2$)$_m$—, —O—, —S—, —S(=O)—, —S(=O)$_2$—, —S(=O) (=NR$^1$)—, —C(=O)—, —C(=N—OR$^1$)—, —C(=O)O—, —OC(=O)—, —C(=O) C(=O)—, —C(=O) NR$^1$—, —NR$^1$C(=O)—, —OC(=O) NR$^1$—, —NR$^1$C(=O) O—, —NR$^1$C(=O) NR$^1$—, —S(=O)$_2$NR$^1$—, —NR$^1$S(=O)$_2$—, —NR$^1$—, or —N(OR$^1$)—;

$L^{11}$ is a bond, substituted or unsubstituted —(CH$_2$CH$_2$O)$_n$— or substituted or unsubstituted —(OCH$_2$CH$_2$)$_n$—;

each $R^1$ is independently H or substituted or unsubstituted $C_1$-$C_6$ alkyl;

R comprises a lipid, nucleic acid, amino acid, protein, or lipid nanoparticle;

m is an integer selected from 1 to 10; and n is an integer selected from 1 to 200, wherein each of the A groups is a N-acetylgalactosamine moiety.

2. The compound of claim 1, or a stereoisomer or a salt thereof, wherein each of $L^1$, $L^3$, $L^4$, and $L^7$ comprises unsubstituted $C_1$-$C_6$ alkylene;

each of $L^2$, $L^5$, and $L^8$ comprises —C(=O)NH— or —NHC(=O)—;

each of $L^6$ and L' comprises unsubstituted $C_1$-$C_6$ alkylene;

$L^{10}$ is —(CH$_2$)$_{1-3}$—, —CH$_2$CH$_2$O— or —CH$_2$O—;

$L^{11}$ is —(CH$_2$CH$_2$O)$_n$— or —(OCH$_2$CH$_2$)$_n$—, where n is an integer selected from 1 to 50;

$L^{12}$ is —NHC(=O)O— or —NHC(=O)—; and

R is selected from the group consisting of dialkylglycerolyl, diacylglycerolyl, sterol, n-alkyl comprising $C_{10}$-$C_{30}$ carbon atoms, branched alkyl comprising $C_{10}$-$C_{30}$ carbon atoms or tocopherol.

3. The compound of claim 2, or a stereoisomer or salt thereof, wherein each of $L^1$, $L^3$, $L^4$, and $L^7$ comprises —(CH$_2$)$_4$—.

4. The compound of claim 2, or a stereoisomer or salt thereof, wherein each of $L^6$ and $L^9$ comprises —(CH$_2$)$_3$—.

5. The compound of claim 1, or a stereoisomer or a salt thereof, wherein the R comprises one or more of fatty alcohols, fatty acids, glycerolipids, glycerophospholipids, sphingolipids, saccharolipids, polyketides, or sterols or derivatives thereof.

6. The compound of claim 1, or a stereoisomer or salt thereof, wherein R is

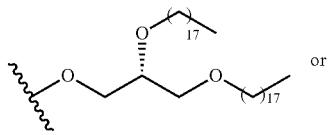 or

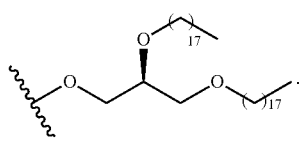

7. The compound of claim 6, or a stereoisomer or salt thereof, wherein R is
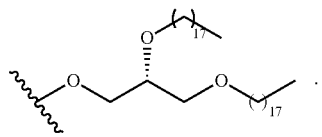
8. The compound of claim 1, or a stereoisomer or salt thereof, wherein
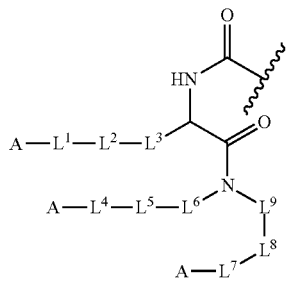
is
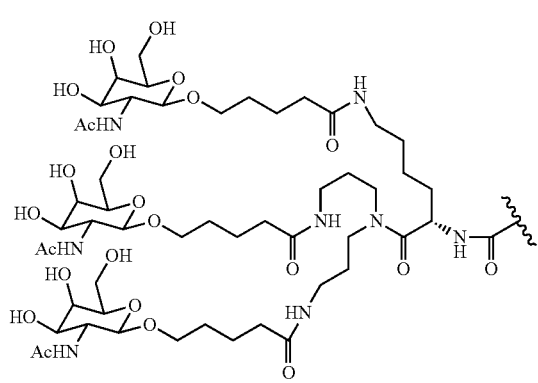
or
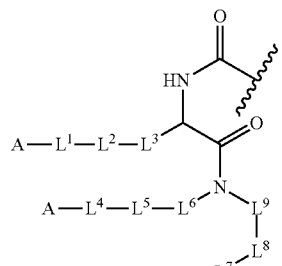
9. The compound of claim 8, or a stereoisomer or salt thereof, wherein
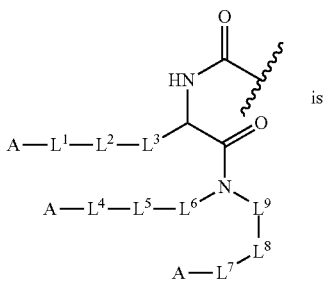 is
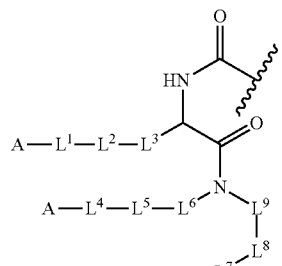
10. The compound of claim 1, or a stereoisomer or salt thereof, wherein R is
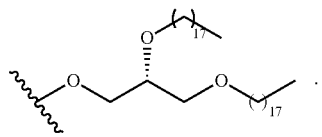
and wherein is
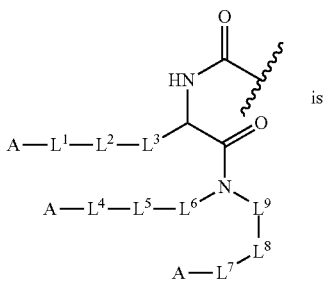

is
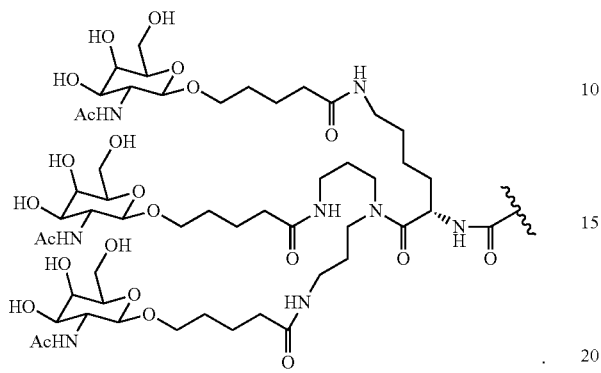
11. The compound of claim 1, or stereoisomer or salt thereof, wherein A is
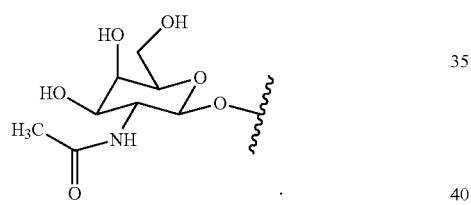
12. The compound of claim 1, or a stereoisomer or salt thereof, wherein $L^{11}$ is —$(CH_2CH_2O)_n$—, and wherein n is an integer from 42 to 46.
13. The compound of claim 1, or a stereoisomer or a salt thereof, wherein the compound is a compound selected from the following:
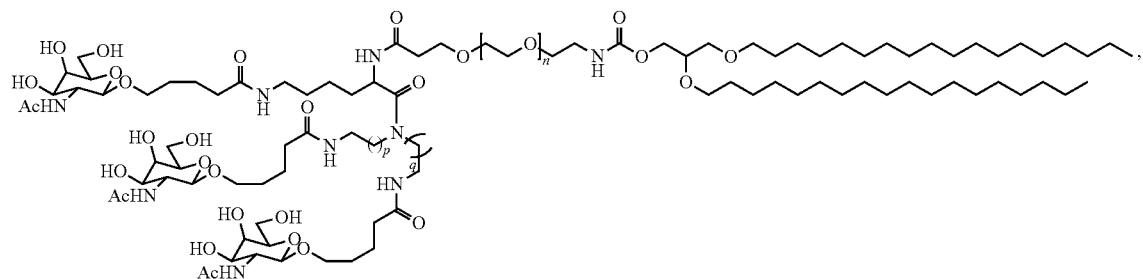

wherein each of the p and q is independently an integer from 1 to 5, and n is an integer from 1 to 50;
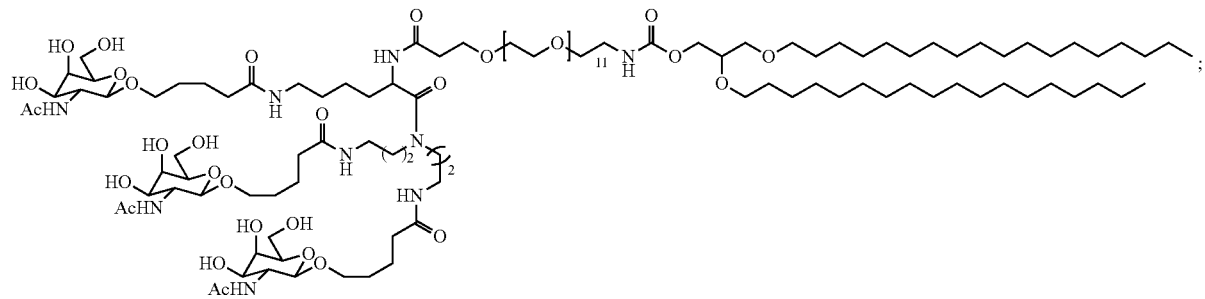
1002
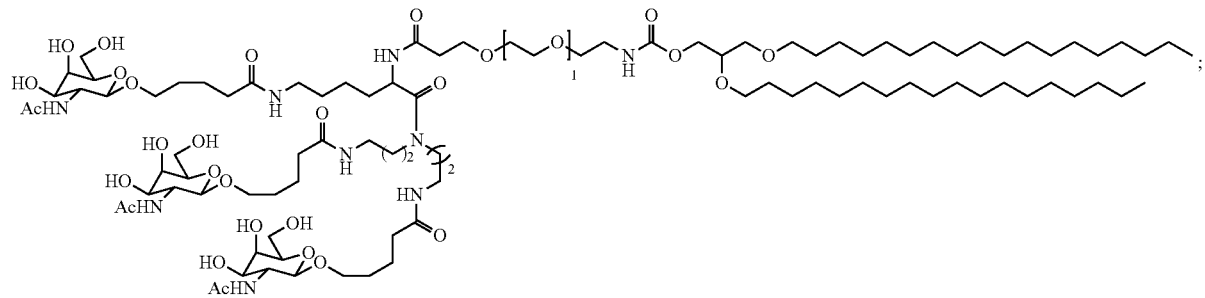
1003
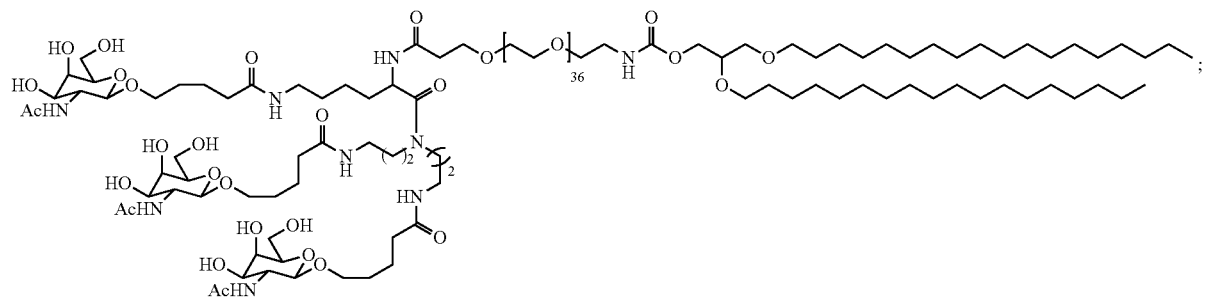
1004
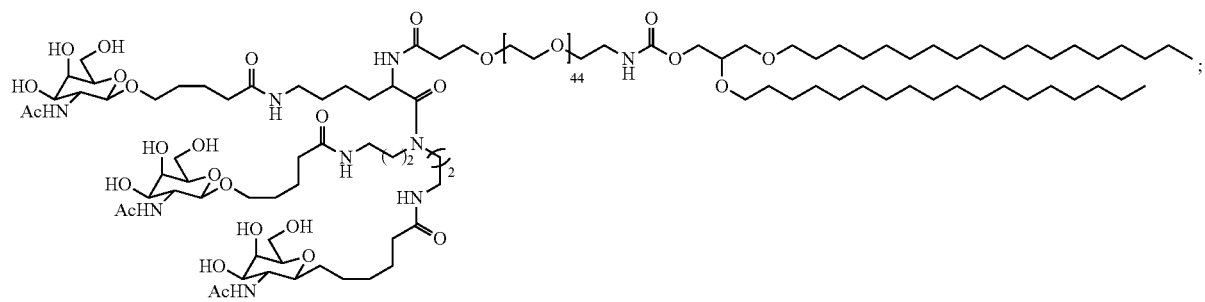
1005

-continued
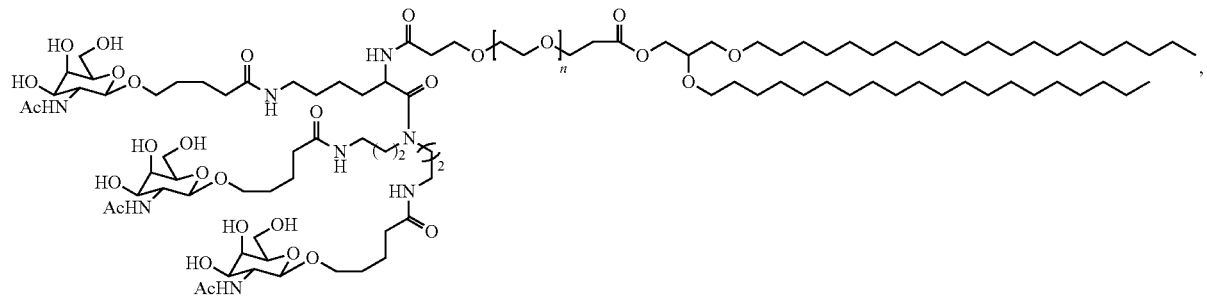
wherein n is an integer from 1 to 50;
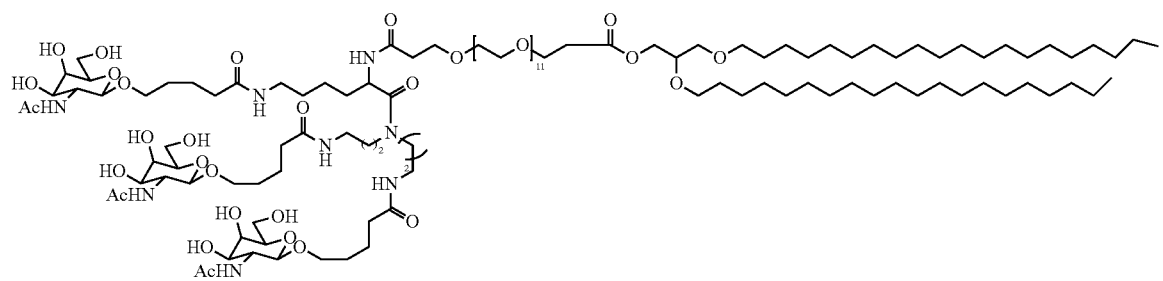
;
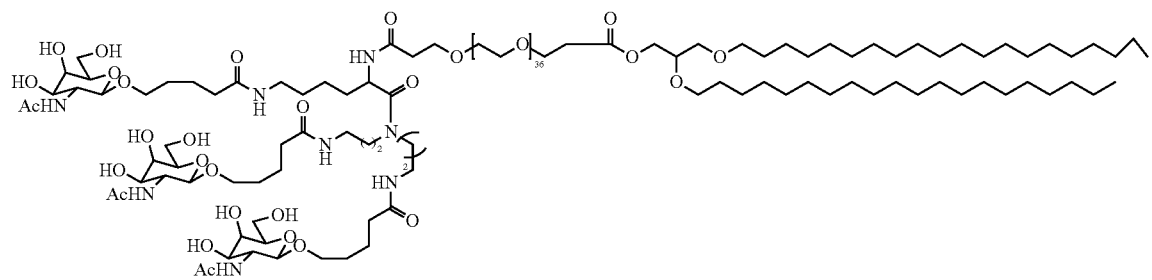
;
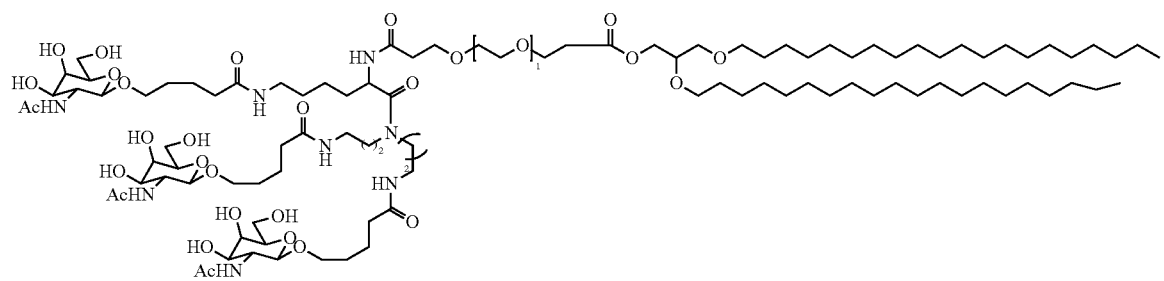
;
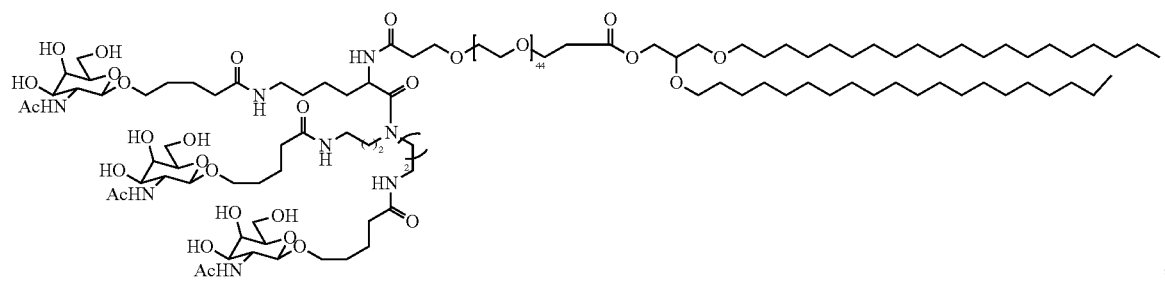
;

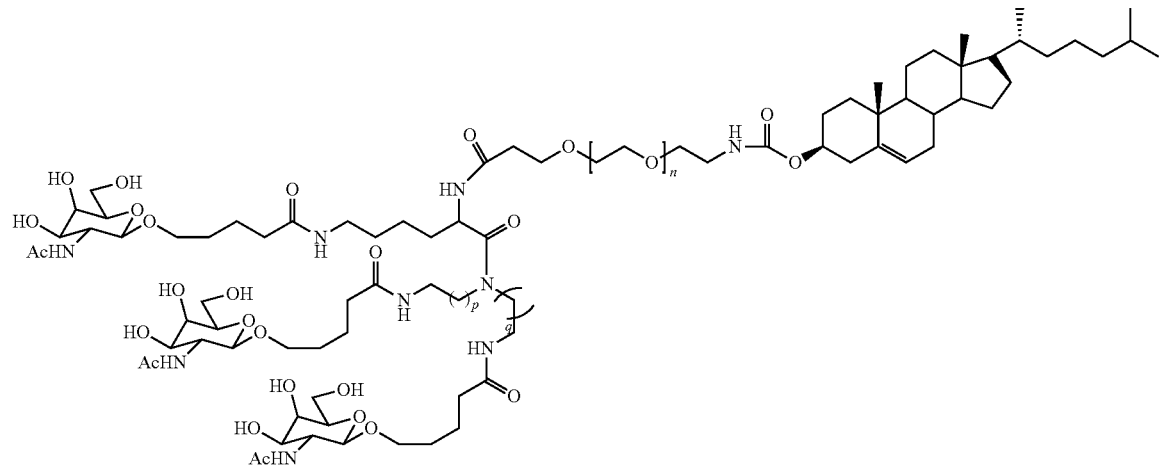
wherein each of the p and q is independently an integer from 1 to 5, and n is an integer from 1 to 50;
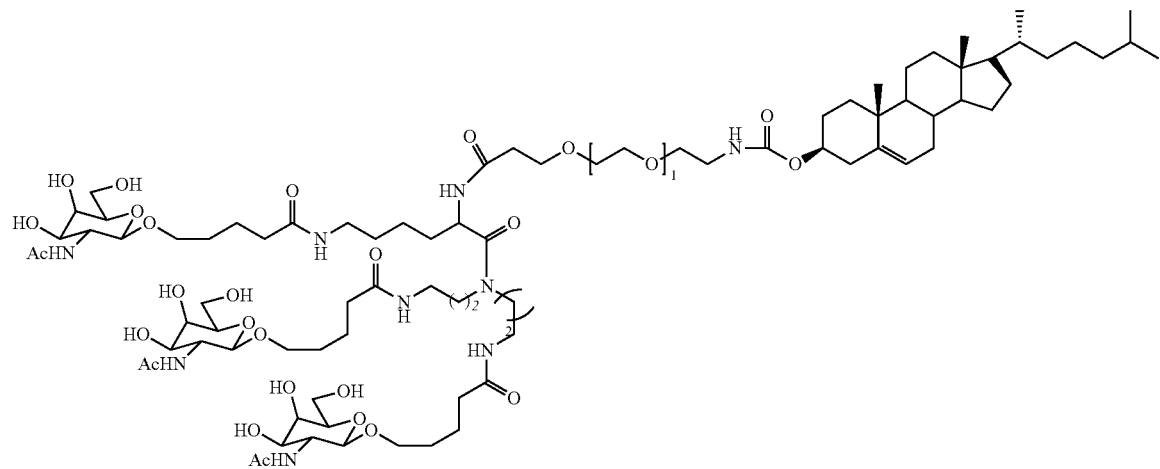
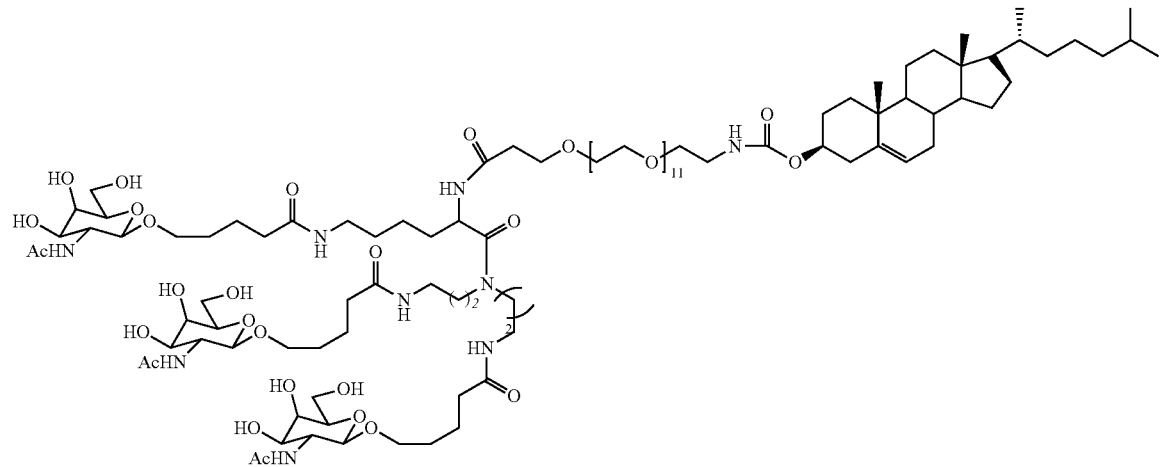

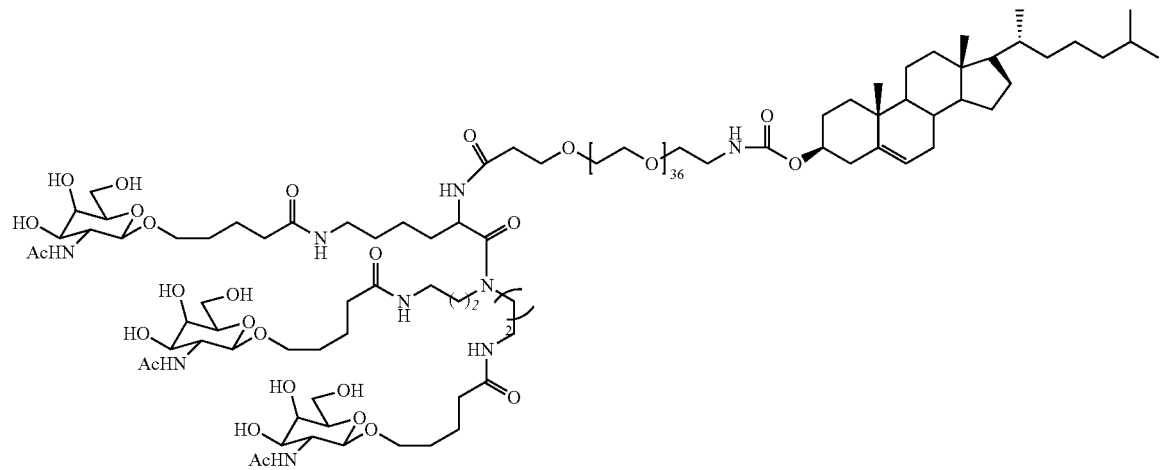
;
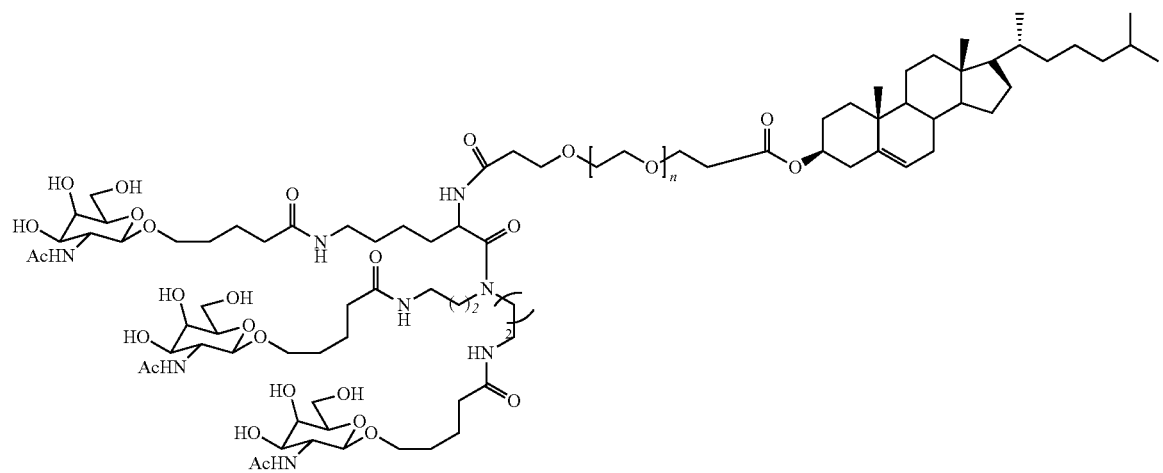
wherein n is an integer from 1 to 50;
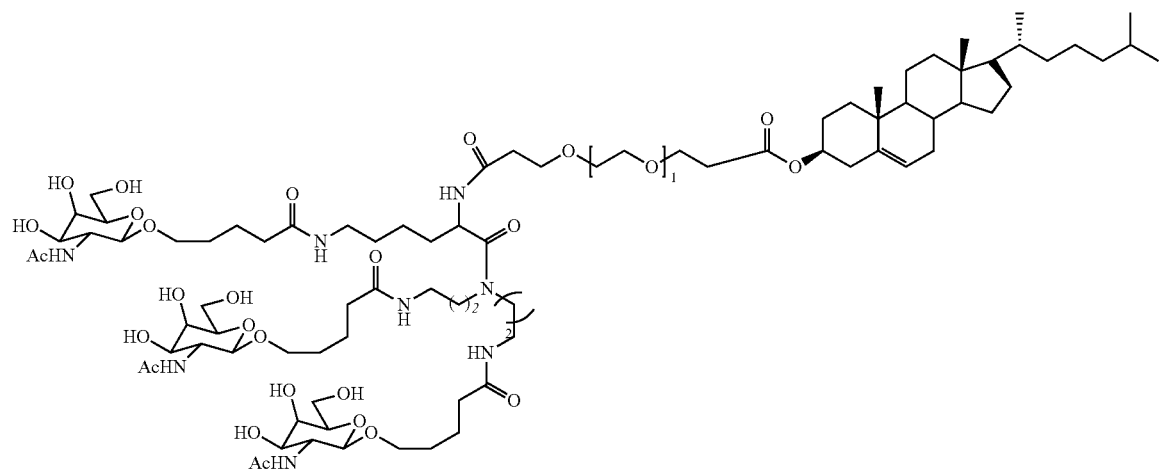
;

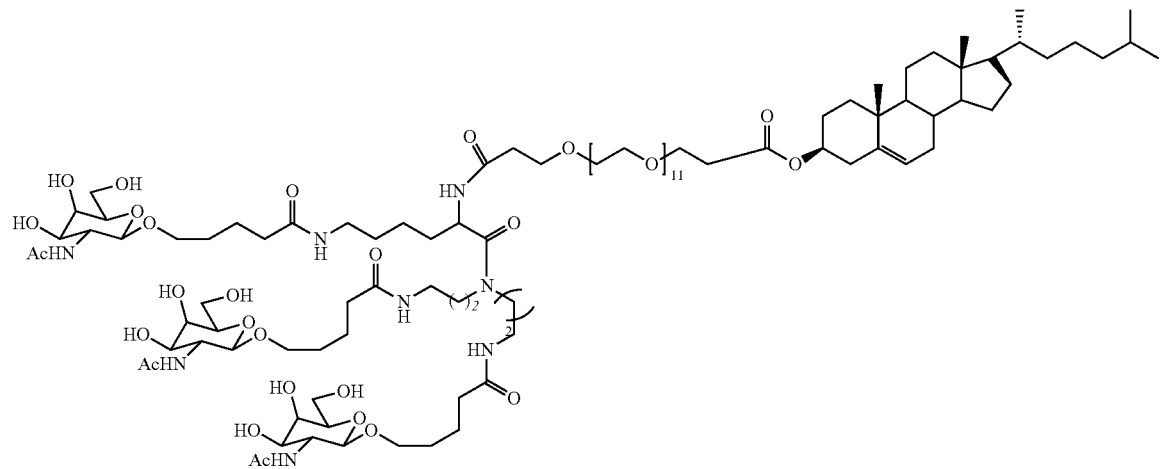
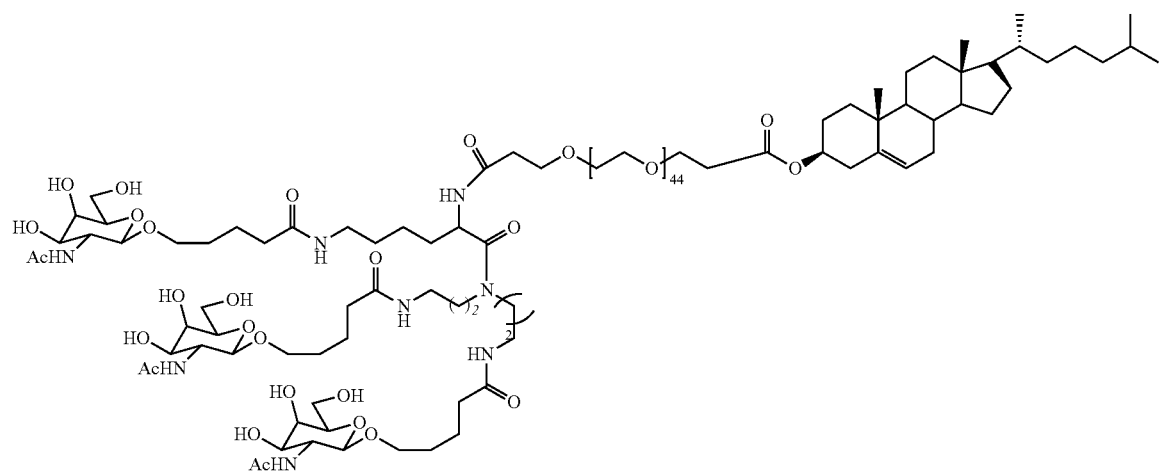
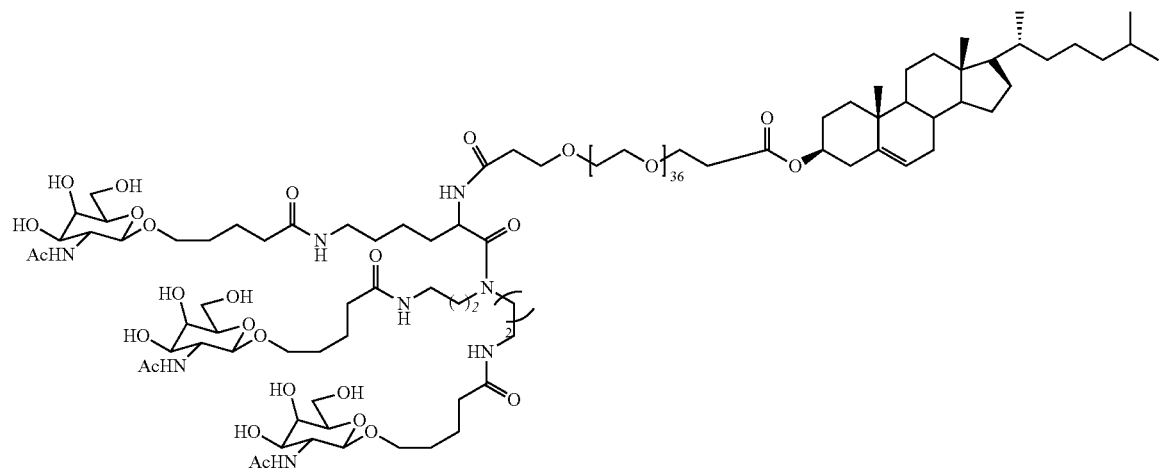

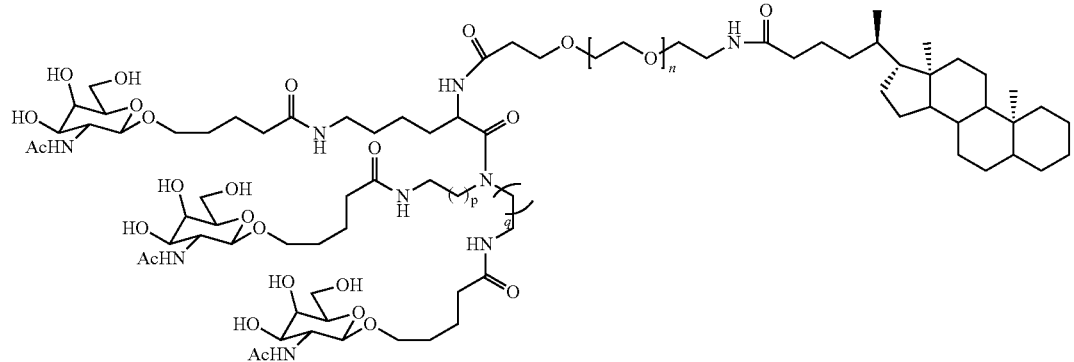
wherein each of the p and q is independently an integer from 1 to 5, and n is an integer from 1 to 50;

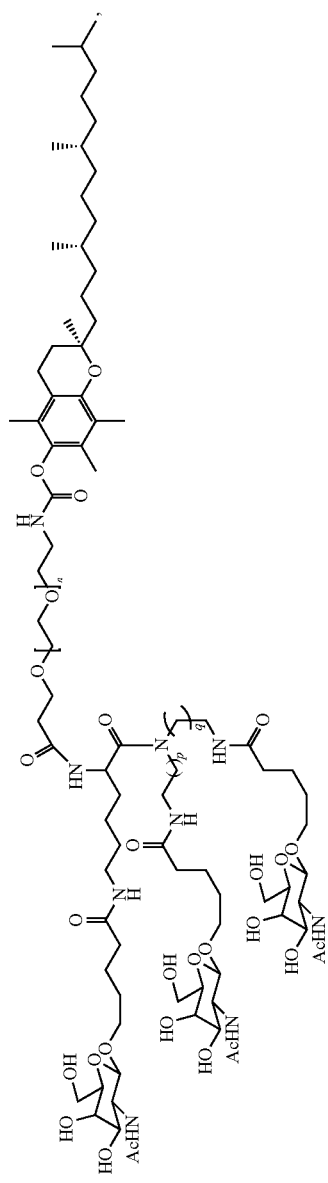

wherein each of the p and q is independently an integer from 1 to 5, and n is an integer from 1 to 50;
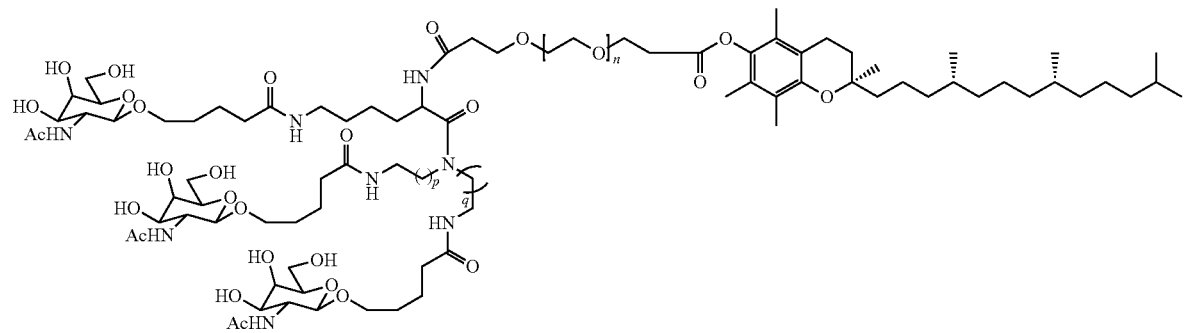
1066
wherein each of the p and q is independently an integer from 1 to 5, and n is an integer from 1 to 50;
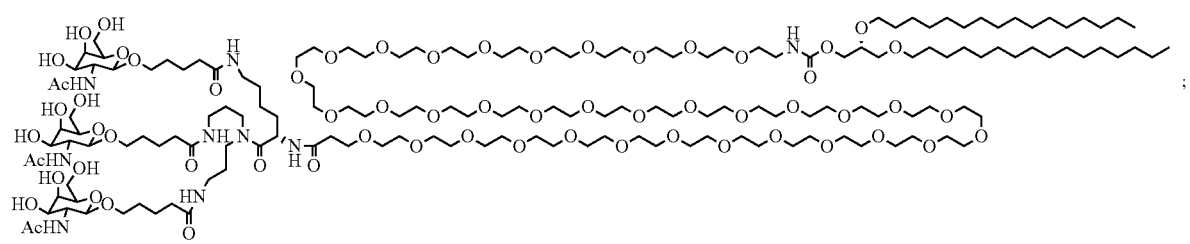
1075
;
1076
;
1077
;
1078
;

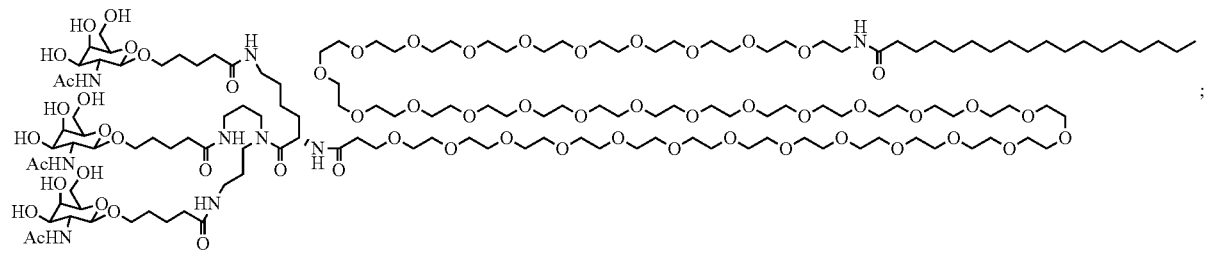
1079
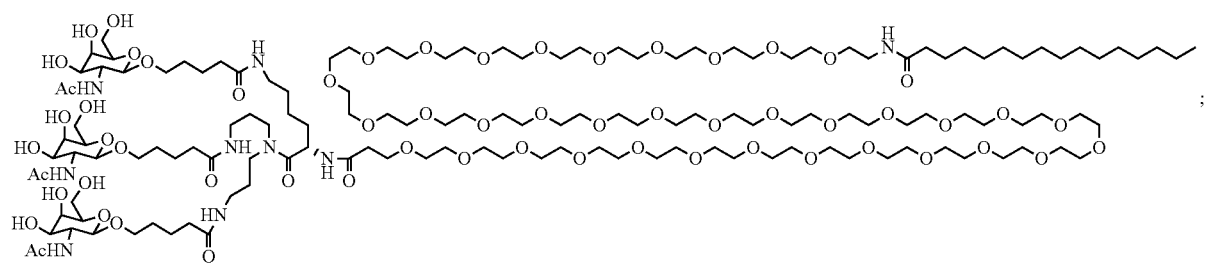
1080
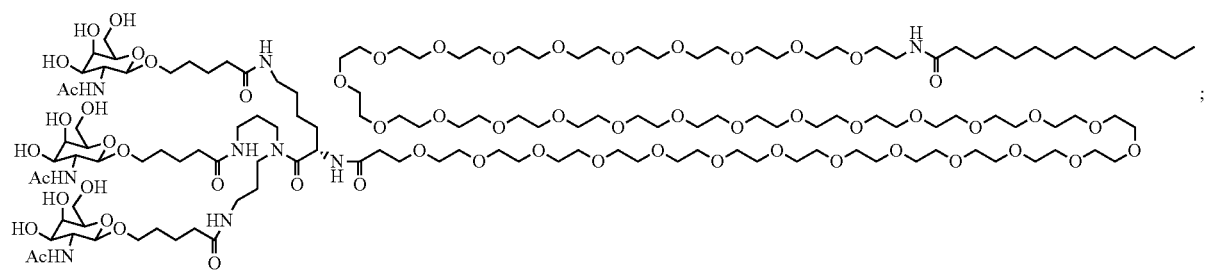
1081
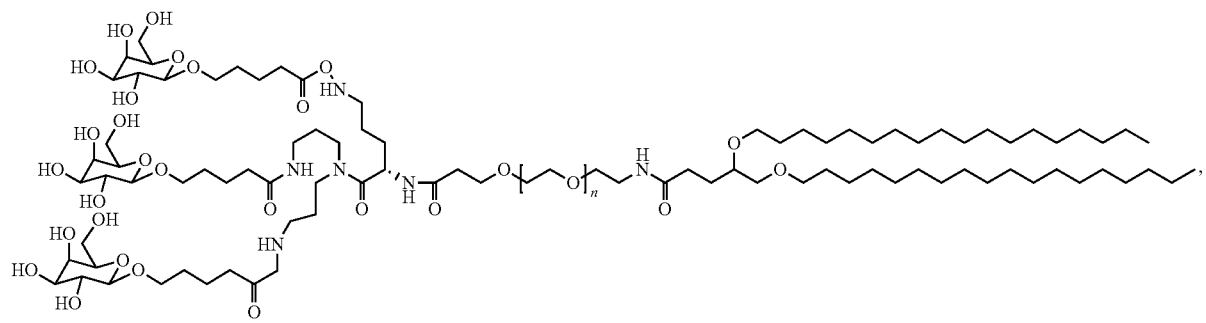
1082 wherein n is an integer from 1-50;
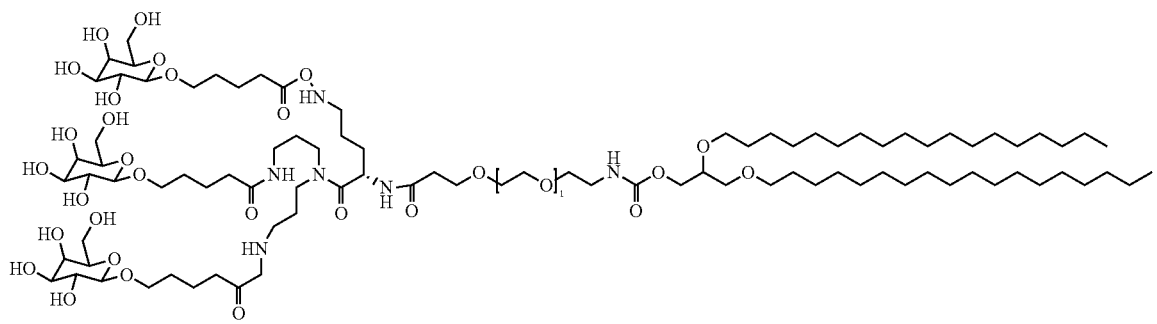
1083
;
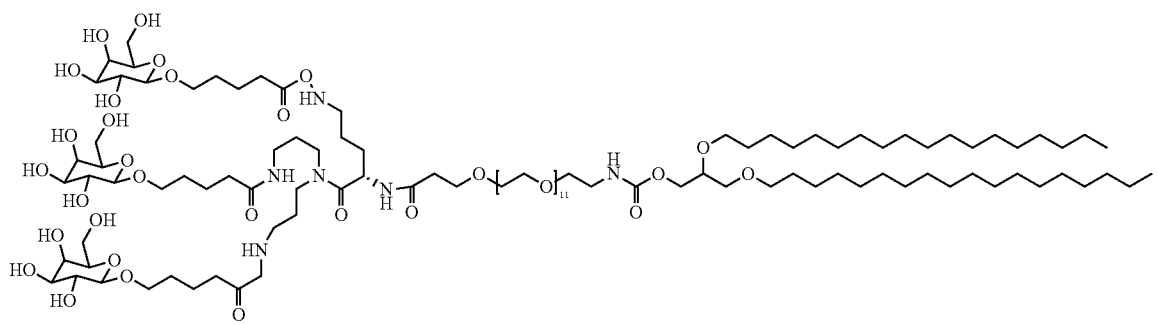
1084
; and
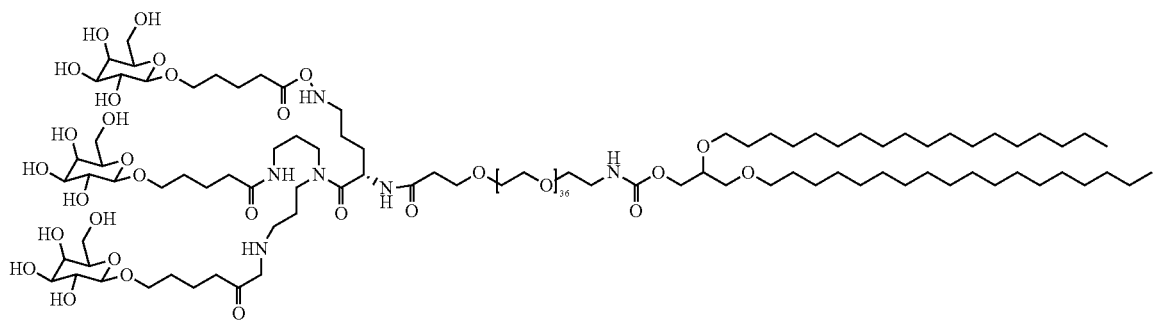
1085
.
14. The compound of claim 1, or a stereoisomer or a salt thereof, wherein the compound is
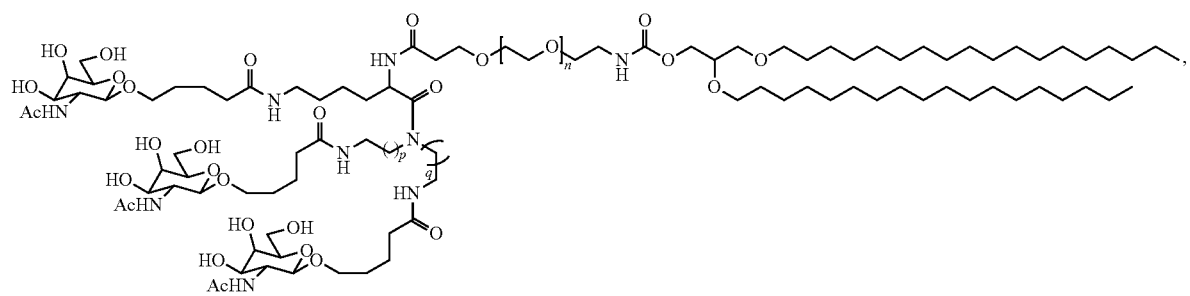

wherein each of the p and q is independently an integer from 1 to 5, and n is an integer from 33 to 39.

15. The compound of claim 14, or a stereoisomer or a salt thereof, wherein each p and q are 2, and n is 34.

16. The compound of claim 14, or a stereoisomer or a salt thereof, wherein each p and q are 2, and n is 35.

17. The compound of claim 1, or a stereoisomer or a salt thereof, wherein the compound is

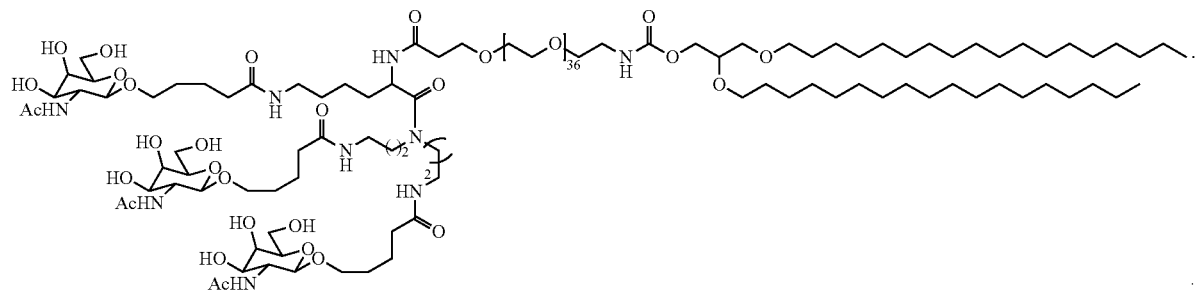

1004

18. The compound of claim 1, or a stereoisomer or salt thereof, wherein R is

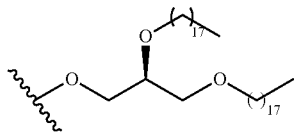

and wherein

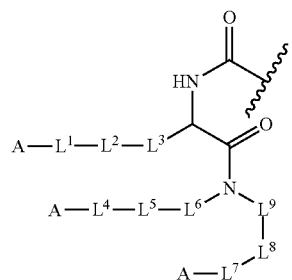

is

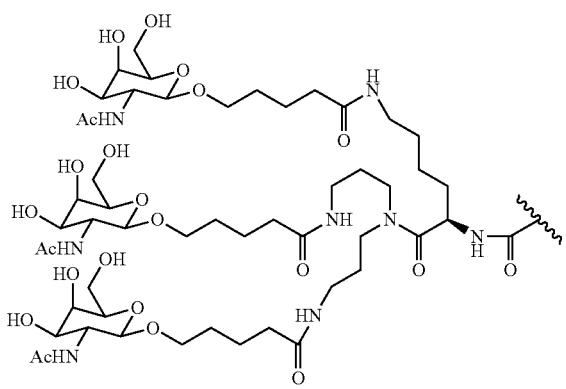 [SMILES: *C(=O)N[C@H](CCCCNC(=O)CCCCOC1OC(CO)C(O)C(O)C1NC(C)=O)C(=O)N(CCCNC(=O)CCCCOC1OC(CO)C(O)C(O)C1NC(C)=O)CCCNC(=O)CCCCOC1OC(CO)C(O)C(O)C1NC(C)=O]

19. The compound of claim 1, or a stereoisomer or salt thereof, wherein R is

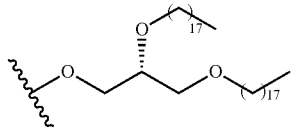

and wherein

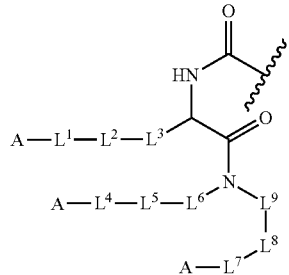

is

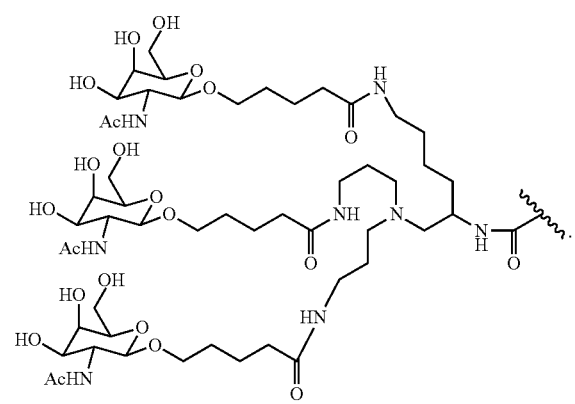 [SMILES: *C(=O)NC(CCCCNC(=O)CCCCOC1OC(CO)C(O)C(O)C1NC(C)=O)CN(CCCNC(=O)CCCCOC1OC(CO)C(O)C(O)C1NC(C)=O)CCCNC(=O)CCCCOC1OC(CO)C(O)C(O)C1NC(C)=O]

20. The compound of claim 1, or a stereoisomer or salt thereof, wherein R is
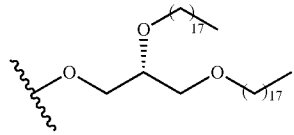
and wherein
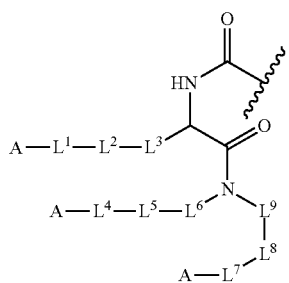
is
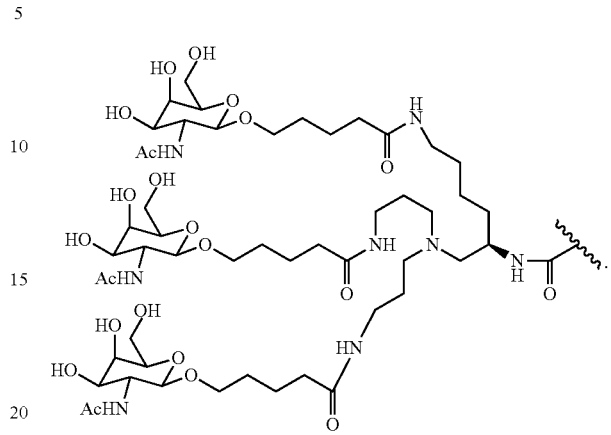
* * * * *

SEQUENCE LISTING

```
Sequence total quantity: 126
SEQ ID NO: 1            moltype = AA  length = 1362
FEATURE                 Location/Qualifiers
source                  1..1362
                        mol_type = protein
                        organism = Streptococcus pyogenes
SEQUENCE: 1
MDKKYSIGLD IGTNSVGWAV ITDEYKVPSK KFKVLGNTDR HSIKKNLIGA LLFDSGEAEA   60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENTTKG QKNSRERMKR  780
IEEGIKELGS QILKEHPVEN TQLQNEKLYL YYLQNGRDMY VDQELDINRL SDYDVDHIVP  840
QSFLKDDSID NKVLTRSDKN RGKSDNVPSE EVVKKMKNYW RQLLNAKLIT QRKFDNLTKA  900
ERGGLSELDK AGFIKRQLVE TRQITKHVAQ ILDSRMNTKY DENDKLIREV KVITLKSKLV  960
SDFRKDFQFY KVREINNYHH AHDAYLNAVV GTALIKKYPK LESEFVYGDY KVYDVRKMIA 1020
KSEEIGKATA KYFFYSNIMN FFKTEITLAN GEIRKRPLIE TNGETGEIVW DKGRDFATVR 1080
KVLSMPVNIV KKTEVTGGFS KESILPKRNS DKLIARKKDW DPKKYGGFDS PTVAYSVLVV 1140
AKVEKGKSKK LKSVKELLGI TIMERSSFEK NPIDFLEAKG YKEVKKDLII KLPKYSLFEL 1200
ENGRKRMLAS AGELQKGNEL ALPSKYVNFL YLASHYEKLK GSPEDNEQKQ LFVEQHKYHL 1260
DEIIEQISEF SKRVILADAN LDKVLSAYNK HRDKPIREQA ENIIHLFTLT NLGAPAAFKY 1320
```

FDTTIDRKRY TSTKEVLDAT LIHQSITGLY ETRIDLSQLG GD            1362

```
SEQ ID NO: 2           moltype = DNA   length = 4107
FEATURE                Location/Qualifiers
source                 1..4107
                       mol_type = genomic DNA
                       organism = Streptococcus pyogenes
SEQUENCE: 2
atggataaga aatactcaat aggcttagat atcggcacaa atagcgtcgg atgggcggtg   60
atcactgatg aatataaggt tccgtctaaa aagttcaagg ttctgggaaa tacagaccgc  120
cacagtatca aaaaaaatct tatagggct cttttatttg acagtggaga gacagcggaa  180
gcgactcgtc tcaaacggac agctcgtaga aggtatacac gtcggaagaa tcgtatttgt  240
tatctacagg agatttttc aaatgagatg gcgaaagtag atgatagttt ctttcatcga  300
cttgaagagt ctttttggt ggaagaagac aagaagcatg aacgtcatcc tatttttgga  360
aatatagtag atgaagttgc ttatcatgag aaatatccaa ctatctatca tctgcgaaaa  420
aaattggtag attctactga taaagcggat ttgcgcttaa tctatttggc cttagcgcat  480
atgattaagt ttcgtggtca ttttttgatt gagggagatt taaatcctga taatagtgat  540
gtggacaaac tatttatcca gttggtacaa acctacaatc aattatttga agaaaaccct  600
attaacgcaa gtggagtaga tgctaaagcg attctttctg cacgattgag taaatcaaga  660
cgattagaaa atctcattgc tcagctcccc ggtgagaaga aaaatggctt atttgggaat  720
ctcattgctt tgtcattggg tttgaccct aatttttaaat caaattttga tttggcagaa  780
gatgctaaat tacagctttc aaaagatact tacgatgatg atttagataa ttattgggcg  840
caaattggag atcaatatgc tgatttgttt ttggcagcta agaatttatc agatgctatt  900
ttactttcag atatcctaag agtaaatact gaaataacta aggctcccct atcagcttca  960
atgattaaac gctacgatga acatcatcaa gacttgactc ttttaaaagc tttagttcga 1020
caacaacttc cagaaaagta taaagaaatc tttttttgatc aatcaaaaaa cggatatgca 1080
ggttatattg atgggggagc tagccaagaa gaatttataa aatttatcaa accaatttta 1140
gaaaaaatgg atggtactga ggaattattg gtgaaactaa atcgtgaaga tttgctgcgc 1200
aagcaacgga cctttgacaa cggctctatt ccccatcaaa ttcacttggg tgagctgcat 1260
gctattttga gaagacaaga agactttat ccattttaa aagacaatcg tgagaagatt 1320
gaaaaaatct tgactttcg aattcctat tatgttggtc cattggcgcg tggcaatagt 1380
cgttttgcat ggatgactcg gaagtctgaa gaaacaatta ccccatggaa ttttgaagaa 1440
gttgtcgata aggtgcttc agctcaatca tttattgaac gcatgacaaa ctttgataaa 1500
aatcttccaa atgaaaaagt actaccaaaa catgtttgc tttatgagta tttacggtt 1560
tataacgaat tgacaaaggt caaatatgtt actgaaggaa tgcgaaaacc agcatttctt 1620
tcaggtgaac agaagaaagc cattgttgat ttactcttca aaacaaatcg aaaagtaacc 1680
gttaagcaat aaaagaaga ttatttcaaa aaaatagaat gttttgatag tgttgaaatt 1740
tcaggagttg aagatagatt taatgcttca ttaggtacct accatgattt gctaaaaatt 1800
attaaagata aagttttttt ggataatgaa gaaaatgaag atatcttaga ggatattgtt 1860
ttaacattga cctattttga agataggagg atgattgagg aaagacttaa aacatatgct 1920
cacctctttg atgataaggt gatgaaacag cttaaacgtc gccgttatac tggttgggga 1980
cgtttgtctc gaaaattgat taatggtatt agggataagc aatctggcaa aacaatatta 2040
gatttttga aatcagatgg ttttgccaat cgcaattta ttcagctgat ccatgatgat 2100
agtttgacat ttaaagaaga cattcaaaaa gcacaagtgt ctggacaagg cgatagttta 2160
catgaacata ttgcaaattt agctggtagc cctgctatta aaaaggtat tttacagact 2220
gtaaaagttg ttgatgaatt ggtcaaagta atggggcggc ataagccaga aaatatcgtt 2280
attgaaatgg cacgtgaaaa tcagacaact caaaagggcc agaaaaattc gcgagagcgt 2340
atgaaacgaa tcgaagaagg tatcaaagaa ttaggaagtc agattcttaa agagcatcct 2400
gttgaaaata ctcaattgca aaatgaaaag ctctatctct attatctcca aaatggaaga 2460
gacatgtatg tggaccaaga attagatatt aatcgtttaa gtgattatga tgtcgatcac 2520
attgttccac aaagttttcct taaagacgat tcaataaca ataaggtctt aacgcgttct 2580
gataaaaatc gtggtaaatc ggataacgtt ccagtgaag aagtagtcaa aaagatgaaa 2640
aactattgga gacaacttct aaacgccaag ttaatcactc aacgtaagtt tgataattta 2700
acgaaagctg aacgtggagg tttgagtgaa cttgataaag ctggttttat caaacgccaa 2760
ttggttgaaa ctcgccaaat cactaagcat gtggcacaaa ttttggatag tcgcatgaat 2820
actaaatacg atgaaaatga taaacttatt cgagaggtta agtgattac cttaaaatct 2880
aaattagttt ctgacttccg aaaagatttc caattctata aagtacgtga gattaacaat 2940
taccatcatg cccatgatgc gtatctaaat gccgtcgttg gaactgcttt gattaagaaa 3000
tatccaaaac ttgaatcgga gtttgtctat ggtgattata aagtttatga tgttcgtaaa 3060
atgattgcta agtctgagca agaaataggc aaagcaaccg caaatatttt cttttactct 3120
aatatcatga acttcttcaa aacagaaatt acacttgcaa atggagagat tcgcaaacgc 3180
cctctaatcg aaactaatgg ggaaactgga gaaattgtct gggataaagg gcgagatttt 3240
gccacagtgc gcaaagtatt gtccatgccc caagtcaata ttgtcaagaa aacagaagta 3300
cagacaggcg gattctcaa ggagtcaatt taccaaaaa gaaattcgga caagcttatt 3360
gctcgtaaaa aagactggga tccaaaaaaa tatggtggtt tgatagtcc aacggtagct 3420
tattcagtcc tagtggttgc taaggtggaa aagggaaat cgaagaagtt aaaatccgtt 3480
aaagagttac tagggatcac aattatgaa agaagttcct ttgaaaaaaa tccgattgac 3540
ttttagaag ctaaaggata taaggaagtt aaaaaagact aatcattaa actacctaaa 3600
tatagtcttt ttgagttaga aaacggtcgt aaacggtcg tggctagtgc cggagaatta 3660
caaaaaggaa atgagctggc tctgccaagc aaatatgtga atttttata tttagctagt 3720
cattatgaaa agttgaaggg tagtccagaa gataacgaac aaaaacaatt gtttgtggag 3780
cagcataagc attatttaga tgagattatt gagcaaatca gtgaatttc taagcgtgtt 3840
attttagcag atgccaattt agataaagtt cttagtgcat ataacaaaca tagagacaaa 3900
ccaatcagtg aacaagcaga aatattatt catttttta cgttgacgaa tctgggaact 3960
cccgctgctt ttaaatattt tgatacaaca attgatcgta aacgatatac gtctacaaaa 4020
gaagttttag atgccactct tatccatcaa tccatcactg gtctttatga aacacgcatt 4080
gatttgagtc agctagggag tgactga                                     4107

SEQ ID NO: 3           moltype = AA   length = 7
```

```
FEATURE              Location/Qualifiers
source               1..7
                     mol_type = protein
                     note = synthetic polypeptide
                     organism = Simian virus 40
SEQUENCE: 3
PKKKRKV                                                                              7

SEQ ID NO: 4         moltype = AA   length = 7
FEATURE              Location/Qualifiers
source               1..7
                     mol_type = protein
                     organism = synthetic construct
SEQUENCE: 4
PKKKRRV                                                                              7

SEQ ID NO: 5         moltype = AA   length = 16
FEATURE              Location/Qualifiers
source               1..16
                     mol_type = protein
                     note = nucleoplasmin bipartite NLS sequence
                     organism = unidentified
SEQUENCE: 5
KRPAATKKAG QAKKKK                                                                    16

SEQ ID NO: 6         moltype = AA   length = 1775
FEATURE              Location/Qualifiers
source               1..1775
                     mol_type = protein
                     organism = synthetic construct
SEQUENCE: 6
MSEVEFSHEY WMRHALTLAK RAWDEREVPV GAVLVHNNRV IGEGWNRPIG RHDPTAHAEI        60
MALRQGGLVM QNYRLIDATL YVTLEPCVMC AGAMIHSRIG RVVFGARDAK TGAAGSLMDV       120
LHHPGMNHRV EITEGILADE CAALLSDFFR MRRQEIKAPK KAQSSTDSGG SSGGSSGSET       180
PGTSESATPE SSGGSSGGSS EVEFSHEYWM RHALTLAKRA RDEREVPVGA VLVLNNRVIG       240
EGWNRAIGLH DPTAHAEIMA LRQGGLVMQN YRLIDATLYV TFEPCVMCAG AMIHSRIGRV       300
VFGVRNAKTG AAGSLMDVLH YPGMNHRVEI TEGILADECA ALLCYFFRMP RQVFNAQKKA       360
QSSTDSGGSS GGSSGSETPG TSESATPESS GGSSGGSDKK YSIGLAIGTN SVGWAVITDE       420
YKVPSKKFKV LGNTDRHSIK KNLIGALLFD SGETAEATRL KRTARRRYTR RKNRICYLQE       480
IFSNEMAKVD DSFFHRLEES FLVEEDKKHE RHPIFGNIVD EVAYHEKYPT IYHLRKKLVD       540
STDKADLRLI YLALAHMIKF RGHFLIEGDL NPDNSDVDKL FIQLVQTYNQ LFEENPINAS       600
GVDAKAILSA RLSKSRRLEN LIAQLPGEKK NGLFGNLIAL SLGLTPNFKS NFDLAEDAKL       660
QLSKDTYDDD LDNLLAQIGD QYADLFLAAK NLSDAILLSD ILRVNTEITK APLSASMIKR       720
YDEHHQDLTL LKALVRQQLP EKYKEIFFDQ SKNGYAGYID GGASQEEFYK FIKPILEKMD       780
GTEELLVKLN REDLLRKQRT FDNGSIPHQI HLGELHAILR RQEDFYPFLK DNREKIEKIL       840
TFRIPYYVGP LARGNSRFAW MTRKSEETIT PWNFEEVVDK GASAQSFIER MTNFDKNLPN       900
EKVLPKHSLL YEYFTVYNEL TKVKYVTEGM RKPAFLSGEQ KKAIVDLLFK TNRKVTVKQL       960
KEDYFKKIEC FDSVEISGVE DRFNASLGTY HDLLKIIKDK DFLDNEENED ILEDIVLTLT      1020
LFEDREMIEE RLKTYAHLFD DKVMKQLKRR RYTGWGRLSR KLINGIRDKQ SGKTILDFLK      1080
SDGFANRNFM QLIHDDSLTF KEDIQKAQVS GQGDSLHEHI ANLAGSPAIK KGILQTVKVV      1140
DELVKVMGRH KPENIVIEMA RENQTTQKGQ KNSRERMKRI EEGIKELGSQ ILKEHPVENT      1200
QLQNEKLYLY YLQNGRDMYV DQELDINRLS DYDVDHIVPQ SFLKDDSIDN KVLTRSDKNR      1260
GKSDNVPSEE VVKKMKNYWR QLLNAKLITQ RKFDNLTKAE RGGLSELDKA GFIKRQLVET      1320
RQITKHVAQI LDSRMNTKYD ENDKLIREVK VITLKSKLVS DFRKDFQFYK VREINNYHHA      1380
HDAYLNAVVG TALIKKYPKL ESEFVYGDYK VYDVRKMIAK SEQEIGKATA KYFFYSNIMN      1440
FFKTEITLAN GEIRKRPLIE TNGETGEIVW DKGRDFATVR KVLSMPQVNI VKKTEVQTGG      1500
FSKESILPKR NSDKLIARKK DWDPKKYGGF DSPTVAYSVL VVAKVEKGKS KKLKSVKELL      1560
GITIMERSSF EKNPIDFLEA KGYKEVKKDL IIKLPKYSLF ELENGRKRML ASAGELQKGN      1620
ELALPSKYVN FLYLASHYEK LKGSPEDNEQ KQLFVEQHKH YLDEIIEQIS EFSKRVILAD      1680
ANLDKVLSAY NKHRDKPIRE QAENIIHLFT LTNLGAPAAF KYFDTTIDRK RYTSTKEVLD      1740
ATLIHQSITG LYETRIDLSQ LGGDSGGSPK KKRKV                                 1775

SEQ ID NO: 7         moltype = RNA   length = 13
FEATURE              Location/Qualifiers
source               1..13
                     mol_type = other RNA
                     organism = synthetic construct
SEQUENCE: 7
aaaaaaaaaa aaa                                                                       13

SEQ ID NO: 8         moltype = RNA   length = 13
FEATURE              Location/Qualifiers
source               1..13
                     mol_type = other RNA
                     organism = synthetic construct
SEQUENCE: 8
tttttttttt ttt                                                                       13

SEQ ID NO: 9         moltype = RNA   length = 13
```

-continued

```
FEATURE                 Location/Qualifiers
source                  1..13
                        mol_type = other RNA
                        organism = synthetic construct
SEQUENCE: 9
aaaaaaaaaa aaa                                                          13

SEQ ID NO: 10           moltype = RNA   length = 13
FEATURE                 Location/Qualifiers
source                  1..13
                        mol_type = other RNA
                        organism = synthetic construct
SEQUENCE: 10
tttttttttt ttt                                                          13

SEQ ID NO: 11           moltype = RNA   length = 13
FEATURE                 Location/Qualifiers
source                  1..13
                        mol_type = other RNA
                        organism = synthetic construct
SEQUENCE: 11
aaaaaaaaaa aaa                                                          13

SEQ ID NO: 12           moltype = RNA   length = 13
FEATURE                 Location/Qualifiers
source                  1..13
                        mol_type = other RNA
                        organism = synthetic construct
SEQUENCE: 12
tttttttttt ttt                                                          13

SEQ ID NO: 13           moltype = RNA   length = 24
FEATURE                 Location/Qualifiers
source                  1..24
                        mol_type = other RNA
                        organism = synthetic construct
SEQUENCE: 13
aaaaaaaaaa aaaaaaaaaa aaaa                                              24

SEQ ID NO: 14           moltype = RNA   length = 24
FEATURE                 Location/Qualifiers
source                  1..24
                        mol_type = other RNA
                        organism = synthetic construct
SEQUENCE: 14
tttttttttt tttttttttt tttt                                              24

SEQ ID NO: 15           moltype = RNA   length = 24
FEATURE                 Location/Qualifiers
source                  1..24
                        mol_type = other RNA
                        organism = synthetic construct
SEQUENCE: 15
aaaaaaaaaa aaaaaaaaaa aaaa                                              24

SEQ ID NO: 16           moltype = RNA   length = 24
FEATURE                 Location/Qualifiers
source                  1..24
                        mol_type = other RNA
                        organism = synthetic construct
SEQUENCE: 16
tttttttttt tttttttttt tttt                                              24

SEQ ID NO: 17           moltype = RNA   length = 24
FEATURE                 Location/Qualifiers
source                  1..24
                        mol_type = other RNA
                        organism = synthetic construct
SEQUENCE: 17
aaaaaaaaaa aaaaaaaaaa aaaa                                              24

SEQ ID NO: 18           moltype = RNA   length = 24
FEATURE                 Location/Qualifiers
source                  1..24
                        mol_type = other RNA
                        organism = synthetic construct
SEQUENCE: 18
tttttttttt tttttttttt tttt                                              24
```

-continued

| | | |
|---|---|---|
| SEQ ID NO: 19<br>FEATURE<br>source | moltype = RNA length = 13<br>Location/Qualifiers<br>1..13<br>mol_type = other RNA<br>organism = synthetic construct | |
| SEQUENCE: 19<br>aaaaaaaaaa aaa | | 13 |
| SEQ ID NO: 20<br>FEATURE<br>source | moltype = RNA length = 13<br>Location/Qualifiers<br>1..13<br>mol_type = other RNA<br>organism = synthetic construct | |
| SEQUENCE: 20<br>tttttttttt ttt | | 13 |
| SEQ ID NO: 21<br>FEATURE<br>source | moltype = RNA length = 13<br>Location/Qualifiers<br>1..13<br>mol_type = other RNA<br>organism = synthetic construct | |
| SEQUENCE: 21<br>aaaaaaaaaa aaa | | 13 |
| SEQ ID NO: 22<br>FEATURE<br>source | moltype = RNA length = 13<br>Location/Qualifiers<br>1..13<br>mol_type = other RNA<br>organism = synthetic construct | |
| SEQUENCE: 22<br>tttttttttt ttt | | 13 |
| SEQ ID NO: 23<br>FEATURE<br>source | moltype = RNA length = 13<br>Location/Qualifiers<br>1..13<br>mol_type = other RNA<br>organism = synthetic construct | |
| SEQUENCE: 23<br>aaaaaaaaaa aaa | | 13 |
| SEQ ID NO: 24<br>FEATURE<br>source | moltype = RNA length = 13<br>Location/Qualifiers<br>1..13<br>mol_type = other RNA<br>organism = synthetic construct | |
| SEQUENCE: 24<br>tttttttttt ttt | | 13 |
| SEQ ID NO: 25<br>FEATURE<br>source | moltype = RNA length = 24<br>Location/Qualifiers<br>1..24<br>mol_type = other RNA<br>organism = synthetic construct | |
| SEQUENCE: 25<br>aaaaaaaaaa aaaaaaaaaa aaaa | | 24 |
| SEQ ID NO: 26<br>FEATURE<br>source | moltype = RNA length = 24<br>Location/Qualifiers<br>1..24<br>mol_type = other RNA<br>organism = synthetic construct | |
| SEQUENCE: 26<br>tttttttttt tttttttttt tttt | | 24 |
| SEQ ID NO: 27<br>FEATURE<br>source | moltype = RNA length = 24<br>Location/Qualifiers<br>1..24<br>mol_type = other RNA<br>organism = synthetic construct | |
| SEQUENCE: 27<br>aaaaaaaaaa aaaaaaaaaa aaaa | | 24 |
| SEQ ID NO: 28<br>FEATURE<br>source | moltype = RNA length = 24<br>Location/Qualifiers<br>1..24<br>mol_type = other RNA<br>organism = synthetic construct | |
| SEQUENCE: 28<br>tttttttttt tttttttttt tttt | | 24 |

```
SEQ ID NO: 29          moltype = RNA   length = 24
FEATURE                Location/Qualifiers
source                 1..24
                       mol_type = other RNA
                       organism = synthetic construct
SEQUENCE: 29
aaaaaaaaaa aaaaaaaaaa aaaa                                          24

SEQ ID NO: 30          moltype = RNA   length = 24
FEATURE                Location/Qualifiers
source                 1..24
                       mol_type = other RNA
                       organism = synthetic construct
SEQUENCE: 30
tttttttttt tttttttttt tttt                                          24

SEQ ID NO: 31          moltype = RNA   length = 13
FEATURE                Location/Qualifiers
source                 1..13
                       mol_type = other RNA
                       organism = synthetic construct
SEQUENCE: 31
aaaaaaaaaa aaa                                                      13

SEQ ID NO: 32          moltype = RNA   length = 13
FEATURE                Location/Qualifiers
source                 1..13
                       mol_type = other RNA
                       organism = synthetic construct
SEQUENCE: 32
tttttttttt ttt                                                      13

SEQ ID NO: 33          moltype = RNA   length = 13
FEATURE                Location/Qualifiers
source                 1..13
                       mol_type = other RNA
                       organism = synthetic construct
SEQUENCE: 33
aaaaaaaaaa aaa                                                      13

SEQ ID NO: 34          moltype = RNA   length = 13
FEATURE                Location/Qualifiers
source                 1..13
                       mol_type = other RNA
                       organism = synthetic construct
SEQUENCE: 34
tttttttttt ttt                                                      13

SEQ ID NO: 35          moltype = RNA   length = 13
FEATURE                Location/Qualifiers
source                 1..13
                       mol_type = other RNA
                       organism = synthetic construct
SEQUENCE: 35
aaaaaaaaaa aaa                                                      13

SEQ ID NO: 36          moltype = RNA   length = 13
FEATURE                Location/Qualifiers
source                 1..13
                       mol_type = other RNA
                       organism = synthetic construct
SEQUENCE: 36
tttttttttt ttt                                                      13

SEQ ID NO: 37          moltype = RNA   length = 24
FEATURE                Location/Qualifiers
source                 1..24
                       mol_type = other RNA
                       organism = synthetic construct
SEQUENCE: 37
aaaaaaaaaa aaaaaaaaaa aaaa                                          24

SEQ ID NO: 38          moltype = RNA   length = 24
FEATURE                Location/Qualifiers
source                 1..24
                       mol_type = other RNA
                       organism = synthetic construct
SEQUENCE: 38
```

-continued

```
tttttttttt tttttttttt tttt                                          24

SEQ ID NO: 39           moltype = RNA   length = 24
FEATURE                 Location/Qualifiers
source                  1..24
                        mol_type = other RNA
                        organism = synthetic construct
SEQUENCE: 39
aaaaaaaaaa aaaaaaaaaa aaaa                                          24

SEQ ID NO: 40           moltype = RNA   length = 24
FEATURE                 Location/Qualifiers
source                  1..24
                        mol_type = other RNA
                        organism = synthetic construct
SEQUENCE: 40
tttttttttt tttttttttt tttt                                          24

SEQ ID NO: 41           moltype = RNA   length = 24
FEATURE                 Location/Qualifiers
source                  1..24
                        mol_type = other RNA
                        organism = synthetic construct
SEQUENCE: 41
aaaaaaaaaa aaaaaaaaaa aaaa                                          24

SEQ ID NO: 42           moltype = RNA   length = 24
FEATURE                 Location/Qualifiers
source                  1..24
                        mol_type = other RNA
                        organism = synthetic construct
SEQUENCE: 42
tttttttttt tttttttttt tttt                                          24

SEQ ID NO: 43           moltype = RNA   length = 13
FEATURE                 Location/Qualifiers
source                  1..13
                        mol_type = other RNA
                        organism = synthetic construct
SEQUENCE: 43
aaaaaaaaaa aaa                                                      13

SEQ ID NO: 44           moltype = DNA   length = 13
FEATURE                 Location/Qualifiers
source                  1..13
                        mol_type = other DNA
                        organism = synthetic construct
misc_feature            1..13
                        note = DNA/RNA hybrid sequence
modified_base           1
                        mod_base = OTHER
                        note = uracil
modified_base           3
                        mod_base = OTHER
                        note = uracil
modified_base           5
                        mod_base = OTHER
                        note = uracil
modified_base           7
                        mod_base = OTHER
                        note = uracil
modified_base           11
                        mod_base = OTHER
                        note = uracil
modified_base           13
                        mod_base = OTHER
                        note = uracil
SEQUENCE: 44
tttttttttt ttt                                                      13

SEQ ID NO: 45           moltype = RNA   length = 13
FEATURE                 Location/Qualifiers
source                  1..13
                        mol_type = other RNA
                        organism = synthetic construct
SEQUENCE: 45
aaaaaaaaaa aaa                                                      13

SEQ ID NO: 46           moltype = DNA   length = 13
```

```
FEATURE              Location/Qualifiers
misc_feature         1..13
                     note = DNA/RNA hybrid sequence
source               1..13
                     mol_type = other DNA
                     organism = synthetic construct
modified_base        1
                     mod_base = OTHER
                     note = uracil
modified_base        3
                     mod_base = OTHER
                     note = uracil
modified_base        5
                     mod_base = OTHER
                     note = uracil
modified_base        7
                     mod_base = OTHER
                     note = uracil
modified_base        9
                     mod_base = OTHER
                     note = uracil
modified_base        11
                     mod_base = OTHER
                     note = uracil
modified_base        13
                     mod_base = OTHER
                     note = uracil
SEQUENCE: 46
tttttttttt ttt                                                                   13

SEQ ID NO: 47        moltype = RNA   length = 13
FEATURE              Location/Qualifiers
source               1..13
                     mol_type = other RNA
                     organism = synthetic construct
SEQUENCE: 47
aaaaaaaaaa aaa                                                                   13

SEQ ID NO: 48        moltype = DNA   length = 13
FEATURE              Location/Qualifiers
misc_feature         1..13
                     note = DNA/RNA hybrid sequence
source               1..13
                     mol_type = other DNA
                     organism = synthetic construct
modified_base        1
                     mod_base = OTHER
                     note = uracil
modified_base        3
                     mod_base = OTHER
                     note = uracil
modified_base        5
                     mod_base = OTHER
                     note = uracil
modified_base        7
                     mod_base = OTHER
                     note = uracil
modified_base        9
                     mod_base = OTHER
                     note = uracil
modified_base        11
                     mod_base = OTHER
                     note = uracil
modified_base        13
                     mod_base = OTHER
                     note = uracil
SEQUENCE: 48
tttttttttt ttt                                                                   13

SEQ ID NO: 49        moltype = RNA   length = 24
FEATURE              Location/Qualifiers
source               1..24
                     mol_type = other RNA
                     organism = synthetic construct
SEQUENCE: 49
aaaaaaaaaa aaaaaaaaaa aaaa                                                       24

SEQ ID NO: 50        moltype = DNA   length = 24
FEATURE              Location/Qualifiers
```

```
misc_feature         1..24
                     note = DNA/RNA hybrid sequence
source               1..24
                     mol_type = other DNA
                     organism = synthetic construct
modified_base        1
                     mod_base = OTHER
                     note = uracil
modified_base        2
                     mod_base = OTHER
                     note = uracil
modified_base        4
                     mod_base = OTHER
                     note = uracil
modified_base        6
                     mod_base = OTHER
                     note = uracil
modified_base        8
                     mod_base = OTHER
                     note = uracil
modified_base        10
                     mod_base = OTHER
                     note = uracil
modified_base        12
                     mod_base = OTHER
                     note = uracil
modified_base        14
                     mod_base = OTHER
                     note = uracil
modified_base        16
                     mod_base = OTHER
                     note = uracil
modified_base        18
                     mod_base = OTHER
                     note = uracil
modified_base        20
                     mod_base = OTHER
                     note = uracil
modified_base        22
                     mod_base = OTHER
                     note = uracil
modified_base        24
                     mod_base = OTHER
                     note = uracil
SEQUENCE: 50
tttttttttt tttttttttt tttt                                              24

SEQ ID NO: 51        moltype = RNA  length = 24
FEATURE              Location/Qualifiers
source               1..24
                     mol_type = other RNA
                     organism = synthetic construct
SEQUENCE: 51
aaaaaaaaaa aaaaaaaaaa aaaa                                              24

SEQ ID NO: 52        moltype = DNA  length = 24
FEATURE              Location/Qualifiers
misc_feature         1..24
                     note = DNA/RNA hybrid sequence
source               1..24
                     mol_type = other DNA
                     organism = synthetic construct
modified_base        1
                     mod_base = OTHER
                     note = uracil
modified_base        2
                     mod_base = OTHER
                     note = uracil
modified_base        4
                     mod_base = OTHER
                     note = uracil
modified_base        6
                     mod_base = OTHER
                     note = uracil
modified_base        8
                     mod_base = OTHER
                     note = uracil
modified_base        10
                     mod_base = OTHER
```

```
modified_base           note = uracil
                        12
                        mod_base = OTHER
                        note = uracil
modified_base           14
                        mod_base = OTHER
                        note = uracil
modified_base           16
                        mod_base = OTHER
                        note = uracil
modified_base           22
                        mod_base = OTHER
                        note = uracil
modified_base           20
                        mod_base = OTHER
                        note = uracil
modified_base           18
                        mod_base = OTHER
                        note = uracil
modified_base           24
                        mod_base = OTHER
                        note = uracil
SEQUENCE: 52
tttttttttt tttttttttt tttt                                              24

SEQ ID NO: 53           moltype = RNA  length = 24
FEATURE                 Location/Qualifiers
source                  1..24
                        mol_type = other RNA
                        organism = synthetic construct
SEQUENCE: 53
aaaaaaaaaa aaaaaaaaaa aaaa                                              24

SEQ ID NO: 54           moltype = DNA  length = 24
FEATURE                 Location/Qualifiers
misc_feature            1..24
                        note = DNA/RNA hybrid sequence
source                  1..24
                        mol_type = other DNA
                        organism = synthetic construct
modified_base           1
                        mod_base = OTHER
                        note = uracil
modified_base           2
                        mod_base = OTHER
                        note = uracil
modified_base           4
                        mod_base = OTHER
                        note = uracil
modified_base           6
                        mod_base = OTHER
                        note = uracil
modified_base           8
                        mod_base = OTHER
                        note = uracil
modified_base           10
                        mod_base = OTHER
                        note = uracil
modified_base           12
                        mod_base = OTHER
                        note = uracil
modified_base           14
                        mod_base = OTHER
                        note = uracil
modified_base           16
                        mod_base = OTHER
                        note = uracil
modified_base           18
                        mod_base = OTHER
                        note = uracil
modified_base           20
                        mod_base = OTHER
                        note = uracil
modified_base           22
                        mod_base = OTHER
                        note = uracil
modified_base           24
                        mod_base = OTHER
                        note = uracil
```

-continued

```
SEQUENCE: 54
tttttttttt tttttttttt tttt                                          24

SEQ ID NO: 55           moltype = RNA   length = 13
FEATURE                 Location/Qualifiers
source                  1..13
                        mol_type = other RNA
                        organism = synthetic construct
SEQUENCE: 55
aaaaaaaaaa aaa                                                      13

SEQ ID NO: 56           moltype = DNA   length = 13
FEATURE                 Location/Qualifiers
source                  1..13
                        mol_type = other DNA
                        organism = synthetic construct
SEQUENCE: 56
tttttttttt ttt                                                      13

SEQ ID NO: 57           moltype = RNA   length = 13
FEATURE                 Location/Qualifiers
source                  1..13
                        mol_type = other RNA
                        organism = synthetic construct
SEQUENCE: 57
aaaaaaaaaa aaa                                                      13

SEQ ID NO: 58           moltype = DNA   length = 13
FEATURE                 Location/Qualifiers
misc_feature            1..13
                        note = DNA/RNA hybrid sequence
source                  1..13
                        mol_type = other DNA
                        organism = synthetic construct
modified_base           3
                        mod_base = OTHER
                        note = uracil
SEQUENCE: 58
tttttttttt ttt                                                      13

SEQ ID NO: 59           moltype = RNA   length = 13
FEATURE                 Location/Qualifiers
source                  1..13
                        mol_type = other RNA
                        organism = synthetic construct
SEQUENCE: 59
aaaaaaaaaa aaa                                                      13

SEQ ID NO: 60           moltype = DNA   length = 13
FEATURE                 Location/Qualifiers
source                  1..13
                        mol_type = other DNA
                        organism = synthetic construct
SEQUENCE: 60
tttttttttt ttt                                                      13

SEQ ID NO: 61           moltype = RNA   length = 24
FEATURE                 Location/Qualifiers
source                  1..24
                        mol_type = other RNA
                        organism = synthetic construct
SEQUENCE: 61
aaaaaaaaaa aaaaaaaaaa aaaa                                          24

SEQ ID NO: 62           moltype = DNA   length = 24
FEATURE                 Location/Qualifiers
source                  1..24
                        mol_type = other DNA
                        organism = synthetic construct
SEQUENCE: 62
tttttttttt tttttttttt tttt                                          24

SEQ ID NO: 63           moltype = RNA   length = 24
FEATURE                 Location/Qualifiers
source                  1..24
                        mol_type = other RNA
                        organism = synthetic construct
SEQUENCE: 63
aaaaaaaaaa aaaaaaaaaa aaaa                                          24
```

```
SEQ ID NO: 64            moltype = DNA   length = 24
FEATURE                  Location/Qualifiers
source                   1..24
                         mol_type = other DNA
                         organism = synthetic construct
SEQUENCE: 64
tttttttttt tttttttttt tttt                                              24

SEQ ID NO: 65            moltype = RNA   length = 24
FEATURE                  Location/Qualifiers
source                   1..24
                         mol_type = other RNA
                         organism = synthetic construct
SEQUENCE: 65
aaaaaaaaaa aaaaaaaaaa aaaa                                              24

SEQ ID NO: 66            moltype = DNA   length = 24
FEATURE                  Location/Qualifiers
source                   1..24
                         mol_type = other DNA
                         organism = synthetic construct
SEQUENCE: 66
tttttttttt tttttttttt tttt                                              24

SEQ ID NO: 67            moltype = RNA   length = 100
FEATURE                  Location/Qualifiers
source                   1..100
                         mol_type = other RNA
                         organism = synthetic construct
SEQUENCE: 67
ggctgatgag gccgcacatg gttttagagc tagaaatagc aagttaaaat aaggctagtc       60
cgttatcaac ttgaaaaagt ggcaccgagt cggtgctttt                            100

SEQ ID NO: 68            moltype = RNA   length = 100
FEATURE                  Location/Qualifiers
source                   1..100
                         mol_type = other RNA
                         organism = synthetic construct
SEQUENCE: 68
ggctgatgag gccgcacatg gttttagagc tagaaatagc aagttaaaat aaggctagtc       60
cgttatcaac ttgaaaaagt ggcaccgagt cggtgctttt                            100

SEQ ID NO: 69            moltype = RNA   length = 115
FEATURE                  Location/Qualifiers
source                   1..115
                         mol_type = other RNA
                         organism = synthetic construct
SEQUENCE: 69
ggctgatgag gccgcacatg gttttagagc tagaaatagc aagttaaaat aaggctagtc       60
cgttatcaac ttgaaaaagt ggcaccgagt cggtgctttt ttcctttgtt tttgc           115

SEQ ID NO: 70            moltype = RNA   length = 115
FEATURE                  Location/Qualifiers
source                   1..115
                         mol_type = other RNA
                         organism = synthetic construct
SEQUENCE: 70
cctttgtttt tgcttggctg atgaggccgc acatggtttt agagctagaa atagcaagtt       60
aaaataaggc tagtccgtta tcaacttgaa aaagtggcac cgagtcggtg ctttt           115

SEQ ID NO: 71            moltype = RNA   length = 13
FEATURE                  Location/Qualifiers
misc_feature             1..13
                         note = Description of Artificial Sequence: Synthetic
                          oligonucleotide
source                   1..13
                         mol_type = other RNA
                         organism = synthetic construct
SEQUENCE: 71
gcaaaaacaa agg                                                          13

SEQ ID NO: 72            moltype = RNA   length = 13
FEATURE                  Location/Qualifiers
source                   1..13
                         mol_type = other RNA
                         organism = synthetic construct
SEQUENCE: 72
gcaaaaacaa agg                                                          13
```

```
SEQ ID NO: 73           moltype = RNA  length = 130
FEATURE                 Location/Qualifiers
source                  1..130
                        mol_type = other RNA
                        organism = synthetic construct
SEQUENCE: 73
cctttgtttt tgcttggctg atgaggccgc acatggtttt agagctagaa atagcaagtt    60
aaaataaggc tagtccgtta tcaacttgaa aaagtggcac cgagtcggtg cttttttcct   120
ttgttttgc                                                           130

SEQ ID NO: 74           moltype = RNA  length = 13
FEATURE                 Location/Qualifiers
source                  1..13
                        mol_type = other RNA
                        organism = synthetic construct
SEQUENCE: 74
gcaaaaacaa agg                                                       13

SEQ ID NO: 75           moltype = RNA  length = 13
FEATURE                 Location/Qualifiers
source                  1..13
                        mol_type = other RNA
                        organism = synthetic construct
SEQUENCE: 75
gcaaaaacaa agg                                                       13

SEQ ID NO: 76           moltype = DNA  length = 116
FEATURE                 Location/Qualifiers
misc_feature            1..116
                        note = DNA/RNA hybrid sequence
source                  1..116
                        mol_type = other DNA
                        organism = synthetic construct
modified_base           7
                        mod_base = OTHER
                        note = uracil
modified_base           19
                        mod_base = OTHER
                        note = uracil
modified_base           22..25
                        mod_base = OTHER
                        note = uracil
modified_base           31
                        mod_base = OTHER
                        note = uracil
modified_base           37
                        mod_base = OTHER
                        note = uracil
modified_base           44..45
                        mod_base = OTHER
                        note = uracil
modified_base           50
                        mod_base = OTHER
                        note = uracil
modified_base           56
                        mod_base = OTHER
                        note = uracil
modified_base           59
                        mod_base = OTHER
                        note = uracil
modified_base           63..64
                        mod_base = OTHER
                        note = uracil
modified_base           66
                        mod_base = OTHER
                        note = uracil
modified_base           71..72
                        mod_base = OTHER
                        note = uracil
modified_base           80
                        mod_base = OTHER
                        note = uracil
modified_base           90
                        mod_base = OTHER
                        note = uracil
modified_base           94
                        mod_base = OTHER
                        note = uracil
```

| | | |
|---|---|---|
| modified_base | 97..100 | |
| | mod_base = OTHER | |
| | note = uracil | |
| modified_base | 106..108 | |
| | mod_base = OTHER | |
| | note = uracil | |
| modified_base | 110 | |
| | mod_base = OTHER | |
| | note = uracil | |
| modified_base | 111..114 | |
| | mod_base = OTHER | |
| | note = uracil | |
| modified_base | 4 | |
| | mod_base = OTHER | |
| | note = uracil | |

SEQUENCE: 76
```
ggctgatgag gccgcacatg gttttagagc tagaaatagc aagttaaaat aaggctagtc   60
cgttatcaac ttgaaaaagt ggcaccgagt cggtgctttt tttcctttgt ttttgc      116
```

| | | |
|---|---|---|
| SEQ ID NO: 77 | moltype = RNA  length = 13 | |
| FEATURE | Location/Qualifiers | |
| source | 1..13 | |
| | mol_type = other RNA | |
| | organism = synthetic construct | |

SEQUENCE: 77
```
gcaaaaacaa agg                                                     13
```

| | | |
|---|---|---|
| SEQ ID NO: 78 | moltype = DNA  length = 116 | |
| FEATURE | Location/Qualifiers | |
| misc_feature | 1..116 | |
| | note = DNA/RNA hybrid sequence | |
| source | 1..116 | |
| | mol_type = other DNA | |
| | organism = synthetic construct | |
| modified_base | 3..5 | |
| | mod_base = OTHER | |
| | note = uracil | |
| modified_base | 7..11 | |
| | mod_base = OTHER | |
| | note = uracil | |
| modified_base | 20 | |
| | mod_base = OTHER | |
| | note = uracil | |
| modified_base | 23 | |
| | mod_base = OTHER | |
| | note = uracil | |
| modified_base | 35 | |
| | mod_base = OTHER | |
| | note = uracil | |
| modified_base | 38..41 | |
| | mod_base = OTHER | |
| | note = uracil | |
| modified_base | 47 | |
| | mod_base = OTHER | |
| | note = uracil | |
| modified_base | 53 | |
| | mod_base = OTHER | |
| | note = uracil | |
| modified_base | 60..61 | |
| | mod_base = OTHER | |
| | note = uracil | |
| modified_base | 66 | |
| | mod_base = OTHER | |
| | note = uracil | |
| modified_base | 72 | |
| | mod_base = OTHER | |
| | note = uracil | |
| modified_base | 75 | |
| | mod_base = OTHER | |
| | note = uracil | |
| modified_base | 79..80 | |
| | mod_base = OTHER | |
| | note = uracil | |
| modified_base | 82 | |
| | mod_base = OTHER | |
| | note = uracil | |
| modified_base | 87..88 | |
| | mod_base = OTHER | |
| | note = uracil | |

```
modified_base          96
                       mod_base = OTHER
                       note = uracil
modified_base          106
                       mod_base = OTHER
                       note = uracil
modified_base          110
                       mod_base = OTHER
                       note = uracil
modified_base          113..116
                       mod_base = OTHER
                       note = uracil
SEQUENCE: 78
cctttgtttt tgctttggct gatgaggccg cacatggttt tagagctaga aatagcaagt   60
taaaataagg ctagtccgtt atcaacttga aaaagtggca ccgagtcggt gctttt      116

SEQ ID NO: 79          moltype = RNA  length = 13
FEATURE                Location/Qualifiers
source                 1..13
                       mol_type = other RNA
                       organism = synthetic construct
SEQUENCE: 79
gcaaaaacaa agg                                                      13

SEQ ID NO: 80          moltype = DNA  length = 132
FEATURE                Location/Qualifiers
misc_feature           1..132
                       note = DNA/RNA hybrid sequence
source                 1..132
                       mol_type = other DNA
                       organism = synthetic construct
modified_base          3..5
                       mod_base = OTHER
                       note = uracil
modified_base          7..11
                       mod_base = OTHER
                       note = uracil
modified_base          20
                       mod_base = OTHER
                       note = uracil
modified_base          23
                       mod_base = OTHER
                       note = uracil
modified_base          35
                       mod_base = OTHER
                       note = uracil
modified_base          38..41
                       mod_base = OTHER
                       note = uracil
modified_base          47
                       mod_base = OTHER
                       note = uracil
modified_base          53
                       mod_base = OTHER
                       note = uracil
modified_base          60..61
                       mod_base = OTHER
                       note = uracil
modified_base          65
                       mod_base = OTHER
                       note = uracil
modified_base          72
                       mod_base = OTHER
                       note = uracil
modified_base          75
                       mod_base = OTHER
                       note = uracil
modified_base          79..80
                       mod_base = OTHER
                       note = uracil
modified_base          82
                       mod_base = OTHER
                       note = uracil
modified_base          87..88
                       mod_base = OTHER
                       note = uracil
modified_base          96
                       mod_base = OTHER
                       note = uracil
```

```
modified_base           106
                        mod_base = OTHER
                        note = uracil
modified_base           110
                        mod_base = OTHER
                        note = uracil
modified_base           113..116
                        mod_base = OTHER
                        note = uracil
modified_base           122..124
                        mod_base = OTHER
                        note = uracil
modified_base           126..130
                        mod_base = OTHER
                        note = uracil
SEQUENCE: 80
cctttgtttt tgctttggct gatgaggccg cacatggttt tagagctaga aatagcaagt    60
taaaataagg ctagtccgtt atcaacttga aaaagtggca ccgagtcggt gcttttttc   120
ctttgttttt gc                                                       132

SEQ ID NO: 81           moltype = RNA   length = 13
FEATURE                 Location/Qualifiers
source                  1..13
                        mol_type = other RNA
                        organism = synthetic construct
SEQUENCE: 81
gcaaaaacaa agg                                                       13

SEQ ID NO: 82           moltype = RNA   length = 13
FEATURE                 Location/Qualifiers
source                  1..13
                        mol_type = other RNA
                        organism = synthetic construct
SEQUENCE: 82
gcaaaaacaa agg                                                       13

SEQ ID NO: 83           moltype = RNA   length = 103
FEATURE                 Location/Qualifiers
source                  1..103
                        mol_type = other RNA
                        organism = synthetic construct
SEQUENCE: 83
tttggctgat gaggccgcac atggttttag agctagaaat agcaagttaa aataaggcta    60
gtccgttatc aacttgaaaa agtggcaccg agtcggtgct ttt                     103

SEQ ID NO: 84           moltype = RNA   length = 103
FEATURE                 Location/Qualifiers
source                  1..103
                        mol_type = other RNA
                        organism = synthetic construct
SEQUENCE: 84
tttggctgat gaggccgcac atggttttag agctagaaat agcaagttaa aataaggcta    60
gtccgttatc aacttgaaaa agtggcaccg agtcggtgct ttt                     103

SEQ ID NO: 85           moltype = RNA   length = 103
FEATURE                 Location/Qualifiers
source                  1..103
                        mol_type = other RNA
                        organism = synthetic construct
SEQUENCE: 85
tttggctgat gaggccgcac atggttttag agctagaaat agcaagttaa aataaggcta    60
gtccgttatc aacttgaaaa agtggcaccg agtcggtgct ttt                     103

SEQ ID NO: 86           moltype = RNA   length = 103
FEATURE                 Location/Qualifiers
source                  1..103
                        mol_type = other RNA
                        organism = synthetic construct
SEQUENCE: 86
tttggctgat gaggccgcac atggttttag agctagaaat agcaagttaa aataaggcta    60
gtccgttatc aacttgaaaa agtggcaccg agtcggtgct ttt                     103

SEQ ID NO: 87           moltype = DNA   length = 103
FEATURE                 Location/Qualifiers
misc_feature            1..103
                        note = DNA/RNA hybrid sequence
source                  1..103
                        mol_type = other DNA
                        organism = synthetic construct
```

```
modified_base      7
                   mod_base = OTHER
                   note = uracil
modified_base      10
                   mod_base = OTHER
                   note = uracil
modified_base      22
                   mod_base = OTHER
                   note = uracil
modified_base      25..28
                   mod_base = OTHER
                   note = uracil
modified_base      34
                   mod_base = OTHER
                   note = uracil
modified_base      40
                   mod_base = OTHER
                   note = uracil
modified_base      47..48
                   mod_base = OTHER
                   note = uracil
modified_base      53
                   mod_base = OTHER
                   note = uracil
modified_base      59
                   mod_base = OTHER
                   note = uracil
modified_base      62
                   mod_base = OTHER
                   note = uracil
modified_base      66..67
                   mod_base = OTHER
                   note = uracil
modified_base      69
                   mod_base = OTHER
                   note = uracil
modified_base      74..75
                   mod_base = OTHER
                   note = uracil
modified_base      83
                   mod_base = OTHER
                   note = uracil
modified_base      93
                   mod_base = OTHER
                   note = uracil
modified_base      97
                   mod_base = OTHER
                   note = uracil
modified_base      100..103
                   mod_base = OTHER
                   note = uracil
SEQUENCE: 87
tttggctgat gaggccgcac atggttttag agctagaaat agcaagttaa aataaggcta   60
gtccgttatc aacttgaaaa agtggcaccg agtcggtgct ttt                   103

SEQ ID NO: 88        moltype = DNA   length = 103
FEATURE              Location/Qualifiers
misc_feature         1..103
                     note = DNA/RNA hybrid sequence
source               1..103
                     mol_type = other DNA
                     organism = synthetic construct
modified_base        7
                     mod_base = OTHER
                     note = uracil
modified_base        10
                     mod_base = OTHER
                     note = uracil
modified_base        22
                     mod_base = OTHER
                     note = uracil
modified_base        25..28
                     mod_base = OTHER
                     note = uracil
modified_base        34
                     mod_base = OTHER
                     note = uracil
modified_base        40
                     mod_base = OTHER
```

|   |   |
|---|---|
| modified_base | 47..48 |
|   | mod_base = OTHER |
|   | note = uracil |
| modified_base | 53 |
|   | mod_base = OTHER |
|   | note = uracil |
| modified_base | 59 |
|   | mod_base = OTHER |
|   | note = uracil |
| modified_base | 62 |
|   | mod_base = OTHER |
|   | note = uracil |
| modified_base | 66..67 |
|   | mod_base = OTHER |
|   | note = uracil |
| modified_base | 69 |
|   | mod_base = OTHER |
|   | note = uracil |
| modified_base | 74..75 |
|   | mod_base = OTHER |
|   | note = uracil |
| modified_base | 83 |
|   | mod_base = OTHER |
|   | note = uracil |
| modified_base | 93 |
|   | mod_base = OTHER |
|   | note = uracil |
| modified_base | 97 |
|   | mod_base = OTHER |
|   | note = uracil |
| modified_base | 100..103 |
|   | mod_base = OTHER |
|   | note = uracil |
| SEQUENCE: 88 | |

```
tttggctgat gaggccgcac atggttttag agctagaaat agcaagttaa aataaggcta   60
gtccgttatc aacttgaaaa agtggcaccg agtcggtgct ttt                    103
```

|   |   |
|---|---|
| SEQ ID NO: 89 | moltype = DNA  length = 103 |
| FEATURE | Location/Qualifiers |
| misc_feature | 1..103 |
|   | note = DNA/RNA hybrid sequence |
| source | 1..103 |
|   | mol_type = other DNA |
|   | organism = synthetic construct |
| modified_base | 7 |
|   | mod_base = OTHER |
|   | note = uracil |
| modified_base | 10 |
|   | mod_base = OTHER |
|   | note = uracil |
| modified_base | 22 |
|   | mod_base = OTHER |
|   | note = uracil |
| modified_base | 25..28 |
|   | mod_base = OTHER |
|   | note = uracil |
| modified_base | 34 |
|   | mod_base = OTHER |
|   | note = uracil |
| modified_base | 40 |
|   | mod_base = OTHER |
|   | note = uracil |
| modified_base | 47..48 |
|   | mod_base = OTHER |
|   | note = uracil |
| modified_base | 53 |
|   | mod_base = OTHER |
|   | note = uracil |
| modified_base | 59 |
|   | mod_base = OTHER |
|   | note = uracil |
| modified_base | 62 |
|   | mod_base = OTHER |
|   | note = uracil |
| modified_base | 66..67 |
|   | mod_base = OTHER |
|   | note = uracil |
| modified_base | 69 |

```
                        mod_base = OTHER
                        note = uracil
modified_base           74..75
                        mod_base = OTHER
                        note = uracil
modified_base           83
                        mod_base = OTHER
                        note = uracil
modified_base           93
                        mod_base = OTHER
                        note = uracil
modified_base           97
                        mod_base = OTHER
                        note = uracil
modified_base           100..103
                        mod_base = OTHER
                        note = uracil
SEQUENCE: 89
tttggctgat gaggccgcac atggttttag agctagaaat agcaagttaa aataaggcta    60
gtccgttatc aacttgaaaa agtggcaccg agtcggtgct ttt                     103

SEQ ID NO: 90           moltype = DNA  length = 103
FEATURE                 Location/Qualifiers
misc_feature            1..103
                        note = DNA/RNA hybrid sequence
source                  1..103
                        mol_type = other DNA
                        organism = synthetic construct
modified_base           7
                        mod_base = OTHER
                        note = uracil
modified_base           10
                        mod_base = OTHER
                        note = uracil
modified_base           22
                        mod_base = OTHER
                        note = uracil
modified_base           25..28
                        mod_base = OTHER
                        note = uracil
modified_base           34
                        mod_base = OTHER
                        note = uracil
modified_base           40
                        mod_base = OTHER
                        note = uracil
modified_base           47..48
                        mod_base = OTHER
                        note = uracil
modified_base           53
                        mod_base = OTHER
                        note = uracil
modified_base           59
                        mod_base = OTHER
                        note = uracil
modified_base           62
                        mod_base = OTHER
                        note = uracil
modified_base           66..67
                        mod_base = OTHER
                        note = uracil
modified_base           69
                        mod_base = OTHER
                        note = uracil
modified_base           74..75
                        mod_base = OTHER
                        note = uracil
modified_base           83
                        mod_base = OTHER
                        note = uracil
modified_base           93
                        mod_base = OTHER
                        note = uracil
modified_base           97
                        mod_base = OTHER
                        note = uracil
modified_base           100..103
                        mod_base = OTHER
                        note = uracil
```

-continued

```
SEQUENCE: 90
tttggctgat gaggccgcac atggttttag agctagaaat agcaagttaa aataaggcta    60
gtccgttatc aacttgaaaa agtggcaccg agtcggtgct ttt                     103

SEQ ID NO: 91            moltype = DNA   length = 103
FEATURE                  Location/Qualifiers
misc_feature             1..103
                         note = DNA/RNA hybrid sequence
source                   1..103
                         mol_type = other DNA
                         organism = synthetic construct
modified_base            4
                         mod_base = OTHER
                         note = uracil
modified_base            7
                         mod_base = OTHER
                         note = uracil
modified_base            19
                         mod_base = OTHER
                         note = uracil
modified_base            22..25
                         mod_base = OTHER
                         note = uracil
modified_base            31
                         mod_base = OTHER
                         note = uracil
modified_base            37
                         mod_base = OTHER
                         note = uracil
modified_base            44..45
                         mod_base = OTHER
                         note = uracil
modified_base            50
                         mod_base = OTHER
                         note = uracil
modified_base            56
                         mod_base = OTHER
                         note = uracil
modified_base            59
                         mod_base = OTHER
                         note = uracil
modified_base            63..64
                         mod_base = OTHER
                         note = uracil
modified_base            66
                         mod_base = OTHER
                         note = uracil
modified_base            71..72
                         mod_base = OTHER
                         note = uracil
modified_base            80
                         mod_base = OTHER
                         note = uracil
modified_base            90
                         mod_base = OTHER
                         note = uracil
modified_base            94
                         mod_base = OTHER
                         note = uracil
modified_base            97..100
                         mod_base = OTHER
                         note = uracil
SEQUENCE: 91
ggctgatgag gccgcacatg gttttagagc tagaaatagc aagttaaaat aaggctagtc    60
cgttatcaac ttgaaaaagt ggcaccgagt cggtgctttt ttt                     103

SEQ ID NO: 92            moltype = DNA   length = 103
FEATURE                  Location/Qualifiers
misc_feature             1..103
                         note = DNA/RNA hybrid sequence
source                   1..103
                         mol_type = other DNA
                         organism = synthetic construct
modified_base            4
                         mod_base = OTHER
                         note = uracil
modified_base            7
                         mod_base = OTHER
                         note = uracil
```

```
modified_base        19
                     mod_base = OTHER
                     note = uracil
modified_base        22..25
                     mod_base = OTHER
                     note = uracil
modified_base        31
                     mod_base = OTHER
                     note = uracil
modified_base        37
                     mod_base = OTHER
                     note = uracil
modified_base        44..45
                     mod_base = OTHER
                     note = uracil
modified_base        50
                     mod_base = OTHER
                     note = uracil
modified_base        56
                     mod_base = OTHER
                     note = uracil
modified_base        59
                     mod_base = OTHER
                     note = uracil
modified_base        63..64
                     mod_base = OTHER
                     note = uracil
modified_base        66
                     mod_base = OTHER
                     note = uracil
modified_base        71..72
                     mod_base = OTHER
                     note = uracil
modified_base        80
                     mod_base = OTHER
                     note = uracil
modified_base        90
                     mod_base = OTHER
                     note = uracil
modified_base        94
                     mod_base = OTHER
                     note = uracil
modified_base        97..100
                     mod_base = OTHER
                     note = uracil
SEQUENCE: 92
ggctgatgag gccgcacatg gttttagagc tagaaatagc aagttaaaat aaggctagtc    60
cgttatcaac ttgaaaaagt ggcaccgagt cggtgctttt ttt                     103

SEQ ID NO: 93        moltype = RNA   length = 106
FEATURE              Location/Qualifiers
source               1..106
                     mol_type = other RNA
                     organism = synthetic construct
SEQUENCE: 93
ggctgatgag gccgcacatg gttttagagc tagaaatagc aagttaaaat aaggctagtc    60
cgttatcaac ttgaaaaagt ggcaccgagt cggtgctttt tttttt                  106

SEQ ID NO: 94        moltype = RNA   length = 106
FEATURE              Location/Qualifiers
source               1..106
                     mol_type = other RNA
                     organism = synthetic construct
SEQUENCE: 94
ggctgatgag gccgcacatg gttttagagc tagaaatagc aagttaaaat aaggctagtc    60
cgttatcaac ttgaaaaagt ggcaccgagt cggtgctttt tttttt                  106

SEQ ID NO: 95        moltype = RNA   length = 106
FEATURE              Location/Qualifiers
source               1..106
                     mol_type = other RNA
                     organism = synthetic construct
SEQUENCE: 95
ggctgatgag gccgcacatg gttttagagc tagaaatagc aagttaaaat aaggctagtc    60
cgttatcaac ttgaaaaagt ggcaccgagt cggtgctttt tttttt                  106

SEQ ID NO: 96        moltype = DNA   length = 140
FEATURE              Location/Qualifiers
misc_feature         1..140
```

```
                        note = DNA/RNA hybrid sequence
source                  1..140
                        mol_type = other DNA
                        organism = synthetic construct
modified_base           24
                        mod_base = OTHER
                        note = uracil
modified_base           27
                        mod_base = OTHER
                        note = uracil
modified_base           39
                        mod_base = OTHER
                        note = uracil
modified_base           42..45
                        mod_base = OTHER
                        note = uracil
modified_base           51
                        mod_base = OTHER
                        note = uracil
modified_base           57
                        mod_base = OTHER
                        note = uracil
modified_base           64..65
                        mod_base = OTHER
                        note = uracil
modified_base           70
                        mod_base = OTHER
                        note = uracil
modified_base           76
                        mod_base = OTHER
                        note = uracil
modified_base           79
                        mod_base = OTHER
                        note = uracil
modified_base           83..84
                        mod_base = OTHER
                        note = uracil
modified_base           86
                        mod_base = OTHER
                        note = uracil
modified_base           91..92
                        mod_base = OTHER
                        note = uracil
modified_base           100
                        mod_base = OTHER
                        note = uracil
modified_base           110
                        mod_base = OTHER
                        note = uracil
modified_base           114
                        mod_base = OTHER
                        note = uracil
modified_base           117..120
                        mod_base = OTHER
                        note = uracil
SEQUENCE: 96
aaaaaaaaaa aaaaaatttt ggctgatgag gccgcacatg gttttagagc tagaaatagc    60
aagttaaaat aaggctagtc cgttatcaac ttgaaaaagt ggcaccgagt cggtgctttt   120
tttaaaaaaa aaaaaaaaaa                                               140

SEQ ID NO: 97           moltype = RNA   length = 17
FEATURE                 Location/Qualifiers
source                  1..17
                        mol_type = other RNA
                        organism = synthetic construct
SEQUENCE: 97
tttttttttt ttttttt                                                   17

SEQ ID NO: 98           moltype = RNA   length = 117
FEATURE                 Location/Qualifiers
source                  1..117
                        mol_type = other RNA
                        organism = synthetic construct
SEQUENCE: 98
ggctgatgag gccgcacatg gttttagagc tagaaatagc aagttaaaat aaggctagtc    60
cgttatcaac ttgaaaaagt ggcaccgagt cggtgctttt aaaaaaaaaa aaaaaaa     117

SEQ ID NO: 99           moltype = RNA   length = 17
FEATURE                 Location/Qualifiers
```

```
source                  1..17
                        mol_type = other RNA
                        organism = synthetic construct
SEQUENCE: 99
tttttttttt ttttttt                                                          17

SEQ ID NO: 100          moltype = RNA   length = 120
FEATURE                 Location/Qualifiers
source                  1..120
                        mol_type = other RNA
                        organism = synthetic construct
SEQUENCE: 100
ggctgatgag gccgcacatg gttttagagc tagaaatagc aagttaaaat aaggctagtc            60
cgttatcaac ttgaaaaagt ggcaccgagt cggtgctttt aaaaaaaaaa aaaaaaaaaa           120

SEQ ID NO: 101          moltype = RNA   length = 17
FEATURE                 Location/Qualifiers
source                  1..17
                        mol_type = other RNA
                        organism = synthetic construct
SEQUENCE: 101
tttttttttt ttttttt                                                          17

SEQ ID NO: 102          moltype = RNA   length = 120
FEATURE                 Location/Qualifiers
source                  1..120
                        mol_type = other RNA
                        organism = synthetic construct
SEQUENCE: 102
ggctgatgag gccgcacatg gttttagagc tagaaatagc aagttaaaat aaggctagtc            60
cgttatcaac ttgaaaaagt ggcaccgagt cggtgctttt aaaaaaaaaa aaaaaaaaaa           120

SEQ ID NO: 103          moltype = RNA   length = 20
FEATURE                 Location/Qualifiers
source                  1..20
                        mol_type = other RNA
                        organism = synthetic construct
SEQUENCE: 103
tttttttttt tttttttttt                                                       20

SEQ ID NO: 104          moltype = DNA   length = 20
FEATURE                 Location/Qualifiers
source                  1..20
                        mol_type = other DNA
                        note = protospacer sequence
                        organism = unidentified
SEQUENCE: 104
caggttccat gggatgctct                                                       20

SEQ ID NO: 105          moltype = DNA   length = 20
FEATURE                 Location/Qualifiers
source                  1..20
                        mol_type = other DNA
                        note = protospacer sequence
                        organism = unidentified
SEQUENCE: 105
ggctgatgag gccgcacatg                                                       20

SEQ ID NO: 106          moltype = DNA   length = 20
FEATURE                 Location/Qualifiers
source                  1..20
                        mol_type = other DNA
                        note = protospacer sequence
                        organism = unidentified
SEQUENCE: 106
cccataccttt ggagcaacgg                                                      20

SEQ ID NO: 107          moltype = DNA   length = 20
FEATURE                 Location/Qualifiers
source                  1..20
                        mol_type = other DNA
                        note = protospacer sequence
                        organism = unidentified
SEQUENCE: 107
cccataccttt ggagcaacgg                                                      20

SEQ ID NO: 108          moltype = DNA   length = 20
FEATURE                 Location/Qualifiers
source                  1..20
```

```
                            mol_type = other DNA
                            note = protospacer sequence
                            organism = unidentified
SEQUENCE: 108
cccatacctt ggagcaacgg                                                    20

SEQ ID NO: 109              moltype = DNA  length = 20
FEATURE                     Location/Qualifiers
source                      1..20
                            mol_type = other DNA
                            note = protospacer sequence
                            organism = unidentified
SEQUENCE: 109
cccatacctt ggagcaacgg                                                    20

SEQ ID NO: 110              moltype = DNA  length = 20
FEATURE                     Location/Qualifiers
source                      1..20
                            mol_type = other DNA
                            note = protospacer sequence
                            organism = unidentified
SEQUENCE: 110
cccgcacctt ggcgcagcgg                                                    20

SEQ ID NO: 111              moltype = DNA  length = 20
FEATURE                     Location/Qualifiers
source                      1..20
                            mol_type = other DNA
                            note = protospacer sequence
                            organism = unidentified
SEQUENCE: 111
gagatacctg agtaactttc                                                    20

SEQ ID NO: 112              moltype = DNA  length = 20
FEATURE                     Location/Qualifiers
source                      1..20
                            mol_type = other DNA
                            note = protospacer sequence
                            organism = unidentified
SEQUENCE: 112
gagatacctg agtaactttc                                                    20

SEQ ID NO: 113              moltype = DNA  length = 20
FEATURE                     Location/Qualifiers
source                      1..20
                            mol_type = other DNA
                            note = protospacer sequence
                            organism = unidentified
SEQUENCE: 113
gagatacctg agtaactttc                                                    20

SEQ ID NO: 114              moltype = AA  length = 6
FEATURE                     Location/Qualifiers
source                      1..6
                            mol_type = protein
                            note = 6xHis tag
                            organism = synthetic construct
SEQUENCE: 114
HHHHHH                                                                   6

SEQ ID NO: 115              moltype = RNA  length = 200
FEATURE                     Location/Qualifiers
misc_feature                1..200
                            note = this sequence may encompass 1-200 nucleotides
source                      1..200
                            mol_type = other RNA
                            organism = synthetic construct
SEQUENCE: 115
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa        120
aaaaaaaaaa aaaaaaaaaa aaaaaaaaaa aaaaaaaaaa aaaaaaaaaa aaaaaaaaaa        180
aaaaaaaaaa aaaaaaaaaa                                                    200

SEQ ID NO: 116              moltype = RNA  length = 200
FEATURE                     Location/Qualifiers
misc_feature                1..200
                            note = this sequence may encompass 1-200 nucleotides
source                      1..200
                            mol_type = other RNA
```

```
                            organism = synthetic construct
SEQUENCE: 116
tttttttttt tttttttttt tttttttttt tttttttttt tttttttttt tttttttttt    60
tttttttttt tttttttttt tttttttttt tttttttttt tttttttttt tttttttttt   120
tttttttttt tttttttttt tttttttttt tttttttttt tttttttttt tttttttttt   180
tttttttttt tttttttttt                                                200

SEQ ID NO: 117          moltype = DNA   length = 200
FEATURE                 Location/Qualifiers
misc_feature            1..200
                        note = this sequence may encompass 1-200 nucleotides
source                  1..200
                        mol_type = other DNA
                        organism = synthetic construct
SEQUENCE: 117
tttttttttt tttttttttt tttttttttt tttttttttt tttttttttt tttttttttt    60
tttttttttt tttttttttt tttttttttt tttttttttt tttttttttt tttttttttt   120
tttttttttt tttttttttt tttttttttt tttttttttt tttttttttt tttttttttt   180
tttttttttt tttttttttt                                                200

SEQ ID NO: 118          moltype = RNA   length = 50
FEATURE                 Location/Qualifiers
misc_feature            1..50
                        note = this sequence may encompass 3-50 nucleotides
source                  1..50
                        mol_type = other RNA
                        organism = synthetic construct
SEQUENCE: 118
tttttttttt tttttttttt tttttttttt tttttttttt tttttttttt               50

SEQ ID NO: 119          moltype = RNA   length = 20
FEATURE                 Location/Qualifiers
misc_feature            1..20
                        note = this sequence may encompass 3-20 nucleotides
source                  1..20
                        mol_type = other RNA
                        organism = synthetic construct
SEQUENCE: 119
tttttttttt tttttttttt                                                20

SEQ ID NO: 120          moltype = RNA   length = 15
FEATURE                 Location/Qualifiers
misc_feature            1..15
                        note = this sequence may encompass 3-15 nucleotides
source                  1..15
                        mol_type = other RNA
                        organism = synthetic construct
SEQUENCE: 120
tttttttttt ttttt                                                     15

SEQ ID NO: 121          moltype = RNA   length = 100
FEATURE                 Location/Qualifiers
source                  1..100
                        mol_type = other RNA
                        organism = synthetic construct
SEQUENCE: 121
caggttccat gggatgctct gttttagagc tagaaatagc aagttaaaat aaggctagtc    60
cgttatcaac ttgaaaaagt ggcaccgagt cggtgctttt                          100

SEQ ID NO: 122          moltype = RNA   length = 100
FEATURE                 Location/Qualifiers
source                  1..100
                        mol_type = other RNA
                        organism = synthetic construct
SEQUENCE: 122
ggctgatgag gccgcacatg gttttagagc tagaaatagc aagttaaaat aaggctagtc    60
cgttatcaac ttgaaaaagt ggcaccgagt cggtgctttt                          100

SEQ ID NO: 123          moltype = RNA   length = 100
FEATURE                 Location/Qualifiers
source                  1..100
                        mol_type = other RNA
                        organism = synthetic construct
SEQUENCE: 123
cccatacctt ggagcaacgg gttttagagc tagaaatagc aagttaaaat aaggctagtc    60
cgttatcaac ttgaaaaagt ggcaccgagt cggtgctttt                          100

SEQ ID NO: 124          moltype = RNA   length = 99
FEATURE                 Location/Qualifiers
```

```
source               1..99
                     mol_type = other RNA
                     organism = synthetic construct
SEQUENCE: 124
cccatacttg gagcaacggg tttagagct agaaatagca agttaaaata aggctagtcc  60
gttatcaact tgaaaaagtg gcaccgagtc ggtgctttt                        99

SEQ ID NO: 125       moltype = RNA  length = 100
FEATURE              Location/Qualifiers
source               1..100
                     mol_type = other RNA
                     organism = synthetic construct
SEQUENCE: 125
cccgcaccttt ggcgcagcgg gttttagagc tagaaatagc aagttaaaat aaggctagtc 60
cgttatcaac ttgaaaaagt ggcaccgagt cggtgctttt                       100

SEQ ID NO: 126       moltype = RNA  length = 100
FEATURE              Location/Qualifiers
source               1..100
                     mol_type = other RNA
                     organism = synthetic construct
SEQUENCE: 126
gagatacctg agtaactttc gttttagagc tagaaatagc aagttaaaat aaggctagtc 60
cgttatcaac ttgaaaaagt ggcaccgagt cggtgctttt                       100
```